United States Patent
Kemp et al.

(10) Patent No.: US 8,895,313 B2
(45) Date of Patent: Nov. 25, 2014

(54) LIGANDS FOR AGGREGATED TAU MOLECULES

(75) Inventors: Steven John Kemp, Aberdeen (GB); Lynda Jane Storey, Aberdeen (GB); John Mervyn David Storey, Aberdeen (GB); Janet Rickard, Aberdeen (GB); Charles Robert Harrington, Aberdeen (GB); Claude Michel Wischik, Aberdeen (GB); Scott Clunas, Aberdeen (GB); Tobias Kerst Heinrich, Berlin (DE)

(73) Assignee: Wista Laboratories Ltd., Singapore (SG)

( * ) Notice: Subject to any disclaimer, the term of this patent is extended or adjusted under 35 U.S.C. 154(b) by 12 days.

(21) Appl. No.: 13/063,525

(22) PCT Filed: Sep. 23, 2009

(86) PCT No.: PCT/GB2009/002260
§ 371 (c)(1),
(2), (4) Date: Mar. 11, 2011

(87) PCT Pub. No.: WO2010/034982
PCT Pub. Date: Apr. 1, 2010

(65) Prior Publication Data
US 2011/0171739 A1    Jul. 14, 2011

Related U.S. Application Data

(60) Provisional application No. 61/099,376, filed on Sep. 23, 2008.

(51) Int. Cl.
*G01N 33/50* (2006.01)
*C07D 277/66* (2006.01)
(Continued)

(52) U.S. Cl.
CPC .......... *G01N 33/6896* (2013.01); *C07D 471/04*

(58) Field of Classification Search
USPC ............... 436/86, 501, 503, 91, 98, 106, 119; 548/178, 154; 546/270.1, 121
See application file for complete search history.

(56) References Cited

U.S. PATENT DOCUMENTS 3,615,639 A    10/1971    Carpenter et al.
(Continued)

FOREIGN PATENT DOCUMENTS

CH    542 266    11/1973
(Continued)

OTHER PUBLICATIONS

Beta Amyloid Induces Paired Helical Filament-like Tau Filaments in Tissue Culture Alessandra Ferrari, Federic Hoerndli, Thomas Baechi, Roger M Nitsch, and jurgen Gotz J. Biol. Chem. 2003 278:40162-40168.*

(Continued)

*Primary Examiner* — Krishnan S Menon
*Assistant Examiner* — Dwan A Gerido
(74) *Attorney, Agent, or Firm* — Foley & Lardner LLP

(57) ABSTRACT

Provided are certain benzothiazole, imidazothiazole, imidazopyrimidine and imidazopyridine compounds, including, for example: formula (I) and pharmaceutically and physiologically acceptable salts, hydrates, and solvates thereof. Such compounds can be used as diagnostic ligands or labels of tau protein and PHF.

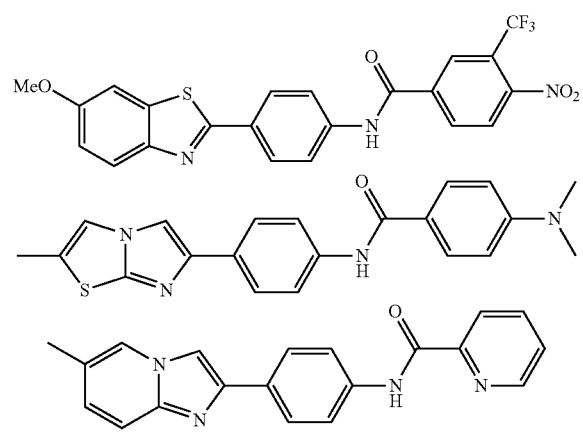

36 Claims, 6 Drawing Sheets

(51) Int. Cl.
C07D 417/12 (2006.01)
C07D 513/04 (2006.01)
C07D 471/04 (2006.01)
C07D 487/04 (2006.01)
G01N 33/68 (2006.01)(2013.01); G01N 2800/2821 (2013.01);

(Continued)

(52) U.S. Cl.
CPC ............ C07D 487/04 (2013.01); C07D 277/66 (2013.01); G01N 2333/4709 (2013.01); C07D 513/04 (2013.01); C07D 417/12 (2013.01)
USPC ............... 436/91; 436/98; 436/106; 436/119; 548/178; 548/154; 546/270.1; 546/121

(56) References Cited

U.S. PATENT DOCUMENTS

| | | | |
|---|---|---|---|
| 4,220,760 | A | 9/1980 | Erckel et al. |
| 4,508,903 | A | 4/1985 | Heiss |
| 6,034,246 | A | 3/2000 | Stevens et al. |
| 2003/0069261 | A1 | 4/2003 | Marzabadi et al. |
| 2007/0086949 | A1 | 4/2007 | Prasad et al. |
| 2007/0232661 | A1 | 10/2007 | Beachy et al. |

FOREIGN PATENT DOCUMENTS

| | | |
|---|---|---|
| EP | 0002042 A1 | 5/1979 |
| EP | 0 287 909 | 10/1988 |
| EP | 1 277 729 A1 | 1/2003 |
| EP | 1 547 996 A1 | 6/2005 |
| EP | 1 574 500 A1 | 9/2005 |
| GB | 941048 | 11/1963 |
| JP | 6826622 | 12/1965 |
| JP | 6908114 | 12/1965 |
| JP | 6826622 | 11/1968 |
| JP | 51-102186 A | 8/1976 |
| JP | 51-102186 A | 9/1976 |
| JP | 2004-67659 | 3/2004 |
| NL | 6615211 | 10/1966 |
| RU | 2 364 597 C1 | 8/2009 |
| SU | 1190986 A | 11/1985 |
| WO | WO 01/10854 A1 | 2/2001 |
| WO | WO 02/055720 A2 | 7/2002 |
| WO | WO 02/075318 A2 | 9/2002 |
| WO | WO 2004/083195 A1 | 9/2004 |
| WO | WO 2006/014381 A2 | 2/2006 |
| WO | WO 2006/014382 A1 | 2/2006 |
| WO | WO 2007/019346 A1 | 2/2007 |
| WO | WO 2007/020400 A1 | 2/2007 |
| WO | WO 2008/014266 A2 | 1/2008 |
| WO | WO 2008/029152 A2 | 3/2008 |
| WO | WO 2010/129620 A1 | 11/2010 |

OTHER PUBLICATIONS

Heiser, et al., "Identification of benzothiazoles as potential polyglutamine aggregation inhibitors of Huntington's disease by using an automated filter retardation assay," Proceedings of the National Academy of Sciences of the United States of America, 2002, 99 (Suppl. 4).

Pauchard et al., "Anil synthesis. 16. Preparation of styryl derivatives of 2-phenylimidazo[1,2-a]pyridine," Helvetica Chimica Acta, 1978, pp. 129-141, vol. 61, No. 1.

International Search Report received in the corresponding International Patent Application No. PCT/GB2009/002260, dated Jan. 29, 2010.

Siegrist et al., "uber eine neue Synthese zur Darstellung heterocyclisch substituierter Stilbenverbindungen, die Anil-Synthese", Helv. Chim. Acta. 1967, 50, 906-957.

Agdeppa et al., "Binding Characteristics of Radiofluorinated 6-Dialkylamino-2- Naphthylethylidene Derivatives as Positron Emission Tomography Imaging Probes for _-Amyloid Plaques in Alzheimer's Disease", *J Neurosci*. 2001, 21(24), RC189.

Agdeppa et al., "2-Dialkylamino-6-Acylmalononitrile Substituted Naphthalenes (DDNP Analogs): Novel Diagnostic and Therapeutic Tools in Alzheimer's Disease", *Mol Imaging Biol*. 2003; 5, 404-17.

Bacskai et al., "Four-dimensional multiphoton imaging of brain entry, amyloid binding, and clearance of an amyloid-_ligand in transgenic mice",*PNAS*, 2003, 100, 12462-12467.

Berndt et al.,"Synthesis of a [18F] fluorobenzothiazole as potential amyloid imaging agent", *J. Label Compd. Radiopharm*, 2008, 51 137-145.

Billeau et al., "Spectral Assignments and Reference Data-1H and 13C chemical shifts for 2-aryl and 2-N-arylamino benzothiazole derivatives", Magn. Reson. Chem., 2006, 44, 102-105.

Cai et al., "Synthesis and Evaluation of Two 18F-Labeled 6-Iodo-2-(4¢-N,N-dimethylamino) phenylimidazo[1,2-a]pyridine Derivatives as Prospective Radioligands for â-Amyloid in Alzheimer's Disease", *J Med Chem*, 2004, 47, 2208-2218.

Cai et al., "Synthesis and Structure-Affinity Relationships of New 4-(6-Iodo-H-imidazol[1,2-a]pyridin-2-yl)-N-dimethylbenzeneamine Derivatives as Ligands for Human β-Amyloid Plaques", *J. Med. Chem.* 2007, 50, 4746-4758.

Cai et al., "Synthesis and Evaluation of N-Methyl and S-Methyl11 C-Labeled 6-Methylthio-2-(4'-N,N-dimethylamino)phenylimidazo[1,2-] pyridines as Radioligands fro Imaging β-Amyloid Plaques in Alzheimer's Disease", *J. Med. Chem.* 2008, 51, 148-158.

Chandra et al., "Design, synthesis, and structure—activity relationship of novel thiophene derivatives for b-amyloid plaque imaging", *Bioorg Med Chem Lett*, 2006, 16, 1350-1352.

Chandra et al.,"New Diphenylacetylenes as Probes for Positron Emission Tomographic Imaging of Amyloid Plaques",*J. Med. Chem.* 2007, 50, 2415-2423.

Chang et al., "Synthesis and evaluation of benzothiophene derivatives as ligands fro imaging β-amyloid plaques in Alzheimer's disease", *Nuclear Medicine and Biology*, 2006, 33, 811-820.

Chen et al., „Synthesis and biological evaluation of 99m Tc, Re-monoamine-monoamide conjugated to 2-(4-aminophenyl) benzothiazole as potential probes for β-amyloid plaques in the brain, *Bioorg Med Chem Lett*, 2008, 18, 1442-1445.

Chua et al., Antitumor Benzothiazoles. 7. Synthesis of 2-(4-Acylaminophenyl)benzothiazoles and Investigations into the Role of Acetylation in the Antitumor Activities of the Parent Amines, J. Med. Chem. 1999, 42(3), 381-392.

Flaherty et al., "Polyfluorinated Bis-styrylbenzene β-Amyloid Plaque Binding Ligands", *J. Med. Chem*., 2007, 50 (20), 4986-4992.

Furumoto et al., " Recent Advances in the Development of Amyloid Imaging Agents", *Curr Top Med Chem*, 2007, 7, 1773-1789.

Hausner et al., "Synthesis of 5- and 6-substituted 2-(4-dimethy Iminophenyl)-1,3-benzoxazoles and their in vitro and in vivo evaluation as imaging agents fro amyloid plaque", Bioorg Med Chem, 2009, 19(2) 543-545.

Hintersteiner et al.,"Bringing amyloid into focus", *-Nat Biotechnol*, 2005, 23, 577-83.

Honson et al., "Differentiating Alzheimer disease-associated aggregates with small molecules", *Neurobiology of Disease*, 2007, 28, 251-260.

Ishii et al., <<Chrysamine G and its derivative reduce amyloid β-induced neurotoxicity in mice, *Neuroscience Letters*, 2002, 333, 5-8.

Klunk et al., "Imaging Aβ Plaques in Living Transgenic Mice with Multiphoton Microscopy and Methyoxy-X04, a Systemically Administered Congo Red Derivative", *Journal of Neuropathology & Experimental Neurology*. 2002, 61, 797-805.

Klunk et al., "Uncharged thioflavin-T derivatives bind to amyloid-beta protein with high affinity and readily enter the brain", *Life Sciences*, 2001, 69, 1471-1484.

Kung et al., "Detection of Amyloid Plaques by Radioligands for Aβ40 and Aβ42", *J Mol Neurosci*. 2003, 20, 15-24.

Kung et al., "Radioiodinated Styrylbenzene Derivatives as Potential SPECT Imaging Agents for Amyloid Plaque Detection in alzheimer's Disease", *J Mol Neurosci*., 2002, 19, 7-10.

(56) References Cited

OTHER PUBLICATIONS

Lai et al., "Examination of Phosphorylated Tau Protein as a PHF-Precursor at Early Stage Alzheimer's Disease", *Neurobiol. Aging*, 1995, 16, 433-445.

Lee et al., "Synthesis and evaluation of stilbenylbenzoxazole and stilbenylbenzothiazole derivatives for detecting β-amyloid fibrils", *Bioorg. Med. Chem. Lett*,. 2008, 18, 1534-1537.

Lee et al., "Isomerization of (Z,Z) to (E,E)1-Bromo-2,5-bis-(3-hydroxycarbonyl-4-hydroxy)-styrylbenzene in Strong Base: Probes for Amyloid Plaques in the Brain", *J Med Chem, 2001*, 44, 2270-2275.

Lee et al., "Dimethylamino-fluorenes: ligands for detecting _-amyloid plaques in the brain", *Nuclear Medicine and Biology*, 2003, 30, 573-580.

Levine III et al., "Multiple ligand binding sites on Aβ(1-40) fibrils", *Amyloid*, 2005, 12, 5-14.

Li et al., "Solid-Phase Synthesis of Styryl Dyes and their Application as Amyloid Sensors", *Angew Chem Int Ed*, 2004, 43, 6331-6335.

Li et al., "Styryl-Based Compounds as Potential in vivo Imaging Agents for b-Amyloid Plaques", *ChemBioChem*, 2007, 8, 1679-1687.

Lin et al., "Degenerate nonlinear absorption and optical power limiting properties of asymmetrically substituted stilbenoid chromophores", J Materials Chem 2004, 14, 982.

Lockhart et al., "Evidence for the Presence of Three Distinct Binding Sites for the Thioflavin T Class of Alzheimer's Disease PET Imaging Agents on _-Amyloid Peptide Fibrils ", *J Biol Chem*, 2005, 280, 7677-7684.

Higuchi et al., "19 F and 1H MRI Detection of amyloid βplaques in vivo ", *Nature Neuroscience*, 2005, 8, 527-533.

Mathis et al., "A Lipophilic Thioflavin-T Derivative for Positron Emission Tomography (PET) Imaging of Amyloid in Brain", *Bioorg Med Chem Lett*, 2002, 12, 295-298.

Mathis et al., "Synthesis and Evaluation of 11C-Labeled 6-Substituted 2-Arylbenzothiazoles as Amyloid Imaging Agents", *J. Med. Chem.*, 2003, 46, 13, 2740-2754.

Nesterov et al., "In Vivo Optical Imaging of Amyloid Aggregates in Brain: Design of Fluorescent Markers", *Angew. Chem.*, 2005, 117, 5588-5592.

Okamura et al.,"Quinoline and Benzimidazole Derivatives: Candidate Probes for In Vivo Imaging of Tau Pathology in Alzheimer's Disease", *J Neuroscience*, 2004, 24, 2535-2541.

Okamura et al., "Styrylbenzoxazole Derivatives for In Vivo Imaging of Amyloid Plaques in the Brain" *The Journal of Neuroscience*, 2005, 47, 10857-10862.

Ono et al., "Aurones serve as probes of b-amyloid plaques in Alzheimer's disease", *Biochemical and Biophysical Research Communications*, 2007, 361, 116-121.

Ono et al., "Structure—activity relationship of chalcones and related derivatives as ligands for detecting of b-amyloid plaques in the brain", *Bioorg Med Chem*, 2007, 15, 6388-6396.

Ono et al., "Synthesis and characterization of styrylchromone derivatives as b-amyloid imaging agents" *Bioorg Med Chem*, 2007, 15, 444-450.

Ono et al., "Novel chalcones as probes for in vivo imaging of b-amyloid plaques in Alzheimer's brains", *Bioorg. Med. Chem.*, 2007, 15, 6802-6809.

Ono et al., "Radioiodinated Flavones for in Vivo Imaging of â-Amyloid Plaques in the Brain", *J Med Chem*, 2005, 48, 7253-7260.

Ono et al., "Novel Benzofuran Derivaties for PET Imaging of β-Amyloid Plaques in Alzheimer's disease Brains", *J Med Chem*, 2006, 49, 2725-2730.

Ono et al., "Synthesis and biological evaluation of (E)-3-styrylpyridine derivatives as amyloid imaging agents for Alzheimer's disease", *Nuclear Medicine and Biology*, 2005, 32, 329-335.

Ono et al., "C-labeled stilbene derivaties as Aβ-aggregate-specific PET imaging agents fro Alzheimer's disease", *Nuclear Medicine and Biology*, 2003, 30, 565-571.

Osman et al., "Heterocyclic Compounds, Part II PRepareation of some New Disperse Benzothiazole Dyes", Journal of Chemistry of the United Arab Republic, 1971, vol. 14, pp. 475,476, 483,484.

Poduslo et al., "Design and Chemical Synthesis of a Magnetic Resonance Contrast Agent with Enhanced in Vitro Binding, High Blood-Brain Barrier Permeability, and in ViVo Targeting to Alzheimer's Disease Amyloid Plaques ", *Biochemistry*, 2004, 43, 6064-6075.

Qu et al., "Novel Styrylpyridines as Probes for SPEFCT Imaging of Amyloid Plaques", *J Med Chem*, 2007, 50, 2157-2165.

Qu et al., "Quick Assembly of 1,4-Diphenyltriazoles as Probes Targeting â-Amyloid Aggregates in Alzheimer's Disease", *J Med Chem*, 2007, 50, 3380-3387.

Rowe et al., *Lancet Neurol.*, 2008, 7, 129-35.

Ryu et al., "Curcumin and Dehydrozingerone Derivatives: Synthesis, Radiolabeling, and Evaluation for â-Amyloid Plaque Imaging", *J Med Chem*, 2006, 49, 6111-6119.

Sato et al., "Fluoro-substitute4d and 13 C-labeled styrylbenzene derivatives for detecting brain amyloid plaques", *Eur J Med Chem*, 2004, 39, 573-578.

Serdons et al., "Synthesis and evaluation of a 99mTc-BAN-phenylbenzothiazole conjugate as a potential in vivo tracer for visuation of amyloid β", *Bioorg Med Chem Lett*, 2007, 17, 6086-6090.

Shao et al., Synthesis and two-photon absorption properties of novel heterocycle-based organic molecules, J. Mater. Chem. 2005, 15 (42), 4502-4506.

Shimadzu et al., "Novel probes for imaging amyloid-b: F-18 and C-11 labeling of 2-(4-aminostyryl)benzoxazole derivatives", *J Label Compd Radiopharm*2004, 47, 181-190.

Siegrist et al.,"uber eine neue Synthese zur Darstellung heterocyclisch substituierter Stilbenverbindungen, die Anil-Synthese", Helv. Chim. Acta. 1967, 50, 906-957.

Stephenson et al., "Fluoro-pegylated (FPEG) Imaging Agents Targeting Aâ Aggregates",*Bioconjugate Chemistry*, 2007, 18, 238-246.

Wang et al., "Synthesis and Evaluation of 2-(3'-Iodo-4'-aminophenyl)-6-hydroxybenzothiazole for In Vivo Quantitation of Amyloid Deposits in Alzheimer's Disease", *J Mol Neurosci.* 2002, 19, 11-16.

Wei et al., "Development of Novel Amyloid Imaging Agents Based Upon Thioflavin S", *Curr Alzheimer Res*, 2005, 2, 109-14.

Wu et al., "Dibenzothiazoles as novel amyloid-imaging agents", *Bioorg Med Chem*, 2007, 15, 2789-2796.

Zeng et al., "Synthesis and evaluation of two 18F-labeled imidazo[1,2-a]pyridine analogues as potential agents for imaging b-amyloid in Alzheimer's disease",*Bioorg Med Chem Lett*, 2006, 16, 3015-3018.

Zhang et al.,"F-18 Stilbenes as PET Imaging Agents for Detecting β-Amyloid Plaques in the Brain", *J Med Chem*, 2005, 48, 5980-5988.

Zhang et al., "F-18 Polyethyleneglycol stilbenes as PET imaging agents targeting Aβ aggregates in the brain", *Nuclear Medicine and Biology*, 2005, 32, 799-809.

Zhang et al., "F-labeled Styrylpyridines as PET agents for amyloid plaque imaging", *Nuclear Medicine and Biology*, 2007, 34, 89-97.

Zhuang et al., "Structure-Activity Relationship of Imidazo [1.2-a] pyridines as Llgands for Detecting β-Amyoid Plaques in the Brain", *J Med Chem*, 2003, 46, 237-243.

Zhuang et al., "Synthesis of Biphenyltrienes as Probes for â-Amyloid Plaques", *J Med Chem*, 2006, 49, 2841-2844.

Zhuang et al., "IBOX(2-(4_-dimethylaminophenyI)-6-iodobenzoxazole): a ligand for imaging amyloid plaques in the brain",*Nuclear Medicine and Biology*, 2001, 28, 887-894.

Zhuang et al., "Biphenyls labeled with technetium 99m for imaging h-amyloid plaques in the brain", *Nuclear Medicine and Biology*, 2005, 32, 171-184.

Serpell, "Alzheimer's Amyloid Fibrils: Structure and Assembly," Biochimica et Biophysica Acta 1502 (2000) pp. 16-30.

Diaz-Hernadez et al., "Biochemical, Ultrastructural, and Reversibility Studies on Huntingtin Filaments Isolated from Mouse and Human Brain," The Journal of Neuroscience 24(42), Oct. 20, 2004, pp. 9361-9371.

(56) References Cited

OTHER PUBLICATIONS

DiFiglia et al., "Aggregation of Huntingtin in Neuronal Intranuclear Inclusions and Dystrophic Neurites in Brain," Science 277, Sep. 26, 1997, pp. 1190-1993.

Esiri, "Chapter 2—The Neuropathology of Alzheimer's Disease," Neurobiology of Alzheimer's Disease, 2001, pp. 33-37.

Morgan et al., "Structure and Function of Amyloid in Alzheimer's Disease," Progress in Neurobiology 74 (2004) pp. 323-349.

Notice of Reasons for Rejection mailed Jan. 28, 2014 in Japan Application No. 2011-527403 (translation), 3 pgs.

\* cited by examiner (CO-1)

(HC-1)

(CO-2)

(HC-2)

LIGANDS FOR AGGREGATED TAU MOLECULES

CROSS REFERENCE TO RELATED APPLICATIONS

This application is the U.S. National Phase of International Application No. PCT/GB2009/002260, filed 23 Sep. 2009, which was published in English on 1 Apr. 2010, as WO 2010/034982; and claims the benefit of U.S. Provisional Application No. 61/099,376, filed 23 Sep. 2008, the contents of which are hereby incorporated by reference in their entirety.

TECHNICAL FIELD

The present invention pertains generally to materials, methods and models relating to the labelling and detection of neurofibrillary tangles. In addition, it concerns ligands suitable for neuropathological staging and their use in the diagnosis, prognosis or treatment of diseases such as Alzheimer's Disease (AD).

BACKGROUND

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Conditions of dementia such as Alzheimer's disease (AD) are frequently characterised by a progressive accumulation of intracellular and/or extracellular deposits of proteinaceous structures such as β-amyloid plaques and neurofibrillary tangles (NFTs) in the brains of affected patients. The appearance of these lesions largely correlates with pathological neurofibrillary degeneration and brain atrophy, as well as with cognitive impairment (see, e.g., Mukaetova-Ladinska, E. B., et al., 2000).

In AD, both neuritic plaques and NFTs contain paired helical filaments (PHFs), of which a major constituent is the microtubule-associated protein tau (see, e.g., Wischik et al., 1988). Plaques also contain extracellular β-amyloid fibrils derived from the abnormal processing of amyloid precursor protein (APP) (see, e.g., Kang et al., 1987). An article by Wischik et al. (in 'Neurobiology of Alzheimer's Disease') discusses in detail the putative role of tau protein in the pathogenesis of neurodegenerative dementias. Loss of the normal form of tau, accumulation of pathological PHFs, and loss of synapses in the mid-frontal cortex all correlate with associated cognitive impairment. Furthermore, loss of synapses and loss of pyramidal cells both correlate with morphometric measures of tau-reactive neurofibrillary pathology, which parallels, at a molecular level, an almost total redistribution of the tau protein pool from a soluble to a polymerised form (i.e., PHFs) in Alzheimer's disease.

Tau exists in alternatively-spliced isoforms, which contain three or four copies of a repeat sequence corresponding to the microtubule-binding domain (see, e.g., Goedert, M., et al., 1989; and Goedert, M., et al., 1989). Tau in PHFs is proteolytically processed to a core domain (see, e.g., Wischik, C. M., et al., 1988; Wischik et al., 1988; Novak, M., et al., 1993) which is composed of a phase-shifted version of the repeat domain; only three repeats are involved in the stable tau-tau interaction (see, e.g., Jakes, R., et al., 1991). Once formed, PHF-like tau aggregates act as seeds for the further capture and provide a template for proteolytic processing of full-length tau protein (see, e.g., Wischik et al., 1996).

The phase shift which is observed in the repeat domain of tau incorporated into PHFs suggests that the repeat domain undergoes an induced conformational change during incorporation into the filament. During the onset of AD, it is envisaged that this conformational change could be initiated by the binding of tau to a pathological substrate, such as damaged or mutated membrane proteins (see, e.g., Wischik, C. M., et al., 1997, in "Microtubule-associated proteins: modifications in disease").

In the course of their formation and accumulation, PHFs first assemble to form amorphous aggregates within the cytoplasm, probably from early tau oligomers which become truncated prior to, or in the course of, PHF assembly (see, e.g., Mena, R., et al., 1995; Mena, R., et al., 1996). These filaments then go on to form classical intracellular NFTs. In this state, the PHFs consist of a core of truncated tau and a fuzzy outer coat containing full-length tau (see, e.g., Wischik et al., 1996). The assembly process is exponential, consuming the cellular pool of normal functional tau and inducing new tau synthesis to make up the deficit (see, e.g., Lai, R. Y. K., et al., 1995). Eventually, functional impairment of the neurone progresses to the point of cell death, leaving behind an extracellular NFT. Cell death is highly correlated with the number of extracellular NFTs (see, e.g., Wischik et al., in 'Neurobiology of Alzheimer's Disease'). As tangles are extruded into the extracellular space, there is progressive loss of the fuzzy outer coat of the neurone with corresponding loss of N-terminal tau immunoreactivity, but preservation of tau immunoreactivity associated with the PHF core (see, e.g., Bondareff, W. et al., 1994).

Measurements of tau and β-amyloid peptides, in lumbar-puncture CSF samples, have been combined to add value in the diagnosis of AD (see, for example, Galasko et al. (1998); Hulstaert et al. (1999); Andreasen et al. (2001)) and to discriminate between AD and controls, and between AD and other degenerative dementias (Hampel et al. (2004)). The validation of such tests, however, with neuropathologically confirmed cases and cases at different stages of development has been limited thus far (Clark et al. (2003); Grossmann, et al. (2005); Engelborghs et al. (2008)). Although such tests and others (Wischik et al. (2001); Carretero et al. (1995)) may provide supportive data towards a diagnosis, lumbar-puncture is more invasive than nuclear medicine-based approaches, and carries a higher risk (see, for example, Villareal, D. T. et al. (1998); Marin, D. B. et al. (1998); and Kuller, L. H. et al., (1998)). EEG-neurological diagnosis has also been developed (see, for example, Vargha-Khadem, F. et al. (1997); Willingham, D. B. (1997); Lakmache, Y. et al. (1995); and Hodges, J. R. et al. (1999)), but in this regard there remains a need for cheap instrumentation which can be used at the point of clinician contact.

In developing a treatment aimed specifically at preventing neurofibrillary degeneration of the Alzheimer-type, there is a critical need to develop, in parallel, non-invasive means of selecting patients for treatment, and monitoring their response to the treatment, according to a defined and reproducible definition of disease progression.

WO 02/075318 discloses ligands for aggregated paired helical filament (PHF). The ligands may be used to label aggregated tau, and particularly extracellular aggregated tau present in neurofibrillary tangles.

Structures presented include those of the sulphonated-benzothiazole compounds shown below:

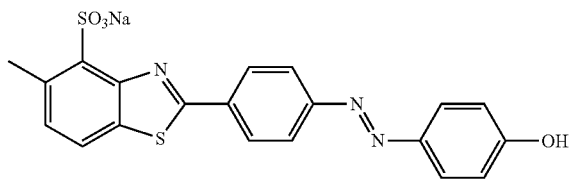

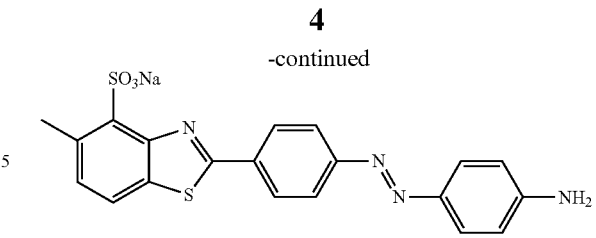

CH 542 266 discloses benzothiazole compounds for use in the textile industries. A compound disclosed is the benzothiazole structure shown below (identified as compound 73):

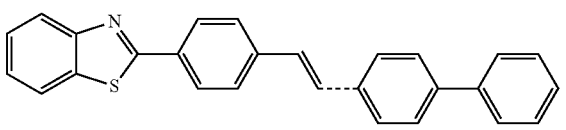

WO 01/10854 discloses benzothiazole compounds for use as optical brighteners. A compound disclosed is the benzothiazole structure shown below (identified as compound 10):

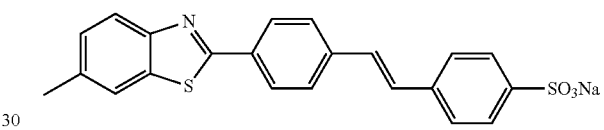

WO 2006/014382 discloses benzothiazole compounds for use in methods for imaging areas of amyloid deposition in patients exhibiting dementia in pre-diagnosed states. A compound disclosed is the benzothiazole structure shown below (identified as compound 43):

| Code No. | Structure |
|---|---|
| P-001 | -phenyl-F) |

Lee et al. *Bioorg. Med. Chem. Lett.* 2008, 18, 1534 discloses benzothiazole compounds for use in detecting β-amyloid fibrils. A number of compounds are disclosed as intermediates for the benzothiazole imaging agents, and two example intermediates are shown below:

| Code No. | Structure |
|---|---|
| P-002 | ![structure](HO-benzothiazole-phenyl-CH=CH-phenyl-NH2) |
| P-003 | ![structure](HO-benzothiazole-phenyl-CH=CH-phenyl-NHCH3) |

WO 2007/020400 discloses benzothiazole compounds for use as in vivo imaging agents for amyloid. A compound disclosed is the benzothiazole structure shown below (identified as compound 8):

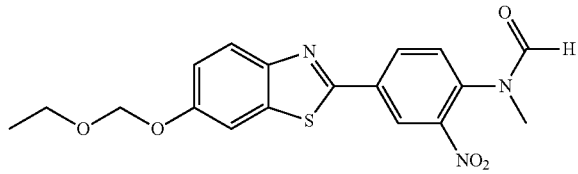 [SMILES: CCOCOc1ccc2nc(-c3ccc(N(C)C=O)c([N+](=O)[O-])c3)sc2c1]

Also described are intermediates for the preparation of the benzothiazole imaging agents. The intermediates have the general formula shown below (identified as compounds of formula (IIa)):

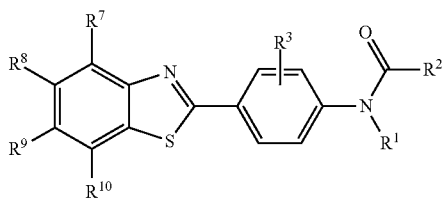

wherein
—$R^1$ is selected from $C_{1-6}$alkyl, $C_{2-6}$alkenyl, and $C_{2-6}$alkynyl;
—$R^2$ is selected from hydrogen, $C_{1-10}$alkyl, $C_{1-10}$haloalkyl, $C_{6-14}$aryl, $C_{6-14}$arylalkyl, —$(CH_2CH_2O)_q$—$CH_3$ wherein q is an integer of from 1 to 10;
—$R^3$ is a leaving group; and
—$R^7$, —$R^8$, —$R^9$, and —$R^{10}$ are selected from a list of substituents.

Notwithstanding these disclosures, it will be appreciated that the provision of one or more compounds, not previously specifically identified as being effective labels for PHF, would provide a contribution to the art.

DISCLOSURE OF THE INVENTION

The present inventors have now identified certain compounds that, e.g., bind to paired helical filaments and/or are useful in the detection of diseases such as Alzheimer's disease (AD). The present invention provides new and alternative ligands for the detection of these structures.

The invention therefore relates to methods, uses, compositions and other materials employing these compounds as PHF ligands. The invention further provides processes for making these compounds.

These and other aspects of the invention are discussed in more detail hereinafter.

COMPOUNDS

Figure 1:
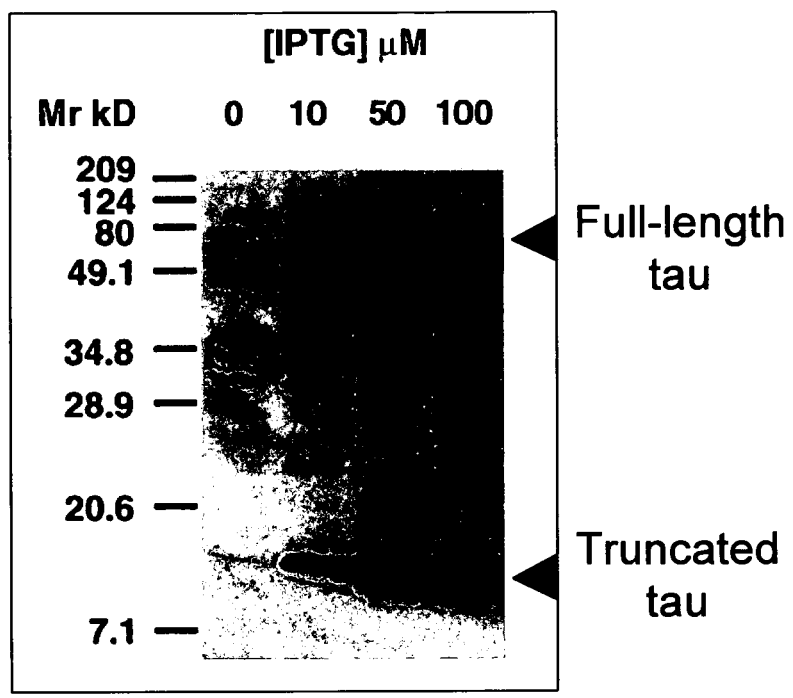
FIG. 1 shows an example of the cellular assay for tau aggregation. Low-level constitutive expression of truncated tau is increased when the expression of full-length tau is induced with IPTG. Truncated tau is derived from full-length tau that is captured by truncated tau and subjected to proteolysis and further tau capture.

One aspect of the present invention relates to certain 1,4-disubstituted-benzene compounds (for convenience, collectively referred to herein as "DSB compounds"), which are structurally related to N-(4-benzothiazol-2-yl-phenyl)-benzamide.

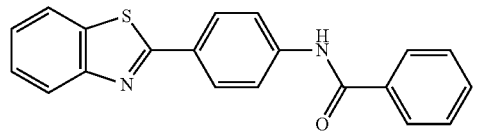

N-(4-Benzothiazol-2-yl-phenyl)-benzamide

In one embodiment, the compounds are selected from compounds of the following formula, and pharmaceutically and physiologically acceptable salts, hydrates, and solvates thereof:

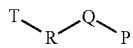

wherein
—R— is independently selected from:

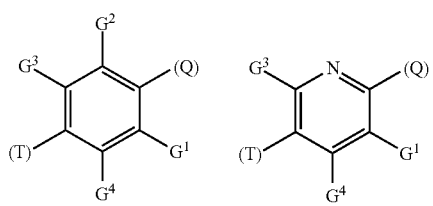

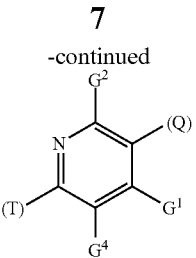

wherein (T) indicates the point of attachment to -T;
and (Q) indicates the point of attachment to -Q-;
-Q- is independently selected from:
—NHC(O)—; —$NR^1$C(O)—;
—C(O)NH—; —C(O)$NR^1$—;
—N=N—;
—CH=CH—;
—$CR^1$=CH—; —CH=$CR^1$—;
—$CR^1$=$CR^1$—;
—N=CH—; —CH=N—;
each —$R^1$ is independently unsubstituted saturated aliphatic $C_{1-4}$alkyl;
—P is independently selected from:

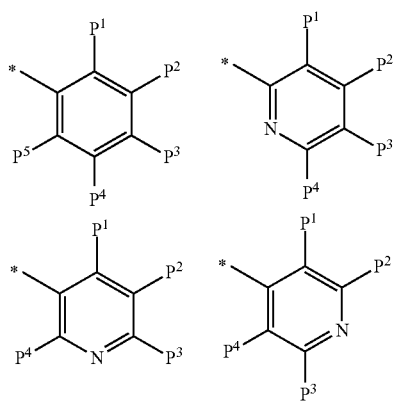

where the asterisk indicates the point of attachment;
-T is independently selected from:

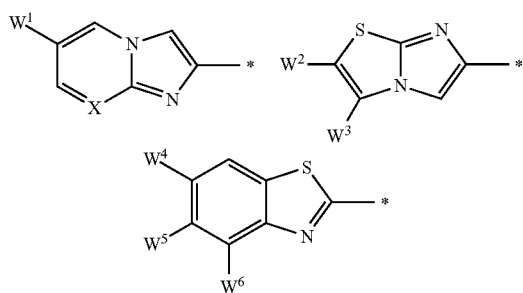

where the asterisk indicates the point of attachment;
and X is independently N or CH;
—$W^1$ is independently —H or —$W^A$;
—$W^2$ is independently —H or —$W^A$;
—$W^3$ is independently —H or —$W^A$;
—$W^4$ is independently —H or —$W^A$;
—$W^5$ is independently —H or —$W^A$;
—$W^6$ is independently —H or —$W^A$;

where —$W^A$ is independently selected from:
—F, —Cl, —Br, —I,
—OH, —$W^{A1}$, —O—$W^{A1}$,
—$NH_2$, —NH$W^{A1}$, and —N($W^{A1}$)$_2$;
and —$W^{A1}$ is independently selected from:
unsubstituted saturated aliphatic $C_{1-4}$alkyl,
—$CF_3$,
—$CH_2CH_2OH$, and
—$CH_2CH_2N(Me)_2$;
-$G^1$ is independently —H or -$G^A$;
-$G^2$ is independently —H or -$G^A$;
where -$G^A$ is independently selected from:
—F, —Cl, —Br, —I,
—$CF_3$, —$OCF_3$,
—OH, —$OR^2$;
—[O—$CH_2CH_2]_n$—$R^{B2}$, where n is 2 to 6;
-$G^3$ is independently —H or -$G^B$;
-$G^4$ is independently —H or -$G^B$
where -$G^B$ is independently selected from:
—F, —Cl, —Br, —I,
—$CF_3$, —$OCF_3$,
—OH, —$OR^2$;
—[O—$CH_2CH_2]_n$—$R^{B2}$, where n is 2 to 6;
wherein:
—$P^1$ is independently —H or —$P^A$;
—$P^2$ is independently —H or —$P^B$;
—$P^3$ is independently —H or —$P^C$;
—$P^4$ is independently —H or —$P^B$;
—$P^5$ is independently —H or —$P^A$;
and wherein:
each —$P^A$, each —$P^B$, and each —$P^C$ is independently:
—F, —Cl, —Br, —I,
—$R^2$,
—$CF_3$, —$OCF_3$,
—OH, -$L^1$-OH,
—$OR^2$, -$L^1$-$OR^2$,
—SH, —$SR^2$,
—CN,
—$NO_2$,
—$NH_2$, —$NHR^2$, —$NR^2_2$, —$NR^3R^4$,
—NHOH,
-$L^1$-$NH_2$, -$L^1$-$NHR^2$, -$L^1$-$NR^2_2$, -$L^1$-$NR^3R^4$,
—O-$L^1$-$NH_2$, —O-$L^1$-$NHR^2$, —O-$L^1$-$NR^2_2$, —O-$L^1$-$NR^3R^4$,
—C(=O)OH, —C(=O)$OR^2$,
—OC(=O)$R^2$,
—C(=O)$NH_2$, —C(=O)$NHR^2$, —C(=O)$NR^2_2$, —C(=O)$NR^3R^4$,
—NHC(=O)$R^2$, —$NR^2$C(=O)$R^2$, —C(=O)$NHOR^2$, —C(=O)$NR^2OR^2$,
—NHC(=O)$OR^2$, —$NR^2$C(=O)$OR^2$,
—OC(=O)$NH_2$, —OC(=O)$NHR^2$, —OC(=O)$NR^2_2$, —OC(=O)$NR^3R^4$,
—C(=O)$R^2$,
—NHC(=O)$NH_2$, —NHC(=O)$NHR^2$,
—NHC(=O)$NR^2_2$, —NHC(=O)$NR^3R^4$,
—$NR^2$C(=O)$NH_2$, —$NR^2$C(=O)$NHR^2$,
—$NR^2$C(=O)$NR^2_2$, —$NR^2$C(=O)$NR^3R^4$,
—NHS(=O)$_2R^2$, —$NR^2$S(=O)$_2R^2$,
—S(=O)$_2NH_2$, —S(=O)$_2NHR^2$, —S(=O)$_2NR^2_2$,
—S(=O)$_2NR^3R^4$,
—S(=O)$R^2$, —S(=O)$_2R^2$, —OS(=O)$_2R^2$, or —S(=O)$_2OR^2$
wherein:
each -$L^1$- is independently saturated aliphatic $C_{1-5}$alkylene;

in each group —NR$^3$R$^4$, —R$^3$ and —R$^4$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N, O, or S;

each —R$^2$ is independently:
—R$^{A1}$, —R$^{A2}$, —R$^{A3}$, —R$^{A4}$, —R$^{A5}$, —R$^{A6}$, —R$^{A7}$, —R$^{A8}$,
-L$^A$-R$^{A4}$, -L$^A$-R$^{A5}$, -L$^A$-R$^{A6}$, or -L$^A$-R$^{A8}$;

wherein:
each —R$^{A1}$ is independently saturated aliphatic C$_{1-6}$alkyl;
each —R$^{A2}$ is independently aliphatic C$_{2-6}$alkenyl;
each —R$^{A3}$ is independently aliphatic C$_{2-6}$alkynyl;
each —R$^{A4}$ is independently saturated C$_{3-6}$cycloalkyl;
each —R$^{A8}$ is independently C$_{3-6}$cycloalkenyl;
each —R$^{A8}$ is independently non-aromatic C$_{3-7}$heterocyclyl;
each —R$^{A7}$ is independently C$_{6-10}$carboaryl;
each —R$^{A8}$ is independently C$_{6-10}$heteroaryl;
each -L$^A$- is independently saturated aliphatic C$_{1-3}$alkylene;

and wherein:
each —R$^{A4}$, —R$^{A5}$, —R$^{A6}$, —R$^{A7}$, and —R$^{A8}$ is optionally substituted, for example, with one or more substituents —R$^{B1}$ and/or one or more substituents —R$^{B2}$, and
each —R$^{A1}$, —R$^{A2}$, —R$^{A3}$, and -L$^A$- is optionally substituted, for example, with one or more substituents —R$^{B2}$, wherein:
each —R$^{B1}$ is independently saturated aliphatic C$_{1-4}$alkyl, phenyl, or benzyl;
each —R$^{B2}$ is independently:
—F, —Cl, —Br, —I,
—CF$_3$, —OCF$_3$,
—OH, -L$^C$-OH, —O-L$^C$-OH,
—OR$^{C1}$, -L$^C$-OR$^{C1}$, —O-L$^C$-OR$^{C1}$,
—SH, —SR$^{C1}$,
—CN,
—NO$_2$,
—NH$_2$, —NHR$^{C1}$, —NR$^{C1}_2$, —NR$^{C2}$R$^{C3}$,
-L$^C$-NH$_2$, -L$^C$-NHR$^{C1}$, -L$^C$-NR$^{C1}_2$, or -L$^C$-NR$^{C2}$R$^{C3}$,
—O-L$^C$-NH$_2$, —O-L$^C$-NHR$^{C1}$, —O-L$^C$-NR$^{C1}_2$, —O-L$^C$-NR$^{C2}$R$^{C3}$,
—C(=O)OH, —C(=O)OR$^{C1}$,
—OC(=O)R$^{C1}$,
—C(=O)R$^{C1}$,
—C(=O)NH$_2$, —C(=O)NHR$^{C1}$, —C(=O)NR$^{C1}_2$, —C(=O)NR$^{C2}$R$^{C3}$,
—NHC(=O)R$^{C1}$, —NR$^{C1}$C(=O)R$^{C1}$,
—NHS(=O)$_2$R$^{C1}$, —NR$^{C1}$S(=O)$_2$R$^{C1}$,
—S(=O)$_2$NH$_2$, —S(=O)$_2$NHR$^{C1}$, —S(=O)$_2$NR$^{C1}_2$, —S(=O)$_2$NR$^{C2}$R$^{C3}$, or
—S(=O)$_2$R$^{C1}$;

wherein:
each —R$^{C1}$ is independently unsubstituted saturated aliphatic C$_{1-4}$alkyl, phenyl, or benzyl;
each -L$^C$- is independently unsubstituted saturated aliphatic C$_{1-5}$alkylene; and
in each group —NR$^{C2}$R$^{C3}$, —R$^{C2}$ and —R$^{C3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N, O, or S.

Optional Provisos

In one or more aspects of the present invention (e.g., compounds, compositions, compounds for use in therapy, use of compounds in the manufacture of a medicament, methods, methods of treatment, etc.), the compounds are optionally as defined herein, but with one or more optional provisos, as defined herein.

In one embodiment, the compound is a compound as defined herein, with the proviso that the compound is not a compound selected from P-001 through P-015.

| Code No. | Citation | Structure |
| --- | --- | --- |
| P-001 | Klunk et al. WO 2006/014382 | 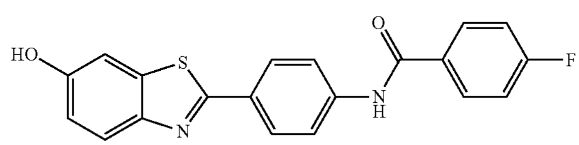 |
| P-002 | Lee et al. Bioorg. Med. Chem. Lett. 2008, 18, 1534 | 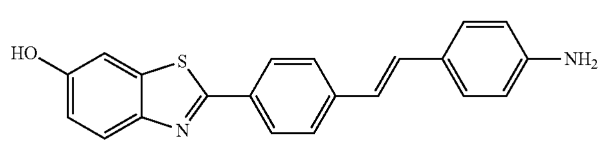 [SMILES: Nc1ccc(/C=C/c2ccc(-c3nc4ccc(O)cc4s3)cc2)cc1] |
| P-003 | Lee et al. Bioorg. Med. Chem. Lett. 2008, 18, 1534 | 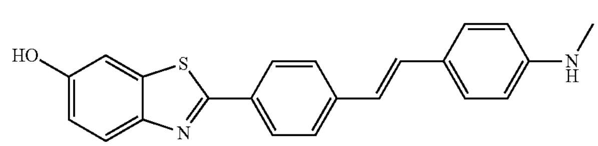 [SMILES: CNc1ccc(/C=C/c2ccc(-c3nc4ccc(O)cc4s3)cc2)cc1] |
| P-004 | Lee et al. Bioorg. Med. Chem. Lett. 2008, 18, 1534 | 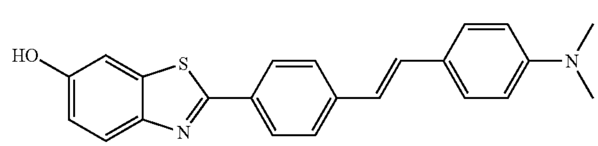 [SMILES: CN(C)c1ccc(/C=C/c2ccc(-c3nc4ccc(O)cc4s3)cc2)cc1] |

-continued

| Code No. | Citation | Structure |
|---|---|---|
| P-005 | Lee et al. Bioorg. Med. Chem. Lett. 2008, 18, 1534 | 6-hydroxybenzothiazol-2-yl-phenyl-CH=CH-phenyl-NH₂ |
| P-006 | Lee et al. Bioorg. Med. Chem. Lett. 2008, 18, 1534 | 6-hydroxybenzothiazol-2-yl-phenyl-CH=CH-phenyl-NHMe |
| P-007 | Lee et al. Bioorg. Med. Chem. Lett. 2008, 18, 1534 | 6-hydroxybenzothiazol-2-yl-phenyl-CH=CH-phenyl-NMe₂ |
| P-008 | Lee et al. Bioorg. Med. Chem. Lett. 2008, 18, 1534 | 6-methoxybenzothiazol-2-yl-phenyl-CH=CH-phenyl-NO₂ |
| P-009 | Lee et al. Bioorg. Med. Chem. Lett. 2008, 18, 1534 | 5-methoxybenzothiazol-2-yl-phenyl-CH=CH-phenyl-NO₂ |
| P-010 | Lee et al. Bioorg. Med. Chem. Lett. 2008, 18, 1534 | 6-methoxybenzothiazol-2-yl-phenyl-CH=CH-phenyl-NH₂ |
| P-011 | Lee et al. Bioorg. Med. Chem. Lett. 2008, 18, 1534 | 6-methoxybenzothiazol-2-yl-phenyl-CH=CH-phenyl-NHMe |
| P-012 | Lee et al. Bioorg. Med. Chem. Lett. 2008, 18, 1534 | 6-methoxybenzothiazol-2-yl-phenyl-CH=CH-phenyl-NMe₂ |
| P-013 | Lee et al. Bioorg. Med. Chem. Lett. 2008, 18, 1534 | 5-methoxybenzothiazol-2-yl-phenyl-CH=CH-phenyl-NH₂ |
| P-014 | Lee et al. Bioorg. Med. Chem. Lett. 2008, 18, 1534 | 5-methoxybenzothiazol-2-yl-phenyl-CH=CH-phenyl-NHMe |
| P-015 | Lee et al. Bioorg. Med. Chem. Lett. 2008, 18, 1534 | 5-methoxybenzothiazol-2-yl-phenyl-CH=CH-phenyl-NMe₂ |

In one embodiment, the compound is a compound as defined herein, with the proviso that the compound is not a compound selected from P-001 through P-015.

In one embodiment, the compound is a compound as defined herein, with the proviso that the compound is not a compound selected from P-001 through P-015, and salts, hydrates, and solvates thereof.

In one or more aspects of the present invention (e.g., relating to defined uses and methods such as compounds for use in labelling tau aggregates, use of compounds in the manufacture of a diagnostic, methods of prognosis or diagnosis or staging, etc.), the compounds are optionally as defined herein, but without any of the above provisos, that is, without a proviso regarding P-001 through P-015.

For example, a reference to a particular group of compounds "without the proviso regarding P-001 through P-015" (e.g., for use in diagnosis) is intended to be a reference to the compounds as defined, but wherein the definition no longer includes the indicated proviso. In such cases, it is as if the indicated proviso has been deleted from the definition of compounds, and the definition has been expanded to encompass those compounds which otherwise would have been excluded by the indicated proviso.

In one embodiment, the compound is a compound as defined herein, with the proviso that the compound is not a compound where -T is:

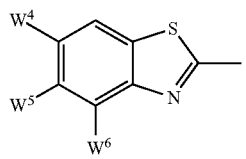

—R— is:

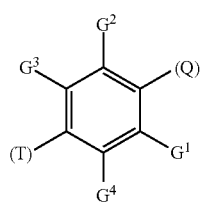

and —P is:

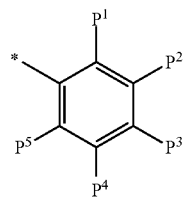

and —$W^4$ is —H, -Q- is —CH=CH—, -$G^1$, -$G^2$, -$G^3$, and -$G^4$ are all —H, and (i) —$P^1$, —$P^2$, —$P^4$ and —$P^5$ are all —H, and —$P^3$ is —$R^{41}$; or (ii) one of —$P^1$, —$P^2$, —$P^3$, $P^4$ and —$P^5$ is —$R^{47}$, and the others of —$P^1$, —$P^2$, —$P^3$, $P^4$ and —$P^5$ are —H.

Preferred Compounds

In one embodiment, the compound is independently selected from:

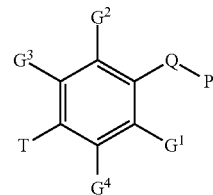

wherein -Q-, —P, -T-, -$G^1$, -$G^2$, -$G^3$ and -$G^4$ are as defined above.

In one embodiment, the compound is independently selected from:

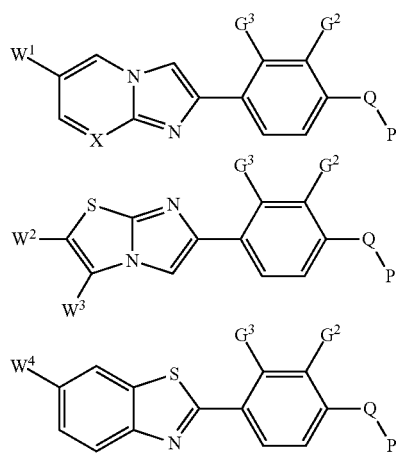

wherein -Q-, —P, X, —$W^1$, —$W^2$, —$W^3$, —$W^4$, -$G^2$, and -$G^3$ are as defined above.

Benzothiazole Compounds

In one embodiment, the compound is independently:

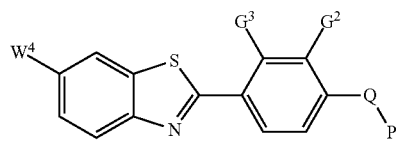

wherein -Q-, —P, -$G^2$, and -$G^3$ are as defined above.

In one embodiment, the compound is independently selected from:

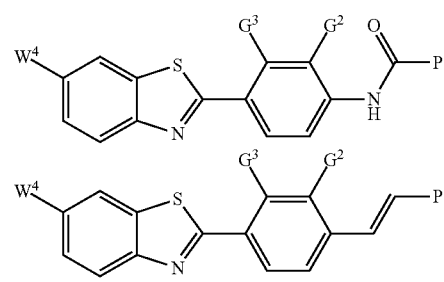

-continued

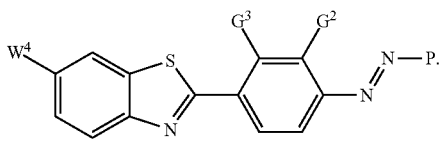

In one embodiment, the compound is independently:

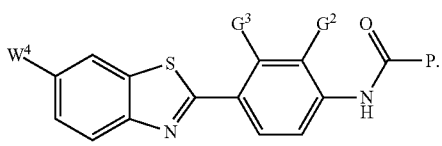

In one embodiment, the compound is independently:

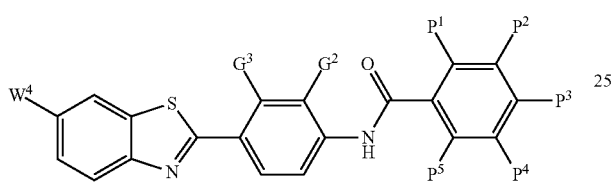

wherein —P¹, —P², —P³, —P⁴, and —P⁵ are as defined above.

In one embodiment, the compound is independently:

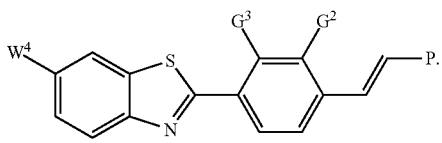

In one embodiment, the compound is independently:

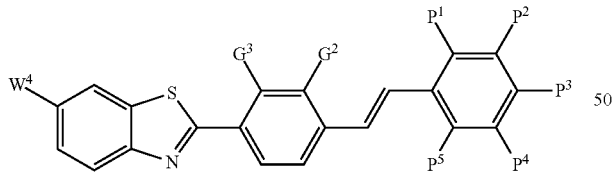

wherein —P¹, —P², —P³, —P⁴, and —P⁵ are as defined above.

In one embodiment, the compound is independently:

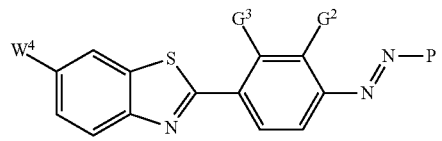

In one embodiment, the compound is independently:

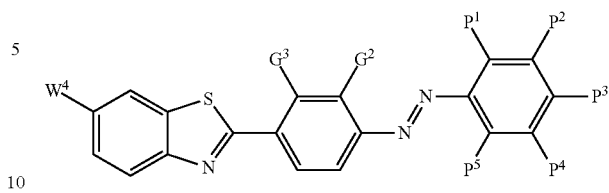

wherein —P¹, —P², —P³, —P⁴, and —P⁵ are as defined above.

In one embodiment, the compound is independently:

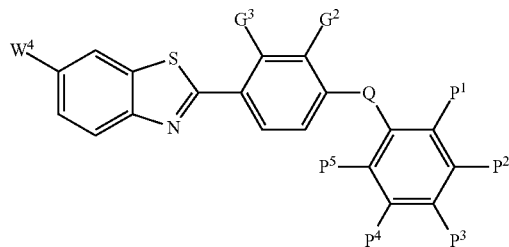

wherein —P¹, —P², —P³, —P⁴, and —P⁵ are as defined above.

Imidazo[2,1-b][1,3]thiazole Compounds

In one embodiment, the compound is independently:

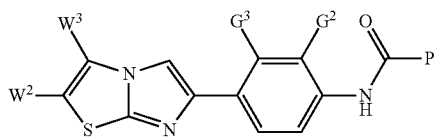

wherein —P, —W², —W³, -G², and -G³ are as defined above.

In one embodiment, the compound is independently:

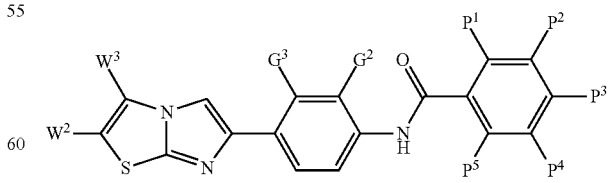

wherein —W², —W³, -G², -G³, —P¹, —P², —P³, —P⁴, and —P⁵ are as defined above.

Imidazo[2,1-b][1,3]thiazole and Imidazo[1,2-a]pyridine Compounds

In one embodiment, the compound is independently:

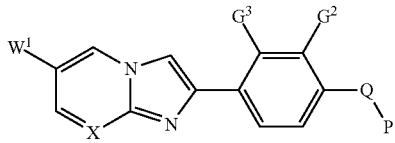

wherein -Q-, —P, —W$^1$, X, -G$^2$, and -G$^3$ are as defined above.

In one embodiment, the compound is independently:

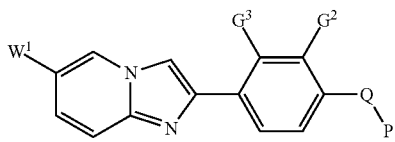

wherein -Q-, —P, —W$^1$, -G$^2$, and -G$^3$ are as defined above.

In one embodiment, the compound is independently:

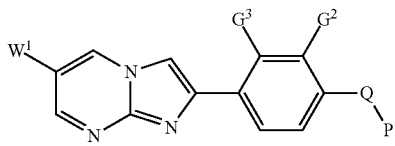

wherein -Q-, —P, —W$^1$, -G$^2$, and -G$^3$ are as defined above.

In one embodiment, the compound is independently selected from:

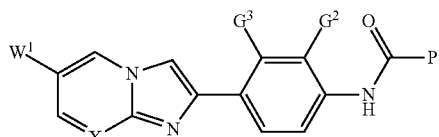

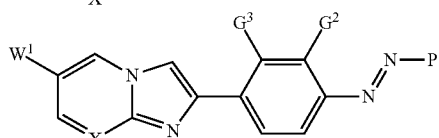

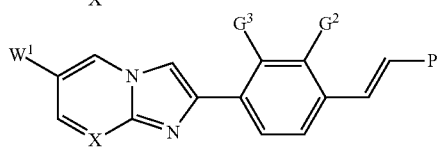

wherein —P, —W$^1$, X, -G$^2$, and -G$^3$ are as defined above.

In one embodiment, the compound is independently:

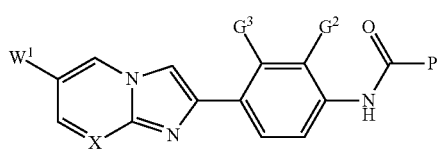

wherein —P, —W$^1$, X, -G$^2$, and -G$^3$ are as defined above.

In one embodiment, the compound is independently:

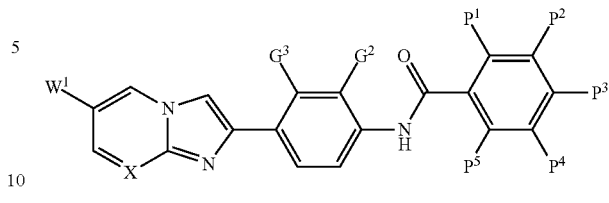

wherein —P$^1$, —P$^2$, —P$^3$, —P$^4$, and —P$^5$ are as defined above.

In one embodiment, the compound is independently:

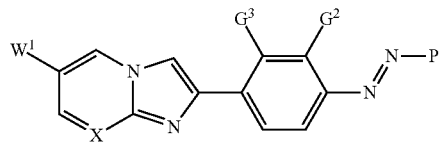

wherein —P, —W$^1$, X, -G$^2$, and -G$^3$ are as defined above.

In one embodiment, the compound is independently:

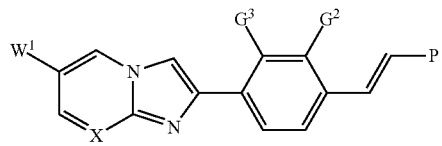

wherein —P, —W$^1$, X, -G$^2$, and -G$^3$ are as defined above.

Halogenated Compounds

In one embodiment, the DSB compound is a compound of formula (I) with the proviso that the compound comprises a —F, —Cl, —Br or —I group.

In one embodiment, the DSB compound is a compound of formula (I) with the proviso that the compound comprises a —F group.

In one embodiment, the DSB compound is a compound of formula (I) with the proviso that the compound comprises a —$^{19}$F group.

In one embodiment, the DSB compound is a compound of formula (I) with the proviso that the compound comprises a —Cl, —Br or —I group.

In one embodiment, the group —P is substituted with a —F group or is substituted with a group comprising a —F group. Thus, one of —P$^1$, —P$^2$, —P$^3$, —P$^4$, and —P$^5$, if present, may be —F, or one of —P$^A$, —P$^B$ or —P$^C$ comprises a —F group.

In one embodiment, the group -T is substituted with a —F group or is substituted with a group comprising a —F group. Thus, —W$^A$ is —F, or —W$^{A1}$ comprises a —F group.

In one embodiment, the group —R— is substituted with a —F group or is substituted with a group comprising a —F group. Thus, -G$^4$ is —F or -G$^4$ comprises a —F group.

The Group —R—

In one embodiment, —R— is independently selected from:

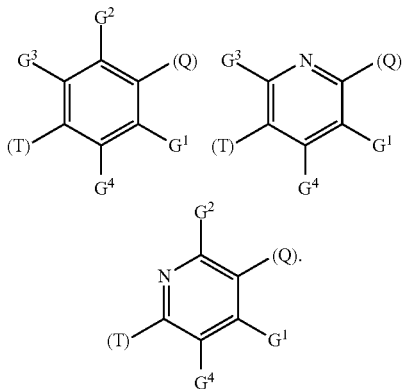

In one embodiment, —R— is independently selected from:

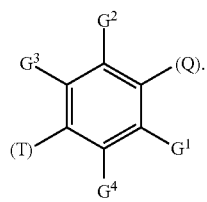

In one embodiment, —R— is independently selected from:

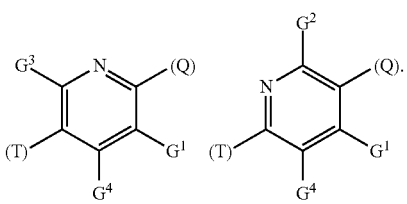

The Group -Q-

In one embodiment, -Q- is independently selected from:
—NHC(O)—; —NR¹C(O)—;
—C(O)NH—; —C(O)NR¹—;
—N=N—;
—CH=CH—;
—CR¹=CH—; —CH=CR¹—;
—CR¹=CR¹—;
—N=C—; —C=N—.

In one embodiment, -Q- is independently selected from:
—NHC(O)—; —NR¹C(O)—;
—N=N—;
—CH=CH—;
—N=C—; —C=N—.

In one embodiment, -Q- is independently selected from:
—NHC(O)—;
—N=N—;
—CH=CH—;
—N=C—.

In one embodiment, -Q- is independently selected from:
—NHC(O)—;
—N=N—;
—CH=CH—.

In one embodiment, -Q- is independently selected from —NHC(O)— and —NR¹C(O)—.

In one embodiment, -Q- is independently —NHC(O)—.

In one embodiment, -Q- is independently selected from —N=N—, —CH=CH—, and —N=C—.

In one embodiment, -Q- is independently —N=N—.

In one embodiment, -Q- is independently:

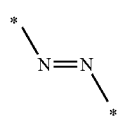

where the asterisks indicate the points of attachment.

In one embodiment, -Q- is independently —CH=CH—.

In one embodiment, -Q- is independently:

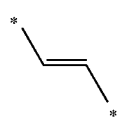

where the asterisks indicate the points of attachment.

In one embodiment, -Q- is independently —N=C—.

In one embodiment, -Q- is independently:

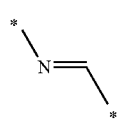

where the asterisks indicate the points of attachment.

The Group —R¹

In one embodiment, each —R¹, where present, is independently unsubstituted saturated aliphatic $C_{1-4}$alkyl.

In one embodiment, each —R¹, where present, is independently -Me.

In one embodiment, each —R¹, where present, is independently -Et.

The Group —P

In one embodiment, —P is independently selected from:

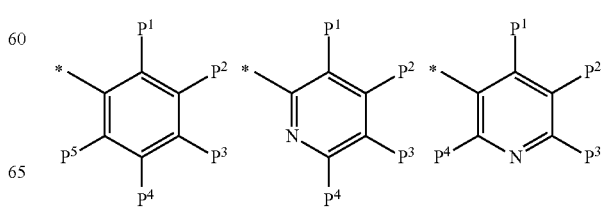

-continued

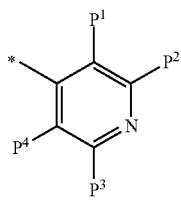

where the asterisk indicates the point of attachment.
In one embodiment, —P is independently:

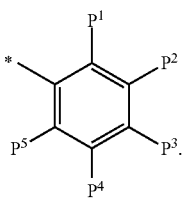

In one embodiment, —P is independently selected from:

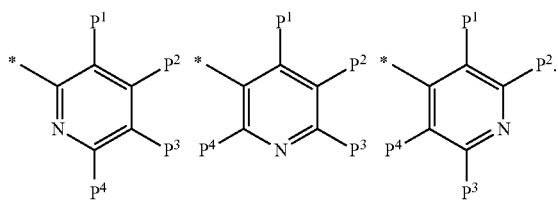

In one embodiment, —P is independently:

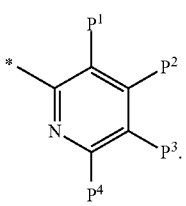

In one embodiment, —P is independently:

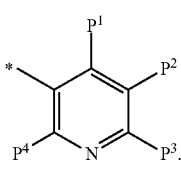

In one embodiment, —P is independently:

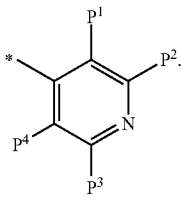

The Group -T
In one embodiment, -T is independently selected from:

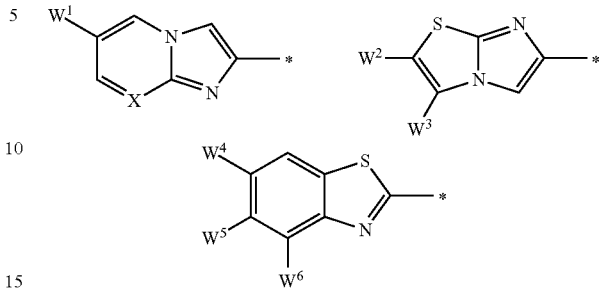

where X is independently N or CH.
In one embodiment, -T is independently:

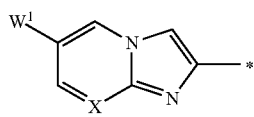

where X is independently N or CH.
In one embodiment, -T is independently:

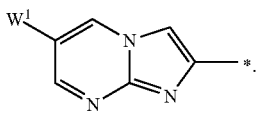

In one embodiment, -T is independently:

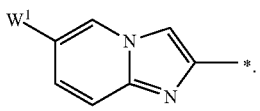

In one embodiment, -T is independently:

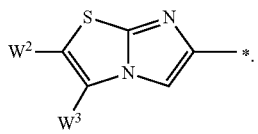

In one embodiment, -T is independently:

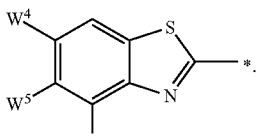

The Group —$W^1$
In one embodiment, —$W^1$ is independently —H or —$W^4$.
In one embodiment, —$W^1$ is independently —H.
In one embodiment, —$W^1$ is independently —$W^4$.

The Group —$W^2$

In one embodiment, —$W^2$ is independently —H or —$W^A$.
In one embodiment, —$W^2$ is independently —H.
In one embodiment, —$W^2$ is independently —$W^A$.

The Group —$W^3$

In one embodiment, —$W^3$ is independently —H or —$W^A$.
In one embodiment, —$W^3$ is independently —H.
In one embodiment, —$W^3$ is independently —$W^A$.

The Group —$W^4$

In one embodiment, —$W^4$ is independently —H or —$W^A$.
In one embodiment, —$W^4$ is independently —H.
In one embodiment, —$W^4$ is independently —$W^A$.

The Group —$W^5$

In one embodiment, —$W^5$ is independently —H or —$W^A$.
In one embodiment, —$W^5$ is independently —H.
In one embodiment, —$W^5$ is independently —$W^A$.

The Group —$W^6$

In one embodiment, —$W^6$ is independently —H or —$W^A$.
In one embodiment, —$W^6$ is independently —H.
In one embodiment, —$W^6$ is independently —WA.

The Groups —$W^2$, and —$W^3$

In one embodiment, at least one of —$W^2$ and —$W^3$ is —$W^A$.
In one embodiment, one of —$W^2$ and —$W^3$ is —$W^A$.
In one embodiment, —$W^2$ is —$W^A$.
In one embodiment, —$W^3$ is —$W^A$.

The Groups —$W^4$, —$W^5$, and —$W^6$

In one embodiment, at least one of —$W^4$, —$W^5$ and —$W^6$ is —$W^A$.
In one embodiment, one of —$W^4$, —$W^5$ and —$W^6$ is —$W^A$.
In one embodiment, —$W^4$ is —$W^A$.
In one embodiment, —$W^5$ is —$W^A$.
In one embodiment, —$W^6$ is —$W^A$.

The Group —$W^A$

In one embodiment, —$W^A$, where present, is independently selected from:
—F, —Cl, —Br, —I,
—OH, —$W^{A1}$, —O—$W^{A1}$,
—$NH_2$, —$NHW^{A1}$, and —$N(W^{A1})_2$.

In one embodiment, —$W^A$, where present, is independently selected from:
—OH, —$W^{A1}$, —O—$W^{A1}$,
—$NH_2$, —$NHW^{A1}$, and —$N(W^{A1})_2$.

In one embodiment, —$W^A$, where present, is independently selected from —OH, —$W^{A1}$, and —O—$W^{A1}$.

In one embodiment, —$W^A$, where present, is independently selected from —$W^{A1}$ and —O—$W^{A1}$.

In one embodiment, —$W^A$, where present, is independently selected from: —OH and —O—$W^{A1}$.

In one embodiment, —$W^A$, where present, is independently —$W^{A1}$.

In one embodiment, —$W^A$, where present, is independently —O—$W^{A1}$.

In one embodiment, —$W^A$, where present, is independently —OH.

In one embodiment, —$W^A$, where present, is independently selected from —$NH_2$, —$NHW^{A1}$, and —$N(W^{A1})_2$.

In one embodiment, —$W^A$, where present, is independently —$NH_2$.

In one embodiment, —$W^A$, where present, is independently —$NHW^{A1}$.

In one embodiment, —$W^A$, where present, is independently —$N(W^{A1})_2$.

In one embodiment, —$W^A$, where present, is independently selected from —F, —Cl, —Br, and —I.

In one embodiment, —$W^A$, where present, is independently —F or —I.

In one embodiment, —$W^A$, where present, is independently —F.

The Group —$W^{A1}$

In one embodiment, —$W^{A1}$, where present, is independently selected from:
unsubstituted saturated aliphatic $C_{1-4}$alkyl,
—$CF_3$,
—$CH_2CH_2OH$, and
—$CH_2CH_2N(Me)_2$.

In one embodiment, —$W^{A1}$, where present, is independently selected from unsubstituted saturated aliphatic $C_{1-4}$alkyl and —$CF_3$.

In one embodiment, —$W^{A1}$, where present, is independently unsubstituted saturated aliphatic $C_{1-4}$alkyl.

In one embodiment, —$W^{A1}$, where present, is independently -Me.

In one embodiment, —$W^{A1}$, where present, is independently -Et.

In one embodiment, —$W^{A1}$, where present, is —$CF_3$.

In one embodiment, —$W^{A1}$, where present, is independently —$CH_2CH_2OH$.

In one embodiment, —$W^{A1}$, where present, is independently —$CH_2CH_2N(Me)_2$.

The Groups -$G^2$, -$G^3$, and -$G^4$

In one embodiment, at least one of -$G^1$, -$G^4$, and -$G^2$ and $G^3$, where present, is not —H.

In one embodiment, one of -$G^1$, -$G^4$, and -$G^2$ and $G^3$, where present, is not —H.

In one embodiment, -$G^1$, -$G^4$, and -$G^2$ and $G^3$, where present, are each independently —H.

The Group -$G^1$

In one embodiment, -$G^1$ is independently —H or -$G^A$.
In one embodiment, -$G^1$ is independently —H.
In one embodiment, -$G^1$ is independently -$G^A$.

The Group -$G^2$

In one embodiment, -$G^2$, where present, is independently —H or -$G^A$.
In one embodiment, -$G^2$, where present, is independently —H.
In one embodiment, -$G^2$, where present, is independently -$G^A$.

The Group -$G^3$

In one embodiment, -$G^3$, where present, is independently —H or -$G^B$.
In one embodiment, -$G^3$, where present, is independently —H.
In one embodiment, -$G^3$, where present, is independently -$G^B$.

The Group -$G^4$

In one embodiment, -$G^4$ is independently —H or -$G^B$.
In one embodiment, -$G^4$ is independently —H.
In one embodiment, -$G^4$ is independently -$G^B$.

The Group -$G^A$

In one embodiment, -$G^A$, where present, is independently selected from
—F, —Cl, —Br, —I,
—$CF_3$, —$OCF_3$,
—OH, —$OR^2$;
—[O—$CH_2CH_2]_n$—$R^{B2}$, where n is 2 to 6.

In one embodiment, -$G^A$, where present, is independently selected from
—F,
—$CF_3$, —$OCF_3$,
—OH, —$OR^2$;
—[O—$CH_2CH_2]_n$—$R^{B2}$, where n is 2 to 6.

In one embodiment, -$G^A$, where present, is independently selected from
—F,
—$CF_3$, —$OCF_3$,
—OH, —$OR^2$.

In one embodiment, -$G^A$, where present, is independently selected from
—F, —Cl, —Br, —I,
—OH, —$OR^2$.

In one embodiment, -$G^A$, where present, is independently selected from —F, —Cl, —Br, and —I.

In one embodiment, -$G^A$, where present, is independently —F.

In one embodiment, -$G^A$, where present, is independently selected from —OH and —$OR^2$.

In one embodiment, -$G^A$, where present, is independently —OH.

In one embodiment, -$G^A$, where present, is independently —$OR^2$.

In one embodiment, -$G^A$, where present, is independently —[O—$CH_2CH_2]_n$—$R^{B2}$, where n is 2 to 6.

The Group -$G^B$

In one embodiment, -$G^B$, where present, is independently selected from
—F, —Cl, —Br, —I,
—$CF_3$, —$OCF_3$,
—OH, —$OR^2$;
—[O—$CH_2CH_2]_n$—$R^{B2}$, where n is 2 to 6.

In one embodiment, -$G^B$, where present, is independently selected from
—F,
—$CF_3$, —$OCF_3$,
—OH, —$OR^2$;
—[O—$CH_2CH_2]_n$—$R^{B2}$, where n is 2 to 6.

In one embodiment, -$G^B$, where present, is independently selected from:
—$CF_3$, —$OCF_3$,
—OH, —$OR^2$;
—[O—$CH_2CH_2]_n$—$R^{B2}$, where n is 2 to 6.

In one embodiment, -$G^B$, where present, is independently selected from:
—$CF_3$, —$OCF_3$,
—OH, —$OR^2$.

In one embodiment, -$G^B$, where present, is independently selected from —F, —Cl, —Br, and —I.

In one embodiment, -$G^B$, where present, is independently —F.

In one embodiment, -$G^B$, where present, is independently selected from —$CF_3$ and —$OCF_3$.

In one embodiment, -$G^B$, where present, is independently —$CF_3$ and —$OCF_3$.

In one embodiment, -$G^B$, where present, is independently —$OCF_3$.

In one embodiment, -$G^B$, where present, is independently selected from —OH and —$OR^2$.

In one embodiment, -$G^B$, where present, is independently —OH.

In one embodiment, -$G^B$, where present, is independently —$OR^2$.

In one embodiment, -$G^B$, where present, is independently —$OCH_2CH_2N(Me)_2$.

In one embodiment, -$G^B$, where present, is independently —[O—$CH_2CH_2]_n$—$R^{B2}$, where n is 2 to 6.

In one embodiment, -$G^B$, where present, is independently —[O—$CH_2CH_2]_3$—OMe.

The Group n

In one embodiment, n, where applicable, is independently 2 to 6.

In one embodiment, n, where applicable, is independently 2 to 4.

In one embodiment, n, where applicable, is independently 2.

In one embodiment, n, where applicable, is independently 3.

The Groups —$P^1$, —$P^2$, —$P^3$, —$P^4$, and —$P^5$

In one embodiment, at least one of —$P^1$, —$P^2$, —$P^3$, —$P^4$, and —$P^5$, if present, is —$P^A$, —$P^B$ or —$P^C$ where appropriate.

In one embodiment, one of —$P^1$, —$P^2$, —$P^3$, —$P^4$, and —$P^5$, if present, is —$P^A$, —$P^B$ or —$P^C$ where appropriate.

In one embodiment, at least one of —$P^1$, —$P^2$, —$P^3$, —$P^4$, and —$P^5$, if present, is not —H.

In one embodiment, one of —$P^1$, —$P^2$, —$P^3$, —$P^4$, and —$P^5$, if present, is not —H.

In one embodiment, —$P^1$, —$P^2$, —$P^3$, and —$P^4$, and —$P^5$, where present, are each independently —H.

In one embodiment, one of —$P^1$, —$P^2$, —$P^3$, and —$P^4$, and —$P^5$, where present, is independently —F.

The Group —$P^1$

In one embodiment, —$P^1$ is independently —H or —$P^A$.

In one embodiment, —$P^1$ is independently —H.

In one embodiment, —$P^1$ is independently —$P^A$.

In one embodiment, —$P^1$ is the same as —$P^5$, where present.

The Group —$P^2$

In one embodiment, —$P^2$ is independently —H or —$P^B$.

In one embodiment, —$P^2$ is independently —H.

In one embodiment, —$P^2$ is independently —$P^B$.

In one embodiment, —$P^2$ is the same as —$P^4$.

The Group —$P^3$

In one embodiment, —$P^3$ is independently —H or —$P^C$.

In one embodiment, —$P^3$ is independently —H.

In one embodiment, —$P^3$ is independently —$P^C$.

The Group —$P^4$

In one embodiment, —$P^4$ is independently —H or —$P^B$.

In one embodiment, —$P^4$ is independently —H.

In one embodiment, —$P^4$ is independently —$P^B$.

The Group —$P^5$

In one embodiment, —$P^5$, where present, is independently —H or —$P^A$.

In one embodiment, —$P^5$, where present, is independently —H.

In one embodiment, —$P^5$, where present, is independently —$P^A$.

The Groups —$P^A$, —$P^B$, and —$P^C$

In one embodiment, each —$P^A$, each —$P^B$, and each —$P^C$, where present, is independently selected from:
—F, —Cl, —Br, —I,
—$R^2$,
—$CF_3$, —$OCF_3$,
—OH, -$L^1$-OH,
—$OR^2$, -$L^1$-$OR^2$, —O-$L^1$-$OR^2$,
—$NO_2$,
—$NH_2$, —$NHR^2$, —$NR^2_2$, —$NR^3R^4$,
—NHOH,
—C(=O)OH, —C(=O)$OR^2$,
—OC(=O)$R^2$,
—C(=O)$NH_2$, —C(=O)$NHR^2$, —C(=O)$NR^2_2$,
—C(=O)$NR^3R^4$,
—NHC(=O)$R^2$, —$NR^2$C(=O)$R^2$,
—C(=O)$NHOR^2$, —C(=O)$NR^2OR^2$,
—NHC(=O)$OR^2$, —$NR^2$C(=O)$OR^2$, —OC(=O)NH$_2$, —OC(=O)NHR$^2$, —OC(=O)NR$^2_2$,
—OC(=O)NR$^3$R$^4$,
—C(=O)R$^2$,
—S(=O)R$^2$, —S(=O)$_2$R$^2$, —OS(=O)$_2$R$^2$, or —S(=O)$_2$OR$^2$.

In one embodiment, each —P$^A$, each —P$^B$, and each —P$^C$, where present, is independently selected from:
- —F, —Cl, —Br, —I,
- —CF$_3$, —OCF$_3$,
- —OH, -L$^1$-OH,
- —OR$^2$, -L$^1$-OR$^2$, —O-L$^1$-OR$^2$,
- —NO$_2$,
- —NH$_2$, —NHR$^2$, —NR$^2_2$, —NR$^3$R$^4$,
- —NHOH,
- —C(=O)OH, —C(=O)OR$^2$,
- —OC(=O)R$^2$,
- —NHC(=O)R$^2$, —NR$^2$C(=O)R$^2$.

The Group —P$^A$

In one embodiment, each —P$^A$, where present, is independently selected from:
- —F, —Cl, —Br, —I,
- —CF$_3$, —OCF$_3$,
- —OH, -L$^1$-OH,
- —OR$^2$, -L$^1$-OR$^2$, —O-L$^1$-OR$^2$,
- —NO$_2$,
- —NH$_2$, —NHR$^2$, —NR$^2_2$, —NR$^3$R$^4$.

In one embodiment, each —P$^A$, where present, is independently selected from:
- —F,
- —CF$_3$, —OCF$_3$,
- —OH,
- —OR$^2$,
- —NO$_2$,
- —NH$_2$, —NHR$^2$, —NR$^2_2$, —NR$^3$R$^4$.

In one embodiment, each —P$^B$, where present, is independently selected from —F, —Cl, —Br, and —I.

In one embodiment, each —P$^B$, where present, is independently —F.

In one embodiment, each —P$^A$, where present, is independently selected from —CF$_3$ and —OCF$_3$.

In one embodiment, each —P$^A$, where present, is independently —CF$_3$.

In one embodiment, each —P$^A$, where present, is independently —OCF$_3$.

In one embodiment, each —P$^A$, where present, is independently selected from —OH and -L$^1$-OH.

In one embodiment, each —P$^A$, where present, is independently —OH.

In one embodiment, each —P$^A$, where present, is independently -L$^1$-OH.

In one embodiment, each —P$^A$, where present, is independently selected from —OR$^2$, -L$^1$-OR$^2$, and —O-L$^1$-OR$^2$.

In one embodiment, each —P$^A$, where present, is independently —OR$^2$.

In one embodiment, each —P$^A$, where present, is independently —OMe.

In one embodiment, each —P$^A$, where present, is independently —O(CH$_2$)$_3$—CF$_3$.

In one embodiment, each —P$^A$, where present, is independently —O(CH$_2$)$_n$—F, where n is from 2 to 6.

In one embodiment, each —P$^A$, where present, is independently —O(CH$_2$)$_2$—F.

In one embodiment, each —P$^A$, where present, is independently selected from -L$^1$-OR$^2$ and —O-L$^1$-OR$^2$.

In one embodiment, each —P$^A$, where present, is independently selected from:
- —NO$_2$,
- —NH$_2$, —NHR$^2$, —NR$^2_2$, —NR$^3$R$^4$.

In one embodiment, each —P$^A$, where present, is independently —NO$_2$.

In one embodiment, each —P$^A$, where present, is independently selected from —NH$_2$, —NHR$^2$, —NR$^2_2$, and —NR$^3$R$^4$.

In one embodiment, each —P$^A$, where present, is independently selected from —NH$_2$, —NHR$^2$, and —NR$^2_2$.

In one embodiment, each —P$^A$, where present, is independently —NR$^3$R$^4$.

In one embodiment, each —P$^A$, where present, is independently selected from —NH$_2$, —NHR$^2$, and —NR$^2_2$.

In one embodiment, each —P$^A$, where present, is independently —NH$_2$.

In one embodiment, each —P$^A$, where present, is independently —NHR$^2$.

In one embodiment, each —P$^A$, where present, is independently —NHMe.

In one embodiment, each —P$^A$, where present, is independently —NH—(CH$_2$)$_n$—F, where n is from 2 to 6.

In one embodiment, each —P$^A$, where present, is independently —NH—(CH$_2$)$_n$—F, where n is 2, 3 or 4.

In one embodiment, each —P$^A$, where present, is independently —NR$^2_2$.

In one embodiment, each —P$^A$, where present, is independently —NMe$_2$.

In one embodiment, each —P$^A$, where present, is independently —R$^2$.

The Group —P$^B$

In one embodiment, each —P$^B$, where present, is independently selected from:
- —F, —Cl, —Br, —I,
- —CF$_3$, —OCF$_3$,
- —OH, -L$^1$-OH,
- —OR$^2$, -L$^1$-OR$^2$,
- —NO$_2$,
- —NH$_2$, —NHR$^2$, —NR$^2_2$, —NR$^3$R$^4$.

In one embodiment, each —P$^B$, where present, is independently selected from:
- —F,
- —CF$_3$, —OCF$_3$,
- —OH,
- —OR$^2$,
- —NO$_2$,
- —NH$_2$, —NHR$^2$, —NR$^2_2$, —NR$^3$R$^4$.

In one embodiment, each —P$^B$, where present, is independently selected from:
- —F,
- —CF$_3$, —OCF$_3$,
- —NO$_2$,
- —NH$_2$, —NHR$^2$, —NR$^2_2$, —NR$^3$R$^4$.

In one embodiment, each —P$^B$, where present, is independently selected from —F, —Cl, —Br, and —I.

In one embodiment, each —P$^B$, where present, is independently —F.

In one embodiment, each —P$^B$, where present, is independently selected from —CF$_3$ and —OCF$_3$.

In one embodiment, each —P$^B$, where present, is independently —CF$_3$.

In one embodiment, each —P$^B$, where present, is independently —OCF$_3$.

In one embodiment, each —P$^B$, where present, is independently selected from —OH and -L$^1$-OH.

In one embodiment, each —P$^B$, where present, is independently —OH.

In one embodiment, each —P$^B$, where present, is independently -L$^1$-OH.

In one embodiment, each —$P^B$, where present, is independently selected from —$OR^2$, -$L^1$-$OR^2$, and —O-$L^1$-$OR^2$.

In one embodiment, each —$P^B$, where present, is independently —$OR^2$.

In one embodiment, each —$P^B$, where present, is independently selected from -$L^1$-$OR^2$ and —O-$L^1$-$OR^2$.

In one embodiment, each —$P^B$, where present, is independently —O(CH$_2$)$_n$—F, where n is from 2 to 6.

In one embodiment, each —$P^B$, where present, is independently —O(CH$_2$)$_2$—F.

In one embodiment, each —$P^B$, where present, is independently selected from:
—NO$_2$,
—NH$_2$, —NHR$^2$, —NR$^2{}_2$, —NR$^3$R$^4$.

In one embodiment, each —$P^B$, where present, is independently —NO$_2$.

In one embodiment, each —$P^B$, where present, is independently selected from —NH$_2$, —NHR$^2$, —NR$^2{}_2$, and —NR$^3$R$^4$.

In one embodiment, each —$P^B$, where present, is independently selected from —NH$_2$, —NHR$^2$, and —NR$^2{}_2$.

In one embodiment, each —$P^B$, where present, is independently —NR$^3$R$^4$.

In one embodiment, each —$P^B$, where present, is independently selected from —NH$_2$, —NHR$^2$, and —NR$^2{}_2$.

In one embodiment, each —$P^B$, where present, is independently —NH$_2$,

In one embodiment, each —$P^B$, where present, is independently —NHR$^2$.

In one embodiment, each —$P^B$, where present, is independently —NHMe.

In one embodiment, each —$P^B$, where present, is independently —NH—(CH$_2$)$_n$—F, where n is from 2 to 6.

In one embodiment, each —$P^B$, where present, is independently —NH—(CH$_2$)$_n$—F, where n is 2, 3 or 4.

In one embodiment, each —$P^B$, where present, is independently —NR$^2{}_2$.

In one embodiment, each —$P^B$, where present, is independently —NMe$_2$.

In one embodiment, each —$P^B$, where present, is independently —R$^2$.

The Group —$P^C$

In one embodiment, each —$P^C$, where present, is independently selected from:
—F, —Cl, —Br, —I,
—CF$_3$, —OCF$_3$,
—OH, -$L^1$-OH,
—OR$^2$, -$L^1$-OR$^2$,
—NO$_2$,
—NH$_2$, —NHR$^2$, —NR$^2{}_2$, —NR$^3$R$^4$,
—NHOH,
—C(=O)OH, —C(=O)OR$^2$,
—OC(=O)R$^2$,
—NHC(=O)R$^2$, —NR$^2$C(=O)R$^2$.

In one embodiment, each —$P^C$, where present, is independently selected from:
—F, —Cl, —Br, —I,
—CF$_3$, —OCF$_3$,
—OH,
—OR$^2$,
—NO$_2$,
—NH$_2$, —NHR$^2$, —NR$^2{}_2$, —NR$^3$R$^4$,
—NHOH,
—OC(=O)R$^2$,
—NHC(=O)R$^2$.

In one embodiment, each —$P^C$, where present, is independently selected from —F, —Cl, —Br, and —I.

In one embodiment, each —$P^C$, where present, is independently selected from —F, —Cl, and —Br.

In one embodiment, each —$P^C$, where present, is independently —F.

In one embodiment, each —$P^C$, where present, is independently selected from —CF$_3$ and —OCF$_3$.

In one embodiment, each —$P^C$, where present, is independently —CF$_3$.

In one embodiment, each —$P^C$, where present, is independently —OCF$_3$.

In one embodiment, each —$P^C$, where present, is independently selected from —OH and -$L^1$-OH.

In one embodiment, each —$P^C$, where present, is independently —OH.

In one embodiment, each —$P^C$, where present, is independently -$L^1$-OH.

In one embodiment, each —$P^C$, where present, is independently selected from —OR$^2$, -$L^1$-OR$^2$, and —O-$L^1$-OR$^2$.

In one embodiment, each —$P^C$, where present, is independently —OR$^2$.

In one embodiment, each —$P^C$, where present, is independently —OMe.

In one embodiment, each —$P^C$, where present, is independently —O(CH$_2$)$_2$—OH.

In one embodiment, each —$P^C$, where present, is independently —O(CH$_2$)$_n$—F, where n is from 2 to 6.

In one embodiment, each —$P^C$, where present, is independently —O(CH$_2$)$_2$—F.

In one embodiment, each —$P^C$, where present, is independently —O(CH$_2$)$_n$—CF$_3$, where n is from 1 to 6.

In one embodiment, each —$P^C$, where present, is independently —O(CH$_2$)$_n$—CF$_3$, where n is 1, 2 or 3.

In one embodiment, each —$P^C$, where present, is independently selected from -$L^1$-OR$^2$ and In one embodiment, each —$P^C$, where present, is independently selected from:
—NO$_2$,
—NH$_2$, —NHR$^2$, —NR$^2{}_2$, —NR$^3$R$^4$,
—NHOH.

In one embodiment, each —$P^C$, where present, is independently —NO$_2$.

In one embodiment, each —$P^C$, where present, is independently —NHOH.

In one embodiment, each —$P^C$, where present, is independently selected from —NH$_2$, —NHR$^2$, —NR$^2{}_2$, —NR$^3$R$^4$ and —NHOH.

In one embodiment, each —$P^C$, where present, is independently selected from —NH$_2$, —NHR$^2$, —NR$^2{}_2$, and —NR$^3$R$^4$.

In one embodiment, each —$P^C$, where present, is independently selected from —NH$_2$, —NHR$^2$, and —NR$^2{}_2$.

In one embodiment, each —$P^C$, where present, is independently —NR$^3$R$^4$.

In one embodiment, each —$P^C$, where present, is independently selected from —NH$_2$, —NHR$^2$, and —NR$^2{}_2$.

In one embodiment, each —$P^C$, where present, is independently —NH$_2$,

In one embodiment, each —$P^C$, where present, is independently —NHR$^2$.

In one embodiment, each —$P^C$, where present, is independently —NHMe.

In one embodiment, each —$P^C$, where present, is independently —NH—(CH$_2$)$_n$—CF$_3$, where n is from 1 to 6.

In one embodiment, each —$P^C$, where present, is independently —NH—(CH$_2$)$_n$—CF$_3$, where n is 2, 3 or 4.

In one embodiment, each —$P^C$, where present, is independently —NH—(CH$_2$)$_n$—F, where n is from 2 to 6.

In one embodiment, each —$P^C$, where present, is independently —NH—$(CH_2)_n$—F, where n is 2, 3 or 4.

In one embodiment, each —$P^C$, where present, is independently —$NR^2_2$.

In one embodiment, each —$P^C$, where present, is independently —$NMe_2$.

In one embodiment, each —$P^C$, where present, is independently selected from —C(=O)OH and —C(=O)$OR^2$.

In one embodiment, each —$P^C$, where present, is independently —C(=O)OH.

In one embodiment, each —$P^C$, where present, is independently —C(=O)$OR^2$.

In one embodiment, each —$P^C$, where present, is independently —OC(=O)Me.

In one embodiment, each —$P^C$, where present, is independently selected from —NHC(=O)$R^2$ and —$NR^2$C(=O)$R^2$.

In one embodiment, each —$P^C$, where present, is independently —NHC(=O)$R^2$.

In one embodiment, each —$P^C$, where present, is independently —NHC(=O)$CF_3$.

In one embodiment, each —$P^C$, where present, is independently —$NR^2$C(=O)$R^2$.

In one embodiment, each —$P^C$, where present, is independently —$R^2$.

The Group -$L^1$-

In one embodiment, each -$L^1$-, where present, is independently unsubstituted saturated aliphatic $C_{1-5}$alkylene.

In one embodiment, each -$L^1$-, where present, is —$CH_2$—.

In one embodiment, each -$L^1$-, where present, is —$CH_2CH_2$—.

The Group —$R^2$

In one embodiment, each —$R^2$, where present, is independently:

—$R^{A1}$, —$R^{A2}$, —$R^{A3}$, —$R^{A4}$, —$R^{A5}$, —$R^{A6}$, —$R^{A7}$, —$R^{A8}$,

-$L^A$-$R^{A4}$, -$L^A$-$R^{A5}$, -$L^A$-$R^{A6}$, -$L^A$-$R^{A7}$, or -$L^A$-$R^{A8}$;

and each —$R^{A4}$, —$R^{A5}$, —$R^{A6}$, —$R^{A7}$, and —$R^{A8}$ is optionally substituted, for example, with one or more substituents —$R^{B1}$ and/or one or more substituents —$R^{B2}$, and each —$R^{A1}$, —$R^{A2}$, —$R^{A3}$, and -$L^A$- is optionally substituted, for example, with one or more substituents —$R^{B2}$.

In one embodiment, each —$R^2$, where present, is independently —$R^{A1}$.

The Group —$R^{A1}$

In one embodiment, each —$R^{A1}$, where present, is independently optionally substituted saturated aliphatic $C_{1-6}$alkyl.

In one embodiment, each —$R^{A1}$, where present, is independently optionally substituted saturated aliphatic $C_{1-4}$alkyl.

In one embodiment, each —$R^{A1}$, where present, is independently unsubstituted saturated aliphatic $C_{1-6}$alkyl.

In one embodiment, each —$R^{A1}$, where present, is independently unsubstituted saturated aliphatic $C_{1-4}$alkyl.

In one embodiment, each —$R^{A1}$, where present, is unsubstituted -Me.

In one embodiment, each —$R^{A1}$, where present, is unsubstituted -Et.

In one embodiment, each —$R^{A1}$, where present, is unsubstituted —Pr.

In one embodiment, each —$R^{A1}$, where present, is optionally substituted -Me.

In one embodiment, each —$R^{A1}$, where present, is optionally substituted -Et.

In one embodiment, each —$R^{A1}$, where present, is optionally substituted —Pr.

In one embodiment, each where present, is optionally substituted -Bu.

In one embodiment, each —$R^{A1}$, where present, is —$CF_3$.

In one embodiment, each —$R^{A1}$, where present, is —$CH_2CF_3$.

In one embodiment, each —$R^{A1}$, where present, is —$CH_2CH_2CF_3$.

In one embodiment, each —$R^{A1}$, where present, is —$CH_2CH_2CH_2CF_3$.

In one embodiment, each —$R^{A1}$, where present, is —$CH_2F$.

In one embodiment, each —$R^{A1}$, where present, is —$CH_2CH_2F$.

In one embodiment, each —$R^{A1}$, where present, is —$CH_2CH_2CH_2F$.

In one embodiment, each —$R^{A1}$, where present, is —$CH_2CH_2N(Me)_2$.

The Group —$R^{B2}$

In one embodiment, each —$R^{B2}$, where present, is independently selected from:

—F, —Cl, —Br, —I,

—$CF_3$, —$OCF_3$,

—OH, -$L^C$-OH, —O-$L^C$-OH,

—$OR^{C1}$, -$L^C$-$OR^{C1}$, —O-$L^C$-$OR^{C1}$,

—NHS(=O)$_2R^{C1}$, —$NR^2$S(=O)$_2R^{C1}$.

In one embodiment, each —$R^{B2}$, where present, is independently selected from:

—F, —Cl, —Br, —I,

—$CF_3$, —$OCF_3$,

—OH, -$L^C$-OH, —O-$L^C$-OH,

—$OR^{C1}$, -$L^C$-$OR^{C1}$, —O-$L^C$-$OR^{C1}$.

In one embodiment, each —$R^{B2}$, where present, is independently selected from:

—F, —Cl, —Br, —I,

—$CF_3$, —$OCF_3$,

—OH, —O-$L^C$-OH,

—$OR^{C1}$, -$L^C$-$OR^{C1}$, —O-$L^C$-$OR^{C1}$.

In one embodiment, each —$R^{B2}$, where present, is independently selected from:

—F, —Cl, —Br, —I,

—$CF_3$, —$OCF_3$.

In one embodiment, each —$R^{B2}$, where present, is independently selected from —F, —Cl, —Br, and —I.

In one embodiment, each —$R^{B2}$, where present, is independently selected from —$CF_3$ and —$OCF_3$.

In one embodiment, each —$R^{B2}$, where present, is independently —F and —$CF_3$.

In one embodiment, each —$R^{B2}$, where present, is independently —F.

In one embodiment, each —$R^{B2}$, where present, is independently —$CF_3$.

In one embodiment, each —$R^{B2}$, where present, is independently selected from:

—OH, -$L^C$-OH, —O-$L^C$-OH,

—$OR^{C1}$, -$L^C$-$OR^{C1}$, —O-$L^C$-$OR^{C1}$.

In one embodiment, each —$R^{B2}$, where present, is independently selected from:

—OH, —O-$L^C$-OH, $OR^{C1}$, —O-$L^C$-$OR^{C1}$.

In one embodiment, each —$R^{B2}$, where present, is independently selected —OH or —$OR^{C1}$.

In one embodiment, each —$R^{B2}$, where present, is independently selected from —O-$L^C$-OH and —O-$L^C$-$OR^{C1}$.

In one embodiment, each —$R^{B2}$, where present, is independently —O-$L^C$-OH.

In one embodiment, each —$R^{B2}$, where present, is independently —O-$L^C$-$OR^{C1}$.

The Group -L$^C$

In one embodiment, each -L$^C$-, where present, is independently unsubstituted saturated aliphatic C$_{1-5}$alkylene.

In one embodiment, each -L$^C$-, where present, is independently —CH$_2$CH$_2$—.

The Group —R$^{C1}$

In one embodiment, each —R$^{C1}$, where present, is independently unsubstituted saturated aliphatic C$_{1-4}$alkyl, phenyl, or benzyl.

In one embodiment, each —R$^{C1}$, where present, is independently unsubstituted saturated aliphatic C$_{1-4}$alkyl.

In one embodiment, each —R$^{C1}$, where present, is independently -Me.

In one embodiment, each —R$^{C1}$, where present, is independently unsubstituted phenyl.

In one embodiment, each —R$^{C1}$, where present, is independently unsubstituted benzyl.

Combinations

Each and every compatible combination of the embodiments described above is explicitly disclosed herein, as if each and every combination was individually and explicitly recited.

Physicochemical Properties

The preferred physicochemical property ranges for enhancing blood brain barrier permeation are discussed in more detail hereinafter. However based on existing CNS active agents, the following are preferred criteria for the DSB compounds described herein:

Molecular Weight

In one embodiment, the DSB compound has a molecular weight of from 330 to 600.

In one embodiment, the bottom of the range is from 350, 375, 400, or 425.

In one embodiment, the top of the range is 600, 575, 550, 525, 500 or 450.

In one embodiment, the range is 375 to 575.

In one embodiment, the DSB compound has a molecular weight of 500 or less.

In one embodiment, the DSB compound has a molecular weight of 450 or less.

miLog P

In one embodiment, the DSB compound has a miLog P of from 2.0 to 5.3.

In one embodiment, the bottom of the range is from 2.8, 2.9, 3.0, or 3.1.

In one embodiment, the top of the range is 5.0, 5.1, 5.2, 5.3, 4.5, or 4.0.

In one embodiment, the range is 3.0 to 5.1.

In one embodiment, the DSB compound has a miLog P of from 2.0 to 5.0.

In one embodiment, the DSB compound has a miLog P of from 2.0 to 4.0.

Log D

In one embodiment, the DSB compound has a Log D of from 2.0 to 5.0.

In one embodiment, the DSB compound has a Log D of from 2.0 to 4.0.

Log D is the ratio of the equilibrium concentration of all species (unionised and ionised) of the molecule in octanol to the same molecules in the water phase at 25° C.

In one embodiment, Log D is the ratio of the equilibrium concentration of all species (unionised and ionised) of the molecule in octanol to the same molecules in the water phase at 25° C. and pH 7.4.

Topological Polar Surface Area

In one embodiment, the DSB compound has a topological polar surface area of from 45 to 95 Å$^2$.

In one embodiment, the bottom of the range is from 50, 55, or 60.

In one embodiment, the top of the range is 70, 75, 80, 85, or 90.

In one embodiment, the range is 55 to 75.

In one embodiment, the DSB compound has a topological polar surface area of 90 Å$^2$ or less.

In one embodiment, the DSB compound has a topological polar surface area of 70 Å$^2$ or less.

Hydrogen Bond Donors

In one embodiment, the DSB compound has 3 or less hydrogen bond donors.

In one embodiment, the DSB compound has 2 or less hydrogen bond donors.

In one embodiment, the DSB compound has 1 or no hydrogen bond donors.

Examples of Specific Embodiments

In one embodiment, the compounds are selected from compounds of the formulae below and pharmaceutically acceptable salts, hydrates, and solvates thereof.

Compounds where -Q- is —NHC(O)—; —NR$^1$C(O)—; —C(O)NH—; or —C(O)NR$^1$—

Benzothiazole Compounds

Non-Fluorinated Methoxy-Amides

| Code | Book No. | Structure |
|---|---|---|
| ABMA-01 | SKT01-13 | 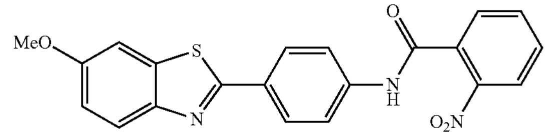 |
| ABMA-02 | SKT01-23 | 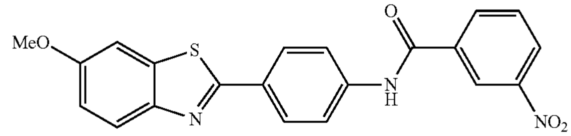 [SMILES: COc1ccc2nc(-c3ccc(NC(=O)c4cccc([N+](=O)[O-])c4)cc3)sc2c1] |

-continued

| Code | Book No. | Structure |
|---|---|---|
| ABMA-03 | SKT01-9 | MeO-benzothiazole-C6H4-NH-C(O)-C6H4-NO2 (para) |
| ABMA-04 | SKT01-99 | MeO-benzothiazole-C6H4-NH-C(O)-C6H4-NH2 (ortho) |
| ABMA-05 | SKT01-41 | MeO-benzothiazole-C6H4-NH-C(O)-C6H4-NH2 (meta) |
| ABMA-06 | SKT01-21 | MeO-benzothiazole-C6H4-NH-C(O)-C6H4-NH2 (para) |
| ABMA-07 | SKT01-103 | MeO-benzothiazole-C6H4-NH-C(O)-C6H4-N(Me)2 (ortho) |
| ABMA-08 | SKT01-63 | MeO-benzothiazole-C6H4-NH-C(O)-C6H4-N(Me)2 (meta) |
| ABMA-09 | SKT01-61 | MeO-benzothiazole-C6H4-NH-C(O)-C6H4-N(Me)2 (para) |
| ABMA-10 | SKT01-155 | MeO-benzothiazole-C6H4-NH-C(O)-C6H4-OC(O)CH3 (para) |
| ABMA-11 | SKT01-161 | MeO-benzothiazole-C6H4-NH-C(O)-C6H4-OH (para) |
| ABMA-12 | SKT04-87 | MeO-benzothiazole-C6H4-NH-C(O)-C6H3(NO2)-OC(O)CH3 |

| Code | Book No. | Structure |
|---|---|---|
| ABMA-13 | SKT04-89 | (6-methoxybenzothiazol-2-yl)phenyl-N-(4-hydroxy-3-nitrobenzamide) |
| ABMA-14 | SKT03-141 | (6-methoxybenzothiazol-2-yl)phenyl-N-(4-(dimethylamino)-3-nitrobenzamide) |
| ABMA-15 | SKT03-137 | (6-methoxybenzothiazol-2-yl)phenyl-N-(3,4-dinitrobenzamide) |
| ABMA-16 | SKT03-33 | (6-methoxybenzothiazol-2-yl)phenyl-N-(4-(2-hydroxyethoxy)benzamide) |

In one embodiment, the compound is independently selected from:
ABMA-04; ABMA-05; ABMA-06; ABMA-07; ABMA-08; ABMA-09; ABMA-10; ABMA-11; ABMA-13; ABMA-14; ABMA-15; and ABMA-16.

In one embodiment, the compound is independently selected from:
ABMA-04; ABMA-05; ABMA-06; ABMA-07; ABMA-08; ABMA-09; ABMA-10; ABMA-11; and ABMA-13.

Fluorinated Methoxy-Amides

| Code | Book No. | Structure |
|---|---|---|
| ABFMA-01 | SK2033-50 | (6-methoxybenzothiazol-2-yl)phenyl-N-(2-(trifluoromethyl)benzamide) |
| ABFMA-02 | SK2033-49 | (6-methoxybenzothiazol-2-yl)phenyl-N-(3-(trifluoromethyl)benzamide) |
| ABFMA-03 | SK2033-47 | (6-methoxybenzothiazol-2-yl)phenyl-N-(4-(trifluoromethyl)benzamide) |
| ABFMA-04 | SKT04-155 | (6-methoxybenzothiazol-2-yl)phenyl-N-(4-methoxy-3-(trifluoromethyl)benzamide) |

-continued
| Code | Book No. | Structure |
|---|---|---|
| ABFMA-05 | SKT05-7 | 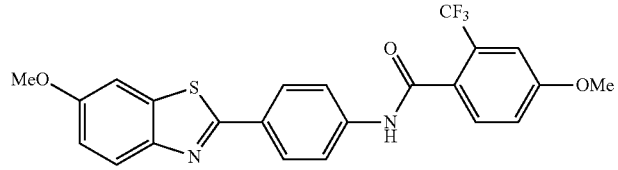 |
| ABFMA-06 | SKT05-9 | 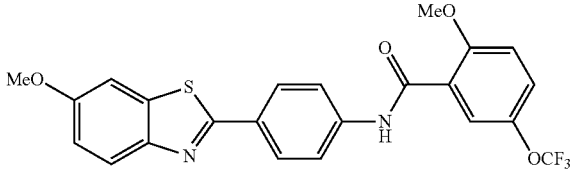 [SMILES: COc1ccc2nc(-c3ccc(NC(=O)c4cc(OC(F)(F)F)ccc4OC)cc3)sc2c1] |
| ABFMA-07 | SKT04-173 | 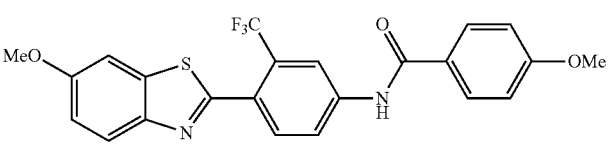 [SMILES: COc1ccc(C(=O)Nc2ccc(-c3nc4ccc(OC)cc4s3)c(C(F)(F)F)c2)cc1] |
| ABFMA-08 | SKT05-33 | 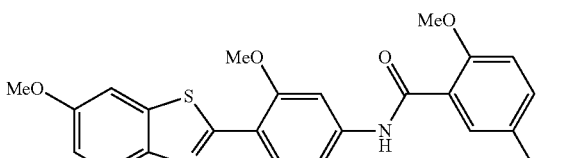 |
| ABFMA-09 | SKT05-31 | 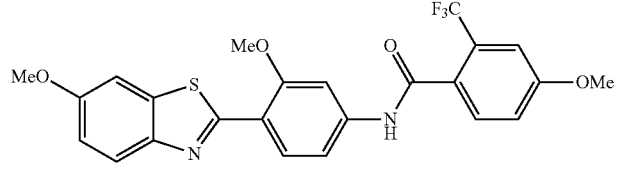 [SMILES: COc1ccc(C(=O)Nc2ccc(-c3nc4ccc(OC)cc4s3)c(OC)c2)c(C(F)(F)F)c1] |
| ABFMA-10 | SKT05-21 | 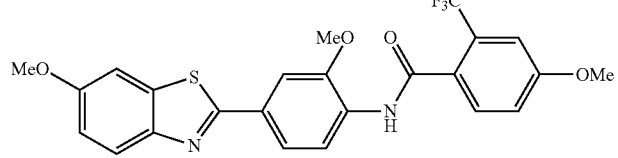 |
| ABFMA-11 | SKT04-175 | 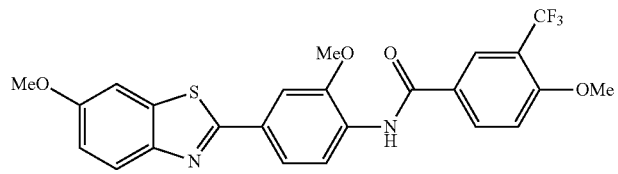 [SMILES: COc1ccc2nc(-c3ccc(NC(=O)c4ccc(OC)c(C(F)(F)F)c4)c(OC)c3)sc2c1] |
| ABFMA-12 | SKT02-103 | 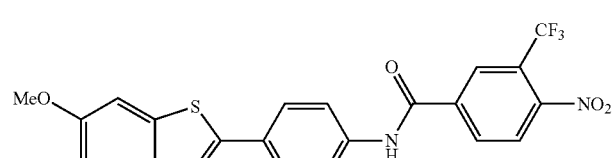 |
| ABFMA-13 | SKT02-169 | 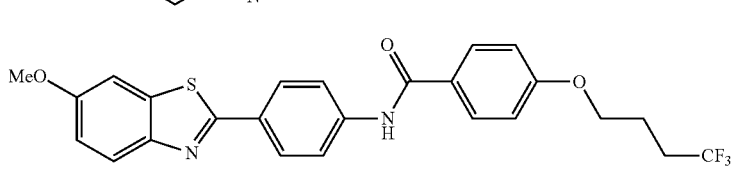 |

| Code | Book No. | Structure |
|---|---|---|
| ABFMA-14 | SKT03-39 | (6-methoxybenzothiazol-2-yl)phenyl-NH-C(O)-phenyl-O-CH2-CF3 |
| ABFMA-15 | SKT01-157 | (6-methoxybenzothiazol-2-yl)phenyl-NH-C(O)-phenyl(3-CF3, 4-NH2) |
| ABFMA-16 | SKT01-149 | (6-methoxybenzothiazol-2-yl)phenyl-NH-C(O)-phenyl(2-CF3, 4-NH2) |
| ABFMA-17 | SKT02-31 | (6-methoxybenzothiazol-2-yl)phenyl-NH-C(O)-phenyl(3-CF3, 4-NMe2) |
| ABFMA-18 | SKT01-159 | (6-methoxybenzothiazol-2-yl)phenyl-NH-C(O)-phenyl(2-CF3, 4-NMe2) |
| ABFMA-19 | SKT02-25 | (6-methoxybenzothiazol-2-yl)phenyl-NH-C(O)-phenyl-O-CH2-CF3 |
| ABFMA-20 | SKT01-137 | (6-methoxybenzothiazol-2-yl)phenyl-NH-C(O)-phenyl(2-CF3, 4-NO2) |

In one embodiment, the compound is independently selected from:
ABFMA-04; ABFMA-05; ABFMA-06; ABFMA-07; ABFMA-08; ABFMA-09; ABFMA-11; ABFMA-12; ABFMA-14; ABFMA-15; and ABFMA-17.

In one embodiment, the compound is independently selected from ABFMA-15 and ABFMA-12.

Monohalo Methoxy-Amides

| Code | Book No. | Structure |
|---|---|---|
| ABMFMA-01 | SKT02-135 | (6-methoxybenzothiazol-2-yl)phenyl-NH-C(O)-phenyl-4-F |

-continued
| Code | Book No. | Structure |
|---|---|---|
| ABMFMA-02 | SKT04-137 | 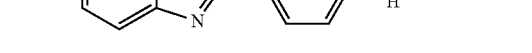 |
| ABMFMA-03 | SKT04-111 | 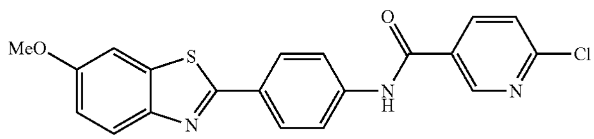 |
| ABMFMA-04 | SKT05-63 | 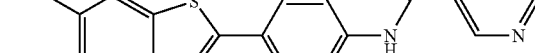 |
| ABMFMA-05 | SKT03-99 | 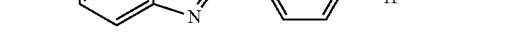 |
| ABMFMA-06 | SKT03-75 | 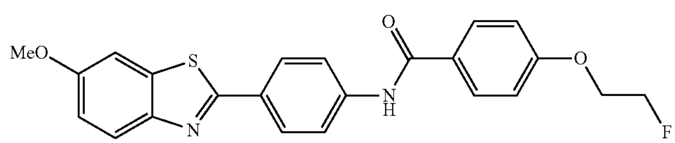 [SMILES: COc1ccc2nc(-c3ccc(NC(=O)c4ccc(OCCF)cc4)cc3)sc2c1] |
| ABMFMA-07 | SKT03-93 | 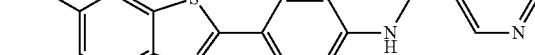 |
| ABMFMA-08 | SKT04-33 | 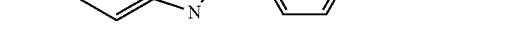 |
| ABMFMA-09 | SKT04-29 | 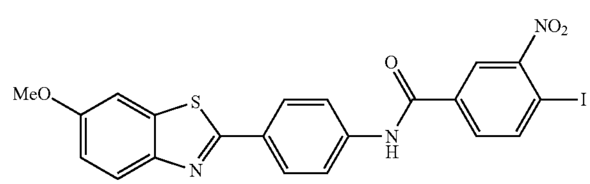 [SMILES: COc1ccc2nc(-c3ccc(NC(=O)c4ccc(I)c([N+](=O)[O-])c4)cc3)sc2c1] |
| ABMFMA-10 | SKT05-37 | 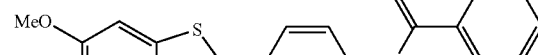 |

In one embodiment, the compound is independently selected from:

ABMFMA-02; ABMFMA-03; ABMFMA-04; ABMFMA-05; ABMFMA-07; ABMFMA-08; ABMFMA-09; and ABMFMA-10.

In one embodiment, the compound is independently selected from:

ABMFMA-02; ABMFMA-03; ABMFMA-05; ABMFMA-08 and ABMFMA-09.

Non-Fluorinated Hydroxy-Amides

| Code | Book No. | Structure |
|---|---|---|
| ABHA-01 | SKT01-101 | 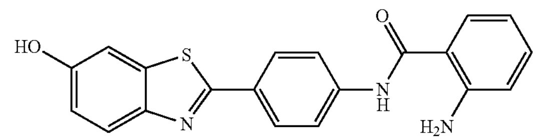 [SMILES: Nc1ccccc1C(=O)Nc1ccc(-c2nc3ccc(O)cc3s2)cc1] |
| ABHA-02 | SKT01-77 | 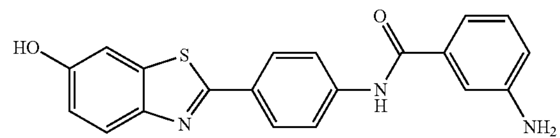 |
| ABHA-03 | SKT01-57 | 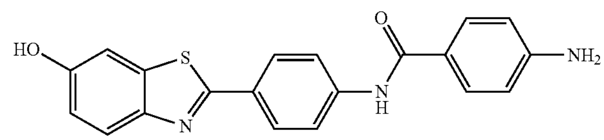 [SMILES: Nc1ccc(C(=O)Nc2ccc(-c3nc4ccc(O)cc4s3)cc2)cc1] |
| ABHA-04 | SKT01-111 | 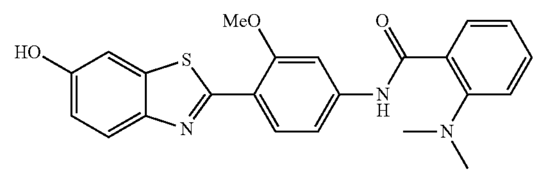 [SMILES: COc1cc(NC(=O)c2ccccc2N(C)C)ccc1-c1nc2ccc(O)cc2s1] |
| ABHA-05 | SKT02-177 | 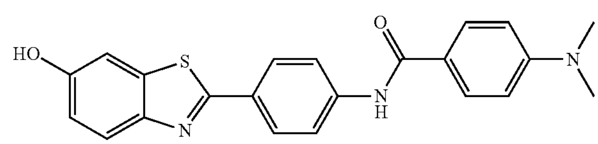 [SMILES: CN(C)c1ccc(C(=O)Nc2ccc(-c3nc4ccc(O)cc4s3)cc2)cc1] |

In one embodiment, the compound is independently selected from:

ABHA-01; ABHA-02; ABHA-03; and ABHA-05.

In one embodiment, the compound is independently selected from:

ABHA-01; ABHA-02 and ABHA-03.

Fluorinated Hydroxy-Amides

| Code | Book No. | Structure |
|---|---|---|
| ABFHA-01 | SKT03-07 | 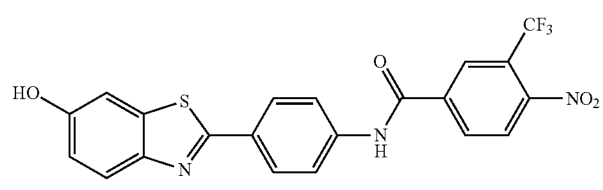 |
| ABFHA-02 | SKT02-45 | 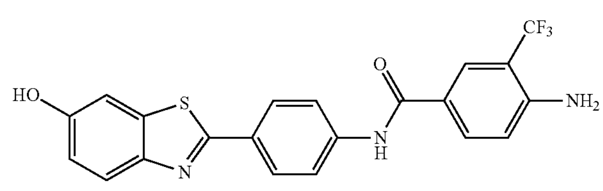 [SMILES: O=C(Nc1ccc(-c2nc3ccc(O)cc3s2)cc1)c1ccc([N+](=O)[O-])c(C(F)(F)F)c1] |

-continued

| Code | Book No. | Structure |
|---|---|---|
| ABFHA-03 | SKT02-149 | 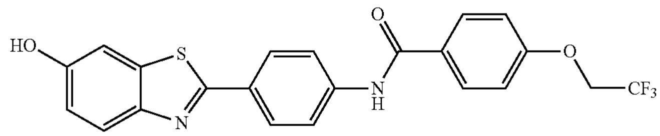 [SMILES: O=C(Nc1ccc(-c2nc3ccc(O)cc3s2)cc1)c1ccc(OCC(F)(F)F)cc1] |
| ABFHA-04 | SKT03-41 | 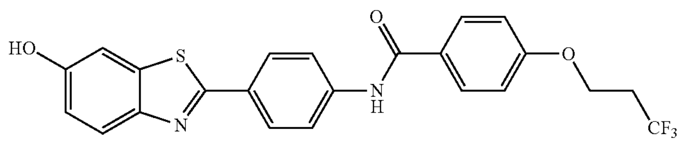 [SMILES: O=C(Nc1ccc(-c2nc3ccc(O)cc3s2)cc1)c1ccc(OCCC(F)(F)F)cc1] |
| ABFHA-05 | SKT02-171 | 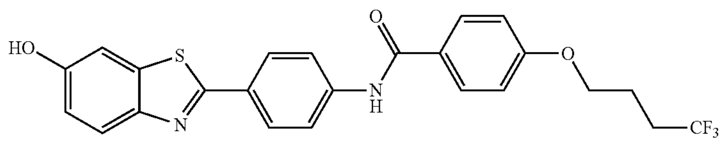 [SMILES: O=C(Nc1ccc(-c2nc3ccc(O)cc3s2)cc1)c1ccc(OCCCC(F)(F)F)cc1] |
| ABFHA-06 | SKT05-39 | 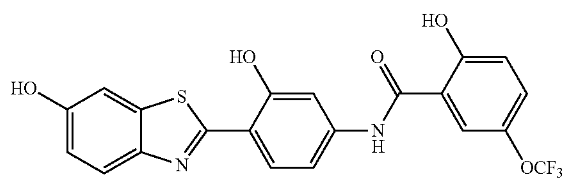 [SMILES: O=C(Nc1ccc(-c2nc3ccc(O)cc3s2)c(O)c1)c1cc(OC(F)(F)F)ccc1O] |
| ABFHA-07 | SKT02-163 | 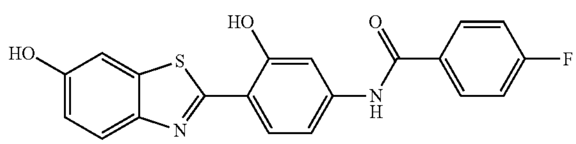 [SMILES: O=C(Nc1ccc(-c2nc3ccc(O)cc3s2)c(O)c1)c1ccc(F)cc1] |
| ABFHA-08 | SKT05-17 | 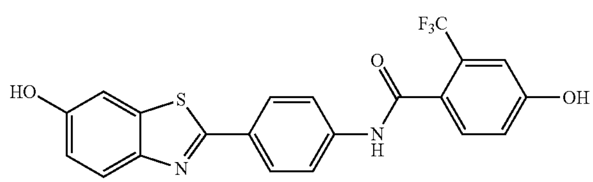 [SMILES: O=C(Nc1ccc(-c2nc3ccc(O)cc3s2)cc1)c1ccc(O)cc1C(F)(F)F] |
| ABFHA-09 | SKT05-13 | 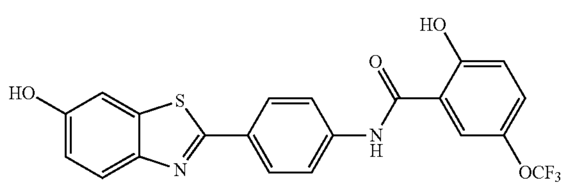 [SMILES: O=C(Nc1ccc(-c2nc3ccc(O)cc3s2)cc1)c1cc(OC(F)(F)F)ccc1O] |
| ABFHA-10 | SKT04-179 | 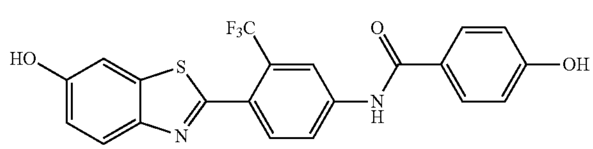 [SMILES: O=C(Nc1ccc(-c2nc3ccc(O)cc3s2)c(C(F)(F)F)c1)c1ccc(O)cc1] |
| ABFHA-11 | SKT03-129 | 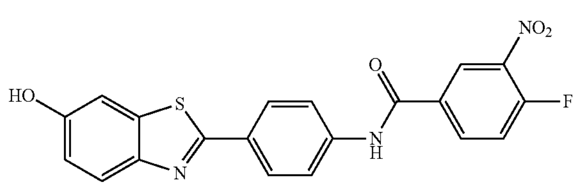 [SMILES: O=C(Nc1ccc(-c2nc3ccc(O)cc3s2)cc1)c1ccc(F)c([N+](=O)[O-])c1] |

In one embodiment, the compound is independently selected from:
ABFHA-01; ABFHA-02; ABFHA-03; ABFHA-05; ABFHA-06; ABFHA-07; ABFHA-08; ABFHA-09; ABFHA-10 and ABFHA-11.

In one embodiment, the compound is independently selected from:
ABFHA-01; ABFHA-02; ABFHA-03; ABFHA-05; ABFHA-06; ABFHA-08; ABFHA-09; ABFHA-10 and ABFHA-11.

Non-Fluorinated Methyl-Amides

| Code | Book No. | Structure |
|---|---|---|
| ABAA-01 | SK2033-51 | 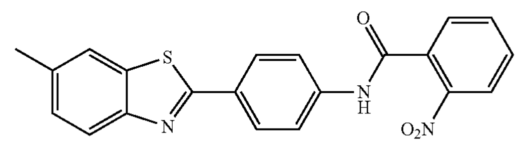 [SMILES: Cc1ccc2nc(-c3ccc(NC(=O)c4ccccc4[N+](=O)[O-])cc3)sc2c1] |
| ABAA-02 | SK2033-46 | 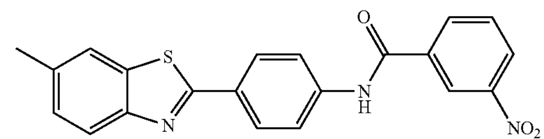 [SMILES: Cc1ccc2nc(-c3ccc(NC(=O)c4cccc([N+](=O)[O-])c4)cc3)sc2c1] |
| ABAA-03 | SK2033-67 | 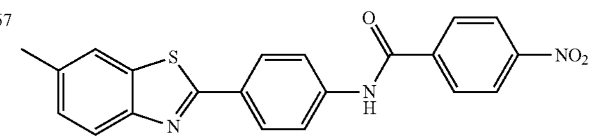 |
| ABAA-04 | SK2033-55 | 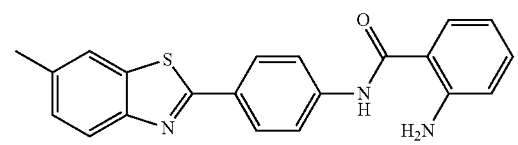 [SMILES: Cc1ccc2nc(-c3ccc(NC(=O)c4ccccc4N)cc3)sc2c1] |
| ABAA-05 | SK2033-72 | 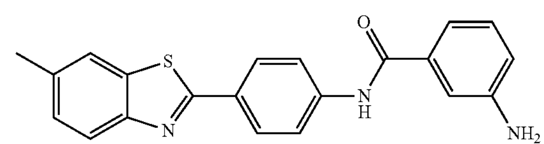 [SMILES: Cc1ccc2nc(-c3ccc(NC(=O)c4cccc(N)c4)cc3)sc2c1] |
| ABAA-06 | LS-T107 | 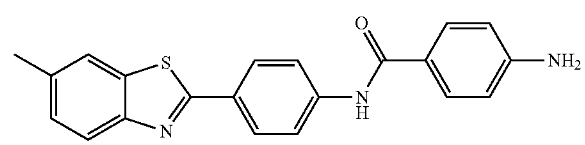 |
| ABAA-07 | SKT01-5 | 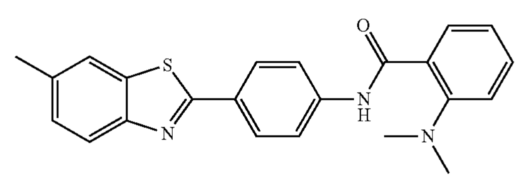 [SMILES: Cc1ccc2nc(-c3ccc(NC(=O)c4ccccc4N(C)C)cc3)sc2c1] |
| ABAA-08 | SK2033-93 | 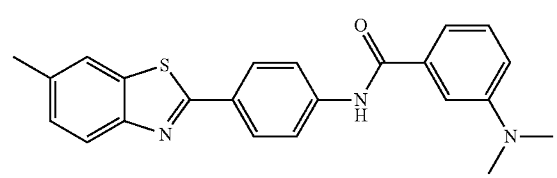 |
| ABAA-09 | SK2033-71 | 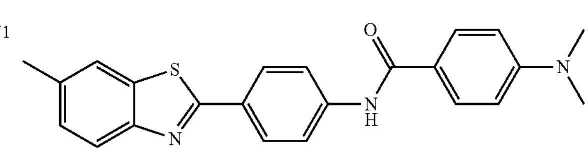 |

| Code | Book No. | Structure |
|---|---|---|
| ABAA-10 | SK696-32 | 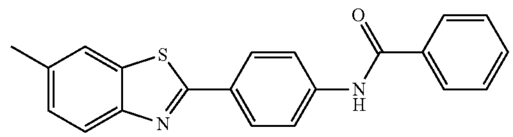 [SMILES: Cc1ccc2nc(-c3ccc(NC(=O)c4ccccc4)cc3)sc2c1] |
| ABAA-11 | SK696-54 | 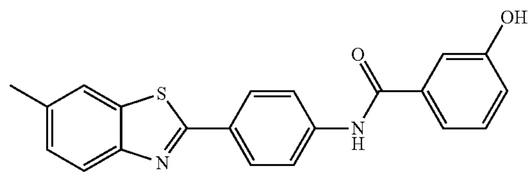 [SMILES: Cc1ccc2nc(-c3ccc(NC(=O)c4cccc(O)c4)cc3)sc2c1] |
| ABAA-12 | SK2033-94 | 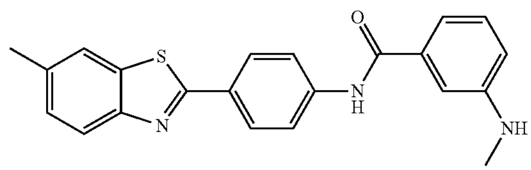 [SMILES: CNc1cccc(C(=O)Nc2ccc(-c3nc4ccc(C)cc4s3)cc2)c1] |

In one embodiment, the compound is independently selected from:
ABAA-01; ABAA-02; ABAA-03; ABAA-06; ABAA-09; ABAA-10 and ABAA-11.

In one embodiment, the compound is independently selected from:
ABAA-06; ABAA-10 and ABAA-11.

Dimethylamine-Amides

| Code | Book No. | Structure |
|---|---|---|
| ABDMAA-01 | SKT03-171 | 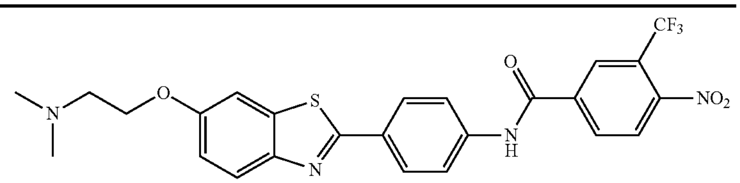 |
| ABDMAA-02 | SKT03-171.01 | 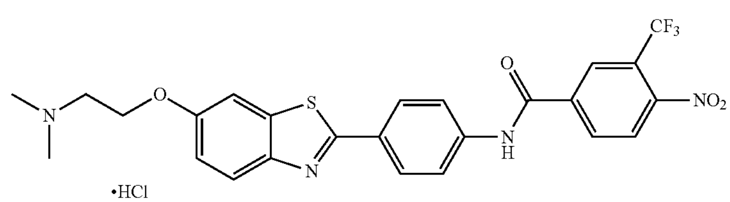 [SMILES: CN(C)CCOc1ccc2nc(-c3ccc(NC(=O)c4ccc([N+](=O)[O-])c(C(F)(F)F)c4)cc3)sc2c1 ; Cl] |

Unsubstituted-Amides

| Code | Book No. | Structure |
|---|---|---|
| AUB-01 | SKT04-127 | 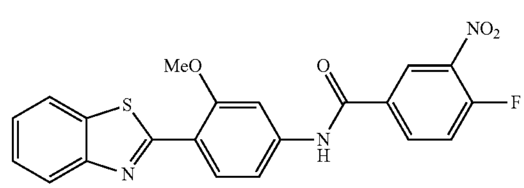 [SMILES: COc1cc(NC(=O)c2ccc(F)c([N+](=O)[O-])c2)ccc1-c1nc2ccccc2s1] |

| Code | Book No. | Structure |
|---|---|---|
| AUB-02 | SKT04-143 | 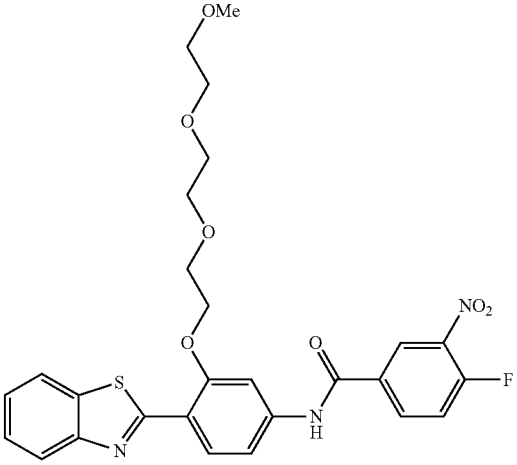 [SMILES: COCCOCCOCCOc1cc(NC(=O)c2ccc(F)c([N+](=O)[O-])c2)ccc1-c1nc2ccccc2s1] |
| AUB-03 | SKT04-163 | 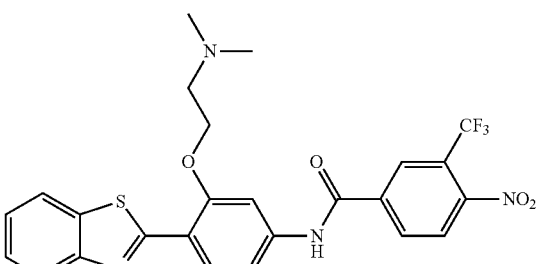 |
Imidazo[1,2-a]pyridine Compounds
| Code | Book No. | Structure |
|---|---|---|
| AIPN-01 | SKT05-123 | 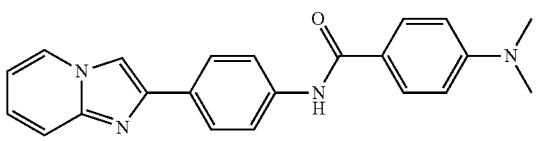 [SMILES: CN(C)c1ccc(C(=O)Nc2ccc(-c3cn4ccccc4n3)cc2)cc1] |
| AIPN-02 | SKT05-93 | 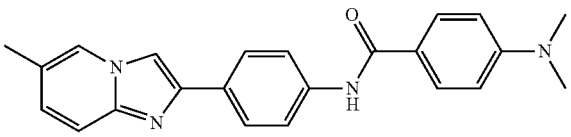 |
| AIPN-03 | SKT05-107 | 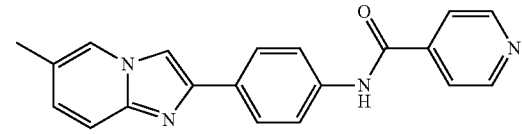 [SMILES: Cc1ccc2nc(-c3ccc(NC(=O)c4ccncc4)cc3)cn2c1] |
| AIPN-04 | SKT05-171 | 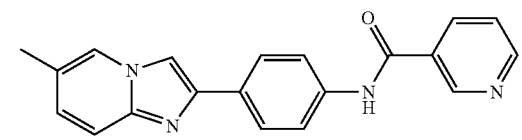 [SMILES: Cc1ccc2nc(-c3ccc(NC(=O)c4cccnc4)cc3)cn2c1] |

| Code | Book No. | Structure |
|---|---|---|
| AIPN-05 | SKT06-5 | 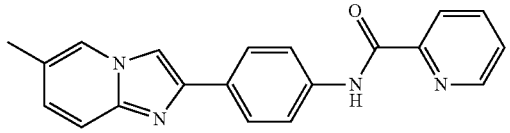 |
| AIPN-06 | SKT05-169 | 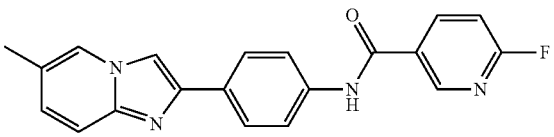 [SMILES: Cc1ccc2nc(-c3ccc(NC(=O)c4ccc(F)nc4)cc3)cn2c1] |
| AIPN-07 | SKT06-53 | 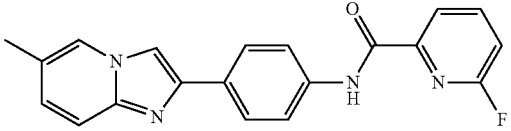 [SMILES: Cc1ccc2nc(-c3ccc(NC(=O)c4cccc(F)n4)cc3)cn2c1] |
| AIPN-08 | SKT06-63 | 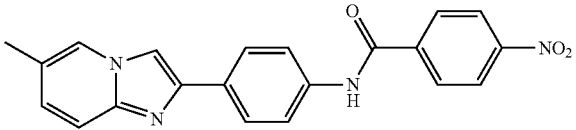 |
| AIPN-09 | SKT05-165 | 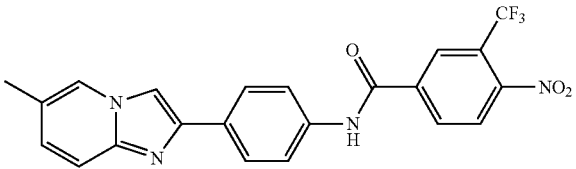 [SMILES: Cc1ccc2nc(-c3ccc(NC(=O)c4ccc([N+](=O)[O-])c(C(F)(F)F)c4)cc3)cn2c1] |
| AIPN-10 | SKT05-173 | 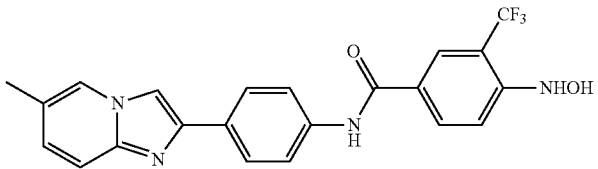 |
| AIPN-11 | SKT06-71 | 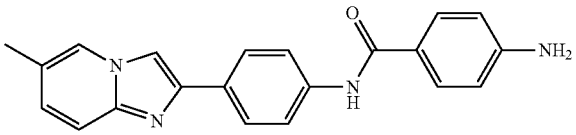 [SMILES: Cc1ccc2nc(-c3ccc(NC(=O)c4ccc(N)cc4)cc3)cn2c1] |
| AIPN-12 | SKT06-67 | 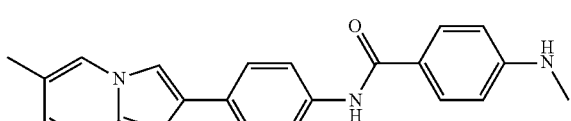 |
| AIPN-13 | SKT06-7 | 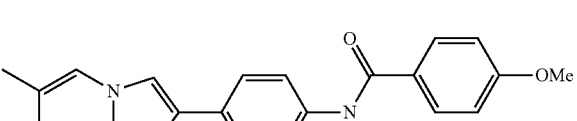 |
| AIPN-14 | SKT06-11 | 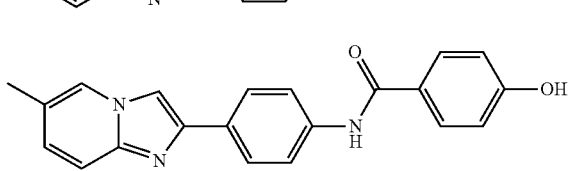 |

-continued
| Code | Book No. | Structure |
|------|----------|-----------|
| AIPN-15 | SKT06-25 | 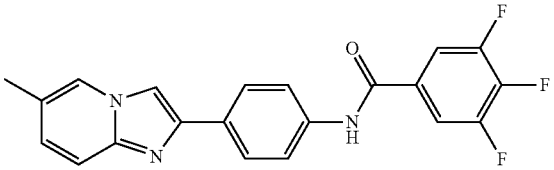 [SMILES: Cc1ccc2nc(-c3ccc(NC(=O)c4cc(F)c(F)c(F)c4)cc3)cn2c1] |
| AIPN-16 | SKT06-29 | 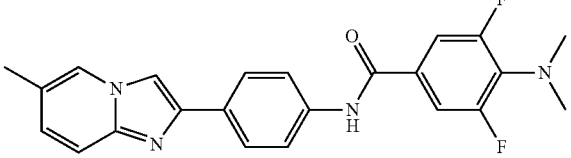 |
| AIPN-17 | SKT06-15 | 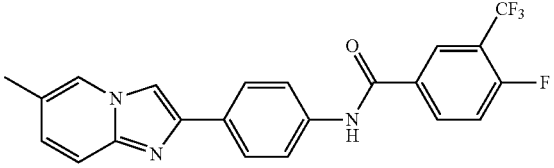 |
| AIPN-18 | SKT06-13 | 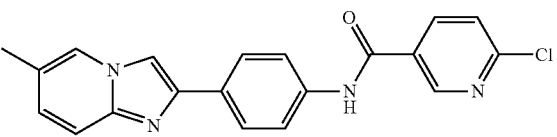 |
| AIPN-19 | SKT06-35 | 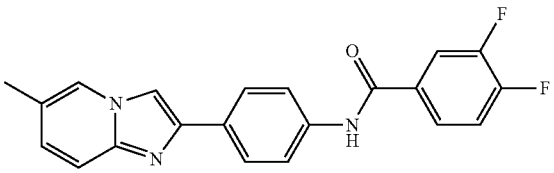 [SMILES: Cc1ccc2nc(-c3ccc(NC(=O)c4ccc(F)c(F)c4)cc3)cn2c1] |
| AIPN-20 | SKT06-55 | 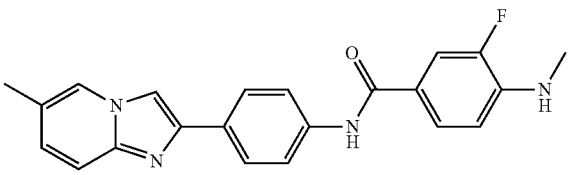 |
| AIPN-21 | SKT06-59 | 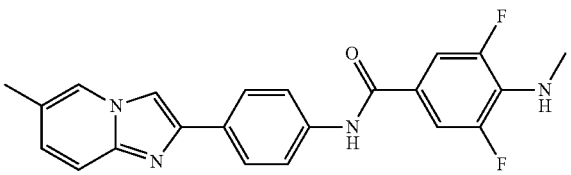 |
| AIPN-22 | SKT06-39 | 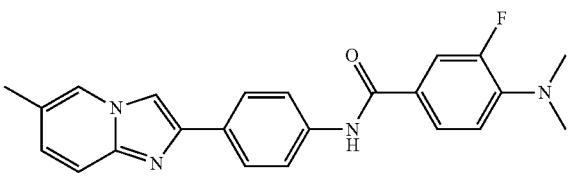 |
| AIPN-23 | SKT06-49 | 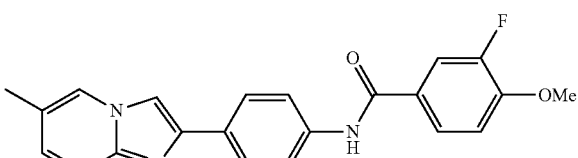 |

| Code | Book No. | Structure |
|---|---|---|
| AIPN-24 | SKT06-45 | (6-methylimidazo[1,2-a]pyridin-2-yl)phenyl-N-(3,5-difluoro-4-methoxybenzamide) |
| AIPN-25 | SKT06-79 | (6-methylimidazo[1,2-a]pyridin-2-yl)phenyl-N-(2,6-difluoro-4-methoxybenzamide) |
| AIPN-26 | SKT06-51 | (6-methylimidazo[1,2-a]pyridin-2-yl)phenyl-N-(3,5-difluoro-4-hydroxybenzamide) |
| AIPN-27 | SKT06-57 | (6-methylimidazo[1,2-a]pyridin-2-yl)phenyl-N-(3-fluoro-4-hydroxybenzamide) |
| AIPN-28 | SKT06-61 | (6-methylimidazo[1,2-a]pyridin-2-yl)phenyl-N-(3-trifluoromethyl-4-methoxybenzamide) |
| AIPN-29 | SKT06-103 | (6-methylimidazo[1,2-a]pyridin-2-yl)phenyl-N-(2-fluoro-4-hydroxybenzamide) |
| AIPN-30 | SKT06-99 | (6-methylimidazo[1,2-a]pyridin-2-yl)phenyl-N-(3-trifluoromethyl-4-methylaminobenzamide) |
| AIPN-31 | SKT06-81 | (6-methylimidazo[1,2-a]pyridin-2-yl)phenyl-N-(2-fluoro-4-methoxybenzamide) |

In one embodiment, the compound is independently selected from:
AIPN-01; AIPN-02; AIPN-05; AIPN-07; AIPN-08; AIPN-09; AIPN-10; AIPN-11; AIPN-12; AIPN-13; AIPN-14; AIPN-15; AIPN-16; AIPN-18; AIPN-19; AIPN-20; AIPN-21; AIPN-22; AIPN-23; AIPN-24; AIPN-25; AIPN-26; AIPN-27; AIPN-28; AIPN-29; AIPN-30; and AIPN-31.

In one embodiment, the compound is independently selected from:
AIPN-01; AIPN-02; AIPN-05; AIPN-07; AIPN-08; AIPN-09; AIPN-10; AIPN-11; AIPN-12; AIPN-13; AIPN-14; AIPN-16; AIPN-18; AIPN-20; AIPN-21; AIPN-22; AIPN-23; AIPN-24; AIPN-25; AIPN-26; AIPN-27; AIPN-28; AIPN-29; AIPN-30; and AIPN-31.

Additionally or alternatively, the imidazo[1,2-a]pyridine compound is independently selected from:

| Code | Book No. | Structure |
|---|---|---|
| AIPN-32 | SKT08-153 | 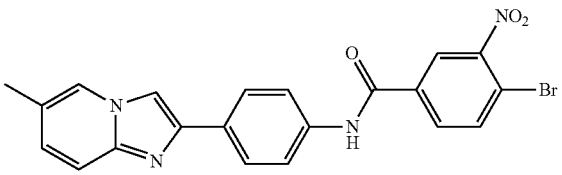 [SMILES: Cc1ccc2nc(-c3ccc(NC(=O)c4ccc(Br)c([N+](=O)[O-])c4)cc3)cn2c1] |
| AIPN-33 | SKT08-165 | 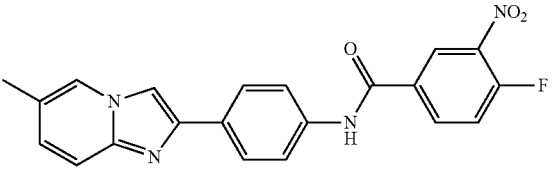 |
| AIPN-34 | SKT06-155 | 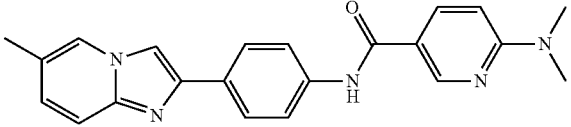 |
| AIPN-35 | SKT06-153 | 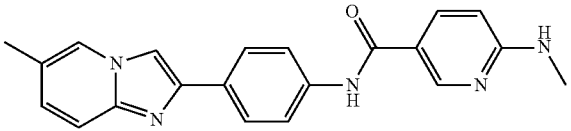 |
| AIPN-36 | SKT06-141 | 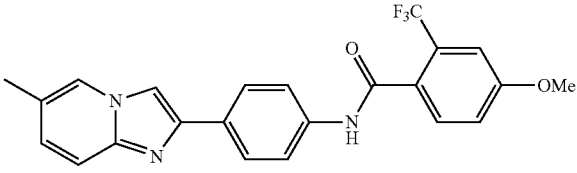 [SMILES: COc1ccc(C(=O)Nc2ccc(-c3cn4cc(C)ccc4n3)cc2)c(C(F)(F)F)c1] |
| AIPN-37 | SKT06-137 | 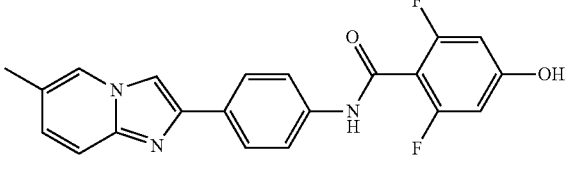 |
| AIPN-38 | SKT06-131 | 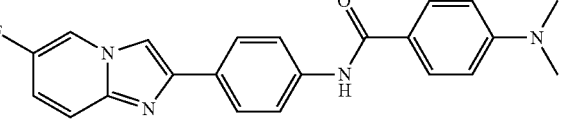 |
| AIPN-39 | SKT06-165 | 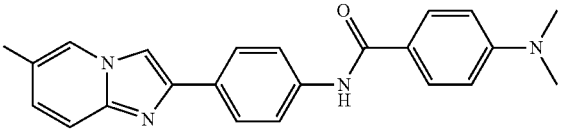 |

In one embodiment, the compound is independently additionally or alternatively selected from AIPN-38 and AIPN-39.

Imidazo[1,2-a]pyrimidine Compounds

| Code | Book No. | Structure |
|---|---|---|
| AIPM-01 | SKT05-95 | 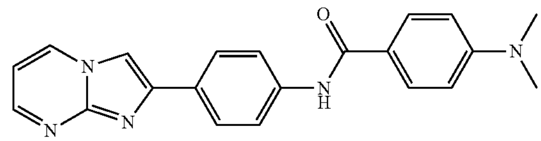 [SMILES: CN(C)c1ccc(C(=O)Nc2ccc(-c3cn4cccnc4n3)cc2)cc1] |

Imidazo[2,1-b][1,3]thiazole Compounds

| Code | Book No. | Structure |
|---|---|---|
| AIT-01 | SKT05-149 | 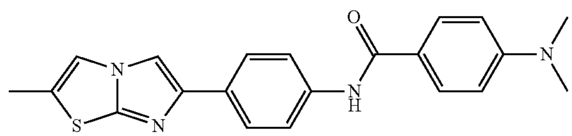 |
| AIT-02 | SKT05-143 | 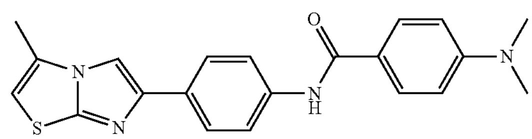 [SMILES: Cc1csc2nc(-c3ccc(NC(=O)c4ccc(N(C)C)cc4)cc3)cn12] |

Compounds where -Q- is —CH=CH—; —CR$^1$=CH—; —CH=CR$^1$—; or —CR$^1$=CR$^1$—

Benzothiazole Compounds

Non-Fluorinated Methyl-Alkenes

| Code | Book No. | Structure |
|---|---|---|
| BEMA-01 | SK696-39 | 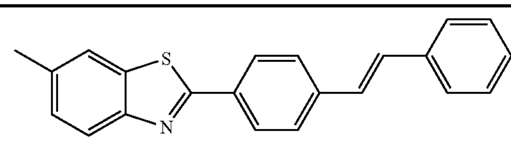 |
| BEMA-02 | SKT01-15 | 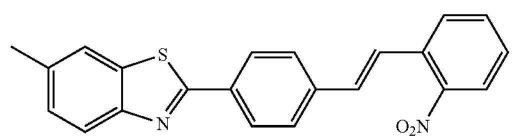 |
| BEMA-03 | SKT01-53 | 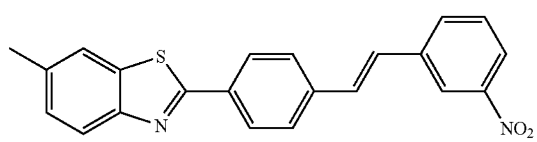 [SMILES: Cc1ccc2nc(-c3ccc(/C=C/c4cccc([N+](=O)[O-])c4)cc3)sc2c1] |
| BEMA-04 | SKT01-3 | 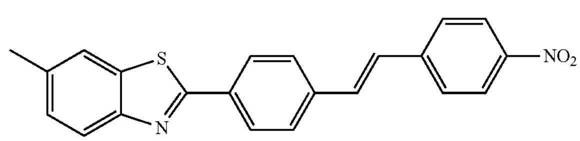 [SMILES: Cc1ccc2nc(-c3ccc(/C=C/c4ccc([N+](=O)[O-])cc4)cc3)sc2c1] |
| BEMA-05 | SKT01-55 | 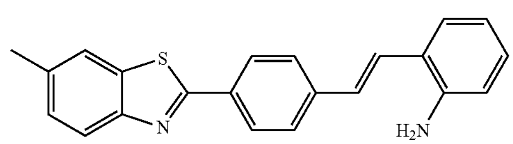 |

-continued

| Code | Book No. | Structure |
|---|---|---|
| BEMA-06 | SKT01-69 | (structure: 6-methylbenzothiazole-phenyl-CH=CH-phenyl-3-NH₂) |
| BEMA-07 | SKT01-17 | (structure: 6-methylbenzothiazole-phenyl-CH=CH-phenyl-4-NH₂) |
| BEMA-08 | SK2033-30 | (structure: 6-methylbenzothiazole-phenyl-CH=CH-phenyl-4-N(Me)₂) |
| BEMA-09 | SK696-62 | (structure: 6-methylbenzothiazole-phenyl-CH=CH-phenyl-2-OH) |
| BEMA-10 | SK696-57 | (structure: 6-methylbenzothiazole-phenyl-CH=CH-phenyl-3-OH) |
| BEMA-11 | SK696-43 | (structure: 6-methylbenzothiazole-phenyl-CH=CH-phenyl-4-OH) |
| BEMA-12 | SK2033-29 | (structure: 6-methylbenzothiazole-phenyl-CH=CH-phenyl-3-OMe) |

In one embodiment, the compound is independently selected from:
BEMA-02; BEMA-03; BEMA-04; BEMA-07 and BEMA-10.

In one embodiment, the compound is independently BEMA-10.

Non-Fluorinated Methoxy-Alkenes

| Code | Book No. | Structure |
|---|---|---|
| BEMOA-01 | SKT01-71 | (structure: 6-methoxybenzothiazole-phenyl-CH=CH-phenyl-2-NO₂) |
| BEMOA-02 | SKT01-73 | (structure: 6-methoxybenzothiazole-phenyl-CH=CH-phenyl-3-NO₂) |

-continued

| Code | Book No. | Structure |
|---|---|---|
| BEMOA-03 | SKT02-67 | MeO-benzothiazole-C6H4-CH=CH-C6H4-NO2 |
| BEMOA-04 | SKT01-109 | MeO-benzothiazole-C6H4-CH=CH-C6H4(o-NH2) |
| BEMOA-05 | SKT01-107 | MeO-benzothiazole-C6H4-CH=CH-C6H4(m-NH2) |
| BEMOA-06 | SKT01-189 | MeO-benzothiazole-C6H4-CH=CH-C6H4-NH2 |
| BEMOA-07 | SKT03-57 | MeO-benzothiazole-C6H4-CH=CH-C6H4-N(Me)2 |
| BEMOA-08 | SKT03-91 | MeO-benzothiazole-C6H4-CH=CH-C6H3(NO2)(Cl) |
| BEMOA-09 | SKT03-107 | MeO-benzothiazole-C6H4-CH=CH-C6H3(NO2)(OH) |

In one embodiment, the compound is independently selected from:
  BEMOA-01; BEMOA-02; BEMOA-03; BEMOA-04; BEMOA-05; BEMOA-07 and BEMOA-08.

In one embodiment, the compound is independently selected from BEMOA-03 and BEMOA-05.

Additionally or alternatively, the non-fluorinated methoxy-alkene compound is independently selected from:

| Code | Book No. | Structure |
|---|---|---|
| BEMOA-10 | SKT08-143 | MeO-benzothiazole-C6H4-CH=CH-C6H4-O-CH2CH2-OH |

Fluorinated Methoxy-Alkenes

| Code | Book No. | Structure |
|------|----------|-----------|
| BEFA-01 | SK2033-44 | 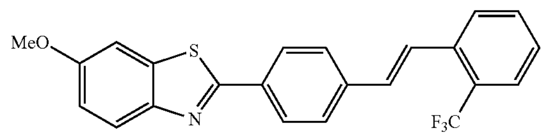 [SMILES: COc1ccc2nc(-c3ccc(/C=C/c4ccccc4C(F)(F)F)cc3)sc2c1] |
| BEFA-02 | SK2033-42 | 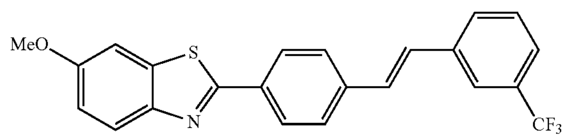 |
| BEFA-03 | SK2033-40 | 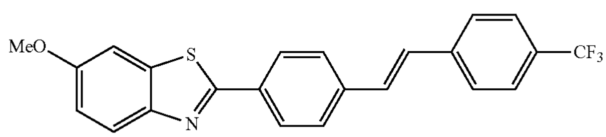 [SMILES: COc1ccc2nc(-c3ccc(/C=C/c4ccc(C(F)(F)F)cc4)cc3)sc2c1] |
| BEFA-04 | SKT02-17 | 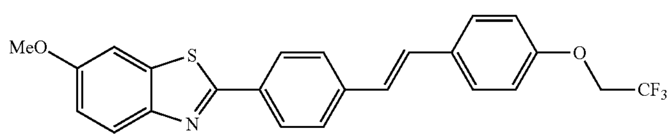 [SMILES: COc1ccc2nc(-c3ccc(/C=C/c4ccc(OCC(F)(F)F)cc4)cc3)sc2c1] |
| BEFA-05 | SKT02-11 | 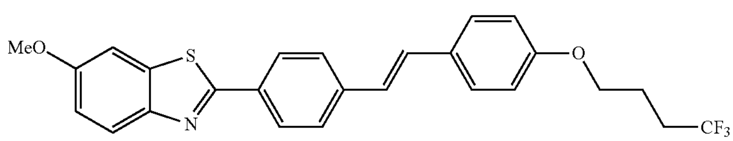 [SMILES: COc1ccc2nc(-c3ccc(/C=C/c4ccc(OCCCC(F)(F)F)cc4)cc3)sc2c1] |
| BEFA-06 | SKT02-117 | 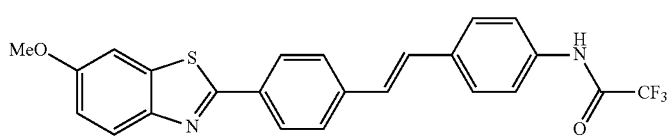 [SMILES: COc1ccc2nc(-c3ccc(/C=C/c4ccc(NC(=O)C(F)(F)F)cc4)cc3)sc2c1] |
| BEFA-07 | SKT02-153 | 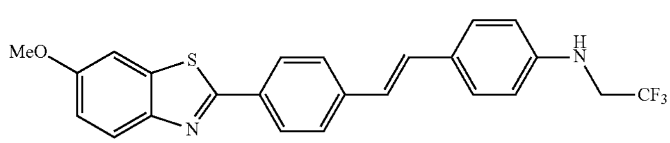 [SMILES: COc1ccc2nc(-c3ccc(/C=C/c4ccc(NCC(F)(F)F)cc4)cc3)sc2c1] |
| BEFA-08 | SKT02-119 | 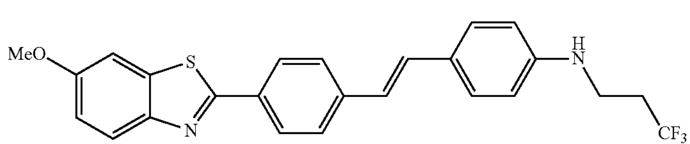 [SMILES: COc1ccc2nc(-c3ccc(/C=C/c4ccc(NCCC(F)(F)F)cc4)cc3)sc2c1] |
| BEFA-09 | SKT02-81 | 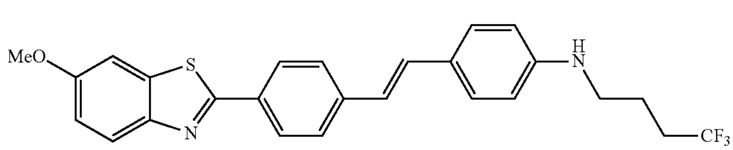 [SMILES: COc1ccc2nc(-c3ccc(/C=C/c4ccc(NCCCC(F)(F)F)cc4)cc3)sc2c1] |
| BEFA-10 | SKT02-137 | 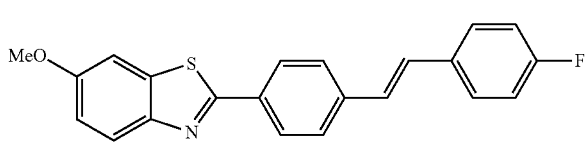 [SMILES: COc1ccc2nc(-c3ccc(/C=C/c4ccc(F)cc4)cc3)sc2c1] |

-continued

| Code | Book No. | Structure |
|---|---|---|
| BEFA-11 | SKT03-167 | 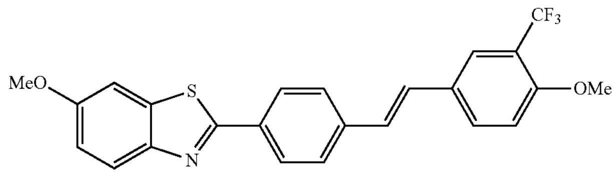 [SMILES: COc1ccc2nc(-c3ccc(/C=C/c4ccc(OC)c(C(F)(F)F)c4)cc3)sc2c1] |
| BEFA-12 | SKT03-77 | 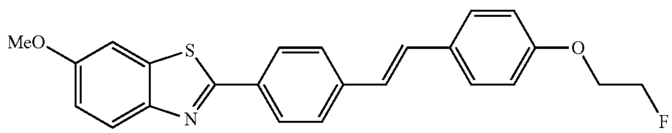 [SMILES: COc1ccc2nc(-c3ccc(/C=C/c4ccc(OCCF)cc4)cc3)sc2c1] |
| BEFA-13 | SKT04-187 | 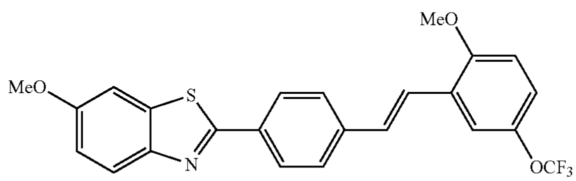 [SMILES: COc1ccc2nc(-c3ccc(/C=C/c4cc(OC(F)(F)F)ccc4OC)cc3)sc2c1] |
| BEFA-14 | SKT04-159 | 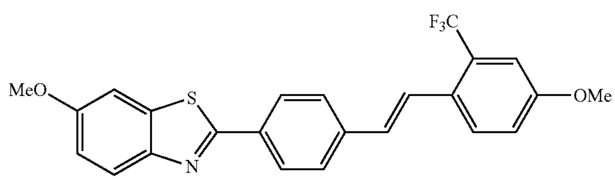 [SMILES: COc1ccc(/C=C/c2ccc(-c3nc4ccc(OC)cc4s3)cc2)c(C(F)(F)F)c1] |

In one embodiment, the compound is independently selected from:
BEFA-05; BEFA-06; BEFA-07; BEFA-08; BEFA-10; BEFA-11; BEFA-13; and BEFA-14.

In one embodiment, the compound is independently selected from:
BEFA-06; and BEFA-10.

Monofluoro and Fluorinated Hydroxy-Alkenes

| Code | Book No. | Structure |
|---|---|---|
| BEHF-01 | SKT02-165 | 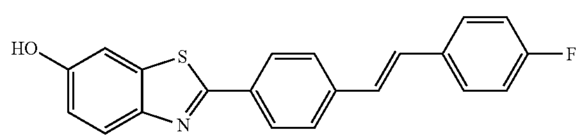 [SMILES: Oc1ccc2nc(-c3ccc(/C=C/c4ccc(F)cc4)cc3)sc2c1] |
| BEHF-02 | SKT02-155 | 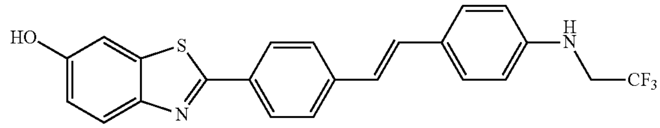 [SMILES: Oc1ccc2nc(-c3ccc(/C=C/c4ccc(NCC(F)(F)F)cc4)cc3)sc2c1] |
| BEHF-03 | SKT02-127 | 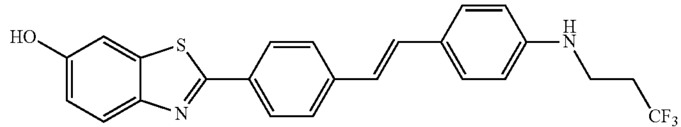 [SMILES: Oc1ccc2nc(-c3ccc(/C=C/c4ccc(NCCC(F)(F)F)cc4)cc3)sc2c1] |
| BEHF-04 | SKT02-111 | 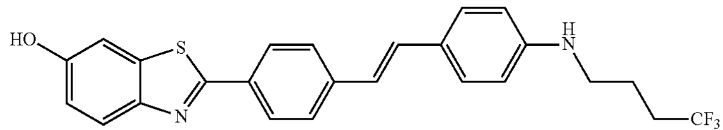 [SMILES: Oc1ccc2nc(-c3ccc(/C=C/c4ccc(NCCCC(F)(F)F)cc4)cc3)sc2c1] |

| Code | Book No. | Structure |
|---|---|---|
| BEHF-05 | SKT02-51 | 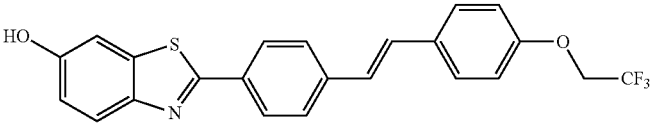 [SMILES: Oc1ccc2nc(-c3ccc(/C=C/c4ccc(OCC(F)(F)F)cc4)cc3)sc2c1] |
| BEHF-06 | SKT05-05 | 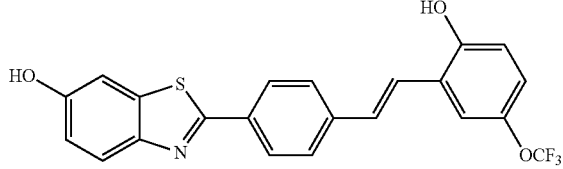 [SMILES: Oc1ccc2nc(-c3ccc(/C=C/c4cc(OC(F)(F)F)ccc4O)cc3)sc2c1] |
| BEHF-07 | SKT04-169 | 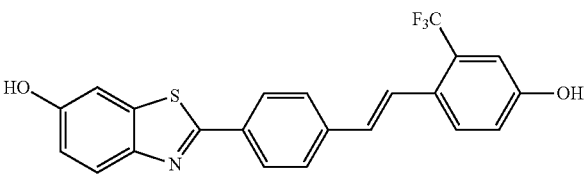 [SMILES: Oc1ccc(/C=C/c2ccc(-c3nc4ccc(O)cc4s3)cc2)c(C(F)(F)F)c1] |

In one embodiment, the compound is independently selected from:
BEHF-01; BEHF-02; BEHF-03; BEHF-05; BEHF-06 and BEHF-07.

In one embodiment, the compound is independently selected from:
BEHF-01; BEHF-02; BEHF-06 and BEHF-07.

Imidazo[1,2-a]pyridine Compounds

| Code | Book No. | Structure |
|---|---|---|
| IEPN-01 | SKT06-117 | 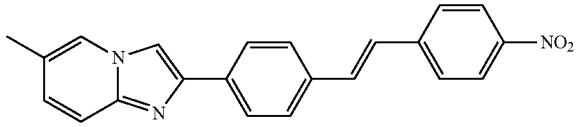 [SMILES: Cc1ccc2nc(-c3ccc(/C=C/c4ccc([N+](=O)[O-])cc4)cc3)cn2c1] |

Additionally or alternatively, the imidazo[1,2-a]pyridine compound is selected from:

| Code | Book No. | Structure |
|---|---|---|
| IEPN-02 | SKT06-161 | 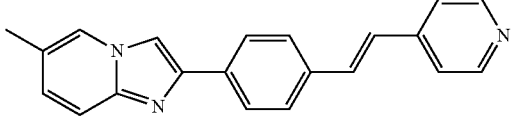 |
| IEPN-03 | SKT07-81 | 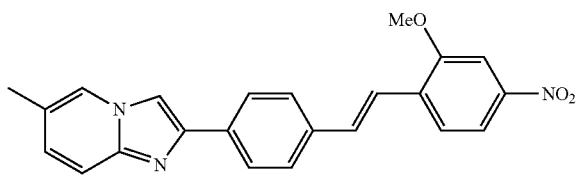 [SMILES: COc1cc([N+](=O)[O-])ccc1/C=C/c1ccc(-c2cn3cc(C)ccc3n2)cc1] |

-continued
| Code | Book No. | Structure |
|---|---|---|
| IEPN-04 | SKT07-115 | 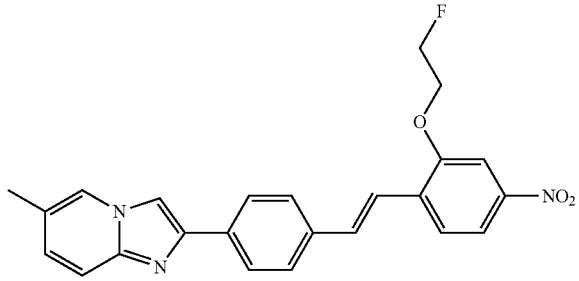 [SMILES: Cc1ccc2nc(-c3ccc(/C=C/c4ccc([N+](=O)[O-])cc4OCCF)cc3)cn2c1] |
| IEPN-05 | SKT07-131 | 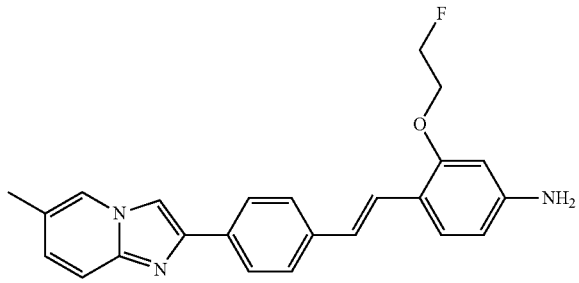 |
| IEPN-06 | SKT07-113 | 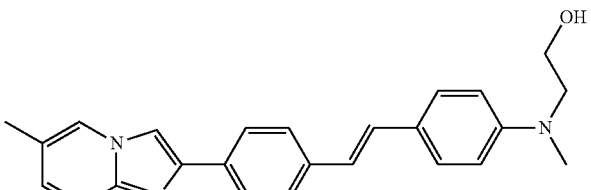 |
| IEPN-07 | SKT08-137 | 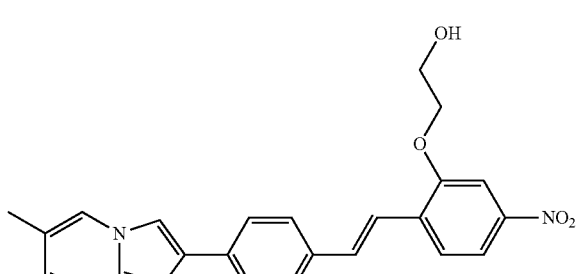 |
Compounds where -Q- is —N═N—
Benzothiazole Compounds
| Code | Book No. | Structure |
|---|---|---|
| BDF-01 | LS-T192 | 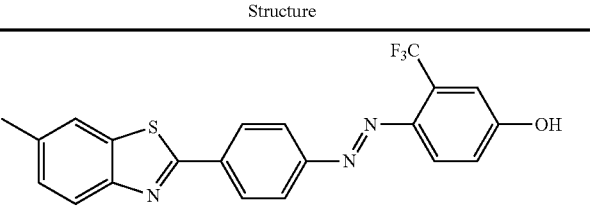 |
| BDF-02 | LS-T191 | 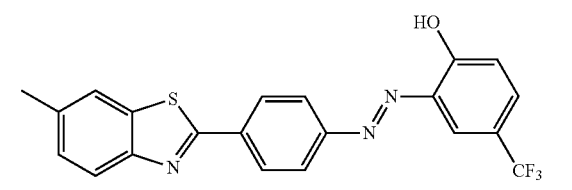 [SMILES: Cc1ccc2nc(-c3ccc(/N=N/c4cc(C(F)(F)F)ccc4O)cc3)sc2c1] |

-continued

| Code | Book No. | Structure |
|---|---|---|
| BDF-03 | LS-T209 | 6-MeO-benzothiazol-2-yl–C6H4–N=N–C6H3(2-CF3)(4-OH) |
| BDF-04 | LS-T213 | 6-HO-benzothiazol-2-yl–C6H4–N=N–C6H3(2-CF3)(4-OH) |
| BDF-05 | LS-T245 | 5-HO-benzothiazol-2-yl–C6H4–N=N–C6H3(2-CF3)(4-OH) |
| BDF-06 | LS-T256 | 6-(Me2N)-benzothiazol-2-yl–C6H4–N=N–C6H3(2-CF3)(4-OH) |
| BDF-07 | LS-T210 | 6-(F3CO)-benzothiazol-2-yl–C6H4–N=N–C6H4–OH |
| BDF-08 | LS-T214 | 6-Me-benzothiazol-2-yl–C6H4–N=N–C6H2(2,6-(CF3)2)(4-OH) |
| BDF-09 | LS-T229 | 5-(F3CO)-benzothiazol-2-yl–C6H4–N=N–C6H4–OH |
| BDF-10 | LS-T235A | 5-MeO-benzothiazol-2-yl–C6H4–N=N–C6H3(2-OH)(4-CF3) |
| BDF-11 | LS-T235B | 5-MeO-benzothiazol-2-yl–C6H4–N=N–C6H3(2-CF3)(4-OH) |

-continued

| Code | Book No. | Structure |
|---|---|---|
| BDF-12 | LS-T236A | 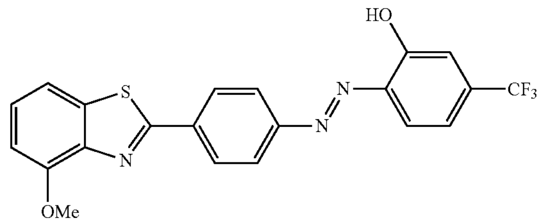 [SMILES: COc1cccc2sc(-c3ccc(/N=N/c4ccc(C(F)(F)F)cc4O)cc3)nc12] |
| BDF-13 | LS-T236B | 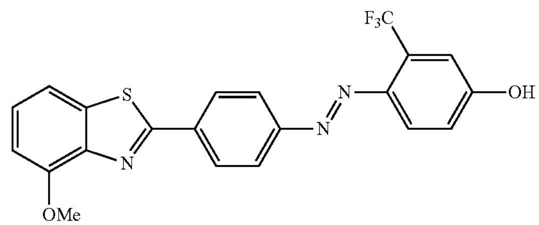 [SMILES: COc1cccc2sc(-c3ccc(/N=N/c4ccc(O)cc4C(F)(F)F)cc3)nc12] |
| BDF-14 | LS-T274 | 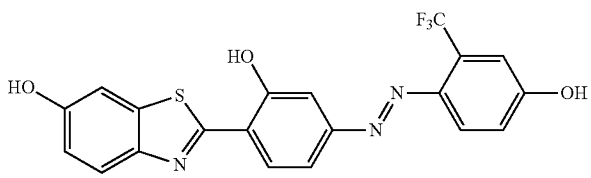 [SMILES: Oc1ccc(/N=N/c2ccc(-c3nc4ccc(O)cc4s3)c(O)c2)c(C(F)(F)F)c1] |
| BDF-15 | LS-T272 | 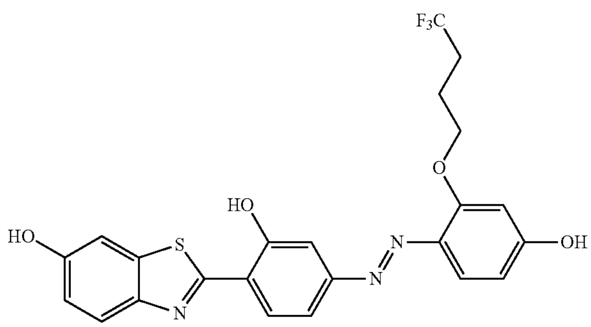 [SMILES: Oc1ccc(/N=N/c2ccc(-c3nc4ccc(O)cc4s3)c(O)c2)c(OCCCC(F)(F)F)c1] |
| BDF-16 | LS-T288 | 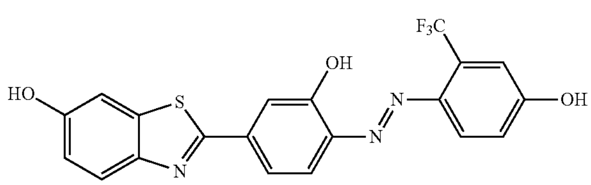 [SMILES: Oc1ccc(/N=N/c2ccc(-c3nc4ccc(O)cc4s3)cc2O)c(C(F)(F)F)c1] |
| BDF-17 | LS-T289 | 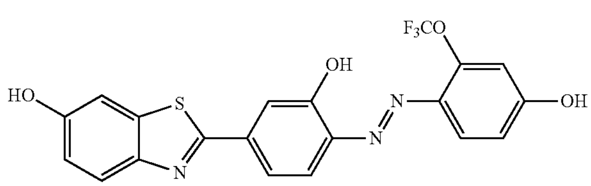 [SMILES: Oc1ccc(/N=N/c2ccc(-c3nc4ccc(O)cc4s3)cc2O)c(OC(F)(F)F)c1] |

In one embodiment, the compound is independently selected from:

BDF-01; BDF-02; BDF-03; BDF-04; BDF-05; BDF-06; BDF-07; BDF-10; BDF-11; BDF-12; BDF-13; BDF-14; BDF-15; BDF-16 and BDF-17.

Additionally or alternatively, the benzothiazole compound is independently selected from:

| Code | Book No. | Structure |
|------|----------|-----------|
| BDF-18 | SC598 | MeO-benzothiazole-C6H4-N=N-C6H4-O-CH2CH2-F |
| BDF-19 | SC588 | MeO-benzothiazole-C6H4-N=N-C6H4-O-CH2CH2-OH |

Imidazo[1,2-a]pyridine Compounds

| Code | Book No. | Structure |
|------|----------|-----------|
| DPN-001 | SKT05-163 | methyl-imidazo[1,2-a]pyridine-C6H4-N=N-C6H4-N(CH3)2 |

Substantially Purified Forms

One aspect of the present invention pertains to DSB compounds, as described herein, in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to a equimolar mixture of enantiomers (i.e., a racemic mixture, a racemate). In one embodiment, the substantially purified form refers to one enantiomer, e.g., optically pure enantiomer.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the substantially purified form is at least 60% optically pure (i.e., 60% of the compound, on a molar basis, is the desired stereoisomer or enantiomer, and 40% is the undesired stereoisomer or enantiomer), e.g., at least 70% optically pure, e.g., at least 80% optically pure, e.g., at least 90% optically pure, e.g., at least 95% optically pure, e.g., at least 97% optically pure, e.g., at least 98% optically pure, e.g., at least 99% optically pure.

Isomers

Certain compounds may exist in one or more particular geometric, optical, enantiomeric, diastereomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

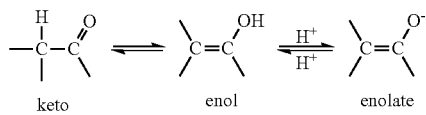

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like. Also F may be in any isotopic form, including $^{18}F$ and $^{19}F$.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Unless indicated to the contrary, the groups —N=N—, —CH=CH—; —CR$^1$=CH—; —CH=CR$^1$—; and —CR$^1$=CR$^1$— may be cis or trans.

In one embodiment, the group —N=N—, where present, may be cis or trans.

In one embodiment, the group —N=N—, where present, is cis.

In one embodiment, the group —N=N—, where present is trans.

For example:

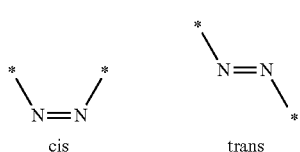

where the asterisks indicate the points of attachment

In one embodiment, the groups —CH=CH—; —CR$^1$=CH—; —CH=CR$^1$—; and —CR$^1$=CR$^1$—, where present, may be cis or trans.

In one embodiment, the group —CH=CH—; —CR$^1$=CH—; —CH=CR$^1$—; and —CR$^1$=CR$^1$—, where present, is cis.

In one embodiment, the group —CH=CH—; —CR$^1$=CH—; —CH=CR$^1$—; and —CR$^1$=CR$^1$—, where present is trans.

For example,

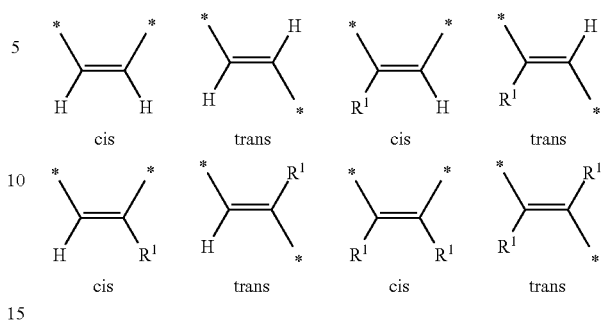

where the asterisks indicate the points of attachment.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," J. Pharm. Sci., Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

In one embodiment, the salt is independently selected from the following acids: hydrochloric and methanesulfonic.

Unless otherwise specified, a reference to a particular compound also includes salt forms thereof.

Solvates and Hydrates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999).

A wide variety of such "protecting," "blocking," or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH-Psec); or, in suitable cases (e.g., cyclic amines), as a nitroxide radical (>N—O.).

For example, a carboxylic acid group may be protected as an ester for example, as: an C$_{1-7}$alkyl ester (e.g., a methyl ester; a t-butyl ester); a C$_{1-7}$haloalkyl ester (e.g., a C$_{1-7}$trihaloalkyl ester); a triC$_{1-7}$alkylsilyl-C$_{1-7}$alkyl ester; or a C$_{5-20}$aryl-C$_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

Proform

It may be convenient or desirable to prepare, purify, and/or handle the compound in the form of a proform. The term "proform," as used herein, pertains to a compound which, when metabolised (e.g., in vivo), yields the desired active compound. Typically, the proform is inactive, or less active than the desired active compound, but may provide advantageous handling, administration, or metabolic properties.

For example, some proforms are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some proforms are activated enzymatically to yield the active compound, or a compound which, upon further chemical reaction, yields the active compound (for example, as in ADEPT, GDEPT, LIDEPT, etc.). For example, the proform may be a sugar derivative or other glycoside conjugate, or may be an amino acid ester derivative.

Compositions

One aspect of the present invention pertains to a composition (e.g., a diagnostic composition) comprising a DSB compound, as described herein, and a physiologically acceptable carrier, diluent, or excipient.

Another aspect of the present invention pertains to a method of preparing a composition (e.g., a diagnostic composition) comprising admixing a DSB compound, as described herein, and a physiologically acceptable carrier, diluent, or excipient.

Pharmaceutical and Diagnostic Compositions

Another aspect of the invention pertains to a pharmaceutical or diagnostic composition comprising a DSB compound as described herein.

Another aspect of the invention pertains to a pharmaceutical or diagnostic composition comprising a DSB compound as described herein, and a physiologically acceptable carrier, diluent, or excipient.

Another aspect of the invention pertains to a method of preparing a pharmaceutical or diagnostic composition comprising admixing a DSB compound as described herein and a physiologically acceptable carrier, diluent, or excipient.

Examples of suitable physiologically acceptable carriers, diluents, and excipients are the pharmaceutically acceptable ones described below.

Uses

The compounds described herein (e.g., without a proviso) are useful, for example, in methods and models relating to the labelling and detection of neurofibrillary tangles, and in particular paired helical filaments.

Methods of Labelling PHF and Aggregated Tau

In one aspect, the present invention provides a method of labelling PHF, comprising contacting the PHF with a DSB compound and detecting the presence of said compound. Methods of use may be performed e.g. by analogy to the use of the ligands described previously (see, for example, Mena et al., (1995); Mena et al. (1996); Lai, R. et al.; Bondareff, W. et al.; Resch, J. F. et al.; Novak, M. et al.; Wischik, C. W. et al., (1996); and Wischik C. W. et al. (1989)).

In one aspect, the present invention thus provides a method of labelling aggregated tau or tau-like molecules, comprising contacting the aggregated tau molecules with a DSB compound and detecting the presence of said compound. Methods of use may be performed e.g. by analogy to the use of the ligands described previously (see, for example, Mena et al. (1995); Mena et al. (1996); Lai, R. et al.; Bondareff, W. et al.; Resch, J. F. et al.; Novak, M. et al.; Wischik, C. W. et al. (1996); and Wischik C. W. et al. (1989)).

Where used herein, the term "tau protein" refers generally to any protein of the tau protein family. Tau proteins are characterised as being one among a larger number of protein families which co-purify with microtubules during repeated cycles of assembly and disassembly (Shelanski et al. (1973) Proc. Natl. Acad. Sci. USA, 70., 765-768), and are known as microtubule-associated-proteins (MAPs). Members of the tau family share the common features of having a characteristic N-terminal segment, sequences of approximately 50 amino acids inserted in the N-terminal segment, which are developmentally regulated in the brain, a characteristic tandem repeat region consisting of 3 or 4 tandem repeats of 31-32 amino acids, and a C-terminal tail See, for example, Wischik, et al. (2001) and loc. cit.).

"Tau like" molecules include, for instance, MAP2, which is the predominant microtubule-associated protein in the somatodendritic compartment (Matus, A., in "*Microtubules*" [Hyams and Lloyd, eds.] pp 155-166, John Wiley and Sons, NY). MAP2 isoforms are almost identical to tau protein in the tandem repeat region, but differ substantially both in the sequence and extent of the N-terminal domain (Kindler and Garner (1994) Mol. Brain. Res. 26, 218-224). Nevertheless, aggregation in the tandem-repeat region is not selective for the tau repeat domain. Thus it will be appreciated that any discussion herein in relation to tau protein or tau-tau aggregation should be taken as relating also to tau-MAP2 aggregation, MAP2-MAP2 aggregation and so on.

The DSB compound may be conjugated, chelated, or otherwise associated with, a further group or entity which has a diagnostic, prognostic or therapeutic purpose or effect, e.g. to a fluorescent group which thus enables visualisation of neurofibrillary tangles to which the ligand binds.

Diagnostic Ligands

The DSB compounds are capable of acting as ligands or labels of tau protein (or aggregated tau protein). In particular the DSB compounds will have utility in methods of medical imaging.

There are various methods by which aggregated tau can be visualised in vivo. These include the use of ligands where the DSB incorporates $^{19}$F (MRI scans), $^{18}$F (Positron Emission Tomography (PET) scans) or a stable nitroxyl free radical (MRI and Proton-Electron Double Resonance Imaging (PEDRI) contrast agent). Also included is the use of ligands incorporating an I radioisotope (single photon emission computed tomography, SPECT).

Use of the agents described herein in any of these methods is embraced by the present invention.

Thus, in one embodiment, the DSB compound is a ligand of tau protein (or aggregated tau protein).

Such DSB compounds (ligands) may incorporate, be conjugated to, be chelated with, or otherwise be associated with, other chemical groups, such as stable and unstable detectable isotopes, radioisotopes, positron-emitting atoms, magnetic resonance labels, dyes, fluorescent markers, antigenic groups, therapeutic moieties, or any other moiety that may aid in a prognostic, diagnostic or therapeutic application.

For example, as noted above, in one embodiment, the DSB compound is as defined above, but with the additional limitation that the compound incorporates, is conjugated to, is chelated with, or is otherwise associated with one or more (e.g., 1, 2, 3, 4, etc.) isotopes, radioisotopes, positron-emitting atoms, magnetic resonance labels, dyes, fluorescent markers, antigenic groups, or therapeutic moieties.

In one embodiment, the DSB compound is a ligand as well as a label, e.g., a label for tau protein (or aggregated tau protein), and incorporates, is conjugated to, is chelated with, or is otherwise associated with, one or more (e.g., 1, 2, 3, 4, etc.) detectable labels.

For example, in one embodiment, the DSB compound is as defined above, but with the additional limitation that the compound incorporates, is conjugated to, is chelated with, or is otherwise associated with, one or more (e.g., 1, 2, 3, 4, etc.) detectable labels.

Labelled DSB compounds (e.g., when ligated to tau protein or aggregated tau protein) may be visualised or detected by any suitable means, and the skilled person will appreciate that any suitable detection means as is known in the art may be used.

For example, the DSB compound (ligand-label) may be suitably detected by incorporating a positron-emitting atom (e.g., $^{11}$C) (e.g., as a carbon atom of one or more alkyl group substituents, e.g., methyl group substituents) and detecting the compound using positron emission tomography (PET) as is known in the art.

Generally, radiotracers for use in PET studies must be synthesised and imaged within a time frame compatible with the half-life of the isotope, typically within two half-lives after the radioisotope is produced.

$^{18}$F has a 110 minute half life, which allows sufficient time for relatively complex synthetic manipulations and for biological studies. An additional advantage is that $^{18}$F has a low positron energy, and its maximum range (2.4 mm) allows for the sharpest imaging with high resolution PET. For these reasons, the F-containing DSB compounds described herein include those compounds where one or more F atoms, where present, is an $^{18}$F atom.

$^{18}$F may be introduced into a ligand using, for example, fluoride ion or [$^{18}$F]F$_2$. Fluoride ion is the more desirable of the two because it can be produced without added carrier. In principle, 100% of the isotope can be incorporated into the tracer. In contrast, the maximum radiochemical yield when [$^{18}$F]F$_2$ is used as a precursor is around 50%, because only one of the fluorine atoms in the fluorine molecule is labelled and typically only one atom of fluorine is incorporated.

A key requirement for successful radiofluorinations is how to maintain [$^{18}$F]fluoride solubility. [$^{18}$F]fluoride is initially available after production in an aqueous solution of potassium carbonate. The water is then removed as an azeotrope, usually with acetonitrile. However, the potassium ion possesses limited solubility in some reaction solvents. The addition of the aminopolyether Kryptofix 2.2.2 (K$_{222}$) improves potassium ion solubility and as a consequence greatly enhances nucleophilic radiofluorinations with [$^{18}$F]fluoride on both aliphatic and aromatic substrates.

As a final practical consideration, the labelled product can be separated from any unreacted material by HPLC. This is usually necessary to provide material of high specific activity.

In one aspect of the invention there is provided the use of the DSB compounds as in vivo imaging agents for PHF, and PHF tau protein.

The DSB compounds may be used in a method determining the stage of neurofibrillary degeneration associated with a tauopathy in a subject believed to suffer from the disease, which method comprises the steps of:
(i) introducing into the subject a DSB compounds capable of labelling aggregated paired helical filament (PHF) tau protein,
(ii) determining the presence and\or amount of DSB compound bound to extracellular aggregated PHF tau in the medial temporal lobe of the brain of the subject,
(iii) correlating the result of the determination made in (ii) with the extent of neurofibrillary degeneration in the subject.

The determination in step (ii) may be used to establish the density ligand binding.

The correlation in step (iii) may be made by reference to historical data.

The tauopathy may be Alzheimer Disease (AD).

The DSB compounds may be capable of crossing the blood brain barrier.

The determination of (ii) above is made based on extracellular aggregated tau. In general terms, for the purposes of the present invention, this may be determined from extracellular tangles.

It has previously been shown from histological studies that, during the course of aggregation, tau protein acquires binding sites for compounds such as thiazin red and thioflavin-S (see Mena et al. (1995) Mena et al. (1996)). The binding site can be shown to exist within the tangle itself, and not in extraneous proteins (Wischik C. W. et al., (1989)). Thus both intracellular and extracellular tangles are labelled to some extent by such ligands, as judged histologically.

However, for the avoidance of doubt, ligands may be visualised or detected by any suitable means, and the skilled person will appreciate that any suitable detection means as is known in the art could be substituted for these examples Such methods may be based on those described in WO 02/075318.

Examples of Diagnostic Ligands

In one embodiment, the diagnostic ligands are selected from compounds of the formulae below and pharmaceutically acceptable salts, hydrates, and solvates thereof.

| Code | Related To | Structure |
|---|---|---|
| DL-001 | ABMFMA-05 | 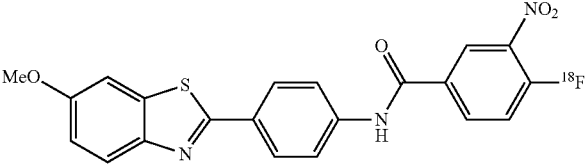 [SMILES: COc1ccc2nc(-c3ccc(NC(=O)c4ccc([18F])c([N+](=O)[O-])c4)cc3)sc2c1] |
| DL-002 | ABMFMA-02 | 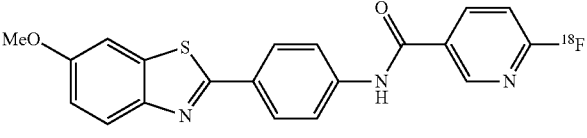 [SMILES: COc1ccc2nc(-c3ccc(NC(=O)c4ccc([18F])nc4)cc3)sc2c1] |
| DL-003 | AIPN-33 | 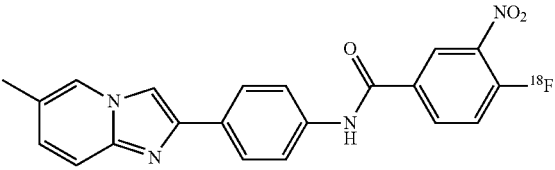 [SMILES: Cc1ccc2nc(-c3ccc(NC(=O)c4ccc([18F])c([N+](=O)[O-])c4)cc3)cn2c1] |
| DL-004 | AIPN-06 | 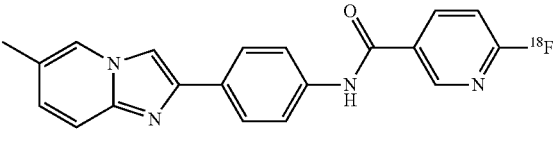 |
| DL-005 | IEPN-04 | 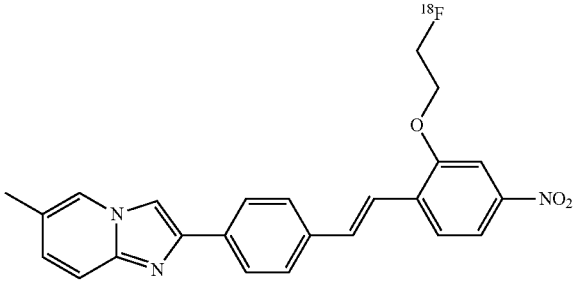 [SMILES: Cc1ccc2nc(-c3ccc(/C=C/c4ccc([N+](=O)[O-])cc4OCC[18F])cc3)cn2c1] |

| Code | Related To | Structure |
|---|---|---|
| DL-006 | BEFA-12 | MeO-[benzothiazole]-[phenyl]-CH=CH-[phenyl]-O-CH$_2$CH$_2$-$^{18}$F |
| DL-007 | BDF-18 | MeO-[benzothiazole]-[phenyl]-N=N-[phenyl]-O-CH$_2$CH$_2$-$^{18}$F |

Additional Methods for Labelling PHF and Tau

The present invention provides a method of labelling paired helical filaments (PHFs), the method comprising contacting the PHFs with a DSB compound as described herein and detecting the presence of said compound.

The method may be performed in vivo. Where the method is an in vivo method, the compound is administered to a subject. The subject may be a mammal. In one embodiment, the subject is a rodent. In another embodiment, the subject is a human subject.

Alternatively, the method may be performed in vitro.

The PHFs may be isolated from a subject as described herein. In one embodiment, the PHFs are isolated from the brain of a subject. The PHFs may be taken from the IFII fraction of a brain sample, for example as described by C. M. Wischik (Thesis "The structure and biochemistry of paired helical filaments in Alzheimer's disease" Part I and II; Cambridge University, 1989).

In one embodiment, the brain sample includes a sample from the medial temporal lobe i.e. E2/Trans (Entorhinal cortex layer 2/transitional entorhinal cortex) and E4/HC (Entorhinal cortex layer 4 and hippocampus) regions, and also neocortical structures (F/T/P regions—frontal, temporal, parietal) of the brain.

In one embodiment, the PHFs are isolated from the brain of a subject having Alzheimer's disease, or a subject that is suspected of having Alzheimer's disease. The subject may be a human subject.

The DSB compound may be used alone, or may be formulated in a composition with suitable carriers, diluents, excipients, etc. as described herein.

The presence of the DSB compound may be detected using techniques that are suitable for the type of compound employed.

The DSB compound may be detected by fluorescence spectroscopy. Such methods are suitable for use with DSB compounds that are capable of fluorescence.

The DSB compound may be detected by radiation count. Such methods are suitable for use with DSB compounds that comprise a radiolabel.

The presence of the DSB compound may be detected by a competition assay whereby the displacement of a known ligand for PHFs by the DSB compound is monitored, including quantified, by changes in a detectable. The known ligand may be a fluorescent ligand. The displacement of the known ligand from the PHFs may be monitored, and optionally quantified, by fluorescence spectroscopy. Such methods are suitable for use with DSB compounds that are not capable of fluorescence, or compounds that fluoresce under conditions or at wavelengths that do not interfere with the fluorescence signal detectable from the known ligand.

In one embodiment, the presence of the DSB compound is detected by displacement of a detectable known ligand from the PHFs. The known ligand may be a fluorescent ligand.

The displacement of the known ligand from the PHFs by the DSB compound may be detected by a reduction in fluorescent activity. In one embodiment, the known ligand is capable of increased fluorescence when bound to PHF.

In one embodiment, the known ligand is primulin.

In one embodiment, the DSB compound has a greater affinity for PHF than primulin.

In one embodiment, a compound comprising an $^{18}$F radiolabel may be detected using a radiation counter, for example a gamma-counter.

Other methods for detecting DSB compounds of the invention include those set in the Diagnostic Ligands section herein.

The present invention also provides a method for labelling aggregated tau or tau-like molecules, comprising contacting the aggregated tau molecules with a DSB compound and detecting the presence of said compound.

The method may be performed in vivo or in vitro. Where the method is an in vivo method, the compound is administered to a subject. The subject may be a mammal. In one embodiment, the subject is a rodent. In another embodiment, the subject is a human subject.

In one embodiment, the DSB compound is contacted with aggregated tau or tau-like molecules within a brain sample from a subject. In one embodiment, the subject is a non-human subject capable of expressing full-length human tau. The subject may be a transgenic rodent expressing full-length human tau having a double mutation P301S/G335D.

In one embodiment, the aggregated tau or tau-like molecules is prepared in a cell line expressing full-length tau ("T40") and/or PHF-core tau fragment (12 kD fragment). The cell line may be a fibroblast cell line. In one embodiment, the cell line is a 3T6 cell line.

In one embodiment, the DSB compound is prepared and then contacted with the PHFs or aggregated tau or tau-like molecules, or administered to a subject, within 14 days of its preparation.

The DSB compound may be contacted or administered within 7 days, 2 days, 24 hours, 12 hours, 6 hours or 3 hours of its preparation.

The DSB compound may be administered to a subject, and the distribution of the DSB compound in one or more organs of the subject monitored.

In one embodiment, the distribution of the DSB compound in the brain is monitored.

The DSB compound may reach a maximum concentration in the brain at least 10 minutes, 5 minutes, or 2 minutes after administration to the subject.

The amount of DSB compound remaining in the brain may reach a level of 50% of the maximum concentration in the brain at 120 min at most, 60 min at most, or 30 min at most after administration.

The total amount of DSB compound in the brain as a percentage of the initial dose administered to the subject is at least 1%, at least 2%, at least 3% or at least 4% of the total amount of DSB compound administered. The time point for measuring the total amount may be the time point at which the amount in the brain reaches a maximum concentration. Alternatively, the time point may be 1, 2, 5 or 10 minutes after administration.

In one embodiment, the DSB compound is at least substantially dissolved in a solution comprising an aprotic solvent. The aprotic solvent may be DMSO. The DSB compound may be at least substantially dissolved in a solution comprising at least 1% DMSO, at least 5% DMSO or at least 10% DMSO. The solution may be an aqueous solution.

The In one embodiment, the DSB compound is at least substantially dissolved in a solution comprising a protic solvent. The protic solvent may be methanol or ethanol. The DSB compound may be at least substantially dissolved in a solution comprising at least 10% of the protic solvent, at least 25% of the protic solvent or at least 50% of the protic solvent. In one embodiment, the solution is an aqueous solution comprising a protic solvent and an aprotic solvent.

Kits

One aspect of the invention pertains to a kit comprising (a) a DSB compound as described herein, or a composition comprising a DSB compound as described herein, e.g., preferably provided in a suitable container and/or with suitable packaging; and (b) instructions for use, e.g., written instructions on how to administer the compound or composition.

Diagnostic Uses

The DSB compound, or a composition comprising such a compound, may be provided for use in a method of diagnosis, prognosis or treatment of the human or animal body by therapy, especially in relation to a condition such as AD as described herein.

In a further aspect, the present invention provides a method of diagnosis or prognosis, the method comprising administering to the mammal a diagnostically- or prognostically-effective amount of one or more DSB compounds as described herein. This aspect embraces such compounds for use in a method of diagnosis or prognosis. Both in vitro and in vivo uses are encompassed by this aspect. In vitro methods may be performed by (i) obtaining a sample of appropriate tissue from a subject; (ii) contacting the sample with a DSB compound; (iii) detecting the amount and\or localisation of the DSB compound bound to the sample (iv) correlating the result of (iii) with the stage or severity of the disease in the subject.

The method may be performed in the context of a clinical trial to assess the efficacy of a tau aggregation inhibitor.

In a further aspect, the present invention provides the use of a DSB compound in the manufacture of a composition for the diagnosis, prognosis or therapy of a disease as described above.

The disease or condition may be e.g. AD, or an AD-like condition, or any other condition in which aggregated protein molecules are implicated.

Notably it is not only Alzheimer's Disease in which tau protein (and aberrant function or processing thereof) may play a role. The pathogenesis of neurodegenerative disorders such as Pick's disease and Progressive Supranuclear Palsy (PSP) appears to correlate with an accumulation of pathological truncated tau aggregates in the dentate gyrus and stellate pyramidal cells of the neocortex, respectively. Other dementias include frontotemporal dementia (FTD); parkinsonism linked to chromosome 17 (FTDP-17); disinhibition-dementia-parkinsonism-amyotrophy complex (DDPAC); pallido-ponto-nigral degeneration (PPND); Guam-ALS syndrome; pallido-nigro-luysian degeneration (PNLD); cortico-basal degeneration (CBD) and others (see Wischik et al. 2001, loc. cit, for detailed discussion—especially Table 5.1). All of these diseases, which are characterized primarily or partially by abnormal tau aggregation, are referred to herein as "tauopathies".

Routes of Administration

The DSB compound or pharmaceutical composition comprising the DSB compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be an animal, a mammal, a placental mammal, a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutan, gibbon), or a human.

Furthermore, the subject/patient may be any of its forms of development, for example, a foetus.

In one preferred embodiment, the subject/patient is a human. In other embodiments, the subject/patient is not a human.

Suitable subjects may be selected on the basis of conventional factors. Thus the initial selection of a patient may involve any one or more of: rigorous evaluation by experienced clinician; exclusion of non-AD diagnosis as far as possible by supplementary laboratory and other investigations; objective evaluation of level of cognitive function using neuropathologically validated battery.

Formulations

While it is possible for the DSB compound to be administered alone, it is preferable to present it as a physiologically acceptable formulation.

The following comments are made with respect to pharmaceutical formulations, but apply mutatis mutandis to diagnostic ones.

Thus there is a provided a pharmaceutical formulation (e.g., composition, preparation, medicament) comprising at least one DSB compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one IBD compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences,* 18th edition, Mack Publishing Company, Easton, Pa., 1990; and *Handbook of Pharmaceutical Excipients,* 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Chemical Synthesis

Several methods for the chemical synthesis of DSB compounds of the present invention are described herein. These and/or other well known methods may be modified and/or adapted in known ways in order to facilitate the synthesis of additional compounds within the scope of the present invention.

General Procedures

In one approach, the DSB compounds may be prepared in a process comprising the coupling of compound A with compound B:

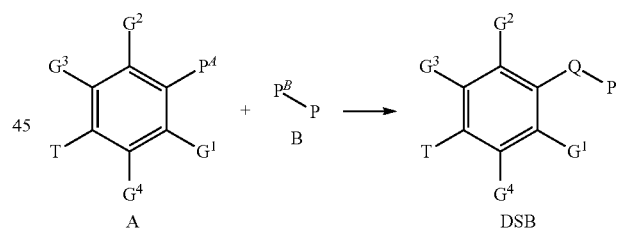

where —$P^A$ and —$P^B$ are suitable reactive functional groups, and -T, —P, and -$G^1$ to -$G^4$ are as defined according to the DSB compounds of the invention, and protected forms thereof.

In one embodiment, —$P^A$ and —$P^B$ are amide-coupling partners. The product of the coupling reaction is an amide bond i.e. -Q- is —NHC(O)—; —NR$^1$C(O)—; —C(O)NH—; or —C(O)NR$^1$—. Thus, one of —$P^A$ and —$P^B$ may be —C(O)OH, or an activated form thereof, and the other may be —NH$_2$ or —NHR$^1$.

In one embodiment, —$P^A$ is —NH$_2$ or —NHR$^1$. In one embodiment, —$P^A$ is —NH$_2$.

In one embodiment, —$P^B$ is —C(O)OH or —C(O)Cl.

In one embodiment, —$P^A$ and —$P^B$ are alkene-coupling partners. The product of the coupling reaction is an alkene bond i.e. -Q- is —CH=CH—; —CR$^1$=CH—; —CH=CR$^1$—; or —CR$^1$=CR$^1$—.

In one embodiment, —P^A and —P^B the alkene-coupling partners may be Wittig or Wittig-like coupling partners, for example Horner-Wadsworth-Emmons coupling partners.

Thus, one of —P^A and —P^B may be —C(O)H or —C(O)R^1, and the other may be a phosphonate.

In one embodiment, one of —P^A and —P^B is —C(O)H.

In one embodiment, the other of —P^A and —P^B is —P(O)(OEt)_2.

In one embodiment, —P^B is —C(O)H.

In one embodiment, the other of —P^A is —P(O)(OEt)_2.

In one embodiment, —P^A and —P^B the alkene-coupling partners may be Heck or Heck-like coupling partners.

Thus, one of —P^A and —P^B may be alkenyl, for example H_2C=CH—, and the other may be —Cl, —Br, —I, —N_2^+X^- (where X is Cl or BF_4) or —OTf.

A and B are coupled in the presence of a catalyst, typically a palladium catalyst, such as Pd or Pd(OAc)_2. A base may also be used.

In one embodiment, —P^A and —P^B are diazo-coupling partners. The product of the coupling reaction is a diazo bond i.e. -Q- is —N=N—.

In one embodiment, —P^A and —P^B are imine-coupling partners. The product of the coupling reaction is an imine bond i.e. -Q- is —N=CH— or —CH=N—. Thus, one of —P^A and —P^B may be —NH_2 and the other may be —C(=O)H.

Preparation of Fluorinated Compounds

In certain embodiments, the present invention pertain to DSB compounds having a —F group, and in further embodiments, there are provided DSB compounds having a —$^{18}$F group.

In one general method, DSB compounds having a —F group may be prepared from a DSB compounds having a —OH group. The —OH group may be converted to an activated leaving group. The activated leaving group is activated for substitution with a —F nucleophile. Reaction of the compound having an activated leaving group with a source of fluoride nucleophile yields a DSB compounds having a —F group. Where the fluoride nucleophile is a —$^{18}$F nucleophile, the product of the reaction is DSB compound having a —$^{18}$F group.

The activated leaving group includes those groups familiar to those in the art, such as mesylate (—OS(O)_2CH_3) and tosylate (—OS(O)_2PhCH_3). A DSB compound having a —OH group may be reacted with mesylate halide or tosylate haldide to from the DSB compound having In one embodiment, the —OH group is a substituent on a saturated aliphatic alkyl group, for example a saturated aliphatic $C_{1-6}$alkyl group substituted with —OH, or a linker to an —OH group such as a saturated aliphatic $C_{1-5}$alkylene linker to an —OH group.

Examples of groups suitable for use include those where —W^{A1} is —CH_2CH_2OH, one of —P^A, —P^B, or —P^C is -L^1-OH, -G^A or -G^B is [O—CH_2CH_2]_n—R^{B2} and —R^{B2} is -L^C-OH, —O-L^C-OH or —OH, or where —R^{B2} is -L^C-OH or —O-L^C-OH, where such groups are present.

The present invention provides methods for the preparation of DSB compounds where compound A is coupled with compound B, as described above, to form a product compound having the group -Q-. Compound A or compound B may comprise a —F group. This —F group may be carried through any remaining synthesis steps to appear in the final DSB product. Examples of compounds of formula A and B having an —F group are given throughout the present specification.

EXAMPLES

The following examples are provided solely to illustrate the present invention and are not intended to limit the scope of the invention, as described herein.

General Methods
Amide Coupling

In this reaction, an amine and an acid chloride are coupled to give the corresponding amide, as shown in the scheme below

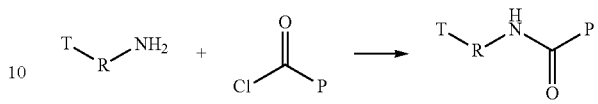

where T-, —R— and —P are as previously defined.

In a typical reaction, an amine (1 equiv.) is reacted with an acid chloride (X equiv.) in the presence of excess base, typically an organic base such as pyridine or diisopropylethylamine, to yield the corresponding amide product, which may be isolated after a work-up, including, for example, extraction, filtration, column chromatography, crystallisation and/or drying. The reaction may be performed at elevated temperature, for example at reflux, and optionally under an inert atmosphere, for example under argon. The reaction may be performed in an organic solvent, for example THF, or may be performed neat in an organic base.

The acid chloride may be generated from the carboxylic acid with, for example, thionyl chloride. The acid chloride may be used crude in the amide coupling reaction.

In a representative example, 2-nitro-N-[4-(6-methoxybenzothiazol-2-yl)-phenyl]-benzamide was prepared as described below.

2-Nitro-N-[4-(6-methoxybenzothiazol-2-yl)-phenyl]-benzamide

Book No.: SKT01-13

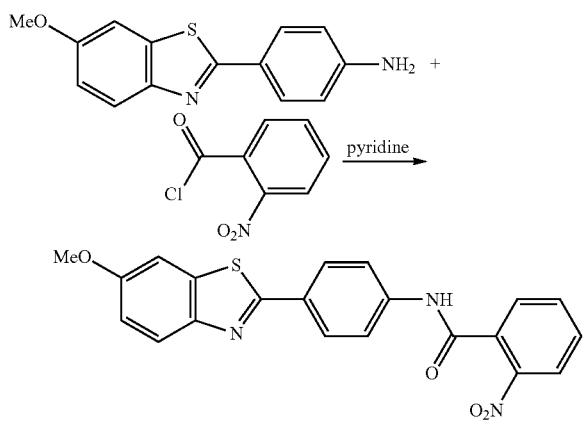

To a stirred solution of 2-(4-aminophenyl)-6-methoxybenzothiazole (0.30 g, 1.17 mmol) in dry pyridine (15 ml) at room temperature was added 2-nitrobenzoyl chloride (0.24 g, 1.29 mmol) in one portion under an atmosphere of argon. The reaction mixture was heated at 90° C. for 7 h and on cooling to room temperature it was added to water (150 ml). The precipitate was collected by filtration and dried under vacuum at 50° C. overnight to give the title compound (0.42 g, 88%) as a colourless solid.

Nitro Reduction

In this reaction, a nitro functional group is converted to the corresponding amine group. Typically, a nitro compound (1 equiv.) is reacted with tin (II) chloride dihydrate (8 equiv.) in a solvent, for example ethanol, to give, after an appropriate work-up, the corresponding amine compound. The work-up may include the steps of basification, separation, extraction, filtration, column chromatography, crystallisation and/or drying. The reaction may be performed at elevated temperature, for example at reflux, and optionally under an inert atmosphere, for example under argon.

In a representative example, 2-amino-N-[4-(6-methoxy-benzothiazol-2-yl)-phenyl]-benzamide was prepared as described below.

2-Amino-N-[4-(6-methoxybenzothiazol-2-yl)-phenyl]-benzamide

Book No.: SKT01-99

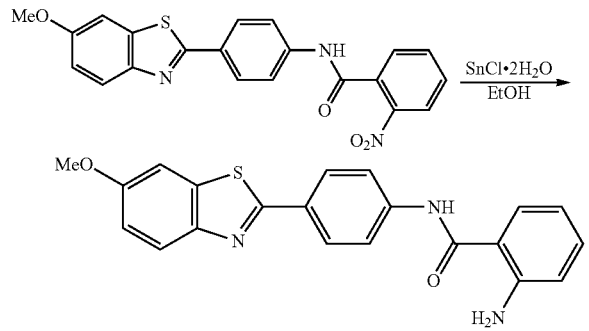

A mixture of 2-nitro-N-[4-(6-methoxybenzothiazol-2-yl)-phenyl]-benzamide (1.0 g, 2.47 mmol) and tin (II) chloride dihydrate (4.45 g, 19.74 mmol) in EtOH (20 ml) was heated under reflux for 6 h. On cooling to room temperature, the reaction mixture was made basic by addition of sat. $NaHCO_3$ solution and then extracted with EtOAc (4×50 ml). The combined organic extracts were washed with brine (80 ml), dried ($Na_2SO_4$) and the solvent removed under reduced pressure to give the title compound (0.79 g, 85%) as a pale yellow needles after recrystallisation from EtOH.

Demethylation

In this reaction, an aryl methoxy functional group is converted to the corresponding aryl hydroxy group. Typically, an aryl methoxy compound (1 equiv.) is reacted with $BBr_3$ in a solvent, for example DCM, to give, after work-up, the corresponding aryl hydroxyl compound. The work-up may include the steps of basification, separation, acidification, extraction, filtration, column chromatography, crystallisation and/or drying. The reaction may be performed at reduced temperature, for example at 0° C. or −78° C.

In a representative example, 2-amino-N-[4-(6-hydroxy-benzothiazol-2-yl)-phenyl]-benzamide was prepared as described below.

4-Amino-N-[4-(6-hydroxybenzothiazol-2-yl)-phenyl]-benzamide

Book No.: SKT01-57

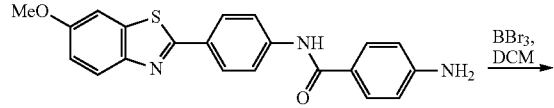

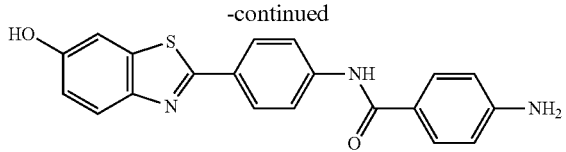

To a stirred suspension of 4-amino-N-[4-(6-methoxybenzothiazol-2-yl)-phenyl]-benzamide (50 mg, 0.13 mmol) in dry DCM (3 ml) at room temperature was added dropwise $BBr_3$ (1.0 M solution in DCM, 0.67 ml, 0.67 mmol) and the reaction mixture stirred at room temperature for 2.5 h. The reaction was then quenched by the dropwise addition of MeOH, and the reaction mixture poured into ammonia solution (25 ml), the aqueous phase separated, neutralized by addition of 1 M HCl and extracted with EtOAc (4×60 ml). The combined organic extracts were dried ($Na_2SO_4$) and the solvent removed under reduced pressure to give a solid which was purified by flash chromatography (1:1 Hexane/EtOAc followed by EtOAc) to give the title compound (27 mg, 56%) as a tan-coloured solid.

Alkene Formation

In this reaction, a phosphonate and an aldehyde are reacted in the presence of a base to give an alkene product, for example as shown in the scheme below

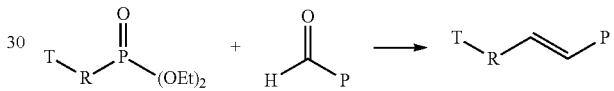

where T-, —R— and —P are as previously defined.

In a typical reaction, a phosphonate (1 equiv.) is reacted with an aldehyde (1 equiv.) in the presence of a base (2 equiv.), for example sodium methoxide, sodium hydride or potassium t-butoxide, in an organic solvent, for example MeOH or THF, to yield the corresponding alkene product, which may be isolated after a work-up, including, for example, acidification, extraction, filtration, column chromatography, crystallisation and/or drying. The reaction may be performed at reduced temperature, for example at 0° C. or −78° C., or elevated temperature, for example at reflux.

In a representative example, 2-{4-[2-(2-nitrophenyl)-vinyl]-phenyl}-6-methoxybenzo thiazole was prepared as described below.

2-{4-[2-(2-Nitrophenyl)-vinyl]-phenyl}-6-methoxybenzothiazole

Book No.: SKT01-71

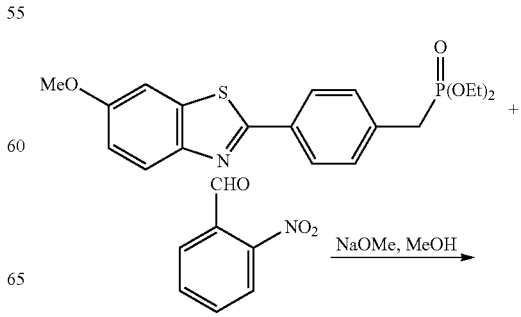

-continued

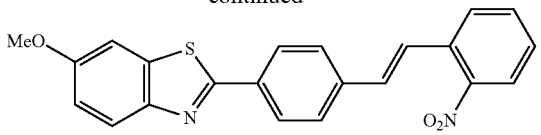

To a stirred solution of diethyl 4-(6-methoxylbenzothiazol-2-yl)benzylphosphonate (0.10 g, 0.25 mmol) and 2-nitrobenzaldehyde (0.39 g, 0.25 mmol) in dry MeOH (10 ml) at 0° C. was added dropwise a solution of 0.5 M sodium methoxide (1.02 ml, 0.51 mmol). The reaction mixture was then allowed to rise to room temperature and heated under reflux for 18 h. The reaction mixture was cooled to room temperature and water (30 ml) was added followed by 1 M HCl until the reaction mixture became acidic. The reaction mixture was then extracted with DCM (3×80 ml) and the combined organic extracts washed with brine (50 ml) and dried ($Na_2SO_4$). The solvent was removed under reduced pressure to give a solid which was purified by flash chromatography (DCM) to give the title compound (0.043 g, 43%) as a yellow solid.

Amination

In this reaction, a primary amine is converted to a tertiary amine. In a typical reaction, a primary amine (1 equiv.) is reacted with an aldehyde (10 equiv.), for example paraformaldehyde, in the presence of a reducing agent, for example sodium cyanoborohydride (5 equiv.) to yield the corresponding tertiary amine product, which may be isolated after a work-up, including, for example, basification, extraction, filtration, column chromatography, crystallisation and/or drying. The reaction may be performed in an organic solvern, such as AcOH.

In a representative example, 2-dimethylamino-N-[4-(6-methoxybenzothiazol-2-yl)-phenyl]-benzamide was prepared as described below.

2-Dimethylamino-N-[4-(6-methoxybenzothiazol-2-yl)-phenyl]-benzamide

Book No.: SKT01-103

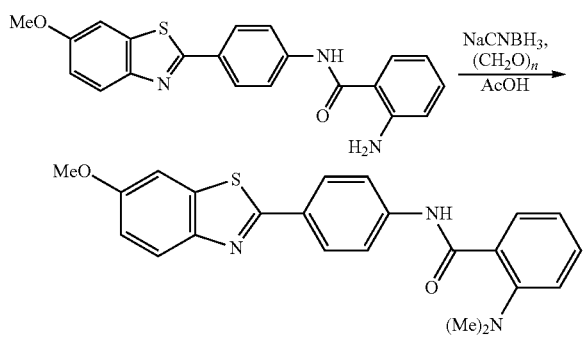

Sodium cyanoborohydride (84 mg, 1.33 mmol) was added in one portion to a stirred mixture of 2-amino-N-[4-(6-methoxybenzothiazol-2-yl)-phenyl]-benzamide (100 mg, 0.266 mmol) and paraformaldehyde (80 mg, 2.66 mmol) in AcOH (2 ml). The reaction mixture was stirred at room temperature for 18 h and then added to water (30 ml) and made alkaline (pH 8-9) by the addition of sodium bicarbonate. This was extracted with DCM (3×30 ml) and the combined organic extracts were washed with brine (25 ml), dried ($Na_2SO_4$) and the solvent removed under reduced pressure to give a yellow residue. This was purified by flash chromatography (2:1 Hexane/EtOAc) to give the title compound (63 mg, 59%) as a colourless solid.

Thioamide Formation

In this reaction, an amide is converted to a thioamide. In a typical reaction, an amide (1 equiv.) is dissolved in hot toluene (dry, 40 vol) and Lawesson's reagent (1.5 equiv.) added. The reaction is heated to 80° C. under argon for 2 h. The reaction is then cooled to rt and filtered. The resulting precipitate is washed with EtOAc then dried under reduced pressure to give the corresponding crude thioamide product. Column chromatography is performed to obtain pure target material.

Potassium Ferricyanide Benzothiazole Formation

In this reaction, a thiobenzamide is converted to a benzothiazole in the presence of potassium ferricyanide. In a typical reaction, a thiobenzamide (1 equiv) is dissolved in NaOH (1.5 M, 39 equiv.) and the solution cooled to 5° C. with ice. Potassium ferricyanide in water (20%, 15 vol) is added and the reaction stirred at it for 18 h. The mixture is filtered and the solid washed with $H_2O$. The solid is dissolved in DCM (20 vol), dried ($Na_2SO_4$) and the solvent removed under reduced pressure to give the crude benzothiazole product. Column chromatography may be carried out in order to obtain the pure target material.

Diazo Coupling

In this reaction, an aryl amine and an arene, for example a phenol, are coupled through formation of a diazo linkage. In a typical reaction, an aryl amine (1 equiv.) is dissolved in MeOH (10 vol) and the solution cooled to 5° C. in ice. HCl (3 equiv, 2 M) is then added to the solution. $NaNO_2$ in $H_2O$ (10 vol) is added drop-wise. The reaction is stirred at 5° C. for 10 min. In a separate flask the arene (1 equiv) is added to $H_2O$ (20 vol). $Na_2CO_3$ (2 equiv.), followed by NaOH (1 equiv.) is added and the resulting suspension added dropwise to the diazonium salt. The reaction is stirred for 30 min, before it is extracted with EtOAc (3×20 vol). The combined organics are washed with $H_2O$ (10 vol), brine (10 vol) and dried ($Na_2SO_4$). The solvent is removed under reduced pressure to give the crude target material which may be purified by column chromatography.

Compounds where -Q- is NHC(O)—; —$NR^1$C(O)—; —C(O)NH—; or —C(O)$NR^1$—

Intermediates

5-Methoxy-2-aminobenzenethiol

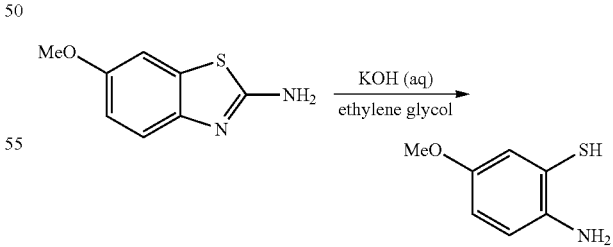

A mixture of 2-amino-6-methoxybenzothiazole (15 g, 83.2 mmol), ethylene glycol (20.23 g, 0.33 mol) and 50% w/v KOH (100 ml) was heated under reflux for 24 h. On cooling to room temperature, toluene (60 ml) was added and the reaction mixture was cooled in an ice-bath and acidified with acetic acid (final pH 5-6). The reaction mixture was extracted with toluene (5×300 ml) and the combined organic extracts were washed with brine (2×200 ml), dried (MgSO$_4$) and the solvent removed under reduced pressure to give the title compound (11.1 g, 86%) as a yellow solid which was used without further purification.

$^1$H NMR (250 MHz, CDCl$_3$/DMSO-d$_6$) δ 3.21 (s, 3H), 6.13 (d, J=8.8 Hz, 1H), 6.30 (d, J=8.8 Hz, 1H), 6.39 (s, 1H); $^{13}$C NMR (62.5 MHz, CDCl$_3$) δ 55.87, 113.61, 115.41, 116.47, 119.00, 140.58, 152.52.

The experimental data agreed with those reported previously by Mathis et al. and Haugwitz et al.

2-(4-Nitrophenyl)-6-methoxybenzothiazole

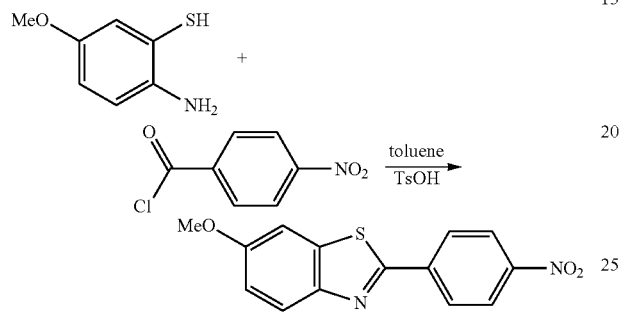

A mixture of 2-amino-5-methoxybenzenethiol (5.0 g, 32.2 mmol) and 4-nitrobenzoyl chloride (6.0 g, 32.2 mmol) in toluene (250 ml) was heated under reflux with a catalytic amount of 4-toluenesulphonic acid in a Dean-Stark trap for 6 h. On cooling to room temperature the precipitate was collected by filtration, washed with toluene and recrystallised from AcOH to give the title compound (7.0 g, 76%) as a pale yellow solid.

$^1$H NMR (400 MHz, CDCl$_3$) δ 3.88 (s, 3H), 7.11 (dd, J=8.9, 2.4 Hz, 1H), 7.34 (d, J=2.4 Hz, 1H), 7.96 (d, J=8.9 Hz, 1H), 8.16 (d, J=8.9 Hz, 2H), 8.29 (d, J=8.9 Hz, 2H);

$^{13}$C NMR (100 MHz, CDCl$_3$) δ 55.88, 104.00, 116.64, 124.32, 124.51, 127.83, 137.09, 139.39, 148.69, 148.73, 158.58, 162.19.

The experimental data agreed with those reported previously by Kashiyama et al. and Shi et al.

2-(4-Nitrophenyl-2-trifluoromethyl)-6-methoxybenzothiazole

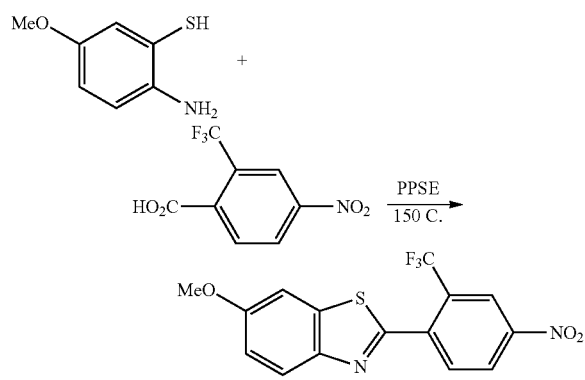

A thoroughly mixed paste of 2-amino-5-methoxybenzenethiol (1.0 g, 6.44 mmol) and 4-nitro-2-trifluoromethyl-benzoic acid (1.51 g, 6.44 mmol) in trimethylsilylpolyphosphate (PPSE) (5 ml) was stirred and heated at 150° C. under an atmosphere of argon for 3 h. On cooling to room temperature the reaction mixture was a solid mass which was dissolved in DCM and adsorbed onto silica and purified on a short plug of silica (1:1 Hexane/EtOAc). The first eluting fractions were collected and the solvent removed under reduced pressure to give an orange solid (1.5 g) which was further purified by flash chromatography (3:1 Hexane/EtOAc) to give the title compound (0.85 g, 37%) as a yellow solid.

PPSE was obtained from commercial sources. Alternatively, PPSE may be prepared according to the methods described by Imamoto et al.

$^1$H NMR (400 MHz, CDCl$_3$) δ 3.88 (s, 3H), 7.14 (dd, J=8.9, 2.4 Hz, 1H), 7.36 (d, J=2.7 Hz, 1H), 7.94 (d, J=8.5 Hz, 1H), 8.01 (d, J=8.9 Hz, 1H), 8.46 (dd, J=8.5, 2.0 Hz, 1H), 8.67 (d, J=2.4 Hz, 1H); $^{13}$C NMR (62.5 MHz, CDCl$_3$) δ 55.93, 103.50, 116.75, 122.41 (q, J$_{CF}$=274 Hz), 122.63 (q, J$_{CF}$=5.9 Hz), 124.81, 126.39, 130.61 (q, J$_{CF}$=33 Hz), 133.98, 137.85, 138.95, 148.06, 158.59, 158.87.

2-(4-Nitrophenyl-3-trifluoromethyl)-6-methoxybenzothiazole

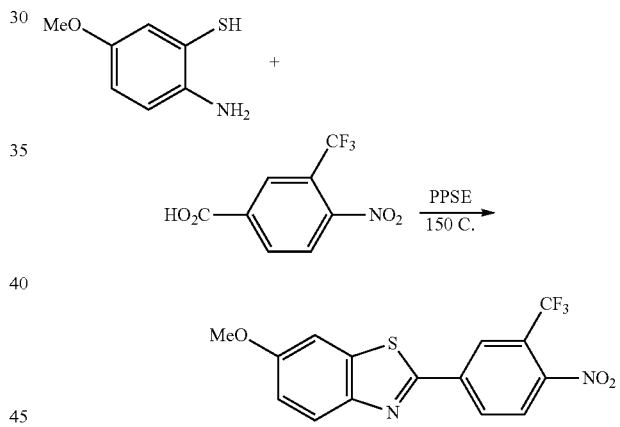

A thoroughly mixed paste of 2-amino-5-methoxybenzenethiol (2.0 g, 12.88 mmol) and 4-nitro-3-trifluoromethyl-benzoic acid (3.03 g, 12.88 mmol) in trimethylsilylpolyphosphate (10 ml) was stirred and heated at 150° C. under an atmosphere of argon for 2 h. On cooling to room temperature the reaction mixture was dissolved in DCM (100 ml) and washed with 1 M HCl (2×50 ml), sat. NaHCO$_3$ (2×50 ml), brine (80 ml) and dried (Na$_2$SO$_4$). The solvent was removed under reduced pressure to give a brown solid which was purified by flash chromatography (2:1 Hexane/EtOAc) to give the title compound (2.36 g, 52%) as a yellow solid.

$^1$H NMR (250 MHz, CDCl$_3$) δ 3.90 (s, 3H), 7.14 (dd, J=9.1, 2.4 Hz, 1H), 7.34 (d, J=2.1 Hz, 1H), 7.95 (d, J=8.5 Hz, 1H), 7.97 (d, J=8.8 Hz, 1H), 8.24 (d, J=8.5 Hz, 1H), 8.47 (s, 1H); $^{13}$C NMR (62.5 MHz, CDCl$_3$) δ 55.88, 103.95, 116.95, 121.75 (q, J$_{CF}$=274 Hz), 124.68, 124.75 (q, J$_{CF}$=35 Hz), 126.00, 126.30, 130.83, 137.10, 137.97, 148.17, 148.55, 158.84, 160.38.

2-(2-Methoxy-4-nitrophenyl)-6-methoxybenzothiazole

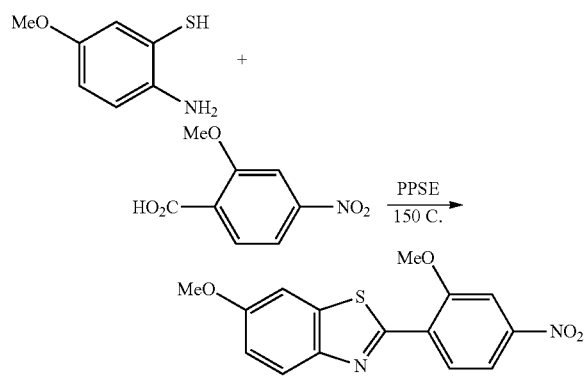

A thoroughly mixed paste of 2-amino-5-methoxybenzenethiol (2.0 g, 12.88 mmol) and 2-methoxy-4-nitrobenzoic acid (2.54 g, 12.88 mmol) in trimethylsilylpolyphosphate (10 ml) was stirred and heated at 150° C. under an atmosphere of argon for 30 min. On cooling to room temperature, the reaction mixture was suspended in DCM/MeOH and an orange solid was collected by filtration. The filtrate was washed with 1 M HCl (2×50 ml), sat. NaHCO$_3$ (2×50 ml), brine (70 ml) and dried (Na$_2$SO$_4$). The solvent was removed under reduced pressure to give a solid which was combined with that collected and recrystallised from AcOH to give the title compound (3.43 g, 83%) as a yellow solid.

$^1$H NMR (250 MHz, CDCl$_3$) δ 3.90 (s, 3H), 4.15 (s, 3H), 7.13 (dd, J=9.1, 2.1 Hz, 1H), 7.36 (d, J=2.1 Hz, 1H), 7.89 (s, 1H), 7.97 (m, 2H), 8.66 (d, J=8.5 Hz, 1H); $^{13}$C NMR (62.5 MHz, CDCl$_3$) δ 55.84, 56.38, 103.24, 106.87, 116.22, 116.45, 124.09, 128.27, 129.79, 138.00, 146.84, 149.09, 156.71, 157.97, 158.13.

2-(3-Methoxy-4-nitrophenyl)-6-methoxybenzothiazole

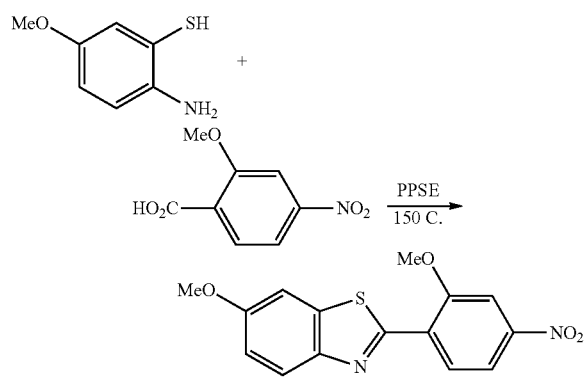

A thoroughly mixed paste of 2-amino-5-methoxybenzenethiol (2.0 g, 12.88 mmol) and 3-methoxy-4-nitrobenzoic acid (2.54 g, 12.88 mmol) in trimethylsilylpolyphosphate (10 ml) was stirred and heated at 150° C. under an atmosphere of argon for 2 h. On cooling to room temperature, the reaction mixture was suspended in DCM (300 ml) and adsorbed onto flash silica and initially purified using a plug of flash silica eluting with DCM, then DCM/EtOAc (6:1). Further purification of the collected fractions by flash chromatography (20:1 DCM/Hexane) gave the title compound (1.32 g, 32%) as a yellow solid.

$^1$H NMR (400 MHz, CDCl$_3$) δ 3.88 (s, 3H), 4.07 (s, 3H), 7.10 (dd, J=8.9, 2.4 Hz, 1H), 7.34 (d, J=2.4 Hz, 1H), 7.54 (dd, J=8.5, 1.7 Hz, 1H), 7.84 (d, 1H, J=1.7 Hz, 1H), 7.92 (d, J=8.5 Hz, 1H), 7.95 (d, J=8.5 Hz, 1H); $^{13}$C NMR (62.5 MHz, CDCl$_3$) δ 55.88, 56.86, 104.02, 111.50, 116.56, 119.08, 124.37, 126.56, 137.01, 139.15, 140.24, 148.58, 153.50, 158.51, 162.44.

2-(2-Methoxy-4-nitrophenyl)benzothiazole

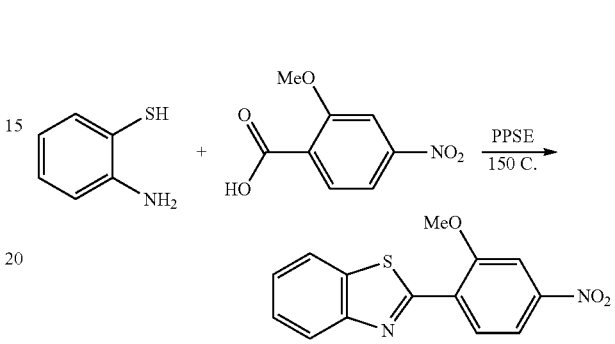

A thoroughly mixed paste of 2-aminobenzenethiol (0.63 g, 5.07 mmol) and 2-methoxy-4-nitrobenzoic acid (1.0 g, 5.07 mmol) in trimethylsilylpolyphosphate (5 ml) was stirred and heated at 150° C. under an atmosphere of argon for 1.5 h. On cooling to room temperature the reaction mixture was a solid mass to which was added DCM (35 ml) and Et$_2$O (50 ml). The solid was broken up and collected by filtration, then recrystallised from AcOH and dried under high vacuum for 18 h to give the title compound (0.90 g, 62%) as a yellow solid.

$^1$H NMR (250 MHz, CDCl$_3$) δ 4.16 (s, 3H), 7.40-7.46 (m, 1H), 7.51-7.56 (m, 1H), 7.91 (s, 1H), 7.93-8.05 (m, 2H), 8.12 (d, J=7.9 Hz, 1H), 8.72 (d, J=8.5 Hz, 1H); $^{13}$C NMR (62.5 MHz, CDCl$_3$) δ 56.39, 106.84, 116.11, 121.42, 123.42, 125.61, 126.49, 127.93, 130.21, 136.37, 149.40, 152.05, 157.04, 160.45.

2-(4-Amino-2-methoxyphenyl)benzothiazole

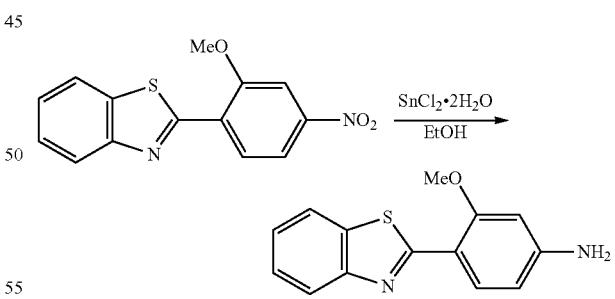

Prepared as described in the Nitro Reduction section using 2-(2-methoxy-4-nitrophenyl)benzothiazole (0.1 g, 0.35 mmol) and tin (II) dichloride dihydrate (0.63 g, 2.8 mmol) in EtOH (12 ml) to give the title compound (0.086 g, 96%) as a pale orange solid after work-up and flash chromatography (2:1 Hexane/THF).

$^1$H NMR (250 MHz, CDCl$_3$) δ 3.99 (br s, 5H), 6.30 (d, J=1.5 Hz, 1H), 6.41 (dd, J=8.5, 1.5 Hz, 1H), 7.25-7.32 (m, 1H), 7.39-7.46 (m, 1H), 7.85 (d, J=7.9 Hz, 1H), 7.99 (d, J=7.9 Hz, 1H), 8.31 (d, J=8.5 Hz, 1H); $^{13}$C NMR (62.5 MHz,

CDCl₃) δ 55.51, 97.48, 107.97, 113.01, 121.06, 121.98, 123.83, 125.69, 130.95, 135.49, 150.42, 152.21, 158.90, 163.89

2-(2-Hydroxy-4-nitrophenyl)benzothiazole

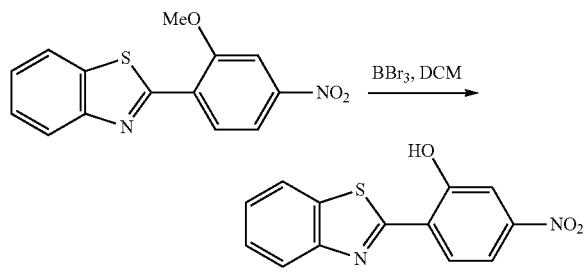

Prepared as described in the Demethylation section above using 2-(2-methoxy-4-nitrophenyl)benzothiazole (0.5 g, 1.75 mmol) in dry DCM (30 ml) was added dropwise at room temperature and BBr₃ (1.0 M solution in DCM, 8.8 ml, 8.8 mmol). The reaction mixture was stirred at room temperature for 18 h. The reaction was quenched by addition of MeOH (5 ml) and extracted with 8% w/v NaOH (5×35 ml). The combined aqueous extracts were acidified with 6 M HCl and extracted with EtOAc (3×70 ml). The combined organic extracts were washed with brine (40 ml), dried (Na₂SO₄) and the solvent removed under reduced pressure to give a solid which was purified by flash chromatography (1:1 Hexane/EtOAc) to give the title compound (0.47 g, 99%) as a pale yellow solid after work-up and flash chromatography (1:1 Hexane/EtOAc).

¹H NMR (250 MHz, CDCl₃) δ 7.49-7.53 (m, 1H), 7.55-7.61 (m, 1H), 7.78-7.95 (m, 2H), 7.95-7.98 (m, 2H), 8.06 (d, J=7.9 Hz, 1H), 12.95 (s, 1H); ¹³C NMR (62.5 MHz, CDCl₃) δ 113.24, 114.14, 121.78, 122.79, 126.65, 127.34, 129.03, 132.99, 149.79, 151.40, 158.28, 166.88 (1 missing).

2-[2-(1,3-Benzothiazol-2-yl)-5-nitrophenoxy]-N,N-dimethylethanamine

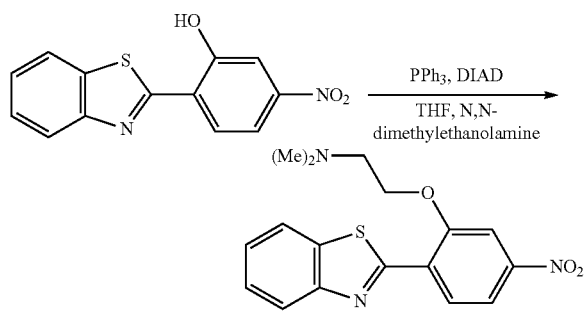

To a stirred mixture of 2-(2-hydroxy-4-nitrophenyl)benzothiazole (0.15 g, 0.55 mmol), triphenylphosphine (0.216 g, 0.825 mmol) and N,N-dimethylethanolamine (0.059 g, 0.66 mmol) in dry THF (10 ml) at 0° C. was added dropwise DIAD (0.167 g, 0.825 mmol). The reaction mixture was stirred at 0° C. for 0.5 h, then left to rise to room temperature overnight. The solvent was removed under reduced pressure and the residue was purified by flash chromatography (20:1 DCM/MeOH) to give the title compound (0.089 g, 47%) as a yellow solid.

¹H NMR (250 MHz, CDCl₃) δ 2.41 (s, 6H), 2.98-3.03 (m, 2H), 4.36-4.40 (m, 2H), 7.39-7.45 (m, 1H), 7.49-7.55 (m, 1H), 7.89-7.96 (m, 3H), 8.10 (d, J=7.6 Hz, 1H), 8.71 (d, J=8.5 Hz, 1H); ¹³C NMR (62.5 MHz, CDCl₃) δ 46.18, 57.93, 68.47, 107.63, 116.11, 121.42, 123.42, 125.60, 126.48, 128.05, 130.30, 136.36, 149.34, 151.99, 156.37, 160.47.

The reaction conditions employed were based on the methods described by Malamas et al. and Mann et al. for the reaction of 4-hydroxybenzaldehydes with aliphatic alcohols.

2-[2-{2-(2-(2-Methoxyethoxy)ethoxy)ethoxy}-4-nitrophenyl]-1,3-benzothiazole

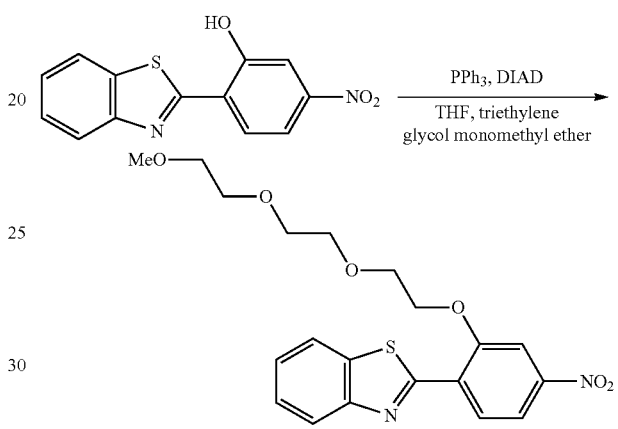

To a stirred mixture of 2-(2-hydroxy-4-nitrophenyl)benzothiazole (0.15 g, 0.55 mmol), triphenylphosphine (0.216 g, 0.825 mmol) and triethylene glycol monomethyl ether (0.108 g, 0.66 mmol) in dry THF (10 ml) at 0° C. was added dropwise DIAD (0.167 g, 0.825 mmol). The reaction mixture was stirred at 0° C. for 0.5 h, then left to rise to room temperature overnight. The solvent was removed under reduced pressure and the residue was purified by flash chromatography (1:1 Hexane/EtOAc) to give the title compound (0.176 g, 76%) as a yellow solid.

¹H NMR (250 MHz, CDCl₃) δ 3.32 (s, 3H), 3.47-3.52 (m, 2H), 3.61-3.67 (m, 2H), 3.68-3.75 (m, 2H), 3.76-3.84 (m, 2H), 4.06-4.10 (m, 2H), 4.44-4.48 (m, 2H), 7.39-7.45 (m, 1H), 7.49-7.55 (m, 1H), 7.92-7.96 (m, 3H), 8.10 (d, J=7.9 Hz, 1H), 8.71 (d, J=8.5 Hz, 1H);

¹³C NMR (62.5 MHz, CDCl₃) δ 59.05, 69.34 (2×C), 70.68, 70.79, 70.99, 71.94, 107.91, 116.19, 121.44, 123.41, 125.58, 126.45, 128.11, 130.22, 136.48, 149.31, 152.02, 156.39, 160.56.

The reaction conditions employed were based on the methods described by Zhang et al. for the reaction of polyethyleneglycols with phenolic compounds.

2-(4-Aminophenyl)-6-methoxybenzothiazole

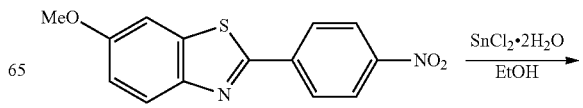

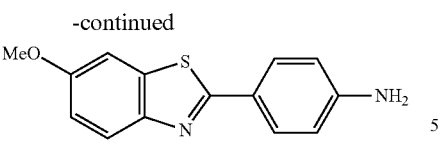

Prepared as described in the Nitro Reduction section using 2-(4-nitrophenyl)-6-methoxybenzothiazole (5.0 g, 17.5 mmol) and tin (II) dichloride dihydrate (31.5 g, 0.14 mol) in EtOH (150 ml) to give the title compound (4.2 g, 93%) as a colourless solid after work-up and recrystallisation from EtOH.

$^1$H NMR (250 MHz, CDCl$_3$) δ 3.86 (s, 3H), 3.96 (s, 2H), 6.71 (d, J=8.5 Hz, 2H), 7.04 (dd, J=8.5, 2.4 Hz, 1H), 7.31 (d, J=2.4 Hz, 1H), 7.83 (d, J=8.5 Hz, 2H), 7.87 (d, J=8.5 Hz, 2H); $^{13}$C NMR (62.5 MHz, CDCl$_3$) δ 55.82, 104.34, 114.84, 115.10, 123.00, 124.20, 128.81, 135.92, 148.84, 148.87, 157.29, 166.15. The experimental data agreed with those reported previously by Mathis et al. and Shi et al.

2-(4-Amino-2-trifluoromethylphenyl)-6-methoxy-benzothiazole

Prepared as described in the Nitro Reduction section using 2-(4-nitro-2-trifluoromethylphenyl)-6-methoxybenzothiazole (0.6 g, 1.69 mmol) and tin (II) dichloride dihydrate (3.06 g, 13.56 mmol) in EtOH (35 ml) to give the title compound (0.51 g, 93%) as a colourless solid after work-up and flash chromatography (30:1 DCM/EtOAc).

$^1$H NMR (250 MHz, CDCl$_3$) δ 3.88 (s, 3H), 4.08 (br s, 2H), 6.83 (d, J=8.2 Hz, 1H), 7.04 (s, 1H), 7.10 (dd, J=8.8, 2.4 Hz, 1H), 7.34 (d, J=2.4 Hz, 1H), 7.48 (d, J=8.2 Hz, 1H), 7.96 (d, J=8.8 Hz, 1H); $^{13}$C NMR (62.5 MHz, CDCl$_3$) δ 55.85, 103.69, 112.69 (q, J$_{CF}$=4.9 Hz), 115.61, 116.78, 122.01, 123.59 (q, J$_{CF}$=274 Hz), 124.00, 130.00 (q, J$_{CF}$=31 Hz), 133.73, 137.55, 147.89, 148.02, 157.75, 162.86.

2-(4-Amino-3-trifluoromethylphenyl)-6-methoxy-benzothiazole

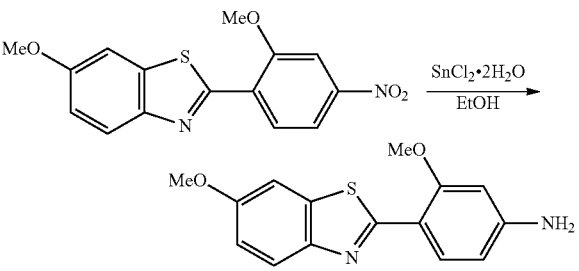

Prepared as described in the Nitro Reduction section using 2-(4-nitro-3-trifluoromethyl phenyl)-6-methoxybenzothiazole (1.0 g, 2.82 mmol) and tin (II) dichloride dihydrate (5.1 g, 22.6 mmol) in EtOH (50 ml) to give the title compound (0.84 g, 91%) as a pale orange solid after work-up and flash chromatography (2:1 Hexane/EtOAc).

$^1$H NMR (400 MHz, CDCl$_3$) δ 3.84 (s, 3H), 4.44 (br s, 2H), 6.76 (d, J=8.4 Hz, 1H), 7.03 (dd, J=8.8, 2.4 Hz, 1H), 7.28 (d, J=2.4 Hz, 1H), 7.85 (d, J=8.8 Hz, 1H), 7.91 (dd, J=8.4, 2.0 Hz, 1H), 8.07 (d, J=2.0 Hz, 1H); $^{13}$C NMR (62.5 MHz, CDCl$_3$) δ 55.84, 104.26, 113.70 (q, J$_{CF}$=30.3 Hz), 115.54, 117.26, 123.22, 123.41, 124.55 (q, J$_{CF}$=272 Hz), 125.99 (q, J$_{CF}$=3.9 Hz), 131.71, 135.88, 146.33, 148.44, 157.60, 164.59.

2-(4-Amino-2-methoxyphenyl)-6-methoxybenzothiazole

Prepared as described in the Nitro Reduction section using 2-(2-methoxy-4-nitrophenyl)-6-methoxybenzothiazole (1.0 g, 3.13 mmol) and tin (II) dichloride dihydrate (5.66 g, 25.08 mmol) in EtOH (50 ml) to give the title compound (0.79 g, 89%) as a pale yellow solid after work-up and recrystallisation from EtOH.

$^1$H NMR (400 MHz, DMSO-d$_6$) δ 3.76 (s, 3H), 3.87 (s, 3H), 5.82, (br s, 2H), 6.27 (dd, J=8.5, 1.7 Hz, 1H), 6.29 (d, J=1.7 Hz, 1H), 6.98 (dd, J=8.9, 2.4 Hz, 1H), 7.50 (d, J=2.4 Hz, 1H), 7.71 (d, J=8.9 Hz, 1H), 7.99 (d, J=8.5 Hz, 1H); $^{13}$C NMR (100.5 MHz, DMSO-d$_6$) δ 56.01, 56.24, 96.71, 104.78, 107.72, 110.09, 115.43, 122.43, 130.18, 136.59, 147.01, 153.53, 156.85, 158.99, 161.62.

2-(4-Amino-3-methoxyphenyl)-6-methoxybenzothiazole

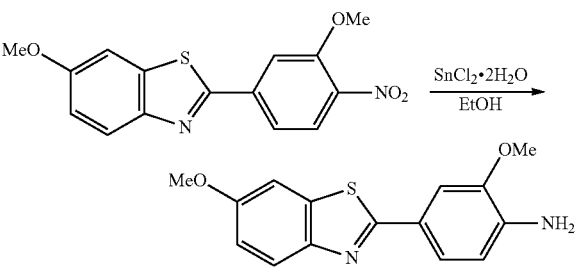

Prepared as described in the Nitro Reduction section using 2-(3-methoxy-4-nitrophenyl)-6-methoxybenzothiazole (0.5 g, 1.56 mmol) and tin (II) dichloride dihydrate (2.61 g, 11.58 mmol) in EtOH (35 ml) to give the title compound (0.41 g, 91%) as a pale orange solid after work-up and flash chromatography (2:1 Hexane/THF).

$^1$H NMR (400 MHz, DMSO-$d_6$) δ 3.87 (s, 3H), 3.97 (s, 3H), 4.12 (br s, 2H), 6.72 (d, J=7.9 Hz, 1H), 7.04 (dd, J=8.8, 2.4 Hz, 1H), 7.31 (d, J=2.4 Hz, 1H), 7.40 (dd, J=7.9, 1.2, Hz 1H), 7.56 (d, J=1.2 Hz, 1H), 7.87 (d, J=8.8 Hz, 1H); $^{13}$C NMR (62.5 MHz, CDCl$_3$) δ 55.74, 55.81, 104.33, 108.55, 114.06, 115.09, 121.48, 122.93, 124.12, 135.95, 139.17, 147.12, 148.76, 157.27, 166.46.

4-(1,3-Benzothiazol-2-yl)-3-[2-(dimethylamino)ethoxy]aniline

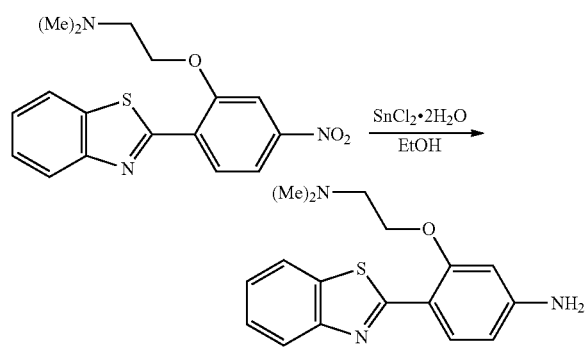

Prepared as described in the Nitro Reduction section using 2-[2-(1,3-benzothiazol-2-yl)-5-nitrophenoxy]-N,N-dimethylethanamine (0.073 g, 0.21 mmol) and tin (II) dichloride dihydrate (0.38 g, 1.7 mmol) in EtOH (7 ml) to give the title compound (0.05 g, 75%) as a cream-coloured solid after work-up and flash chromatography (MeOH).

$^1$H NMR (400 MHz, CDCl$_3$) δ 2.36 (s, 6H), 2.94 (t, J=6.5 Hz, 2H), 3.98 (br s, 2H), 4.21 (t, J=6.5 Hz, 2H), 6.25 (d, J=2.4 Hz, 1H), 6.37 (dd, J=8.5, 2.4 Hz, 1H), 7.24-7.28 (m, 1H), 7.37-7.41 (s, 1H), 7.84 (d, J=8.2 Hz, 1H), 7.95 (d, J=8.2 Hz, 1H), 8.29 (d, J=8.5 Hz, 1H); $^{13}$C NMR (62.5 MHz, CDCl$_3$) δ 46.15, 58.05, 67.52, 98.25, 108.03, 113.26, 120.95, 121.93, 123.72, 125.59, 130.97, 135.46, 150.21, 152.18, 158.04, 163.74.

4-(1,3-Benzothiazol-2-yl)-3-[2-{2-(2-methoxyethoxy)ethoxy}ethoxy]aniline

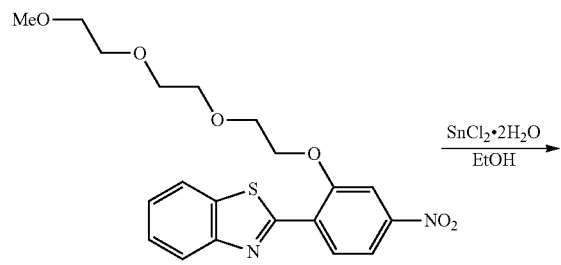

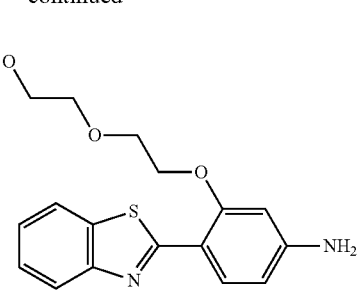

Prepared as described in the Nitro Reduction section using 2-[2-{2-(2-methoxyethoxy)ethoxy)ethoxy}-4-nitrophenyl]-1,3-benzothiazole (0.15 g, 0.36 mmol) and tin (II) dichloride dihydrate (0.65 g, 2.87 mmol) in EtOH (12 to give the title compound (0.13 g, 92%) as a viscous, yellow oil after work-up and flash chromatography (EtOAc).

$^1$H NMR (250 MHz, CDCl$_3$) δ 3.30 (s, 3H), 3.47-3.49 (m, 2H), 3.59-3.62 (m, 2H), 3.62-3.65 (m, 2H), 3.73-3.75 (m, 2H), 3.95-3.97 (m, 2H), 4.10-4.28 (m, 4H), 6.19 (s, 1H), 6.33 (d, J=8.5 Hz, 1H), 7.23-7.29 (m, 1H), 7.37-7.43 (m, 1H), 7.84 (d, J=7.9 Hz, 1H), 7.96 (d, J=7.9 Hz, 1H), 8.27 (d, J=8.5 Hz, 1H); $^{13}$C NMR (62.5 MHz, CDCl$_3$) δ 58.99, 68.23, 69.55, 70.54, 70.69, 70.80, 71.89, 98.26, 108.15, 112.79, 121.05, 121.89, 123.73, 125.66, 130.81, 135.55, 150.75, 152.11, 158.09, 164.03.

2-Methoxy-5-(trifluoromethoxy)benzoic acid

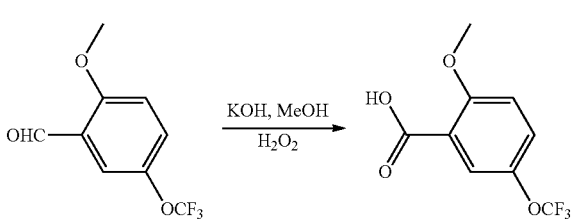 [SMILES: COc1ccc(OC(F)(F)F)cc1C=O ; "H2O2" ; COc1ccc(OC(F)(F)F)cc1C(=O)O]

To a stirred solution of 2-methoxy-5-trifluoromethoxybenzaldehyde (2.0 g, 9.09 mmol) and 50% KOH (4.1 ml) in MeOH (15 ml) at 65° C. was added dropwise hydrogen peroxide (30%, 7.4 ml) over 20 min. The reaction mixture was then stirred at 65° C. for 10 min., cooled to room temperature, acidified with 1 M HCl, and extracted with Et$_2$O (3×40 ml). The combined organic extracts were washed with brine (35 ml), dried (Na$_2$SO$_4$) and the solvent removed under reduced pressure to give a pale yellow viscous oil which solidified at room temperature overnight to give the title compound (1.95 g, 91%) as a pale yellow solid.

$^1$H NMR (250 MHz, CDCl$_3$) δ 4.07 (s, 3H), 7.07 (d, J=9.2 Hz, 1H), 7.41 (dd, J=9.2, 2.1 Hz, 1H), 7.99 (d, J=2.1 Hz, 1H), 8.80-11.0 (vbr s, 1H); $^{13}$C NMR (100.5 MHz, DMSO-$d_6$) δ 57.22, 113.13, 118.95, 120.41 (q, $J_{CF}$=258 Hz), 126.20, 127.83, 143.22, 156.68, 164.82.

The oxidation of aromatic aldehydes to aromatic acids is described by Cong et al.

4-(2,2,2-Trifluoroethoxy)benzaldehyde

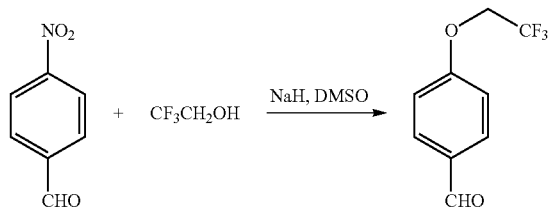

To a stirred suspension of sodium hydride (60% dispersion in mineral oil, 0.87 g, 21.8 mmol) in DMSO (20 ml) was added trifluoroethanol (3.97 g, 39.7 mmol) at 10-15° C. under an atmosphere of argon. The reaction mixture was stirred at this temperature for 20 min then 4-nitrobenzaldehyde (3.0 g, 19.85 mmol) was added in one portion. The reaction mixture was stirred at 10-15° C. for 3 h then at room temperature for 60 h. Brine (100 ml) was added cautiously to the reaction mixture followed by extraction with $Et_2O$ (3×70 ml). The combined organic extracts were washed with water, dried ($MgSO_4$) and the solvent removed under reduced pressure to give an oil which was purified by flash chromatography (3:1 Hexane/EtOAc) to give a yellow oil which solidified on standing at room temperature to give the title compound (1.76 g, 43%) as a yellow solid.

$^1$H NMR (250 MHz, $CDCl_3$) δ 4.42 (q, J=7.9 Hz, 2H), 7.04 (d, J=8.5 Hz, 2H), 7.85 (d, J=8.5 Hz, 2H); $^{13}$C NMR (62.5 MHz, $CDCl_3$) δ 65.5 (q, $J_{CF}$=36 Hz), 115.02, 123.02 (q, $J_{CF}$=277 Hz), 131.34, 132.01, 161.82, 190.62.

The experimental data agreed with those reported previously by Idoux et al. (1983) and Idoux et al. (1985).

4-(2,2,2-Trifluoroethoxy)benzoic acid

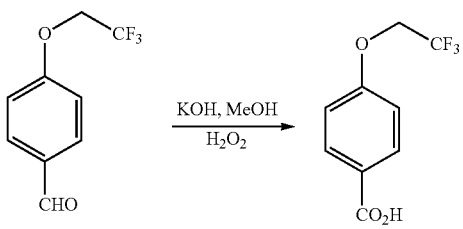 [SMILES: O=Cc1ccc(OCC(F)(F)F)cc1 ; "H2O2" ; O=C(O)c1ccc(OCC(F)(F)F)cc1]

To a stirred solution of 50% w/v KOH (1.2 ml) and 4-(2,2,2-trifluoroethoxy)-benzaldehyde (0.6 g, 2.94 mmol) in MeOH (5 ml) at 65° C. was added dropwise over 20 min aqueous hydrogen peroxide (30 wt. % in water, 2.4 ml). On completion of the addition the reaction mixture was heated at 65° C. for a further 10 min. On cooling to room temperature, the reaction mixture was acidified with 1 M HCl and extracted with $Et_2O$ (3×30 ml). The combined organic extracts were washed with brine (20 ml), dried ($Na_2SO_4$) and the solvent removed under reduced pressure to give the title compound (0.59 g, 91%) as a pale yellow solid which was used without further purification.

$^1$H NMR (250 MHz, acetone-$d_6$) δ 4.80 (q, J=7.9 Hz, 2H), 7.18 (d, J=8.5 Hz, 2H), 8.05 (d, J=8.5 Hz, 2H); $^{13}$C NMR (62.5 MHz, acetone-$d_6$) δ 66.34 (q, $J_{CF}$=35 Hz), 115.36, 124.72 (q, $J_{CF}$=277 Hz), 125.31, 132.78, 161.79, 167.00.

The reaction conditions employed were based on the methods described by Cong et al.

4-(3,3,3-Trifluoropropoxy)benzaldehyde

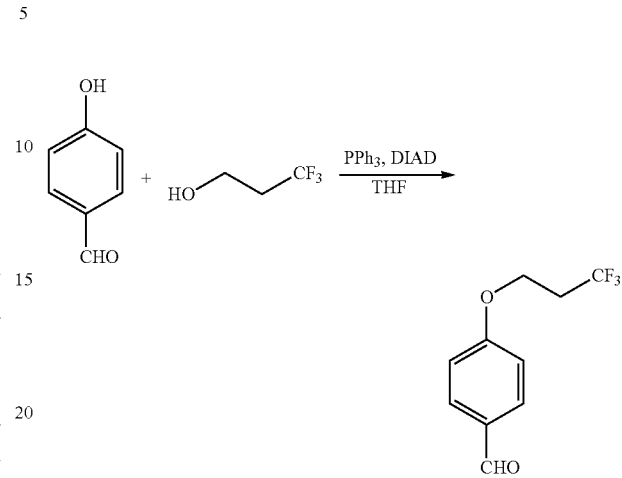

To a stirred solution of 4-hydroxybenzaldehyde (0.36 g, 2.93 mmol), 3,3,3-trifluoropropanol (0.5 g, 4.39 mmol) and triphenylphosphine (1.15 g, 4.39 mmol) in dry THF (10 ml) at 0° C. under an atmosphere of argon was added dropwise diisopropylazodicarboxylate (0.89 g, 4.39 mmol). On completion of the addition, the reaction mixture was stirred at room temperature for 60 h. The solvent was removed under reduced pressure and the residue was purified by flash chromatography (4:1 Hexane/EtOAc) to give the title compound (0.25 g, 46%) as a colourless solid.

$^1$H NMR (250 MHz, $CDCl_3$) δ 2.57-2.75 (m, 2H), 4.27 (t, J=6.4 Hz, 2H), 6.99 (d, J=8.5 Hz, 2H), 7.84 (d, J=8.5 Hz, 2H), 9.89 (s, 1H); $^{13}$C NMR (62.5 MHz, $CDCl_3/DMSO-d_6$) 33.82 (q, $J_{CF}$=28.3 Hz), 60.87, 113.87, 123.91, 125.79 (q, $J_{CF}$=276 Hz), 131.78, 161.50, 168.12.

The reaction conditions employed were based on the methods described by Malamas et al. and Mann et al.

4-(3,3,3-Trifluoropropoxy)benzoic acid

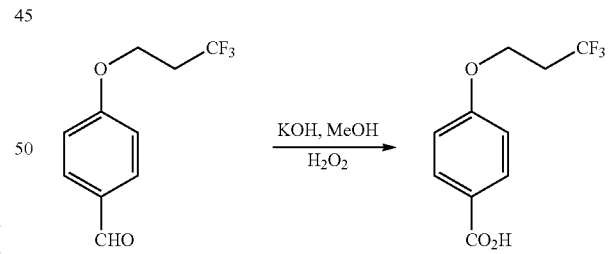

To a stirred solution of 50% w/v KOH (0.8 ml) and 4-(3,3,3-trifluoropropoxy)benzaldehyde (0.4 g, 1.83 mmol) in MeOH (4 ml) at 65° C. was added dropwise over 20 min aqueous hydrogen peroxide (30 wt. % in water, 1.5 ml). On completion of the addition the reaction mixture was heated at 65° C. for a further 10 min. On cooling to room temperature, the reaction mixture was acidified with 1 M HCl and extracted with $Et_2O$ (3×25 ml). The combined organic extracts were washed with brine (25 ml), dried ($Na_2SO_4$) and the solvent removed under reduced pressure to give the title compound (0.36 g, 83%) as a colourless solid which was used without further purification.

$^1$H NMR (250 MHz, CDCl$_3$/DMSO-d$_6$) δ 2.42-2.60 (m, 2H), 4.10 (t, J=6.4 Hz, 2H), 6.76 (d, J=8.8 Hz, 2H), 7.85 (d, J=8.8 Hz, 2H); $^{13}$C NMR (62.5 MHz, CDCl$_3$/DMSO-d$_6$) δ 33.71 (q, J$_{CF}$=29.3 Hz), 60.80, 113.83, 123.84, 125.78 (q, J$_{CF}$=276 Hz), 131.67, 161.42, 167.92.

Ethyl 4-(4,4,4-trifluorobutoxy)benzoate

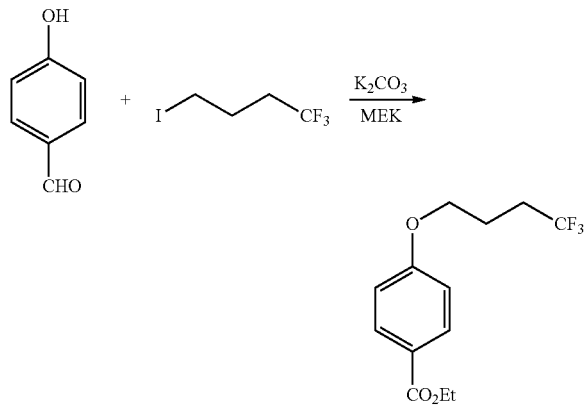

A mixture of ethyl 4-hydroxybenzoate (0.46 g, 2.80 mmol), 1-iodo-4,4,4-trifluorobutane (0.67 g, 2.80 mmol) and anhydrous K$_2$CO$_3$ (1.16 g, 8.40 mmol) in methyl ethyl ketone (5 ml) was heated under reflux for 4 h under an atmosphere of argon. On cooling to room temperature, the solvent was removed under reduced pressure and the residue was partitioned between water (15 ml) and Et$_2$O (30 ml). The organic layer was separated, and the aqueous phase extracted with Et$_2$O (2×20 ml). The combined organic extracts were washed with brine (15 ml) and dried (Na$_2$SO$_4$). The solvent was removed under reduced pressure to give a solid which was purified by flash chromatography (3:1 Hexane/EtOAc) to give the title compound (0.67 g, 87%) as a colourless solid.

$^1$H NMR (250 MHz, CDCl$_3$) δ 1.36 (t, J=7.0 Hz, 3H), 2.00-2.11 (m, 2H), 2.21-2.40 (m, 2H), 4.05 (t, J=5.8 Hz, 2H), 4.33 (q, J=7.0 Hz, 2H), 6.88 (d, J=8.8 Hz, 2H), 7.98 (d, J=8.8 Hz, 2H); $^{13}$C NMR (62.5 MHz, CDCl$_3$) δ 14.36, 22.09 (q, J$_{CF}$=2.9 Hz), 30.67 (q, J$_{CF}$=29 Hz), 60.70, 66.15, 113.95, 123.30, 127.06 (q, J$_{CF}$=276 Hz), 131.61, 162.22, 166.31.

The reaction conditions employed were based on the methods described by Pez et al. for the alkylation of 4-hydroxybenzaldehyde with iodoalkanes.

4-(4,4,4-Trifluorobutoxy)benzoic acid

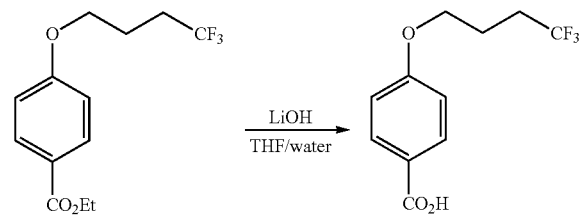 [SMILES: CCOC(=O)c1ccc(OCCCC(F)(F)F)cc1 ; "LiOH" ; O=C(O)c1ccc(OCCCC(F)(F)F)cc1]

To a stirred solution of ethyl 4-(4,4,4-trifluorobutoxy)benzoate (0.60 g, 2.17 mmol) in THF/water (3:1 v/v, 15 ml) at room temperature was added LiOH (0.11 g, 4.34 mmol) in one portion. The reaction mixture was stirred at room temperature for 18 h, then EtOH (15 ml) was added to give a clear solution and stirring was continued for 48 h. The solvents were removed under reduced pressure and to the residue was added water (30 ml). This was extracted with DCM (30 ml) and the aqueous phase was then acidified with 1 M HCl and extracted with EtOAc (3×30 ml). The combined organic extracts were washed with brine (30 ml) and dried (Na$_2$SO$_4$). The solvent was removed under reduced pressure to give the title compound (0.51 g, 95%) as a colourless solid which was used without further purification.

$^1$H NMR (250 MHz, acetone-d$_6$) δ 2.03-2.14 (m, 2H), 2.37-2.56 (m, 2H), 4.21 (t, J=5.8 Hz, 2H), 7.05 (d, J=8.8 Hz, 2H), 7.99 (d, J=8.8 Hz, 2H); $^{13}$C NMR (62.5 MHz, CDCl$_3$/DMSO-d$_6$) δ 21.88 (q, J$_{CF}$=1.9 Hz), 30.41 (q, J$_{CF}$=29 Hz), 65.93, 113.77, 123.39, 127.00 (q, J$_{CF}$=276 Hz), 131.65, 161.98, 168.03.

4-(2-Fluoroethoxy)benzaldehyde

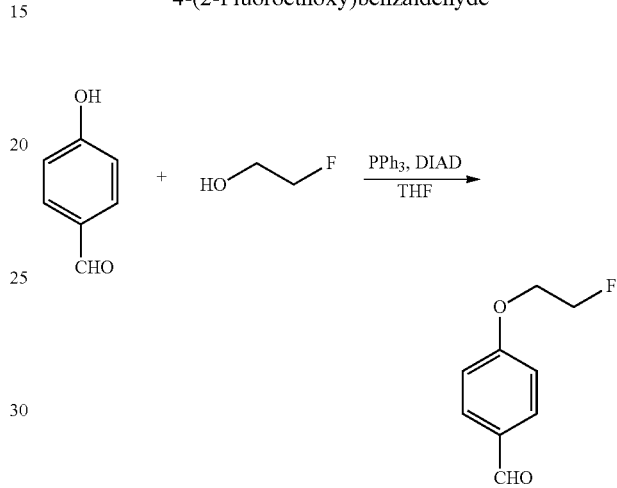

To a mixture of 4-hydroxybenzaldehyde (1.45 g, 11.9 mmol), triphenylphosphine (6.87 g, 26.2 mmol) and 2-fluoroethanol (1.68 g, 26.2 mmol) in dry THF (70 ml) at 0° C., was added DIAD (5.29 g, 26.2 mmol) dropwise. The reaction mixture was stirred at 0° C. for 1 h then allowed to rise to room temperature and stirred for 48 h. The solvent was removed under reduced pressure and the residue was purified by flash chromatography (5:1 DCM/Hexane) to give the title compound (0.807 g, 40%) as a colourless solid.

$^1$H NMR (250 MHz, CDCl$_3$) δ 4.28 (dist d of t, J$_{HF}$=28 Hz, J$_{HH}$=4.0 Hz, 2H), 4.77 (dist d of t, J$_{HF}$=47 Hz, J$_{HH}$=4.0 Hz, 2H), 7.01 (d, J=8.8 Hz, 2H), 7.83 (d, J=8.8 Hz, 2H), 9.87 (s, 1H); $^{13}$C NMR (62.5 MHz, CDCl$_3$) δ 67.33 (d, J$_{CF}$=19.5 Hz), 81.59 (d, J$_{CF}$=172 Hz), 114.85, 130.38, 132.06, 163.36, 190.86.

The reaction conditions employed were based on the methods described by Malamas et al. and Mann et al.

4-(2-Fluoroethoxy)benzoic acid

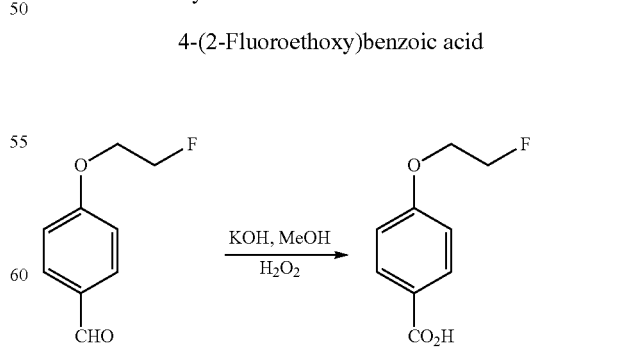

To a stirred solution of 50% w/v KOH (1.3 ml) and 4-(2-fluoroethoxy)benzaldehyde (0.5 g, 2.98 mmol) in MeOH (6 ml) at 65° C. was added dropwise over 20 min aqueous hydrogen peroxide (30 wt. % in water, 2.45 ml). On completion of the addition the reaction mixture was heated at 65° C. for a further 10 min. On cooling to room temperature, the reaction mixture was acidified with 1 M HCl and extracted with Et$_2$O (3×30 ml). The combined organic extracts were washed with brine (30 ml), dried (Na$_2$SO$_4$) and the solvent removed under reduced pressure to give a solid which was purified by flash chromatography (1:1 Hexane/EtOAc) to give the title compound (0.278 g, 63%) as a colourless solid.

$^1$H NMR (250 MHz, CDCl$_3$/DMSO-d$_6$) δ 4.09 (dist d of t, J$_{HF}$=28 Hz, J$_{HH}$=3.0 Hz, 2H), 4.59 (dist d of t, J$_{HF}$=47 Hz, J$_{HH}$=3.0 Hz, 2H), 6.76 (d, J=8.2 Hz, 2H), 7.82 (d, J=8.2 Hz, 2H); $^{13}$C NMR (62.5 MHz, CDCl$_3$/DMSO-d$_6$) δ 67.06 (d, J$_{CF}$=19.5 Hz), 81.64 (d, J$_{CF}$=170 Hz), 113.94, 123.73, 131.73, 161.82, 168.08.

The reaction conditions employed were based on the methods described by Gong et al. for the oxidation of aromatic aldehydes to aromatic acids.

Benzothiazole Compounds
Non-Fluorinated Methoxy-Amides

2-Nitro-N-[4-(6-methoxybenzothiazol-2-yl)-phenyl]-benzamide

Book No.: SKT01-13

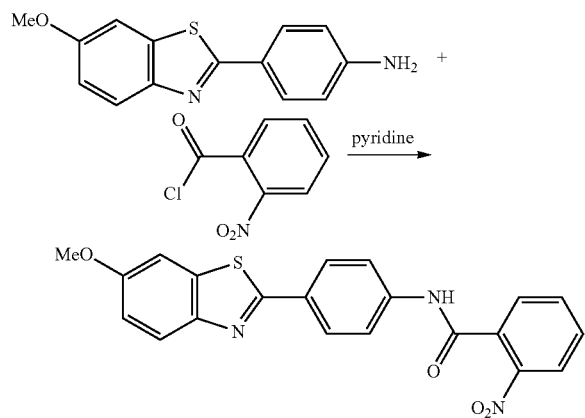

Prepared as described in the Amide Coupling section above.

$^1$H NMR (250 MHz, CDCl$_3$/DMSO-d$_6$) δ 3.15 (s, 3H), 6.34 (dd, J=8.8, 1.8 Hz, 1H), 6.74 (d, J=1.8 Hz, 1H), 6.96-7.02 (m, 2H), 7.07-7.15 (m, 4H), 7.27 (d, J=8.5 Hz, 2H), 7.40 (d, J=8.5 Hz, 1H), 10.08 (s, 1H); $^{13}$C NMR (62.5 MHz, CDCl$_3$/DMSO-d$_6$) δ 55.26, 103.91, 115.21, 119.54, 122.79, 123.72, 127.17, 128.52, 128.87, 130.26, 132.52, 133.38, 135.61, 140.78, 146.08, 147.91, 157.09, 163.98, 164.10 (split carbonyl).

3-Nitro-N-[4-(6-methoxybenzothiazol-2-yl)-phenyl]-benzamide

Book No.: SKT01-23

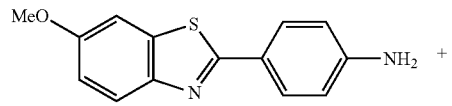

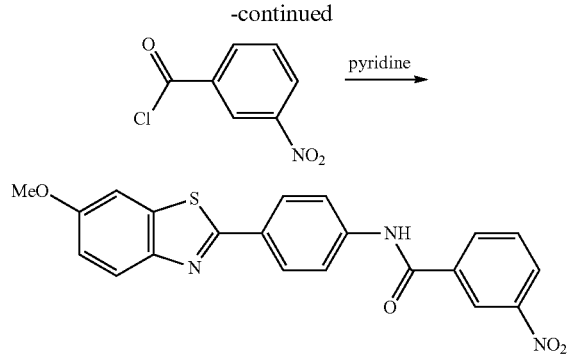

Prepared as described in the Amide Coupling section above using 2-(4-aminophenyl)-6-methoxybenzothiazole (0.25 g, 0.98 mmol) and 3-nitrobenzoyl chloride (0.20 g, 1.07 mmol) in dry pyridine (15 ml) to give the title compound (0.38 g, 96%) as a colourless solid after work-up.

$^1$H NMR (250 MHz, CDCl$_3$/DMSO-d$_6$) δ 3.22 (s, 3H), 6.41 (dd, J=8.8, 1.8 Hz, 1H), 6.79 (d, J=1.8 Hz, 1H), 7.10 (t, J=7.9 Hz, 1H), 7.21 (d, J=8.8 Hz, 1H), 7.34 (m, 4H), 7.74 (d, J=8.8 Hz, 1H), 7.78 (d, J=8.8 Hz, 1H), 8.29 (br s, 1H), 10.01 (s, 1H); $^{13}$C NMR (62.5 MHz, CDCl$_3$/DMSO-d$_6$) δ 55.31, 103.89, 115.24, 120.38, 122.37, 122.82, 125.69, 127.07, 128.70, 129.31, 133.92, 135.69, 135.92, 140.74, 147.52, 147.97, 157.15, 163.19, 164.13.

4-Nitro-N-[4-(6-methoxybenzothiazol-2-yl)-phenyl]-benzamide

Book No.: SKT01-9

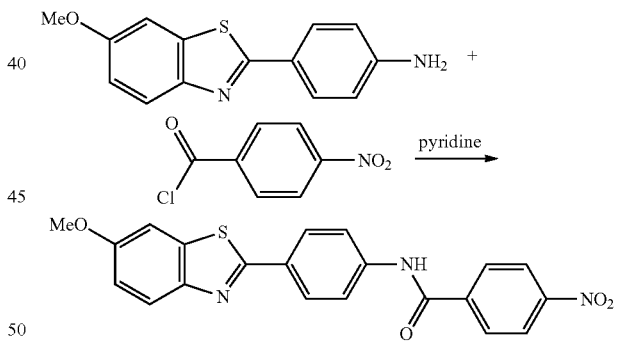

Prepared as described in the Amide Coupling section above using 2-(4-aminophenyl)-6-methoxybenzothiazole (0.30 g, 1.17 mmol) and 4-nitrobenzoyl chloride (0.24 g, 1.29 mmol) in dry pyridine (15 ml) to give the title compound (0.369 g, 78%) as fine yellow needles after work-up and recrystallisation from 1,2-dichloroethane.

$^1$H NMR (250 MHz, CDCl$_3$/DMSO-d$_6$) δ 3.15 (s, 3H), 6.34 (dd, J=8.8, 1.8 Hz, 1H), 6.73 (d, J=1.8 Hz, 1H), 7.13 (d, J=8.8 Hz, 1H), 7.26 (m, 4H), 7.51 (d, J=8.5 Hz, 2H), 7.60 (d, J=8.8 Hz, 2H), 9.92, (s, 1H); $^{13}$C NMR (62.5 MHz, CDCl$_3$/DMSO-d$_6$) δ 55.25, 103.89, 115.23, 120.26, 122.79, 122.90, 127.01, 128.64, 128.87, 135.63, 140.02, 140.69, 147.91, 148.90, 157.09, 163.59, 163.99.

2-Amino-N-[4-(6-methoxybenzothiazol-2-yl)-phenyl]-benzamide

Book No.: SKT01-99

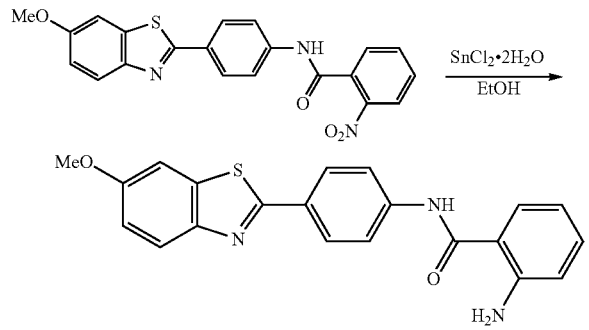

Prepared as described in the Nitro Reduction section using 3-nitro-N-[4-(6-methoxybenzo thiazol-2-yl)-phenyl]-benzamide (0.33 g, 0.81 mmol) and tin (II) chloride dihydrate (1.47 g, 6.51 mmol) in EtOH (20 ml) give the title compound (0.24 g, 79%) as a pale yellow solid after work-up.

$^1$H NMR (400 MHz, DMSO-d$_6$) δ 3.79 (s, 3H), 5.30 (s, 2H), 6.71 (dd, J=7.9, 2.1 Hz, 1H), 7.02-7.08 (m, 3H), 7.09-7.13 (m, 1H), 7.64 (d, J=2.7 Hz, 1H), 7.86 (d, J=8.8 Hz, 1H), 7.91 (d, J=8.8 Hz, 2H), 7.96 (d, J=8.8 Hz, 2H), 10.31 (s, 1H); $^{13}$C NMR (62.5 MHz, CDCl$_3$/DMSO-d$_6$) δ 55.32, 103.89, 113.42, 115.19, 115.85, 117.31, 119.95, 122.79, 127.06, 128.00, 128.56, 135.64, 141.51, 147.33, 147.46, 148.02, 157.09, 164.41, 166.56.

4-Amino-N-[4-(6-methoxybenzothiazol-2-yl)-phenyl]-benzamide

Book No.: SKT01-21

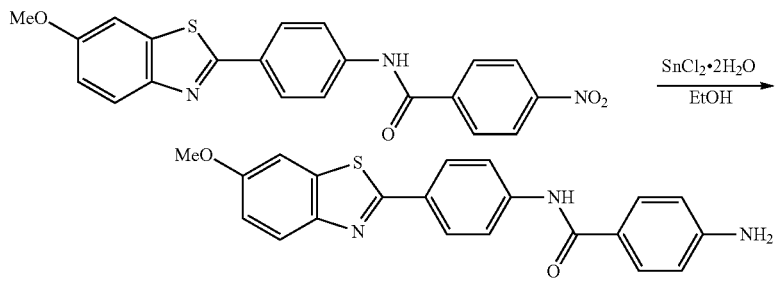

Prepared as described in the Nitro Reduction section above.

$^1$H NMR (250 MHz, CDCl$_3$/DMSO-d$_6$) δ 3.31 (s, 3H), 6.08 (t, J=7.6 Hz, 1H), 6.21 (d, J=8.2 Hz, 1H), 6.50 (dd, J=8.8, 2.1 Hz, 1H), 6.64 (t, J=7.6 Hz, 1H), 6.84 (d, J=2.1 Hz, 1H), 7.10 (d, J=7.9 Hz, 1H), 7.30 (d, J=9.1 Hz, 1H), 7.35 (d, J=8.8 Hz, 2H), 7.41 (d, J=8.8 Hz, 2H), 9.51 (s, 1H); $^{13}$C NMR (62.5 MHz, CDCl$_3$/DMSO-d$_6$) δ 55.39, 103.92, 115.149, 115.211, 115.47, 116.55, 120.23, 122.85, 127.10, 128.07, 128.58, 132.07, 135.74, 141.50, 148.13, 149.21, 157.15, 164.57, 168.03.

Prepared as described in the Nitro Reduction section using 4-nitro-N-[4-(6-methoxybenzothiazol-2-yl)-phenyl]-benzamide (0.31 g, 0.765 mmol) and tin (II) chloride dihydrate (1.38 g, 6.12 mmol) in EtOH (5 ml) to give the title compound (0.212 g, 74%) as a pale yellow solid after work-up.

$^1$H NMR (250 MHz, DMSO-d$_6$) δ 3.84 (s, 3H), 5.84 (s, 2H), 6.61 (d, J=8.5 Hz, 2H), 7.11 (dd, J=8.8, 2.4 Hz, 1H), 7.69 (d, J=2.4 Hz, 1H), 7.75 (d, J=8.2 Hz, 2H), 7.90 (d, J=8.8 Hz, 1H), 7.96 (dist d, J=8.8 Hz, 2H), 7.99 (dist d, J=8.8 Hz, 2H), 10.06 (s, 1H); $^{13}$C NMR (100.5 MHz, DMSO-d$_6$) δ 55.18, 103.94, 112.45, 115.07, 119.65, 120.99, 122.59, 126.84, 127.26, 129.14, 135.44, 141.93, 147.85, 151.57, 156.90, 164.23, 165.36.

3-Amino-N-[4-(6-methoxybenzothiazol-2-yl)-phenyl]-benzamide

Book No.: SKT01-41

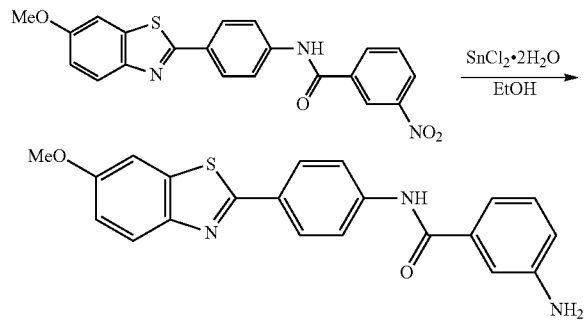

2-Dimethylamino-N-[4-(6-methoxybenzothiazol-2-yl)-phenyl]-benzamide

Book No.: SKT01-103

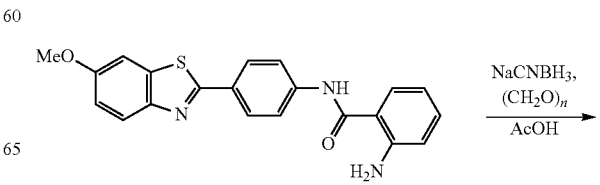

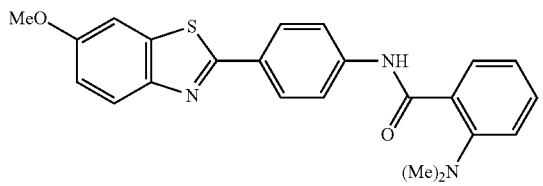

Prepared as described in the Amination section.
¹H NMR (250 MHz, CDCl₃) δ 2.84 (s, 6H), 3.87 (s, 3H), 7.08 (dd, J=8.9, 2.4 Hz, 1H), 7.27 (d, J=8.2 Hz, 1H), 7.32 (m, 2H), 7.50 (dt, J=8.5, 1.5 Hz, 1H), 7.80 (d, J=8.8 Hz, 2H), 7.92 (d, J=8.8 Hz, 1H), 8.03 (d, J=8.5 Hz, 2H), 8.28 (dd, J=7.6, 1.5 Hz, 1H), 12.57 (s, 1H); ¹³C NMR (62.5 MHz, CDCl₃) δ 45.60, 55.84, 104.20, 115.54, 120.00, 120.55, 123.47, 125.32, 127.40, 128.17, 129.12, 131.75, 132.74, 135.31, 141.11, 148.78, 152.21, 157.63, 164.27, 165.28.

The dimethylation of aniline compounds is described by Ono et al.

3-Dimethylamino-N-[4-(6-methoxybenzothiazol-2-yl)-phenyl]-benzamide

Book No.: SKT01-63

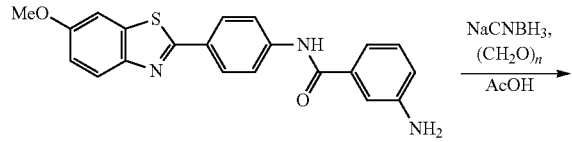

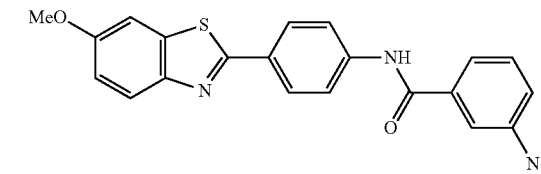

Prepared as described in the Amination section using sodium cyanoborohydride (67 mg, 1.06 mmol), 3-amino-N-[4-(6-methoxybenzothiazol-2-yl)-phenyl]-benzamide (80 mg, 0.213 mmol) and paraformaldehyde (64 mg, 2.13 mmol) in AcOH (2 ml) to give the title compound as colourless plates (53 mg, 62%) after recrystallisation from EtOH.

¹H NMR (250 MHz, CDCl₃) δ 3.02 (s, 6H), 3.88 (s, 3H), 6.91 (dd, J=8.2, 2.1 Hz, 1H), 6.78 (d, J=8.8 Hz, 2H), 7.05-7.12 (m, 2H), 7.29-7.36 (m, 3H), 7.92 (d, J=8.8 Hz, 1H), 8.03 (dist d, J=8.8 Hz, 3H); ¹³C NMR (62.5 MHz, CDCl₃) δ 40.68, 55.85, 104.20, 111.55, 114.14, 115.61, 115.96, 120.01, 123.53, 128.14, 129.46, 129.67, 135.61, 136.33, 140.25, 148.70, 150.61, 157.69, 166.48 (1 missing).

The dimethylation of aniline compounds is described by Ono et al.

4-Dimethylamino-N-[4-(6-methoxybenzothiazol-2-yl)-phenyl]-benzamide

Book No.: SKT01-61

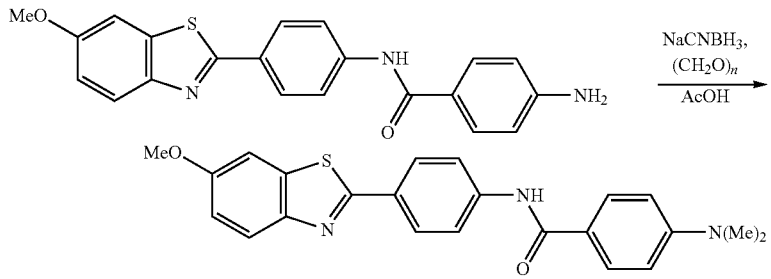

Prepared as described in the Amination section using sodium cyanoborohydride (67 mg, 1.06 mmol), 4-amino-N-[4-(6-methoxybenzothiazol-2-yl)-phenyl]-benzamide (80 mg, 0.213 mmol) and paraformaldehyde (64 mg, 2.13 mmol) in AcOH (2 ml) to give the title compound (49 mg, 57%) as colourless needles after recrystallisation from EtOH.

¹H NMR (250 MHz, CDCl₃/DMSO-d₆) δ 2.19 (s, 6H), 3.02 (s, 3H), 5.88 (d, J=8.8 Hz, 2H), 6.22 (dd, J=8.8, 2.1 Hz, 1H), 6.66 (d, J=2.1 Hz, 1H), 7.01 (d, J=8.8 Hz, 1H), 7.06 (d, J=8.8 Hz, 2H), 7.12 (m, 4H), 9.21 (s, 1H); ¹³C NMR (62.5 MHz, CDCl₃/DMSO-d₆) δ 39.41, 55.17, 103.95, 110.16, 115.09, 119.68, 120.50, 122.57, 126.82, 127.27, 128.94, 135.41, 141.85, 147.82, 151.99, 156.88, 164.18, 165.22.

4-Acetoxy-N-[4-(6-methoxybenzothiazol-2-yl)-phenyl]-benzamide

Book No.: SKT01-155

Prepared as described in the Amide Coupling section above using 2-(4-aminophenyl)-6-methoxybenzothiazole (0.25 g, 0.976 mmol) and 4-acetoxybenzoyl chloride (0.22 g, 1.07 mmol) in dry pyridine (10 ml) to give the title compound (0.385 g, 94%) as a colourless solid after work-up.

$^1$H NMR (250 MHz, DMSO-d$_6$) δ 1.55 (s, 3H), 3.10 (s, 3H), 6.30 (dd, J=9.1, 2.1 Hz, 1H), 6.46 (d, J=8.5 Hz, 2H), 6.71 (d, J=2.1 Hz, 1H), 7.09 (d, J=8.8 Hz, 1H), 7.21 (m, 4H), 7.27 (d, J=8.2 Hz, 2H), 9.66 (s, 1H); $^{13}$C NMR (62.5 MHz, CDCl$_3$/DMSO-d$_6$) δ 20.56, 55.22, 103.91, 115.15, 119.96, 121.17, 122.69, 126.95, 128.10, 128.89, 132.01, 135.55, 141.20, 147.88, 152.66, 157.01, 164.07, 164.79, 168.19.

4-Hydroxy-N-[4-(6-methoxybenzothiazol-2-yl)-phenyl]-benzamide

Book No.: SKT01-161

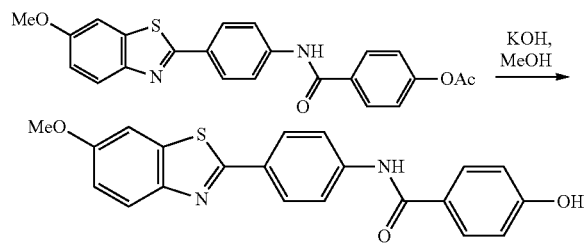

A mixture of 4-acetoxy-N-[4-(6-methoxybenzothiazol-2-yl)-phenyl]-benzamide (0.31 g, 0.74 mmol) and Na$_2$CO$_3$ (0.24 g, 2.22 mmol) in MeOH (15 ml) and water (7 ml) was stirred at room temperature for 18 h. Water (25 ml) was added to the reaction mixture followed by acidification with 1 M HCl and the precipitate was collected by filtration. Purification by flash chromatography (3:1 DCM/EtOAc) gave the title compound (0.22 g, 78%) as a colourless solid.

$^1$H NMR (250 MHz, DMSO-d$_6$) δ 3.84 (s, 3H), 6.87 (d, J=7.9 Hz, 2H), 7.10 (d, J=9.1 Hz, 1H), 7.68 (s, 1H), 7.86-7.94 (m, 3H), 7.94-8.01 (m, 4H), 10.16 (s, 1H), 10.27 (s, 1H); $^{13}$C NMR (62.5 MHz, CDCl$_3$/DMSO-d$_6$) δ 55.18, 103.91, 114.53, 115.10, 119.82, 122.62, 124.88, 126.87, 127.62, 129.39, 135.49, 141.62, 147.85, 156.93, 160.44, 164.17, 165.21.

4-Acetoxy-3-nitro-N-[4-(6-methoxybenzothiazol-2-yl)-phenyl]-benzamide

Book No.: SKT04-87

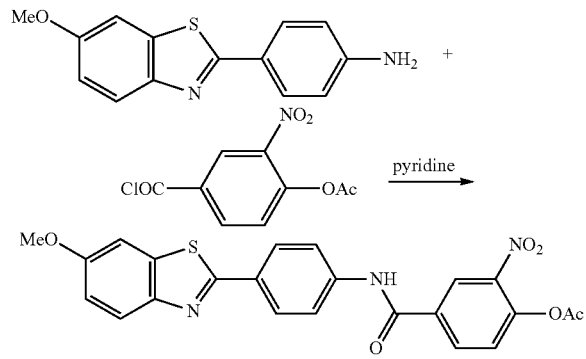

A mixture of 4-acetoxy-3-nitrobenzoic acid (0.44 g, 1.95 mmol) and thionyl chloride (5 ml) was heated under reflux for 1.5 h. The reaction mixture was cooled to room temperature and excess reagent was removed under reduced pressure to give the crude acid chloride. The amide was prepared as described in the Amide Coupling section above using the acid chloride and 2-(4-aminophenyl)-6-methoxybenzothiazole (0.50 g, 1.95 mmol) in dry THF (25 ml) containing diisopropylethylamine (0.302 g, 2.34 mmol) to give the title compound (0.728 g, 86%) as a tan-coloured solid after work-up.

$^1$H NMR (250 MHz, DMSO-d$_6$) δ 2.38 (s, 3H), 3.85 (s, 3H), 7.12 (dd, J=8.8, 2.1 Hz, 1H), 7.68 (d, J=8.8 Hz, 1H), 7.71 (d, J=2.1 Hz, 1H), 7.92 (d, J=8.8 Hz, 1H), 7.97 (d, J=8.8 Hz, 2H), 0.07 (d, J=8.8 Hz, 2H), 8.40 (dd, J=8.5, 1.8 Hz, 1H), 8.73 (d, J=1.8 Hz, 1H), 10.83 (s, 1H); $^{13}$C NMR (62.5 MHz, CDCl$_3$/DMSO-d$_6$) δ 20.44, 55.39, 103.91, 115.32, 120.43, 122.91, 125.02, 127.20, 128.84, 133.17, 134.29, 135.78, 140.72, 140.95, 145.60, 148.03, 157.24, 162.66, 164.31, 167.69 (1 missing).

4-Hydroxy-3-nitro-N-[4-(6-methoxybenzothiazol-2-yl)-phenyl]-benzamide

Book No.: SKT04-89

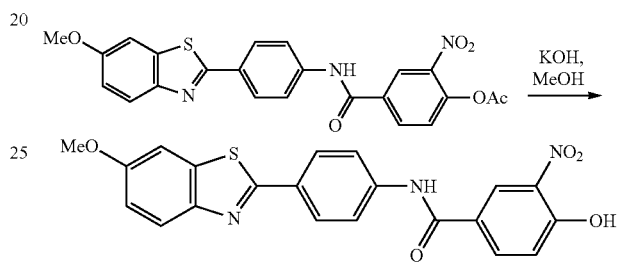

A mixture of 4-acetoxy-3-nitro-N-[4-(6-methoxybenzothiazol-2-yl)-phenyl]-benzamide (0.20 g, 0.464 mmol) and potassium hydroxide (0.081 g, 1.45 mmol) in MeOH (10 ml) was stirred vigorously at room temperature for 1.5 h. The reaction mixture was then acidified with 1 M HCl and extracted with EtOAc (3×20 ml). The combined organic extracts were washed with water (20 ml), brine (20 ml) and dried over Na$_2$SO$_4$. The solvent was removed under reduced pressure to give a solid which was purified by flash chromatography (3:2 Hexane/THF) to give the title compound (0.052 g, 29%) as a yellow solid.

$^1$H NMR (250 MHz, DMSO-d$_6$) δ 3.84 (s, 3H), 7.12 (dd, J=8.8, 1.8 Hz, 1H), 7.26 (d, J=8.8 Hz, 1H), 7.70 (d, J=1.8 Hz, 1H), 7.91 (d, J=8.8 Hz, 1H), 7.96 (d, J=8.8 Hz, 2H), 8.04 (d, J=8.8 Hz, 2H), 8.17 (dd, J=8.8, 1.8 Hz, 1H), 8.59 (d, J=1.8 Hz, 1H), 10.57 (s, 1H), 11.84 (br s, 1H); $^{13}$C NMR (62.5 MHz, CDCl$_3$/DMSO-d$_6$) δ 55.28, 103.88, 115.21, 119.15, 120.23, 122.77, 124.95, 125.49, 127.01, 128.33, 134.85, 134.94, 135.63, 141.03, 147.94, 155.36, 157.09, 163.06, 164.20.

Fluorinated Methoxy-Amides

2-Trifluoromethyl-N-[4-(6-methoxybenzothiazol-2-yl)-phenyl]-benzamide

Book No.: SK2033-50

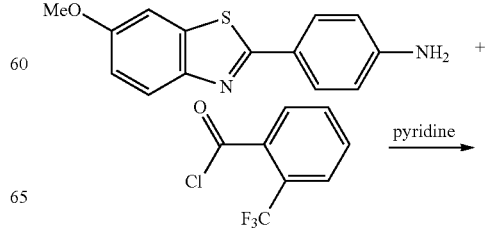

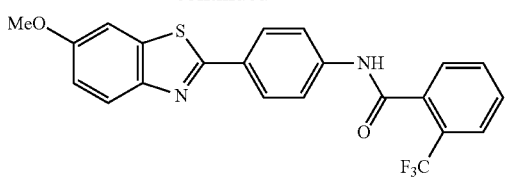

Prepared as described in the Amide Coupling section using 2-(4-aminophenyl)-6-methoxybenzothiazole (0.06 g, 0.23 mmol) and 2-trifluoromethylbenzoyl chloride (0.054 g, 0.26 mmol) in dry pyridine (7.5 ml) give the title compound (0.093 g, 93%) as a pale yellow solid after work-up.

$^1$H NMR (400 MHz, DMSO-d$_6$) δ 3.85 (s, 3H), 7.12 (dd, J=9.0, 2.0 Hz, 1H), 7.69-7.58 (m, 3H), 7.79-7.83 (m, 1H), 7.87-7.89 (m, 3H), 7.92 (d, J=8.6 Hz, 1H), 8.04 (d, J=8.2 Hz, 2H), 10.87 (s, 1H); $^{13}$C NMR (100 MHz, DMSO-d$_6$) δ 56.19, 105.32, 116.29, 120.33, 123.66, 124.23 (q, J$_{CF}$=274 Hz), 126.30 (q, J$_{CF}$=31.1 Hz), 126.86 (q, J$_{CF}$=4.6 Hz), 128.12, 128.96, 129.02, 130.71, 133.15, 136.32, 141.68, 148.53, 157.85, 164.71, 166.29 (1 missing).

3-Trifluoromethyl-N-[4-(6-methoxybenzothiazol-2-yl)-phenyl]-benzamide

Book No.: SK2033-49

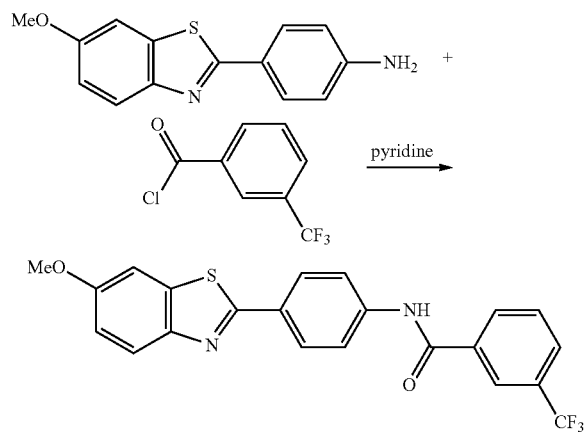

Prepared as described in the Amide Coupling section using 2-(4-aminophenyl)-6-methoxybenzothiazole (0.06 g, 0.23 mmol) and 3-trifluoromethylbenzoyl chloride (0.054 g, 0.26 mmol) in dry pyridine (7.5 ml) to give the title compound (0.085 g, 85%) as a colourless solid after work-up.

$^1$H NMR (400 MHz, DMSO-d$_6$) δ 3.84 (s, 3H), 7.11 (dd, J=9.0, 2.0 Hz, 1H), 7.69 (d, J=2.0 Hz, 1H), 7.79 (t, J=7.8 Hz, 1H), 7.91 (d, J=9.0 Hz, 1H), 7.97-7.99 (m, 3H), 8.05 (d, J=8.6 Hz, 2H), 8.29 (d, J=7.8 Hz, 1H), 8.32 (s, 1H), 10.73 (s, 1H); $^{13}$C NMR (100 MHz, DMSO-d$_6$) δ 56.18, 105.32, 116.29, 121.09, 123.64, 124.42 (q, J$_{CF}$=272.5 Hz), 124.81 (q, J$_{CF}$=3.9 Hz), 127.99, 128.79, 128.99, 129.66 (q, J$_{CF}$=32.7 Hz), 130.23, 132.42, 135.98, 136.32, 141.72, 148.53, 157.85, 164.73, 164.75.

4-Trifluoromethyl-N-[4-(6-methoxybenzothiazol-2-yl)-phenyl]-benzamide

Book No.: SK2033-47

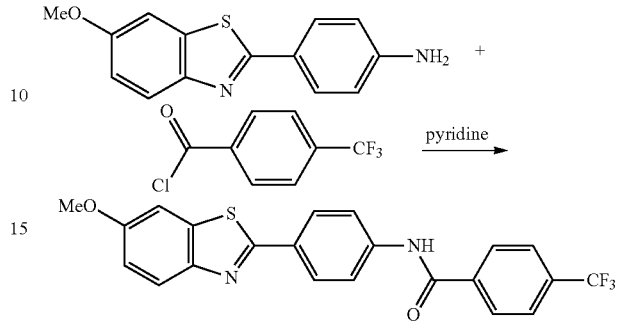

Prepared as described in the Amide Coupling section using 2-(4-aminophenyl)-6-methoxybenzothiazole (0.06 g, 0.23 mmol) and 4-trifluoromethylbenzoyl chloride (38 μl, 0.054 g, 0.26 mmol) in dry pyridine (8 ml) give the title compound (0.093 g, 93%) as a colourless solid after work-up.

$^1$H NMR (250 MHz, DMSO-d$_6$) δ 3.85 (s, 3H), 7.12 (d, J=8.8 Hz, 1H), 7.69 (s, 1H), 7.85-7.97 (m, 3H), 7.97-8.07 (m, 4H), 8.18 (d, J=7.6 Hz, 2H), 10.75 (s, 1H); $^{13}$C NMR (100 MHz, DMSO-d$_6$) δ 56.20, 105.33, 114.06, 116.31, 121.04, 123.65, 124.35 (q, J$_{CF}$=272.4 Hz), 125.91 (q, J$_{CF}$=3.9 Hz), 127.98, 128.79, 129.01, 129.17, 131.99 (q, J$_{CF}$=31.9 Hz), 136.32, 141.69, 148.51, 157.85, 164.75.

3-Trifluoromethyl-N-[4-(6-methoxy-1,3-benzothiazol-2-yl)phenyl]-4-(methoxy)benzamide Book No.: SKT04-155

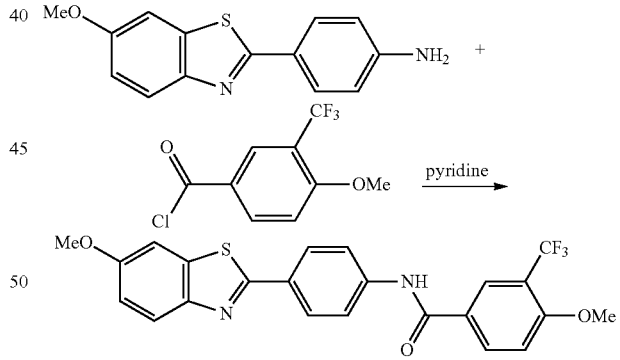

Prepared as described in the Amide Coupling section using 2-(4-aminophenyl)-6-methoxybenzothiazole (0.5 g, 1.95 mmol) and 4-methoxy-3-trifluoromethylbenzoyl chloride (0.47 g, 1.95 mmol) in dry pyridine (15 ml) to give the title compound (0.77 g, 87%) as pale yellow feathery crystals after work-up and recrystallisation from acetic acid.

$^1$H NMR (400 MHz, DMSO-d$_6$) δ 3.79 (s, 3H), 3.94 (s, 3H), 7.06 (dd, J=8.9, 2.4 Hz, 1H), 7.37 (d, J=8.9 Hz, 1H), 7.63 (d, J=2.4 Hz, 1H), 7.85 (d, J=8.9 Hz, 1H), 7.92 (d, J=8.9 Hz, 2H), 7.98 (d, J=8.9 Hz, 2H), 8.23 (s, 1H), 8.25 (d, J=8.9 Hz, 1H), 10.5 (s, 1H); $^{13}$C NMR (62.5 MHz, CDCl$_3$/DMSO-d$_6$) δ 55.46, 56.01, 103.94, 111.47, 115.33, 117.49 (q, J$_{CF}$=31.2 Hz), 120.40, 122.93, 123.12 (q, J$_{CF}$=273 Hz), 126.27, 126.87

(q, $J_{CF}$=3.9 Hz), 127.23, 128.49, 133.62, 135.81, 141.25, 148.10, 157.27, 159.55, 164.24, 164.62.

2-Trifluoromethyl-N-[4-(6-methoxy-1,3-benzothiazol-2-yl)phenyl]-4-(methoxy)benzamide Book No.: SKT05-7

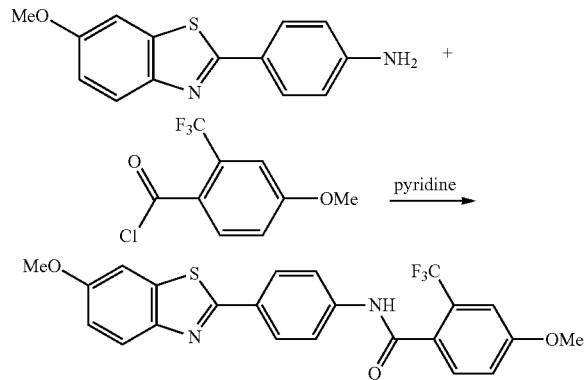

A stirred mixture of 4-methoxy-2-trifluoromethylbenzoic acid (0.50 g, 2.27 mmol) and thionyl chloride (9 ml) was heated under reflux for 4 h. After cooling to room temperature, the excess reagent was removed under reduced pressure to give crude acid chloride. The amide was prepared as described in the Amide Coupling section using the crude 4-methoxy-5-trifluoromethylbenzoyl chloride and 2-(4-aminophenyl)-6-methoxybenzo thiazole (0.58 g, 2.27 mmol) in dry pyridine (15 ml) to give the title compound (0.478 g, 46%) as pale yellow needles after work-up and recrystallisation from acetic acid.

$^1$H NMR (250 MHz, DMSO-$d_6$) δ 3.85 (s, 3H), 3.89 (s, 3H), 7.12 (dd, J=8.8, 2.4 Hz, 1H), 7.30-7.38 (m, 2H), 7.64-7.77 (m, 2H), 7.88 (d, J=8.8 Hz, 2H), 7.92 (d, J=8.8 Hz, 1H), 8.03 (d, J=8.8 Hz, 2H), 10.81 (s, 1H); $^{13}$C NMR (62.5 MHz, CDCl$_3$/DMSO-$d_6$) δ 55.35, 55.45, 103.91, 112.08 (q, $J_{CF}$=4.9 Hz), 115.26, 116.02, 119.65, 122.85, 122.99 (q, $J_{CF}$=274 Hz), 127.20, 128.04, 128.40 (q, $J_{CF}$=32 Hz), 128.45, 130.13, 135.71, 141.08, 148.02, 157.16, 159.91, 164.32, 165.64.

2-Methoxy-N-[4-(6-methoxy-1,3-benzothiazol-2-yl)phenyl]-5-(trifluoromethoxy)benzamide Book No.: SKT05-9

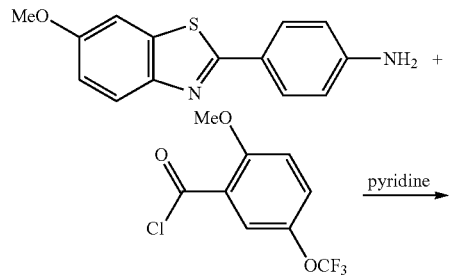

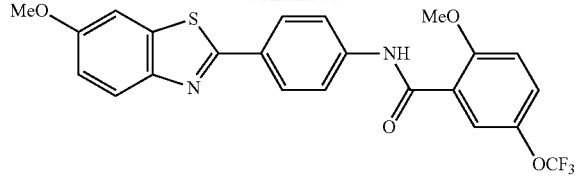

A stirred mixture of 2-methoxy-5-trifluoromethoxybenzoic acid (0.50 g, 2.12 mmol) and thionyl chloride (9 ml) was heated under reflux for 4 h. After cooling to room temperature, the excess reagent was removed under reduced pressure to give crude acid chloride. The amide was prepared as described in the Amide Coupling section using the crude acid chloride and 2-(4-aminophenyl)-6-methoxybenzothiazole (0.54 g, 2.12 mmol) in dry pyridine (15 ml) to give the title compound (0.607 g, 60%) as pale yellow crystals after recrystallisation from dioxane.

$^1$H NMR (250 MHz, DMSO-$d_6$) δ 3.85 (s, 3H), 3.91 (s, 3H), 7.12 (dd, J=8.8, 2.4 Hz, 1H), 7.29 (d, J=8.8 Hz, 1H), 7.53 (dd, J=8.8, 2.1 Hz, 1H), 7.59 (br s, 1H), 7.71 (d, J=2.4 Hz, 1H), 7.90 (d, J=8.5 Hz, 1H), 7.92 (d, J=8.8 Hz, 2H), 8.03 (d, J=8.8 Hz, 2H), 10.55 (s, 1H); $^{13}$C NMR (62.5 MHz, CDCl$_3$) δ 55.82, 56.91, 104.14, 112.80, 115.63, 120.40, 120.52 (q, $J_{CF}$=258 Hz), 122.77, 123.52, 125.33, 126.14, 128.10, 129.73, 136.33, 140.11, 143.38, 148.69, 155.50, 157.69, 161.73, 165.00.

N-[3-Trifluoromethyl-4-(6-methoxy-1,3-benzothiazol-2-yl)phenyl]-4-(methoxy)benzamide Book No.: SKT04-173

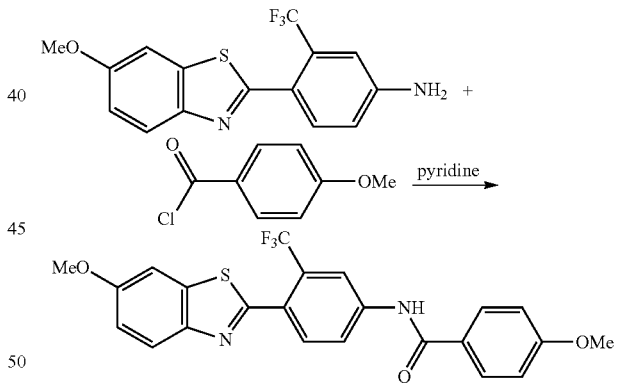

Prepared as described in the Amide Coupling section using 2-(4-amino-2-trifluoromethyl phenyl)-6-methoxybenzothiazole (0.10 g, 0.31 mmol) and 4-methoxybenzoyl chloride (0.053 g, 0.31 mmol) in dry pyridine (5 ml)° C. give the title compound (0.12 g, 85%) as a cream solid after work-up and recrystallisation from acetic acid.

$^1$H NMR (250 MHz, CDCl$_3$) δ 3.86 (s, 3H), 3.89 (s, 3H), 6.95 (d, J=8.8 Hz, 2H), 7.12 (dd, J=8.8, 2.4 Hz, 1H), 7.36 (d, J=2.4 Hz, 1H), 7.67 (d, J=8.2 Hz, 1H), 7.86 (d, J=8.8 Hz, 2H), 7.97 (d, J=8.2 Hz, 1H), 8.01 (d, J=8.8 Hz, 1H), 8.05 (s, 1H), 8.21 (s, 1H); $^{13}$C NMR (62.5 MHz, CDCl$_3$) δ 55.56, 55.88, 103.61, 114.15, 116.00, 118.11 (q, $J_{CF}$=4.9 Hz), 122.45, 123.32 (q, $J_{CF}$=274 Hz), 124.22, 126.14, 127.94, 129.15, 129.69 (q, $J_{CF}$=31 Hz), 133.36, 137.63, 139.84, 147.92, 157.99, 161.81, 162.95, 165.49.

2-Methoxy-N-[3-methoxy-4-(6-methoxy-1,3-benzothiazol-2-yl)phenyl]-5-(trifluoromethoxy)benzamide Book No.: SKT05-33

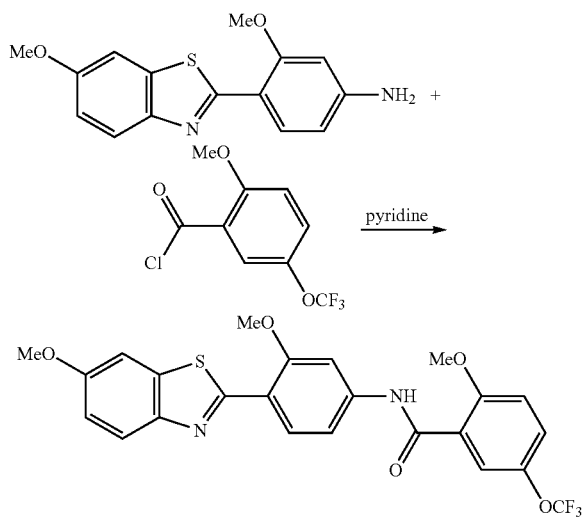

A stirred mixture of 2-methoxy-5-trifluoromethoxybenzoic acid (0.248 g, 1.05 mmol) and thionyl chloride (4 ml) was heated under reflux for 4 h. After cooling to room temperature, the excess reagent was removed under reduced pressure to give the crude acid chloride. The amide was prepared as described in the Amide Coupling section using the crude acid chloride and 3-methoxy-4-(6-methoxy-1,3-benzothiazol-2-yl)aniline (0.30 g, 1.05 mmol) in dry pyridine (8 ml) to give the title compound (0.389 g, 73%) as an almost colourless solid after work-up and recrystallisation from acetic acid.

$^1$H NMR (400 MHz, DMSO-d$_6$) δ 3.79 (s, 3H), 3.88 (s, 3H), 3.98 (s, 3H), 7.06 (dd, J=8.8, 2.4 Hz, 1H), 7.25 (d, J=8.8 Hz, 1H), 7.41 (dd, J=8.8, 2.4 Hz, 1H), 7.49 (dd, J=8.8, 2.4 Hz, 1H), 7.55 (d, J=2.4 Hz, 1H), 7.61 (d, J=2.4 Hz, 1H), 7.76 (d, J=2.4 Hz, 1H), 7.85 (d, J=8.8 Hz, 1H), 8.29 (d, J=8.8 Hz, 1H), 10.48 (s, 1H); $^{13}$C NMR (62.5 MHz, CDCl$_3$) δ5.79 (2×C), 56.89, 103.46, 103.63, 112.26, 112.80, 115.41, 118.37, 120.51 (q, J$_{CF}$=258 Hz), 122.68, 123.00, 125.21, 126.20, 129.23, 137.29, 141.02, 143.34, 146.78, 155.52, 157.21, 157.72, 160.59, 161.85.

2-Trifluoromethyl-N-[3-methoxy-4-(6-methoxy-1,3-benzothiazol-2-yl)phenyl]-4-(methoxy)benzamide Book No.: SKT05-31

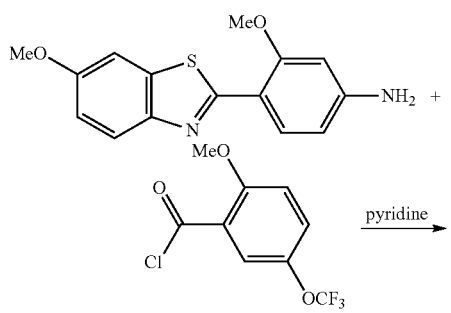

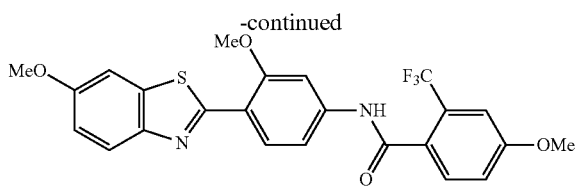

A stirred mixture of 4-methoxy-2-trifluoromethylbenzoic acid (0.23 g, 1.05 mmol) and thionyl chloride (4 ml) was heated under reflux for 3 h. After cooling to room temperature, the excess reagent was removed under reduced pressure to give the crude acid chloride. The amide was prepared as described in the Amide Coupling section using the crude acid chloride and 3-methoxy-4-(6-methoxy-1,3-benzothiazol-2-yl)aniline (0.30 g, 1.05 mmol) in dry pyridine (8 ml) to give the title compound (0.398 g, 78%) as very pale yellow feathery crystals after work-up and recrystallisation from acetic acid.

$^1$H NMR (250 MHz, CDCl$_3$/DMSO-d$_6$) δ 3.49 (s, 3H), 3.51 (s, 3H), 3.67 (s, 3H), 6.67 (d, J=8.8 Hz, 1H), 6.76 (d, J=8.5 Hz, 1H), 6.86 (s, 1H), 6.95 (d, J=8.8 Hz, 1H), 6.99 (s, 1H), 7.22 (d, J=8.8 Hz, 1H), 7.46 (s, 1H), 7.49 (d, J=8.8 Hz, 1H), 7.97 (d, J=8.5 Hz, 1H), 9.98 (s, 1H); $^{13}$C NMR (62.5 MHz, CDCl$_3$/DMSO-d$_6$) δ 55.49 (2×C), 55.57, 102.90, 103.22, 112.10, 112.28 (q, J$_{CF}$=5 Hz), 115.19, 116.06, 117.32, 122.55, 123.14 (q, J$_{CF}$=274 Hz), 128.19, 128.76 (q, J$_{CF}$=32 Hz), 128.84, 130.29, 136.76, 142.15, 146.17, 156.90, 157.13, 160.13, 160.25, 166.00.

2-Trifluoromethyl-N-[2-methoxy-4-(6-methoxy-1,3-benzothiazol-2-yl)phenyl]-4-(methoxy)benzamide Book No.: SKT05-21

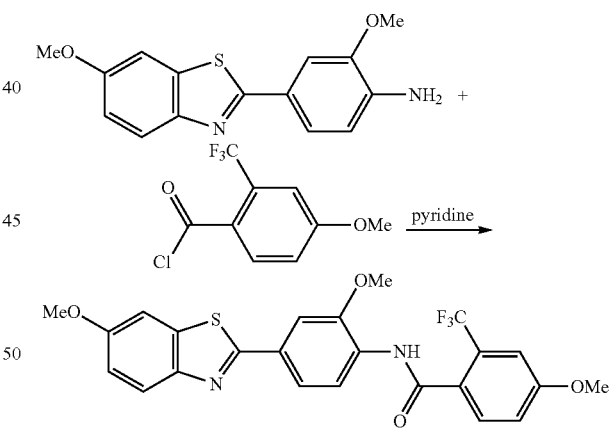

A stirred mixture of 4-methoxy-2-trifluoromethylbenzoic acid (0.15 g, 0.69 mmol) and thionyl chloride (4 ml) was heated under reflux for 3.5 h. After cooling to room temperature, the excess reagent was removed under reduced pressure to give the crude acid chloride. The amide was prepared as described in the Amide Coupling section using the crude acid chloride and 3-methoxy-4-(6-methoxy-1,3-benzothiazol-2-yl)aniline (0.20 g, 0.69 mmol) in dry pyridine (5 ml) to give the title compound (0.13 g, 38%) as a pale yellow solid after work-up and flash chromatography (2:1 Hexane/EtOAc).

$^1$H NMR (400 MHz, DMSO-d$_6$) δ 3.81 (s, 3H), 3.84 (s, 3H), 3.90 (s, 3H), 7.08 (dd, J=8.8, 2.4 Hz, 1H), 7.25-7.27 (m, 2H), 7.57 (d, J=8.2 Hz, 1H), 7.61 (d, J=8.5 Hz, 1H), 7.65 (d,

J=8.2 Hz, 1H), 7.65 (d, J=8.8 Hz, 1H), 7.90 (d, J=8.8 Hz, 1H), 8.13 (d, J=8.2 Hz, 1H), 9.73 (s, 1H); $^{13}$C NMR (62.5 MHz, CDCl$_3$/DMSO-d$_6$) δ 55.40, 55.46, 55.74, 103.92, 108.01, 112.32 (q, J$_{CF}$=3.9 Hz), 115.23, 116.33, 119.81, 120.16, 122.88, 122.97 (q, J$_{CF}$=273 Hz), 127.40, 128.14 (q, J$_{CF}$=32 Hz), 129.23, 129.37, 130.21, 135.75, 147.79, 148.81, 157.24, 160.13, 164.34, 165.31.

3-Trifluoromethyl-N-[2-methoxy-4-(6-methoxy-1,3-benzothiazol-2-yl)phenyl]-4-(methoxy)benzamide Book No.: SKT04-175

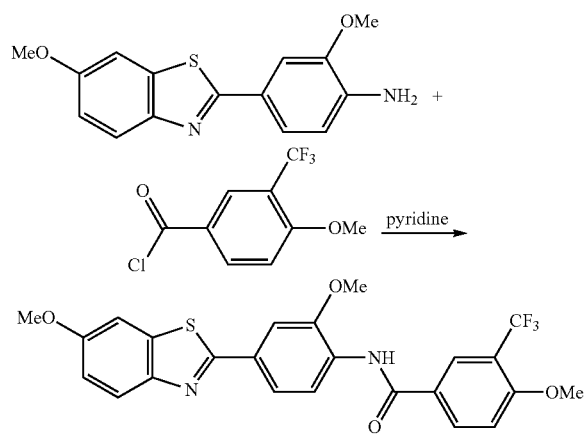

Prepared as described in the Amide Coupling section using 2-(4-amino-3-methoxyphenyl)-6-methoxybenzothiazole (0.13 g, 0.45 mmol) 4-methoxy-3-trifluoromethylbenzoyl chloride (0.11 g, 0.45 mmol) in dry pyridine (5 ml) to give the title compound (0.18 g, 79%) as a colourless solid after work-up and recrystallisation from acetic acid.

$^1$H NMR (400 MHz, CDCl$_3$) δ 3.88 (s, 3H), 3.98 (s, 3H), 4.07 (s, 3H), 7.07 (dd, J=8.8, 2.4 Hz, 1H), 7.09 (d, J=8.8 Hz, 1H), 7.33 (d, J=2.1 Hz, 1H), 7.57 (dd, J=8.5, 1.2 Hz, 1H), 7.73 (s, 1H), 7.91 (d, J=8.8 Hz, 1H), 8.05 (dd, J=8.8, 2.1 Hz, 1H), 8.12 (s, 1H), 8.58 (s, 1H), 8.59 (d, J=8.2 Hz, 1H); $^{13}$C NMR (62.5 MHz, CDCl$_3$) δ 55.83, 56.32 (2×C), 104.17, 107.96, 111.98, 115.69, 119.05 (q, J$_{CF}$=32 Hz), 119.56, 121.16, 123.12 (q, J$_{CF}$=273 Hz), 123.44, 126.55 (q, J$_{CF}$=4.9 Hz), 126.68, 129.37, 129.88, 132.55, 136.33, 148.30, 148.45, 157.75, 160.25, 163.62, 165.30.

4-Nitro-3-trifluoromethyl-N-[4-(6-methoxybenzothiazol-2-yl)-phenyl]-benzamide

Book No.: SKT02-103

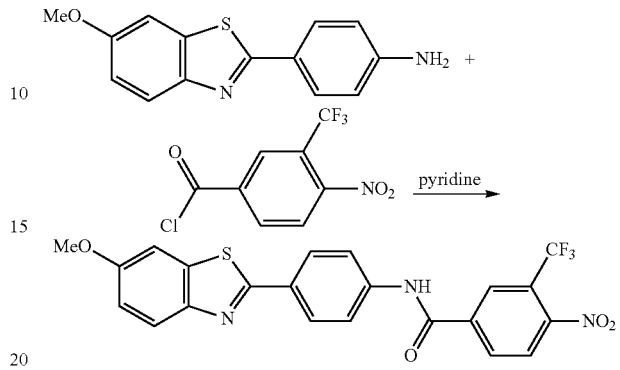

A mixture of 4-nitro-3-trifluoromethylbenzoic acid (0.46 g, 1.95 mmol) and thionyl chloride (0.47 g, 4.0 mmol) in chloroform (5 ml) was heated under reflux for 5 h. The reaction mixture was cooled to room temperature and the excess reagent and solvent was removed under reduced pressure to give the crude acid chloride. The amide was prepared as described in the Amide Coupling section above using the crude acid chloride and 2-(4-aminophenyl)-6-methoxybenzothiazole (0.50 g, 1.95 mmol) in dry pyridine (25 ml) to give the title compound (0.84 g, 91%) as an orange solid after work-up.

$^1$H NMR (250 MHz, DMSO-d$_6$) δ 3.85 (s, 3H), 7.13 (dd, J=2.1, 8.8 Hz, 1H), 7.71 (d, J=2.1 Hz, 1H), 7.92 (d, J=8.8 Hz, 1H), 7.97 (d, J=8.8 Hz, 2H), 8.08 (d, J=8.8 Hz, 2H), 8.35 (d, J=8.5 Hz, 1H), 8.50 (d, J=8.8 Hz, 1H), 8.54 (s, 1H), 10.94 (s, 1H); $^{13}$C NMR (100.5 MHz, DMSO-d$_6$) δ 56.23, 105.42, 116.26, 121.24, 121.88 (q, J$_{CF}$=33.5 Hz), 122.37 (q, J$_{CF}$=274 Hz), 123.67, 126.13, 127.86 (q, J$_{CF}$=5.4 Hz), 127.99, 129.45, 134.37, 136.39, 139.16, 141.28, 148.60, 149.24, 157.95, 163.12, 164.64.

4-Nitro-3-trifluoromethyl-N-[4-(6-(2-dimethylaminoethoxy)-benzothiazol-2-yl)-phenyl]-benzamide Book No.: SKT03-171

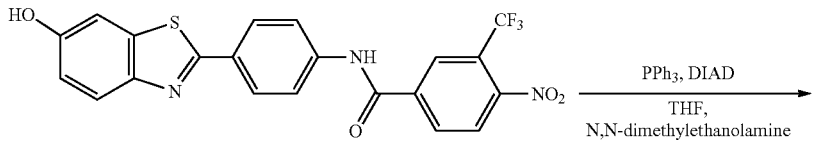

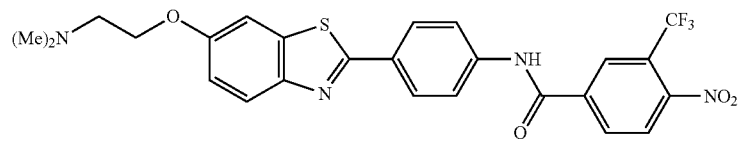

To a stirred mixture of 4-nitro-3-trifluoromethyl-N-[4-(6-hydroxybenzothiazol-2-yl)-phenyl]-benzamide (0.05 g, 0.109 mmol), triphenylphosphine (0.043 g, 0.163 mmol) and N,N-dimethylethanolamine (0.015 g, 0.163 mmol) in dry THF (5 ml) at 0° C. was added dropwise DIAD (0.033 g, 0.163 mmol). The reaction mixture was stirred at 0° C. for 1 h, then left to rise to room temperature overnight. The solvent was removed under reduced pressure and the residue was purified by flash chromatography (1:1 Hexane/EtOAc followed by 3:1 EtOAc/MeOH) to give the title compound (0.029 g, 50%) as a yellow solid.

$^1$H NMR (250 MHz, DMSO-$d_6$) δ 2.50 (s, 6H), 2.70 (t, J=5.8 Hz, 2H), 4.15 (t, J=5.8 Hz, 2H), 7.14 (dd, J=8.5, 2.7 Hz, 1H), 7.75 (d, J=2.7 Hz, 1H), 7.92 (d, J=8.5 Hz, 1H), 7.98 (d, J=8.5 Hz, 2H), 8.09 (d, J=8.5 Hz, 2H), 8.36 (d, J=8.5 Hz, 1H), 8.51 (d, J=8.5 Hz, 1H), 8.54 (s, 1H), 10.96 (s, 1H).

N-[4-(1,3-Benzothiazol-2-yl)-3-{2-(dimethylamino)ethoxy}phenyl]-4-fluoro-3-nitrobenzamide Book No.: SKT04-163

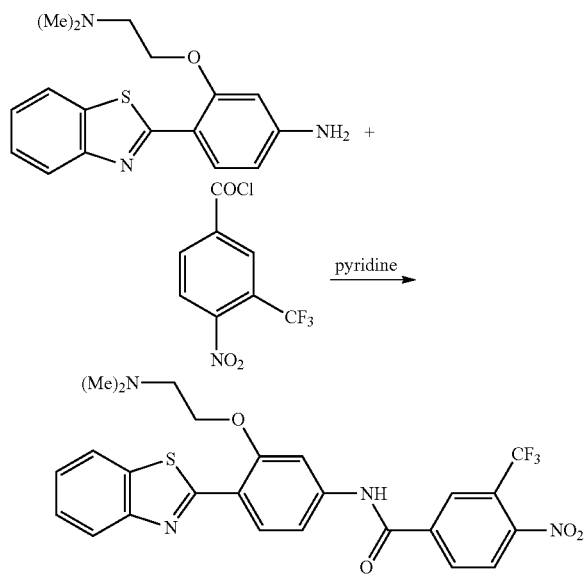

A mixture of 4-nitro-3-trifluoromethylbenzoic acid (0.030 g, 0.128 mmol) and thionyl chloride (1.5 ml) was heated under reflux for 5 h. The reaction mixture was cooled to room temperature and the excess reagent was removed under reduced pressure to give the crude acid chloride. The amide was prepared as described in the Amide Coupling section using the crude acid chloride and 4-(1,3-benzothiazol-2-yl)-3-[2-(dimethylamino)ethoxy]aniline (0.040 g, 0.128 mmol) in dry pyridine (5 ml) to give the title compound (0.045 g, 66%) as a yellow solid after work-up and flash chromatography (12:1 DCM/MeOH).

IR 3437, 3058, 2951, 2831, 2784, 1681, 1602, 1540, 1460, 1429, 1359, 1320, 1253, 1184, 1145, 1047, 967, 923, 856, 760, 731 cm$^{-1}$; $^1$H NMR (400 MHz, CDCl$_3$) δ 2.39 (s, 6H), 2.97 (t, J=6.0 Hz, 2H), 4.33 (t, J=6.0 Hz, 2H), 7.08 (dd, J=8.5, 2.0 Hz, 1H), 7.32 (t, J=7.5 Hz, 1H), 7.43 (t, J=7.2 Hz, 1H), 7.81-7.87 (m, 3H), 7.97 (d, J=8.2 Hz, 1H), 8.11 (d, J=7.9 Hz, 1H), 8.29 (s, 1H), 8.44 (d, J=8.5 Hz, 2H).

4-Nitro-2-trifluoromethyl-N-[4-(6-methoxybenzothiazol-2-yl)-phenyl]-benzamide

Book No.: SKT01-137

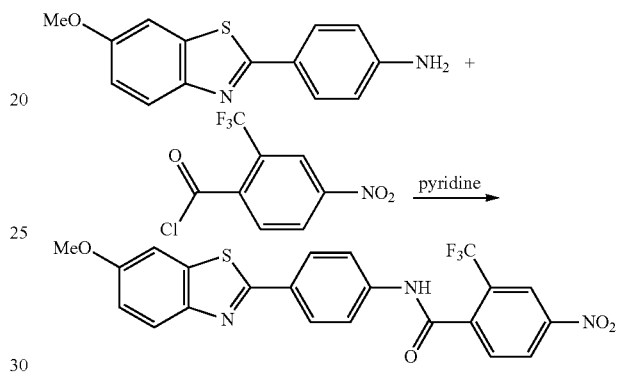

A mixture of 4-nitro-2-trifluoromethylbenzoic acid (0.50 g, 2.13 mmol) and thionyl chloride (0.46 g, 3.83 mmol) in chloroform (5 ml) was heated under reflux for 5 h. The reaction mixture was cooled to room temperature and the excess reagent and solvent was removed under reduced pressure to give the crude acid chloride. The amide was prepared as described in the Amide. Coupling section using the crude acid chloride and 2-(4-aminophenyl)-6-methoxybenzothiazole (0.54 g, 2.13 mmol) in dry pyridine (20 ml) to give the title compound (0.84 g, 83%) as a yellow solid after work-up.

$^1$H NMR (250 MHz, CDCl$_3$) δ 3.90 (s, 3H), 7.09 (dd, J=2.4, 8.8 Hz, 1H), 7.35 (d, J=2.1 Hz, 1H), 7.67 (s, 1H), 7.73 (d, J=8.5 Hz, 2H), 7.93 (d, J=8.2 Hz, 1H), 7.93 (d, J=8.8 Hz, 1H), 8.07 (d, J=8.5 Hz, 2H), 8.51 (dd, J=8.5, 2.1 Hz, 1H), 8.63 (s, 1H); $^{13}$C NMR (62.5 MHz, CDCl$_3$/DMSO-$d_6$) δ 55.54, 103.97, 115.46, 120.13, 121.58, 122.23 (q, $J_{CF}$=274 Hz), 123.11, 126.62, 127.52, 128.71 (q, $J_{CF}$=33 Hz), 129.42, 130.24, 135.97, 140.32, 141.31, 147.61, 148.20, 157.43, 163.86, 164.40.

4-Amino-3-trifluoromethyl-N-[4-(6-methoxybenzothiazol-2-yl)-phenyl]-benzamide

Book No.: SKT01-157

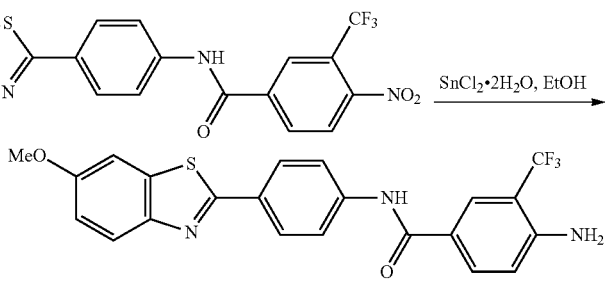

Prepared as described in the Nitro Reduction section using 4-nitro-3-trifluoromethyl-N-[4-(6-methoxybenzothiazol-2-yl)-phenyl]-benzamide (0.35 g, 0.74 mmol) and tin (II) chloride dihydrate (1.33 g, 5.91 mmol) in EtOH (7 ml) to give the title compound (0.24 g, 73%) as a pale yellow solid after work-up and flash chromatography (3:2 Hexane/EtOAc).

IR 3385, 3328, 3069, 2939, 2837, 1661, 1607, 1523, 1488, 1463, 1437, 1407, 1314, 1264, 1225, 1173, 1137, 1056, 1027, 968, 829 cm$^{-1}$. $^1$H NMR (250 MHz, acetone-d$_6$) δ 3.94 (s, 3H), 5.88 (br s, 2H), 7.01 (d, J=8.2 Hz, 1H), 7.15 (dd, J=8.2, 1.6 Hz, 1H), 7.60 (s, 1H), 7.92 (d, J=8.2 Hz, 1H), 8.03-8.11 (m, 5H), 8.16 (s, 1H), 9.72 (s, 1H).

4-Amino-2-trifluoromethyl-N-[4-(6-methoxybenzothiazol-2-yl)-phenyl]-benzamide

Book No.: SKT01-149

1168, 1122, 1045, 1024, 969, 831 cm$^{-1}$. $^1$H NMR (250 MHz, DMSO-d$_6$) δ 3.83 (s, 3H), 5.62 (br s, 2H), 6.78 (d, J=8.5 Hz, 1H), 6.95 (s, 1H), 7.02 (dd, J=8.8, 2.1 Hz, 1H), 7.32 (d, J=8.5 Hz, 1H), 7.43 (d, J=1.8 Hz, 1H), 7.79-7.92 (m, 4H), 7.96 (s, 1H), 10.36 (s, 1H).

4-Dimethylamino-3-trifluoromethyl-N-[4-(6-methoxylbenzothiazol-2-yl)-phenyl]-benzamide Book No.: SKT02-31

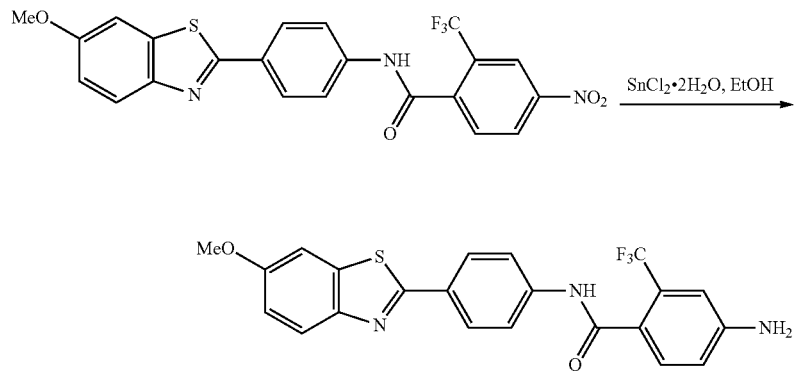

Prepared as described in the Nitro Reduction section using 4-nitro-2-trifluoromethyl-N-[4-(6-methoxybenzothiazol-2-yl)-phenyl]-benzamide (0.50 g, 1.05 mmol) and tin (II) chloride dihydrate (1.90 g, 8.40 mmol) in EtOH (8 ml) to give the title compound (0.32 g, 69%) as a pale yellow solid after work-up and flash chromatography (1:1 Hexane/EtOAc).

IR 3365-3050 (br), 3446, 3261, 3007, 2966, 2936, 2831, 1660, 1631, 1607, 1530, 1490, 1464, 1406, 1325, 1266, 1225,

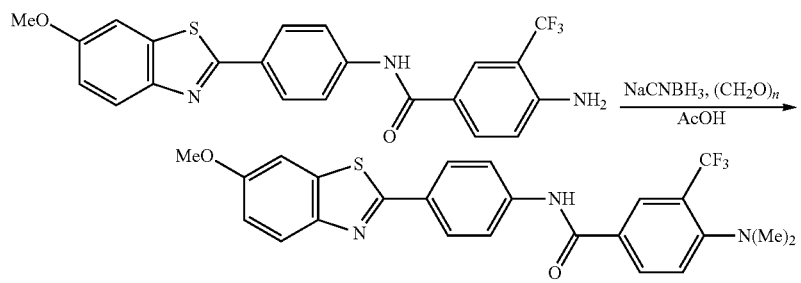

Prepared as described in the Amination section using sodium cyanoborohydride (71 mg, 1.13 mmol), 4-amino-3-trifluoromethyl-N-[4-(6-methoxybenzothiazol-2-yl)-phenyl]-benzamide (100 mg, 0.226 mmol) and paraformaldehyde (68 mg, 2.26 mmol) in AcOH (3 ml to give the title compound (54 mg, 51%) as a colourless solid after work-up and flash chromatography (20:1 DCM/EtOAc).

$^1$H NMR (250 MHz, CDCl$_3$) δ 2.91 (s, 6H), 3.89 (s, 3H), 7.08 (dd, J=8.8, 2.4 Hz, 1H), 7.19 (d, J=8.5 Hz, 1H), 7.34 (d, J=2.4 Hz, 1H), 7.78 (d, J=8.8 Hz, 2H), 7.91-7.96 (m, 3H), 8.04 (d, J=8.8 Hz, 2H), 8.10 (s, 1H); $^{13}$C NMR (62.5 MHz, CDCl$_3$) δ 44.44, 55.84, 104.20, 115.66, 120.26, 120.41, 121.51 (q, J$_{CF}$=30.3 Hz), 123.50, 124.08 (q, J$_{CF}$=273.4 Hz), 126.37, 127.74 (q, J$_{CF}$=5.9 Hz), 128.11, 129.77, 131.22, 136.33, 140.05, 148.61, 155.33, 157.72, 164.40, 164.97.

4-Dimethylamino-2-trifluoromethyl-N-[4-(6-methoxybenzothiazol-2-yl)-phenyl]-benzamide Book No.: SKT01-159

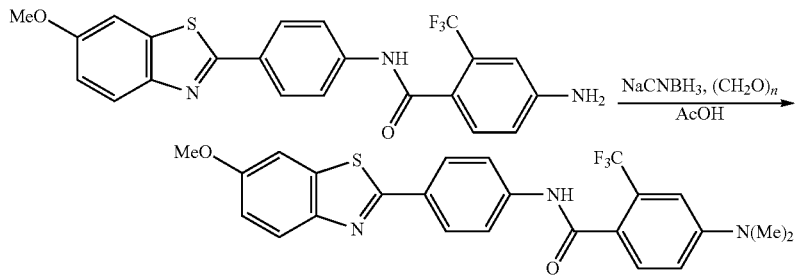

Prepared as described in the Amination section using sodium cyanoborohydride (66 mg, 1.05 mmol), 4-amino-2-trifluoromethyl-N-[4-(6-methoxybenzothiazol-2-yl)-phenyl]-benzamide (100 mg, 0.226 mmol) and paraformaldehyde (63 mg, 2.11 mmol) in AcOH (3 ml) to give the title compound (39 mg, 37%) as a colourless solid after work-up and flash chromatography (20:1 DCM/EtOAc).

$^1$H NMR (400 MHz, DMSO-d$_6$) δ 2.97 (s, 6H), 3.80 (s, 3H), 6.93-6.95 (m, 2H), 7.07 (dd, J=8.8, 2.4 Hz, 1H), 7.50 (d, J=8.5 Hz, 1H), 7.65 (d, J=2.4 Hz, 1H), 7.83 (d, J=8.8 Hz, 2H), 7.86 (d, J=8.5 Hz, 1H), 7.96 (d, J=8.8 Hz, 2H), 10.57 (s, 1H); $^{13}$C NMR (100 MHz, DMSO-d$_6$) δ 40.24, 56.25, 105.49, 109.20 (q, J$_{CF}$=5.4 Hz), 114.41, 116.18, 120.25, 122.91, 123.60, 124.45 (q, J$_{CF}$=274 Hz), 127.99, 128.07 (q, J$_{CF}$=30.4 Hz), 128.58, 130.59, 136.32, 142.29, 148.63, 151.35, 157.89, 164.87, 166.74.

4-(2,2-Trifluoroethoxy)-N-[4-(6-methoxybenzothiazol-2-yl)-phenyl]-benzamide

Book No.: SKT02-25

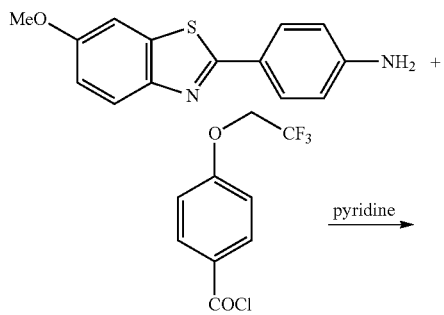

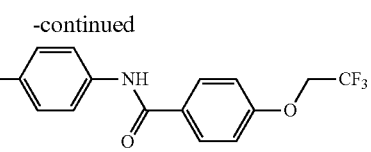

A mixture of 4-(2,2,2-trifluoroethoxy)benzoic acid (0.30 g, 1.35 mmol) and thionyl chloride (0.32 g, 2.72 mmol) in chloroform (5 ml) was heated under reflux for 4 h. The reaction mixture was cooled to room temperature and the excess reagent and solvent was removed under reduced pressure to give the crude acid chloride. The amide was prepared as described in the Amide Coupling section using the crude acid chloride and 2-(4-aminophenyl)-6-methoxybenzothiazole (0.34 g, 1.35 mmol) in dry pyridine (15 ml) to give the title compound (0.56 g, 91%) as a pale yellow solid after work-up.

$^1$H NMR (400 MHz, DMSO-d$_6$) δ 3.79 (s, 3H), 4.82 (q, J=9.0 Hz, 2H), 7.06 (dd, J=9.0, 2.7 Hz, 1H), 7.16 (d, J=9.0 Hz, 2H), 7.63 (d, J=2.7 Hz, 1H), 7.85 (d, J=9.0 Hz, 1H), 7.91 (dist d, J=9.0 Hz, 2H), 7.94-7.98 (m, 4H), 10.38 (s, 1H); $^{13}$C NMR (100.5 MHz, DMSO-d$_6$) δ 56.38 (q, J$_{CF}$=8 Hz), 65.21 (q, J$_{CF}$=34 Hz), 105.50 (q, J$_{CF}$=6 Hz), 115.19, 116.45, 121.12, 123.82, 124.55 (q, J$_{CF}$=278 Hz), 128.09, 128.74, 128.81, 130.50 (q, J$_{CF}$=6 Hz), 136.46, 142.32, 148.69, 158.00, 160.19, 165.10, 165.63.

4-(3,3,3-Trifluoropropoxy)-N-[4-(6-methoxybenzothiazol-2-yl)-phenyl]-benzamide Book No.: SKT03-39

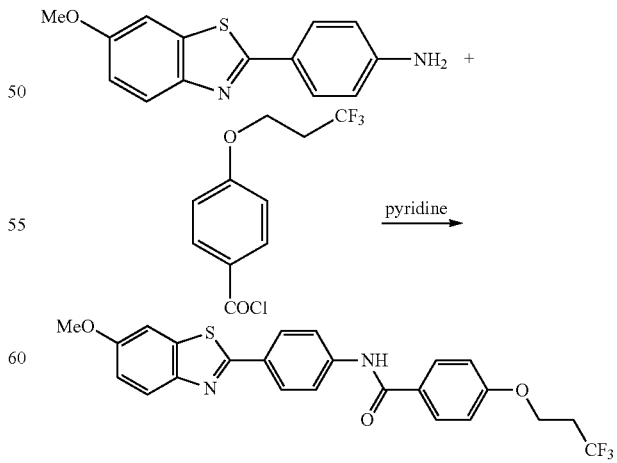

A mixture of 4-(3,3,3-trifluoropropoxy)benzoic acid (0.32 g, 1.39 mmol) and thionyl chloride (0.33 g, 2.78 mmol) in chloroform (5 ml) was heated under reflux for 5 h. The reaction mixture was cooled to room temperature and the excess reagent and solvent was removed under reduced pressure to give the crude acid chloride. The amide was prepared as described in the Amide Coupling section using the crude acid chloride and 2-(4-aminophenyl)-6-methoxybenzothiazole (0.36 g, 1.39 mmol) in dry pyridine (10 ml) to give the title compound (0.59 g, 90%) as a pale yellow solid after work-up.

$^1$H NMR (400 MHz, DMSO-$d_6$) δ 2.74-2.83 (m, 2H), 3.80 (s, 3H), 4.26 (t, J=5.9 Hz, 2H), 7.07 (d, J=9.0 Hz, 2H), 7.07 (dd, J=9.0, 2.7 Hz, 1H), 7.65 (d, J=2.7 Hz, 1H), 7.86 (d, J=9.0 Hz, 1H), 7.92-7.99 (m, 6H), 10.33 (s, 1H); $^{13}$C NMR (100.5 MHz, DMSO-$d_6$) δ 33.40 (q, $J_{CF}$=27 Hz), 56.40, 61.85, 105.56, 114.85, 116.44, 121.85, 123.79, 127.34 (q, $J_{CF}$=277 Hz), 127.78, 128.09, 128.65, 130.47, 136.48, 142.48, 148.75, 158.01, 161.34, 165.07, 165.70.

4-(4,4,4-Trifluorobutoxy)-N-[4-(6-methoxybenzothiazol-2-yl)-phenyl]-benzamide Book No.: SKT02-169

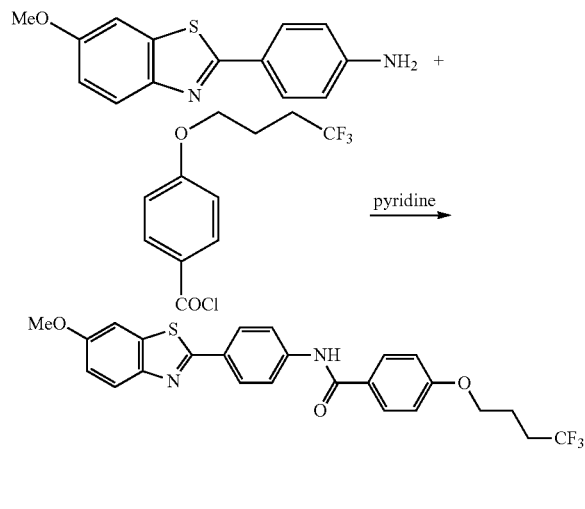

A mixture of 4-(4,4,4-trifluorobutoxy)benzoic acid (0.20 g, 0.806 mmol) and thionyl chloride (0.42 g, 3.54 mmol) in chloroform (5 ml) was heated under reflux for 8 h. The reaction mixture was cooled to room temperature and the excess reagent and solvent was removed under reduced pressure to give the crude acid chloride. The amide was prepared as described in the Amide Coupling section using the crude acid chloride and 2-(4-aminophenyl)-6-methoxybenzothiazole (0.206 g, 0.806 mmol) in dry pyridine (10 ml) to give the title compound (0.343 g, 87%) as a colourless solid after work-up.

$^1$H NMR (400 MHz, DMSO-$d_6$) δ 1.89-1.96 (m, 2H), 2.33-2.45 (m, 2H), 3.80 (s, 3H), 4.09 (t, J=6.1 Hz, 2H), 7.04 (d, J=8.8 Hz, 2H), 7.07 (dd, J=9.1, 2.4 Hz, 1H), 7.64 (d, J=2.4 Hz, 1H), 7.86 (d, J=8.8 Hz, 1H), 7.93 (d, J=8.8 Hz, 2H), 7.94 (d, J=9.1 Hz, 2H), 7.97 (d, J=8.8 Hz, 2H), 10.30 (s, 1H); $^{13}$C NMR (100.5 MHz, DMSO-$d_6$) δ 22.03 (q, $J_{CF}$=6.3 Hz), 29.97 (q, $J_{CF}$=28.05 Hz), 56.24, 66.60, 105.46, 114.66, 116.16, 120.86, 123.58, 127.38, 127.85, 128.05 (q, $J_{CF}$=276.4 Hz), 128.51, 130.21, 136.32, 142.32, 148.63, 157.86, 161.63, 164.89, 165.54.

Monohalo Methoxy-Amides

4-Fluoro-N-[4-(6-methoxybenzothiazol-2-yl)-phenyl]-benzamide

Book No.: SKT02-135

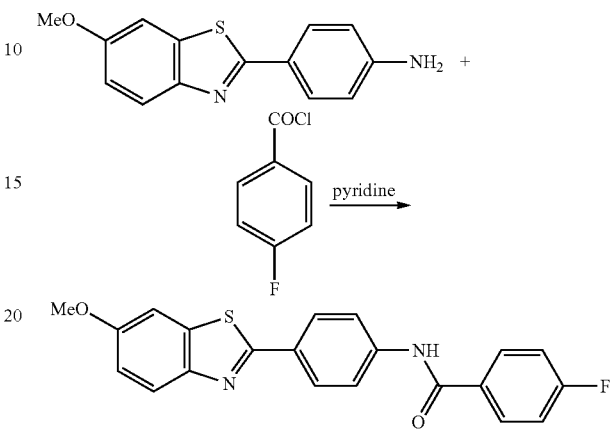

A mixture of 4-fluorobenzoic acid (0.20 g, 1.43 mmol) and thionyl chloride (0.93 g, 7.81 mmol) in chloroform (5 ml) was heated under reflux for 3.5 h. The reaction mixture was cooled to room temperature and the excess reagent and solvent was removed under reduced pressure to give the crude acid chloride. The amide was prepared as described in the Amide Coupling section using the crude acid chloride and 2-(4-aminophenyl)-6-methoxybenzothiazole (0.36 g, 1.43 mmol) in dry pyridine (15 ml) to give the title compound as (0.26 g, 48%) as colourless needles after recrystallisation from EtOAc.

$^1$H NMR (250 MHz, DMSO-$d_6$) δ 3.85 (s, 3H), 7.12 (dd, J=2.1, 8.8 Hz, 1H), 7.40 (t, J=8.8 Hz, 2H), 7.70 (d, J=2.1 Hz, 1H), 7.92 (d, J=8.8 Hz, 1H), 7.98 (d, J=8.8 Hz, 2H), 8.04 (d, J=8.8 Hz, 2H), 8.00-8.10 (m, 2H), 10.55 (s, 1H); $^{13}$C NMR (62.5 MHz, CDCl$_3$/DMSO-$d_6$) δ 55.22, 103.89, 114.73 (d, $J_{CF}$=21.5 Hz), 115.16, 120.01, 122.68, 126.93, 128.10, 130.03 (d, $J_{CF}$=8.8 Hz), 130.67 (d, $J_{CF}$=2.9 Hz), 135.53, 141.16, 147.86, 156.99, 163.97 (d, $J_{CF}$=251 Hz), 164.06, 164.38.

6-Fluoro-N-(4-[6-methoxy-1,3-benzothiazol-2-yl)phenyl]pyridine-3-carboxamide Book No.: SKT04-137

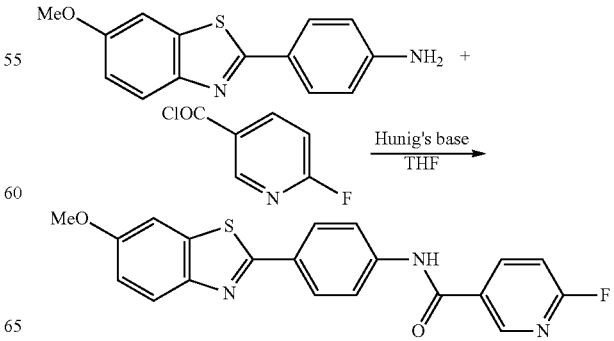

A mixture of 6-fluoronicotinic acid (0.125 g, 0.647 mmol) and thionyl chloride (3 ml) was heated under reflux for 4 h. The reaction mixture was cooled to room temperature and excess reagent was removed under reduced pressure to give the crude acid chloride. The amide was prepared as described in the Amide Coupling section using the crude acid chloride and 2-(4-aminophenyl)-6-methoxybenzothiazole (0.166 g, 0.647 mmol) in dry THF (5 ml) containing diisopropylethylamine (0.10 g, 0.776 mmol to give the title compound (0.195 g, 79%) as colourless crystals after work-up and recrystallisation from dioxane.

$^1$H NMR (400 MHz, DMSO-d$_6$) δ 3.80, (s, 3H), 7.07 (dd, J=8.9, 2.7 Hz, 1H), 7.34 (dd, J=8.5, 2.0 Hz, 1H), 7.66 (d, J=2.4 Hz, 1H), 7.87 (d, J=8.9 Hz, 1H), 7.91 (dd, J=8.9, 2.0 Hz, 2H), 8.01 (dd, J=8.9, 2.0 Hz, 2H), 8.47 (dt, J=8.5, 2.7 Hz, 1H), 8.79 (d, J=2.7 Hz, 1H), 10.67 (s, 1H); $^{13}$C NMR (100.5 MHz, DMSO-d$_6$) δ 56.40, 105.52, 110.22 (d, J$_{CF}$=37 Hz), 116.51, 121.14, 123.85, 128.20, 129.20, 129.77 (d, J$_{CF}$=3.8 Hz), 136.51, 141.79, 142.72 (d, J$_{CF}$=9.2 Hz), 148.58 (d, J$_{CF}$=16.8 Hz), 148.69, 158.04, 163.79, 164.90, 165.04 (d, J$_{CF}$=241 Hz).

6-Chloro-N-(4-[6-methoxy-1,3-benzothiazol-2-yl) phenyl]pyridine-3-carboxamide

Book No.: SKT04-111

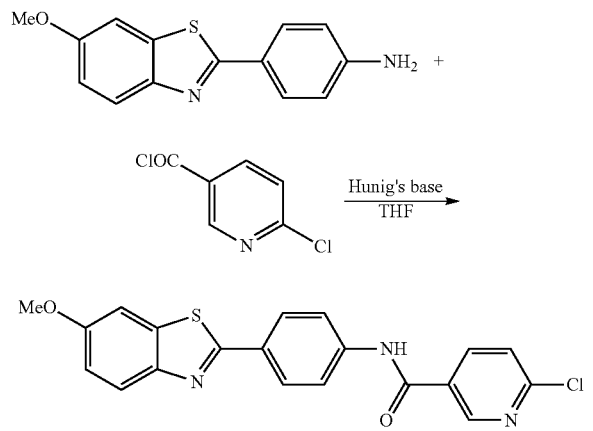

Prepared as described in the Amide Coupling section using 2-(4-aminophenyl)-6-methoxybenzothiazole (0.75 g, 2.93 mmol) and 6-chloronicotinoyl chloride (0.515 g, 2.93 mmol) in dry THF (20 ml) containing diisopropylethylamine (0.45 g, 3.52 mmol) to give the title compound (0.784 g, 68%) as small, colourless crystals after work-up and recrystallisation from dioxane.

$^1$H NMR (250 MHz, DMSO-d$_6$) δ 3.73 (s, 3H), 6.93 (dd, J=8.8, 2.4 Hz, 1H), 7.22 (d, J=2.4 Hz, 1H), 7.25 (s, 1H), 7.35 (d, J=8.5 Hz, 1H), 7.70 (d, J=8.8 Hz, 2H), 7.73 (d, J=8.5 Hz, 1H), 7.85 (d, J=8.5 Hz, 2H), 8.13 (dd, J=8.2, 2.4 Hz, 1H), 8.77, (d, J=1.8 Hz, 1H); $^{13}$C NMR (62.5 MHz, CDCl$_3$/DMSO-d$_6$) δ 55.22, 103.86, 115.21, 120.16, 122.76, 123.53, 127.00, 128.55, 129.14, 135.58, 138.39, 140.63, 147.86, 148.97, 153.08, 157.05, 162.68, 163.95.

6-Bromo-N-(4-[6-methoxy-1,3-benzothiazol-2-yl) phenyl]pyridine-3-carboxamide

Book No.: SKT05-63

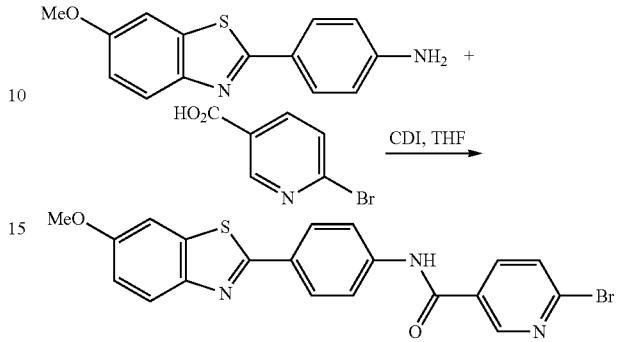

To a solution of 6-bromonicotinic acid (0.16 g, 0.78 mmol) in dry THF (5 ml) was added under an atmosphere of argon 1,1'-carbonyldiimidazole (0.13 g, 0.78 mmol) and the reaction mixture stirred at room temperature for 5 h. To the reaction mixture was added 2-(4-aminophenyl)-6-methoxybenzothiazole (0.2 g, 0.78 mmol) over 2 mins, stirring continued at room temperature for 1 h, then heated under reflux for 18 h. After cooling to room temperature, the reaction mixture was diluted with Et$_2$O (30 ml) and the precipitate was collected by filtration, washed with Et$_2$O (50 ml) and dried under high vacuum to give the title compound (0.101 g, 29%) as an orange solid.

$^1$H NMR (250 MHz, DMSO-d$_6$) δ 3.86 (s, 3H), 7.14 (d, J=8.8 Hz, 1H), 7.72 (s, 1H), 7.87 (d, J=8.2 Hz, 1H), 7.92 (d, J=8.8 Hz, 1H), 7.97 (d, J=8.5 Hz, 2H), 8.07 (d, J=8.5 Hz, 2H), 8.28 (d, J=8.2 Hz, 1H), 8.96 (s, 1H), 10.78 (s, 1H); $^{13}$C NMR (62.5 MHz, CDCl$_3$/DMSO-d$_6$) δ 55.17, 103.91, 115.18, 120.07, 122.69, 126.95, 127.32, 128.44, 129.42, 135.50, 138.02, 140.60, 144.14, 147.79, 149.31, 156.98, 162.71, 163.81.

The reaction conditions employed were based on the methods described by Boschelli et al. for the coupling of 6-bromonicotinic acid with N-methylpiperazine using CDI.

4-Fluoro-3-nitro-N-[4-(6-methoxybenzothiazol-2-yl)-phenyl]-benzamide

Book No.: SKT03-99

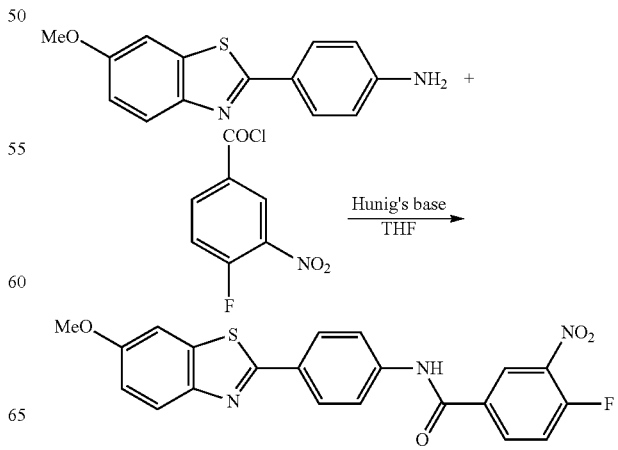

A mixture of 4-fluoro-3-nitrobenzoic acid (0.36 g, 1.95 mmol) and thionyl chloride (0.93 g, 7.81 mmol) in chloroform (5 ml) was heated under reflux for 4 h. The reaction mixture was cooled to room temperature and the excess reagent and solvent was removed under reduced pressure to give the crude acid chloride. The amide was prepared as described in the Amide Coupling section using the crude acid chloride, 2-(4-aminophenyl)-6-methoxybenzothiazole (0.50 g, 1.95 mmol) and Hunig's base (0.28 g, 2.15 mmol) in dry THF (20 ml) to give the title compound (0.49 g, 59%) as a pale yellow solid after work-up.

$^1$H NMR (400 MHz, DMSO-$d_6$) δ 3.80 (s, 3H), 7.06 (dd, J=8.9, 2.7 Hz, 1H), 7.63 (d, J=2.4 Hz, 1H), 7.73 (dd, J=11.3, 8.9 Hz, 1H), 7.85 (d, J=8.9 Hz, 1H), 7.91 (d, J=8.9 Hz, 2H), 7.99 (d, J=8.9 Hz, 2H), 8.36 (m, 1H), 8.72 (dd, J=7.5, 2.4 Hz, 1H), 10.72 (s, 1H); $^{13}$C NMR (100.5 MHz, DMSO-$d_6$) δ 56.38, 105.52, 116.48, 119.54 (d, $J_{CF}$=21 Hz), 121.30, 123.84, 126.53, 128.16, 129.33, 132.02 (d, $J_{CF}$=3.8 Hz), 136.42, 136.53, 137.31 (d, $J_{CF}$=8 Hz), 141.69, 148.72, 157.13 (d, $J_{CF}$=267 Hz), 158.06, 163.27, 164.87.

N-[4-(1,3-Benzothiazol-2-yl)-3-methoxyphenyl]-4-fluoro-3-nitrobenzamide

Book No.: SKT04-127

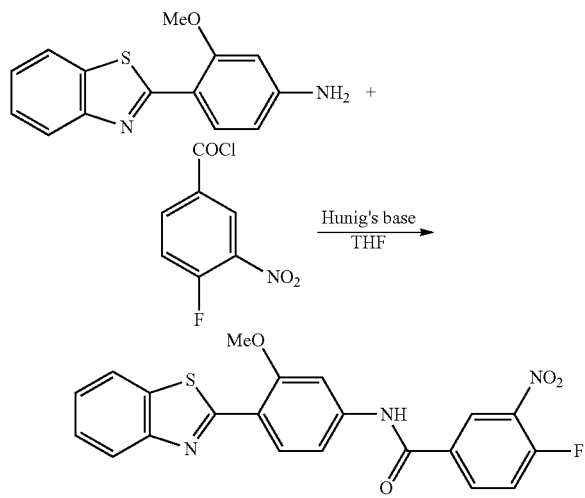

A mixture of 4-fluoro-3-nitrobenzoic acid (0.062 g, 0.336 mmol) and thionyl chloride (5 ml) was heated under reflux for 2 h. The reaction mixture was cooled to room temperature and the excess reagent was removed under reduced pressure to give the crude acid chloride. The amide was prepared as described in the Amide Coupling section using the crude acid chloride, 2-(4-amino-2-methoxyphenyl)benzothiazole (0.086 g, 0.336 mmol) and Hunig's base (0.052 g, 0.403 mmol) in dry THF (5 ml) to give the title compound (0.105 g, 74%) as a pale yellow solid after work-up.

$^1$H NMR (400 MHz, DMSO-$d_6$) δ 4.02 (s, 3H), 7.34-7.38 (m, 1H), 7.45-7.49 (m, 1H), 7.58 (dd, J=8.8, 1.9 Hz, 1H), 7.73-7.78 (m, 2H), 9.97 (d, J=7.8 Hz, 1H), 8.05 (d, J=7.6 Hz, 1H), 8.36-8.39 (m, 1H), 8.89 (d, J=8.8 Hz, 1H), 8.74 (dd, J=7.1, 2.2 Hz, 1H), 10.77 (s, 1H); $^{13}$C NMR (100.5 MHz, DMSO-$d_6$) δ 61.14, 108.85, 117.97, 122.11, 124.08 (d, $J_{CF}$=19.4 Hz), 126.89 (d, $J_{CF}$=10.9 Hz), 127.32 (d, $J_{CF}$=8.5 Hz), 129.80, 131.03, 131.35, 134.28, 136.44 (d, $J_{CF}$=3.9 Hz), 140.29, 141.05, 141.82 (d, $J_{CF}$=7.8 Hz), 147.69, 156.79, 161.72 (d, $J_{CF}$=267 Hz), 162.43, 167.07, 167.86.

N-[4-(1,3-Benzothiazol-2-yl)-3-[2-{2-(2-methoxyethoxy)ethoxy}ethoxy]phenyl]-4-fluoro-3-nitrobenzamide Book No.: SKT04-143

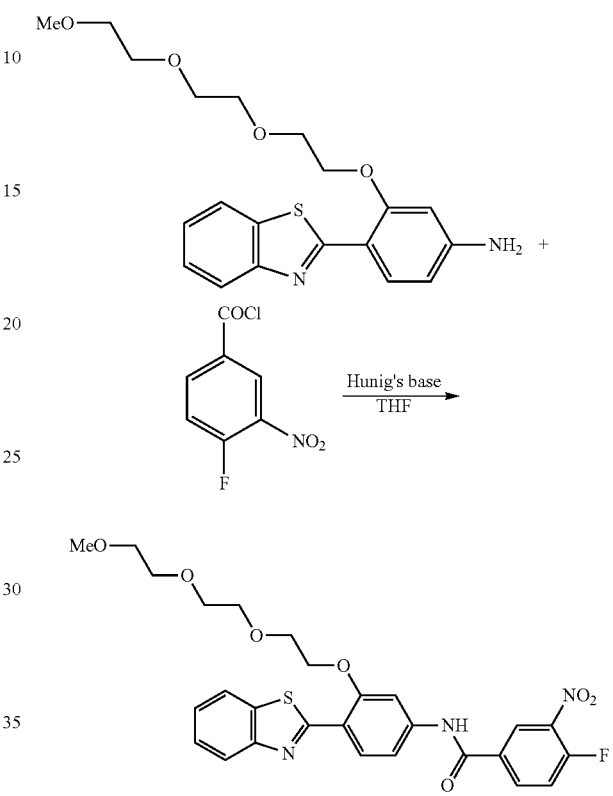

A mixture of 4-fluoro-3-nitrobenzoic acid (0.048 g, 0.257 mmol) and thionyl chloride (2 ml) was heated under reflux for 4 h. The reaction mixture was cooled to room temperature and the excess reagent was removed under reduced pressure to give the crude acid chloride. The amide was prepared as described in the Amide Coupling section above using the crude acid chloride, 4-(1,3-benzothiazol-2-yl)-3-[2-{2-(2-methoxyethoxy)ethoxy}ethoxy]aniline (0.10 g, 0.257 mmol) and Hunig's base (0.040 g, 0.308 mmol) in dry THF (5 ml) to give the title compound (0.140 g, 98%) as a yellow solid after work-up and flash chromatography (EtOAc).

$^1$H NMR (400 MHz, DMSO-$d_6$) δ 3.22 (s, 3H), 3.41-3.43 (m, 2H), 3.54-3.57 (m, 2H), 3.62-3.64 (m, 2H), 3.73-3.76 (m, 2H), 4.04-4.06 (m, 2H), 4.42-4.44 (m, 2H), 7.45 (dt, J=7.0, 1.2 Hz, 1H), 7.55 (dt, J=7.0, 1.2 Hz, 1H), 7.64 (dd, J=8.6, 1.9 Hz 1H), 7.82 (dd, J=10.9, 9.0 Hz, 1H), 7.86 (d, J=1.9 Hz, 1H), 8.06 (d, J=8.2 Hz, 1H), 8.11 (d, J=7.8 Hz, 1H), 8.44-8.48 (m, 1H), 8.48 (d, J=8.6 Hz, 1H), 8.82 (dd, J=7.0, 2.3 Hz, 1H); $^{13}$C NMR (100.5 MHz, DMSO-$d_6$) δ 58.44, 68.87, 69.15, 70.07, 70.35, 70.48, 71.69, 104.85, 113.38, 117.62, 119.39 (d, $J_{CF}$=21 Hz), 122.05, 122.59, 125.07, 126.28, 126.58, 129.63, 131.72 (d, $J_{CF}$=3.9 Hz), 135.76, 136.26 (d, $J_{CF}$=10 Hz), 137.10 (d, $J_{CF}$=7.7 Hz), 142.82, 152.02, 156.93, 156.98 (d, $J_{CF}$=267 Hz), 162.49, 163.14.

4-Chloro-3-nitro-N-[4-(6-methoxybenzothiazol-2-yl)-phenyl]-benzamide

Book No.: SKT03-93

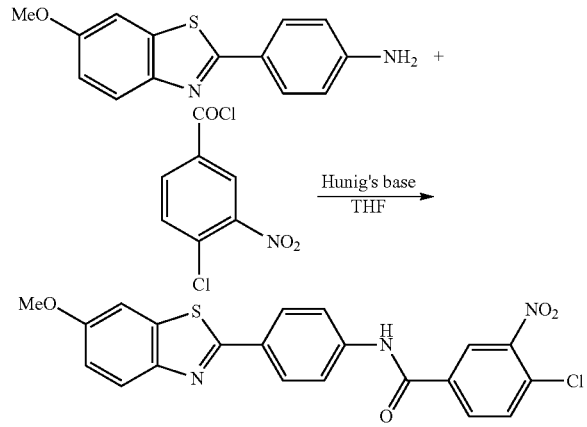

Prepared as described in the Amide Coupling section using 2-(4-aminophenyl)-6-methoxybenzothiazole (0.50 g, 1.95 mmol), 4-chloro-3-nitrobenzoyl chloride (0.43 g, 1.95 mmol) and Hunig's base (0.28 g, 2.15 mmol) in dry THF (20 ml) to give the title compound (0.83 g, 97%) as a yellow solid after work-up.

$^1$H NMR (400 MHz, DMSO-d$_6$) δ 3.79 (s, 3H), 7.07 (dd, J=8.8, 2.7 Hz, 1H), 7.64 (d, J=2.4 Hz, 1H), 7.86 (d, J=9.0 Hz, 1H), 7.92 (d, J=8.5 Hz, 2H), 8.00, dd, J=8.8, 1.9 Hz, 2H), 8.25 (dd, J=8.5, 1.9 Hz, 1H), 8.62 (d, J=1.9 Hz, 1H), 10.81 (s, 1H); $^{13}$C NMR (62.5 MHz, CDCl$_3$/DMSO-d$_6$) δ 55.14, 103.92, 115.21, 120.13, 122.57, 124.50, 126.90, 128.28, 131.34, 132.44, 133.98, 135.38, 140.57, 146.87, 147.47, 156.96, 161.95, 163.84 (1 missing).

4-Bromo-3-nitro-N-[4-(6-methoxybenzothiazol-2-yl)-phenyl]-benzamide

Book No.: SKT04-33

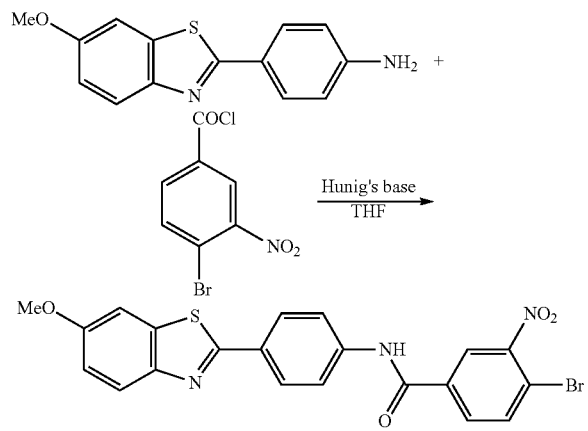

A mixture of 4-bromo-3-nitrobenzoic acid (0.24 g, 0.976 mmol) and thionyl chloride (5 ml) was heated under reflux for 3 h. The reaction mixture was cooled to room temperature and the excess reagent and solvent was removed under reduced pressure to give the crude acid chloride. The amide was prepared as described in the Amide Coupling section using the crude acid chloride, 2-(4-aminophenyl)-6-methoxybenzothiazole (0.25 g, 0.976 mmol) and Hunig's base (0.151 g, 1.17 mmol) in dry THF (10 ml) to give the title compound (0.368 g, 78%) as small yellow crystals after work-up and recrystallisation from DMF.

$^1$H NMR (250 MHz, DMSO-d$_6$) δ 3.85 (s, 3H), 7.13 (dd, J=8.8, 2.4 Hz, 1H), 7.71 (d, J=2.4 Hz, 1H), 7.92 (d, J=8.8 Hz, 1H), 7.96 (d, J=8.8 Hz, 2H), 8.07 (d, J=8.5 Hz, 2H), 8.15 (d, J=8.8 Hz, 1H), 8.18 (dd, J=8.5, 1.8 Hz, 1H), 8.61 (d, J=1.5 Hz, 1H), 10.80 (s, 1H); $^{13}$C NMR (62.5 MHz, CDCl$_3$/DMSO-d$_6$) δ 55.39, 103.89, 115.32, 117.01, 120.44, 122.91, 124.53, 127.18, 128.92, 132.46, 134.71, 134.85, 135.77, 140.58, 148.03, 149.15, 157.24, 162.35, 164.24.

4-Iodo-3-nitro-N-[4-(6-methoxybenzothiazol-2-yl)-phenyl]-benzamide

Book No.: SKT04-29

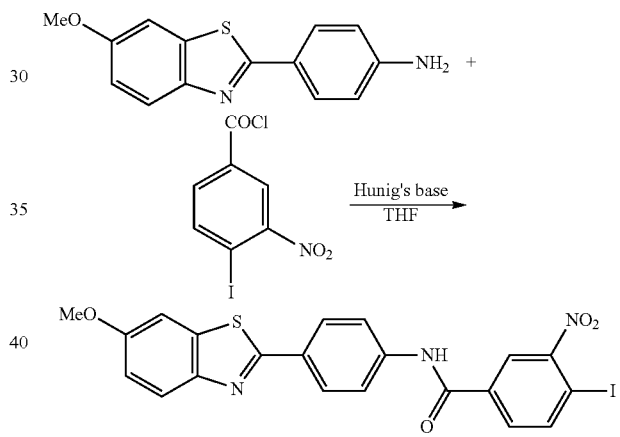

A mixture of 4-iodo-3-nitrobenzoic acid (0.286 g, 0.976 mmol) and thionyl chloride (5 ml) was heated under reflux for 3 h. The reaction mixture was cooled to room temperature and the excess reagent and solvent was removed under reduced pressure to give the crude acid chloride. The amide was prepared as described in the Amide Coupling section using the crude acid chloride, 2-(4-aminophenyl)-6-methoxybenzothiazole (0.25 g, 0.976 mmol) and Hunig's base (0.151 g, 1.17 mmol) in dry THF (10 ml) to give the title compound (0.403 g, 78%) as a yellow solid after work-up.

$^1$H NMR (250 MHz, DMSO-d$_6$) δ 3.85 (s, 3H), 7.13 (dd, J=8.8, 2.4 Hz, 1H), 7.70 (d, J=2.1 Hz, 1H), 7.91 (d, J=8.8 Hz, 1H), 7.94-7.99 (m, 3H), 8.05 (d, J=8.8 Hz, 2H), 8.32 (d, J=8.2 Hz, 1H), 8.52 (d, J=1.8 Hz, 1H), 10.78 (s, 1H); $^{13}$C NMR (62.5 MHz, CDCl$_3$/DMSO-d$_6$) δ 55.29, 91.17, 103.88, 115.26, 120.33, 122.82, 123.86, 127.06, 128.73, 132.15, 135.35, 135.67, 140.58, 141.37, 147.94, 152.64, 157.13, 162.50, 164.06.

4-Dimethylamino-3-nitro-N-[4-(6-methoxybenzothiazol-2-yl)-phenyl]-benzamide

Book No.: SKT03-141

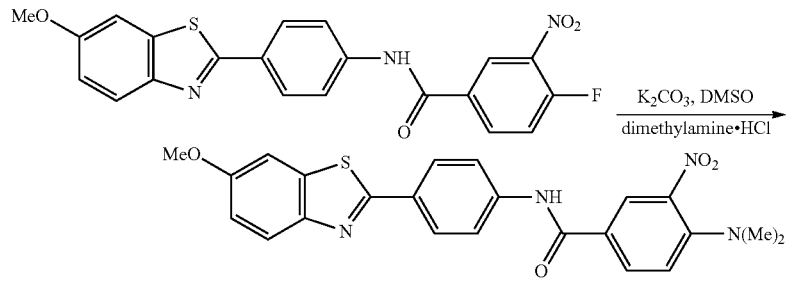

A mixture of 4-fluoro-3-nitro-N-[4-(6-methoxybenzothiazol-2-yl)-phenyl]-benzamide (0.10 g, 0.237 mmol), dimethylamine hydrochloride (0.039 g, 0.474 mmol) and potassium carbonate (0.085 g, 0.616 mmol) in DMSO (4 ml) and water (1 ml) was stirred and heated under reflux for 3 d. The reaction mixture was cooled to room temperature and water (10 ml) added and the resulting precipitate was collected by filtration. Purification by flash chromatography (2:1) EtOAc/Hexane gave the title compound (0.029 g, 27%) as an orange solid.

$^1$H NMR (400 MHz, DMSO-$d_6$) δ 2.94 (s, 6H), 3.85 (s, 3H), 7.12 (dd, J=8.8, 2.4 Hz, 1H), 7.27 (d, J=9.1 Hz, 1H), 7.71 (d, J=2.1 Hz, 1H), 7.91 (d, J=9.1 Hz, 1H), 7.96 (d, J=8.2 Hz, 2H), 8.04 (d, J=8.2 Hz, 2H), 8.10 (dd, J=9.1, 2.1 Hz, 1H), 8.50 (d, J=1.5 Hz, 1H), 10.46 (s, 1H); $^{13}$C NMR (62.5 MHz, CDCl$_3$/DMSO-$d_6$) δ 41.68, 55.31, 103.86, 115.19, 116.56, 120.12, 121.93, 122.77, 126.50, 127.03, 128.13, 132.44, 135.66, 136.31, 141.29, 147.15, 148.00, 157.09, 163.47, 164.34.

The reaction conditions employed were based on the methods described by Ermert et al. for the introduction of dimethylamino group by nucleophilic substitution in DMSO.

3,4-Dinitro-N-[4-(6-methoxybenzothiazol-2-yl)-phenyl]-benzamide

Book No.: SKT03-137

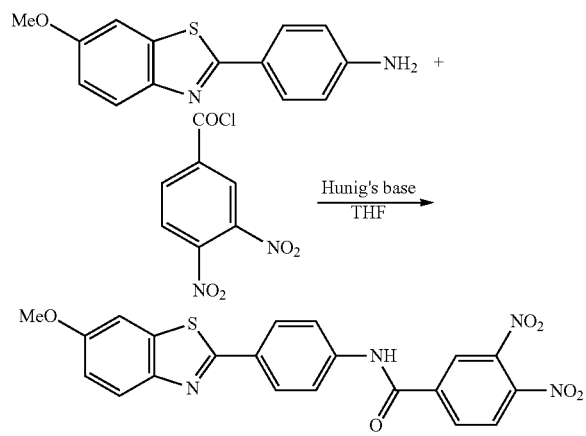

A mixture of 3,4-dinitrobenzoic acid (0.21 g, 0.976 mmol) and thionyl chloride (1 ml) in chloroform (5 ml) was heated under reflux for 4 h. The reaction mixture was cooled to room temperature and excess reagent was removed under reduced pressure to give the crude acid chloride. The amide was prepared as described in the Amide Coupling section using the crude acid chloride, 2-(4-aminophenyl)-6-methoxybenzothiazole (0.25 g, 0.976 mmol) in dry THF (20 ml) containing diisopropylethylamine (0.14 g, 1.07 mmol to give the title compound (0.334 g, 76%) as an orange solid after work-up and flash chromatography (EtOAc followed by (1:1) EtOAc/MeOH).

$^1$H NMR (250 MHz, DMSO-$d_6$) δ 3.86 (s, 3H), 7.13 (dd, J=8.8, 2.1 Hz, 1H), 7.72 (d, J=2.1 Hz, 1H), 7.93 (d, J=8.8 Hz, 1H), 8.00 (d, J=8.8 Hz, 2H), 8.09 (d, J=8.5 Hz, 2H), 8.43 (d, J=8.5 Hz, 1H), 8.54 (d, J=7.9 Hz, 1H), 8.79 (s, 1H), 11.08 (s, 1H); $^{13}$C NMR (62.5 MHz, CDCl$_3$/DMSO-$d_6$) δ 55.18, 103.88, 115.21, 120.32, 122.74, 124.45, 125.21, 126.96, 128.83, 133.42, 135.55, 139.06, 140.25, 141.50, 143.19, 147.79, 157.02, 161.18, 163.75.

4-(2-Fluoroethoxy)-N-[4-(6-methoxybenzothiazol-2-yl)-phenyl]-benzamide

Book No.: SKT03-75

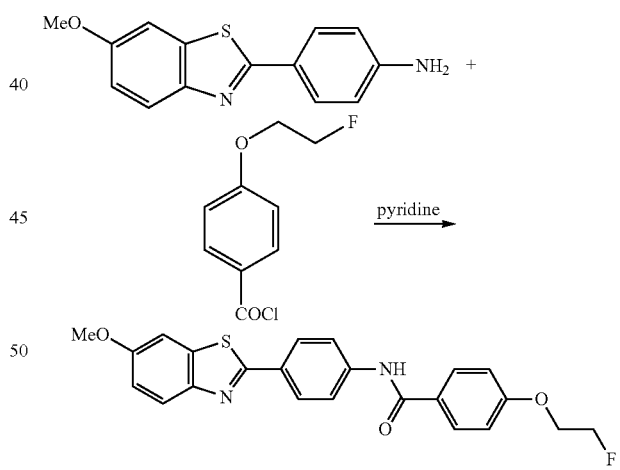

A mixture of 4-(2-fluoroethoxy)benzoic acid (0.20 g, 1.11 mmol) and thionyl chloride (0.53 g, 4.44 mmol) in chloroform (5 ml) was heated under reflux for 5 h. The reaction mixture was cooled to room temperature and the excess reagent and solvent was removed under reduced pressure to give the crude acid chloride. The amide was prepared as described in the Amide Coupling section using the crude acid chloride, and 2-(4-aminophenyl)-6-methoxybenzothiazole (0.28 g, 1.11 mmol) in dry pyridine (10 ml) to give the title compound (0.34 g, 72%) as a pale yellow solid after work-up.

$^1$H NMR (400 MHz, DMSO-$d_6$) δ 3.80 (s, 3H), 4.29 (dist d of t, $J_{HF}$=30 Hz, $J_{HH}$=3.7 Hz, 2H), 4.73 (dist d of t, $J_{HF}$=48

Hz, $J_{HH}$=3.7 Hz, 2H), 7.06 (m, 3H), 7.65 (d, J=2.7 Hz, 1H), 7.86 (d, J=8.8 Hz, 1H), 7.91-7.98 (m, 6H), 10.33 (s, 1H); $^{13}$C NMR (100.5 MHz, DMSO-d$_6$) δ 56.40, 67.97 (d, $J_{CF}$=19 Hz), 82.70 (d, $J_{CF}$=167 Hz), 105.56, 114.86, 116.44, 121.04, 123.79, 127.63, 128.09, 128.64, 130.47, 136.47, 142.48, 148.73, 158.01, 161.65, 165.08, 165.75; LRMS (ESI−) 421 (M$^+$−H, 100%).

4-(2-Hydroxyethoxy)-N-[4-(6-methoxybenzothiazol-2-yl)-phenyl]-benzamide

Book No.: SKT03-33

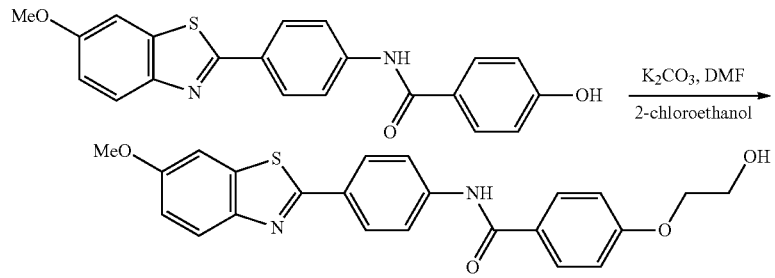

A mixture of 4-hydroxy-N-[4-(6-methoxybenzothiazol-2-yl)-phenyl]-benzamide (0.20 g, 0.53 mmol), chloroethanol (0.064 g, 0.80 mmol) and potassium carbonate (0.26 g, 1.86 mmol) was heated at 100° C. in dry DMF (10 ml) for 18 h. On cooling to room temperature, water (30 ml) was added and the reaction mixture was extracted with EtOAc (7×40 ml). The combined organic extracts were washed with brine (80 ml) and dried (Na$_2$SO$_4$). The solvent was removed under reduced pressure to give the title compound (0.17 g, 76%) as a colourless solid.

$^1$H NMR (400 MHz, DMSO-d$_6$) δ 3.70 (q, J=4.8 Hz, 2H), 3.80 (s, 3H), 4.03 (t, J=4.8 Hz, 2H), 4.87 (t, J=5.1 Hz, 1H), 7.03 (d, J=8.9 Hz, 2H), 7.07 (dd, J=2.4, 8.9 Hz, 1H), 7.64 (d, J=2.7 Hz, 1H), 7.86 (d, J=8.9 Hz, 1H), 7.93-7.98 (m, 6H), 10.33 (s, 1H); $^{13}$C NMR (100.5 MHz, DMSO-d$_6$) δ 56.40, 60.11, 70.48, 105.56, 114.78, 116.42, 121.00, 123.78, 127.18, 128.06, 128.59, 130.43, 136.47, 142.56, 148.75, 158.00, 162.25, 165.09, 165.79.

The reaction conditions employed were based on the methods described by Zhang et al. for the reaction of phenolic compounds with chloroalcohols.

4-Dimethylamino-N-[4-(6-(2-hydroxyethoxy)-benzothiazol-2-yl)-phenyl]-benzamide

Book No.: SKT03-19

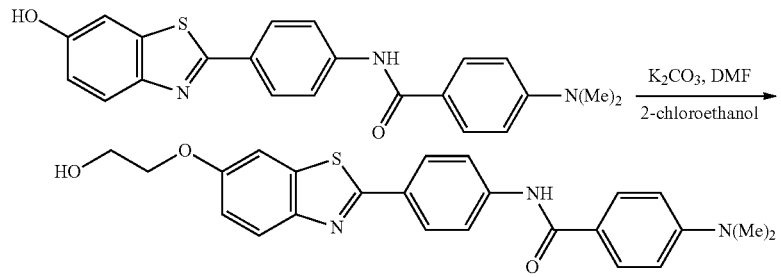

A mixture of (4-dimethylamino-N-[4-(6-hydroxybenzothiazol-2-yl)-phenyl]-benzamide (0.20 g, 0.51 mmol), chloroethanol (0.05 g, 0.62 mmol) and potassium carbonate (0.23 g, 1.63 mmol) was heated at 100° C. in dry DMF (10 ml) for 18 h. On cooling to room temperature, water (30 ml) was added and the reaction mixture was extracted with EtOAc (7×40 ml). The combined organic extracts were washed with brine (80 ml) and dried (Na$_2$SO$_4$). The solvent was removed under reduced pressure to give the title compound (0.117 g, 53%) as a pale yellow solid.

$^1$H NMR (400 MHz, DMSO-d$_6$) δ 2.96 (s, 6H), 3.71 (m, 2H), 4.03 (m, 2H), 4.86 (br s, 1H), 6.72 (d, J=9.2 Hz, 2H), 7.07 (dd, J=8.9, 2.4 Hz, 1H), 7.64 (d, J=2.4 Hz, 1H), 7.85 (d, J=9.2 Hz, 3H), 7.93 (m, 4H), 10.08 (s, 1H); $^{13}$C NMR (62.5 MHz, CDCl$_3$/DMSO-d$_6$) δ 39.50, 59.55, 69.79, 104.70, 110.21, 115.58, 119.77, 120.55, 122.60, 126.89, 127.40, 128.98, 135.44, 141.85, 147.88, 152.04, 156.39, 164.32, 165.39.

The reaction conditions employed were based on the methods described by Zhang et al. for the reaction of phenolic compounds with chloroalcohols.

4-Fluoro-3-trifluoromethyl-N-[4-(6-methoxybenzothiazol-2-yl)-phenyl]-benzamide

Book No.: SKT05-37

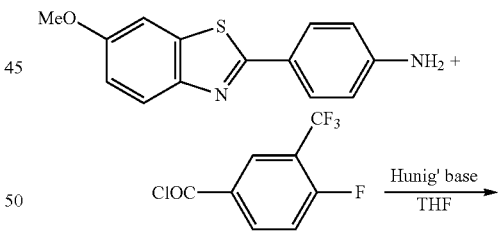

-continued

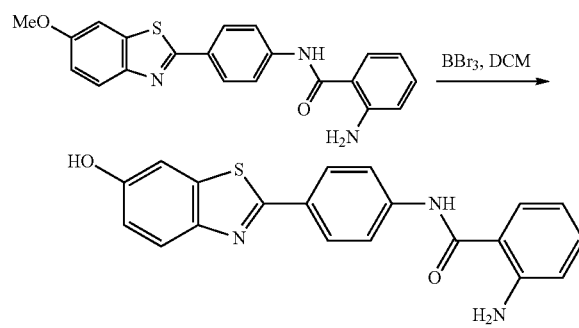

A mixture of 4-fluoro-3-trifluoromethylbenzoic acid (0.32 g, 1.56 mmol) and thionyl chloride (5 ml) was heated under reflux for 4 h. The reaction mixture was cooled to room temperature and excess reagent was removed under reduced pressure to give the crude acid chloride. The amide was prepared as described in the Amide Coupling section using the crude acid chloride and 2-(4-aminophenyl)-6-methoxybenzothiazole (0.40 g, 1.56 mmol) in dry pyridine (12 ml) to give the title compound (0.502 g, 72%) as a colourless solid after recrystallisation from AcOH.

$^1$H NMR (250 MHz, DMSO-$d_6$) δ 3.84 (s, 3H), 7.10 (dd, J=8.8, 2.4 Hz, 1H), 7.66 (s, 1H), 7.72 (m, 1H), 7.90 (d, J=8.8 Hz, 1H), 7.95 (d, J=8.5 Hz, 2H), 8.03 (d, J=8.5 Hz, 2H), 8.38 (d, J=6.1 Hz, 1H), 8.30-8.43 (m, 1H), 10.71 (s, 1H); $^{13}$C NMR (100 MHz, DMSO-$d_6$) δ 56.22, 105.42, 116.21, 117.13 (d of q, $J_{CF}$=32.7, 13.3 Hz), 117.99 (d, $J_{CF}$=21.0 Hz), 121.14, 122.84 (q, $J_{CF}$=272.5 Hz), 123.63, 127.54 (d of q, $J_{CF}$=4.6, 1.5 Hz), 127.92, 129.14, 131.97 (d, $J_{CF}$=3.8 Hz), 135.58 (d, $J_{CF}$=10.1 Hz), 136.37, 141.60, 148.61, 157.92, 161.19 (d of q, $J_{CF}$=258.5, 1.6 Hz), 163.74, 164.71.

Non-Fluorinated Hydroxy-Amides

2-Amino-N-[4-(6-hydroxybenzothiazol-2-yl)-phenyl]-benzamide

Book No.: SKT01-101

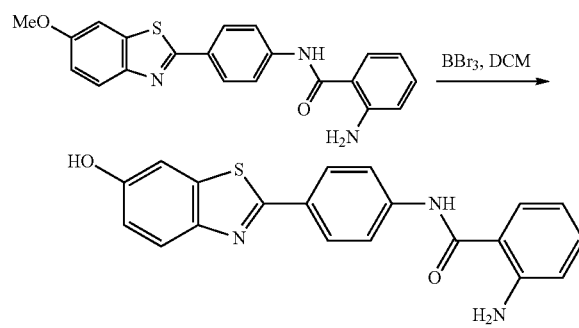

Prepared as described in the Demethylation section using 2-amino-N-[4-(6-methoxy benzothiazol-2-yl)-phenyl]-benzamide (50 mg, 0.13 mmol) in dry DCM (3 ml) and BBr$_3$ (1.0 M solution in DCM, 0.67 ml, 0.67 mmol) to give the title compound (31 mg, 64%) as a colourless solid after work-up and flash chromatography (6:1 Et$_2$O/Hexane).

$^1$H NMR (400 MHz, DMSO-$d_6$) δ 6.42 (br s, 2H), 6.65 (t, J=7.5 Hz, 1H), 6.82 (d, J=8.2 Hz, 1H), 7.03 (dd, J=8.6, 1.2 Hz, 1H), 7.26 (t, J=7.5 Hz, 1H), 7.45 (d, J=1.2 Hz, 1H), 7.71 (d, J=7.5 Hz, 1H), 7.87 (d, J=8.6 Hz, 1H), 7.96 (d, J=8.6 Hz, 2H), 8.03 (d, J=8.6 Hz, 2H), 9.89 (s, 1H), 10.30 (s, 1H); $^{13}$C NMR (100.5 MHz, DMSO-$d_6$) δ 107.25, 115.16, 115.31, 116.46, 116.91, 120.96, 123.65, 127.69, 128.50, 129.29, 132.85, 136.26, 142.13, 147.69, 150.38, 156.04, 163.75, 168.48.

3-Amino-N-[4-(6-hydroxybenzothiazol-2-yl)-phenyl]-benzamide

Book No.: SKT01-77

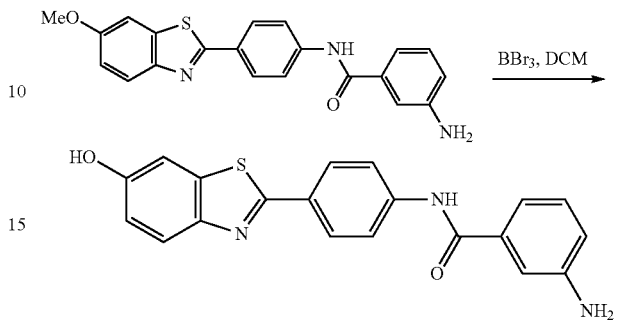

Prepared as described in the Demethylation section using 3-amino-N-[4-(6-methoxybenzothiazol-2-yl)-phenyl]-benzamide (50 mg, 0.13 mmol) in dry DCM (3 ml) and BBr$_3$ (1.0 M solution in DCM, 0.67 ml, 0.67 mmol) to give the title compound (29 mg, 60%) as a pale brown solid after work-up and flash chromatography (1:1 Hexane/EtOAc followed by EtOAc).

$^1$H NMR (250 MHz, DMSO-$d_6$) δ 5.37 (s, 2H), 6.77 (d, J=7.3 Hz, 1H), 6.98 (dd, J=8.5, 2.1 Hz, 1H), 7.07-7.20 (m, 3H), 7.40 (d, J=2.1 Hz, 1H), 7.82 (d, J=8.5 Hz, 1H), 7.93-8.00 (m, 4H), 9.92 (s, 1H), 10.37 (s, 1H); $^{13}$C NMR (62.5 MHz, DMSO-$d_6$) δ 106.80, 112.92, 114.87, 116.04, 117.19, 135.65, 123.21, 147.20, 155.60, 128.88, 163.35, 166.72, 141.71, 147.20, 148.85, 155.60, 163.35, 166.72

4-Amino-N-[4-(6-hydroxybenzothiazol-2-yl)-phenyl]-benzamide

Book No.: SKT01-57

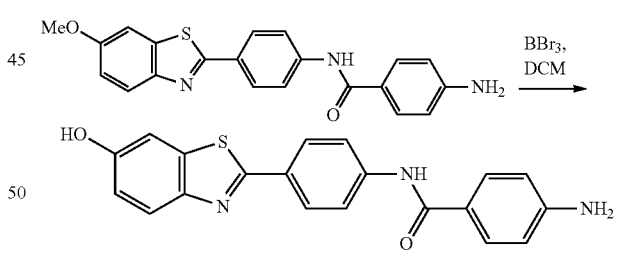

Prepared as described in the Demethylation section using 4-amino-N-[4-(6-methoxybenzothiazol-2-yl)-phenyl]-benzamide (50 mg, 0.13 mmol) in dry DCM (3 ml) and BBr$_3$ (1.0 M solution in DCM, 0.67 ml, 0.67 mmol) to give the title compound (27 mg, 56%) as a tan solid after work-up and flash chromatography (1:1 Hexane/EtOAc followed by EtOAc).

$^1$H NMR (250 MHz, DMSO-$d_6$) δ 5.84 (s, 2H), 6.62 (d, J=8.5 Hz, 2H), 6.98 (dd, J=1.5, 8.8 Hz, 1H), 7.39 (d, J=1.5 Hz, 1H), 7.75 (d, J=8.5 Hz, 2H), 7.82 (d, J=8.8 Hz, 1H), 7.95 (br s, 4H), 9.90 (vbr s, 1H), 10.05 (s, 1H); $^{13}$C NMR (62.5 MHz, CDCl$_3$/DMSO-$d_6$) δ 106.17, 112.65, 115.54, 119.82, 121.00, 122.60, 126.79, 127.48, 129.15, 135.38, 141.64, 146.88, 151.51, 155.11, 163.30, 165.56.

2-Dimethylamino-N-[4-(6-hydroxybenzothiazol-2-yl)-phenyl]-benzamide

Book No.: SKT01-111

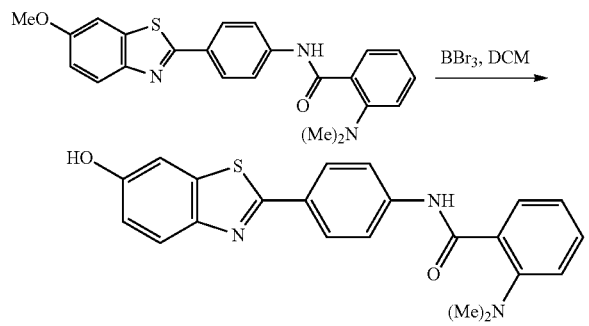

Prepared as described in the Demethylation section using 2-dimethylamino-N-[4-(6-methoxybenzothiazol-2-yl)-phenyl]-benzamide (40 mg, 0.09 mmol) in dry DCM (3 ml) and BBr$_3$ (1.0 M solution in DCM, 0.5 ml, 0.5 mmol) to give the title compound (23 mg, 59%) as a colourless solid after work-up and flash chromatography (4:1 DCM/EtOAc followed by EtOAc)

$^1$H NMR (250 MHz, DMSO-d$_6$) δ 2.82 (s, 6H), 6.93 (d, J=8.5 Hz, 1H), 7.11 (m, 1H), 7.23 (d, J=8.5 Hz, 1H), 7.28 (s, 1H), 7.44 (m, 1H), 7.74 (d, J=8.5 Hz, 1H), 7.78-7.85 (m, 3H), 7.85-7.95 (m, 2H), 9.69 (s, 1H), 11.81 (s, 1H); $^{13}$C NMR (100.5 MHz, CDCl$_3$/DMSO-d$_6$) δ 44.88, 107.08, 116.46, 119.91, 120.32, 123.21, 123.58, 127.73, 127.98, 129.00, 130.88, 132.48, 136.35, 141.74, 147.85, 152.12, 156.14, 163.74, 165.87.

4-Dimethylamino-N-[4-(6-hydroxybenzothiazol-2-yl)-phenyl]-benzamide

Book No.: SKT02-177

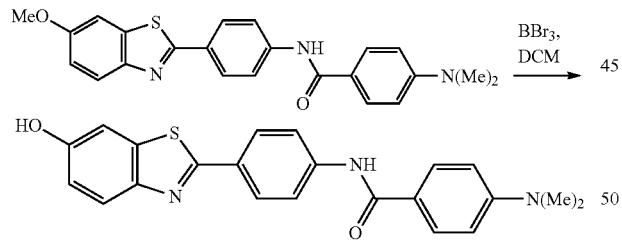

Prepared as described in the Demethylation section using 4-dimethylamino-N-[4-(6-methoxybenzothiazol-2-yl)-phenyl]-benzamide (0.50 g, 1.24 mmol) in dry DCM (50 ml) and BBr$_3$ (1.0 M solution in DCM, 6.2 ml, 6.2 mmol) to give the title compound (0.45 g, 93%) as a yellow solid after work-up and flash chromatography (4:1 DCM/EtOAc followed by EtOAc).

$^1$H NMR (250 MHz, DMSO-d$_6$) δ 3.00 (s, 6H), 6.75 (d, J=8.5 Hz, 2H), 7.00 (d, J=9.1 Hz, 1H), 7.43 (s, 1H), 7.79 (d, J=8.5 Hz, 1H), 7.92-8.02 (m, 5H), 10.07 (s, 1H), 10.24 (s, 1H); $^{13}$C NMR (100.5 MHz, DMSO-d$_6$) δ 40.59, 107.23, 111.20, 116.50, 120.68, 121.07, 123.51, 127.61, 128.10, 129.87, 136.11, 142.63, 147.57, 152.98, 156.21, 163.68, 165.85

Fluorinated Hydroxy-Amides

4-Nitro-3-trifluoromethyl-N-[4-(6-hydroxybenzothiazol-2-yl)-phenyl]-benzamide Book No.: SKT03-7

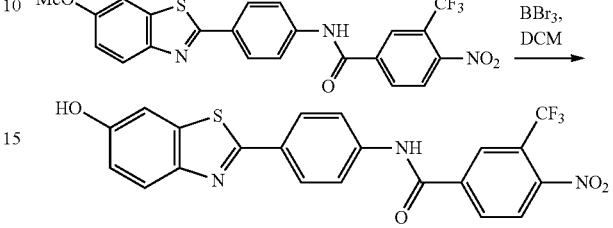

Prepared as described in the Demethylation section using 4-nitro-3-trifluoromethyl-N-[4-(6-methoxybenzothiazol-2-yl)-phenyl]-benzamide (0.10 g, 0.21 mmol) in dry DCM (10 ml) and BBr$_3$ (1.0 M solution in DCM, 1.1 ml, 1.1 mmol) to give the title compound (0.07 g, 71%) as a yellow solid after work-up and flash chromatography (3:1 EtOAc/Hexane).

$^1$H NMR (400 MHz, DMSO-d$_6$) δ 6.93 (dd, J=8.5, 2.4 Hz, 1H), 7.35 (d, J=2.4 Hz, 1H), 7.78 (d, J=8.5 Hz, 1H), 7.91 (dd, J=8.9, 2.0 Hz, 2H), 8.00 (dd, J=8.9, 2.0 Hz, 2H), 8.30 (d, J=8.2 Hz, 1H), 8.44 (dd, J=8.2, 1.7 Hz, 1H), 8.48 (s, 1H), 9.82 (s, 1H), 10.86 (s, 1H); $^{13}$C NMR (100.5 MHz, DMSO-d$_6$) δ 107.46, 116.74, 121.20, 121.35, 122.01 (q, J=33 Hz), 123.92, 126.44, 128.09, 129.69, 134.65, 136.52, 139.39, 141.32, 147.82, 149.38, 156.33, 163.41, 163.66 (1 missing).

4-Amino-3-trifluoromethyl-N-[4-(6-hydroxybenzothiazol-2-yl)-phenyl]-benzamide Book No.: SKT02-45

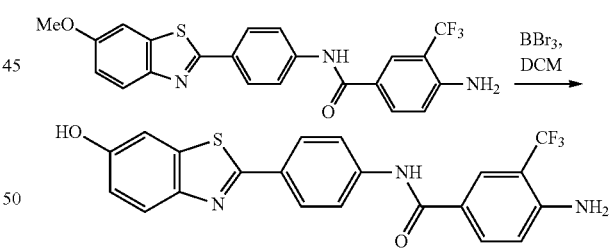

Prepared as described in the Demethylation section using 4-amino-3-trifluoromethyl-N-[4-(6-methoxybenzothiazol-2-yl)-phenyl]-benzamide (0.30 g, 0.68 mmol) in dry DCM (10 ml) and BBr$_3$ (1.0 M solution in DCM, 5.42 ml, 5.42 mmol) to give the title compound (0.064 g, 22%) as an orange solid after work-up and flash chromatography (3:1 DCM/EtOAc).

IR 3610-2880 (br), 3378, 3259, 1650, 1611, 1525, 1502, 1486, 1456, 1439, 1406, 1318, 1277, 1243, 1181, 1144, 1110, 1051, 974, 907, 832 cm$^{-1}$; $^1$H NMR (250 MHz, acetone-d$_6$) δ 5.85 (s, 2H), 7.02 (d, J=8.8 Hz, 1H), 7.07 (dd, J=8.8, 2.1 Hz, 1H), 7.45 (d, J=2.1 Hz, 1H), 7.84 (d, J=8.8 Hz, 1H), 7.98-8.08 (m, 5H), 8.16 (s, 1H), 8.81 (br s, 1H), 9.71 (s, 1H).

4-(2,2,2-Trifluoroethoxy)-N-[4-(6-hydroxybenzothiazol-2-yl)-phenyl]-benzamide Book No.: SKT02-149

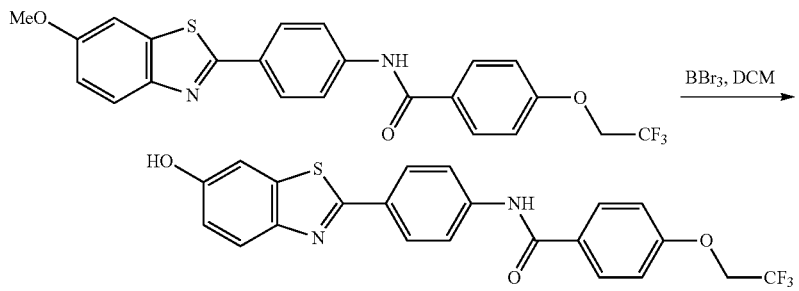

Prepared as described in the Demethylation section using 4-(2,2,2-trifluoroethoxy)-N-[4-(6-methoxybenzothiazol-2-yl)-phenyl]-benzamide (0.20 g, 0.437 mmol) in dry DCM (15 ml) and BBr$_3$ (1.0 M solution in DCM, 2.18 ml, 2.18 mmol) to give the title compound (0.174 g, 89%) as a colourless solid after work-up and flash chromatography (3:1 EtOAc/Hexane).

$^1$H NMR (250 MHz, DMSO-d$_6$) δ 4.90 (q, J=8.8 Hz, 2H), 6.98 (dd, J=8.8, 2.1 Hz, 1H), 7.22 (d, J=8.5 Hz, 2H), 7.40 (d, J=2.1 Hz, 1H), 7.83 (d, J=8.5 Hz, 1H), 7.95-8.04 (m, 6H), 9.86 (s, 1H), 10.42 (s, 1H); $^{13}$C NMR (62.5 MHz, CDCl$_3$/DMSO-d$_6$) δ 64.81 (q, J$_{CF}$=35 Hz), 106.24, 113.94, 115.63, 120.10, 122.74, 123.07 (q, J$_{CF}$=278 Hz), 126.95, 128.30, 128.36, 129.62, 135.63, 141.19, 147.12, 155.28, 159.27, 163.28, 164.90.

yl)-phenyl]-benzamide (0.30 g, 0.63 mmol) in dry DCM (30 ml) and BBr$_3$ (1.0 M solution in DCM, 3.2 ml, 3.2 mmol) to give the title compound (0.103 g, 35%) as a pale orange solid after work-up and flash chromatography (20:1 DCM/MeOH).

$^1$H NMR (400 MHz, DMSO-d$_6$) δ 2.74-2.83 (m, 2H), 4.26 (t, J=5.8 Hz, 2H), 6.93 (dd, J=8.8, 2.4 Hz, 1H), 7.07 (d, J=8.8 Hz, 2H), 7.35 (d, J=2.4 Hz, 1H), 7.77 (d, J=8.8 Hz, 1H), 7.91-7.97 (m, 6H), 9.81 (s, 1H), 10.33 (s, 1H); $^{13}$C NMR (62.5 MHz, CDCl$_3$/DMSO-d$_6$) δ 33.22 (q, J$_{CF}$=28 Hz), 60.67 (q, J$_{CF}$=3.9 Hz), 106.27, 113.61, 115.63, 120.10, 122.76, 125.73 (q, J$_{CF}$=276 Hz), 126.96, 127.31, 128.27, 129.54, 135.64, 141.26, 147.16, 155.28, 160.36, 163.34, 165.14.

4-(3,3,3-Trifluoropropoxy)-N-[4-(6-hydroxybenzothiazol-2-yl)-phenyl]-benzamide Book No.: SKT03-41

4-(4,4,4-Trifluorobutoxy)-N-[4-(6-hydroxybenzothiazol-2-yl)-phenyl]-benzamide Book No.: SKT02-171

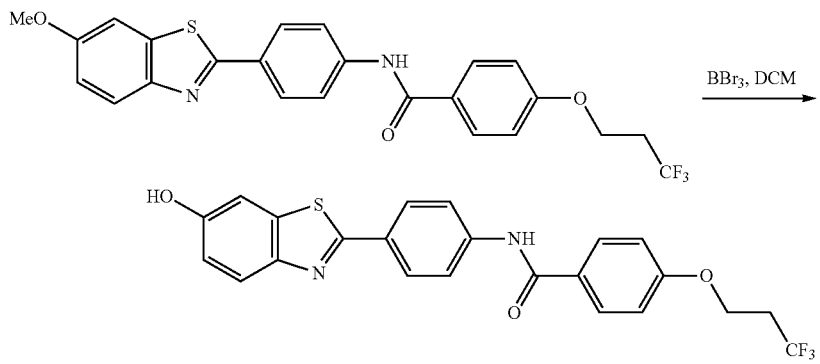

Prepared as described in the Demethylation section using 4-(3,3,3-trifluoropropoxy)-N-[4-(6-methoxybenzothiazol-2-

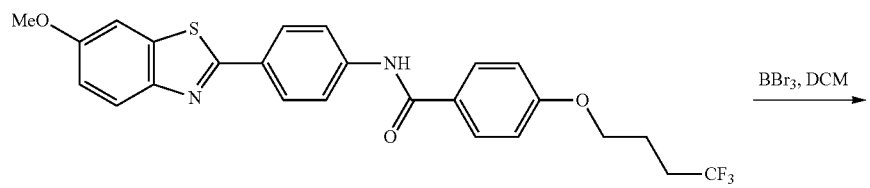

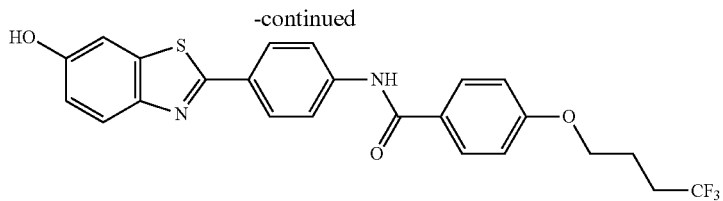

-continued

Prepared as described in the Demethylation section using 4-(4,4,4-trifluorobutoxy)-N-[4-(6-methoxybenzothiazol-2-yl)-phenyl]-benzamide (0.10 g, 0.206 mmol) in dry DCM (10 ml) and BBr$_3$ (1.0 M solution in DCM, 1.0 ml, 1.0 mmol) to give the title compound (17 mg g, 17%) as a yellow solid after work-up, flash chromatography (3:1 EtOAc/Hexane) and recrystallisation from EtOAc.

$^1$H NMR (250 MHz, DMSO-d$_6$) δ 1.94-2.01 (m, 2H), 2.40-2.55 (m, 2H), 4.13 (t, J=5.5 Hz, 2H), 6.97 (d, J=8.8 Hz, 1H), 7.08 (d, J=8.2 Hz, 2H), 7.39 (s, 1H), 7.81 (d, J=8.8 Hz, 1H), 7.91-8.05 (m, 6H), 9.84 (s, 1H), 10.35 (s, 1H); $^{13}$C NMR (100.5 MHz, DMSO-d$_6$) δ 22.01 (q, J$_{CF}$=3.1 Hz), 29.95 (q, J$_{CF}$=28.0 Hz), 66.60, 107.24, 114.69, 116.53, 120.94, 123.64, 127.34, 127.73, 128.04 (q, J$_{CF}$=276 Hz), 128.68, 130.20, 136.27, 142.06, 147.70, 156.03, 161.63, 163.79, 165.63.

2-Hydroxy-N-[3-hydroxy-4-(6-hydroxy-1,3-benzothiazol-2-yl)phenyl]-5-(trifluoromethoxy)benzamide Book No.: SKT05-39

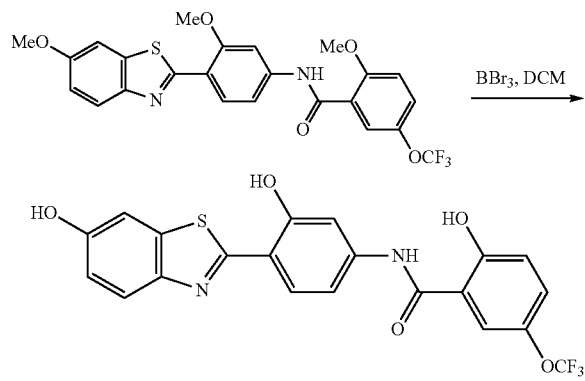

Prepared as described in the Demethylation section using 2-methoxy-N-[3-methoxy-4-(6-methoxy-1,3-benzothiazol-2-yl)phenyl]-5-(trifluoromethoxy)benzamide (0.30 g, 0.595 mmol) in dry DCM (12 ml) and BBr$_3$ (1.0M in DCM, 1.9 ml, 1.9 mmol) at −78° C. under an atmosphere of argon. Additional BBr$_3$ (1.0 M in DCM, 1.9 ml, 1.9 mmol) was added dropwise and the reaction mixture stirred at room temperature for 4 d to give the title compound (88 mg, 32%) as a pale yellow solid after work-up and flash chromatography (4:2:0.3 Hexane/EtOAc/MeOH).

$^1$H NMR (400 MHz, DMSO-d$_6$) δ 6.98 (dd, J=9.0, 2.3 Hz, 1H), 7.09 (d, J=9.0 Hz, 1H), 7.26 (dd, J=8.6, 0.9 Hz, 1H), 7.39 (d, J=2.3 Hz, 1H), 7.43 (dd, J=9.0, 2.3 Hz, 1H), 7.62 (d, J=0.9 Hz, 1H), 7.82 (d, J=9.0 Hz, 1H), 7.84 (d, J=2.3 Hz, 1H), 7.96 (d, J=8.6 Hz, 1H), 9.74 (s, 1H), 10.54 (s, 1H), 11.68 (s, 1H), 11.2-12.2 (br s, 1H); $^{13}$C NMR (100.5 MHz, DMSO-d$_6$) δ 106.96, 108.30, 112.56, 114.88, 116.55, 119.08, 120.39, 120.70 (q, J$_{CF}$=255 Hz), 122.50, 122.91, 126.76, 129.05, 135.54, 140.87, 141.67, 145.45, 155.96, 156.69, 157.00, 162.73, 164.92.

4-Fluoro-N-[4-(6-hydroxybenzothiazol-2-yl)-phenyl]-benzamide

Book No.: SKT02-163

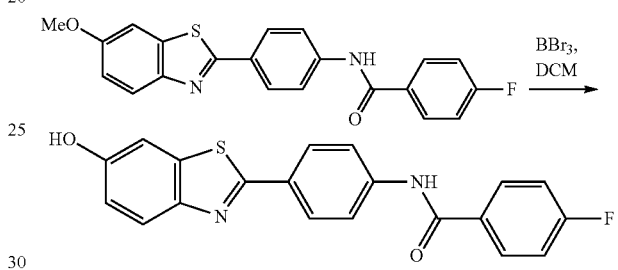

Prepared as described in the Demethylation section using 4-fluoro-N-[4-(6-methoxybenzo thiazol-2-yl)-phenyl]-benzamide (100 mg, 0.26 mmol) in dry DCM (10 ml) and BBr$_3$ (1.0 M solution in DCM, 1.3 ml, 1.3 mmol) to give the title compound (96 mg, 99%) as a pale yellow solid after work-up and flash chromatography (1:1 Hexane/EtOAc).

$^1$H NMR (400 MHz, DMSO-d$_6$) δ 6.93 (dd, J=8.5, 2.4 Hz, 1H), 7.34 (t, J=8.8 Hz, 2H), 7.35 (d, J=2.4 Hz, 1H), 7.77 (d, J=8.5 Hz, 1H), 7.91 (d, J=8.8 Hz, 2H), 7.96 (d, J=8.8 Hz, 2H), 8.01 (dd, J=8.8, 5.5 Hz, 2H), 9.82 (s, 1H), 10.48 (s, 1H); $^{13}$C NMR (62.5 MHz, CDCl$_3$/DMSO-d$_6$) δ 106.30, 114.86 (d, J$_{CF}$=22.5 Hz), 115.69, 120.23, 122.80, 127.04, 128.56, 130.12 (d, J$_{CF}$=8.8 Hz), 130.84 (d, J$_{CF}$=1.9 Hz), 135.71, 141.03, 147.18, 155.33, 163.34, 164.21 (d, J$_{CF}$=252 Hz), 164.74.

The title compound is set out in WO 2006/014382.

2-Trifluoromethyl-N-[4-(6-hydroxy-1,3-benzothiazol-2-yl)phenyl]-4-(hydroxy)benzamide Book No.: SKT05-17

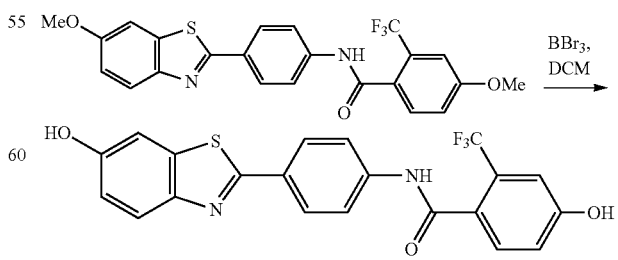

Prepared as described in the Demethylation section using 2-trifluoromethyl-N-[4-(6-methoxy-1,3-benzothiazol-2-yl)

phenyl]-4-(methoxy)benzamide (0.30 g, 0.655 mmol) in dry DCM (15 ml) and BBr₃ (1.0M in DCM, 1.4 ml, 1.4 mmol) at −78° C. under an atmosphere of argon. Stirring was continued at −78° C. for 1 h, and then the reaction mixture was allowed to rise to room temperature overnight. A further volume of BBr₃ (1.0 M in DCM, 1.4 ml, 1.4 mmol) was added and the reaction mixture stirred at room temperature for 24 h to give the title compound (0.175 g, 62%) as a colourless solid after work-up and flash chromatography (15:1 DCM/MeOH).

¹H NMR (250 MHz, DMSO-d₆) δ 6.99 (dd, J=8.5, 2.1 Hz, 1H), 7.13 (d, J=8.5 Hz, 1H), 7.17 (s, 1H), 7.41 (d, J=2.1 Hz, 1H), 7.59 (d, J=8.5 Hz, 1H), 7.83 (d, J=8.5 Hz, 2H), 7.88 (s, 1H), 7.99 (d, J=8.5 Hz, 2H), 9.60-10.64 (vbr s, 2H), 10.70 (s, 1H); ¹³C NMR (62.5 MHz, CDCl₃/DMSO-d₆) δ 106.16, 112.96 (q, $J_{CF}$=3.9 Hz), 115.55, 117.77, 119.43, 122.71, 123.04 (q, $J_{CF}$=274 Hz), 126.37, 126.93, 128.04 (q, $J_{CF}$=32 Hz), 128.31, 129.99, 135.52, 140.98, 147.01, 155.25, 158.48, 162.94, 165.78.

Synthesis of 2-hydroxy-N-[4-(6-hydroxy-1,3-benzothiazol-2-yl)phenyl]-5-(trifluoromethoxy)benzamide Book No.: SKT05-13

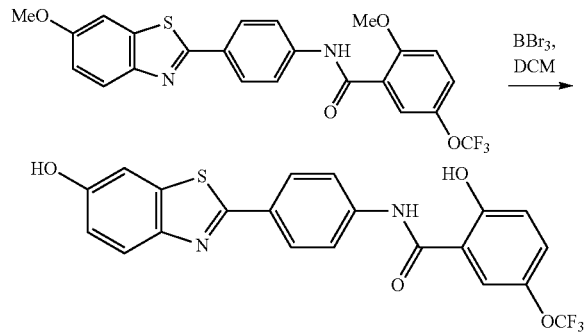

Prepared as described in the Demethylation section using (2-methoxy-N-[4-(6-methoxy-1,3-benzothiazol-2-yl)phenyl]-5-(trifluoromethoxy)benzamide (0.30 g, 0.633 mmol) in dry DCM (15 ml) and BBr₃ (1.0 M in DCM, 1.4 ml, 1.4 mmol) at −78° C. under an atmosphere of argon. A further volume of BBr₃ (1.0 M in DCM, 1.4 ml, 1.4 mmol) was added and the reaction mixture stirred at room temperature for 24 h to give the title compound (0.255 g, 90%) as a colourless solid after work-up and flash chromatography (10:1 DCM/MeOH).

¹H NMR (400 MHz, DMSO-d₆) δ 6.93 (dd, J=8.9, 2.4 Hz, 1H), 7.05 (d, J=8.9 Hz, 1H), 7.40 (d, J=2.4 Hz, 1H), 7.39-7.42 (m, 1H), 7.78 (d, J=8.9 Hz, 1H), 7.80 (m, 1H), 7.84 (d, J=8.5 Hz, 2H), 7.97 (d, J=8.5 Hz, 2H), 9.83 (s, 1H), 10.58 (s, 1H), 11.35-12.08 (vbr s, 1H); ¹³C NMR (100.5 MHz, DMSO-d₆) δ 107.44, 116.73, 119.21, 120.65, 120.85 (q, $J_{CF}$=256 Hz), 121.39, 122.79, 123.94, 127.10, 128.10, 129.50, 136.50, 140.92, 140.99, 147.82, 156.31, 156.87, 163.69, 165.09.

4-Hydroxy-N-[4-(6-hydroxy-1,3-benzothiazol-2-yl)-3-(trifluoromethyl)phenyl]benzamide Book No.: SKT04-179

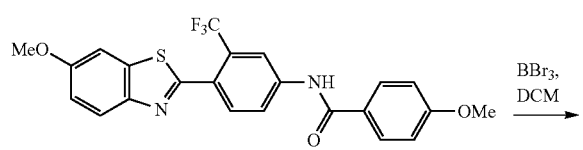

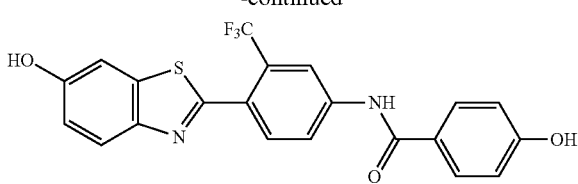

Prepared as described in the Demethylation section using N-[3-trifluoromethyl-4-(6-methoxy-1,3-benzothiazol-2-yl)phenyl]-4-(methoxy)benzamide (90 mg, 0.196 mmol) in dry DCM (5 ml) and BBr₃ (1.0 M solution in DCM, 0.413 ml, 0.413 mmol) at −78° C. to give the title compound (68 mg, 81%) as a colourless solid after work-up and flash chromatography (1:1 Hexane/EtOAc).

¹H NMR (250 MHz, CD₃OD) δ 6.90 (d, J=8.2 Hz, 2H), 7.05 (d, J=8.8 Hz, 1H), 7.34 (s, 1H), 7.70 (d; J=8.2 Hz, 1H), 7.85 (d, J=8.2 Hz, 1H), 7.88 (d, J=8.2 Hz, 2H), 8.11 (d, J=8.2 Hz, 1H), 8.36 (s, 1H); ¹³C NMR (62.5 MHz, CDCl₃/DMSO-d₆) δ 106.20, 115.32, 116.22, 118.31 (q, $J_{CF}$=2.9 Hz), 122.54, 123.54 (q, $J_{CF}$=274 Hz), 123.83, 125.41, 126.98, 128.87 (q, $J_{CF}$=31 Hz), 129.87, 132.86, 137.44, 141.06, 147.06, 155.69, 161.01, 161.17, 166.43.

4-Fluoro-3-nitro-N-[4-(6-hydroxybenzothiazol-2-yl)-phenyl]-benzamide

Book No.: SKT03-129

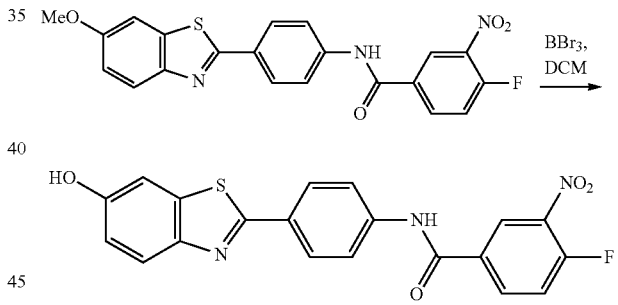

Prepared as described in the Demethylation section using 4-fluoro-3-nitro-N-[4-(6-methoxybenzothiazol-2-yl)-phenyl]-benzamide (0.10 g, 0.24 mmol) in dry DCM (10 ml) and BBr₃ (1.0 M solution in DCM, 1.2 ml, 1.2 mmol) to give the title compound (0.062 g, 63%) as a colourless solid after work-up and flash chromatography (2:1 Hexane/EtOAc, then 2:1:0.1 EtOAc/Hexane/MeOH and finally eluting with 4:1 EtOAc/MeOH).

¹H NMR (250 MHz, DMSO-d₆) δ 6.99 (dd, J=8.8, 2.1 Hz, 1H), 7.42 (d, J=2.1 Hz, 1H), 7.83 (d, J=8.8 Hz, 2H), 7.97 (d, J=8.8 Hz, 2H), 8.04 (d, J=8.5 Hz, 2H), 8.40-8.45 (m, 1H), 8.79 (dd, $J_{HH}$=1.2, $J_{HF}$=7.0 Hz, 1H), 9.91 (s, 1H), 10.83 (s, 1H); ¹³C NMR (62.5 MHz, CDCl₃/DMSO-d₆) δ 106.24, 115.68, 118.18 (d, $J_{CF}$=21.5 Hz), 120.46, 122.77, 125.68, 126.90, 128.92, 131.16 (d, $J_{CF}$=3.9 Hz), 135.52 (d, $J_{CF}$=11.7 Hz), 135.61, 136.36 (d, $J_{CF}$=7.8 Hz), 140.43, 147.09, 155.33, 156.41 ($J_{CF}$=269 Hz), 162.18, 162.97.

Non-Fluorinated Methyl-Amides

N-[4-(6-methylbenzothiazol-2-yl)-phenyl]-benzamide

Book No.: SK696-32

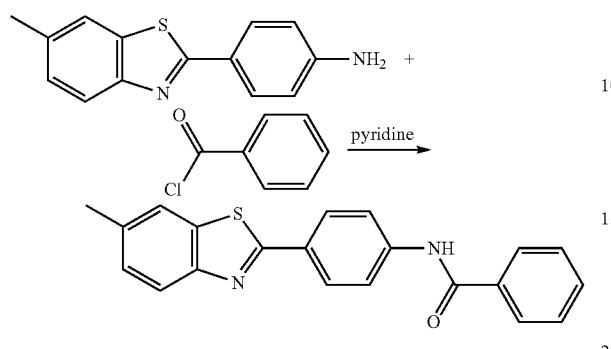

Prepared as described in the Amide Coupling section using 2-(4-aminophenyl)-6-methylbenzothiazole (1.0 g, 4.16 mmol) and benzoyl chloride (0.58 g, 4.16 mmol) in dry THF (10 ml) containing triethylamine (0.46 g, 4.58 mmol) to give the title compound (1.23 g, 86%) as a colourless solid after work-up.

$^1$H NMR (400 MHz, DMSO-$d_6$) δ 2.44 (s, 3H), 7.34 (dd, J=8.2, 1.2 Hz, 1H), 7.53-7.56 (m, 2H), 7.59-7.63 (m, 1H), 7.89-7.91 (m, 2H), 7.96-7.99 (m, 4H), 8.06 (d, J=9.0 Hz, 2H), 10.55 (s, 1H); $^{13}$C NMR (100 MHz, DMSO-$d_6$) δ 21.47, 120.95, 122.19, 122.65, 128.12, 128.21, 128.45, 128.64, 128.87, 132.21, 135.00, 135.19, 135.48, 142.38, 152.32, 166.29, 166.32.

2-Nitro-N-[4-(6-methylbenzothiazol-2-yl)-phenyl]-benzamide

Book No.: SK2033-51

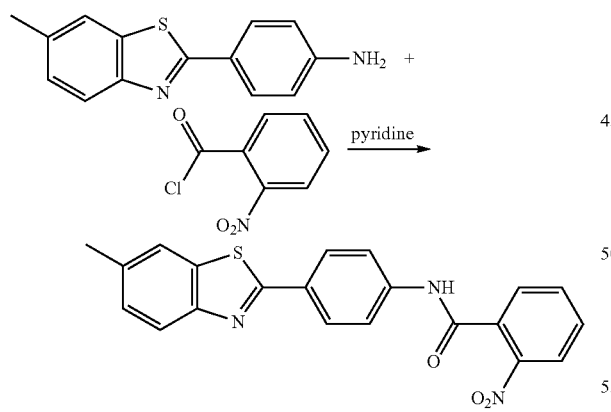

Prepared as described in the Amide Coupling section using 2-(4-aminophenyl)-6-methylbenzothiazole (0.59 g, 2.45 mmol) and 2-nitrobenzoyl chloride (0.50 g, 2.69 mmol) in dry pyridine (10 ml) to give the title compound (0.94 g, 98%) as tan-coloured crystals after recrystallisation from 1,2-dichloroethane.

$^1$H NMR (250 MHz, DMSO-$d_6$) δ 2.45 (s, 3H), 7.34 (d, J=8.2 Hz, 1H), 7.75-7.93 (m, 7H), 8.08 (d, J=8.2 Hz, 2H), 8.18 (d, J=7.9 Hz, 1H), 10.99 (s, 1H); $^{13}$C NMR (62.5 MHz, CDCl$_3$/DMSO-$d_6$) δ 21.15, 119.73, 121.11, 121.949, 123.83, 127.55, 128.98, 130.29, 132.76, 133.47, 134.48, 134.80, 141.08, 146.17, 151.68, 164.38, 165.80.

3-Nitro-N-[4-(6-methylbenzothiazol-2-yl)-phenyl]-benzamide

Book No.: SK2033-46

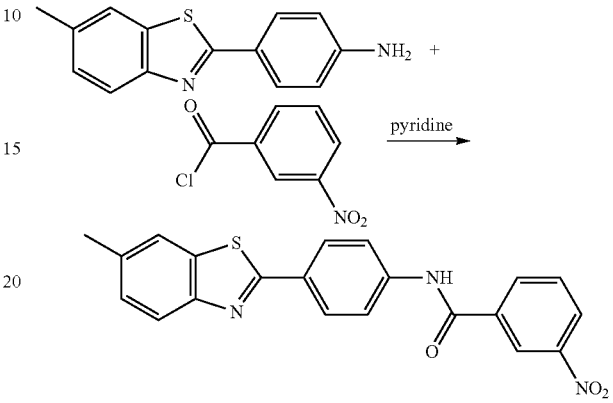

Prepared as described in the Amide Coupling section using 2-(4-aminophenyl)-6-methylbenzothiazole (0.5 g, 2.08 mmol) and 3-nitrobenzoyl chloride (0.77 g, 4.06 mmol) in dry pyridine (10 ml) to give the title compound (0.75 g, 93%) after work-up and flash chromatography (2:1 Hexane/EtOAc, then 1:1 Hexane/EtOAc, then EtOAc).

$^1$H NMR (250 MHz, DMSO-$d_6$) δ 2.43 (s, 3H), 7.32 (d, J=8.2 Hz, 1H), 7.80-7.84 (m, 2H), 7.88 (d, J=8.5 Hz, 1H), 7.98 (d, J=8.8 Hz, 2H), 8.06 (d, J=8.8 Hz, 2H), 8.41-8.43 (m, 2H), 8.80 (s, 1H), 10.82 (s, 1H); $^{13}$C NMR (62.5 MHz, CDCl$_3$/DMSO-$d_6$) δ 21.1, 120.46, 121.09, 121.95, 122.46, 125.77, 127.38, 127.57, 128.73, 129.32, 134.49, 134.79, 136.00, 141.02, 147.60, 151.68, 163.31, 165.78.

4-Nitro-N-[4-(6-methylbenzothiazol-2-yl)-phenyl]-benzamide

Book No.: SK2033-67

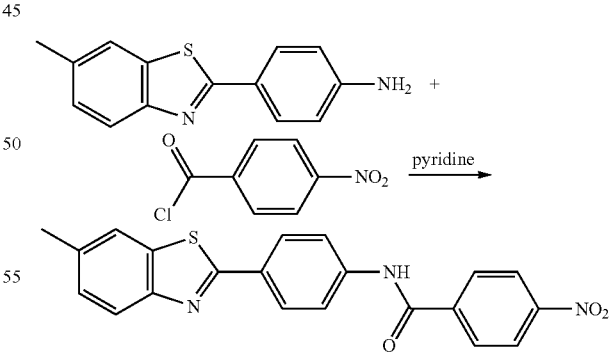

Prepared as described in the Amide Coupling section using 1,2-dichloroethane 2-(4-aminophenyl)-6-methylbenzothiazole (2.5 g, 10.4 mmol) and 4-nitrobenzoyl chloride (2.12 g, 11.4 mmol) in dry pyridine (30 ml) to give the title compound (4.0 g, 99%) as small tan-coloured needles after recrystallisation from DMF/water.

$^1$H NMR (250 MHz, CDCl$_3$/DMSO-$d_6$) δ 1.79 (s, 3H), 6.59 (d, J=8.5 Hz, 1H), 7.04 (s, 1H), 7.15 (d, J=8.2 Hz, 1H), 7.28 (d, J=8.8 Hz, 2H), 7.34 (d, J=8.5 Hz, 2H), 7.54 (d, J=8.5 Hz, 2H), 7.63 (d, J=8.5 Hz, 2H), 9.96 (s, 1H); $^{13}$C NMR (62.5 MHz, CDCl$_3$/DMSO-d$_6$) δ 20.98, 120.27, 121.05, 121.86, 122.91, 127.27, 127.48, 128.59, 128.89, 134.35, 134.65, 140.04, 140.94, 148.92, 151.60, 163.65, 165.53.

For reference, see Weisswange et al.

2-Amino-N-[4-(6-methylbenzothiazol-2-yl)-phenyl]-benzamide

Book No.: SK2033-55

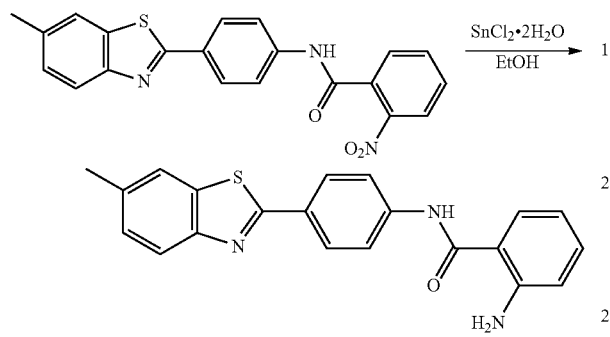

Prepared as described in the Nitro Reduction section using 2-nitro-N-[4-(6-methylbenzothiazol-2-yl)-phenyl]-benzamide (0.5 g, 1.28 mmol) and tin (II) chloride dihydrate (1.45 g, 6.42 mmol) in EtOH (50 ml) to give the title compound (0.063 g, 14%) as a tan needles after recrystallisation from EtOH.

$^1$H NMR (250 MHz, DMSO-d$_6$) δ 2.44 (s, 3H), 6.40 (s, 2H), 6.57-6.63 (m, 1H), 6.77 (d, J=8.2 Hz, 1H), 7.19-7.25 (m, 1H), 7.34 (d, J=8.5 Hz, 1H), 7.66 (d, J=8.2 Hz, 1H), 7.89-7.92 (m, 2H), 7.94 (d, J=8.5 Hz, 2H), 8.04 (d, J=8.5 Hz, 2H), 10.30 (s, 1H); $^{13}$C NMR (100.5 MHz, DMSO-d$_6$) δ 21.40, 116.00, 116.22, 116.99, 120.46, 121.25, 122.17, 127.71 (C×2), 128.55, 128.70, 132.40, 134.82, 134.94, 141.64, 148.98, 152.05, 166.49, 168.25.

3-Amino-N-[4-(6-methylbenzothiazol-2-yl)-phenyl]-benzamide

Book No.: SK2033-72

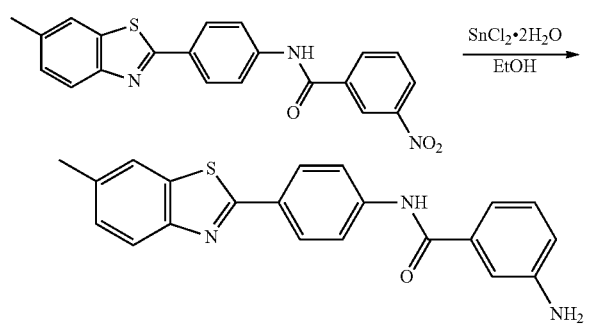

Prepared as described in the Nitro Reduction section using 3-nitro-N-[4-(6-methylbenzothiazol-2-yl)-phenyl]-benzamide (0.30 g, 0.77 mmol) and tin (II) chloride dihydrate (1.39 g, 6.16 mmol) in EtOH (25 ml) to give the title compound (0.131 g, 47%) as a pale yellow solid after flash chromatography (1:1 Hexane/EtOAc).

$^1$H NMR (400 MHz, DMSO-d$_6$) δ 2.39 (s, 3H), 5.31 (s, 2H), 6.72 (dd, J=7.9, 2.1 Hz, 1H), 7.03-7.07 (m, 2H), 7.08-7.12 (m, 1H), 7.28 (d, J=8.5 Hz, 1H), 7.83-7.86 (m, 2H), 7.94 (d, J=8.8 Hz, 2H), 7.98 (d, J=8.8 Hz, 2H), 10.37 (s, 1H); $^{13}$C NMR (62.5 MHz, CDCl$_3$/DMSO-d$_6$) δ 20.96, 113.13, 115.38, 117.03, 119.85, 121.02, 121.76, 127.17, 127.41, 127.79, 128.42, 134.29, 134.51, 135.49, 141.78, 147.83, 151.62, 165.76, 166.53.

4-Amino-N-[4-(6-methylbenzothiazol-2-yl)-phenyl]-benzamide

Book No.: LS-T107

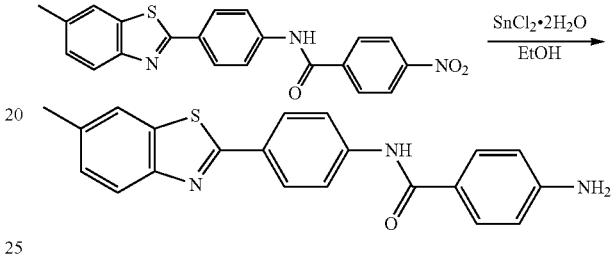

Prepared as described in the Nitro Reduction section using 4-nitro-N-[4-(6-methylbenzothiazol-2-yl)-phenyl]-benzamide (0.39 g, 1.0 mmol) and tin (II) chloride dihydrate (1.13 g, 5.0 mmol) in EtOH (20 ml) to give the title compound (0.30 g, 83%) as a pale yellow solid.

$^1$H NMR (250 MHz, DMSO-d$_6$) δ 2.44 (s, 3H), 5.85 (s, 2H), 6.61 (d, J=8.2 Hz, 2H), 7.33 (d, J=8.5 Hz, 1H), 7.75 (d, J=8.2 Hz, 2H), 7.80-7.92 (m, 2H), 7.97 (d, J=8.5 Hz, 2H), 8.02 (d, J=8.5 Hz, 2H), 10.07 (s, 1H); $^{13}$C NMR (62.5 MHz, CDCl$_3$/DMSO-d$_6$) δ 20.98, 112.73, 119.73, 121.02, 121.48, 121.73, 127.17, 127.38, 129.23, 134.29, 134.45, 142.18, 151.33, 151.65, 165.58, 165.87 (1 missing).

2-Dimethylamino-N-[4-(6-methylbenzothiazol-2-yl)-phenyl]-benzamide

Book No.: SKT01-5

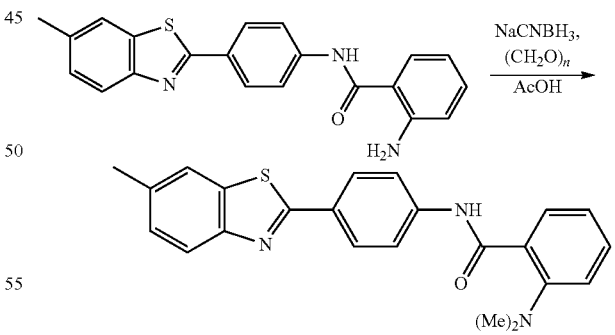

Prepared as described in the Amination section using sodium cyanoborohydride (0.35 g, 5.55 mmol), 2-amino-N-[4-(6-methyl benzothiazol-2-yl)-phenyl]-benzamide (0.40 g, 1.11 mmol) and paraformaldehyde (0.34 g, 11.13 mmol) in AcOH (10 ml) to give the title compound (0.312 g, 73%) as pale yellow crystals after recrystallisation from EtOH.

$^1$H NMR (250 MHz, CDCl$_3$) δ 2.49 (s, 3H), 2.86 (s, 6H), 7.25-7.35 (m, 3H), 7.48-7.55 (m, 1H), 7.67 (s, 1H), 7.81 (d, J=8.5 Hz, 2H), 7.93 (d, J=8.2 Hz, 1H), 8.08 (d, J=8.5 Hz, 2H), 8.28 (dd, J=7.6, 1.5, Hz 1H), 12.58 (s, 1H); $^{13}$C NMR (62.5 MHz, CDCl$_3$) δ 21.60, 45.60, 120.01, 120.57, 121.39, 122.43, 125.35, 127.40, 127.93, 128.41, 129.01, 131.76, 132.76, 135.04, 135.19, 141.34, 152.18, 164.31, 166.74 (1 missing).

The reaction conditions employed were based on the methods described by Ono et al. for the dimethylation of aniline compounds.

3-Dimethylamino-N-[4-(6-methylbenzothiazol-2-yl)-phenyl]-benzamide

Book No.: SK2033-93

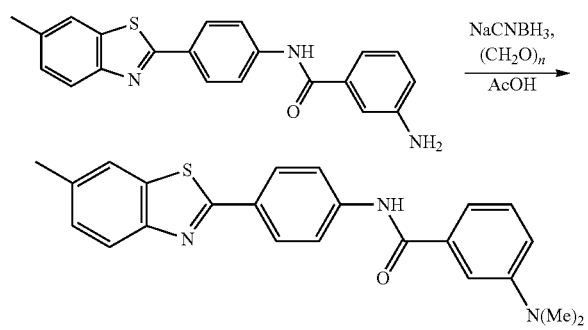

Prepared as described in the Amination section using sodium cyanoborohydride (0.44 g, 6.95 mmol), 3-amino-N-[4-(6-methyl benzothiazol-2-yl)-phenyl]-benzamide (0.50 g, 1.39 mmol) and paraformaldehyde (0.42 g, 13.9 mmol) in AcOH (8 ml) to give the title compound (0.15 g, 28%) as a colourless solid after work-up and flash chromatography (2:1 Hexane/EtOAc).

$^1$H NMR (250 MHz, CDCl$_3$) δ 2.48 (s, 3H), 2.99 (s, 6H), 6.88 (dd, J=8.2, 2.1 Hz, 1H), 7.09 (d, J=7.3 Hz, 1H), 7.26 (m, 2H), 7.32 (d, J=8.5 Hz, 1H), 7.66 (s, 1H), 7.78 (d, J=8.5 Hz, 2H), 7.91 (d, J=8.2 Hz, 1H), 8.05 (d, J=8.5 Hz, 2H), 8.08 (s, 1H); $^{13}$C NMR (62.5 MHz, CDCl$_3$) δ 21.60, 40.54, 111.38, 113.91, 115.82, 120.02, 121.41, 122.52, 127.94, 128.33, 129.45, 129.60, 135.13, 135.26, 135.55, 140.50, 150.75, 152.29, 166.45, 166.63.

The reaction conditions employed were based on the methods described by Ono et al. for the dimethylation of aniline compounds.

4-Dimethylamino-N-[4-(6-methylbenzothiazol-2-yl)-phenyl]-benzamide

Book No.: SK2033-71

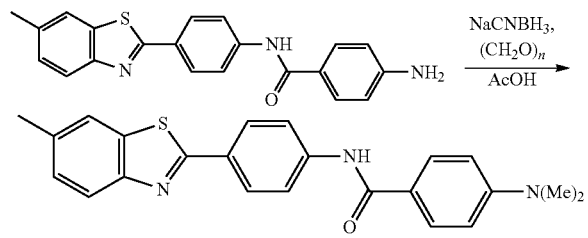

Prepared as described in the Amination section using sodium cyanoborohydride (0.44 g, 6.95 mmol), 4-amino-N-[4-(6-methylbenzothiazol-2-yl)-phenyl]-benzamide (0.50 g, 1.39 mmol) and paraformaldehyde (0.42 g, 13.9 mmol) in AcOH (8 ml) to give the title compound (0.04 g, 7%) as a colourless solid after work-up and flash chromatography (3:1 Hexane/EtOAc).

$^1$H NMR (250 MHz, DMSO-d$_6$) δ 2.44 (s, 3H), 3.00 (s, 6H), 6.77 (d, J=7.9 Hz, 2H), 7.33 (d, J=8.2 Hz, 1H), 7.84-7.92 (m, 4H), 7.98 (dist d, J=8.5 Hz, 2H), 8.03 (dist d, J=8.5 Hz, 2H), 10.17 (s, 1H); $^{13}$C NMR (62.5 MHz, CDCl$_3$/DMSO-d$_6$) δ 39.42, 110.04, 110.15, 119.64, 120.49, 120.99, 121.61, 127.03, 127.17, 127.31, 128.92, 129.06, 134.11, 134.31, 142.10, 151.50, 151.96, 165.22, 165.64.

The reaction conditions employed were based on the methods described by Ono et al. for the dimethylation of aniline compounds.

3-Hydroxy-N-[4-(6-methyl-1,3-benzothiazol-2-yl) phenyl]benzamide

Book No.: SK696-54

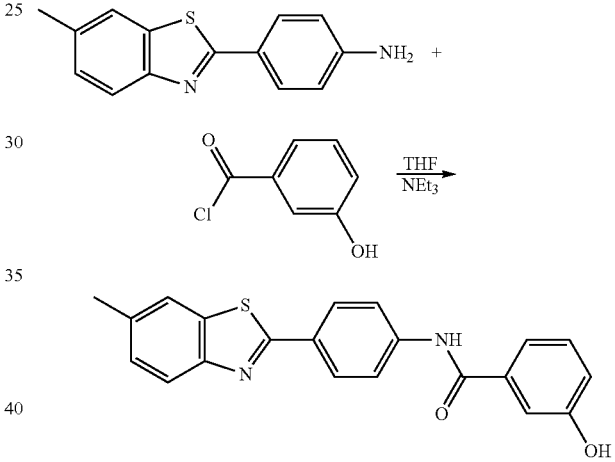

To a stirred solution of 3-hydroxybenzoic acid (0.69 g, 5.0 mmol) in 1:1 THF/DCM (20 ml) was added thionyl chloride (0.65 g, 5.5 mmol) and a drop of DMF. The reaction mixture was heated under reflux for 2.5 h. The reaction mixture was cooled to room temperature and the mixture was transferred by cannula to a stirred solution of dehydrothiotoluidine (1.20 g, 5.0 mmol) in THF (20 ml) at 0° C. The mixture was stirred at 0° C. for 2 h then left to rise to room temperature overnight. The yellow precipitate was collected by filtration under vacuum and washed with THF and water (600 ml). The solid was dried at 80° C. in the oven for 5 h to give the title compound (0.59 g, 33%) as a pale yellow solid.

$^1$H NMR (400 MHz, DMSO-d$_6$) δ 2.44 (s, 3H), 7.02 (dd, J=7.8, 1.6 Hz, 1H), 7.32 (d, J=7.8 Hz, 1H), 7.35-7.37 (m, 2H), 7.42 (d, J=7.8 Hz, 1H), 7.85 (s, 1H), 7.89 (d, J=8.3 Hz, 1H), 7.99 (d, J=8.6 Hz, 2H), 8.04 (d, J=8.6 Hz, 2H), 9.69 (br s, 1H), 10.38 (s, 1H); $^{13}$C NMR (100 MHz, DMSO-d$_6$) δ 21.47, 115.14, 118.77, 119.23, 120.90, 122.16, 122.64, 128.09, 128.43, 128.57, 129.89, 134.99, 135.46, 136.61, 142.42, 152.33, 157.89, 166.33 (1 missing).

3-(Methylamino)-N-[4-(6-methyl-1,3-benzothiazol-2-yl)phenyl]benzamide

Book No.: SK2033-94

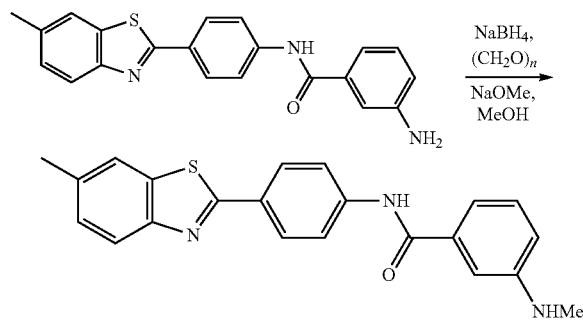

To a stirred mixture of 3-amino-N-[4-(6-methylbenzothiazol-2-yl)-phenyl]-benzamide (0.50 g, 1.39 mmol) and paraformaldehyde (0.059 g, 1.95 mmol) in MeOH (15 ml) at 0° C. was added dropwise a solution of sodium methoxide in MeOH (0.5 M, 3.9 ml, 1.95 mmol). The reaction mixture was then heated under reflux for 1 h. The reaction mixture was cooled to room temperature, sodium borohydride (0.081 g, 2.09 mmol) was added and heating was continued under reflux for 1 h. The reaction mixture was cooled to 0° C. amd 1 M NaOH solution (10 ml) was added, followed by extraction with DCM (3×70 ml). The combined organic extracts were dried ($Na_2SO_4$) and the solvent removed under reduced pressure to give an almost colourless solid. This was purified by flash chromatography (1:1 Hexane/EtOAc) to give the title compound (0.096 g, 18%) as a colourless solid.

$^1$H NMR (400 MHz, DMSO-$d_6$) δ 2.45 (s, 3H), 2.75 (d, J=5.2 Hz, 3H), 5.82 (q, J=5.1 Hz, 1H), 6.75 (dd, J=8.2, 2.0 Hz, 1H), 7.08 (m, 1H), 7.14 (d, J=7.4 Hz, 1H), 7.21-7.25 (m, 1H), 7.33 (dd, J=8.6, 1.6 Hz, 1H), 7.88 (s, 1H), 7.89 (d, J=8.6 Hz, 1H), 7.98 (d, J=8.6 Hz, 2H), 8.04 (d, J=8.6 Hz, 2H), 10.31 (s, 1H); $^{13}$C NMR (100 MHz, DMSO-$d_6$) 21.47, 30.20, 111.07, 115.16, 115.47, 120.87, 122.19, 122.63, 128.09, 128.44, 129.27, 134.98, 135.46, 136.08, 142.56, 150.45, 152.33, 166.36, 167.100.

Imidazo[2,1-b][1,3]thiazole Intermediates

2-Methyl-6-(4-nitrophenyl)imidazo[2,1-b][1,3]thiazole

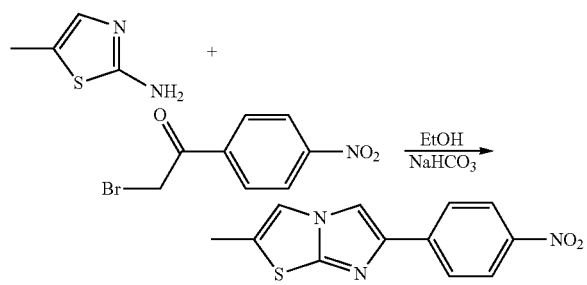

A mixture of 2-amino-5-methylthiazole (0.24 g, 2.11 mmol) and 2-bromo-4'-nitroacetophenone (0.5 g, 2.05 mmol) in EtOH (20 ml) was heated under reflux for 16 h. The reaction mixture was allowed to cool and sodium bicarbonate (200 mg, 2.38 mmol) was added and heating was continued for 1 h. On cooling to room temperature, the solvent was removed under reduced pressure and the residue dissolved in DCM (75 ml) and washed with water (30 ml), brine (30 ml) and dried ($Na_2SO_4$). The solvent was removed under reduced pressure and the residue was purified by flash chromatography (50:1 DCM/MeOH) to give the title compound (0.143 g, 26%) as a yellow solid.

$^1$H NMR (250 MHz, CDCl$_3$) δ 2.45 (s, 3H), 6.49 (s, 1H), 7.76 (s, 1H), 7.97 (d, J=8.5 Hz), 2H), 8.25 (d, J=8.5 Hz, 2H); $^{13}$C NMR (100.5 MHz, DMSO-$d_6$) δ 13.20, 108.67, 111.25, 124.54, 125.67, 128.65, 141.43, 144.53, 146.37, 150.06.

4-(2-Methylimidazo[2,1-b][1,3]thiazol-6-yl)aniline

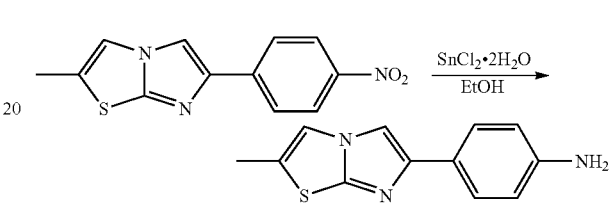

Prepared as described in the Nitro Reduction section using 2-methyl-6-(4-nitrophenyl) imidazo[2,1-b][1,3]thiazole (0.10 g, 0.386 mmol) and tin (II) chloride dihydrate (0.69 g, 3.09 mmol) in EtOH (15 ml) to give a pale orange solid (66 mg, 75%) after work-up and flash chromatography (1:1 DCM/EtOAc).

$^1$H NMR (250 MHz, CDCl$_3$) δ 2.39 (s, 3H), 3.44 (br s, 2H), 6.70 (d, J=8.5 Hz, 2H), 7.08 (s, 1H), 7.47 (s, 1H), 7.59 (d, J=8.5 Hz, 2H); $^{13}$C NMR (62.5 MHz, CDCl$_3$) δ 14.09, 106.20, 115.15, 115.30, 125.04, 125.80, 126.25, 145.69, 146.98, 149.29.

3-Methyl-6-(4-nitrophenyl)imidazo[2,1-b][1,3]thiazole

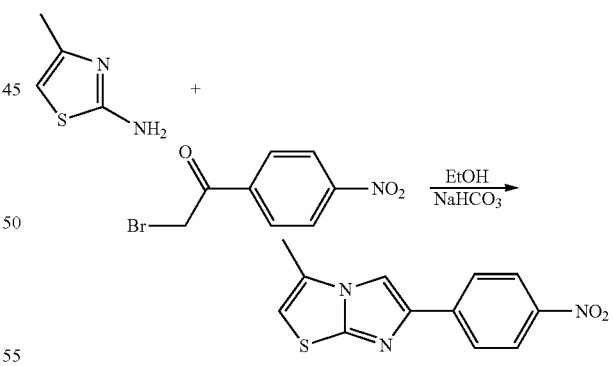

A mixture of 2-amino-4-methylthiazole (0.24 g, 2.11 mmol) and 2-bromo-4'-nitroaceto phenone (0.5 g, 2.05 mmol) in EtOH (20 ml) was heated under reflux for 16 h. The reaction mixture was allowed to cool and sodium bicarbonate (200 mg, 2.38 mmol) was added and heating was continued for 1 h. On cooling to room temperature, the solvent was removed under reduced pressure and DCM (75 ml) was added to the residue. The insoluble material was collected by filtration and purified by flash chromatography (50:1 DCM/MeOH) to give the title compound (0.266 g, 50%) as a yellow solid.

¹H NMR (250 MHz, CDCl₃) δ 2.40 (s, 3H), 7.72 (s, 1H), 8.02 (d, J=8.5 Hz, 2H), 8.21 (d, J=8.5 Hz, 2H), 8.37 (s, 1H); ¹³C NMR (100.5 MHz, DMSO-d₆) δ 14.07, 112.53, 117.16, 124.54, 125.60, 127.20, 141.38, 143.56, 146.29, 149.82

4-(3-Methylimidazo[2,1-b][1,3]thiazol-6-yl)aniline

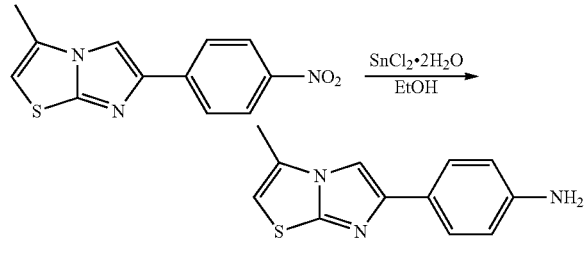

Prepared as described in the Nitro Reduction section using 3-methyl-6-(4-nitrophenyl)imidazo[2,1-b][1,3]thiazole (0.20 g, 0.772 mmol) and tin (II) chloride dihydrate (0.87 g, 3.86 mmol) in EtOH (20 ml) to give the title compound (88 mg, 50%) as a pale orange solid after work-up and flash chromatography (1:1 DCM/EtOAc).

¹H NMR (250 MHz, CDCl₃) δ 2.39 (s, 3H), 3.69 (s, 2H), 6.70 (d, J=8.5 Hz, 2H), 7.07 (s, 1H), 7.46 (s, 1H), 7.59 (d, J=8.5 Hz, 2H); ¹³C NMR (100.5 MHz, DMSO-d₆) δ 13.97, 107.10, 114.38, 117.08, 122.91, 124.78, 126.07, 146.98, 148.04, 148.22.

Imidazo[2,1-b][1,3]thiazole Compounds 4-(Dimethylamino)-N-[4-(2-methylimidazo[2,1-b][1,3]thiazol-6-yl)phenyl]benzamide Book No.: SKT05-149

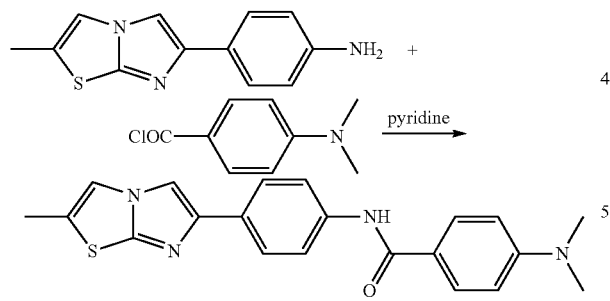

Prepared as described in the Amide Coupling section using 4-(2-methylimidazo[2,1-b][1,3]thiazol-6-yl)aniline (53 mg, 0.231 mmol) and 4-dimethylaminobenzoyl chloride (42 mg, 0.231 mmol) in dry pyridine (4 ml) to give the title compound (76 mg, 87%) as a colourless solid after work-up and flash chromatography (25:1 DCM/MeOH).

¹H NMR (250 MHz, DMSO-d₆) δ 2.43 (s, 3H), 3.01 (s, 6H), 6.78 (d, J=8.5 Hz, 2H), 6.89 (s, 1H), 7.81 (s, 4H), 7.89 (d, J=8.5 Hz, 2H), 8.21 (s, 1H), 9.94 (s, 1H); ¹³C NMR (100.5 MHz, DMSO-d₆) δ 13.31, 40.17, 107.21, 107.64, 111.22, 120.68, 121.53, 125.27, 128.59, 129.56, 129.65, 139.10, 146.74, 148.81, 152.82, 165.55.

4-(Dimethylamino)-N-[4-(3-methylimidazo[2,1-b][1,3]thiazol-6-yl)phenyl]benzamide Book No.: SKT05-143

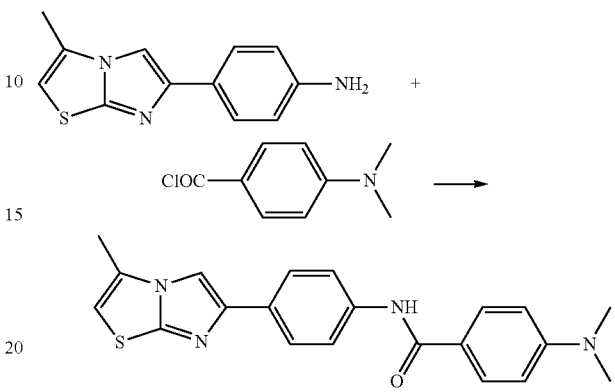

Prepared as described in the Amide Coupling section using 4-(2-methylimidazo[2,1-b][1,3]thiazol-6-yl)aniline (68 mg, 0.297 mmol) and 4-dimethylaminobenzoyl chloride (55 mg, 0.297 mmol) in dry pyridine (5 ml) to give the title compound (74 mg, 66%) as a colourless solid, after work-up and flash chromatography (25:1 DCM/MeOH).

¹H NMR (250 MHz, DMSO-d₆) δ 2.41 (s, 3H), 3.00 (s, 6H), 6.76 (d, J=8.8 Hz, 2H), 7.70 (s, 1H), 7.77 (m, 4H), 7.88 (d, J=8.8 Hz, 2H), 8.08 (s, 1H), 9.92 (s, 1H); ¹³C NMR (100.5 MHz, DMSO-d₆) δ 14.06, 40.17, 109.00, 111.22, 117.15, 120.66, 121.54, 125.17, 125.63, 129.56, 129.60, 139.00, 145.72, 148.55, 152.81, 165.54.

Imidazo[1,2-a]pyrimidine Intermediates 2-(4-Nitrophenyl)imidazo[1,2-a]pyrimidine hydrobromide

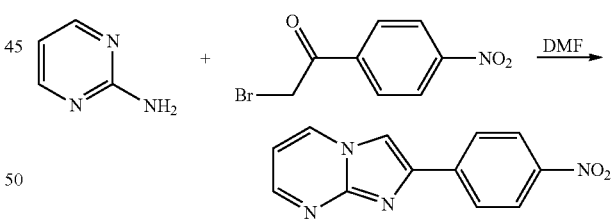

A mixture of 2-aminopyrimidine (0.40 g, 4.22 mmol) and 2-bromo-4'-nitroacetophenone (1.03 g, 4.22 mmol) in DMF (8 ml) was stirred at rt for 16 h. EtOAc (15 ml) was added to the resulting yellow, viscous mixture and the precipitate collected by filtration and washed with EtOAc (50 ml). After drying under high vacuum, a yellow solid was obtained (0.67 g, 51%).

IR 3107, 3073, 1601, 1522, 1508, 1345, 1313, 1241, 1209, 1110, 855, 799, 745 cm⁻¹; ¹H NMR (400 MHz, DMSO-d₆) δ 7.09 (dd, J=6.6, 3.9 Hz, 1H), 8.26 (d, J=9.0 Hz, 2H), 8.32 (d, J=9.0 Hz, 2H), 8.58 (s, 1H), 8.59 (dd, J=3.9, 1.9 Hz, 1H), 8.99 (dd, J=6.6, 1.9 Hz, 1H)

4-Imidazo[1,2-a]pyrimidin-2-yl)aniline

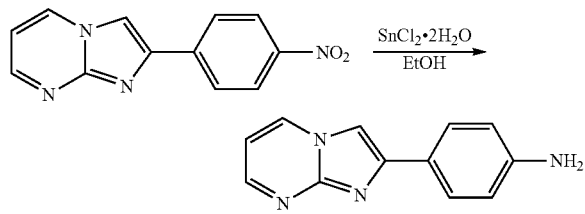

Prepared as described in the Nitro Reduction section using 2-(4-nitrophenyl)imidazo[1,2-a]pyrimidine hydrobromide (0.673 g, 2.18 mmol) and tin (II) chloride dihydrate (2.46 g, 10.89 mmol) in EtOH (50 ml) to give the title compound (0.337 g, 74%) as a pale orange solid after work-up and flash chromatography (4:1 EtOAc/MeOH).

$^1$H NMR (250 MHz, DMSO-$d_6$) δ 5.35 (s, 2H), 6.64 (d, J=8.5 Hz, 2H), 6.95-7.00 (m, 1H), 7.67 (d, J=8.5 Hz, 2H), 8.10 (s, 1H), 8.41-8.44 (m, 1H), 8.86-8.89 (m, 1H); $^{13}$C NMR (100.5 MHz, DMSO-$d_6$) δ 105.57, 108.98, 114.48, 121.50, 127.49, 134.86, 147.49, 148.58, 149.67, 149.83.

Imidazo[1,2-a]pyrimidine Compounds

4-(Dimethylamino)-N-(4-imidazo[1,2-a]pyrimidin-2-ylphenyl)benzamide

Book No.: SKT05-95

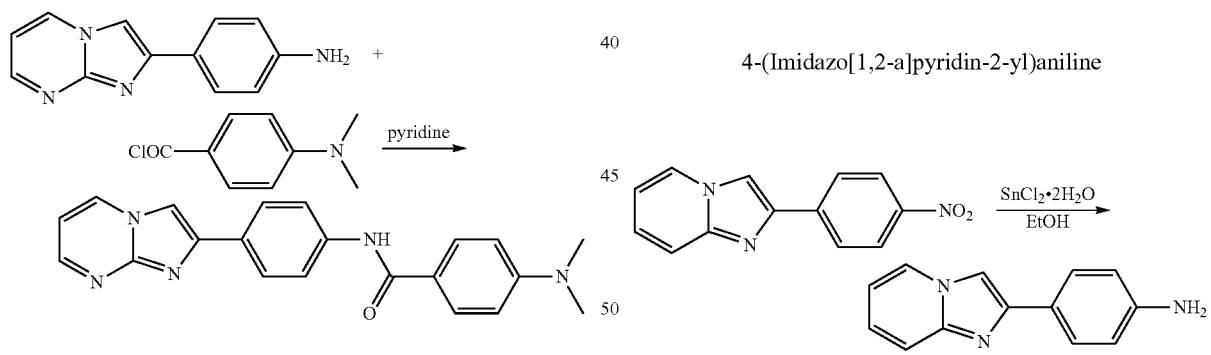

Prepared as described in the Amide Coupling section using 4-imidazo[1,2-a]pyrimidin-2-yl)aniline (80 mg, 0.381 mmol and 4-dimethylaminobenzoyl chloride (70 mg, 0.381 mmol) in dry pyridine (8 ml) flash chromatography (15:1 DCM/MeOH) to give the title compound (49 mg, 36%) as an almost colourless solid after work-up and flash chromatography (15:1 DCM/MeOH).

$^1$H NMR (250 MHz, DMSO-$d_6$) δ 3.00 (s, 6H), 6.77 (d, J=8.5 Hz, 2H), 7.01-7.06 (m, 1H), 7.87-7.98 (m, 6H), 8.31 (s, 1H), 8.49 (bs, 1H), 8.95 (d, J=6.4 Hz, 1H), 9.99 (s, 1H); $^{13}$C NMR (100.5 MHz, DMSO-$d_6$) δ 40.15, 107.22, 109.15, 111.28, 120.73, 121.59, 126.46, 128.59, 129.62, 135.18, 140.34, 145.99, 148.55, 150.37, 152.95, 165.68

Imidazo[1,2-a]pyridine Intermediates

2-(4-Nitrophenyl)imidazo[1,2-a]pyridine

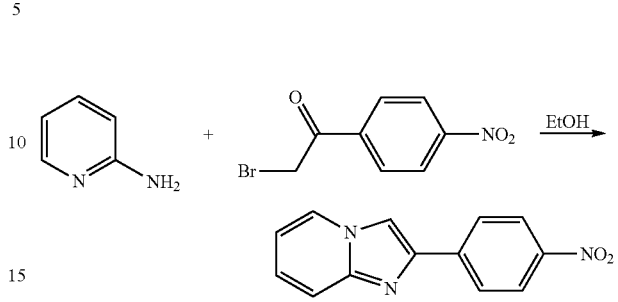

A mixture of 2-aminopyridine (0.20 g, 2.11 mmol) and 2-bromo-4'-nitroacetophenone (0.5 g, 2.05 mmol) in EtOH (25 ml) was heated under reflux for 18 h. The reaction mixture was allowed to cool and sodium bicarbonate (88 mg, 1.05 mmol) was added and heating was continued for 2 h. On cooling to room temperature, the solvent was removed under reduced pressure and the residue was dissolved in DCM (40 ml), washed with water (40 ml), and dried (Na$_2$SO$_4$). The solvent was removed under reduced pressure to give a brown solid which was purified by flash chromatography (15:1 DCM/MeOH) to give the title compound (0.27 g, 54%) as a yellow solid.

$^1$H NMR (250 MHz, CDCl$_3$) δ 6.82-6.87 (m, 1H), 7.21-7.25 (m, 1H), 7.65 (d, J=8.8 Hz, 1H), 7.99 (s, 1H), 8.11 (d, J=8.8 Hz, 2H), 8.12-8.17 (m, 1H), 8.29 (d, J=8.8 Hz, 2H); $^{13}$C NMR (100.5 MHz, DMSO-$d_6$) δ 112.07, 113.31, 117.46, 124.55, 126.28, 126.78, 127.67, 141.02, 142.53, 145.75, 147.02.

4-(Imidazo[1,2-a]pyridin-2-yl)aniline

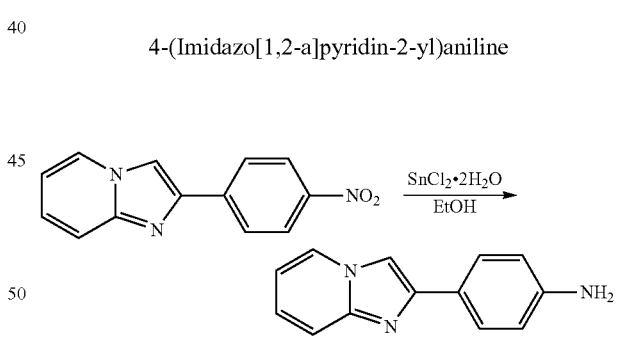

Prepared as described in the Nitro Reduction section using 2-(4-nitrophenyl)imidazo[1,2-a]pyridine (0.216 g, 0.90 mmol) and tin (II) chloride dihydrate (1.02 g, 4.52 mmol) in EtOH (25 ml) to give the title compound (0.144 g, 76%) as a pale yellow solid after work-up and flash chromatography (9:1 EtOAc/DCM).

$^1$H NMR (400 MHz, DMSO-$d_6$) δ 5.21 (br s, 2H), 6.60 (d, J=7.9 Hz, 2H), 6.79 (m, 1H), 7.14 (m, 1H), 7.46 (d, J=8.6 Hz, 1H), 7.61 (d, J=7.9 Hz, 2H), 8.08 (s, 1H), 8.42 (d, J=6.3 Hz, 1H); $^{13}$C NMR (100.5 MHz, DMSO-$d_6$) δ 107.11, 112.06, 114.40, 116.52, 122.24, 124.46, 126.80, 127.07, 145.06, 146.26, 149.01

6-Methyl-2-(4-nitrophenyl)imidazo[1,2-a]pyridine

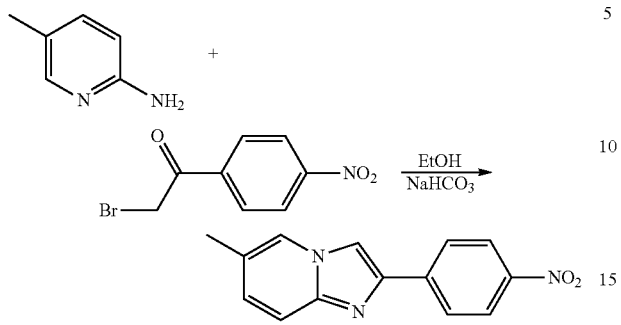

A mixture of 2-amino-5-picoline (0.88 g, 8.19 mmol) and 2-bromo-4'-nitroacetophenone (2.0 g, 8.19 mmol) in EtOH (50 ml) was heated under reflux for 17 h. The reaction mixture was allowed to cool and sodium bicarbonate (840 mg, 9.99 mmol) was added and heating was continued for 18 h. On cooling to room temperature, the solvent was removed under reduced pressure and the residue was purified by flash chromatography (1:1 Hexane/EtOAc) to give the title compound (0.84 g, 40%) as a yellow solid.

$^1$H NMR (250 MHz, DMSO-$d_6$) δ 2.28 (s, 3H), 7.16 (d, J=9.1 Hz, 1H), 7.52 (d, J=9.1 Hz, 1H), 8.19 (d, J=8.8 Hz, 2H), 8.28 (d, J=8.8 Hz, 2H), 8.34 (s, 1H), 8.54 (s, 1H); $^{13}$C NMR (100.5 MHz, DMSO-$d_6$) δ 17.94, 111.74, 116.85, 122.60, 124.50, 124.92, 126.61, 129.29, 141.19, 142.34, 144.84, 146.87.

4-(6-Methylimidazo[1,2-a]pyridin-2-yl)aniline

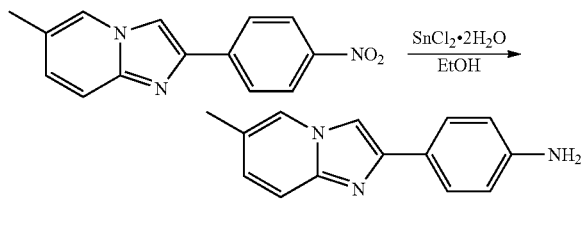

Prepared as described in the Nitro Reduction section using 6-methyl-2-(4-nitrophenyl)imidazo[1,2-a]pyridine (0.423 g, 1.67 mmol) and tin (II) chloride dihydrate (1.89 g, 8.36 mmol) in EtOH (45 ml) to give the title compound (0.216 g, 58%) as a pale orange solid, after work-up and flash chromatography (EtOAc).

$^1$H NMR (250 MHz, CDCl$_3$) δ 2.29 (s, 3H), 3.74 (s, 2H), 6.74 (d, J=8.5 Hz, 2H), 6.95 (d, J=9.1 Hz, 1H), 7.47 (d, J=9.1 Hz, 1H), 7.64 (s, 1H), 7.73 (d, J=8.5 Hz, 2H), 7.85 (s, 1H); $^{13}$C NMR (62.5 MHz, CDCl$_3$/DMSO-$d_6$) δ 17.47, 105.99, 113.97, 115.21, 120.74, 122.06, 123.24, 126.23, 126.79, 143.56, 145.25, 147.55.

6-Fluoro-2-(4-nitrophenyl)imidazo[1,2-a]pyridine

To a stirred mixture of 2-amino-5-fluoropyridine (0.80 g, 7.13 mmol) and sodium bicarbonate (0.60 g, 7.14 mmol) was added a slurry of 2-bromo-4'-bromoacetophenone (1.74 g, 7.13 mmol) in chloroform (10 ml). The stirred reaction mixture was heated under reflux for 20 h. After cooling to room temperature, the precipitate was collected by filtration under vacuum and washed with chloroform (2×40 ml). The solid was then purified by flash chromatography (1:1 Hexane/EtOAc) to give the title compound (0.596 g, 32%) as a brown solid.

$^1$H NMR (250 MHz, CDCl$_3$) δ 7.13-7.21 (m, 1H), 7.59-7.66 (m, 1H), 7.99 (s, 1H), 8.07-8.10 (m, 3H), 8.30 (d, J=8.8 Hz, 2H); $^{13}$C NMR (100.5 MHz, DMSO-$d_6$) δ 113.43 (d, $J_{CF}$=Hz), 114.30 (d, $J_{CF}$=42.0 Hz), 118.17 (d, $J_{CF}$=26.4 Hz), 118.23 (d, $J_{CF}$=10.2 Hz), 124.51, 126.77, 140.61, 143.66, 143.75 (d, $J_{CF}$=Hz), 147.08, 153.26 (d, $J_{CF}$=233.6 Hz).

4-(6-Fluoroimidazo[1,2-a]pyridin-2-yl)aniline

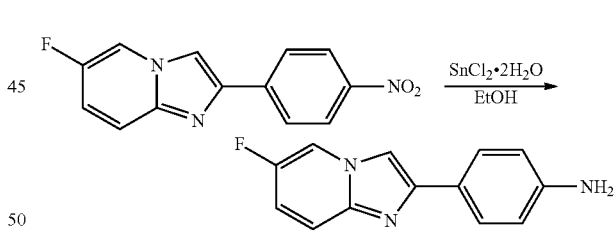

Prepared as described in the Nitro Reduction section using 6-fluoro-2-(4-nitrophenyl)imidazo[1,2-a]pyridine (0.45 g, 1.75 mmol) and tin (II) dichloride dihydrate (1.97 g, 8.75 mmol) in EtOH (25 ml) to give the title compound (0.325 g, 82%) as a pale yellow solid after work-up and flash chromatography (4:1 EtOAc/DCM).

$^1$H NMR (250 MHz, DMSO-$d_6$) δ 5.26 (s, 2H), 6.61 (d J=8.2 Hz, 2H), 7.21-7.28 (m, 1H), 7.51-7.60 (m, 1H), 7.62 (d, J=8.2 Hz, 2H), 8.12 (s, 1H), 8.68 (br s, 1H); $^{13}$C NMR (100.5 MHz, DMSO-$d_6$) δ 108.73 (d, $J_{CF}$=1.5 Hz), 113.48 (d, $J_{CF}$=41 Hz), 114.39, 115.90 (d, $J_{CF}$=25.7 Hz), 117.00 (d, $J_{CF}$=10.1 Hz), 121.90, 142.99, 147.63, 149.18, 152.80 (d, $J_{CF}$=231 Hz).

6-Iodo-2-(4-nitrophenyl)imidazo[1,2-a]pyridine

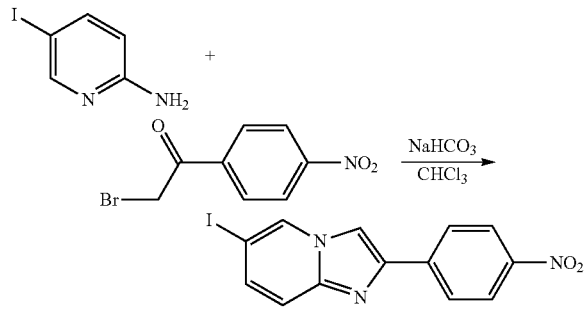

To a stirred mixture of 2-amino-5-iodopyridine (0.80 g, 3.64 mmol) and sodium bicarbonate (0.34 g, 3.99 mmol) was added a slurry of 2-bromo-4'-bromoacetophenone (0.89 g, 3.64 mmol) in chloroform (15 ml). The stirred reaction mixture was heated under reflux for 24 h. After cooling to room temperature, the precipitate was collected by filtration under vacuum and washed with chloroform (2×40 ml), water (40 ml) and then dried at 90° C. for 24 h to give the title compound (0.827 g, 62%) as a pale green solid.

$^1$H NMR (250 MHz, DMSO-$d_6$) δ 7.49 (s, 2H), 8.22 (d, J=8.8 Hz, 2H), 8.31 (d, J=8.2 Hz, 2H), 8.55 (s, 1H), 8.96 (s, 1H); $^{13}$C NMR (100.5 MHz, DMSO-$d_6$) δ 77.10, 111.73, 118.66, 124.53, 126.88, 132.22, 133.78, 140.43, 142.73, 144.27, 147.13.

4-(6-Iodoimidazo[1,2-a]pyridin-2-yl)aniline

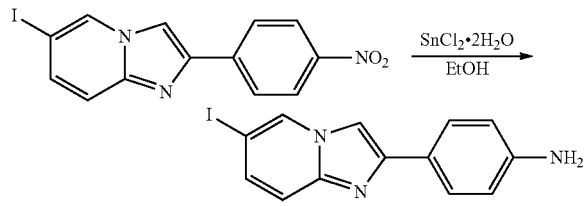

Prepared as described in the Nitro Reduction section using 6-iodo-2-(4-nitrophenyl)imidazo[1,2-a]pyridine (0.45 g, 1.23 mmol) and tin (II) dichloride dihydrate (1.39 g, 6.16 mmol) in EtOH (25 ml) to give the title compound (0.301 g, 73%) as a yellow solid, after work-up and flash chromatography (4:1 EtOAc/DCM).

$^1$H NMR (250 MHz, DMSO-$d_6$) δ 5.27 (s, 2H), 6.60 (d, J=7.6 Hz, 2H), 7.34 (s, 2H), 7.60 (d, J=7.6 Hz, 2H), 8.04 (s, 1H), 8.82 (s, 1H); $^{13}$C NMR (100.5 MHz, DMSO-$d_6$) δ 75.32, 107.03, 114.40, 117.79, 121.57, 127.19, 131.37, 131.93, 143.66, 146.62, 149.28.

6-Methyl-2-phenylimidazo[1,2-a]pyridine

Book No.: SK2033-32

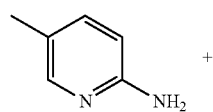

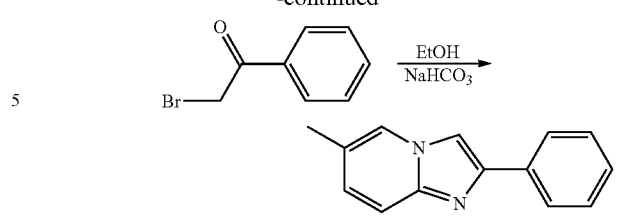

A stirred mixture of 2-amino-5-picoline (0.56 g, 5.22 mmol) and 2-bromoacetophenone (1.0 g, 5.02 mmol) in EtOH (50 ml) was heated under reflux for 2 h. The reaction mixture was left to cool to room temperature and then sodium bicarbonate (0.76 g, 9.04 mmol) was added and the reaction mixture was heated under reflux for 15 h. The solvent was then removed under reduced pressure and the residue was dissolved in EtOAc (70 ml) and washed with water (40 ml). The organic phase was dried ($Na_2SO_4$) and the solvent was removed under reduced pressure to give an orange solid. This solid was purified by flash chromatography (1:1 Hexane/EtOAc) to give the title compound (0.753 g, 70%) as a pale orange solid.

$^1$H NMR (250 MHz, $CDCl_3$) δ 2.30 (s, 3H), 7.01 (d, J=9.5 Hz, 1H), 7.32 (d, J=7.5 Hz, 1H), 7.39-7.45 (m, 2H), 7.53 (d, J=9.5 Hz, 1H), 7.76 (s, 1H), 7.88 (s, 1H), 7.93 (d, J=7.5 Hz, 2H); $^{13}$C NMR (62.5 MHz, $CDCl_3$) δ 18.09, 107.91, 116.75, 121.99, 123.36, 125.92, 127.80, 127.85, 128.72, 133.95, 144.73, 145.39.

2-Fluoroethyl-p-toluenesulphonate

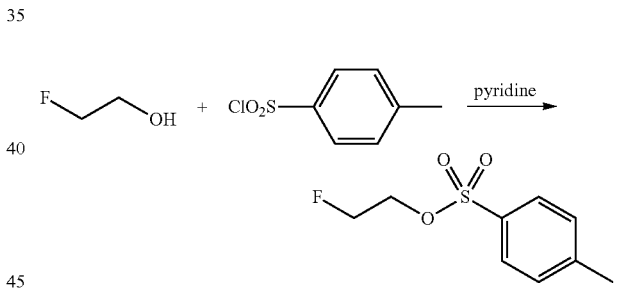

To a stirred solution of 2-fluoroethanol (1.92 g, 29.97 mmol) in dry pyridine (15 ml) under an atmosphere of argon at 0° C. was added p-toluenesulphonyl chloride over 15 min, maintaining the temperature below 5° C. The reaction mixture was then stirred at 0° C. for 4 h, then at room temperature for 12 h. The reaction mixture was cooled to 0° C. and ice (15 g) was added followed by water (40 ml) and EtOAc (50 ml). The organic extract was washed with water (30 ml), 1 M HCl (until aqueous extracts were acidic), 10% sodium carbonate (2×30 ml), brine (40 ml) and dried ($Na_2SO_4$). The solvent was removed under reduced pressure to give the title compound (5.10 g, 78%) as a colourless oil.

$^1$H NMR (250 MHz, $CDCl_3$) δ 2.44 (s, 3H), 4.25 (dist d of t, $J_{HF}$=27 Hz, $J_{HH}$=4.3 Hz, 2H), 4.56 (dist d of t, $J_{HF}$=47 Hz, $J_{HH}$=4.3 Hz, 2H), 7.35 (d, J=8.2 Hz, 2H), 7.79 (d, J=8.2 Hz, 2H); $^{13}$C NMR (62.5 MHz, $CDCl_3$) δ 21.68, 68.52 (d, $J_{CF}$=21.5 Hz), 80.57 (d, $J_{CF}$=174 Hz), 127.99, 129.98, 132.65, 145.21.

Imidazo[1,2-a]pyridine Compounds

4-(Dimethylamino)-N-[4-imidazo[1,2-a]pyridin-2-yl)phenyl]benzamide

Book No.: SKT05-123

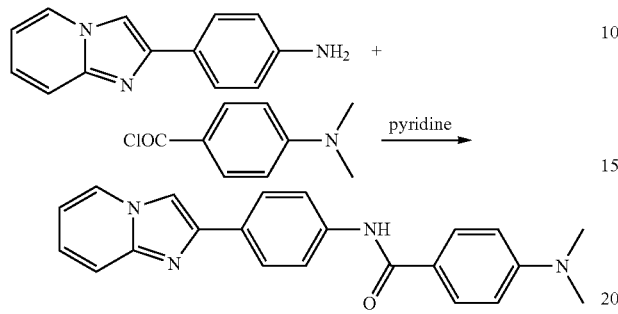

Prepared as described in the Amide Coupling section using 4-(imidazo[1,2-a]pyridin-2-yl)aniline (70 mg, 0.335 mmol) and 4-dimethylaminobenzoyl chloride (62 mg, 0.335 mmol) in dry pyridine (5 ml) to give the title compound (70 mg, 59%) as a pale yellow solid after work-up and flash chromatography (20:1 DCM/MeOH).

$^1$H NMR (400 MHz, DMSO-$d_6$) δ 2.98 (s, 6H), 6.75 (d, J=9.0 Hz, 2H), 6.85 (dd, J=6.7, 0.7 Hz, 1H), 7.21 (dd, J=9.0, 0.7 Hz, 1H), 7.54 (d, J=9.0 Hz, 1H), 7.84 (d, J=8.7 Hz, 2H), 7.88 (d, J=9.0 Hz, 2H), 7.91 (d, J=8.7 Hz, 2H), 8.31 (s, 1H), 8.49 (d, J=6.7 Hz, 1H), 9.93 (s, 1H); $^{13}$C NMR (100.5 MHz, DMSO-$d_6$) δ 40.16, 108.88, 111.23, 112.55, 116.91, 120.68, 121.49, 125.16, 126.22, 127.20, 129.10, 129.61, 139.81, 144.90, 145.23, 152.85, 165.62.

4-(Dimethylamino)-N-[4-(6-methylimidazo[1,2-a]pyridin-2-yl)phenyl]benzamide

Book No.: SKT05-93

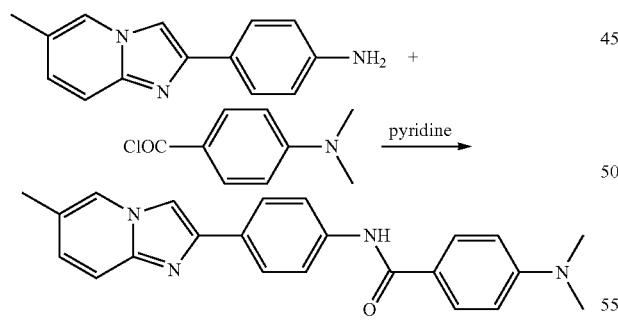

Prepared as described in the Amide Coupling section using 4-(6-methylimidazo[1,2-a]pyridin-2-yl)aniline (70 mg, 0.314 mmol) and 4-dimethylaminobenzoyl chloride (58 mg, 0.314 mmol) in dry pyridine (5 ml) to give the title compound (63 mg, 54%) as a pale yellow solid after work-up and flash chromatography (20:1 DCM/MeOH).

$^1$H NMR (250 MHz, DMSO-$d_6$) δ 2.27 (s, 3H), 3.00 (s, 6H), 6.76 (d, J=8.5 Hz, 2H), 7.08 (d, J=9.5 Hz, 1H), 7.46 (d, J=9.5 Hz, 1H), 7.82-7.92 (m, 6H), 8.23 (s, 1H), 8.30 (s, 1H), 9.95 (s, 1H); $^{13}$C NMR (100.5 MHz, DMSO-$d_6$) δ 17.97, 40.15, 108.62, 111.23, 116.26, 120.67, 121.44, 121.81, 124.60, 126.10, 128.23, 129.16, 129.60, 139.66, 144.24, 144.58, 152.85, 165.64.

N-[4-(6-methylimidazo[1,2-a]pyridin-2-yl)phenyl]pyridine-4-carboxamide

Book No.: SKT05-107

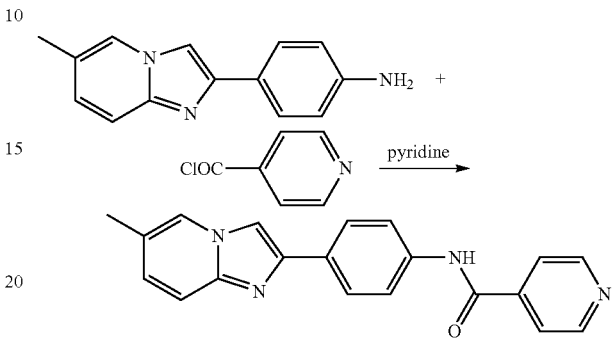

Prepared as described in the Amide Coupling section using 4-(6-methylimidazo[1,2-a]pyridin-2-yl)aniline (70 mg, 0.314 mmol) and isonicotinoyl chloride hydrochloride (56 mg, 0.314 mmol) in dry pyridine (5 ml) to give the title compound (92 mg, 89%) as a pale yellow solid after work-up and flash chromatography (10:1 DCM/MeOH).

$^1$H NMR (250 MHz, DMSO-$d_6$) δ 2.28 (s, 3H), 7.10 (d, J=9.2 Hz, 1H), 7.48 (d, J=9.2 Hz, 1H), 7.85 (d, J=8.2 Hz, 2H), 7.87-7.89 (m, 2H), 7.96 (d, J=8.2 Hz, 2H), 8.27 (s, 1H), 8.32 (s, 1H), 8.80 (d, J=0.6 Hz; 2H), 10.60 (s, 1H); $^{13}$C NMR (62.5 MHz, CDCl$_3$/DMSO-$d_6$) δ 17.24, 107.80, 115.41, 120.12, 120.89, 121.09, 123.58, 125.30, 127.26, 129.46, 137.62, 141.48, 143.48, 143.58, 149.62, 163.30.

N-[4-(6-methylimidazo[1,2-a]pyridin-2-yl)phenyl]pyridine-3-carboxamide

Book No.: SKT05-171

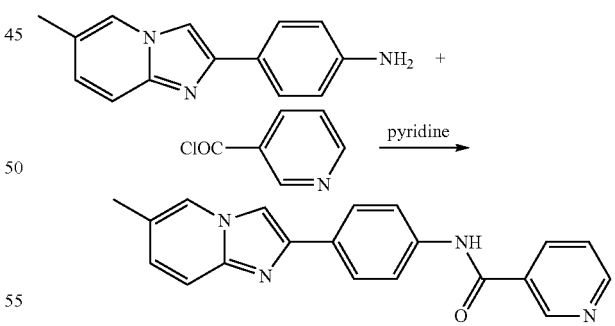

Prepared as described in the Amide Coupling section using 4-(6-methylimidazo[1,2-a]pyridin-2-yl)aniline (70 mg, 0.314 mmol) and nicotinoyl chloride hydrochloride (56 mg, 0.314 mmol in dry pyridine (5 ml) to give the title compound (62 mg, 60%) as a pale yellow solid after work-up and flash chromatography (EtOAc followed by 20:1 EtOAc/MeOH).

$^1$H NMR (400 MHz, DMSO-$d_6$) δ 2.22 (s, 3H), 7.04 (d, J=9.2 Hz, 1H), 7.42 (d, J=9.2 Hz, 1H), 7.53 (dd, J=7.9, 4.9 Hz, 1H), 7.80 (d, J=8.5 Hz, 2H), 7.90 (d, J=8.5 Hz, 2H), 8.20 (s, 1H), 8.25-8.27 (m, 2H), 8.72 (d, J=4.8 Hz, 1H), 9.07 (d, J=2.1

Hz, 1H), 10.48 (s, 1H); $^{13}$C NMR (100.5 MHz, DMSO-d$_6$) δ 18.17, 109.05, 116.59, 121.08, 122.02, 124.17, 124.83, 126.45, 128.45, 130.45, 131.27, 136.12, 138.93, 144.52, 144.63, 149.33, 152.76, 164.66.

N-[4-(6-methylimidazo[1,2-a]pyridin-2-yl)phenyl]pyridine-2-carboxamide

No.: SKT06-5

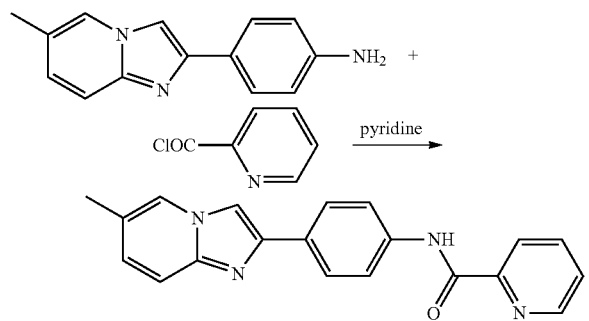

To a stirred suspension of picolinic acid (56 mg, 0.45 mmol) in DCM (1 ml) was added thionyl chloride (2 ml) followed by a drop of DMF. The mixture was stirred at room temperature for 4 h and the excess reagent and solvent was then removed under reduced pressure to give a green solid. The amide was prepared as described in the Amide Coupling section using the crude solid and 4-(6-methylimidazo[1,2-a]pyridin-2-yl)aniline (70 mg, 0.314 mmol) in dry pyridine (4.5 ml) to give the title compound (65 mg, 44%) as a pale yellow solid after work-up and flash chromatography (20:1 DCM/MeOH).

$^1$H NMR (250 MHz, DMSO-d$_6$) δ 2.28 (s, 3H), 7.10 (d, J=9.2 Hz, 1H), 7.49 (d, J=9.2 Hz, 1H), 7.67-7.72 (m, 1H), 7.95 (d, J=8.8 Hz, 2H), 8.00 (d, J=8.8 Hz, 2H), 8.05-8.11 (m, 1H), 8.19 (d, J=7.3 Hz, 1H), 8.27 (s, 1H), 8.31 (s, 1H), 8.76 (d, J=4.6 Hz, 1H), 10.74 (s, 1H); $^{13}$C NMR (100.5 MHz, DMSO-d$_6$) δ 17.94, 108.81, 116.42, 120.80, 121.76, 122.77, 124.61, 126.29, 127.31, 128.16, 130.34, 138.17, 138.55, 144.38, 144.58, 148.87, 150.41, 162.84.

6-Fluoro-N-[4-(6-methylimidazo[1,2-a]pyridin-2-yl)phenyl]pyridine-3-carboxamide Book No.: SKT05-169

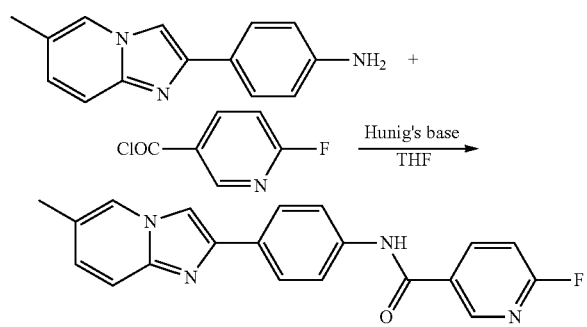

A stirred suspension of 6-fluoronicotinic acid (80 mg, 0.414 mmol) in thionyl chloride (2 ml) was heated under reflux for 4 h. The excess reagent was then removed under reduced pressure to give a crude solid. The amide was prepared as described in the Amide Coupling section using the crude solid and 4-(6-methylimidazo[1,2-a]pyridin-2-yl)aniline (92 mg, 0.414 mmol) in dry THF (13 ml) and diisopropylethylamine (106 µl, 0.608 mmol) to give the title compound (86 mg, 60%) as a colourless solid after work-up and flash chromatography (EtOAc).

$^1$H NMR (400 MHz, DMSO-d$_6$) δ 2.22 (s, 3H), 7.05 (dd, J=9.2, 1.2 Hz, 1H), 7.32 (dd, J=8.5, 2.4 Hz, 1H), 7.42 (d, J=9.2 Hz, 1H), 7.77 (d, J=8.8 Hz, 2H), 7.90 (d, J=8.8 Hz, 2H), 8.20 (s, 1H), 8.26 (s, 1H), 8.46 (dt, J=8.5, 2.4 Hz, 1H), 8.78 (d, J=2.1 Hz, 1H), 10.48 (s, 1H); $^{13}$C NMR (100.5 MHz, DMSO-d$_6$) δ 18.17, 109.06, 109.97, 110.34, 116.58, 121.11, 122.03, 124.84, 126.47, 128.47, 130.00 (d, J$_{CF}$=3.8 Hz), 130.51, 138.80, 142.58 (d, J$_{CF}$=9.1 Hz), 144.56 (d, J$_{CF}$=7.6 Hz), 148.42 (d, J$_{CF}$=16.0 Hz), 163.43, 164.95 (d, J$_{CF}$=239 Hz).

6-Fluoro-N-[4-(6-methylimidazo[1,2-a]pyridin-2-yl)phenyl]pyridine-2-carboxamide Book No.: SKT06-53

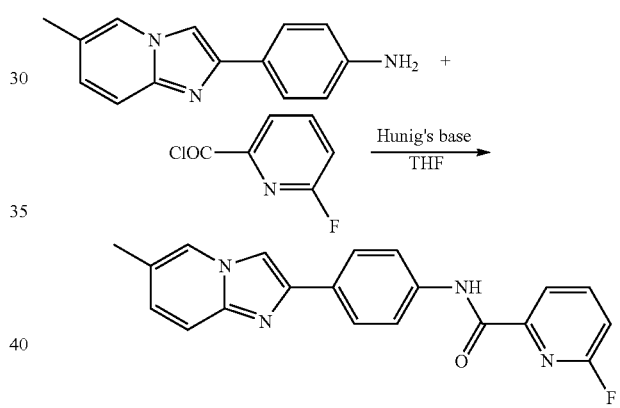

A stirred suspension of 2-fluoropyridine-6-carboxylic acid (86 mg, 0.448 mmol) in thionyl chloride (2 ml) was heated under reflux for 5 h. The excess reagent was then removed under reduced pressure to give a crude solid. The amide was prepared as described in the Amide Coupling section using the crude solid, 4-(6-methylimidazo[1,2-a]pyridin-2-yl)aniline (100 mg, 0.448 mmol) in dry THF (20 ml) and diisopropylethylamine (94 µl, 0.539 mmol) to give the title compound (85 mg, 55%) as a colourless solid, after work-up and flash chromatography (2:1 EtOAc/Hexane).

$^1$H NMR (400 MHz, DMSO-d$_6$) δ 2.23 (s, 3H), 7.05 (dd, J=9.2, 1.7 Hz, 1H), 7.43 (d, J=9.2 Hz, 1H), 7.45 (dd, J=8.3, 1.7 Hz, 1H), 7.87-7.92 (m, 4H), 8.04 (dd, J=7.3, 1.7 Hz, 1H), 8.18-8.24 (m, 1H), 8.22 (s, 1H), 8.27 (s, 1H), 10.48 (s, 1H); $^{13}$C NMR (100.5 MHz, DMSO-d$_6$) δ 17.94, 108.86, 113.54 (d, J$_{CF}$=36.5 Hz), 116.43, 121.05 (d, J$_{CF}$=3.9 Hz), 121.17, 121.76, 124.61, 126.23, 128.17, 130.58, 137.97, 144.30, 144.38, 144.53, 149.23 (d, J$_{CF}$=11.7 Hz), 161.77, 162.12 (d, J$_{CF}$=240.6 Hz).

N-[4-(6-Methylimidazo[1,2-a]pyridin-2-yl)phenyl]-4-nitrobenzamide

Book No.: SKT06-63

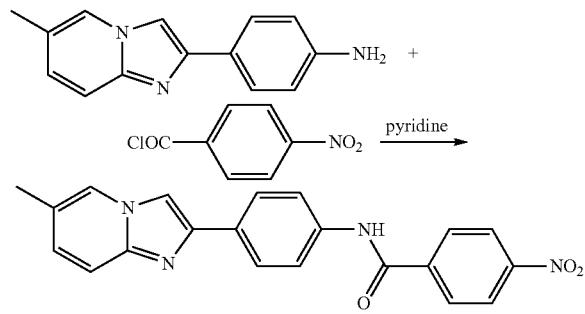

Prepared as described in the Amide Coupling section using 4-(6-methylimidazo[1,2-a]pyridin-2-yl)aniline (0.20 g, 0.897 mmol) and 4-nitrobenzoyl chloride (0.166 g, 0.897 mmol) in dry pyridine (13 ml) to give the title compound (0.266 g, 80%) as a pale yellow solid after work-up and flash chromatography (1:1 EtOAc/MeOH).

$^1$H NMR (400 MHz, DMSO-$d_6$) δ 2.23 (s, 3H), 7.04 (dd, J=9.3, 1.5 Hz, 1H), 7.42 (d, J=9.3 Hz, 1H), 7.81 (d, J=8.8 Hz, 2H), 7.90 (d, J=8.8 Hz, 2H), 8.15 (d, J=8.8 Hz, 2H), 8.21 (s, 1H), 8.26 (s, 1H), 8.33 (d, J=8.8 Hz, 2H), 10.62 (s, 1H); $^{13}$C NMR (100.5 MHz, DMSO-$d_6$) δ 17.95, 108.85, 116.42, 121.09, 121.78, 123.94, 124.63, 126.28, 128.20, 129.66, 130.56, 138.60, 141.12, 144.52, 149.66, 164.27.

N-[4-(6-Methylimidazo[1,2-a]pyridin-2-yl)phenyl]-4-nitro-3-(trifluoromethyl)benzamide Book No.: SKT05-165

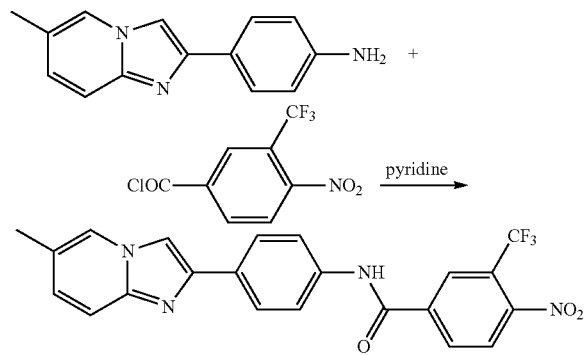

A stirred suspension of 4-nitro-3-trifluoromethylbenzoic acid (0.239 g, 0.986 mmol) in thionyl chloride (4 ml) was heated under reflux for 5 h. The excess reagent was then removed under reduced pressure to give a crude solid. The amide was prepared as described in the Amide Coupling section using the crude solid and 4-(6-methylimidazo[1,2-a]pyridin-2-yl)aniline (0.20 g, 0.897 mmol) in dry pyridine (8 ml) to give the title compound (0.337 g, 85%) as a yellow solid, after work-up and flash chromatography (25:1 DCM/MeOH).

$^1$H NMR (250 MHz, DMSO-$d_6$) δ 2.28 (s, 3H), 7.10 (d, J=9.2 Hz, 1H), 7.48 (d, J=9.2 Hz, 1H), 7.85 (d, J=8.5 Hz, 2H), 7.98 (d, J=8.5 Hz, 2H), 8.27 (s, 1H), 8.32 (s, 1H), 8.35 (d, J=8.8 Hz, 1H), 8.49 (d, J=8.8 Hz, 1H), 8.53 (s, 1H), 10.76 (s, 1H); $^{13}$C NMR (100.5 MHz, DMSO-$d_6$) δ 17.94, 108.91, 116.43, 121.19, 121.80, 121.86 ($J_{CF}$=34 Hz), 122.72 ($J_{CF}$=273 Hz), 124.63, 126.12, 126.33, 127.75 ($J_{CF}$=5.5 Hz), 128.22, 130.80, 134.26, 138.31, 139.47, 144.40, 144.45, 149.14, 162.81; LRMS (ESI+) 486 (M$^+$+2Na, 100%), 441 (M$^+$+H, 34).

N-[4-(6-Methylimidazo[1,2-a]pyridin-2-yl)phenyl]-4-hydroxylamino-3-(trifluoromethyl)benzamide Book No.: SKT05-173

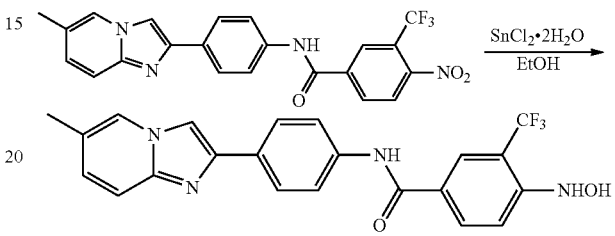

Prepared as described in the Nitro Reduction section using N-[4-(6-methylimidazo[1,2-a]pyridin-2-yl)phenyl]-4-nitro-3-(trifluoromethyl)benzamide (0.25 g, 0.568 mmol) and tin (II) chloride dehydrate (0.64 g, 2.84 mmol) in EtOH (30 ml) to give the title compound (0.20 g, 87%) as a pale yellow solid after work-up and flash chromatography (15:1 DCM/MeOH).

$^1$H NMR (250 MHz, DMSO-$d_6$) δ 2.28 (s, 3H), 7.10 (d, J=9.2 Hz, 1H), 7.40 (d, J=8.5 Hz, 1H), 7.47 (d, J=9.2 Hz, 1H), 7.82 (d, J=8.5 Hz, 2H), 7.93 (d, J=8.5 Hz, 2H), 8.13-8.18 (m, 2H), 8.25 (s, 1H), 8.32 (s, 1H), 9.04 (s, 1H), 9.08 (s, 1H), 10.23 (s, 1H); $^{13}$C NMR (67.5 MHz, CDCl$_3$/DMSO-$d_6$) δ 17.67, 107.55, 111.42 (q, $J_{CF}$=31.2 Hz), 112.94, 115.83, 120.49, 121.47, 123.42, 123.97 (q, $J_{CF}$=272 Hz), 124.62, 125.63, 125.97 (q, $J_{CF}$=5.9 Hz), 127.57, 129.08, 132.51, 138.55, 144.09, 144.40, 150.91, 164.29.

4-Amino-N-[4-(6-methylimidazo[1,2-a]pyridin-2-yl)phenyl]benzamide

Book No.: SKT06-71

Prepared as described in the Nitro Reduction section using N-[4-(6-methylimidazo[1,2-a]pyridin-2-yl)phenyl]-4-nitrobenzamide (0.10 g, 0.269 mmol) and tin (II) chloride dihydrate (0.30 g, 1.34 mmol) in EtOH (15 ml) to give the title compound (0.072 g, 78%) as a pale yellow solid after work-up and flash chromatography (15:1 DCM/MeOH).

$^1$H NMR (250 MHz, DMSO-$d_6$) δ 2.29 (s, 3H), 5.79 (s, 2H), 6.62 (d, J=8.2 Hz, 2H), 7.10 (d, J=9.2 Hz, 1H), 7.47 (d, J=9.2 Hz, 1H), 7.74 (d, J=8.2 Hz, 2H), 7.83 (d, J=8.8 Hz, 2H), 7.90 (d, J=8.8 Hz, 2H), 8.24 (s, 1H), 8.31 (s, 1H), 9.85 (s, 1H);

$^{13}$C NMR (100.5 MHz DMSO-d$_6$) δ 17.97, 108.54, 113.00, 116.33, 120.56, 121.53, 121.69, 124.58, 126.08, 128.08, 129.17, 129.82, 139.75, 144.27, 144.73, 152.61, 165.69.

4-(Methylamino)-N-[4-(6-methylimidazo[1,2-a]pyridin-2-yl)phenyl]benzamide

Book No.: SKT06-67

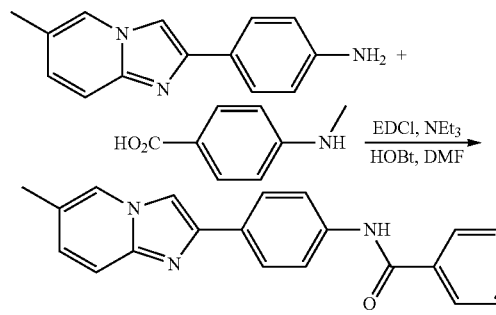

To a stirred solution of 4-(6-methylimidazo[1,2-a]pyridin-2-yl)aniline (0.10 g, 0.448 mmol), 1-hydroxybenzotriazole (0.06 g, 0.448 mmol), 4-methylaminobenzoic acid (0.068 g, 0.448 mmol) and triethylamine (62 µl, 0.045 g, 0.448 mmol) in dry DMF (5 ml) at 0° C. was added 1-ethyl-3-[3-(dimethylaminopropyl]-carbodiimide hydrochloride (0.086 g, 0.448 mmol) under an atmosphere or argon. After 10 min the cooling bath was removed and the reaction mixture was stirred at room temperature for 4 d. The reaction mixture was then added to water (150 ml) with stirring and the precipitate was collected by filtration. Purification by flash chromatography (25:1 DCM/MeOH) gave the title compound (0.053 g, 33%) as an almost colourless solid.

$^1$H NMR (400 MHz, DMSO-d$_6$) δ 2.23 (s, 3H), 2.69 (d, J=4.9 Hz, 3H), 6.30 (q, J=4.9 Hz, 1H), 6.54 (d, J=8.8 Hz, 2H), 7.04 (dd, J=9.3, 1.5 Hz, 1H), 7.41 (d, J=9.3 Hz, 1H), 7.76 (d, J=8.8 Hz, 2H), 7.77 (d, J=8.8 Hz, 2H), 7.84 (d, J=8.8 Hz, 2H), 8.18 (s, 1H), 8.25 (s, 1H), 9.82 (s, 1H); $^{13}$C NMR (100.5 MHz, DMSO-d$_6$) δ 17.93, 29.79, 108.51, 110.94, 116.34, 120.66, 121.48, 121.65, 124.56, 126.10, 128.03, 129.27, 129.73, 139.75, 144.33, 144.83, 153.10, 165.71.

4-Methoxy-N-[4-(6-methylimidazo[1,2-a]pyridin-2-yl)phenyl]benzamide

Book No.: SKT06-7

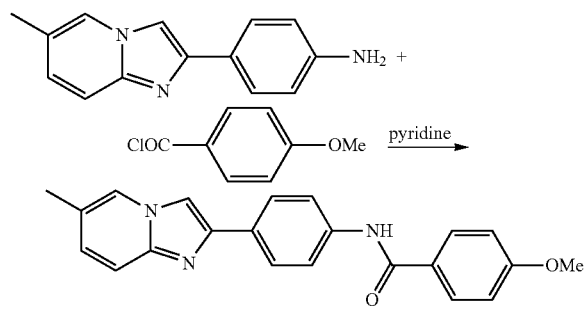

Prepared as described in the Amide Coupling section using 4-(6-methylimidazo[1,2-a]pyridin-2-yl)aniline (70 mg, 0.314 mmol) and 4-methoxybenzoyl chloride (54 mg, 0.314 mmol) in dry pyridine (5 ml) to give the title compound (89 mg, 79%) as a pale yellow solid after work-up and flash chromatography (15:1 DCM/MeOH).

$^1$H NMR (250 MHz, DMSO-d$_6$) δ 2.28 (s, 3H), 3.85 (s, 3H), 7.08 (d, J=8.5 Hz, 2H), 7.10 (d, J=9.2 Hz, 1H), 7.48 (d, J=9.2 Hz, 1H), 7.85 (d, J=8.5 Hz, 2H), 7.93 (d, J=8.5 Hz, 2H), 7.90 (d, J=8.5 Hz, 2H), 8.25 (s, 1H), 8.32 (s, 1H), 10.19 (s, 1H); $^{13}$C NMR (100.5 MHz, DMSO-d$_6$) δ 17.94, 55.90, 108.65, 114.10, 116.39, 120.89, 121.71, 124.59, 126.18, 127.54, 128.10, 129.81, 130.04, 139.30, 144.37, 144.72, 162.42, 165.32.

4-Hydroxy-N-[4-(6-methylimidazo[1,2-a]pyridin-2-yl)phenyl]benzamide

Book No.: SKT06-11

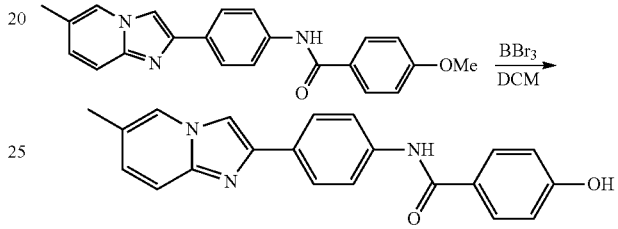

Prepared as described in the Demethylation section using 4-methoxy-N-[4-(6-methylimidazo[1,2-a]pyridin-2-yl)phenyl]benzamide (0.07 g, 0.196 mmol) in dry DCM (5 ml), boron tribromide in DCM (1.0 M, 0.24 ml, 0.24 mmol) at −78° C. The reaction mixture was stirred at −78° C. for 1 h then left to rise to room temperature. After 18 h at room temperature a further volume of boron tribromide in DCM (1.0 M, 0.7 ml, 0.7 mmol) was added and stirring was continued at room temperature to give the title compound (0.043 g, 64%) as a pale yellow solid after work-up and flash chromatography (10:1 DCM/MeOH).

$^1$H NMR (400 MHz, DMSO-d$_6$) δ 2.22 (s, 3H), 6.82 (d, J=8.5 Hz, 2H), 7.04 (dd, J=9.0, 1.5 Hz, 1H), 7.41 (d, J=9.0 Hz, 1H), 7.77 (d, J=8.8 Hz, 2H), 7.82 (d, J=8.5 Hz, 2H), 7.85 (d, J=8.8 Hz, 2H), 8.18 (s, 1H), 8.25 (s, 1H), 10.02 (s, 1H) 9.80-10.81 (br s, 1H); $^{13}$C NMR (100.5 MHz, DMSO-d$_6$) δ 18.17, 108.86, 115.57, 116.53, 120.93, 121.96, 124.79, 126.00, 126.32, 128.37, 129.72, 130.37, 139.60, 144.49, 144.80, 161.25, 165.72.

3,4,5-Trifluoro-N-[4-(6-methylimidazo[1,2-a]pyridin-2-yl)phenyl]benzamide

Book No.: SKT06-25

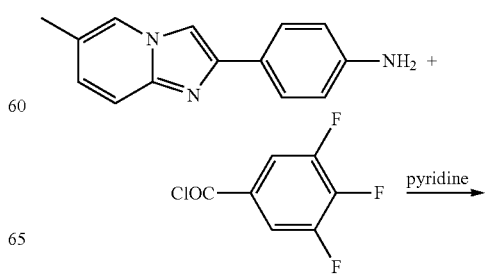

-continued

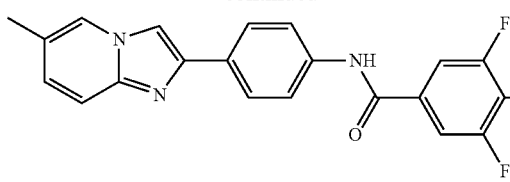

Prepared as described in the Amide Coupling section using 4-(6-methylimidazo[1,2-a]pyridin-2-yl)aniline (0.50 g, 2.24 mmol) and 3,4,5-trifluorobenzoyl chloride (0.436 g, 2.24 mmol) in dry pyridine (20 ml) to give the title compound (0.617 g, 72%) as a colourless solid, after work-up and recrystallisation from AcOH.

$^1$H NMR (250 MHz, DMSO-$d_6$) δ 2.32 (s, 3H), 7.45 (d, J=9.2 Hz, 1H), 6.65 (d, J=9.2 Hz, 1H), 7.86 (d, J=8.8 Hz, 2H), 7.90-7.96 (m, 2H), 7.93 (d, J=8.8 Hz, 2H), 8.43 (s, 1H), 8.48 (s, 1H), 10.51 (s, 1H).

4-(Dimethylamino)-3,5-difluoro-N-[4-(6-methylimidazo[1,2-a]pyridin-2-yl)phenyl]benzamide Book No.: SKT06-29

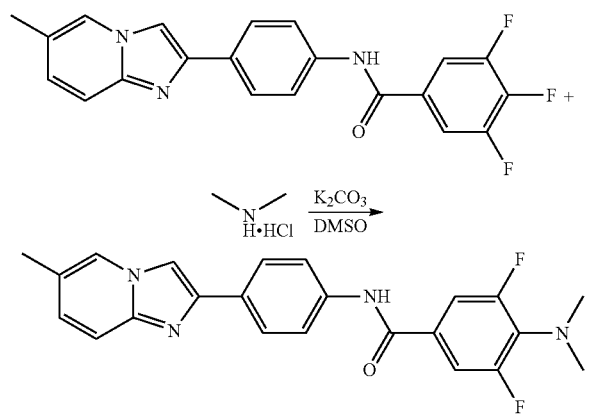

A stirred mixture of 3,4,5-trifluoro-N-[4-(6-methylimidazo[1,2-a]pyridin-2-yl)phenyl]benzamide (0.10 g, 0.26 mmol), dimethylamine hydrochloride (0.087 g, 1.07 mmol) and potassium carbonate (0.147 g, 1.07 mmol) in dry DMSO (3 ml) was heated at 120° C. for 22.5 h. After cooling to room temperature, the reaction mixture was added to water (100 ml) and the precipitate was collected by vacuum filtration, and washed with water (40 ml). The solid was dried in an oven at 95° C., and then purified by flash chromatography (25:1 DCM/MeOH) to give the title compound (0.084 g, 80%) as a colourless solid.

$^1$H NMR (250 MHz, DMSO-$d_6$) δ 2.28 (s, 3H), 2.92 (s, 6H), 7.10 (d, J=8.9 Hz, 1H), 7.47 (d, J=8.9 Hz, 1H), 7.68 (d, $J_{H,F}$=10.1 Hz, 2H), 7.82 (d, J=8.5 Hz, 2H), 7.94 (d, J=8.5 Hz, 2H), 8.26 (s, 1H), 8.32 (s, 1H), 10.22 (s, 1H); $^{13}$C NMR (100.5 MHz, DMSO-$d_6$) δ 17.53, 42.72 (t, $J_{CF}$=3.9 Hz), 107.60, 111.59 (m), 115.67, 120.26, 121.22, 123.45, 125.46, 126.98 (t, $J_{CF}$=7.8 Hz), 127.40, 129.22, 131.58 (t, $J_{CF}$=12.7 Hz), 138.16, 143.89, 144.14, 155.84 (dd, $J_{CF}$=246 Hz, $J_{CF}$=7.8 Hz), 162.68.

4-Fluoro-N-[4-(6-methylimidazo[1,2-a]pyridin-2-yl)phenyl]-3-(trifluoromethyl)benzamide Book No.: SKT06-15

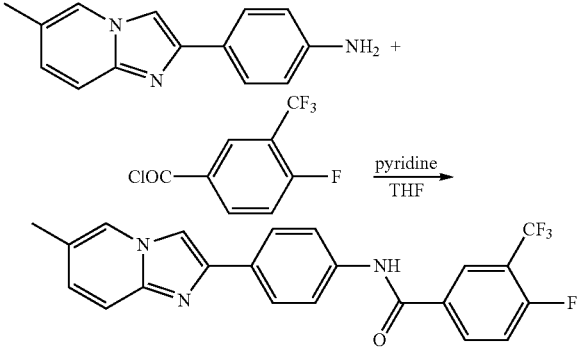

To a stirred solution of 4-fluoro-3-trifluoromethylbenzoic acid (0.103 g, 0.493 mmol) in thionyl chloride (3 ml) was added a drop of DMF and the reaction mixture was then heated under reflux for 2 h. On cooling to room temperature the excess reagent was removed under reduced pressure to give a crude residue. The amide was prepared as described in the Amide Coupling section using the crude residue and 4-(6-methyl imidazo[1,2-a]pyridin-2-yl)aniline (0.10 g, 0.448 mmol) in dry pyridine/THF (1:1, 10 ml) to give the title compound (0.146 g, 79%) as a colourless solid, after work-up and flash chromatography (DCM/EtOAc 1:1).

$^1$H NMR (400 MHz, DMSO-$d_6$) δ 2.26 (s, 3H), 7.08 (dd, J=9.0, 1.2 Hz, 1H), 7.46 (d, J=9.0 Hz, 1H), 7.68-7.76 (m, 1H), 7.82 (d, J=9.0 Hz, 2H), 7.95 (d, J=9.0 Hz, 2H), 8.23 (s, 1H), 8.29 (br s, 1H), 8.33-8.37 (m, 2H), 10.52 (s, 1H); $^{13}$C NMR (100 MHz, DMSO-$d_6$) δ 17.96, 108.85, 116.39, 117.02 (d of q, $J_{CF}$=32.7, 12.5 Hz), 117.99 (d, $J_{CF}$=21.0 Hz), 121.04, 121.80, 122.85 (q, $J_{CF}$=272.4 Hz), 124.63, 126.25, 127.42 (d of q, $J_{CF}$=4.6, 1.6 Hz), 128.23, 130.35, 132.19 (d, $J_{CF}$=3.9 Hz), 135.53 (d, $J_{CF}$=10.2 Hz), 138.62, 144.32, 144.43, 161.08 (d of q, $J_{CF}$=258.4, 1.6 Hz), 163.44 17.96, 108.85, 116.39.

6-Chloro-N-[4-(6-methylimidazo[1,2-a]pyridin-2-yl)phenyl]pyridine-3-carboxamide

Book No.: SKT06-13

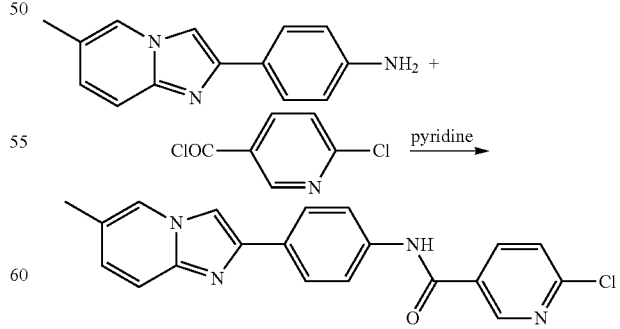

Prepared as described in the Amide Coupling section using 4-(6-methylimidazo[1,2-a]pyridin-2-yl)aniline (0.08 g, 0.359 mmol) and 6-chloronicotinoyl chloride (0.063 g, 0.359 mmol) in dry pyridine (5 ml) to give the title compound (0.087 g, 67%) as a colourless solid after work-up and flash chromatography (20:1 DCM/MeOH).

¹H NMR (250 MHz, DMSO-d₆) δ 2.28 (s, 3H), 7.10 (d, J=9.1 Hz, 1H), 7.47 (d, J=9.1 Hz, 1H), 7.72 (d, J=8.8 Hz, 1H), 7.82 (d, J=8.5 Hz, 2H), 7.95 (d, J=8.5 Hz, 2H), 8.26 (s, 1H), 8.32 (s, 1H), 8.36 (d, J=8.8 Hz, 1H), 8.96 (s, 1H), 10.56 (s, 1H); ¹³C NMR (100.5 MHz, DMSO-d₆) δ 17.97, 108.86, 116.40, 120.92, 121.79, 124.59, 124.63, 126.27, 128.23, 130.42, 130.43, 138.51, 139.50, 144.32, 144.41, 149.77, 153.19, 163.27.

3,4-Difluoro-N-[4-(6-methylimidazo[1,2-a]pyridin-2-yl)phenyl]benzamide

Book No.: SKT06-35

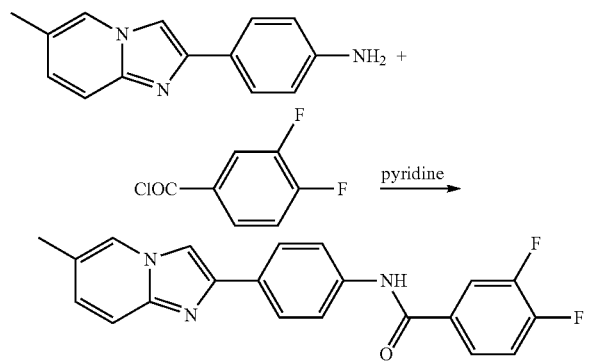

Prepared as described in the Amide Coupling section using 4-(6-methylimidazo[1,2-a]pyridin-2-yl)aniline (0.50 g, 2.24 mmol) and 3,4-difluorobenzoyl chloride (0.395 g, 2.24 mmol) in dry pyridine (20 ml) to give the title compound (0.556 g, 68%) as a colourless solid after work-up and recrystallisation from AcOH.

¹H NMR (250 MHz, DMSO-d₆) δ 2.27 (s, 3H), 7.09 (d, J=9.2 Hz, 1H), 7.46 (d, J=9.2 Hz, 1H), 7.57-7.68 (m, 1H), 7.81 (d, J=8.8 Hz, 2H), 7.83-7.92 (m, 1H), 7.93 (d, J=8.8 Hz, 2H), 8.00-8.08 (m, 1H), 8.24 (s, 1H), 8.30 (s, 1H), 10.38 (s, 1H); ¹³C NMR (100.5 MHz, DMSO-d₆) δ 17.94, 108.79, 116.39, 117.57 (d, $J_{CF}$=18.7 Hz), 118.04 (d, $J_{CF}$=18.1 Hz), 121.04, 121.76, 124.62, 125.68 (dd, $J_{CF}$=7.0 Hz, $J_{CF}$=3.1 Hz), 126.24, 128.18, 130.34, 132.77 (m), 138.69, 144.37, 144.55, 149.57 (dd, $J_{CF}$=237.4 Hz, $J_{CF}$=12.5 Hz), 152.04 (dd, $J_{CF}$=242.1 Hz, $J_{CF}$=13.3 Hz), 163.60.

3-Fluoro-4-(dimethylamino)-N-[4-(6-methylimidazo[1,2-a]pyridin-2-yl)phenyl]benzamide Book No.: SKT06-55

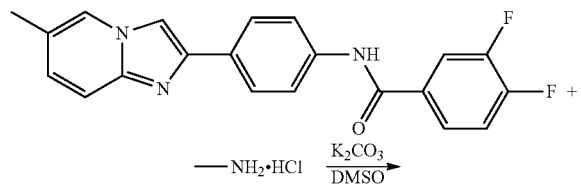

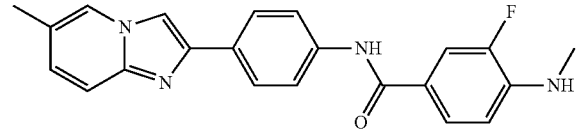

A stirred mixture of 3,4-difluoro-N-[4-(6-methylimidazo[1,2-a]pyridin-2-yl)phenyl]benzamide (0.10 g, 0.275 mmol), methylamine hydrochloride (0.37 g, 5.50 mmol) and potassium carbonate (0.76 g, 5.50 mmol) in dry DMSO (2 ml) was heated at 120° C. for 60 h. After cooling to room temperature, the reaction mixture was added to water (100 ml) and the precipitate was collected by vacuum filtration, and washed with water (40 ml). The solid was dried in an oven at 95° C., then purified by flash chromatography (EtOAc) to give the title compound (0.077 g, 75%) as a colourless solid.

¹H NMR (400 MHz, DMSO-d₆) δ 2.22 (s, 3H), 2.74 (d, J=4.9 Hz, 3H), 6.19-6.21 (m, 1H), 6.68 (t, J=8.8 Hz, 1H), 7.04 (dd, J=9.0, 1.5 Hz, 1H), 7.41 (d, J=9.0 Hz, 1H), 7.65 (dd, J=13.2, 1.7 Hz, 1H), 7.71 (dd, J=8.5, 1.7 Hz, 1H), 7.77 (d, J=8.5 Hz, 2H), 7.85 (d, J=8.5 Hz, 2H), 8.18 (s, 1H), 8.25 (s, 1H), 9.91 (s, 1H); ¹³C NMR (100.5 MHz, DMSO-d₅) δ 17.95, 29.72, 108.61, 110.39 (d, $J_{CF}$=4.6 Hz), 113.89 (d, $J_{CF}$=19.5 Hz), 116.38, 120.78, 121.21 (d, $J_{CF}$=5.4 Hz), 121.70, 124.59, 125.86 (d, $J_{CF}$=1.6 Hz), 126.15, 128.09, 129.58, 139.44, 141.41 (d, $J_{CF}$=12.5 Hz), 144.36, 144.76, 150.29 (d, $J_{CF}$=238 Hz), 164.68 (d, $J_{CF}$=2.3 Hz).

3,5-Difluoro-4-(methylamino)-N-[4-(6-methylimidazo[1,2-a]pyridin-2-yl)phenyl]benzamide Book No.: SKT06-59

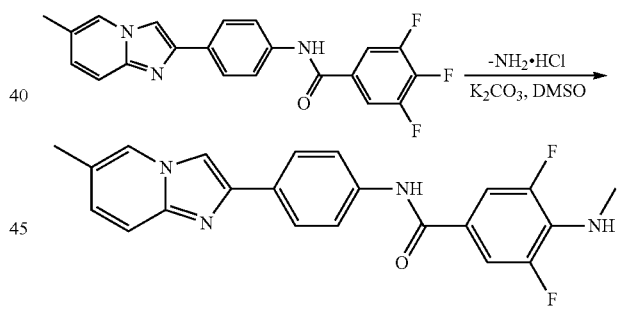

A stirred mixture of 3,4,5-trifluoro-N-[4-(6-methylimidazo[1,2-a]pyridin-2-yl)phenyl]benzamide (0.10 g, 0.26 mmol), methylamine hydrochloride (0.44 g, 6.50 mmol) and potassium carbonate (0.90 g, 6.50 mmol) in dry DMSO (3 ml) was heated at 120° C. for 47 h. After cooling to room temperature, the reaction mixture was added to water (150 ml) and the precipitate was collected by vacuum filtration, and washed with water (40 ml). The solid was dried in an oven at 95° C., then purified by flash chromatography (EtOAc/Hexane 3:1) to give the title compound (0.046 g, 63%) as a colourless solid.

¹H NMR (400 MHz, DMSO-d₆) δ 2.23 (s, 3H), 2.93-2.95 (m, 3H), 5.88-5.91 (m, 1H), 7.04 (dd, J=9.0, 1.5 Hz, 1H), 7.41 (d, J=9.0 Hz, 1H), 7.56 (dist dd, J=9.0, 2.7 Hz, 1H), 7.61 (dist dd, J=9.0, 2.7 Hz, 1H), 7.76 (d, J=8.8 Hz, 2H), 7.86 (d, J=8.8 Hz, 2H), 8.19 (s, 1H), 8.26 (d, J=0.49 Hz, 1H), 9.99 (s, 1H); ¹³C NMR (100.5 MHz, DMSO-d₆) δ 17.97, 32.31 (t, $J_{CF}$=3.8 Hz), 108.71, 111.93 (m), 116.36, 120.55 (t, $J_{CF}$=7.8 Hz), 120.78, 121.75, 124.62, 126.17, 128.16, 129.79, 130.91 (t, $J_{CF}$=14 Hz), 139.03, 144.29, 144.55, 150.97 (dd, $J_{CF}$=239 Hz, $J_{CF}$=10.1 Hz), 163.40.

4-(Dimethylamino)-3-fluoro-N-[4-(6-methylimidazo[1,2-a]pyridin-2-yl)phenyl]benzamide Book No.: SKT06-39

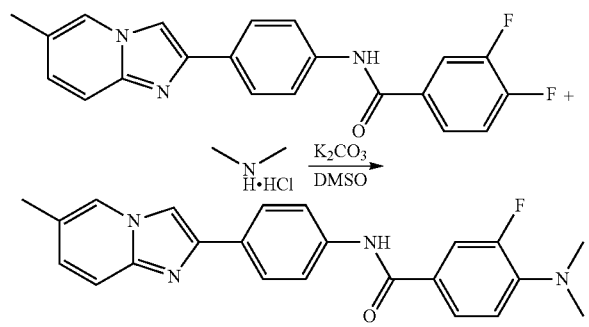

A stirred mixture of 3,4-difluoro-N-[4-(6-methylimidazo[1,2-a]pyridin-2-yl)phenyl]benzamide (0.10 g, 0.275 mmol), dimethylamine hydrochloride (0.045 g, 0.551 mmol) and potassium carbonate (0.080 g, 0.577 mmol) in dry DMSO (3 ml) was heated at 100° C. for 18 h. After cooling to room temperature, the reaction mixture was added to water (100 ml) and the precipitate was collected by vacuum filtration, and washed with water (50 ml). The air-dried solid was then purified by flash chromatography (25:1 DCM/MeOH) to give the title compound (0.066 g, 62%) as a colourless solid.

$^1$H NMR (250 MHz, DMSO-$d_6$) δ 2.28 (s, 3H), 2.93 (s, 6H), 7.01 (t, J=9.2 Hz, 1H), 7.10 (d, J=9.2 Hz, 1H), 7.47 (d, J=9.2 Hz, 1H), 7.73-7.79 (m, 2H), 7.83 (d, J=8.5 Hz, 2H), 7.92 (d, J=8.5 Hz, 2H), 8.25 (s, 1H), 8.32 (s, 1H), 10.10 (s, 1H); $^{13}$C NMR (100.5 MHz, DMSO-$d_6$) δ 17.94, 42.36 (d, J=4.7 Hz), 108.65, 115.92 (d, $J_{CF}$=23.3 Hz), 116.37, 117.20 (d, $J_{CF}$=4.7 Hz), 120.86, 121.71, 124.59, 125.13, 125.15, 125.77 (d, $J_{CF}$=6.2 Hz), 126.17, 128.10, 129.82, 139.19, 143.20 (d, $J_{CF}$=7.7 Hz), 144.52 (d, $J_{CF}$=34.3 Hz), 152.81 (d, $J_{CF}$=243 Hz), 164.30.

3-Fluoro-4-methoxy-N-[4-(6-methylimidazo[1,2-a]pyridin-2-yl)phenyl]benzamide Book No.: SKT06-49

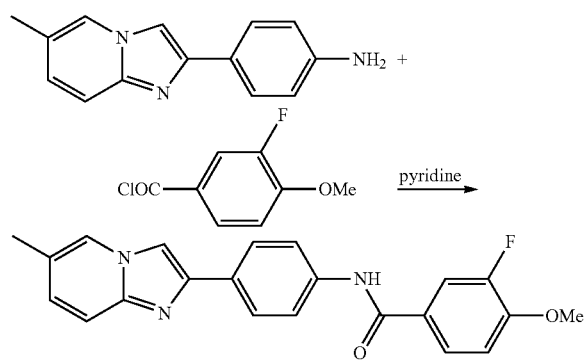

Prepared as described in the Amide Coupling section using 4-(6-methylimidazo[1,2-a]pyridin-2-yl)aniline (0.30 g, 1.34 mmol) and 3-fluoro-4-methoxybenzoyl chloride (0.25 g, 1.34 mmol) in dry pyridine (14 ml) to give the title compound (0.357 g, 71%) as small, colourless needles after work-up, flash chromatography (DCM/MeOH 18:1) and recrystallisation from 1,4-dioxane.

$^1$H NMR (250 MHz, DMSO-$d_6$) δ 2.28 (s, 3H), 3.93 (s, 3H), 7.10 (d, J=9.2 Hz, 1H), 7.33 (m, 1H), 7.47 (d, J=9.2 Hz, 1H), 7.83 (d, J=8.5 Hz, 2H), 7.85-7.91 (m, 2H), 7.93 (d, J=8.5 Hz, 2H), 8.26 (s, 1H), 8.32 (s, 1H), 10.23 (s, 1H); $^{13}$C NMR (100.5 MHz, DMSO-$d_6$) δ 17.96, 56.70, 108.74, 113.71 (d, $J_{CF}$=2.3 Hz), 115.66 (d, $J_{CF}$=19.5 Hz), 116.37, 120.89, 121.75, 124.60, 125.40 (d, $J_{CF}$=3.1 Hz), 126.17, 127.65 (d, $J_{CF}$=5.4 Hz), 128.16, 129.94, 138.98, 144.31, 144.54, 150.39 (d, $J_{CF}$=10.8 Hz), 151.28 (d, $J_{CF}$=244.4 Hz), 164.13.

3,5-Difluoro-4-methoxy-N-[4-(6-methylimidazo[1,2-a]pyridin-2-yl)phenyl]benzamide Book No.: SKT06-45

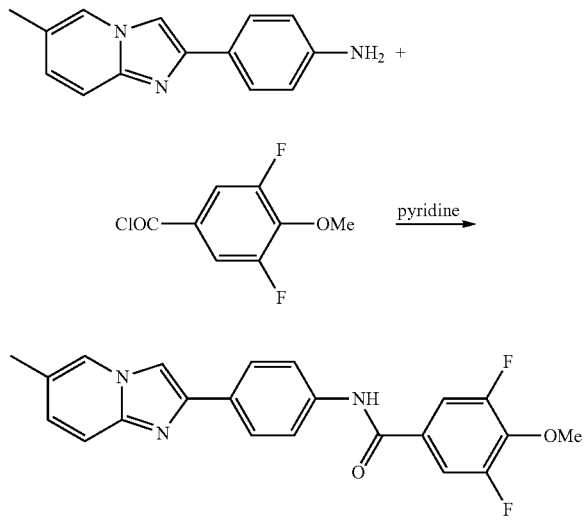

To a stirred solution of 3,5-difluoro-4-methoxybenzoic acid (0.25 g, 1.34 mmol) in thionyl chloride (4 ml) was added a drop of DMF and the reaction mixture was then heated under reflux for 5 h. On cooling to room temperature the excess reagent was removed under reduced pressure to give a crude residue. The amide was prepared as described in the Amide Coupling section using the crude residue and 4-(6-methylimidazo[1,2-a]pyridin-2-yl)aniline (0.30 g, 1.34 mmol) in dry pyridine (14 ml) to give the title compound (0.33 g, 62%) as a pale yellow solid after work-up and flash chromatography (DCM/MeOH 20:1).

$^1$H NMR (400 MHz, DMSO-$d_6$) δ 2.22 (s, 3H), 3.98 (s, 3H), 7.04 (dd, J=9.2, 1.5 Hz, 1H), 7.41 (d, J=9.2 Hz, 1H), 7.78-7.85 (m, 2H), 7.81 (d, J=8.8 Hz, 2H), 7.88 (d, J=8.8 Hz, 2H), 8.21 (s, 1H), 8.26 (s, 1H), 10.44 (s, 1H); $^{13}$C NMR (100.5 MHz, DMSO-$d_6$) δ 18.18, 62.42, 109.06, 113.04 (m), 116.58, 121.22, 121.97, 124.84, 126.35, 128.41, 129.87 (t, $J_{CF}$=Hz), 130.42, 138.87, 139.09 (t, $J_{CF}$=Hz), 144.50, 144.63, 154.86 (dd, $J_{CF}$=246 Hz, $J_{CF}$=6 Hz), 163.12.

2,6-Difluoro-4-methoxy-N-[4-(6-methylimidazo[1,2-a]pyridin-2-yl)phenyl]benzamide Book No.: SKT06-79

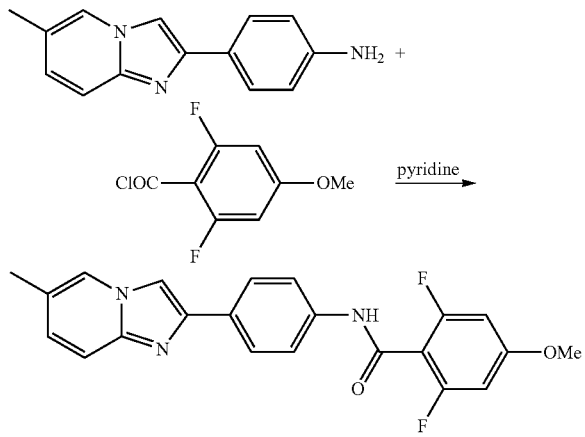

To a stirred solution of 2,6-difluoro-4-methoxybenzoic acid (0.25 g, 1.34 mmol) in thionyl chloride (7 ml) was added a drop of DMF and the reaction mixture was then heated under reflux for 3 h. On cooling to room temperature the excess reagent was removed under reduced pressure to give a crude residue. The amide was prepared as described in the Amide Coupling section using of the crude residue and 4-(6-methylimidazo[1,2-a]pyridin-2-yl)aniline (0.30 g, 1.34 mmol) in dry pyridine (15 ml) to give the title compound (0.24 g, 45%) as a pale yellow solid after work-up and flash chromatography (2:1 EtOAc/Hexane followed by EtOAc then MeOH).

$^1$H NMR (250 MHz, DMSO-d$_6$) δ 2.28 (s, 3H), 3.84 (s, 3H), 6.90 (d, J=10.1 Hz, 2H), 7.10 (d, J=9.2 Hz, 1H), 7.47 (d, J=9.2 Hz, 1H), 7.74 (d, J=8.2 Hz, 2H), 7.93 (d, J=8.2 Hz, 2H), 8.26 (s, 1H), 8.32 (d, J=0.6 Hz, 1H), 10.72 (s, 1H); $^{13}$C NMR (100.5 MHz, DMSO-d$_6$) δ 17.98, 56.88, 98.98 (d, J$_{CF}$ 28.7), 108.58 (t, J$_{CF}$ 22.6), 108.85, 116.39, 119.98, 121.80, 124.63, 126.40, 128.23, 130.31, 138.55, 144.31, 144.38, 158.57, 160.34 (dd, J$_{CF}$ 246 and 11.7), 162.21 (t, J$_{CF}$ 14.8).

3,5-Difluoro-4-hydroxy-N-[4-(6-methylimidazo[1,2-a]pyridin-2-yl)phenyl]benzamide Book No.: SKT06-51

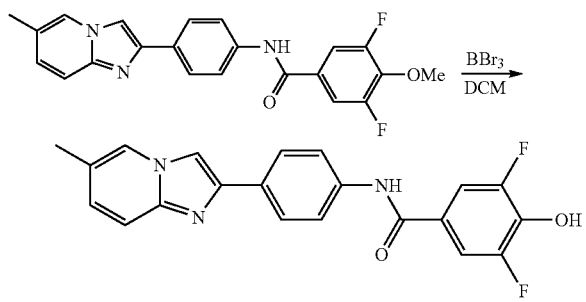

Prepared as described in the Demethylation section above using 3,5-difluoro-4-methoxy-N-[4-(6-methylimidazo[1,2-a]pyridin-2-yl)phenyl]benzamide (0.20 g, 0.509 mmol) in dry DCM (10 ml) and boron tribromide in DCM (1.0 M, 0.62 ml, 0.62 mmol) at −78° C. to give the title compound (0.057 g, 29%) as a colourless solid after work-up and flash chromatography (12:1 DCM/MeOH).

$^1$H NMR (250 MHz, DMSO-d$_6$) δ 2.27 (s, 3H), 7.09 (d, J=9.2 Hz, 1H), 7.46 (d, J=9.2 Hz, 1H), 7.73 (d, J=7.9 Hz, 2H), 7.81 (d, J=8.5 Hz, 2H), 7.93 (d, J=8.5 Hz, 2H), 8.25 (s, 1H), 8.31 (s, 1H), 10.19 (s, 1H), 11.05 (brs, 1H); $^{13}$C NMR (100.5 MHz, DMSO-d$_6$) δ 17.95, 108.76, 112.08 (m), 116.39, 120.99, 121.77, 124.63, 125.10 (t, J$_{CF}$=7.0 Hz), 126.23, 128.18, 130.16, 137.61 (t, J$_{CF}$=16.3 Hz), 138.81, 144.37, 144.58, 152.20 (dd, J$_{CF}$=242 Hz, J$_{CF}$=7.0 Hz), 163.31.

3-Fluoro-4-hydroxy-N-[4-(6-methylimidazo[1,2-a]pyridin-2-yl)phenyl]benzamide

Book No.: SKT06-57

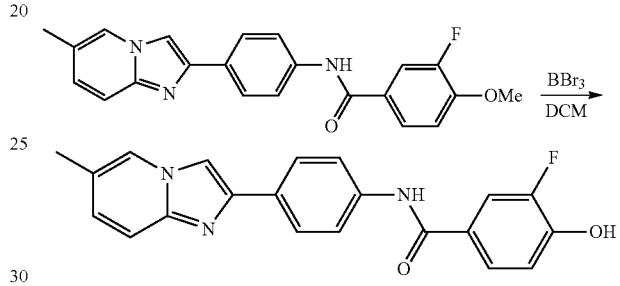

Prepared as described in the Demethylation section above using 3-fluoro-4-methoxy-N-[4-(6-methylimidazo[1,2-a]pyridin-2-yl)phenyl]benzamide (0.20 g, 0.53 mmol) in dry DCM (15 ml) and BBr$_3$ (1.0 M, 1.3 ml, 1.3 mmol) at −78° C. to give the title compound (0.070 g, 36%) as a colourless solid after work-up and flash chromatography (10:1 DCM/MeOH).

$^1$H NMR (400 MHz, DMSO-d$_6$) δ 2.23 (s, 3H), 7.01 (t, J=8.5 Hz, 1H), 7.05 (dd, J=9.3, 1.5 Hz, 1H), 7.42 (d, J=9.3 Hz, 1H), 7.66 (dd, J=8.5, 1.5 Hz, 1H), 7.75-7.78 (m, 1H), 7.77 d, J=8.8 Hz, 2H), 7.86 (d, J=8.8 Hz, 2H), 8.20 (s, 1H), 8.27 (s, 1H), 10.08 (s, 1H), 10.57 (s, 1H); (100.5 MHz, DMSO-d$_6$) δ 17.97, 108.71, 116.17 (d, J$_{CF}$=19.5 Hz), 116.36, 117.73 (d, J$_{CF}$=3.1 Hz), 120.85, 121.77, 124.60, 125.38 (d, J$_{CF}$=2.3 Hz), 126.17, 126.33 (d, J$_{CF}$=4.6 Hz), 128.18, 129.81, 139.12, 144.31, 144.57, 148.76 (d, J$_{CF}$=12.5 Hz), 150.83 (d, J$_{CF}$=241.3 Hz), 164.38 (d, J$_{CF}$=1.6 Hz).

4-Methoxy-3-trifluoromethyl-N-[4-(6-methylimidazo[1,2-a]pyridin-2-yl)phenyl]benzamide Book No.: SKT06-61

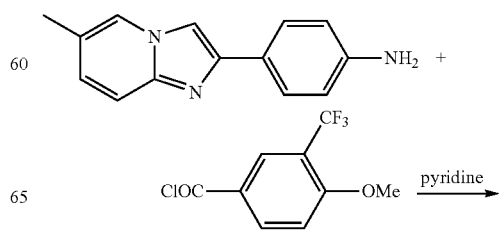

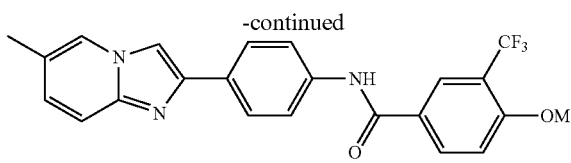

Prepared as described in the Amide Coupling section using 4-(6-methylimidazo[1,2-a]pyridin-2-yl)aniline (0.20 g, 0.897 mmol) and 4-methoxy-3-trifluoromethylbenzoyl chloride (0.21 g, 0.897 mmol) in dry pyridine (15 ml) to give the title compound as a colourless solid (0.147 g, 38%) after work-up and flash chromatography (15:1 EtOAc/Hexane).

$^1$H NMR (400 MHz, DMSO-$d_6$) δ 2.23 (s, 3H), 3.94 (s, 3H), 7.04 (dd, J=9.0, 1.5 Hz, 1H), 7.38 (d, J=8.8 Hz, 1H), 7.42 (d, J=9.0 Hz, 1H), 7.78 (d, J=8.8 Hz, 2H), 7.89 (d, J=8.8 Hz, 2H), 8.20 (s, 1H), 8.22 (dd, J=10.7, 1.9 Hz, 2H), 8.26 (d, J=1.5 Hz, 1H), 10.33 (s, 1H); $^{13}$C NMR (100.5 MHz, CDCl$_3$/DMSO-$d_6$) δ 17.80, 56.05, 107.66, 111.53, 115.97, 117.63 (q, $J_{CF}$=31 Hz), 120.77, 121.73, 123.20 (q, $J_{CF}$=272 Hz), 123.45, 125.85, 126.58, 126.90 (q, $J_{CF}$=3.9 Hz), 127.79, 129.37, 133.45, 138.38, 144.28, 144.43, 159.49, 164.26.

6-(Dimethylamino)-N-[4-(6-methylimidazo[1,2-a]pyridin-2-yl)phenyl]pyridine-3-carboxamide Book No.: SKT06-155

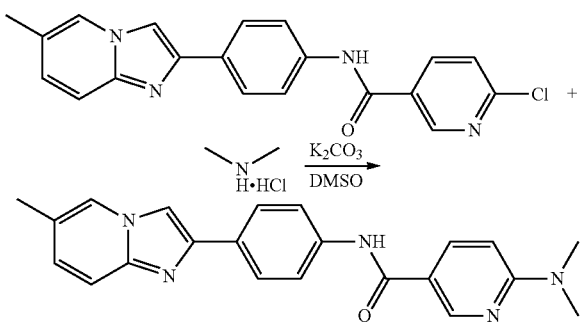

A stirred mixture of 6-chloro-N-[4-(6-methylimidazo[1,2-a]pyridin-2-yl)phenyl]pyridine-3-carboxamide (0.15 g, 0.414 mmol), dimethylamine hydrochloride (0.845 g, 10.36 mmol) and K$_2$CO$_3$ (1.43 g, 10.36 mmol) in dry DMSO (10 ml) was heated at 170° C. for 16 h under an atmosphere of argon. The cooled reaction mixture was added to water (200 ml) and the precipitate was collected by filtration and dried in the air. The solid was purified by flash chromatography (12:1 DCM/MeOH) to give the title compound (0.113 g, 73%) as a pale yellow solid.

$^1$H NMR (250 MHz, DMSO-$d_6$) δ 2.27 (s, 3H), 3.11 (s, 6H), 6.71 (d, J=9.2 Hz, 1H), 7.09 (d, J=9.2 Hz, 1H), 7.46 (d, J=9.2 Hz, 1H), 7.81 (d, J=8.5 Hz, 2H), 7.90 (d, J=8.5 Hz, 2H), 8.07 (dd, J=1.5, 8.5 Hz, 1H), 8.23 (s, 1H), 8.30 (s, 1H), 8.74 (s, 1H), 10.03 (s, 1H); $^{13}$C NMR (100.5 MHz, DMSO-$d_6$) δ 17.98, 38.04, 105.05, 108.64, 116.36, 117.89, 120.68, 121.72, 124.60, 126.14, 128.12, 129.53, 136.99, 139.35, 144.29, 144.63, 148.99, 160.48, 164.66.

6-(Methylamino)-N-[4-(6-methylimidazo[1,2-a]pyridin-2-yl)phenyl]pyridine-3-carboxamide Book No.: SKT06-153

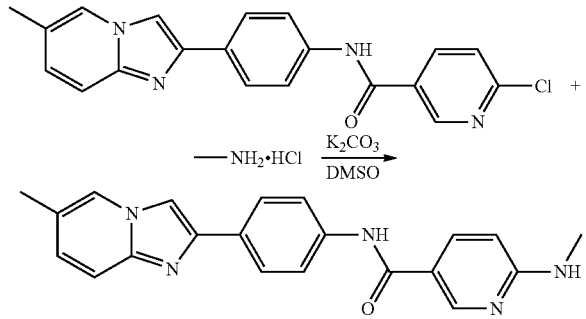

A stirred mixture of 6-chloro-N-[4-(6-methylimidazo[1,2-a]pyridin-2-yl)phenyl]pyridine-3-carboxamide (0.15 g, 0.414 mmol), methylamine hydrochloride (0.69 g, 10.36 mmol) and K$_2$CO$_3$ (1.43 g, 10.36 mmol) in dry DMSO (10 ml) was heated at 170° C. for 17.5 h under an atmosphere of argon. The cooled reaction mixture was added to water (150 ml) and the precipitate was collected by filtration and dried in the air. The solid was purified by flash chromatography (10:1 DCM/MeOH) to give the title compound (0.059 g, 40%) as a pale yellow solid.

$^1$H NMR (400 MHz, DMSO-$d_6$) δ 2.26 (s, 3H), 2.82 (d, J=4.7 Hz, 3H), 6.49 (d, J=9.0 Hz, 1H), 7.08 (dd, J=9.0, 1.6 Hz, 1H), 7.13 (q, J=4.7 Hz, 1H), 7.45 (d, J=9.4 Hz, 1H), 7.79 (d, J=8.6 Hz, 2H), 7.88 (d, J=8.6 Hz, 2H), 7.93 (dd, J=9.0, 2.4 Hz, 1H), 8.22 (s, 1H), 8.29 (s, 1H), 8.66 (d, J=2.4 Hz, 1H), 9.96 (s, 1H); $^{13}$C NMR (100.5 MHz, DMSO-$d_6$) δ 17.98, 28.30, 108.64, 116.36, 118.21, 120.66, 121.73, 124.60, 126.13, 128.12, 129.46, 136.41, 139.41, 144.29, 144.65, 149.38, 161.36, 164.80 (1 missing).

4-Methoxy-N-[4-(6-methylimidazo[1,2-a]pyridin-2-yl)phenyl]-2-(trifluoromethyl)benzamide Book No.: SKT06-141

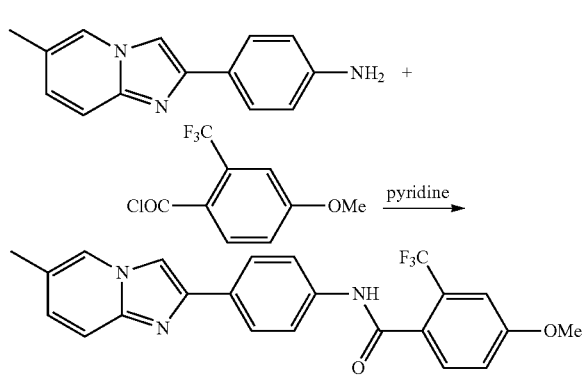

A stirred solution of 4-methoxy-2-trifluoromethylbenzoic acid (0.197 g, 0.897 mmol) in thionyl chloride (5 ml) containing a drop of DMF was heated under reflux for 3 h. The excess reagent was then removed under reduced pressure to give a crude solid. The amide was prepared as described in the Amide Coupling section using the crude solid and 4-(6-methylimidazo[1,2-a]pyridin-2-yl)aniline (0.20 g, 0.897 mmol)

in dry pyridine (15 ml) to give the title compound (0.087 g, 23%) as a colourless solid after work-up and flash chromatography (1:1:0.1 DCM/EtOAc/MeOH).

$^1$H NMR (400 MHz, DMSO-d$_6$) δ 2.25 (s, 3H), 3.88 (s, 3H), 7.07 (dd, J=9.4, 1.5 Hz, 1H), 7.30-7.34 (m, 2H), 7.45 (d, J=9.4 Hz, 1H), 7.64 (d, J=9.4 Hz, 1H), 7.74 (d, J=8.6 Hz, 2H), 7.91 (d, J=8.6 Hz, 2H), 8.22 (s, 1H), 8.28 (d, J=0.7 Hz, 1H), 10.51 (s, 1H); $^{13}$C NMR (100.5 MHz, DMSO-d$_6$) δ 17.97, 56.38, 108.77, 112.59 (q, J$_{CF}$=5.4 Hz), 116.38, 117.65, 120.16, 121.77, 123.92 (q, J$_{CF}$=274 Hz), 124.61, 126.29, 128.12 (q, J$_{CF}$=32 Hz), 128.19, 129.05 (q, J$_{CF}$=2.3 Hz), 130.05, 131.04, 138.98, 144.31, 144.48, 160.39, 165.82.

N-[4-(6-methylimidazo[1,2-a]pyridin-2-yl)phenyl]-2,6-difluoro-4-hydroxybenzamide Book No.: SKT06-137

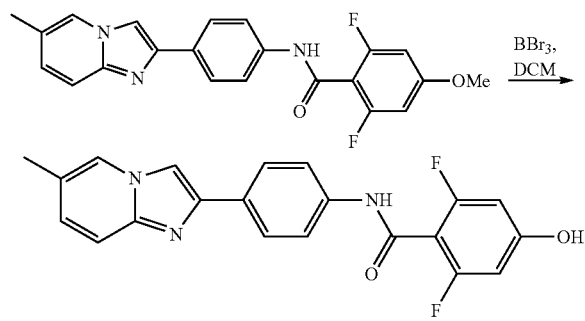

Prepared as described in the Demethylation section above using 2,6-difluoro-4-methoxy-N-[4-(6-methylimidazo[1,2-a]pyridin-2-yl)phenyl]benzamide (0.10 g, 0.254 mmol) in dry DCM (9 ml) and BBr$_3$ in DCM (1.0 M, 1.3 ml, 1.3 mmol) at 0° C. to give the title compound (0.055 g, 57%) as a pale yellow solid after work-up and flash chromatography (15:1 DCM/MeOH followed by 10:1 DCM/MeOH and finally 5:1 DCM/MeOH).

$^1$H NMR (250 MHz, DMSO-d$_6$) δ 2.28 (s, 3H), 6.53 (d, J$_{HF}$=10.7 Hz, 2H), 7.09 (d, J=9.8 Hz, 1H), 7.47 (d, J=9.8 Hz, 1H), 7.73 (d, J=7.9 Hz, 2H), 7.91 (d, J=7.9 Hz, 2H), 8.24 (s, 1H), 8.31 (s, 1H), 10.60 (s, 1H); $^{13}$C NMR (100.5 MHz, DMSO-d$_6$) δ 17.97, 99.73 (d, J$_{CF}$=25.7 Hz), 107.07 (t, J$_{CF}$=22.6 Hz), 108.84, 116.36, 119.93, 121.81, 124.63, 126.38, 128.26, 130.18, 138.62, 144.29, 144.36, 158.85, 160.34 (dd, J$_{CF}$=246 and 11.7 Hz), 160.91 (t, J$_{CF}$=14.8 Hz).

2-Fluoro-4-methoxy-N-[4-(6-methylimidazo[1,2-a]pyridin-2-yl)phenyl]benzamide Book No.: SKT06-81

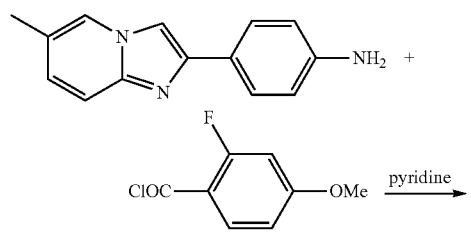

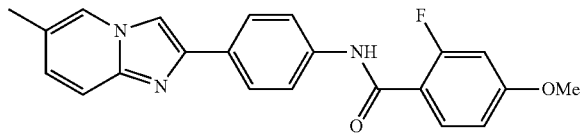

A stirred solution of 2-fluoro-4-methoxybenzoic acid (0.23 g, 1.34 mmol) in thionyl chloride (7 ml) containing a drop of DMF was heated under reflux for 4 h. The excess reagent was then removed under reduced pressure to give a crude solid. The amide was prepared as described in the Amide Coupling section using the crude solid and 4-(6-methylimidazo[1,2-a]pyridin-2-yl)aniline (0.30 g, 1.34 mmol) in dry pyridine (15 ml) to give the title compound (0.323 g, 80%) as a colourless solid after work-up and flash chromatography (EtOAc).

$^1$H NMR (250 MHz, DMSO-d$_6$) δ 2.28 (s, 3H), 3.85 (s, 3H), 6.91 (d, J=9.0 Hz, 1H), 6.97 (d, J=13.1 Hz, 1H), 7.10 (d, J=9.6 Hz, 1H), 7.47 (d, J=8.8 Hz, 1H), 7.66 (t, J=8.8 Hz, 1H), 7.78 (d, J=8.5 Hz, 2H), 7.92 (d, J=7.9 Hz, 2H), 8.25 (s, 1H), 8.31 (s, 1H), 10.26 (s, 1H); $^{13}$C NMR (100.5 MHz, DMSO-d$_6$) δ 17.94, 56.44, 102.34 (d, J$_{CF}$=26.4 Hz), 108.71, 110.99 (d, J$_{CF}$=2.3 Hz), 116.39, 117.28 (d, J$_{CF}$=14.1 Hz), 120.45, 121.73, 124.59, 126.28, 128.12, 130.06, 131.63 (d, J$_{CF}$=4.7 Hz), 138.90, 144.48 (d, J$_{CF}$=24.8 Hz), 160.82 (d, J$_{CF}$=249 Hz), 162.79, 163.00, 163.10.

2-Fluoro-4-hydroxy-N-[4-(6-methylimidazo[1,2-a]pyridin-2-yl)phenyl]benzamide Book No.: SKT06-103

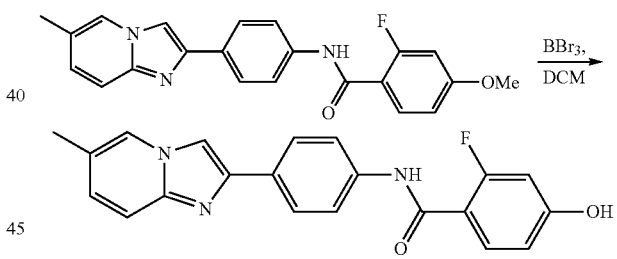

Prepared as described in the Demethylation section above using 2-fluoro-4-methoxy-N-[4-(6-methylimidazo[1,2-a]pyridin-2-yl)phenyl]benzamide (100 mg, 0.267 mmol) in dry DCM (10 ml) and BBr$_3$ in DCM (1.0 M, 1.4 ml, 1.4 mmol) at −78° C. to give the title compound (30 mg, 31%) as a colourless solid after work-up and flash chromatography (10:1 DCM/MeOH).

$^1$H NMR (250 MHz, DMSO-d$_6$) δ 2.28 (s, 3H), 6.63-6.73 (m, 2H), 7.09 (d, J=9.2 Hz, 1H), 7.46 (d, J=9.2 Hz, 1H), 7.55 (t, J=8.5 Hz, 1H), 7.76 (d, J=8.5 Hz, 2H), 7.90 (d, J=8.2 Hz, 2H), 8.23 (s, 1H), 8.31 (s, 1H), 10.13 (s, 1H), 10.47 (s, 1H); $^{13}$C NMR (100.5 MHz, DMSO-d$_6$) δ 17.95, 103.31 (d, J$_{CF}$=24.9 Hz), 108.70, 112.15, 115.68 (d, J$_{CF}$=13.2 Hz), 116.39, 120.43, 121.73, 124.60, 126.27, 128.13, 129.94, 131.83 (d, J$_{CF}$=4.6 Hz), 139.01, 144.50 (d, J$_{CF}$=28.8 Hz), 160.92 (d, J$_{CF}$=248 Hz), 161.73, 161.86, 163.01.

4-(Methylamino)-N-[4-(6-methylimidazo[1,2-a]pyridin-2-yl)phenyl]-3-(trifluoromethyl)benzamide Book No.: SKT06-99

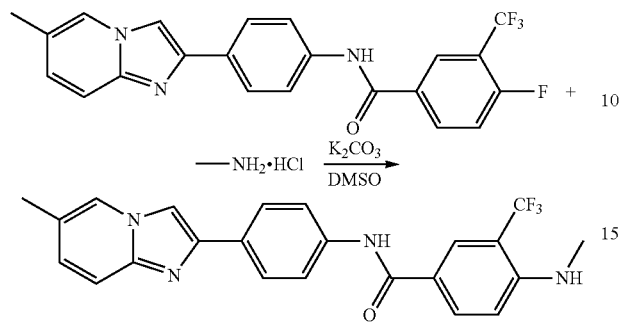

A stirred mixture of 4-fluoro-N-[4-(6-methylimidazo[1,2-a]pyridin-2-yl)phenyl]-3-(trifluoromethyl)benzamide (0.05 g, 0.121 mmol), methylamine hydrochloride (0.20 g, 3.02 mmol) and $K_2CO_3$ (0.42 g, 3.02 mmol) in dry DMSO (5 ml) was heated at 160° C. for 22 h under an atmosphere of argon. The cooled reaction mixture was added to water (100 ml) and the precipitate was collected by filtration under vacuum and dried in the air. The solid was purified by flash chromatography (5:1 EtOAc/Hexane) to give the title compound (0.032 g, 62%) as a pale yellow solid.

$^1$H NMR (250 MHz, DMSO-$d_6$) δ 2.28 (s, 3H), 2.86 (d, J=4.3 Hz, 3H), 6.29-6.31 (q, J=3.9 Hz, 1H), 6.84 (d, J=9.2 Hz, 1H), 7.09 (d, J=9.1 Hz, 1H), 7.47 (d, J=8.8 Hz, 1H), 7.82 (d, J=8.5 Hz, 2H), 7.92 (d, J=8.5 Hz, 2H), 8.12 (br s, 2H), 8.24 (s, 1H), 8.31 (s, 1H), 10.13 (s, 1H); $^{13}$C NMR (100.5 MHz, DMSO-$d_6$) δ 17.96, 30.40, 108.74, 110.86 (q, $J_{CF}$=29.6 Hz), 111.25, 116.20, 119.99, 120.58, 120.87, 121.94, 124.66, 125.21 (q, $J_{CF}$=270 Hz), 126.16, 126.94 (q, $J_{CF}$=6.1 Hz), 128.41, 129.36, 130.80, 133.71, 139.34, 144.17, 144.34, 149.07, 164.60.

4-(Dimethylamino)-N-[4-(6-fluoroimidazo[1,2-a]pyridine-2-yl)phenyl]benzamide Book No.: SKT06-131

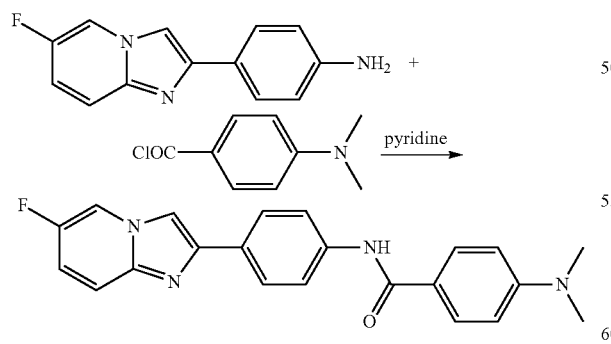

Prepared as described in the Amide Coupling section using 4-(6-fluoroimidazo[1,2-a]pyridin-2-yl)aniline (100 mg, 0.44 mmol) and 4-dimethylaminobenzoyl chloride (81 mg, 0.44 mmol) in dry pyridine (5 ml) to give the title compound (59 mg, 36%) as a pale yellow solid after work-up and flash chromatography (1:1 DCM/EtOAc).

$^1$H NMR (250 MHz, DMSO-$d_6$) δ 3.01 (s, 6H), 6.77 (d, J=8.5 Hz, 2H), 7.31 (t, J=9.2 Hz, 1H), 7.63 (dd, J=9.2, 4.9 Hz, 1H), 7.82-7.93 (m, 6H), 8.33 (s, 1H), 8.75 (br s, 1H), 9.95 (s, 1H); $^{13}$C NMR (100.5 MHz, DMSO-$d_6$) δ 40.15, 110.42 (d, $J_{CF}$=1.5 Hz), 111.28, 113.85 (d, $J_{CF}$=41.2 Hz), 116.75 (d, $J_{CF}$=25.6 Hz), 117.53 (d, $J_{CF}$=9.3 Hz), 120.75, 121.62, 126.26, 128.87, 129.60, 139.99, 143.21, 146.30, 152.94, 152.98 (d, $J_{CF}$=232.8 Hz), 165.66.

4-(Dimethylamino)-N-[4-(6-iodoimidazo[1,2-a]pyridin-2-yl)phenyl]benzamide

Book No.: SKT06-165

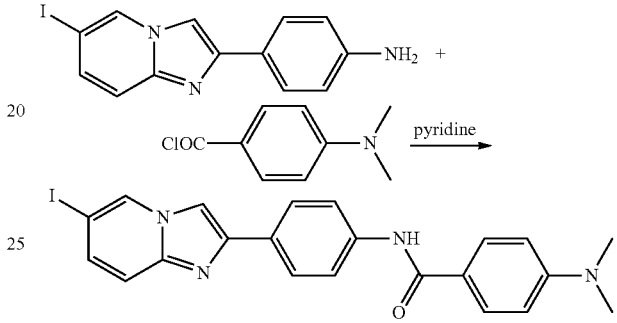

Prepared as described in the Amide Coupling section using 4-(6-iodoimidazo[1,2-a]pyridin-2-yl)aniline (100 mg, 0.298 mmol) and 4-dimethylaminobenzoyl chloride (55 mg, 0.298 mmol) in dry pyridine (5 ml) to give the title compound (45 mg, 31%) as a pale yellow solid after flash chromatography (20:10:1 DCM/EtOAc/MeOH).

$^1$H NMR (250 MHz, DMSO-$d_6$) δ 3.01 (s, 6H), 6.77 (d, J=8.5 Hz, 2H), 7.42 (s, 2H), 7.84-7.89 (m, 6H), 8.26 (s, 1H), 8.90 (s, 1H), 9.96 (s, 1H); $^{13}$C NMR (100.5 MHz, DMSO-$d_6$) δ 76.19, 108.72, 111.21, 118.13, 120.57, 121.44, 126.33, 128.46, 129.61, 131.76, 132.68, 140.06, 143.80, 145.13, 152.85, 165.64 (1 missing).

4-Bromo-N-[4-(6-methylimidazo[1,2-a]pyridin-2-yl)phenyl]-3-nitrobenzamide

Book No.: SKT08-153

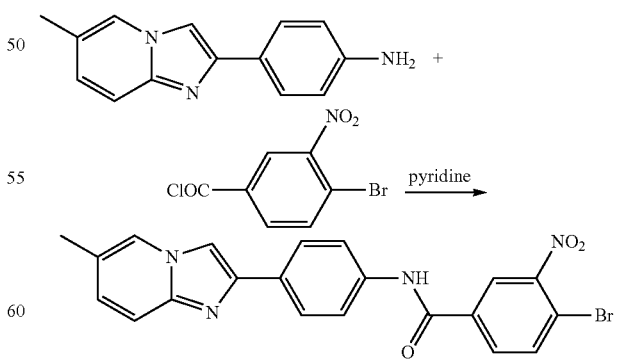

To a stirred suspension of 4-bromo-3-nitrobenzoic acid (0.330 g, 1.344 mmol) in thionyl chloride (7 ml) was added a drop of DMF and the reaction mixture was heated under reflux for 3 h. The excess reagent was then removed under reduced pressure to give a crude solid. The amide was prepared as described in the Amide Coupling section using the crude solid and 4-(6-methylimidazo[1,2-a]pyridin-2-yl)aniline (0.300 g, 1.344 mmol) in dry pyridine (16 ml) to give the title compound (0.448 g, 74%) as a yellow solid after work-up and recrystallisation from DMF/water (1:0.76 v/v).

$^1$H NMR (250 MHz, DMSO-$d_6$) δ 2.27 (s, 3H), 7.10 (d, J=9.5 Hz, 1H), 7.47 (d, J=9.5 Hz, 1H), 7.83 (d, J=8.2 Hz, 2H), 7.95 (d, J=8.2 Hz, 2H), 8.09-8.18 (m, 2H), 8.26 (s, 1H), 8.31 (s, 1H), 8.59 (s, 1H), 10.60 (s, 1H); $^{13}$C NMR (100.5 MHz, DMSO-$d_6$) δ 17.95, 108.90, 116.33, 116.87, 121.10, 121.89, 124.67, 124.97, 126.32, 128.36, 130.46, 133.06, 135.49, 135.96, 138.48, 144.30, 144.34, 149.99, 162.93.

4-Fluoro-N-[4-(6-methylimidazo[1,2-a]pyridin-2-yl)phenyl]-3-nitrobenzamide

Book No.: SKT08-165

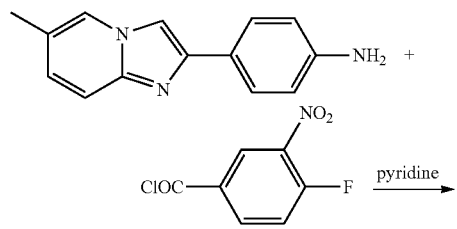

To a stirred suspension of 4-fluoro-3-nitrobenzoic acid (0.254 g, 1.344 mmol) in thionyl chloride (7 ml) was added a drop of DMF and the reaction mixture was heated under reflux for 3 h. The excess reagent was then removed under reduced pressure to give the crude acid chloride. The amide was prepared as described in the Amide Coupling section using the crude acid chloride and 4-(6-methylimidazo[1,2-a]pyridin-2-yl)aniline (0.300 g, 1.344 mmol) in dry pyridine (16 ml) to give the title compound (0.334 g, 64%) as a pale orange solid after work-up and recrystallisation from 1,4-dioxane/water (3.75:1 v/v).

$^1$H NMR (250 MHz, DMSO-$d_6$) δ 2.27 (s, 3H), 7.09 (d, J=9.1 Hz, 1H), 7.47 (d, J=9.1 Hz, 1H), 7.78 (m, 1H), 7.84 (d, J=8.2 Hz, 2H), 7.96 (d, J=8.2 Hz, 2H), 8.25 (s, 1H), 8.30 (s, 1H), 8.35-8.47 (m, 1H), 8.77 (d, J=7.3 Hz, 1H), 10.61 (s, 1H); $^{13}$C NMR (100.5 MHz, DMSO-$d_6$) δ 17.94, 108.85, 116.42, 119.24 (d, $J_{CF}$=21.8 Hz), 121.15, 121.78, 124.63, 126.16, 126.29, 128.19, 130.57, 132.23 (d, $J_{CF}$=3.9 Hz), 136.08 (d, $J_{CF}$=10.2 Hz), 137.18 (d, $J_{CF}$=7.7 Hz), 138.49, 144.392, 144.51, 156.77 (d, $J_{CF}$=266 Hz), 162.77.

Compounds where -Q- is —CH=CH—; —CR$^1$=CH—; —CH=CR$^1$—; or —CR$^1$=CR$^1$—

Benzothiazole Intermediates

5-Methyl-2-aminobenzenethiol

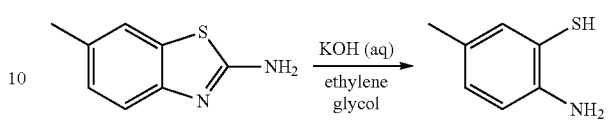

A mixture of 2-amino-6-methylbenzothiazole (15 g, 91.3 mmol), ethylene glycol (22.26 g, 0.36 mol) and 50% w/v KOH (180 ml) was heated under reflux for 62 h. On cooling to room temperature, toluene (60 ml) was added and the reaction mixture was cooled in an ice-bath and acidified with acetic acid (final pH 5-6). The reaction mixture was extracted with toluene (5×300 ml) and the combined organic extracts were washed with brine (2×200 ml), dried (MgSO$_4$) and the solvent removed under reduced pressure to give the title compound (11.1 g, 86%) as a yellow solid which was used without further purification.

$^1$H NMR (250 MHz, CDCl$_3$) δ 2.13 (s, 3H), 4.19 (br s, 2H), 6.64 (d, J=7.9 Hz, 1H), 6.95 (s, 1H), 6.97 (d, J=7.9 Hz, 1H); $^{13}$C NMR (62.5 MHz, CDCl$_3$) δ 20.09, 115.35, 118.92, 127.54, 132.37, 137.09, 146.22.

2-(4-Bromomethyl)phenyl-6-methylbenzothiazole

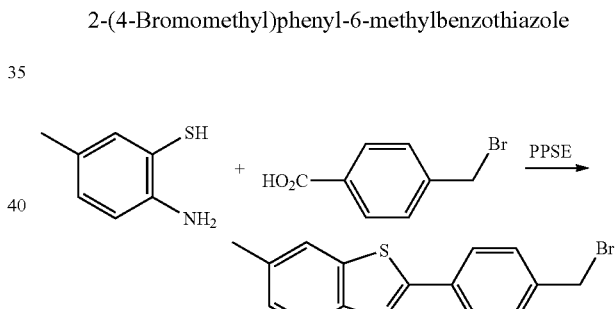

A mixture of 2-amino-5-methylbenzenethiol (0.518 g, 3.73 mmol), 4-bromomethylbenzoic acid (0.80 g, 3.73 mmol) and trimethylsilylpolyphosphate (11.2 ml) was heated under reflux in toluene (20 ml) under an atmosphere of argon for 15 h. The reaction mixture was cooled to room temperature and water (100 ml) was added followed by extraction with chloroform (3×60 ml). The combined organic extracts were washed with brine (60 ml), dried (Na$_2$SO$_4$) and the solvent removed under reduced pressure to give a pale brown solid, which was washed with Et$_2$O (60 ml) to give the title compound (0.816 g, 69%) as a colourless solid.

$^1$H NMR (250 MHz, CDCl$_3$) δ 2.49 (s, 3H), 4.52 (s, 2H), 7.29 (d, J=8.2 Hz, 1H), 7.49 (d, J=8.2 Hz, 2H), 7.67 (s, 1H), 7.94 (d, J=8.2 Hz, 1H), 8.03 (d, J=8.2 Hz, 2H); $^{13}$C NMR (62.5 MHz, CDCl$_3$) δ 21.62, 32.70, 121.42, 122.82, 127.85, 128.11, 129.71, 133.70, 135.22, 135.66, 140.39, 152.16, 166.17; LRMS (ESI) 319.9 (M$^+$($^{81}$Br)+H, 100%), 317.9 (M$^+$($^{79}$Br)+H, 93%).

2-(4-Bromomethyl)phenyl-6-methoxybenzothiazole

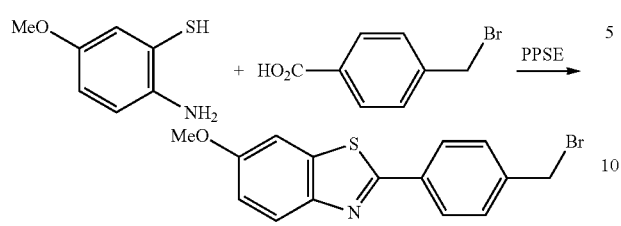

A mixture of 2-amino-5-methoxybenzenethiol (9.25 g, 59.7 mmol) and 4-bromomethylbenzoic acid (12.8 g, 59.7 mmol) in trimethylsilylpolyphosphate (70 ml) was thoroughly mixed then heated at 110° C. under an atmosphere of argon for 3 h. The reaction mixture was cooled to 60° C. and water (25 ml) was added followed by extraction with chloroform (5×80 ml). The combined organic extracts were washed with brine (150 ml), dried ($Na_2SO_4$) and the solvent removed under reduced pressure to give a brown solid which was purified by flash chromatography (4:1 DCM/hexane) to give the title compound (10.9 g, 55%) as a colourless solid.

$^1$H NMR (250 MHz, $CDCl_3$) δ 3.88 (s, 3H), 4.52 (s, 2H), 7.09 (dd, J=8.9, 2.4 Hz, 1H), 7.33 (d, J=2.4 Hz, 1H), 7.48 (d, J=8.2 Hz, 2H), 7.94 (d, J=8.9 Hz, 1H), 8.00 (d, J=8.2 Hz, 2H); $^{13}$C NMR (62.5 MHz, $CDCl_3$) δ 32.75, 55.85, 104.16, 115.85, 123.84, 127.63, 129.70, 133.78, 136.50, 140.13, 148.69, 157.94, 164.66.

The synthesis is described by Yoshino et al.

Diethyl 4-(6-methylbenzothiazol-2-yl)benzylphosphonate

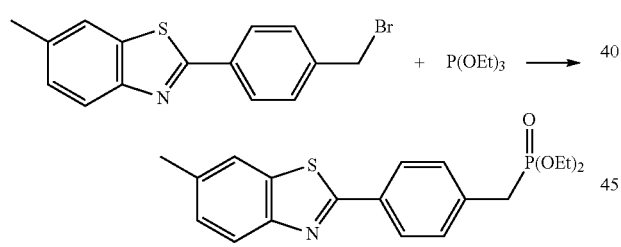

A mixture of 2-(4-bromomethyl)phenyl-6-methylbenzothiazole (0.30 g, 0.94 mmol) and triethyl phosphite (3.5 ml) was heated at 170° C. for 15 min under an atmosphere of argon. On cooling to room temperature, the excess triethyl phosphite was removed by distillation to give a brown oil which solidified on cooling. This solid was purified by flash chromatography (3:1 EtOAc/Hexane) to give the title compound (0.319 g, 90%) as a colourless solid.

$^1$H NMR (250 MHz, $CDCl_3$) δ 1.22 (t, J=7.0 Hz, 6H), 2.45 (s, 3H), 3.18 (d, $J_{HP}$=22 Hz, 2H), 4.01 (m, 4H), 7.25 (dd, J=8.2, 1.2 Hz, 1H), 7.39 (dd, J=8.2, 2.4 Hz, 2H), 7.64 (s, 1H), 7.90 (d, J=8.2 Hz, 1H), 7.99 (d, J=8.2 Hz, 2H); $^{13}$C NMR (62.5 MHz, $CDCl_3$) δ 16.41 (d, $J_{CP}$=5.8 Hz), 21.57, 33.86 (d, $J_{CP}$=138 Hz), 62.29 (d, $J_{CP}$=6.8 Hz), 121.37, 122.66, 127.54, 127.94, 130.40 (d, $J_{CP}$=6.8 Hz), 132.44 (d, $J_{CP}$=1.9 Hz), 134.74 (d, $J_{CP}$=9.8 Hz), 135.28 (d, $J_{CP}$=12.7 Hz), 135.38, 152.23, 166.60.

The synthesis is described by Yoshino et al.

Diethyl 4-(6-methoxybenzothiazol-2-yl)benzylphosphonate

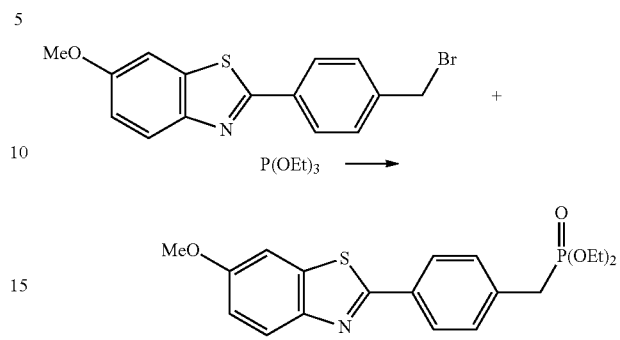

A mixture of 2-(4-bromomethyl)phenyl-6-methoxybenzothiazole (10.0 g, 29.95 mmol) and triethyl phosphite (20 ml) was heated at 130° C. for 4 h under an atmosphere of argon. On cooling to room temperature, the resulting solid was recrystallised from cyclohexane to give the title compound (11.25 g, 96%) as a colourless solid.

$^1$H NMR (250 MHz, $CDCl_3$) δ 1.23 (t, J=7.3 Hz, 6H), 3.18 (d, $J_{HP}$=22 Hz, 2H), 3.86 (s, 3H), 4.01 (m, 4H), 7.06 (dd, J=8.8, 2.4 Hz, 1H), 7.32 (d, J=2.4 Hz, 1H), 7.39 (dd, J=8.2, 2.1 Hz, 2H), 7.91 (d, J=8.8 Hz, 1H), 7.96 (d, J=8.2 Hz, 2H); $^{13}$C NMR (100.5 MHz, $CDCl_3$) δ 16.39 (d, $J_{CP}$=6.2 Hz), 33.83 (d, $J_{CP}$=138 Hz), 55.79, 62.26 (d, $J_{CP}$=7.0 Hz), 104.15, 115.65, 123.65, 127.35 (d, $J_{CP}$=3.1 Hz), 130.38 (d, $J_{CP}$=6.2 Hz), 132.43 (d, $J_{CP}$=3.1 Hz), 134.48 (d, $J_{CP}$=9.3 Hz), 136.37, 148.64, 157.78, 165.16 (d, $J_{CP}$=2.3 Hz).

2-Bromo-1-tert-butyldimethylsiloxyethane

To a stirred solution of bromoethanol (9.912 g, 79.32 mmol) in dry DCM (25 ml) was added in one portion tert-butyldimethylsilyl chloride (13.212 g, 85.03 mmol) and the reaction mixture stirred at room temperature. A solution of triethylamine (8.865 g, 12.3 ml, 87.61 mmol) in dry DCM (40 ml) was then added dropwise over 1 h and 20 min. The reaction mixture was stirred at room temperature for 3 d, then water (30 ml) was added. The organic phase was separated and the aqueous phase was extracted with DCM (2×20 ml). The combined organic extracts were washed with brine (30 ml), dried ($Na_2SO_4$), and the solvent removed under reduced pressure to give a pale yellow oil. Distillation under reduced pressure gave the title compound (10.54 g, 55%) as a colourless oil.

1H NMR (250 MHz, $CDCl_3$) δ 0.08 (s, 6H), 0.90 (s, 9H), 3.34 (t, J=6.41 Hz, 2H), 3.88 (t, J=6.4 Hz); $^{13}$C NMR (62.5 MHz, $CDCl_3$) δ -5.23, 18.35, 25.85, 33.31, 63.54.

Prepared according to method adapted from Kuwabe et al.

4-([2-tert-butyldimethylsiloxy]ethoxy)benzaldehyde

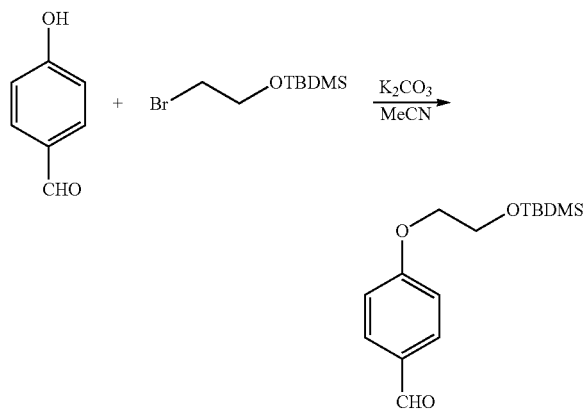

To a stirred suspension of 4-hydroxybenzaldehyde (0.500 g, 4.012 mmol) and anhydrous potassium carbonate (0.833 g, 6.019 mmol) in dry MeCN (15 ml) at room temperature was added 2-bromo-1-tert-butyldimethylsiloxyethane (83%, 1.730 g, 6.019 mmol), and the reaction mixture was heated under reflux for 20.5 h. Water (25 ml) was added and the reaction mixture was extracted with Et$_2$O (4×25 ml). The combined organic extracts were washed with brine (50 ml), dried (Na$_2$SO$_4$), and the solvent was removed under reduced pressure to give a pale yellow oil that was purified by flash chromatography (3:1 Hexane/Et$_2$O) to give the title compound (0.895 g, 79.5%) as a colourless oil.

$^1$H NMR (250 MHz, CDCl$_3$) δ 0.08 (s, 6H), 0.89 (s, 9H), 3.98 (t, J=4.3 Hz, 2H), 4.11 (t, J=4.3 Hz, 2H), 7.00 (d, J=8.5 Hz, 2H), 7.81 (d, J=8.5 Hz, 2H), 9.87 (s, 1H); $^{13}$C NMR (62.5 MHz, CDCl$_3$) δ-5.20, 18.42, 25.90, 61.81, 69.67, 114.88, 129.96, 131.99, 164.09, 190.78.

Prepared according to method adapted from Kuwabe et al.

6-Methoxy-2-(4-{(E)-2-[4-(2-tert-butyldimethylsiloxyethoxy)phenyl]ethenyl}phenyl)-1,3-benzothiazole Book No.: SKT08-101

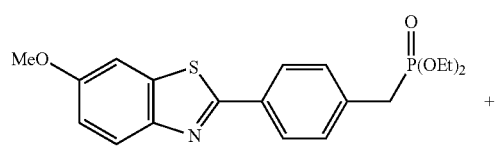

+

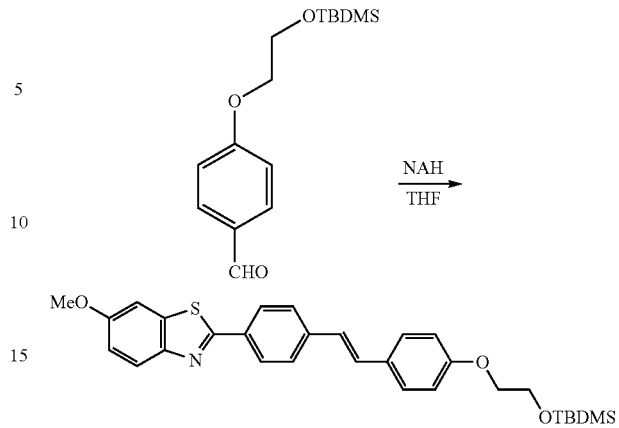

To a flame-dried RB flask under argon was added sodium hydride (68 mg, 60% dispersion in mineral oil, 1.71 mmol). This was washed with dry hexane (3×8 ml) and the flask was then place under high vacuum for 5 min. After placing the flask under argon, dry THF (35 ml) was then added and the suspension was stirred at room temperature for 5 min. Diethyl [4-(6-methoxy-1,3-benzothiazol-2-yl)benzyl]phosphonate (0.558 g, 1.43 mmol) was then added as a solid in several portions over 1 min and the reaction mixture was stirred at room temperature for 30 min before 4-([2-tert-butyldimethylsiloxy]ethoxy)benzaldehyde (0.400 g, 1.43 mmol) was added dropwise over 1 min. The reaction mixture was then heated under reflux for 16.5 h. On cooling to room temperature water (1 ml) was added and the solvent was then removed under reduced pressure to give a yellow solid which was recrystallised from DMF/water (15:1) to give the title compound (0.549 g, 74%) as a yellow solid.

$^1$H NMR (400 MHz, DMSO-d$_6$) δ 0.06 (s, 6H), 0.86 (s, 9H), 3.85 (s, 3H), 3.91 (t, J=4.7 Hz, 2H), 4.06 (t, J=4.7 Hz, 2H), 6.95 (d, J=8.2 Hz, 2H), 7.12 (d, J=9.0 Hz, 1H), 7.15 (d, J=16.4 Hz, 1H), 7.32 (d, J=16.4 Hz, 1H), 7.56 (d, J=8.2 Hz, 2H), 7.69 (m, 1H), 7.71 (d, J=8.2 Hz, 2H), 7.91 (d, J=9.0 Hz, 1H), 8.00 (d, J=8.2 Hz, 2H).

Methanesulphonic acid 2-(4-{(E)-2-[4-(6-methoxy-1,3-benzothiazol-2-yl)phenyl]vinyl}phenoxy)ethyl ester Book No.: SKT08-179

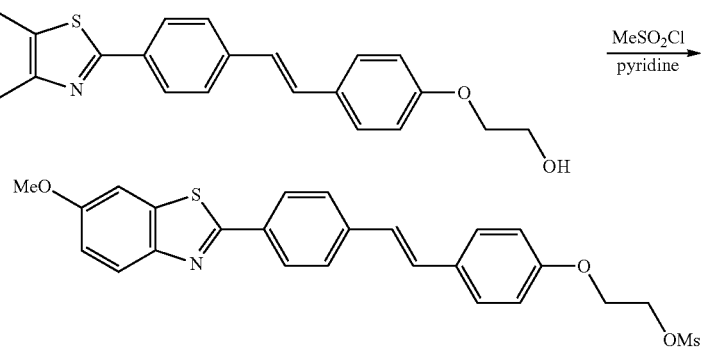

To a stirred solution of 2-(4-{(E)-2-[4-(6-methoxy-1,3-benzothiazol-2-yl)phenyl]ethenyl}phenoxy)ethanol (55.2 mg, 0.137 mmol) in dry pyridine (10 ml) at room temperature was added methanesulphonyl chloride (22.4 μl, 0.287 mmol). After 15 h at room temperature, the reaction mixture was cooled to 0-5° C. and ice water (25 ml) was added resulting in a yellow precipitate which was collected by vacuum filtration and washed with water (4×30 ml) and then dried in the oven at 85° C. for 1.5 h. The yellow solid was then washed with Et₂O (40 ml) and dried at 85° C. for 2 h to give the title compound (53.5 mg, 81%) as a yellow solid.

$^{1}$H NMR (250 MHz, DMSO-d$_{6}$) δ 3.25 (s, 3H), 3.86 (s, 3H), 4.30 (m, 2H), 4.55 (m, 2H), 7.02 (d, J=8.5 Hz, 2H), 7.15 (m, 1H), 7.21 (d, J=16.5 Hz, 1H), 7.37 (d, J=16.5 Hz, 1H), 7.62 (d, J=8.2 Hz, 2H), 7.72 (m, 1H), 7.74 (d, J=8.5 Hz, 2H), 7.94 (d, J=8.8 Hz, 1H), 8.03 (d, J=8.2 Hz, 2H).

Benzothiazole Compounds
Non-Fluorinated Methoxy-Alkenes

2-{4-[2-(2-Nitrophenyl)-vinyl]-phenyl}-6-methoxy-benzothiazole

Book No.: SKT01-71

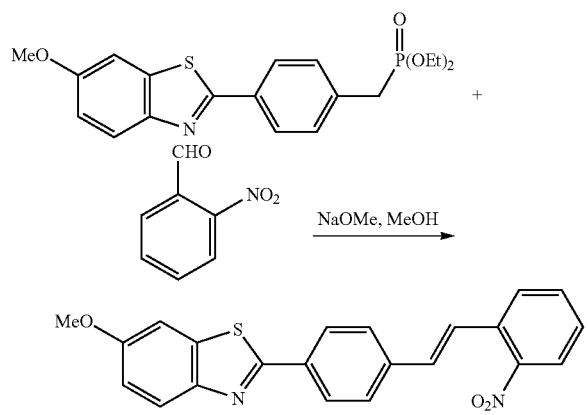

Prepared as described in the Alkene Formation section.

$^{1}$H NMR (250 MHz, CDCl$_{3}$) δ 3.89 (s, 3H), 7.07-7.13 (m, 2H), 7.35 (s, 1H), 7.39-7.45 (m, 1H), 7.59-7.64 (m, 4H), 7.72-7.79 (m, 1H), 7.93-8.00 (m, 2H), 8.04 (d, J=7.9 Hz, 2H); $^{13}$C NMR (62.5 MHz, CDCl$_{3}$) δ 55.85, 104.14, 115.83, 123.81, 124.95, 127.65, 128.28, 128.33, 132.80, 132.89, 133.25, 133.72, 136.51, 138.61, 148.05, 148.79, 157.89, 164.88 (2 missing).

2-{4-[2-(3-Nitrophenyl)-vinyl]-phenyl}-6-methoxy-benzothiazole

Book No.: SKT01-73

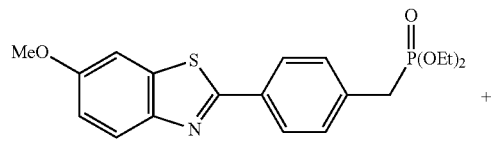

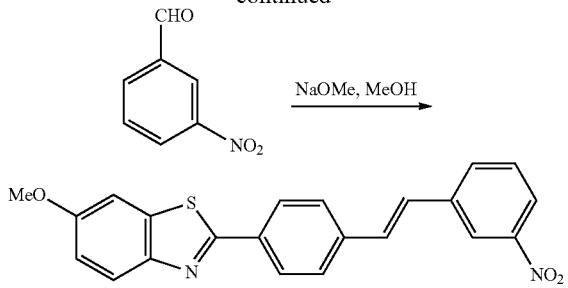

Prepared as described in the Alkene Formation section using diethyl 4-(6-methoxyl benzothiazol-2-yl)benzylphosphonate (0.10 g, 0.25 mmol) and 3-nitrobenzaldehyde (0.39 g, 0.25 mmol) in dry MeOH (10 ml) and 0.5 M sodium methoxide (1.02 ml, 0.51 mmol) to give the title compound as (0.079 g, 80%) yellow, feathery crystals after work-up and recrystallisation from CHCl$_{3}$.

IR 3120, 1603, 1560, 1521, 1489, 1464, 1403, 1358, 1287, 1264, 1225, 1062, 1026, 967, 815 cm$^{-1}$; $^{1}$H NMR (250 MHz, CDCl$_{3}$) δ 3.89 (s, 3H), 7.09 (dd, J=8.8, 2.1 Hz, 1H), 7.20 (dist d, J=18 Hz, 1H), 2.27 (dist d, J=18 Hz, 1H), 7.35 (d, J=2.1 Hz, 1H), 7.50-7.57 (m, 1H), 7.63 (d, J=8.5 Hz, 2H), 7.81 (d, J=7.6 Hz, 1H), 7.95 (d, J=8.8 Hz, 1H), 8.06 (d, J=8.5 Hz, 2H), 8.11 (d, J=8.5 Hz, 1H), 8.39 (s, 1H).

2-{4-[2-(4-Nitrophenyl)-vinyl]-phenyl}-6-methoxy-benzothiazole

Book No.: SKT02-67

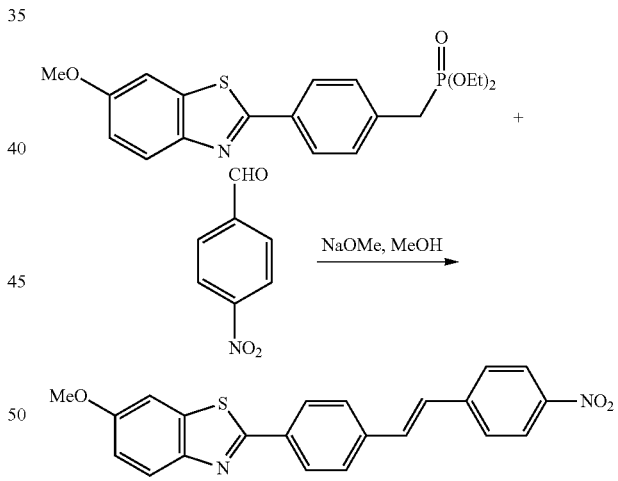

Prepared as described in the Alkene Formation section using diethyl 4-(6-methoxybenzothiazol-2-yl)benzylphosphonate (3.0 g, 7.66 mmol) in dry MeOH (60 ml) and 0.5 M sodium methoxide (30.6 ml, 15.3 mmol) to give the title compound (2.189 g, 74%) as an orange solid after work-up.

$^{1}$H NMR (250 MHz, CDCl$_{3}$) δ 3.89 (s, 3H), 7.10 (dd, J=9.2, 2.1 Hz, 1H), 7.21 (dist d, J=17.7 Hz, 1H), 7.30 (dist d, J=17.7 Hz, 1H), 7.35 (d, J=2.1 Hz, 1H), 7.64 (d, J=8.2 Hz, 2H), 7.65 (d, J=8.5 Hz, 2H), 7.95 (d, J=9.1 Hz, 1H), 8.06 (d, J=8.2 Hz, 2H), 8.23 (d, J=8.5 Hz, 2H); $^{13}$C NMR (62.5 MHz, CDCl$_{3}$/DMSO-d$_{6}$) δ 55.79, 104.09, 115.83, 123.66, 124.12, 127.09, 127.55, 127.71, 132.21, 133.73, 136.40, 138.24, 143.45, 146.84, 148.61, 157.86, 164.58 (1 missing)

2-{4-[2-(2-Aminophenyl)-vinyl]-phenyl}-6-methoxybenzothiazole

Book No.: SKT01-109

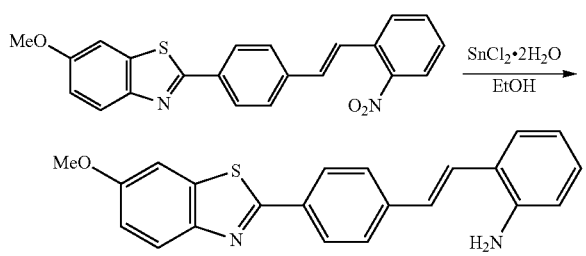

Prepared as described in the Nitro Reduction section using 2-{4-[2-(2-nitrophenyl)-vinyl]-phenyl}-6-methoxylbenzothiazole (0.03 g, 0.077 mmol) and tin (II) chloride dihydrate (0.139 g, 0.618 mmol) in EtOH (3 ml) to give the title compound as a colourless solid (0.019 g, 68%) after work-up and flash chromatography (DCM followed by 6:3:1 DCM/Hexane/EtOAc).

$^{13}$C NMR (100 MHz, DMSO-$d_6$) δ 56.23, 97.72, 105.34, 109.42, 116.51, 120.44, 120.96, 122.85, 123.39, 123.89, 127.52, 128.53, 132.37, 133.57, 136.18, 136.30, 136.53, 148.56, 158.03, 164.61.

2-{4-[2-(3-Aminophenyl)-vinyl]-phenyl}-6-methoxybenzothiazole

Book No.: SKT01-107

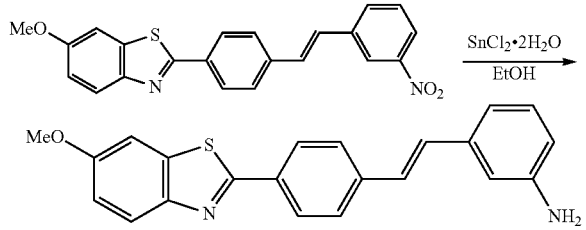

Prepared as described in the Nitro Reduction section using 2-{4-[2-(3-nitrophenyl)-vinyl]-phenyl}-6-methoxylbenzothiazole (0.046 g, 0.118 mmol) and tin (II) chloride dihydrate (0.214 g, 0.947 mmol) in EtOH (3 ml) to give a colourless solid (0.023 g, 54%) after work-up and flash chromatography (3:1 DCM/EtOAc).

$^1$H NMR (250 MHz, CDCl$_3$) δ 3.71 (br s, 2H), 3.91 (s, 3H), 6.71 (dd, J=8.8, 2.1 Hz, 1H), 6.85 (s, 1H), 6.92 (d, J=8.2 Hz, 1H), 7.06-7.20 (m, 4H), 7.34 (d, J=2.1 Hz, 1H), 7.58 (d, J=8.2 Hz, 2H), 7.94 (d, J=8.8 Hz, 1H), 8.01 (d, J=8.5 Hz, 2H); $^{13}$C NMR (62.5 MHz, CDCl$_3$) δ 55.84, 104.16, 113.02, 115.10, 115.71, 117.52, 123.67, 126.98, 127.58, 129.71, 130.36, 132.68, 136.42, 138.05, 139.68, 146.73, 148.79, 157.77, 165.24 (1 missing).

2-{4-[2-(4-Aminophenyl)-vinyl]-phenyl}-6-methoxybenzothiazole

Book No.: SKT01-189

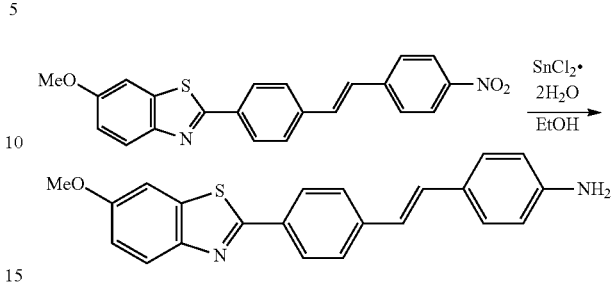

Prepared as described in the Nitro Reduction section using 2-{4-[2-(4-nitrophenyl)-vinyl]-phenyl}-6-methoxybenzothiazole (0.10 g, 0.28 mmol) and tin (II) chloride dihydrate (0.5 g, 2.23 mmol) in EtOH (7 ml) to give the title compound (0.04 g, 43%) as a yellow solid after work-up and flash chromatography (2:1 Hexane/EtOAc).

$^1$H NMR (250 MHz, CDCl$_3$) δ 3.79 (br s, 2H), 3.89 (s, 3H), 6.68 (d, J=8.2 Hz, 2H), 6.94 (dist d, J=16.2 Hz, 1H), 7.07 (d, J=8.5 Hz, 1H), 7.12 (dist d, J=16.2 Hz, 1H), 7.34 (s, 1H), 7.36 (d, J=8.5 Hz, 2H), 7.55 (d, J=8.2 Hz, 2H), 7.93 (d, J=8.8 Hz, 1H), 7.99 (d, J=8.2 Hz, 2H); $^{13}$C NMR (62.5 MHz, CDCl$_3$/DMSO-$d_6$) δ 55.20, 103.84, 113.98, 115.24, 121.72, 122.77, 124.70, 125.80, 126.75, 127.51, 130.32, 130.78, 135.58, 140.04, 147.89, 148.06, 157.05, 164.13.

2-{4-[2-(4-Dimethylaminophenyl)-vinyl]-phenyl}-6-methoxybenzothiazole

Book No.: SKT03-57

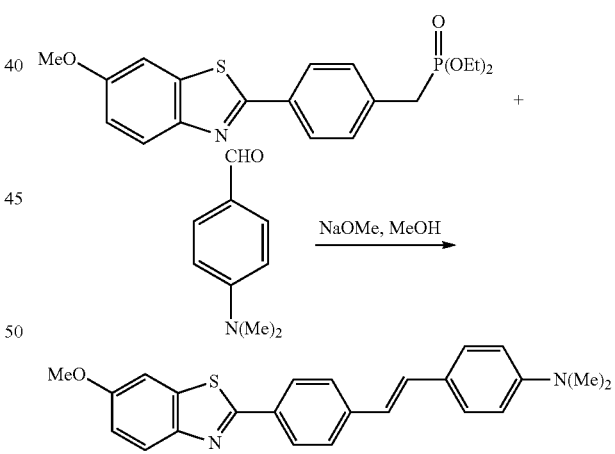

Prepared as described in the Alkene Formation section using diethyl 4-(6-methoxylbenzothiazol-2-yl)benzylphosphonate (0.50 g, 1.28 mmol) and 4-dimethylaminobenzaldehyde (0.21 g, 1.41 mmol) in dry MeOH (10 ml) and 0.5 M sodium methoxide (3.48 ml, 1.74 mmol) to give the title compound (0.187 g, 38%) as a yellow solid after work-up.

$^1$H NMR (250 MHz, CDCl$_3$) δ 2.99 (s, 6H), 3.89 (s, 3H), 6.72 (d, J=8.5 Hz, 2H), 6.93 (d, J=16.2 Hz, 1H), 7.08 (dd, J=8.8, 2.1 Hz, 1H), 7.15 (d, J=16.2 Hz, 1H), 7.35 (d, J=2.1 Hz, 1H), 7.44 (d, J=8.5 Hz, 2H), 7.56 (d, J=8.2 Hz, 2H), 7.93 (d, J=8.8 Hz, 1H), 7.99 (d, J=8.2 Hz, 2H).

2-(4-{(E)-2-[4-(6-methoxy-1,3-benzothiazol-2-yl)phenyl]ethenyl}phenoxy)ethanol Book No.: SKT08-143

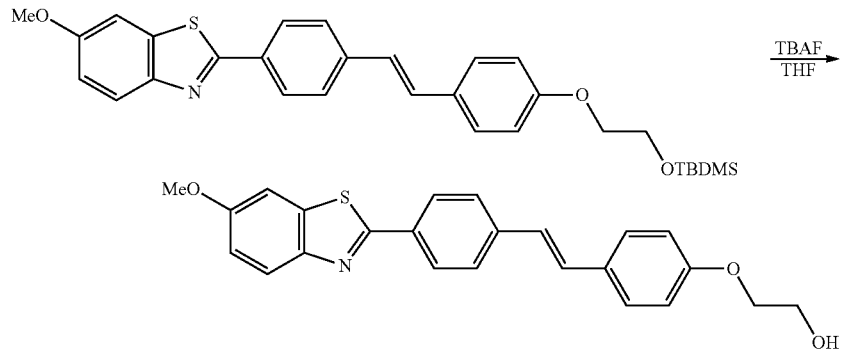

To a stirred solution of 6-methoxy-2-(4-{(E)-2-[4-(2-tert-butyldimethylsiloxyethoxy)phenyl]ethenyl}-1,3-benzothiazole (0.200 g, 0.386 mmol) in dry DMF (5 ml) and dry THF (15 ml) at room temperature was added dropwise TBAF (1 M in THF, 0.85 ml, 0.85 mmol) over 2 min. After 2 h at room temperature, saturated $NH_4Cl$ (30 ml) was added to give a yellow precipitate which was collected by vacuum filtration. The yellow solid was washed with water (2×20 ml) and then left to dry in the air for 2 h. Further drying at 65° C. over 17 h gave the title compound (0.136 g, 87%) as a yellow solid.

IR 3500-3100 (br), 3017, 2941, 2864, 1601, 1558, 1513, 1485, 1462, 1435, 1299, 1252, 1225, 1175, 1083, 1052, 1022, 967, 830, 816 cm$^{-1}$; $^1$H NMR (250 MHz, DMSO-d$_6$) δ 3.69-3.80 (m, 2H), 3.86 (s, 3H), 4.00-4.08 (m, 2H), 4.88 (m, 1H), 6.97 (d, J=8.2 Hz, 2H), 7.13 (d, J=8.8 Hz, 1H), 7.18 9d, J=15.6 Hz, 1H), 7.35 (d, J=15.6 Hz, 1H), 7.59 (d, J=8.2 Hz, 2H), 7.70-7.78 (m, 3H), 7.94 (d, J=8.8 Hz, 1H), 8.02 (d, J=8.2 Hz, 2H).

Fluorinated Methoxy-Alkenes

2-{4-[2-(2-Trifluoromethyl)phenyl)-vinyl]-phenyl}-6-methoxybenzothiazole

Book No.: SK2033-44

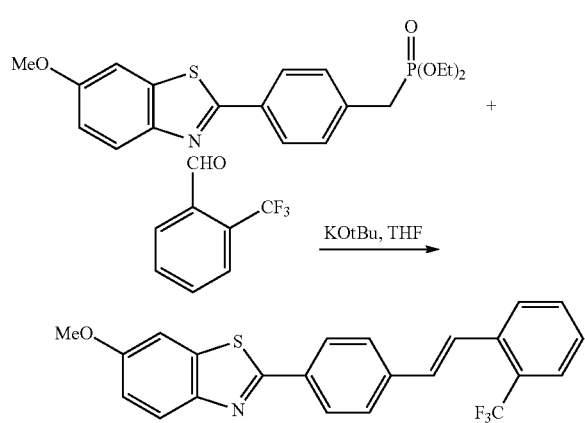

Prepared as described in the Alkene Formation section using diethyl 4-(6-methoxybenzothiazol-2-yl)benzylphosphonate (100 mg, 0.255 mmol) in dry THF (10 ml), 2-trifluorobenzaldehyde (44 mg, 0.255 mmol) in dry THF (5 ml) and potassium t-butoxide (32 mg, 0.280 mmol) in dry THF (5 ml) to give the title compound (77 mg, 73%) as pale yellow plates after work-up, flash chromatography (3:1 DCM/Hexane) and recrystallisation from acetone.

$^1$H NMR (250 MHz, CDCl$_3$) δ 3.89 (s, 3H), 7.07-7.09 (m, 1H), 7.11-7.14 (m, 1H), 7.35 (d, J=2.1 Hz, 1H), 7.39 (d, J=7.6 Hz, 1H), 7.51-7.55 (m, 1H), 7.55-7.65 (m, 3H), 7.68 (d, J=7.9 Hz, 1H), 7.79 (d, J=7.9 Hz, 1H), 7.95 (d, J=8.8 Hz, 1H), 8.04 (d, J=8.2 Hz, 2H); LRMS (ESI+) m/z 412 (M$^+$+H, 100%).

2-{4-[2-(4-Chloro-3-nitrophenyl)-vinyl]-phenyl}-6-methoxybenzothiazole

Book No.: SKT03-91

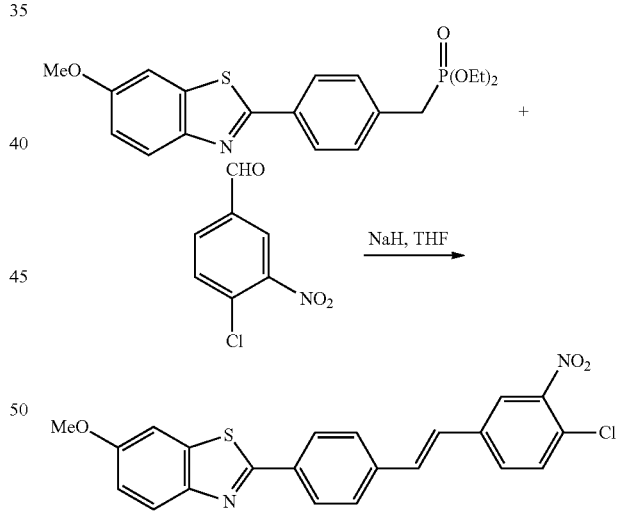

Prepared as described in the Alkene Formation section using sodium hydride (60% dispersion in mineral oil, 0.077 g, 1.92 mmol), diethyl 4-(6-methoxybenzothiazol-2-yl)benzylphosphonate (0.5 g, 1.28 mmol) and 4-chloro-3-nitrobenzaldehyde (0.26 g, 1.41 mmol) in dry THF (20 ml) to give the title compound (0.251 g, 46%) as pale orange needles after work-up and recrystallisation from 1,2-dichloroethane.

$^1$H NMR (250 MHz, DMSO-d$_6$) δ 3.85 (s, 3H), 7.13 (d, J=8.5 Hz, 1H), 7.45 (d, J=17.7 Hz, 1H), 7.60 (d, J=17.7 Hz, 1H), 7.71-7.81 (m, 4H), 7.94 (d, J=8.2 Hz, 2H), 8.05 (d, J=7.0 Hz, 2H), 8.34 (s, 1H); $^{13}$C NMR (100.5 MHz, DMSO-d$_6$) δ 56.23, 105.35, 116.42, 123.38, 123.80, 123.87, 127.20, 127.70, 128.08, 131.55, 131.81, 132.29, 133.21, 136.55, 138.16, 139.10, 148.53, 148.60, 158.09, 164.51.

2-{4-[2-(3-Trifluoromethyl)phenyl)-vinyl]-phenyl}-6-methoxybenzothiazole

Book No.: SK2033-42

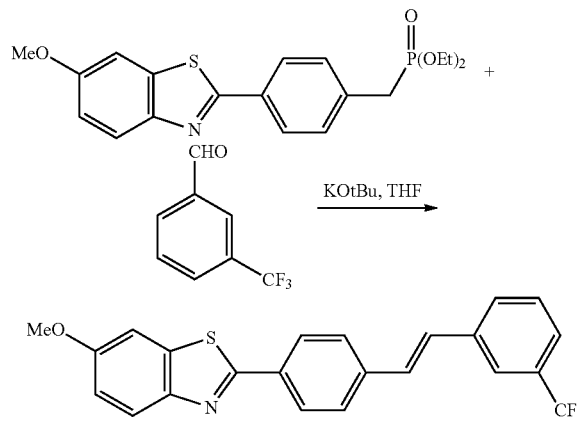

Prepared as described in the Alkene Formation section using diethyl 4-(6-methoxybenzothiazol-2-yl)benzylphosphonate (100 mg, 0.255 mmol) in dry THF (10 ml), potassium t-butoxide (32 mg, 0.280 mmol) in dry THF (5 ml) and 3-trifluorobenzaldehyde (44 mg, 0.255 mmol) in dry THF (5 ml) to give the title compound (78 mg, 74%) as a colourless solid after work-up and flash chromatography (4:1 DCM/Hexane).

$^1$H NMR (250 MHz, acetone-$d_6$) δ 3.87 (s, 3H), 7.08 (d, J=8.5 Hz, 1H), 7.36 (s, 2H), 7.47-7.59 (m, 3H), 7.75 (d, J=8.2 Hz, 2H), 7.80-7.90 (m, 3H), 8.06 (d, J=8.2 Hz, 2H); $^{13}$C NMR (62.5 MHz, CDCl$_3$) δ 55.86, 104.19, 115.83, 123.25, 123.73, 124.40, 127.24, 127.68, 128.56, 129.25, 129.59, 129.76, 131.23 (q, J$_{CF}$=33.2 Hz), 133.22, 136.40, 137.79, 138.90, 148.65, 157.89, 165.02 (1 missing).

2-{4-[2-(4-Trifluoromethyl)phenyl)-vinyl]-phenyl}-6-methoxybenzothiazole

Book No.: SK2033-40

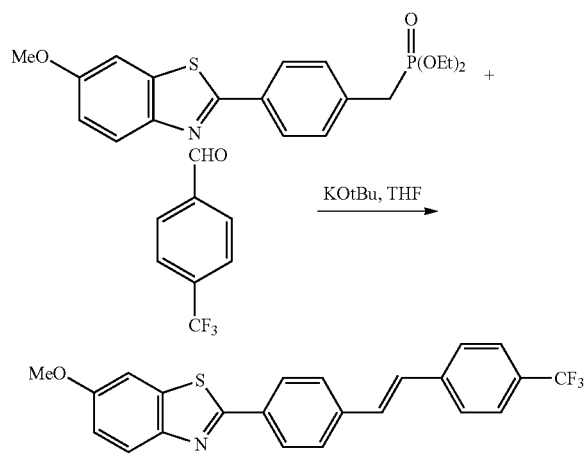

Prepared as described in the Alkene Formation section using diethyl 4-(6-methoxy benzothiazol-2-yl)benzylphosphonate (100 mg, 0.255 mmol) in dry THF (10 ml), potassium t-butoxide (32 mg, 0.280 mmol) in dry THF (5 ml) and 4-trifluorobenzaldehyde (44 mg, 0.255 mmol) in dry THF (5 ml) to give the title compound (51 mg, 49%) as a pale yellow solid after work-up, flash chromatography (4:1 DCM/Hexane) and recrystallisation from acetone.

IR 3022, 2942, 2839, 1606, 1556, 1487, 1462, 1437, 1418, 1326, 1268, 1215, 1164, 1120, 1068, 1028, 1014, 966, 844, 829, 812 cm$^{-1}$; $^1$H NMR (400 MHz, DMSO-$d_6$) δ 3.86 (s, 3H), 7.09 (d, J=8.2 Hz, 1H), 7.39 (s, 2H), 7.56 (s, 1H), 7.65 (d, J=8.2 Hz, 2H), 7.74 (d, J=7.9 Hz, 2H), 7.78 (d, J=8.6 Hz, 2H), 7.88 (d, J=8.6 Hz, 1H), 8.02 (d, J=7.9 Hz, 2H).

2-{4-[2-(4-(2,2,2-Trifluoroethoxy)phenyl)-vinyl]-phenyl}-6-methoxybenzothiazole Book No.: SKT02-17

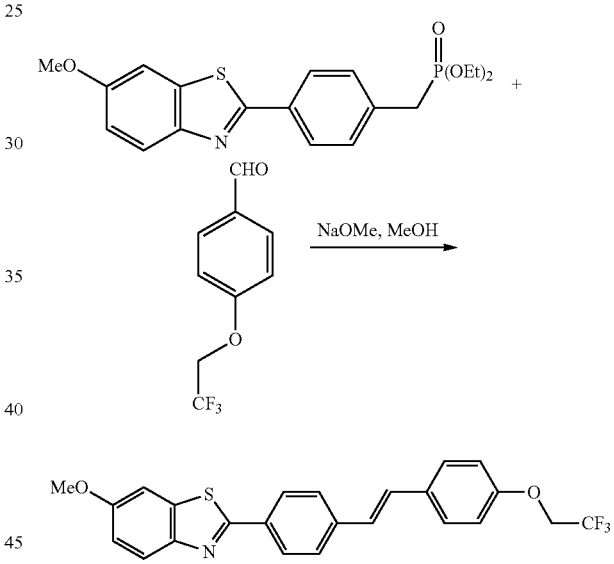

Prepared as described in the Alkene Formation section using diethyl 4-(6-methoxyl benzothiazol-2-yl)benzylphosphonate (0.15 g, 0.38 mmol) in dry MeOH (5 ml), a solution of 0.5 M sodium methoxide (1.54 ml, 0.77 mmol and 4-(2,2,2-trifluoroethoxy)benzaldehyde (0.078 g, 0.38 mmol) to give the title compound (0.132 g, 78%) as small yellow needles after work-up and recrystallisation from 1,2-dichloroethane.

$^1$H NMR (400 MHz, DMSO-$d_6$) δ 3.85 (s, 3H), 4.80 (q, J=9.0H, 2H), 7.09 (d, J=8.6 Hz, 2H), 7.13 (dd, J=9.0, 2.3 Hz, 1H), 7.24 (d, J=16.5 Hz, 1H), 7.37 (d, J=16.5 Hz, 1H), 7.63 (d, J=9.0 Hz, 2H), 7.71 (d, J=2.3 Hz, 1H), 7.74 (d, J=8.2 Hz, 2H), 7.93 (d, J=9.0 Hz, 1H), 8.02 (d, J=8.2 Hz, 2H); $^{13}$C NMR (100 MHz, DMSO-$d_6$) δ 56.28, 65.26 (q, J$_{CF}$=34.3 Hz), 105.46, 115.75, 116.38, 123.79, 126.63, 127.47, 127.67, 128.64, 129.97, 131.54, 132.26, 136.46, 140.30, 148.64, 157.37, 158.04, 164.78 (1 missing).

2-{4-[2-(4-(4,4,4-trifluorobutoxy)phenyl)-vinyl]-phenyl}-6-methoxybenzothiazole Book No.: SKT02-11

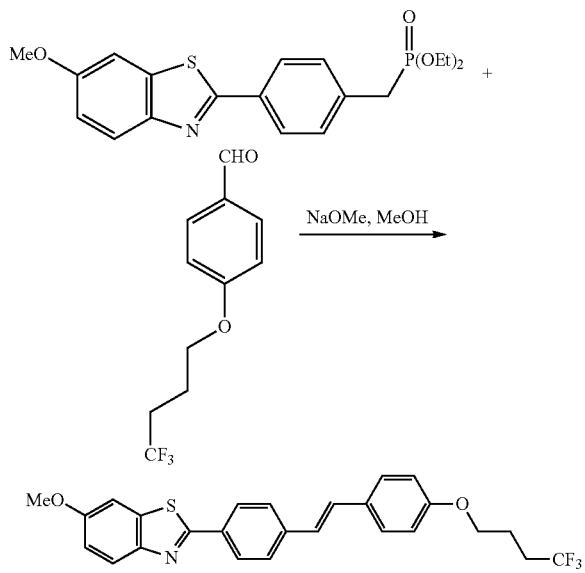

Prepared as described in the Alkene Formation section using diethyl 4-(6-methoxyl benzothiazol-2-yl)benzylphosphonate (0.15 g, 0.38 mmol) in dry MeOH (5 ml), a solution of 0.5 M sodium methoxide (0.92 ml, 0.46 mmol and 4-(4,4,4-trifluorobutoxy)benzaldehyde (0.089 g, 0.38 mmol) to give the title compound (0.108 g, 60%) as small yellow needles after work-up and recrystallisation from 1,2-dichloroethane.

IR 3019, 2942, 2878, 2837, 1603, 1558, 1510, 1462, 1437, 1386, 1247, 1227, 1176, 1151, 1061, 1025, 966, 832 cm$^{-1}$; $^1$H NMR (400 MHz, DMSO-d$_6$) δ 1.90-2.00 (m, 2H), 2.36-2.51 (m, 2H), 3.86 (s, 3H), 4.08 (t, J=6.2 Hz, 2H), 6.98 (d, J=8.6 Hz, 2H), 7.11-7.17 (m, 1H), 7.17 (d, J=16.8 Hz, 1H), 7.33 (d, J=16.8 Hz, 1H), 7.58 (d, J=8.6 Hz, 2H), 7.69 (m, 1H), 7.72 (d, J=8.2 Hz, 2H), 7.93 (d, J=8.6 Hz, 2H), 8.10 (d, J=8.2 Hz, 2H).

2-{4-[2-(4-(N-Trifluoroacetyl)aminophenyl)-vinyl]-phenyl}-6-methoxybenzothiazole Book No.: SKT02-117

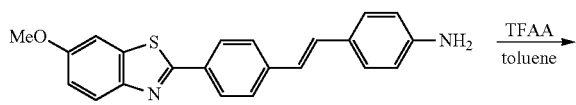

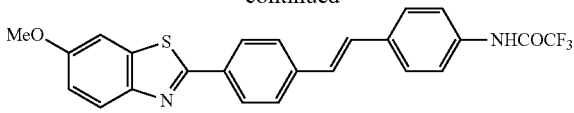

To a stirred suspension of 2-{4-[2-(4-aminophenyl)-vinyl]-phenyl}-6-methoxybenzothiazole (0.20 g, 0.558 mmol) in toluene (10 ml) was added TFAA (0.26 g, 1.23 mmol) and the reaction mixture heated at 80° C. for 18 h. The reaction mixture was cooled to room temperature and DCM (15 ml) and Et$_2$O (40 ml) were added and the precipitate was collected by filtration, washed with Et$_2$O and dried under vacuum at room temperature for 6 h to give the title compound (0.183 g, 72%) as a pale orange solid.

$^1$H NMR (250 MHz, DMSO-d$_6$) δ 3.86 (s, 3H), 7.15 (dd, J=8.8, 2.4 Hz, 1H), 7.32 (dist d, J=17.4 Hz, 1H), (7.41 (dist d, J=17.4 Hz, 1H), 7.67-7.76 (m, 5H), 7.77 (d, J=8.2 Hz, 2H), 7.95 (d, J=8.8 Hz, 1H), 8.05 (d, J=8.2 Hz, 2H), 11.34 (s, 1H); $^{13}$C NMR (100 MHz, DMSO-d$_6$) δ 56.28, 105.45, 116.25 (q, J$_{CF}$=289 Hz), 116.40, 121.69, 123.83, 127.68, 127.69, 127.76, 127.97, 129.84, 132.53, 134.67, 136.49, 140.03, 148.64, 154.88 (q, J$_{CF}$=36.5 Hz), 158.06, 164.71 (1 missing).

2-{4-[2-(4-(N-2,2,2-Trifluoroethyl)aminophenyl)-vinyl]-phenyl}-6-methoxybenzothiazole Book No.: SKT02-153

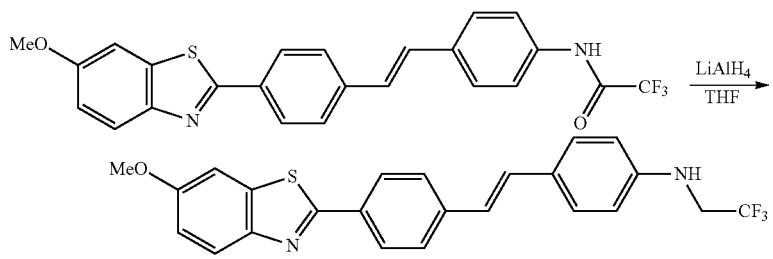

To a stirred suspension of 2-{4-[2-(4-(N-trifluoroacetyl)aminophenyl)-vinyl]-phenyl}-6-methoxybenzothiazole (0.10 g, 0.22 mmol) in dry THF (20 ml) at room temperature was added portionwise lithium aluminium hydride (0.033 g, 0.88 mmol). The reaction mixture was stirred at room temperature for 0.5 h, then heated under reflux for 18 h. The reaction mixture was cooled to 0-5° C. and diluted with Et$_2$O (5 ml). Water (1 ml) was added slowly followed by addition of 15% NaOH (0.2 ml) and the reaction mixture was left to rise to room temperature. To the reaction mixture was added MgSO$_4$ (30 mg) and after 15 mins the salts were collected by filtration. The filtrate was concentrated to give a solid which was stirred with a catalytic amount of iodine in DCM (5 ml). The reaction mixture was washed with water (10 ml), 5% sodium sulphite solution (10 ml) and brine (10 ml) and the solvent removed under reduced pressure to give a solid which was purified by flash chromatography (DCM) to give the title compound (0.060 g, 62%) as an orange solid.

$^1$H NMR (250 MHz, CDCl$_3$) δ 3.76-3.88 (m, 2H), 3.89 (s, 3H), 4.04 (t, J=2.1 Hz, 1H), 6.69 (d, J=8.5 Hz, 2H), 6.95 (dist d, J=17.1 Hz, 1H), 7.08 (d, J=8.8 Hz, 1H), 7.12 (dist d, J=17.1 Hz, 1H), 7.35 (d, J=2.7 Hz, 1H), 7.42 (d, J=8.5 Hz, 2H), 7.56 (d, J=8.2 Hz, 2H), 7.93 (d, J=8.5 Hz, 2H), 8.00 (d, J=8.2 Hz, 2H); $^{13}$C NMR (100.5 MHz, DMSO-d$_6$) δ 44.49 (q, J$_{CF}$=32.7 Hz), 56.26, 105.45, 113.09, 116.31, 123.38, 123.72, 126.24

(q, $J_{CF}$=281 Hz), 126.49, 127.00, 127.64, 128.40, 131.07, 131.59, 136.39, 140.97, 148.25, 148.66, 157.99, 164.91.

2-{4-[2-(4-(N-3,3,3-Trifluoropropyl)aminophenyl)-vinyl]-phenyl}-6-methoxybenzothiazole Book No.: SKT02-119

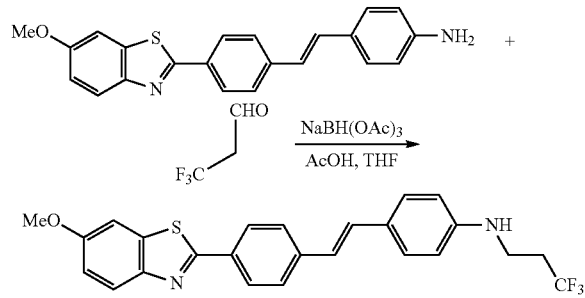

To a stirred solution of 2-{4-[2-(4-aminophenyl)-vinyl]-phenyl}-6-methoxybenzothiazole (0.30 g, 0.838 mmol) in THF (13 ml) at room temperature was added 3,3,3-trifluoropropanal (0.094 g, 0.838 mmol) in one portion. Acetic acid (48 µl, 0.838 mmol) was then added and the reaction mixture stirred for 5 mins before sodium triacetoxyborohydride (0.25 g, 1.17 mmol) was added portionwise over 15 min. Stirring was then continued at room temperature. After 48 h, a further addition of 3,3,3-trifluoropropanal (0.094 g, 0.838 mmol) was made and stirring was continued for 24 h. Sodium bicarbonate (15 ml) was then added and the reaction mixture extracted with EtOAc (4×30 ml), and the combined organic extracts were washed with brine (40 ml) and dried (Na$_2$SO$_4$). The solvent was removed under reduced pressure and the residue was purified by flash chromatography (10:1 DCM/Hexane) to give the title compound (0.149 g, 39%) as an orange solid.

$^1$H NMR (400 MHz, DMSO-d$_6$) δ 2.47-2.59 (m, 2H), 3.33 (q, J=6.7 Hz, 2H), 3.85 (s, 3H), 5.99 (t, J=5.8 Hz, 1H), 6.62 (d, J=8.6 Hz, 2H), 6.99 (d, J=16.4 Hz, 1H), 7.12 (dd, J=8.6, 2.3 Hz, 1H), 7.23 (d, J=16.4 Hz, 1H), 7.41 (d, J=8.2 Hz, 2H), 7.65 (d, J=8.2 Hz, 2H), 7.66 (d, J=2.3 Hz, 1H), 7.91 (d, J=8.6 Hz, 1H), 7.97 (d, J=8.6 Hz, 2H); $^{13}$C NMR (100.5 MHz, DMSO-d$_6$) δ 32.97 (q, $J_{CF}$=26.4 Hz), 36.49 (q, $J_{CF}$=3.1 Hz), 105.43, 112.70, 116.29, 122.78, 123.70, 125.59, 126.91, 127.44 (q, $J_{CF}$=277 Hz), 127.63, 128.59, 131.28, 131.46, 136.38, 141.08, 148.67, 148.80, 157.97, 164.92.

2-{4-[2-(4-(N-4,4,4-Trifluorobutyl)aminophenyl)-vinyl]-phenyl}-6-methoxybenzothiazole Book No.: SKT02-81

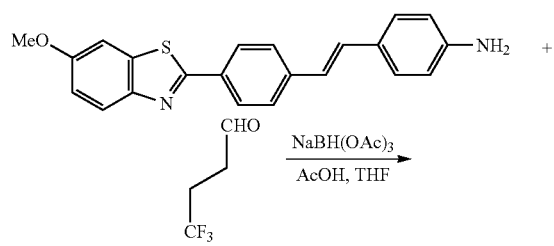

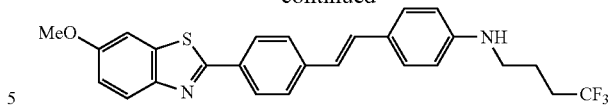

To a stirred solution of 2-{4-[2-(4-aminophenyl)-vinyl]-phenyl}-6-methoxybenzothiazole (0.10 g, 0.28 mmol) in 1,2-dichlorethane (5 ml) at room temperature was added 4,4,4-trifluorobutanal (0.035 g, 0.28 mmol) in one portion. Acetic acid (48 µl, 0.28 mmol) was then added and the reaction mixture stirred for 10 mins before sodium triacetoxyborohydride (0.083 g, 0.39 mmol) was added portionwise over 15 min. Stirring was then continued at room temperature. After 24 h, a further addition of 4,4,4-trifluorobutanal (0.035 g, 0.28 mmol) was made and stirring was continued for 72 h. Sodium bicarbonate (15 ml) was then added and the reaction mixture extracted with EtOAc (3×30 ml) and the combined organic extracts were washed with brine (30 ml) and dried (Na$_2$SO$_4$). The crude solid was dissolved in CHCl$_3$ (8 ml) and stirred with a catalytic amount of iodine for 24 h. The reaction mixture was washed with water (10 ml), 10% sodium sulphite solution (10 ml) and brine (10 ml) and the solvent removed under reduced pressure to give a solid which was purified by flash chromatography (DCM) to give the title compound (0.06 g, 46%) as a yellow solid.

$^1$H NMR (400 MHz, DMSO-d$_6$) δ 1.72-1.79 (m, 2H), 2.27-2.40 (m, 2H), 3.10-3.18 (m, 2H), 3.84 (s, 3H), 5.85-5.97 (m, 1H), 6.59 (d, J=8.6 Hz, 2H), 6.97 (d, J=16.4 Hz, 1H), 7.11 (dd, J=9.0, 2.8 Hz, 1H), 7.21 (d, J=16.4 Hz, 1H), 7.37 (d, J=8.6 Hz, 2H), 7.64 (d, J=8.6 Hz, 2H), 7.66 (d, J=2.8 Hz, 1H), 7.90 (d, J=9.0 Hz, 1H), 7.96 (d, J=8.6 Hz, 2H); $^{13}$C NMR (100.5 MHz, DMSO-d$_6$) δ 21.85 (q, $J_{CF}$=6.2 Hz), 30.89 (q, $J_{CF}$=28.0 Hz), 41.81, 56.25, 105.43, 112.55, 116.27, 122.42, 123.68, 125.07, 126.84, 127.61, 128.55, 129.59, 131.37, 131.39, 136.36, 141.15, 148.66, 149.44, 157.95, 164.93.

2-{4-[2-(4-Fluorophenyl)-vinyl]-phenyl}-6-methoxybenzothiazole

Book No.: SKT02-137

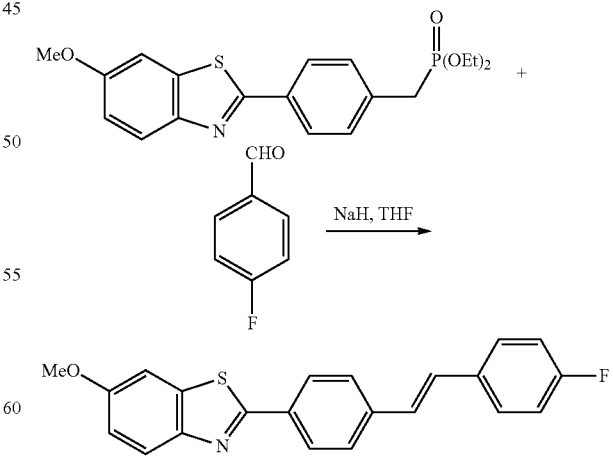

Prepared as described in the Alkene Formation section using NaH (60% dispersion, 0.050 g, 1.02 mmol), diethyl 4-(6-methoxybenzothiazol-2-yl)benzylphosphonate (0.25 g, 0.64 mmol) and 4-fluorobenzaldehyde (0.08 g, 0.64 mmol) in dry THF (5 ml) to give the title compound (0.122 g, 53%) as a pale yellow solid after work-up and recrystallisation from 1,2-dichloroethane.

IR 3021, 2963, 2941, 2837, 1600, 1556, 1507, 1487, 1460, 1435, 1319, 1266, 1237, 1212, 1065, 1026, 966, 840, 822, 807 cm$^{-1}$; $^1$H NMR (250 MHz, CDCl$_3$) δ 3.89 (s, 3H), 7.00-7.11 (m, 4H), 7.17 (dist d, J=15.9 Hz, 1H), 7.35 (d, J=2.1 Hz, 1H), 7.49 (d, J=8.5 Hz, 1H), 7.52 (d, J=8.5 Hz, 1H), 7.59 (d, J=8.2 Hz, 2H), 7.94 (d, J=8.8 Hz, 1H), 8.02 (d, J=8.2 Hz, 2H).

2-{4-[2-(4-Hydroxy-3-nitrophenyl)-vinyl]-phenyl}-6-methoxybenzothiazole

Book No.: SKT03-107

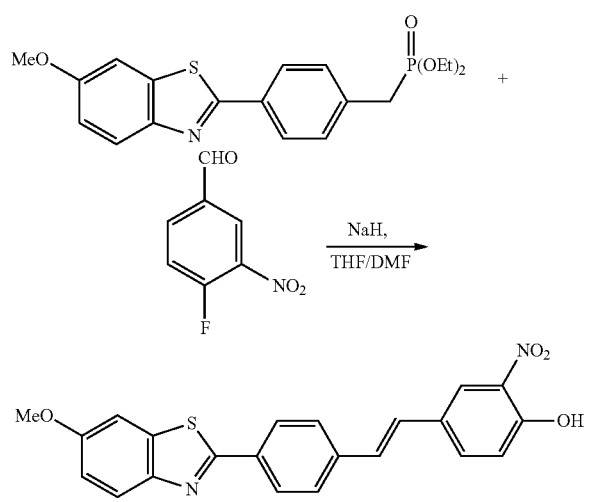

Prepared as described in the Alkene Formation section using sodium hydride (60% dispersion in mineral oil, 0.286 g, 7.15 mmol), diethyl 4-(6-methoxybenzothiazol-2-yl)benzylphosphonate (0.5 g, 1.28 mmol) and 4-fluoro-3-nitrobenzaldehyde (0.24 g, 1.41 mmol) in a mixture of dry DMF (5 ml) and THF (20 ml) to give the title compound (0.10 g, 19%) as a red solid after work-up and flash chromatography (DCM).

$^1$H NMR (400 MHz, DMSO-d$_6$) δ 3.80 (s, 3H), 7.08 (dd, J=8.9, 2.4 Hz, 1H), 7.11 (d, J=8.5 Hz, 1H), 7.25 (d, J=16.4 Hz, 1H), 7.35 (d, J=16.4 Hz, 1H), 7.66 (d, J=2.4 Hz, 1H), 7.69 (d, J=8.5 Hz, 2H), 7.81 (dd, J=8.9, 2.4 Hz, 1H), 7.88 (d, J=8.9 Hz, 1H), 7.98 (d, J=8.2 Hz, 2H), 8.09 (d, J=2.4 Hz, 1H), 11.2 (br s, 1H); $^{13}$C NMR (100.5 MHz, DMSO-d$_6$) δ 56.41, 105.52, 116.65, 120.18, 123.84, 124.01, 127.82, 127.88, 128.65, 129.23, 132.63, 133.45, 136.64, 137.74, 140.11, 148.75, 152.36, 158.19, 164.89 (1 missing).

2-{4-[2-(4-(2-Fluoroethoxy)-phenyl)-vinyl]-phenyl}-6-methoxybenzothiazole

Book No.: SKT03-77

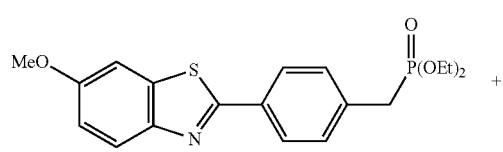

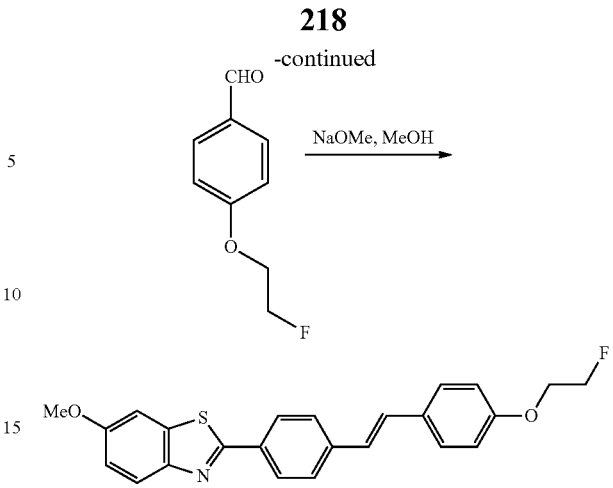

Prepared as described in the Alkene Formation section using diethyl 4-(6-methoxybenzothiazol-2-yl)benzylphosphonate (0.06 g, 0.153 mmol), sodium methoxide (0.5 M solution in MeOH, 0.46 ml, 0.23 mmol) and 4-(2-fluoroethoxy)-benzaldehyde (0.028 g, 0.168 mmol) in dry MeOH (5 ml) to give the title compound (0.048 g, 77%) as a pale yellow solid after work-up.

$^1$H NMR (400 MHz, DMSO-d$_6$) δ 3.85 (s, 3H), 4.27 (dist d of t, J$_{HF}$=30.1 Hz, J$_{HH}$=3.9 Hz, 2H), 4.74 (dist d of t, J$_{HF}$=48.1 Hz, J$_{HH}$=3.9 Hz, 2H), 7.00 (d, J=8.6 Hz, 2H), 7.13 (dd, J=9.0, 2.7 Hz, 1H), 7.18 (d, J=16.4 Hz, 1H), 7.33 (d, J=16.4 Hz, 1H), 7.59 (d, J=9.0 Hz, 2H), 7.69 (d, J=2.7 Hz, 1H), 7.72 (d, J=8.6 Hz, 2H), 7.93 (d, J=9.0 Hz, 1H), 8.01 (d, J=8.6 Hz, 2H).

6-Methoxy-2-(4-{(E)-2-[2-methoxy-5-(trifluoromethoxy)phenyl]ethenyl}phenyl)-1,3-benzothiazole No.: SKT04-187

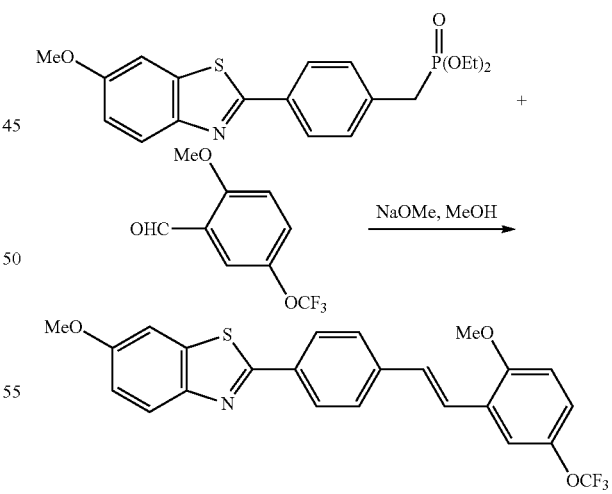

Prepared as described in the Alkene Formation section using diethyl 4-(6-methoxyl benzothiazol-2-yl)benzylphosphonate (0.75 g, 1.92 mmol), a solution of 0.5 M sodium methoxide (7.7 ml, 3.84 mmol) and 2-methoxy-5-trifluoromethoxybenzaldehyde (0.42 g, 1.92 mmol) in dry MeOH (10 ml) to give the title compound (0.732 g, 83%) as a pale yellow solid after work-up.

$^1$H NMR (250 MHz, CDCl$_3$) δ 3.87 (s, 3H), 3.89 (s, 3H), 6.86 (d, J=8.8 Hz, 1H), 7.06-7.14 (m, 3H), 7.33 (d, J=2.1 Hz, 1H), 7.45 (s, 1H), 7.49 (d, J=17 Hz, 1H), 7.60 (d, J=8.2 Hz, 2H), 7.94 (d, J=8.8 Hz, 1H), 8.01 (d, J=8.2 Hz, 2H); $^{13}$C NMR (62.5 MHz, CDCl$_3$) δ 55.81, 55.98, 104.16, 111.61, 115.71, 119.26, 120.67 (q, J$_{CF}$=256 Hz), 121.39, 123.58, 123.69, 127.21, 127.40, 127.54, 129.53, 132.96, 136.45, 139.57, 142.88, 148.81, 155.46, 157.82, 165.13.

6-Methoxy-2-(4-{(E)-2-[4-methoxy-2-(trifluoromethyl)phenyl]ethenyl}phenyl)-1,3-benzothiazole Book No.: SKT04-159

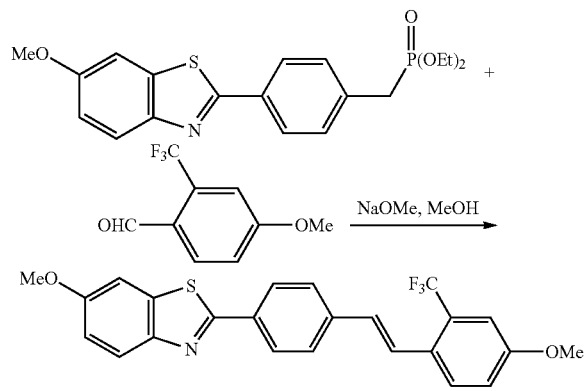

Prepared as described in the Alkene Formation section using diethyl 4-(6-methoxylbenzothiazol-2-yl)benzylphosphonate (0.89 g, 2.28 mmol), a solution of 0.5 M sodium methoxide (9.2 ml, 4.56 mmol) and 4-methoxy-2-trifluoromethylbenzaldehyde (0.47 g, 2.28 mmol) in dry MeOH (10 ml) to give the title compound (0.67 g, 67%) as a yellow/green solid after work-up.

$^1$H NMR (250 MHz, DMSO-d$_6$) δ 3.86 (s, 3H), 3.89 (s, 3H), 6.99 (d, J=16.2 Hz, 1H), 7.05-7.11 (m, 2H), 7.19 (d, J=2.1 Hz, 1H), 7.34 (d, J=2.1 Hz, 1H), 7.48 (d, J=16.2 Hz, 1H), 7.58 (d, J=8.2 Hz, 2H), 7.73 (d, J=8.8 Hz, 1H), 7.94 (d, J=8.8 Hz, 1H), 8.02 (d, J=8.2 Hz, 2H); $^{13}$C NMR (62.5 MHz, CDCl$_3$) δ 55.62, 55.84, 104.16, 111.61 (q, J$_{CF}$=5.9 Hz), 115.72, 117.51, 123.73, 124.16 (q, J$_{CF}$=274 Hz), 125.32, 127.18, 127.60, 128.31, 128.49, 128.79 (q, J$_{CF}$=29.8 Hz), 129.77, 133.03, 136.47, 139.35, 148.83, 157.82, 158.98, 165.08.

6-Methoxy-2-(4-{(E)-2-[4-methoxy-3-(trifluoromethyl)phenyl]ethenyl}phenyl)-1,3-benzothiazole Book No.: SKT03-167

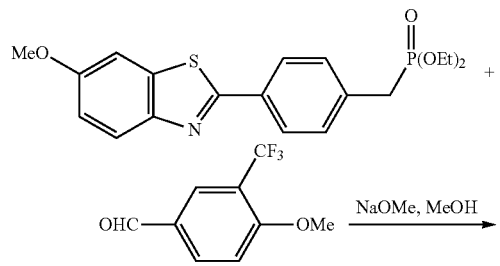

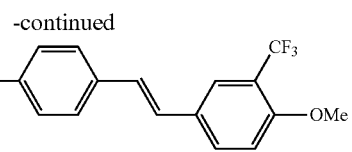

Prepared as described in the Alkene Formation section using diethyl 4-(6-methoxyl benzothiazol-2-yl)benzylphosphonate (0.89 g, 2.28 mmol), a solution of 0.5 M sodium methoxide (9.2 ml, 4.56 mmol) and 4-methoxy-3-trifluoromethylbenzaldehyde (0.47 g, 2.28 mmol) in dry MeOH (15 ml) to give the title compound (0.683 g, 68%) as a pale yellow solid after work-up.

$^1$H NMR (400 MHz, DMSO-d$_6$) δ 3.85 (s, 3H), 3.92 (s, 3H), 7.13 (dd, J=8.6, 2.3 Hz, 1H), 7.29 (d, J=8.6 Hz, 1H), 7.30 (d, J=16.4 Hz, 1H), 7.40 (d, J=16.4 Hz, 1H), 7.68 (d, J=2.3 Hz, 1H), 7.74 (d, J=8.2 Hz, 2H), 7.86-7.91 (m, 2H), 7.92 (d, J=8.6 Hz, 1H), 8.01 (d, J=8.2 Hz, 2H); $^{13}$C NMR (100.5 MHz, DMSO-d$_6$) δ 56.28, 56.83, 105.46, 113.91, 116.39, 117.87 (q, J$_{CF}$=30.4 Hz), 123.81, 124.14 (q, J$_{CF}$=272 Hz), 125.51 (q, J$_{CF}$=5.4 Hz), 127.51, 127.60, 127.68, 128.96, 128.98, 129.87, 132.45, 132.51, 136.48, 140.06, 148.63, 157.18, 158.06, 163.79, 164.74.

Monofluoro and Fluorinated Hydroxy-Alkenes

2-{4-[2-(4-Fluorophenyl)-vinyl]-phenyl}-6-hydroxy-benzothiazole

Book No.: SKT02-165

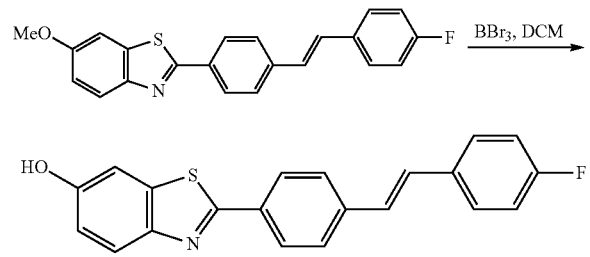

Prepared as described in the Demethylation section above using 2-{4-[2-(4-fluorophenyl)-vinyl]-phenyl}-6-methoxy-benzothiazole (0.080 g, 0.222 mmol) in dry DCM (10 ml) and BBr$_3$ in DCM (1.0 M, 1.10 ml, 1.10 mmol) to give the title compound (0.087 g, 78%) as a yellow solid after work-up and flash chromatography (15:1 DCM/EtOAc).

$^1$H NMR (250 MHz, CDCl$_3$) δ 5.11 (br s, 1H), 6.96-7.09 (m, 4H), 7.17 (d, J=16.2 Hz, 1H), 7.32 (s, 1H), 7.48-7.53 (m, 2H), 7.59 (d, J=8.2 Hz, 2H), 7.91 (d, J=8.8 Hz, 1H), 8.02 (d, J=7.9 Hz, 2H); $^{13}$C NMR (100.5 MHz, DMSO-d$_6$) δ 107.24, 116.13 (d, J$_{CF}$=21.0 Hz), 116.67, 123.91, 127.54, 127.63, 127.86 (d, J$_{CF}$=2.3 Hz), 129.06, 129.14, 129.32, 132.59, 133.86 (d, J$_{CF}$=3.1 Hz), 136.43, 139.78, 147.68, 156.28, 162.31 (d, J$_{CF}$=242.9 Hz).

2-{4-[2-(4-(N-2,2,2-Trifluoroethyl)aminophenyl)-vinyl]-phenyl}-6-hydroxybenzothiazole Book No.: SKT02-155

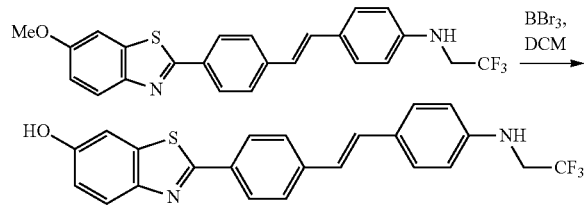

Prepared as described in the Demethylation section above using 2-{4-[2-(4-(N-2,2,2-trifluoroethyl)aminophenyl)-vinyl]-phenyl}-6-methoxybenzothiazole (0.049 g, 0.111 mmol) in dry DCM (10 ml) and BBr$_3$ in DCM (1.0 M, 0.6 ml, 0.60 mmol) to give the title compound (0.050 g, 52%) as a yellow solid after work-up and flash chromatography (4:3 Hexane/EtOAc).

$^1$H NMR (400 MHz, DMSO-d$_6$) δ 2.53-2.66 (m, 2H), 3.37-3.51 (m, 2H), 6.14 (br s, 1H), 6.68 (d, J=8.6 Hz, 2H), 7.05 (dd, J=9.0, 2.3 Hz, 1H), 7.07 (d, J=16.5 Hz, 1H), 7.30 (d, J=16.5 Hz, 1H), 7.46 (s, 1H), 7.47 (d, J=8.6 Hz, 1H), 7.47 (s, 1H), 7.72 (d, J=8.6 Hz, 2H), 7.89 (d, J=9.0 Hz, 1H), 8.01 (d, J=8.6 Hz, 2H), 9.95 (s, 1H); $^{13}$C NMR (100.5 MHz, DMSO-d$_6$) δ 32.98 (q, J$_{CF}$=27.2 Hz), 36.49 (q, J$_{CF}$=3.8 Hz), 107.24, 112.71, 116.60, 122.82, 123.76, 125.62, 126.89, 127.44 (q, J$_{CF}$=277.1 Hz), 127.51, 128.57, 131.17, 131.62, 136.35, 140.88, 147.78, 148.77, 156.19, 163.74.

2-{4-[2-(4-(N-4,4,4-Trifluorobutyl)aminophenyl)-vinyl]-phenyl}-6-hydroxybenzothiazole Book No.: SKT02-111

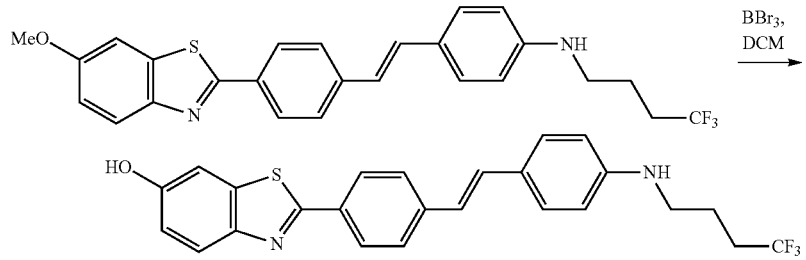

Prepared as described in the Demethylation section above using 2-{4-[2-(4-(N-4,4,4-trifluorobutyl)aminophenyl)-vinyl]-phenyl}-6-methoxybenzothiazole (0.138 g, 0.295 mmol) in dry DCM (10 ml) and BBr$_3$ in DCM (1.0 M, 1.50 ml, 1.50 mmol) to give the title compound (0.095 g, 71%) as a yellow solid after work-up and flash chromatography (3:2 Hexane/EtOAc).

$^1$H NMR (400 MHz, DMSO-d$_6$) δ 1.71-1.79 (m, 2H), 2.27-2.40 (m, 2H), 3.13 (q, J=6.3 Hz, 2H), 5.94 (t, J=5.9 Hz, 1H), 6.59 (d, J=8.6 Hz, 2H), 6.96 (d, J=16.0 Hz, 1H), 6.98 (dd, J=8.6, 2.4 Hz, 1H), 7.20 (d, J=16.0 Hz, 1H), 7.37 (d, J=8.6 Hz, 2H), 7.38 (d, J=2.4 Hz, 1H), 7.63 (d, J=8.2 Hz, 2H), 7.81 (d, J=8.6 Hz, 1H), 7.93 (d, J=8.2 Hz, 2H), 9.76 (s, 1H); $^{13}$C NMR (100.5 MHz, DMSO-d$_6$) δ 21.84 (q, J=Hz), 30.89 (q, J=28.05 Hz), 41.81, 107.23, 112.55, 116.58, 122.45, 123.74, 125.09, 126.82, 127.50, 128.53, 131.27, 131.53, 136.33, 140.94, 147.77, 149.42, 156.17, 163.74.

2-{4-[2-(4-(N-3,3,3-Trifluoropropyl)aminophenyl)-vinyl]-phenyl}-6-hydroxybenzothiazole Book No.: SKT02-127

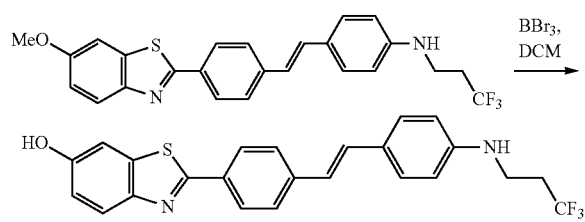

Prepared as described in the Demethylation section above using 2-{4-[2-(4-(N-3,3,3-trifluoropropyl)aminophenyl)-vinyl]-phenyl}-6-methoxybenzothiazole (0.10 g, 0.22 mmol) in dry DCM (10 ml) and BBr$_3$ in DCM (1.0 M, 1.10 ml, 1.10 mmol) to give the title compound (0.037 g, 78%) as a yellow solid after work-up and flash chromatography (15:1 DCM/EtOAc).

$^1$H NMR (400 MHz, DMSO-d$_6$) δ 3.90-4.02 (m, 2H), 6.50 (t, J=1.5 Hz, 1H), 6.76 (d, J=8.2 Hz, 2H), 6.99 (dd, J=1.6, 8.0 Hz, 1H), 7.04 (d, J=16.4 Hz, 1H), 7.24 (d, J=16.4 Hz, 1H), 7.38-7.45 (m, 3H), 7.66 (d, J=8.2 Hz, 2H), 7.83 (d, J=9.0 Hz, 1H), 7.95 (d, J=8.2 Hz, 2H), 9.88 (s, 1H); $^{13}$C NMR (100.5 MHz, DMSO-d$_6$) δ 44.49 (q, J$_{CF}$=32.8 Hz), 107.24, 113.10, 116.61, 123.41, 123.77, 126.24 (q, J$_{CF}$=281 Hz), 126.51, 126.98, 127.51, 128.38, 130.95, 131.75, 136.36, 140.75, 147.77, 148.23, 156.20, 163.72.

2-{4-[2-(4-(2,2,2-Trifluoroethoxy)phenyl)-vinyl]-phenyl}-6-hydroxybenzothiazole Book No.: SKT02-51

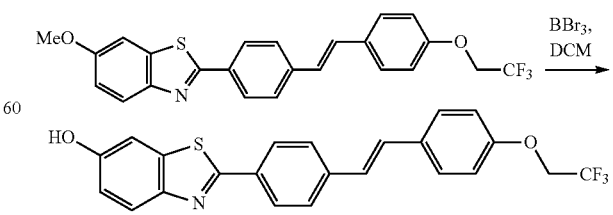

Prepared as described in the Demethylation section above using 2-{4-[2-(4-(2,2,2-trifluoroethoxy)phenyl)-vinyl]-phenyl}-6-methoxybenzothiazole (0.097 g, 0.22 mmol) in dry DCM (5 ml) and BBr₃ in DCM (1.0 M, 1.10 ml, 1.10 mmol) to give the title compound (0.078 g, 83%) as a yellow solid after work-up and flash chromatography (100:1 DCM/MeOH).

¹H NMR (250 MHz, acetone-d₆) δ 4.72 (q, J=9.1 Hz, 2H), 7.01-7.18 (m, 3H), 7.23 (d, J=15.9 Hz, 1H), 7.38 (d, J=15.9 Hz, 1H), 7.47 (d, J=1.8 Hz, 1H), 7.67 (d, J=8.2 Hz, 2H), 7.75 (d, J=8.2 Hz, 2H), 7.87 (d, J=8.5 Hz, 1H), 8.07 (d, J=8.2 Hz, 2H), 8.83 (s, 1H)

2-(4-{(E)-2-[2-Hydroxy-5-(trifluoromethoxy)phenyl]ethenyl}phenyl)-1,3-benzothiazol-6-ol Book No.: SKT05-5

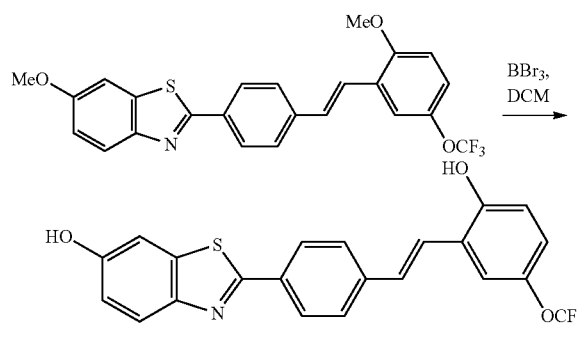

Prepared as described in the Demethylation section above using 6-methoxy-2-(4-{(E)-2-[2-methoxy-5-(trifluoromethoxy)phenyl]ethenyl}phenyl)-1,3-benzothiazole (0.097 g, 0.22 mmol) in dry DCM (20 ml) and BBr₃ in DCM (1.0 M, 1.90 ml, 1.90 mmol) at −78° C. give the title compound (0.308 g, 82%) as a yellow solid after work-up and flash chromatography (20:1 DCM/MeOH).

¹H NMR (250 MHz, CD₃OD) δ 6.86 (d, J=8.8 Hz, 1H), 7.01 (d, J=8.8 Hz, 1H), 7.01 (d, J=8.8 Hz, 1H), 7.26 (d, J=16.5 Hz, 1H), 7.31 (d, J=2.1 Hz, 1H), 7.47 (d, J=2.1 Hz, 1H), 7.55 (d, J=16.5 Hz, 1H), 7.67 (d, J=8.2 Hz, 1H), 7.81 (d, J=8.8 Hz, 1H), 7.98 (d, J=8.2 Hz, 1H); ¹³C NMR (100 MHz, DMSO-d₆) δ 107.24, 116.69, 117.39, 119.69, 120.80 (q, J$_{CF}$=255 Hz), 121.92, 123.89, 124.45, 125.42, 127.58, 127.62, 129.21, 132.75, 136.49, 140.06, 141.56, 147.79, 154.65, 156.33, 163.54.

2-(4-{(E)-2-[4-Hydroxy-2-(trifluoromethyl)phenyl]ethenyl}phenyl)-1,3-benzothiazol-6-ol Book No.: SKT04-169

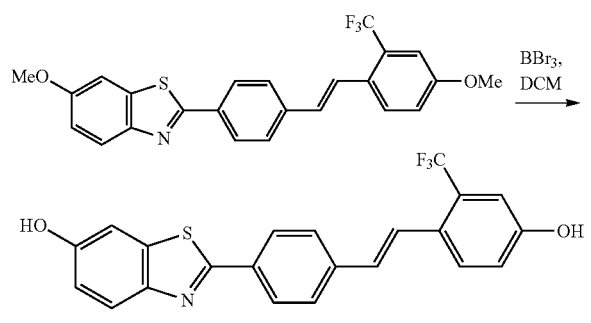

Prepared as described in the Demethylation section above using 6-methoxy-2-(4-{(E)-2-[4-methoxy-2-(trifluoromethyl)phenyl]ethenyl}phenyl)-1,3-benzothiazole (0.30 g, 0.68 mmol) in dry DCM (10 ml) and BBr₃ in DCM (1.0 M, 1.40 ml, 1.40 mmol) at −78° C. give the title compound (0.229 g, 81%) as a yellow solid after work-up and flash chromatography (1:1 Hexane/EtOAc).

¹H NMR (250 MHz, DMSO-d₆) δ 6.99 (dd, J=2.1, 8.5 Hz, 1H), 7.09 (d, J=8.5 Hz, 1H), 7.11 (s, 1H), 7.24 (d, J=17.1 Hz, 1H), 7.31-7.44 (m, 2H), 7.70 (d, J=8.5 Hz, 2H), 7.83-7.91 (m, 2H), 8.03 (d, J=8.5 Hz, 2H), 9.97 (br s, 1H), 10.30 (br s, 1H); ¹³C NMR (100.5 MHz, DMSO-d₆) δ 107.24, 112.97 (q, J$_{CF}$=6.2 Hz), 116.72, 120.06, 123.92, 124.70 (q, J$_{CF}$=274 Hz), 124.97 (q, J$_{CF}$=1.6 Hz), 126.30 (q, J$_{CF}$=1.6 Hz), 127.62, 127.70, 127.72 (q, J$_{CF}$=29.6 Hz), 129.60, 129.73, 132.93, 136.48, 139.55, 147.75, 156.32, 157.86, 163.44.

Non-Fluorinated Methyl-Alkenes

6-Methyl-2-{4-[(E)-2-phenylethenyl]phenyl}-1,3-benzothiazole

Book No.: SK696-39

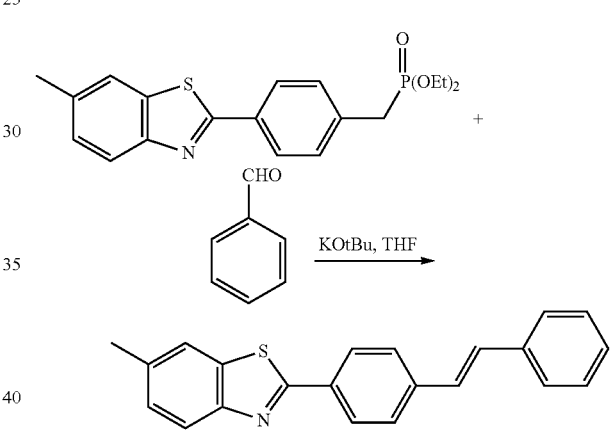

Prepared as described in the Alkene Formation section using diethyl 4-(6-methylbenzothiazol-2-yl)benzylphosphonate (0.30 g, 0.80 mmol) in dry THF (15 ml), potassium t-butoxide (0.10 g, 0.88 mmol) and benzaldehyde (0.085 g, 0.80 mmol) in dry THF (5 ml) to give the title compound (0.16 g, 60%) as a pale yellow solid after work-up and flash chromatography (2:1 Hexane/EtOAc).

¹H NMR (400 MHz, DMSO-d₆) δ 2.47 (s, 3H), 7.28-7.42 (m, 6H), 7.65 (d, J=7.4 Hz, 2H), 7.78 (d, J=7.8 Hz, 2H), 7.92 (s, 1H), 7.93 (d, J=7.8 Hz, 1H), 8.07 (d, J=8.2 Hz, 2H).

2-{4-[2-(2-Nitrophenyl)-vinyl]-phenyl}-6-methyl-benzothiazole

Book No.: SKT01-15

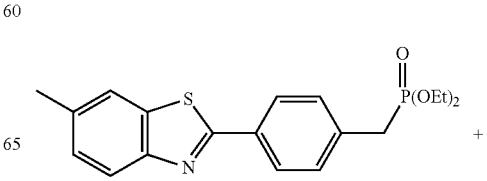

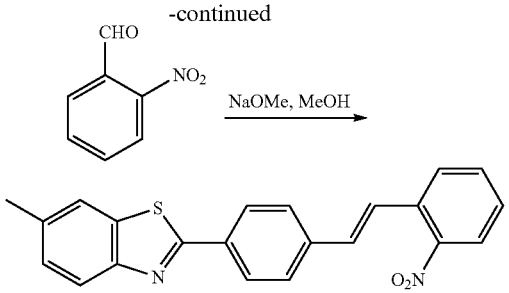

Prepared as described in the Alkene Formation section using diethyl 4-(6-methylbenzothiazol-2-yl)benzylphosphonate (0.30 g, 0.80 mmol), 2-nitrobenzaldehyde (0.12 g, 0.80 mmol) and a solution of 0.5 M sodium methoxide (3.2 ml, 1.60 mmol) in dry MeOH (10 ml) to give the title compound (0.185 g, 62%) as small yellow needles after work-up and recrystallisation from 1,2-dichloroethane.

$^1$H NMR (400 MHz, DMSO-$d_6$) δ 2.46 (s, 3H), 7.36 (dd, J=8.2, 1.2 Hz, 1H), 7.39 (d, J=16.0 Hz, 1H), 7.54-7.58 (m, 1H), 7.60 (d, J=16.0 Hz, 1H), 7.74-7.77 (m, 1H), 7.78 (d, J=8.2 Hz, 2H), 7.92 (br s, 1H), 7.93 (d, J=8.6 Hz, 1H), 7.99 (d, J=7.5 Hz, 1H), 8.00 (dd, J=8.2, 1.2 Hz, 1H), 8.09 (d, J=8.2 Hz, 2H); $^{13}$C NMR (100 MHz, DMSO-$d_6$) δ 21.51, 122.28, 122.92, 124.97, 125.14, 128.00, 128.27, 128.65, 128.74, 129.37, 132.00, 132.85, 133.24, 133.93, 135.16, 135.91, 139.53, 148.50, 152.30, 166.05.

2-{4-[2-(3-Nitrophenyl)-vinyl]-phenyl}-6-methylbenzothiazole

Book No.: SKT01-53

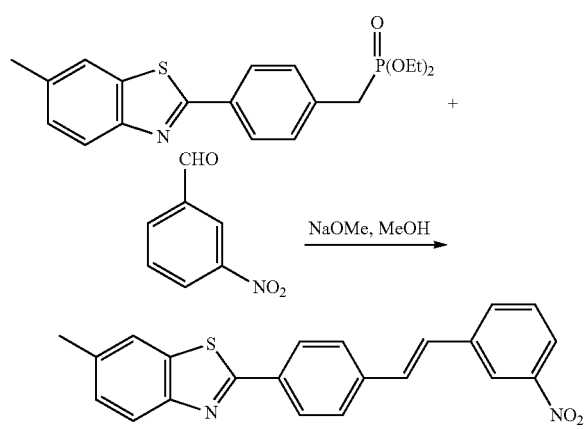

Prepared as described in the Alkene Formation section using diethyl 4-(6-methyl benzothiazol-2-yl)benzylphosphonate (0.16 g, 0.43 mmol), 3-nitrobenzaldehyde (0.064 g, 0.43 mmol) and a solution of 0.5 M sodium methoxide (1.7 ml, 0.85 mmol) in dry MeOH (10 ml) to give the title compound (0.149 g, 94%) as small yellow needles after work-up and recrystallisation from 1,2-dichloroethane.

$^1$H NMR (400 MHz, DMSO-$d_6$) δ 2.45 (s, 3H), 7.36 (d, J=8.6 Hz, 1H), 7.55 (d, J=17.2 Hz, 1H), 7.59 (d, J=17.2 Hz, 1H), 7.66-7.70 (m, 1H), 7.82 (d, J=8.2 Hz, 2H), 7.92 (s, 1H), 7.93 (d, J=8.6 Hz, 1H), 8.08 (d, J=8.2 Hz, 2H), 8.11-8.13 (m, 2H), 8.47 (s, 1H); $^{13}$C NMR (100 MHz, DMSO-$d_6$) δ 21.54, 121.49, 122.31, 122.79, 122.88, 127.92, 128.12, 128.49, 128.65, 130.69, 130.79, 132.90, 133.23, 135.09, 135.86, 139.22, 139.67, 148.83, 152.24, 166.12.

2-{4-[2-(4-Nitrophenyl)-vinyl]-phenyl}-6-methylbenzothiazole

Book No.: SKT01-3

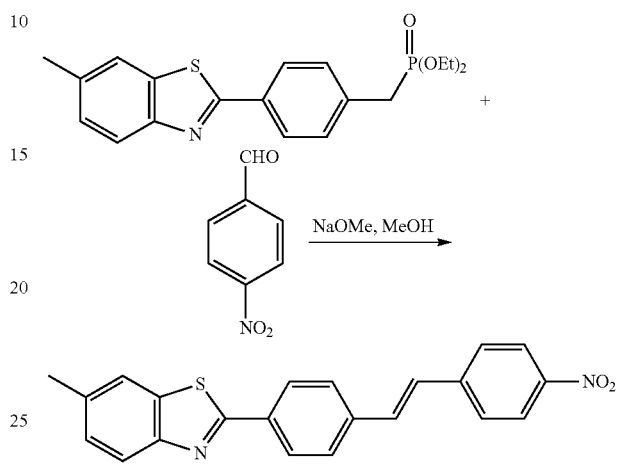

Prepared as described in the Alkene Formation section using diethyl 4-(6-methylbenzothiazol-2-yl)benzylphosphonate (0.324 g, 0.86 mmol), 4-nitrobenzaldehyde (0.13 g, 0.86 mmol) and a solution of 0.5 M sodium methoxide (3.5 ml, 1.75 mmol) in dry MeOH (10 ml) to give the title compound (0.221 g, 69%) as small yellow needles after work-up and recrystallisation from 1,2-dichloroethane.

IR 3023, 1635, 1596, 1587, 1502, 1483, 1332, 1258, 1194, 1109, 968, 943, 873, 834, 825, 810, 748, 722 cm$^{-1}$; $^1$H NMR (250 MHz, DMSO-$d_6$) δ 2.47 (s, 3H), 7.38 (d, J=7.9 Hz, 1H), 7.57 (d, J=17.4 Hz, 1H), 7.65 (d, J=17.4 Hz, 1H), 7.86 (d, J=7.9 Hz, 2H), 7.90-7.97 (m, 4H), 8.12 (d, J=8.2 Hz, 2H), 8.26 (d, J=8.2 Hz, 2H).

2-{4-[2-(2-Aminophenyl)-vinyl]-phenyl}-6-methylbenzothiazole

Book No.: SKT01-55

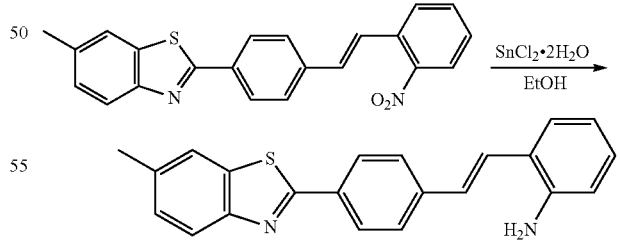

Prepared as described in the Nitro Reduction section using 2-{4-[2-(2-nitrophenyl)-vinyl]-phenyl}-6-methylbenzothiazole (0.10 g, 0.268 mmol) and tin (II) chloride dihydrate (0.48 g, 2.15 mmol) in EtOH (3 ml) to give the title compound (0.036 g, 39%) as a yellow solid after work-up and flash chromatography (20:1 DCM/EtOAc).

$^1$H NMR (250 MHz, CDCl$_3$) δ 2.49 (s, 3H), 3.84 (br s, 2H), 6.73 (d, J=7.9 Hz, 1H), 6.79-6.85 (m, 1H), 7.02 (d, J=16.2 Hz,

1H), 7.09-7.15 (m, 1H), 7.27 (d, J=16.2 Hz, 1H), 7.29 (d, J=7.6 Hz, 1H), 7.43 (d, J=7.6 Hz, 1H), 7.59 (d, J=8.2 Hz, 2H), 7.68 (s, 1H), 7.94 (d, J=8.2 Hz, 1H), 8.05 (d, J=8.2 Hz, 2H); $^{13}$C NMR (62.5 MHz, CDCl$_3$) δ 21.62, 116.47, 119.29, 121.39, 122.65, 125.64, 125.78, 126.92, 127.29, 127.77, 128.00, 129.11, 129.32, 132.69, 135.19, 135.39, 140.10, 144.18, 152.35, 166.63.

2-{4-[2-(3-Aminophenyl)-vinyl]-phenyl}-6-methyl-benzothiazole

Book No.: SKT01-69

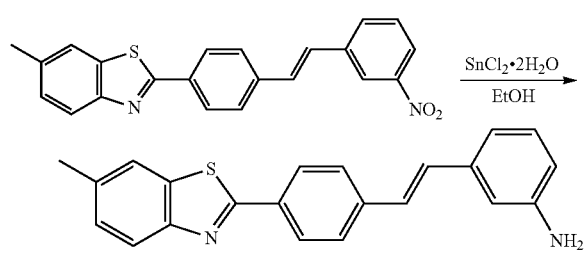

Prepared as described in the Nitro Reduction section using 2-{4-[2-(3-nitrophenyl)-vinyl]-phenyl}-6-methylbenzothiazole (0.12 g, 0.322 mmol) and tin (II) chloride dihydrate (0.58 g, 2.58 mmol) in EtOH (3 ml) to give the title compound (0.078 g, 71%) as a pale yellow solid after work-up and flash chromatography (20:1 DCM/EtOAc).

$^1$H NMR (250 MHz, CDCl$_3$) δ 2.49 (s, 3H), 3.71 (br s, 2H), 6.63 (dd, J=7.9, 1.8 Hz, 1H), 6.87 (s, 1H), 6.95 (d, J=7.6 Hz, 1H), 7.05-7.20 (m, 3H), 7.29 (dd, J=8.2, 1.8 Hz, 1H), 7.59 (d, J=8.2 Hz, 2H), 7.68 (s, 1H), 7.94 (d, J=8.2 Hz, 1H), 8.05 (d, J=8.5 Hz, 2H); $^{13}$C NMR (62.5 MHz, CDCl$_3$) δ 21.63, 113.02, 115.12, 117.54, 121.41, 122.66, 126.98, 127.58, 127.76, 127.99, 129.71, 130.46, 132.66, 135.19, 135.38, 138.03, 139.90, 146.73, 152.37, 166.68.

2-{4-[2-(4-Aminophenyl)-vinyl]-phenyl}-6-methyl-benzothiazole

Book No.: SKT01-17

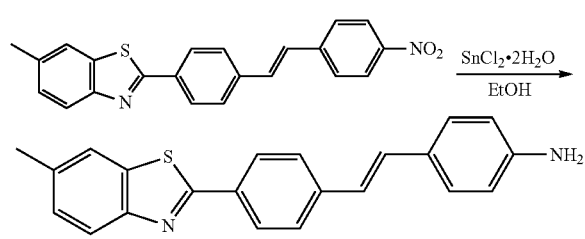

Prepared as described in the Nitro Reduction section using 2-{4-[2-(4-nitrophenyl)-vinyl]-phenyl}-6-methylbenzothiazole (0.15 g, 0.403 mmol) and tin (II) chloride dihydrate (0.73 g, 3.22 mmol) in EtOH (5 ml) to give the title compound (0.113 g, 82%) as a pale yellow solid after work-up and flash chromatography (20:1 DCM/EtOAc).

$^1$H NMR (250 MHz, CDCl$_3$) δ 2.48 (s, 3H), 3.73 (br s, 2H), 6.68 (d, J=8.2 Hz, 2H), 6.94 (d, J=16.0 Hz, 1H), 7.12 (d, J=16.0 Hz, 1H), 7.22-7.41 (m, 3H), 7.57 (d, J=8.2 Hz, 2H), 7.69 (s, 1H), 7.91 (d, J=8.2 Hz, 1H), 8.04 (d, J=8.2 Hz, 2H).

2-{4-[2-(4-Dimethylaminophenyl)-vinyl]-phenyl}-6-methylbenzothiazole

Book No.: SK2033-30

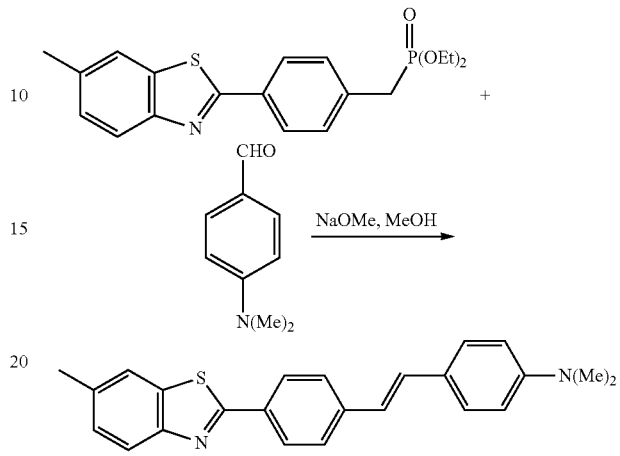

Prepared as described in the Alkene Formation section using diethyl 4-(6-methyl benzothiazol-2-yl)benzylphosphonate (0.05 g, 0.133 mmol) in dry THF (5 ml), potassium t-butoxide (0.03 g, 0.266 mmol) and 4-dimethylaminobenzaldehyde (0.02 g, 0.133 mmol) in dry THF (5 ml) to give the title compound (0.037 g, 75%) as an orange solid after work-up and flash chromatography (4:1 Hexane/Et$_2$O).

IR 3020, 2915, 1605, 1591, 1554, 1523, 1479, 1452, 1415, 1359, 1309, 1256, 1224, 1190, 1180, 1164, 1115, 1062, 965, 949, 827, 812 cm$^{-1}$; $^1$H NMR (400 MHz, acetone-d$_6$) δ 2.49 (s, 3H), 3.00 (s, 6H), 6.77 (d, J=8.6 Hz, 2H), 7.08 (d, J=16.4 Hz, 1H), 7.32 (d, J=16.4 Hz, 1H), 7.36 (d, J=7.4 Hz, 1H), 7.51 (d, J=8.6 Hz, 2H), 7.71 (d, J=8.2 Hz, 2H), 7.86 (s, 1H), 7.90 (d, J=8.2 Hz, 1H), 8.08 (d, J=8.2 Hz, 2H).

2-{(E)-2-[4-(6-Methyl-1,3-benzothiazol-2-yl)phenyl]ethenyl}phenol

Book No.: SK696-62

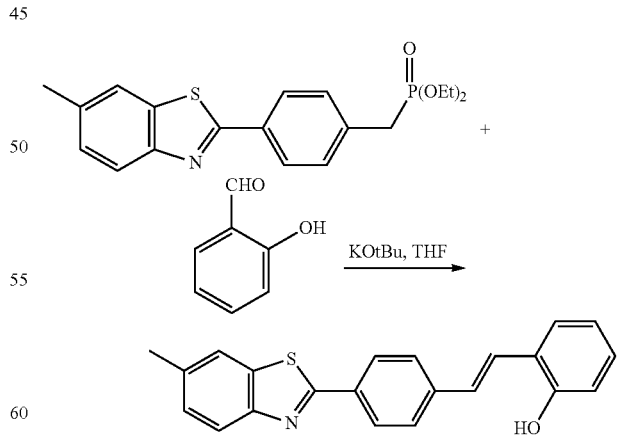

Prepared as described in the Alkene Formation section using diethyl 4-(6-methylbenzothiazol-2-yl)benzylphosphonate (0.30 g, 0.80 mmol) in dry THF (25 ml), potassium t-butoxide (0.19 g, 1.68 mmol) and 2-hydroxybenzaldehyde (0.097 g, 0.80 mmol) in dry THF (10 ml) to give the title compound (0.16 g, 60%) as a yellow solid after work-up and flash chromatography (1:1 Hexane/EtOAc).

$^1$H NMR (400 MHz, DMSO-d$_6$) δ 2.44 (s, 3H), 6.81-6.85 (m, 1H), 6.89 (d, J=7.8 Hz, 1H), 7.10-7.14 (m, 1H), 7.29 (d, J=16.5 Hz, 1H), 7.35 (d, J=8.6 Hz, 1H), 7.56 (d, J=16.5 Hz, 1H), 7.61 (d, J=7.4 Hz, 1H), 7.71 (d, J=8.2 Hz, 2H), 7.89 (s, 1H), 7.92 (d, J=8.6 Hz, 1H), 8.04 (d, J=8.2 Hz, 2H), 9.87 (s, 1H); $^{13}$C NMR (100 MHz, DMSO-d$_6$) δ 21.54, 116.39, 119.81, 122.29, 122.79, 123.87, 126.01, 127.23, 127.42, 127.92, 128.59, 129.63, 131.96, 135.00, 135.72, 141.02, 152.27, 155.76, 166.29 (1 missing).

3-{(E)-2-[4-(6-Methyl-1,3-benzothiazol-2-yl)phenyl]ethenyl}phenol

Book No.: SK696-57

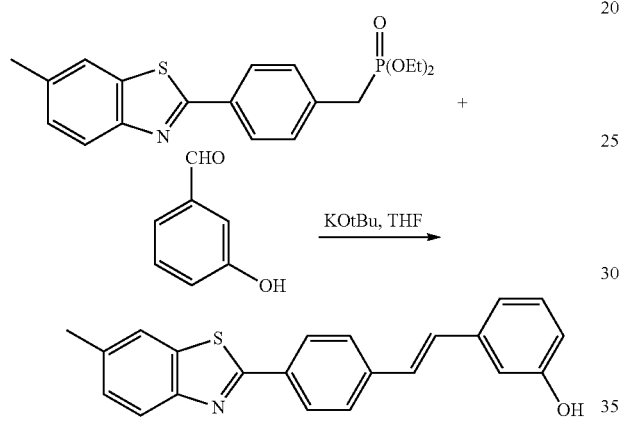

Prepared as described in the Alkene Formation section using diethyl 4-(6-methylbenzothiazol-2-yl)benzylphosphonate (0.30 g, 0.80 mmol) in dry THF (25 ml), potassium t-butoxide (0.19 g, 1.68 mmol) and 3-hydroxybenzaldehyde (0.097 g, 0.80 mmol) in dry THF (10 ml) to give the title compound (0.12 g, 44%) as a yellow solid after work-up and flash chromatography (2:1 Hexane/EtOAc).

$^1$H NMR (400 MHz, DMSO-d$_6$) δ 2.43 (s, 3H), 6.72 (dd, J=7.8, 1.6 Hz, 1H), 7.02 (s, 1H), 7.06 (d, J=7.8 Hz, 1H), 7.17 (d, J=7.9 Hz, 1H), 7.22 (d, J=16.0 Hz, 1H), 7.31 (d, J=16.0 Hz, 1H), 7.34 (d, J=7.8 Hz, 1H), 7.75 (d, J=8.2 Hz, 2H), 7.87 (s, 1H), 7.91 (d, J=8.2 Hz, 1H), 8.03 (d, J=8.2 Hz, 2H), 9.48 (s, 1H); $^{13}$C NMR (100 MHz, DMSO-d$_6$) δ 21.53, 113.79, 115.78, 118.26, 122.26, 122.82, 127.65, 127.71, 127.83, 128.59, 130.16, 130.98, 132.27, 135.03, 135.75, 138.51, 140.33, 152.26, 158.13, 166.23.

4-{(E)-2-[4-(6-Methyl-1,3-benzothiazol-2-yl)phenyl]ethenyl}phenol

Book No.: SK696-43

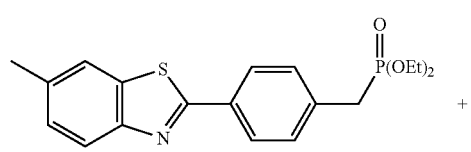

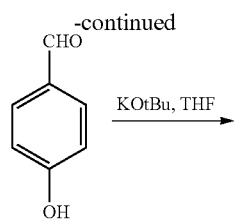
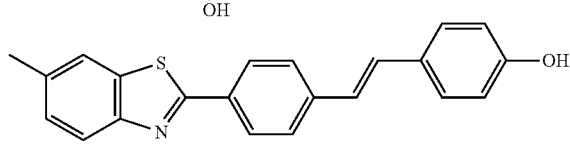

Prepared as described in the Alkene Formation section using diethyl 4-(6-methylbenzothiazol-2-yl)benzylphosphonate (0.10 g, 0.266 mmol) in dry THF (10 ml), potassium t-butoxide (0.063 g, 0.559 mmol) and 4-hydroxybenzaldehyde (0.033 g, 0.266 mmol) in dry THF (5 ml) to give the title compound (0.061 g, 67%) as a pale orange solid after work-up and flash chromatography (2:1 Hexane/EtOAc).

$^1$H NMR (400 MHz, DMSO-d$_6$) δ 2.45 (s, 3H), 6.79 (d, J=8.3 Hz, 2H), 7.08 (d, J=16.5 Hz, 1H), 7.28 (d, J=16.5 Hz, 1H), 7.34 (d, J=8.2 Hz, 1H), 7.46 (d, J=8.3 Hz, 2H), 7.69 (d, J=8.2 Hz, 2H), 7.88 (s, 1H), 7.91 (d, J=8.2 Hz, 1H), 8.02 (d, J=8.2 Hz, 2H), 9.57 (s, 1H); $^{13}$C NMR (100 MHz, DMSO-d$_6$) δ 21.49, 116.14, 122.21, 122.77, 124.61, 127.19, 127.71, 127.85, 128.33, 128.53, 128.69, 130.96, 131.76, 135.67, 140.98, 152.33, 158.25, 166.34.

2-{4-[2-(3-Methoxyphenyl)-vinyl]-phenyl}-6-methylbenzothiazole

Book No.: SK2033-29

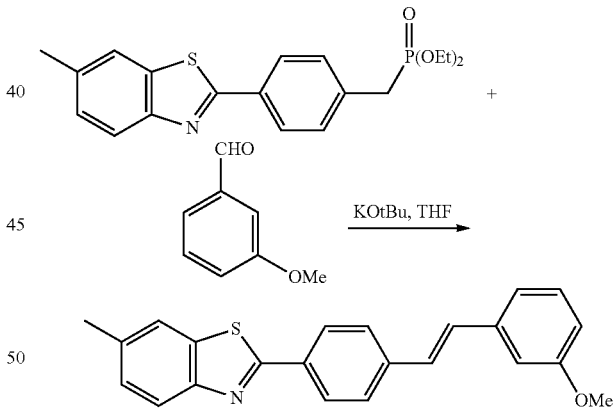

Prepared as described in the Alkene Formation section using diethyl 4-(6-methoxybenzothiazol-2-yl)benzylphosphonate (0.05 g, 0.133 mmol) in dry THF (5 ml), potassium t-butoxide (0.03 g, 0.266 mmol) and 3-methoxybenzaldehyde (0.018 g, 0.133 mmol) in dry THF (5 ml) to give the title compound (0.016 g, 34%) as a yellow solid after work-up and flash chromatography (4:1 Hexane/Et$_2$O).

$^1$H NMR (250 MHz, CDCl$_3$) δ 2.49 (s, 3H), 3.86 (s, 3H), 6.85 (dd, J=8.2, 1.8 Hz, 1H), 7.61 (d, J=8.2 Hz, 2H), 7.68 (s, 1H), 7.94 (d, J=8.2 Hz, 1H), 8.06 (d, J=8.2 Hz, 2H); $^{13}$C NMR (62.5 MHz, CDCl$_3$) δ 21.6, 55.31, 111.90, 113.81, 119.46, 121.39, 122.68, 127.04, 127.77, 128.00, 129.76, 130.18, 132.82, 135.21, 135.41, 138.44, 139.71, 152.35, 159.96, 166.62.

Imidazo[1,2-a]pyridine Intermediates

4-Bromomethylacetophenone

Book No.: SKT05-187

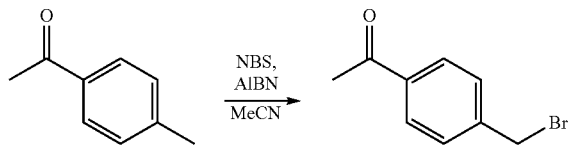

To a stirred solution of 4-methylacetophenone (2.16 g, 15.32 mmol) in MeCN (20 ml) was added N-bromosuccinimide (3.00 g, 16.85 mmol) and AIBN (0.25 g, 1.53 mmol) under an atmosphere of argon. The reaction mixture was then heated at 90° C. for 1.5 h. On cooling to room temperature, the solvent was removed under reduced pressure and toluene (25 ml) was added to the residue which was then filtered under vacuum. The filtrate was then concentrated and purified by flash chromatography (10:1 Hexane/EtOAc followed by 5:1 Hexane/EtOAc) to give the title compound (2.80 g, 86%) as a colourless oil.

IR 3034, 3003, 2969, 1683, 1606, 1573, 1412, 1358, 1267, 1229, 1202, 1181, 1102, 1075, 1017, 959, 843, 821 cm$^{-1}$; $^1$H NMR (250 MHz, CDCl$_3$) δ 2.59 (s, 3H), 4.49 (s, 2H), 7.47 (d, J=8.2 Hz, 2H), 7.92 (d, J=8.2 Hz, 2H); $^{13}$C NMR (62.5 MHz, CDCl$_3$) δ 26.77, 32.22, 128.89, 129.29, 136.87, 142.85, 197.50.

(4-Acetylbenzyl)-phosphonic acid diethyl ester

Book No.: SKT05-191

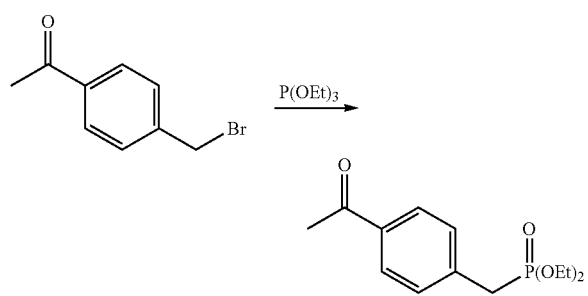

A stirred mixture of 4-bromomethylacetophenone (2.50 g, 11.74 mmol) and triethyl phosphite (10 ml) was heated at 140° C. for 3 h. On cooling to room temperature, the excess triethyl phosphite was removed by distillation and the residue was purified by flash chromatography (EtOAc) to give the title compound (2.49 g, 79%) as a colourless oil.

$^1$H NMR (250 MHz, CDCl$_3$) δ 1.19 (t, J=7.0 Hz, 6H), 2.53 (s, 3H), 3.15 (d, J$_{HP}$=22.2 Hz, 2H), 3.91-4.02 (m, 4H), 7.34 (d, J=7.9 Hz, 2H), 7.85 (d, J=7.9 Hz, 2H); $^{13}$C NMR (62.5 MHz, CDCl$_3$) δ 16.37 (d, J$_{CP}$=5.9 Hz), 26.62, 33.94 (d, J$_{CP}$=137.7 Hz), 62.27 (d, J$_{CP}$=6.8 Hz), 128.56, 129.99 (d, J$_{CP}$=5.9 Hz), 135.73 (d, J$_{CP}$=2.9 Hz), 137.43 (d, J$_{CP}$=9.8 Hz), 197.70.

(4-Bromoacetylbenzyl)-phosphonic acid diethyl ester

Book No.: SKT06-87

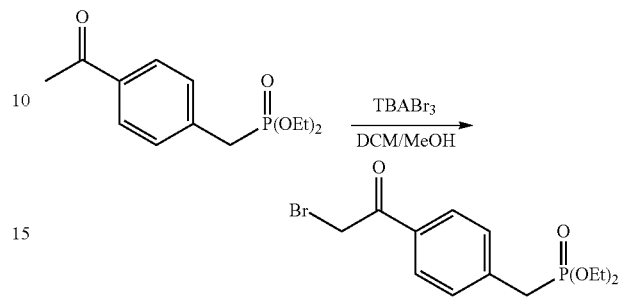

To a stirred solution of (4-acetylbenzyl)-phosphonic acid diethyl ester (2.56 g, 9.48 mmol) in DCM (100 ml) and MeOH (40 ml) at room temperature was added tetra-n-butylammonium tribromide (5.03 g, 10.43 mmol) followed by a drop of concentrated hydrochloric acid. The reaction mixture was stirred at room temperature for 18 h. The solvents were then removed under reduced pressure and the residue was partitioned between Et$_2$O (100 ml) and sat. NaHCO$_3$ (60 ml). The aqueous phase was separated and the organic phase was washed with brine (60 ml) and dried (Na$_2$SO$_4$). The solvent was removed under reduced pressure to give a pale yellow oil which was purified by flash chromatography (3:1 EtOAc/DCM) to give the title compound (2.01 g, 61%) as a colourless oil.

$^1$H NMR (250 MHz, CDCl$_3$) δ 1.23 (t, J=7.0 Hz, 6H), 3.19 (d, J$_{HP}$=22.3 Hz, 2H), 3.95-4.10 (m, 4H), 4.42 (s, 2H), 7.41 (d, J=8.2 Hz, 2H), 7.92 (d, J=8.2 Hz, 2H); $^{13}$C NMR (62.5 MHz, CDCl$_3$) δ 16.38 (d, J$_{CP}$=5.9 Hz), 31.01, 34.08 (d, J$_{CP}$=137 Hz), 39.78, 62.35 (d, J$_{CP}$=6.8 Hz), 129.17, 129.94, 130.24, 130.33, 132.58 (d, J$_{CP}$=2.9 Hz), 138.55 (d, J$_{CP}$=8.8 Hz), 139.21 (d, J$_{CP}$=8.8 Hz), 190.84.

Diethyl[4-(6-methylimidazo[1,2-a]pyridin-2-yl)benzyl]phosphonate

Book No.: SKT06-31

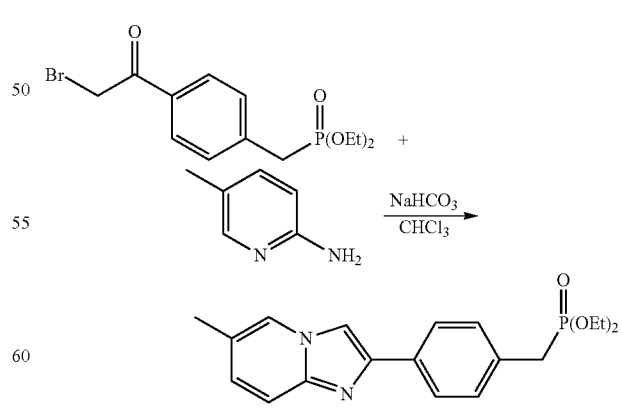

To a stirred mixture of 2-amino-5-picoline (0.62 g, 5.76 mmol) and sodium bicarbonate (0.48 g, 5.76 mmol) in CHCl$_3$ (35 ml) was added a solution of (4-bromoacetylbenzyl)-phosphonic acid diethyl ester in CHCl$_3$ (8 ml). The stirred reaction mixture was heated under reflux for 17 h. After cooling to room temperature, CHCl$_3$ (20 ml) was added to the reaction mixture and this was then washed with water (60 ml). The separated aqueous phase was then extracted with CHCl$_3$ (2×50 ml) and the combined organics were washed with brine (80 ml) and dried (Na$_2$SO$_4$). The solvent was removed under reduced pressure to give an orange, viscous oil which was purified by flash chromatography (EtOAc followed by EtOAc/MeOH 20:1) to give the title compound (1.29 g, 63%) as a colourless solid.

$^1$H NMR (250 MHz, CDCl$_3$) δ 1.23 (t, J=7.0 Hz, 6H), 2.32 (s, 3H), 3.18 (d, J$_{H,P}$=21.7 Hz, 2H), 4.00 (m, 4H), 7.05 (d, J=9.2 Hz, 1H), 7.35 (d, J=7.9 Hz, 2H), 7.57 (d, J=9.2 Hz, 1H), 7.76 (s, 1H), 7.89 (d, J=7.9 Hz, 2H), 7.90 (s, 1H); $^{13}$C NMR (62.5 MHz, CDCl$_3$) δ 16.41 (d, J$_{C,P}$=5.8 Hz), 18.15, 33.65 (d, J$_{C,P}$=138.7 Hz), 62.24 (d, J$_{C,P}$=6.8 Hz), 107.87, 116.76, 122.10, 123.33, 126.05, 127.96, 130.15 (d, J$_{C,P}$=6.8 Hz), 131.13 (d, J$_{C,P}$=8.8 Hz), 132.57 (d, J$_{C,P}$=3.9 Hz), 144.73, 145.08.

2-Hydroxy-4-nitrobenzaldehyde

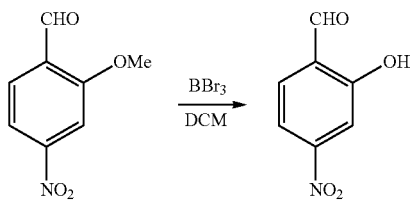

Prepared as described in the Demethylation section above using 2-methoxy-4-nitrobenzaldehyde (1.0 g, 5.52 mmol) in dry DCM (25 ml) and BBr$_3$ in DCM (1.0 M, 16 ml, 16 mmol) to give the title compound (0.70 g, 78%) as tan plates after recrystallisation from EtOH.

$^1$H NMR (250 MHz, CDCl$_3$) δ 7.76-7.85 (m, 3H), 10.04 (s, 1H), 11.14 (s, 1H); $^{13}$C NMR (100.5 MHz, CDCl$_3$) δ 113.49, 114.36, 123.70, 134.79, 152.47, 161.91, 196.01.

2-(2-Fluoroethoxy)-4-nitrobenzaldehyde

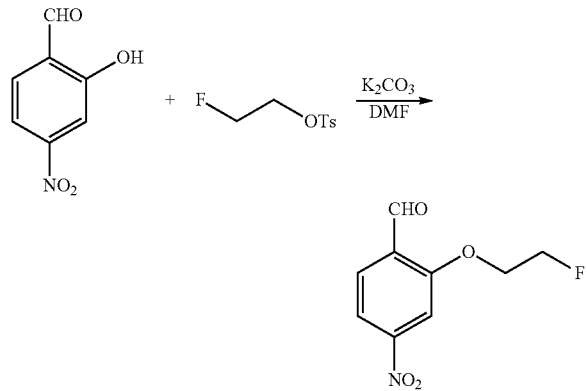

To a stirred solution of 2-hydroxy-4-nitrobenzaldehyde (0.50 g, 2.99 mmol) in dry DMF (15 ml) was added K$_2$CO$_3$ (1.24 g, 8.98 mmol) at room temperature under an atmosphere of argon. To this stirred suspension was added dropwise 2-fluoroethyl-(4-methylbenzene)sulphonate (0.78 g, 3.59 mmol). The reaction mixture was heated to 100° C. for 6 h. The cooled reaction mixture was added to water (250 ml) and extracted with EtOAc (3×75 ml). The combined organics were washed with brine (50 ml), dried (Na$_2$SO$_4$) and the solvent removed under reduced pressure to give a brown solid, which was purified by flash chromatography (3:1 DCM/Hexane) to give the title compound (0.493 g, 77%) as a yellow solid.

$^1$H NMR (250 MHz, CDCl$_3$) δ 4.47 (dist d of t, J$_{HF}$=27 Hz, J$_{HH}$=3.7 Hz, 2H), 4.87 (dist d of t, J$_{HF}$=47 Hz, J$_{HH}$=3.6 Hz, 2H), 7.86 (s, 1H), 7.91 (d, J=9.1 Hz, 1H), 8.01 (d, J=8.2 Hz, 1H), 10.56 (s, 1H); $^{13}$C NMR (100.5 MHz, CDCl$_3$) δ 68.58 (d, J$_{CF}$=20.5 Hz), 81.15 (d, J$_{CF}$=173 Hz), 108.05, 116.25, 128.87, 129.70, 152.05, 160.64, 188.11.

2-([2-tert-Butyldimethylsiloxy]ethoxy)-4-nitrobenzaldehyde

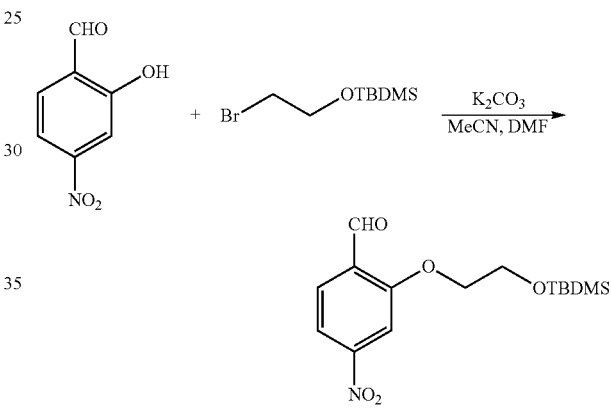

To a stirred suspension of 2-hydroxy-4-nitrobenzaldehyde (0.500 g, 2.992 mmol) and anhydrous potassium carbonate (0.621 g, 4.488 mmol) in dry MeCN (20 ml) at room temperature was added 2-bromo-1-tert-butyldimethylsiloxyethane (83%, 1.293 g, 4.488 mmol), and the reaction mixture was heated under reflux for 40 min which resulted in the appearance of a thick, dark red precipitate. The reaction mixture was left to cool to room temperature and dry DMF (10 ml) was added. The reaction mixture was heated at 100° C. for 4 h and on cooling was added to water (250 ml) and extracted with EtOAc (3×80 ml). The combined organic extracts were washed with water (3×100 ml), brine (100 ml) and dried (Na$_2$SO$_4$) and the solvent was removed under reduced pressure to give a light brown solid which was purified by flash chromatography (2:1 Hexane/Et$_2$O). Recrystallisation from hexane gave the title compound (0.621 g, 64%) as pale yellow crystals.

$^1$H NMR (250 MHz, CDCl$_3$) δ 0.08 (s, 6H), 0.87 (s, 9H), 4.05 (t, J=4.6 Hz, 2H), 4.30 (t, J=4.6 Hz, 2H), 7.83-7.98 (m, 3H), 10.54 (s, 1H); $^{13}$C NMR (62.5 MHz, CDCl$_3$) δ −5.34, 18.32, 25.79, 61.61, 71.08, 108.64, 115.63, 128.81, 129.37, 152.12, 161.53, 188.43.

Method adapted from Kuwabe et al.

4-[2-(Hydroxyethyl)(methyl)amino]benzaldehyde

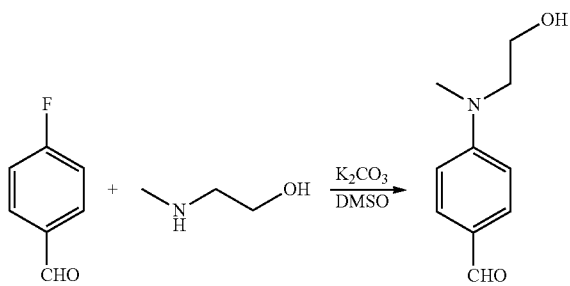

To a stirred solution of 4-fluorobenzaldehyde (5.0 g, 40.29 mmol) and 2-(methylamino)ethanol (3.63 g, 48.34 mmol) in dry DMSO (35 ml) was added $K_2CO_3$ (6.68 g, 48.34 mmol) under an atmosphere of argon. The reaction mixture was then heated at 120° C. for 3 d. The cooled reaction mixture was then added to water (400 ml) and extracted with EtOAc (7×100 ml). The combined organics were washed with brine (2×100 ml), dried ($Na_2SO_4$), and the solvent removed under reduced pressure to give a viscous orange oil which slowly solidified at room temperature. This solid was dissolved in DCM (40 ml) and this solution was then added to hexane (200 ml) to precipitate a yellow solid that was collected by filtration under vacuum. Recrystallisation from toluene gave the title compound (4.47 g, 62%) as small yellow plates.

$^1$H NMR (250 MHz, $CDCl_3$) δ 2.73 (br s, 1H), 3.07 (s, 3H), 3.58 (t, J=5.5 Hz, 2H), 3.82 (t, J=5.5 Hz, 2H), 6.69 (d, J=8.8 Hz, 2H), 7.62 (d, J=8.8 Hz, 2H), 9.60 (s, 1H); $^{13}$C NMR (100.5 MHz, $CDCl_3$) δ 39.25, 54.38, 59.92, 111.16, 125.05, 132.24, 153.96, 190.58.

Method adapted from Lo Meo et al.

4-[N-(2-tert-butyldimethylsilylsilanyloxyethyl)-N-methyl)amino]benzaldehyde

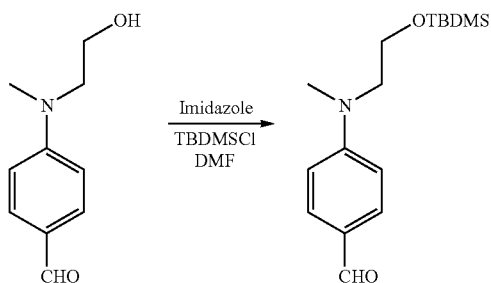 [SMILES: CN(CCO)c1ccc(C=O)cc1 ; CN(CCO[Si](C)(C)C(C)(C)C)c1ccc(C=O)cc1]

To a stirred solution of 4-[2-(hydroxyethyl)(methyl)amino]benzaldehyde (1.50 g, 8.38 mmol) in dry DMF (35 ml) was added imidazole (1.71 g, 25.14 mmol) under an atmosphere of argon. The reaction mixture was stirred at room temperature until everything was in solution then tert-butyldimethylsilyl chloride (2.53 g, 16.76 mmol) was added. The reaction mixture was stirred at room temperature for 3 d, added to water (300 ml) and extracted with $Et_2O$ (3×40 ml). The combined organics were washed with water (3×60 ml), brine (60 ml), dried ($Na_2SO_4$) and the solvent removed under reduced pressure to give a yellow oil. This was purified by flash chromatography to give the title compound (2.22 g, 90%) as a yellow oil.

$^1$H NMR (250 MHz, $CDCl_3$) δ −0.01 (s, 6H), 0.85 (s, 9H), 3.09 (s, 3H), 3.57 (t, J=5.5 Hz, 2H), 3.79 (t, J=5.5 Hz, 2H), 6.71 (d, J=8.8 Hz, 2H), 7.71 (d, J=8.8 Hz, 2H), 9.72 (s, 1H); $^{13}$C NMR (100.5 MHz, $CDCl_3$) δ −5.42, 18.23, 25.85, 39.56, 54.52, 60.43, 111.03, 125.16, 132.10, 153.64, 190.31.

4-[N-(2-tert-butyldimethylsilylsilanyloxyethyl)-N-methyl-4-{(E)-2-[4-(6-methylimidazo[1,2-a]pyridin-2-yl)phenyl]ethenyl}aniline Book No.: SKT07-107

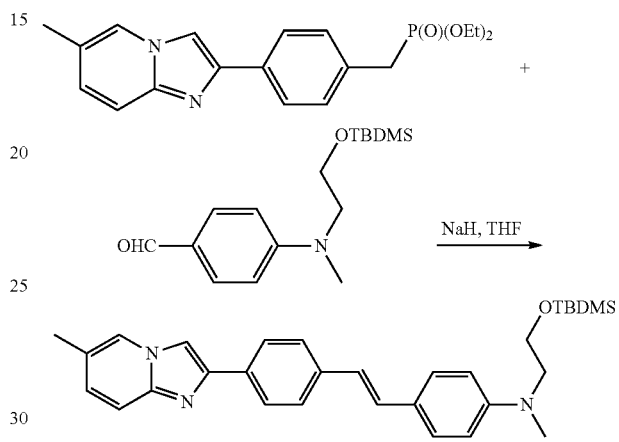

Prepared as described in the Alkene Formation section using sodium hydride (60% dispersion in oil, 27 mg, 0.67 mmol), diethyl[4-(6-methylimidazo[1,2-a]pyridin-2-yl)benzyl phosphonate (200 mg, 0.559 mmol) and 4-[N-(2-tert-butyldimethylsilylsilanyloxyethyl)-N-methyl)amino]benzaldehyde (164 mg, 0.559 mmol) in dry THF (15 ml) to give the title compound (210 mg, 75%) as a pale yellow solid after work-up and flash chromatography (4:1 DCM/EtOAc).

$^1$H NMR (250 MHz, $CDCl_3$) δ 0.02 (s, 6H), 0.88 (s, 9H), 2.32 (s, 3H), 3.02 (s, 3H), 3.49 (t, J=5.5 Hz, 2H), 3.77 (t, J=5.5 Hz, 2H), 6.68 (d, J=7.9 Hz, 2H), 6.91 (d, J=15.6 Hz, 1H), 7.04 (d, J=7.9 Hz, 1H), 7.08 (d, J=15.6 Hz, 1H), 7.40 (d, J=8.5 Hz, 2H), 7.53 (d, J=8.5 Hz, 2H), 7.54-7.59 (m, 1H), 7.76 (s, 1H), 7.89-7.92 (m, 3H); $^{13}$C NMR (100.5 MHz, $CDCl_3$) δ −5.32, 18.20, 18.32, 25.95, 39.30, 54.78, 60.51, 107.79, 111.86, 116.65, 122.15, 123.35, 123.73, 125.29, 126.11, 126.33, 127.74, 127.99, 128.80, 131.89, 137.86, 144.65, 145.19, 148.81.

6-Methyl-2-(4-{(E)-2-[4-nitro-2-(2-tert-butyldimethylsilyloxyethoxy)phenyl]ethenyl}phenyl)imidazo[1,2-a]pyridine Book No.: SKT08-115

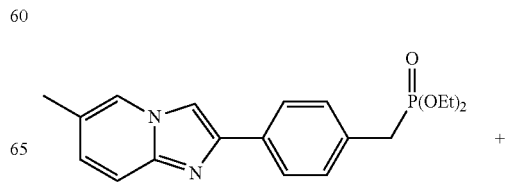

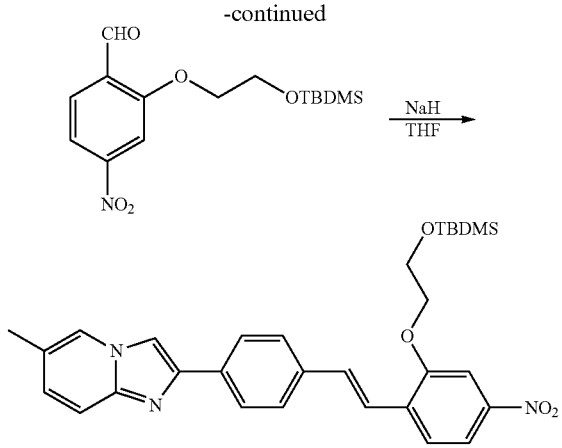

Prepared as described in the Alkene Formation section using sodium hydride (40 mg, 60% dispersion in mineral oil, 1.00 mmol), diethyl [4-(6-methylimidazo[1,2-a]pyridin-2-yl)benzyl]phosphonate (0.300 g, 0.837 mmol) and 2-([2-tert-butyldimethylsiloxy]ethoxy)-4-nitrobenzaldehyde (0.272 g, 0.837 mmol) in dry THF (30 ml) to give the title compound (0.285 g, 64%) as an orange solid after work-up and flash chromatography (2:1 EtOAc/Hexane).

$^1$H NMR (400 MHz, DMSO-$d_6$) δ 0.13 (s, 6H), 0.92 (s, 9H), 3.96 (t, J=5.1 Hz, 2H), 4.10 (t, J=5.1 Hz, 2H), 7.29 (d, J=16.4 Hz, 1H), 7.54 (d, J=16.4 Hz, 1H), 7.63 (d, J=8.2 Hz, 2H), 7.72 (d, J=8.6 Hz, 1H), 7.79 (d, J=2.0 Hz, 1H), 7.83 (s, 1H), 7.86 (dd, J=8.2, 2.0 Hz, 1H), 7.93 (br s, 1H), 7.98 (d, J=8.2 Hz, 2H); $^{13}$C NMR (100.5 MHz, DMSO-$d_6$) δ −5.20, 18.17, 18.40, 25.90, 61.78, 70.57, 107.17, 108.19, 116.27, 116.82, 121.30, 122.32, 123.33, 126.08, 126.19, 127.51, 128.17, 132.89, 133.58, 133.97, 136.40, 144.85, 147.37, 156.20 (1 missing).

Methanesulphonic acid 2-(2-{(E)-2-[4-(6-methyl-1H-imidazo[1,2-a]pyridin-2-yl)phenyl]vinyl}-5-nitrophenoxy)ethyl ester Book No.: SKT08-175

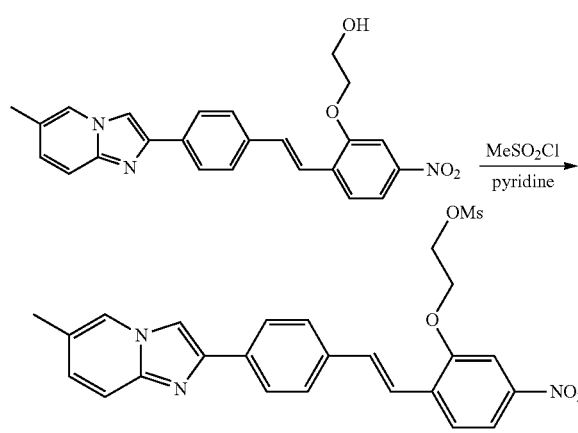

To a stirred solution of 2-(2-{(E)-2-[4-(6-methylimidazo[1,2-a]pyridin-2-yl)phenyl]ethenyl}-5-nitrophenoxy)ethanol (40.2 mg, 0.0968 mmol) in dry pyridine (4 ml) at room temperature was added methanesulphonyl chloride (15.9 μl, 0.203 mmol). After 2.25 h at room temperature, water (25 ml) was added to give a yellow precipitate which was collected by vacuum filtration, washed with water (2×10 ml) and then dried in the oven at 85° C. for 3 h. The yellow solid was purified by flash chromatography (1:1 EtOAc/DCM) to give the title compound (31 mg, 65%) as a yellow solid.

$^1$H NMR (400 MHz, DMSO-$d_6$) δ 2.28 (s, 3H), 3.29 (s, 3H), 4.49-4.52 (m, 2H), 4.69-4.71 (m, 2H), 7.11 (dd, J=9.0, 1.9 Hz, 1H), 7.49 (d, J=9.0 Hz, 1H), 7.55 (d, J=16.4 Hz, 1H), 7.60 (d, J=16.4 Hz, 1H), 7.71 (d, J=8.6 Hz, 2H), 7.84 (d, J=2.4 Hz, 1H), 7.90 (dd, J=8.6, 1.9 Hz, 1H), 7.98 (d, J=8.6 Hz, 2H), 7.60-8.00 (m, 1H), 8.31 (br s, 1H), 8.35 (s, 1H); $^{13}$C NMR (100.5 MHz, DMSO-$d_6$) δ 17.95, 37.54, 67.63, 68.98, 108.18, 109.72, 116.46, 116.99, 121.30, 122.09, 124.70, 126.31, 127.54, 127.87, 128.59, 133.61, 133.93, 134.67, 136.42, 144.14, 144.45, 147.39, 155.69.

Imidazo[1,2-a]pyridine Compounds

6-Methyl-2-{4-[(E)-2-(4-nitrophenyl)ethenyl]phenyl}imidazo[1,2-a]pyridine

Book No.: SKT06-117

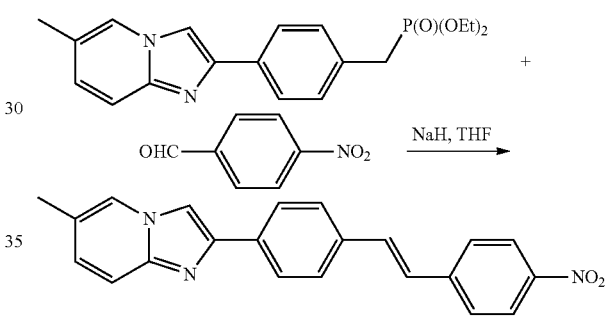

Prepared as described in the Alkene Formation section using sodium hydride (60% dispersion in mineral oil, 7 mg, 0.307 mmol), diethyl[4-(6-methylimidazo[1,2-a]pyridin-2-yl)benzyl phosphonate (100 mg, 0.279 mmol) and 4-nitrobenzaldehyde (42 mg, 0.279 mmol) in THF (5 ml) to give the title compound (24 mg, 24%) as a yellow solid after work-up and flash chromatography (100:1 DCM/MeOH).

$^1$H NMR (250 MHz, DMSO-$d_6$) δ 2.29 (s, 3H), 7.12 (d, J=8.8 Hz, 1H), 7.49 (d, J=15.6 Hz, 1H), 7.50 (d, J=8.5 Hz, 1H), 7.58 (d, J=15.6 Hz, 1H), 7.75 (d, J=8.2 Hz, 2H), 7.88 (d, J=8.5 Hz, 2H), 8.01 (d, J=7.5 Hz, 2H), 8.25 (d, J=8.5 Hz, 2H), 8.33 (s, 1H), 8.37 (s, 1H).

6-Methyl-2-{4-[(E)-2-pyridin-4-ylethenyl]phenyl}imidazo[1,2-a]pyridine

Book No.: SKT06-161

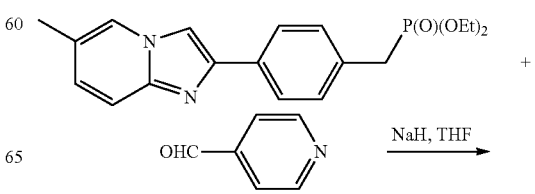

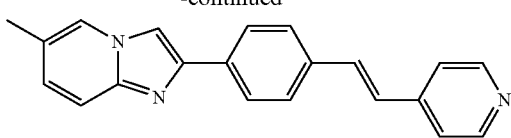

Prepared as described in the Alkene Formation section using sodium hydride (60% dispersion in mineral oil, 25 mg, 0.615 mmol), diethyl[4-(6-methylimidazo[1,2-a]pyridin-2-yl)benzyl phosphonate (0.20 g, 0.559 mmol) and pyridine-4-aldehyde (0.06 g, 0.559 mmol) in dry THF (10 ml) to give the title compound (0.074 g, 42%) as a pale orange solid after work-up and flash chromatography (7:7:1 DCM/EtOAc/MeOH).

IR 3132, 3022, 2919, 1629, 1606, 1590, 1417, 1340, 1273, 1213, 1186, 980, 971, 874, 844, 813, 803, 750 cm$^{-1}$; $^1$H NMR (250 MHz, DMSO-d$_6$) δ 2.29 (s, 3H), 7.12 (dd, J=9.5, 0.6 Hz, 1H), 7.29 (d, J=16.8 Hz, 1H), 7.50 (dd, J=9.5, 0.9 Hz, 1H), 7.52-7.65 (m, 3H), 7.73 (d, J=7.3 Hz, 2H), 8.00 (d, J=7.3 Hz, 2H), 8.34 (dd, J=8.9, 0.6 Hz, 2H), 8.53-8.56 (m, 2H).

2-{4-[(E)-2-(2-methoxy-4-nitrophenyl)ethenyl]phenyl}-6-methylimidazo[1,2-a]pyridine Book No.: SKT07-81

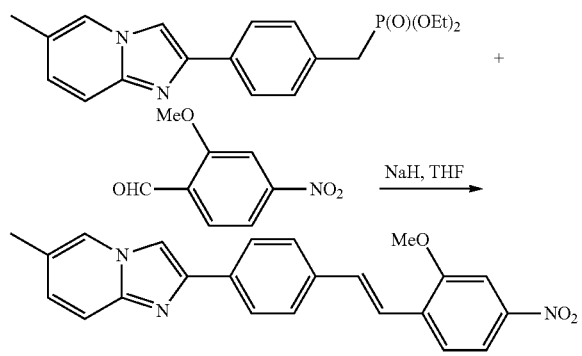

Prepared as described in the Alkene Formation section using sodium hydride (60% dispersion in mineral oil, 33 mg, 0.838 mmol), diethyl[4-(6-methylimidazo[1,2-a]pyridin-2-yl)benzyl phosphonate (250 mg, 0.698 mmol) and 2-methoxy-4-nitrobenzaldehyde (126 mg, 0.698 mmol) in dry THF (15 ml) to give the title compound (199 mg, 74%) as an orange solid after work-up and flash chromatography (25:1 DCM/MeOH).

$^1$H NMR (250 MHz, CDCl$_3$) δ 2.33 (s, 3H), 3.99 (s, 3H), 7.05 (d, J=8.8 Hz, 1H), 7.28 (d, J=16.2 Hz, 1H), 7.50 (d, J=16.2 Hz, 1H), 7.58 (d, J=8.8 Hz, 1H), 7.63 (d, J=8.2 Hz, 2H), 7.71 (d, J=8.8 Hz, 1H), 7.75 (br s, 1H), 7.81 (s, 1H), 7.87 (d, J=8.8 Hz, 1H), 7.91 (s, 1H), 7.97 (d, J=8.2 Hz, 2H); $^{13}$C NMR (62.5 MHz, CDCl$_3$) δ 18.17, 56.08, 105.99, 108.18, 116.27, 116.78, 121.28, 122.45, 123.35, 126.16, 126.27, 127.51, 128.31, 133.03, 133.39, 133.86, 136.45, 144.73, 147.49, 156.81 (1 missing).

2-(4-{(E)-2-[4-nitro-2-(2-fluoroethoxy)phenyl]ethenyl}phenyl)-6-methylimidazo[1,2-a]pyridine Book No.: SKT07-115

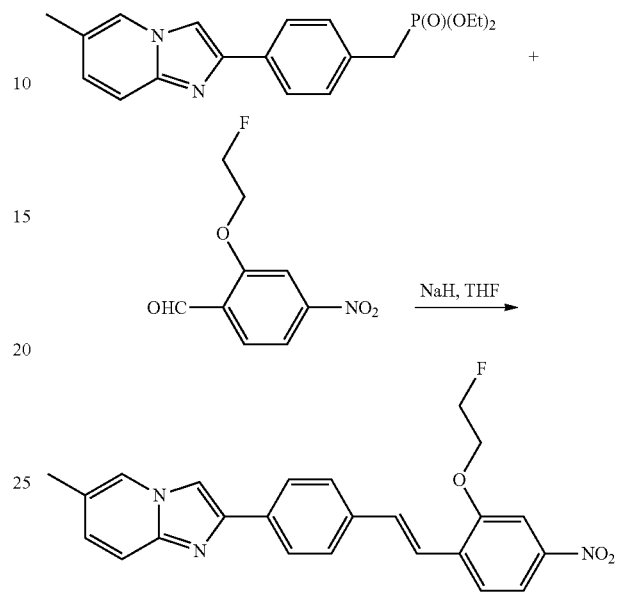

Prepared as described in the Alkene Formation section using sodium hydride (60% dispersion in mineral oil, 27 mg, 0.67 mmol), diethyl[4-(6-methylimidazo[1,2-a]pyridin-2-yl)benzyl phosphonate (200 mg, 0.559 mmol) and 2-(2-fluoroethoxy)-4-nitrobenzaldehyde (119 mg, 0.559 mmol) in dry THF (15 ml) to give the title compound (174 mg, 74%) as an orange solid after work-up and flash chromatography (50:1 DCM/MeOH).

$^1$H NMR (250 MHz, CDCl$_3$) δ 2.32 (s, 3H), 4.39 (dist d of t, J$_{HF}$=28 Hz, J$_{HH}$=3.7 Hz, 2H), 4.89 (dist d of t, J$_{HF}$=47 Hz, J$_{HH}$=3.7 Hz, 2H), 7.04 (d, J=8.8 Hz, 1H), 7.33 (d, J=16.8 Hz, 1H), 7.51 (d, J=16.2 Hz, 1H), 7.55 (d, J=9.2 Hz, 1H), 7.62 (d, J=7.9 Hz, 2H), 7.71-7.75 (m, 2H), 7.82 (s, 1H), 7.88-7.91 (m, 2H), 7.96 (d, J=8.2 Hz, 2H); $^{13}$C NMR (100.5 MHz, CDCl$_3$) δ 18.22, 68.25 (d, J$_{CF}$=20.5 Hz), 81.52 (d, J$_{CF}$=172 Hz), 96.13, 107.15, 108.24, 116.79, 116.92, 121.05, 122.46, 123.36, 126.28, 126.56, 127.60, 128.35, 133.52, 133.86, 136.33, 144.74, 147.23, 155.53 (1 missing).

3-(2-fluoroethoxy)-4-{(E)-2-[4-(6-methylimidazo[1,2-a]pyridin-2-yl)phenyl]ethenyl}aniline Book No.: SKT07-131

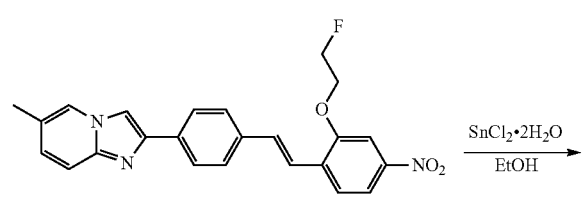

-continued

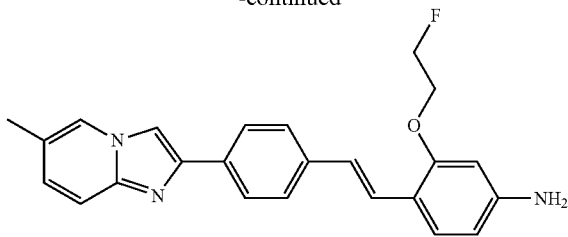

Prepared as described in the Nitro Reduction section using 2-(4-{(E)-2-[4-nitro-2-(2-fluoroethoxy)phenyl]ethenyl}phenyl)-6-methylimidazo[1,2-a]pyridine (81 mg, 0.194 mmol) and tin (II) dichloride dihydrate (219 mg, 0.970 mmol) in EtOH (12 ml) to give the title compound (36 mg, 48%) as an orange solid after work-up and flash chromatography (2:1 EtOAc/DCM).

$^1$H NMR (250 MHz, CDCl$_3$) δ 2.31 (s, 3H), 3.79 (br s, 2H), 4.22 (dist d of t, $J_{HF}$=27 Hz, $J_{HH}$=3.7 Hz, 2H), 4.81 (dist d of t, $J_{HF}$=48 Hz, $J_{HH}$=3.7 Hz, 2H), 6.23 (s, 1H), 6.34 (d, J=7.3 Hz, 1H), 6.99 (d, J=16.5 Hz, 1H), 7.02 (m, 1H), 7.39 (d, J=3.7 Hz, 1H), 7.44 (d, J=3.7 Hz, 1H), 7.55 (d, J=16.5 Hz, 1H), 7.55 (m, 2H), 7.77 (s, 1H), 7.88-7.91 (m, 3H); $^{13}$C NMR (100 MHz, DMSO-d$_6$) δ 17.97, 68.02 (d, $J_{CF}$=18.7 Hz), 82.76 (d, $J_{CF}$=166.5 Hz), 98.94, 107.89, 109.04, 114.47, 116.42, 121.81, 123.63, 124.21, 124.63, 126.24, 126.33, 128.18, 128.24, 132.55, 138.34, 144.69, 150.64, 157.41 (1 missing).

N-(2-Hydroxyethyl)-N-methyl-4-{(E)-2-[4-(6-methylimidazo[1,2-a]pyridin-2-yl)phenyl]ethenyl}aniline Book No.: SKT07-113

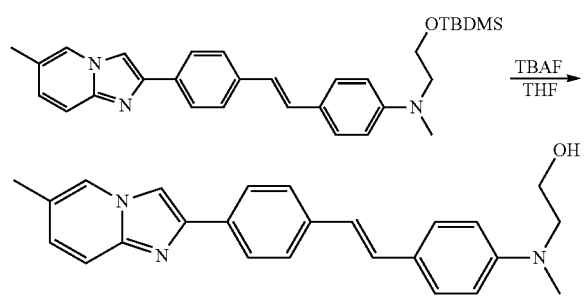

To a stirred suspension of 4-[N-(2-tert-butyldimethylsilylsilanyloxyethyl)-N-methyl-4-{(E)-2-[4-(6-methylimidazo[1,2-a]pyridin-2-yl)phenyl]ethenyl}aniline (0.18 g, 0.362 mmol) in a mixture of dry THF (5 ml) and dry DMF (3 ml) at 0-5° C. was added a solution of TBAF in THF (1 M, 800 µl, 0.800 mmol). The reaction mixture was stirred at 0-5° C. for 5 min and then left to rise to room temperature and stirred for a further 50 min. A solution of saturated ammonium chloride (25 ml) was added to the reaction mixture and this was extracted with DCM/MeOH (1:1, 5×30 ml). The combined organics were washed with brine (40 ml), dried (Na$_2$SO$_4$) and the solvent removed under reduced pressure to give a yellow oil that slowly solidified at room temperature. The solid was purified by flash chromatography (10:1 DCM/MeOH) to give the title compound (0.136 g, 98%) as a yellow solid.

$^1$H NMR (250 MHz, CDCl$_3$) δ 2.28 (s, 3H), 2.96 (s, 3H), 3.42 (t, J=5.2 Hz, 2H), 3.54 (t, J=5.2 Hz, 2H), 4.71 (t, J=5.2 Hz, 1H), 6.70 (d, J=8.5 Hz, 2H), 6.96 (d, J=16.2 Hz, 1H), 7.08-7.19 (m, 2H), 7.42 (d, J=8.5 Hz, 2H), 7.48 (d, J=9.5 Hz, 1H), 7.57 (d, J=8.2 Hz, 2H), 7.90 (d, J=8.2 Hz, 2H), 8.29 (s, 2H); $^{13}$C NMR (100.5 MHz, DMSO-d$_6$) δ 17.96, 39.04, 54.66, 58.68, 109.09, 112.24, 116.44, 121.80, 123.47, 124.60, 124.99, 126.19, 126.53, 128.07, 128.23, 129.13, 132.75, 137.70, 144.42, 144.69, 149.42

2-(2-{(E)-2-[4-(6-methylimidazo[1,2-a]pyridin-2-yl)phenyl]ethenyl}-5-nitrophenoxy)ethanol Book No.: SKT08-137

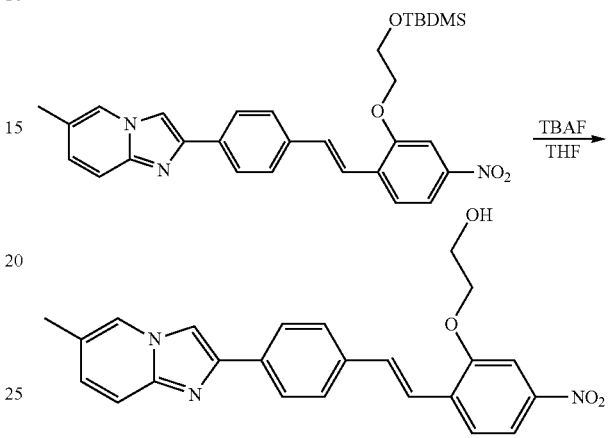

To a stirred solution of 6-methyl-2-(4-{(E)-2-[4-nitro-2-(2-tert-butyldimethylsiloxyethoxy)phenyl]ethenyl}phenyl)imidazo[1,2-a]pyridine (0.200 g, 0.377 mmol) in dry THF (7 ml) at 0-5° C. was added dropwise TBAF (1 M in THF, 0.83 ml, 0.83 mmol) over 5 min. The reaction mixture was stirred at 0-5° C. for 5 min, and then the cooling bath was removed. After 1.5 h, saturated NH$_4$Cl (15 ml) was added and the mixture was transferred to a separating funnel and extracted with DCM/MeOH (3:1, 5×40 ml). The combined organic extracts were washed with brine (2×60 ml) and dried (Na$_2$SO$_4$) and the solvent was removed under reduced pressure to give an orange residue which was purified by flash chromatography (10:1 EtOAc/Hexane) to give the title compound (0.102 g, 65%) as an orange solid.

$^1$H NMR (400 MHz, DMSO-d$_6$) δ 2.27 (s, 3H), 3.81-3.88 (m, 2H), 4.19-4.24 (m, 2H), 5.11 (t, J=5.5 Hz, 1H), 7.11 (d, J=9.0 Hz, 1H), 7.49 (d, J=9.0 Hz, 1H), 7.57 (s, 2H), 7.70 (d, J=7.8 Hz, 2H), 7.81 (s, 1H), 7.85 (d, J=8.2 Hz, 1H), 7.95 (d, J=8.6 Hz, 1H), 7.98 (d, J=7.8 Hz, 2H), 8.30 (s, 1H), 8.34 (s, 1H); $^{13}$C NMR (100 MHz, DMSO-d$_6$) δ 17.99, 59.95, 71.52, 107.75, 109.72, 116.41, 116.53, 121.44, 122.02, 124.69, 126.25, 127.27, 127.95, 128.50, 133.51, 133.67, 134.67, 136.40, 144.18, 144.45, 147.35, 156.44.

Compounds where -Q- is —N═N—

Benzothiazole Intermediates

N-(3-methoxyphenyl)-4-nitrobenzamide

Book No.: LS-T203

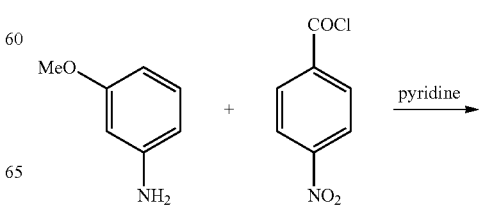

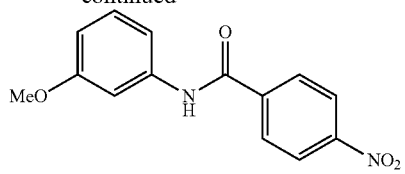

Prepared as described in the Amide Coupling section.
Orange solid (87%). $^1$H NMR (400 MHz, CDCl$_3$) δ 3.83 (s, 3H), 6.74 (dd, J=2.4 Hz, 8.3 Hz, 1H), 7.10 (d, J=8.3 Hz, 1H), 7.28-7.38 (m, 1H), 7.38 (s, 1H), 7.86 (s, 1H), 8.03 (d, J=8.5 Hz, 2H), 8.35 (d, J=8.5 Hz, 2H); LRMS (ESI−) m/z 271.09 (M$^+$−H, 41%), 325.03 (100%).

4-Nitro-N-[3-(trifluoromethoxy)phenyl]benzamide

Book No.: LS-T204

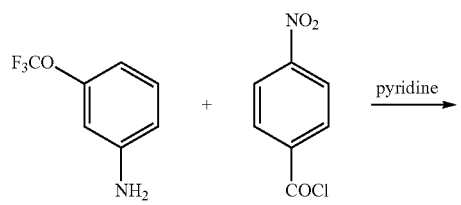

Prepared as described in the Amide Coupling section.
Off-white solid (98%). $^1$H NMR (400 MHz, CDCl$_3$) δ 7.05 (d, J=7.7 Hz, 1H), 7.41 (m, 1H), 7.51 (d, J=8.0 Hz, 1H), 7.69 (s, 1H), 7.89 (s, 1H), 8.02 (d, J=8.5 Hz, 2H), 8.34 (d, J=8.5 Hz, 2H); LRMS (ESI−) m/z 325.02 (M$^+$−H, 100%).

4-Nitro-N-[4-(trifluoromethoxy)phenyl]benzamide

Book No.: LS-T197

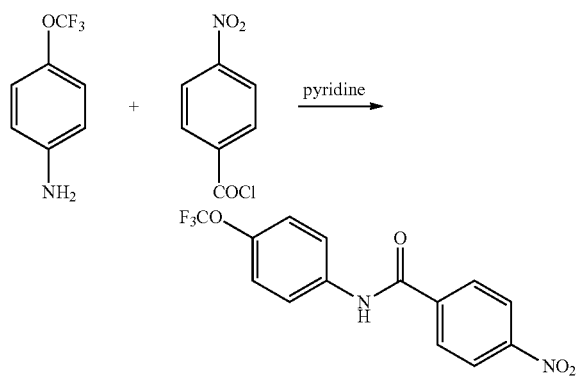

Prepared as described in the Amide Coupling section.
Off-white solid (97%). $^1$H NMR (250 MHz, CDCl$_3$) δ 7.20-7.28 (m, 2H), 7.67 (d, J=9.1 Hz, 2H), 7.88 (bs, 1H), 8.03 (d, J=8.9 Hz, 2H), 8.35 (d, J=8.9 Hz, 2H).

4-Nitro-N-(3-methoxyphenyl)benzenecarbothiamide

Book No.: LS-T205

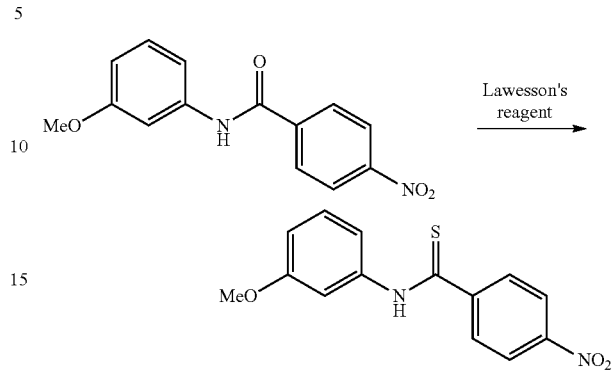

Column chromatography (1:5 EtOAc/40:60 petrol) to give the product as a red/orange solid (82%). $^1$H NMR (400 MHz, CDCl$_3$) δ 3.85 (s, 3H), 6.91-7.07 (m, 2H), 7.17-7.37 (m, 1H), 7.54 (s, 1H), 7.95-8.11 (m, 2H), 8.11-8.29 (m, 2H), 9.09 (s, 1H).

4-Nitro-N-[3-(trifluoromethoxy)phenyl]benzenecarbothiamide

Book No.: LS-T206

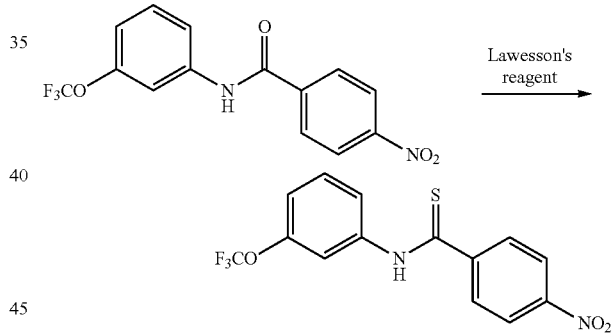

Prepared as described in the Thioamide Formation section.
Column chromatography (1:5 EtOAc/40:60 petrol) to give the product as an orange solid (87%). LRMS (ESI−) m/z 341.00 (M$^+$−H, 85%), 466.92 (100%).

4-Nitro-N-[4-(trifluoromethoxy)phenyl]benzenecarbothiamide

Book No.: LS-T198

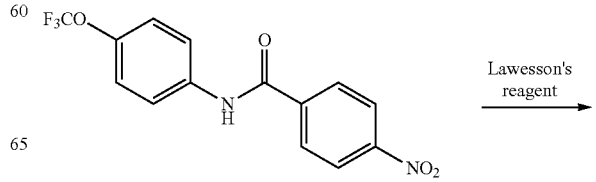

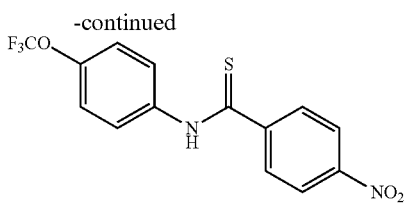

Prepared as described in the Thioamide Formation section.

Column chromatography (1:5 EtOAc/40:60 petrol) to give the product as an orange solid (89%). $^1$H NMR (250 MHz, CDCl$_3$) δ 7.29 (d, J=8.3 Hz, 2H), 7.84 (d, J=8.3 Hz, 2H), 7.93 (d, J=8.5 Hz, 2H), 8.22 (d, J=8.5 Hz, 2H), 9.30 (bs, 1H); $^{13}$C NMR (62.5 MHz, CDCl$_3$) δ 121.3 (2C), 121.9 (2C), 125.2 (2C), 126.1 (2C), 137.4, 147.1, 147.8, 148.7; LRMS (ESI−) m/z 341.04 (M$^+$−H, 100%).

5-Methoxy-2-(4-nitrophenyl)-1,3-benzothiazole

Book No.: LS-T232

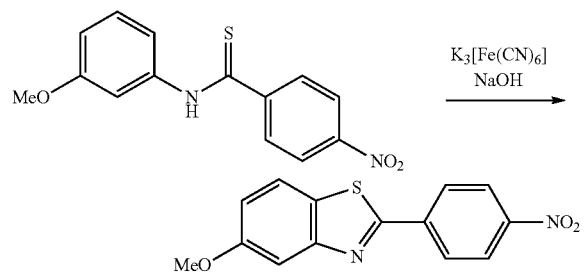

Prepared as described in the Potassium Ferricyanide Benzothiazole Formation section.

Column chromatography (100% toluene) to give the product as a yellow solid (13%). IR (KBr)/cm$^{-1}$: 1603, 1517, 1457, 1344, 1311, 1281, 1159, 1149, 852; $^1$H NMR (250 MHz, CDCl$_3$) δ 3.90 (s, 3H), 7.08 (dd, J=Hz, 2.4 Hz, 8.8 Hz, 1H), 7.55 (d, J=2.4 Hz, 1H), 7.76 (d, J=8.8 Hz, 1H), 8.19 (d, J=8.5 Hz, 2H), 8.30 (d, J=8.5 Hz, 2H); $^{13}$C NMR (100 MHz, CDCl$_3$) δ 55.6, 105.7, 116.8, 122.0, 124.3, 127.4, 128.0, 139.2, 148.9, 155.4, 159.5, 165.9; LRMS (ESI+) m/z 287.42 (M$^+$, 97%), 309.40 (100%).

2-(4-Nitrophenyl)-5-(trifluoromethoxy)-1,3-benzothiazole

Book No.: LS-T208

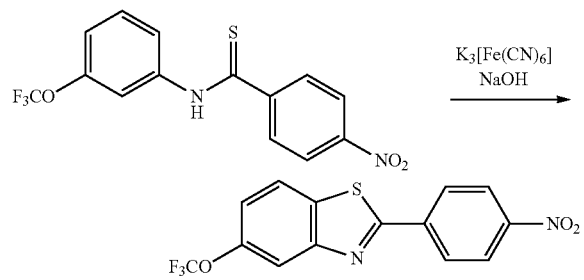

Prepared as described in the Potassium Ferricyanide Benzothiazole Formation section.

Column chromatography (1:4 EtOAc/40:60 petrol) to give the product as a yellow solid (10%). IR (KBr)/cm$^{-1}$: 1607, 1514, 1356, 1302, 1260, 1211, 1151, 1109; $^1$H NMR (250 MHz, CDCl$_3$) δ 7.33 (d, J=8.9 Hz, 1H), 7.93 (d, J=8.9 Hz, 1H), 7.96 (s, 1H), 8.23 (d, J=8.5 Hz, 2H), 8.34 (d, J=8.5 Hz, 2H).

2-(4-Nitrophenyl)-6-(trifluoromethoxy)-1,3-benzothiazole

Book No.: LS-T199

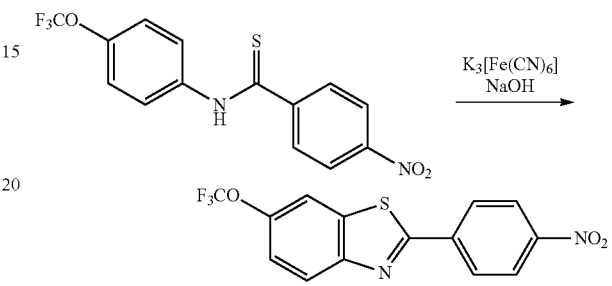

Prepared as described in the Potassium Ferricyanide Benzothiazole Formation section.

Column chromatography (1:5 EtOAc/40:60 petrol) to give the product as a yellow solid (10%). $^1$H NMR (250 MHz, CDCl$_3$) δ 6.43 (dd, J=1.5 Hz, 9.1 Hz, 1H), 7.81 (d, J=0.9 Hz, 1H), 8.11 (d, J=9.1 Hz, 1H), 8.24 (d, J=8.8 Hz, 2H), 8.36 (d, J=8.8 Hz, 2H); LRMS (ESI+) m/z 340.94 (M$^+$+H, 100%).

4-[5-Methoxy-1,3-benzothiazol-2-yl]aniline

Book No.: LS-T226B

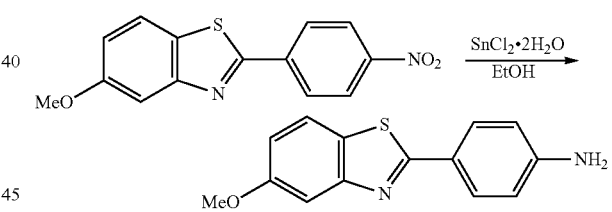

Prepared as described in the Nitro Reduction section.

Column chromatography (1:3 EtOAc/40:60 petrol) to give the product as a yellow solid (45%). $^1$H NMR (400 MHz, CDCl$_3$) δ 3.85 (s, 3H), 3.91 (bs, 2H), 6.68 (d, J=Hz, 8.5 Hz, 2H), 6.92 (dd, J=2.7 Hz, 8.9 Hz, 1H), 7.46 (d, J=2.7 Hz, 1H), 7.64 (d, J=8.9 Hz, 2H), 7.83 (d, J=8.5 Hz, 1H); $^{13}$C NMR (100 MHz, CDCl$_3$) δ 55.5, 105.2, 114.4, 114.7, 121.6, 124.0, 126.3, 128.9, 149.2, 155.4, 158.9, 169.8.

4-[4-Methoxy-1,3-benzothiazol-2-yl]aniline

Book No.: LS-T234

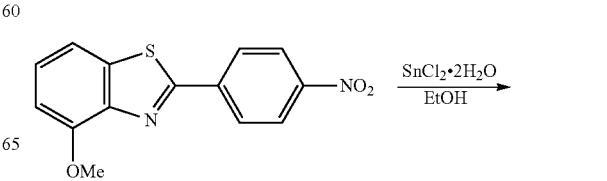

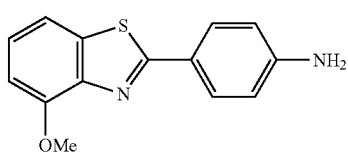

Prepared as described in the Nitro Reduction section.

Column chromatography (1:1 EtOAc/40:60 petrol) to give the product as a yellow solid (39%). IR (KBr)/cm$^{-1}$: 3345, 3211, 1620, 1602, 1567, 1433, 1333, 1308, 1262, 1177, 1051, 973, 826, 729; $^1$H NMR (400 MHz, CDCl$_3$) δ 3.92 (bs, 2H), 4.03 (s, 3H), 6.68 (d, J=Hz, 8.5 Hz, 2H), 6.85 (dd, J=1.0 Hz, 8.6 Hz, 1H), 7.20-7.24 (m, 2H), 7.40 (dd, J=1.0 Hz, 8.5 Hz, 1H), 7.90 (d, J=8.5 Hz, 2H); LRMS (ESI+) m/z 257.48 (M$^+$+H, 100%).

4-[5-(Trifluoromethoxy)-1,3-benzothiazol-2-yl]aniline

Book No.: LS-T225

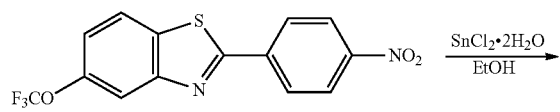

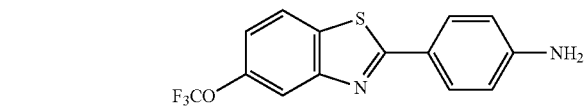

Prepared as described in the Nitro Reduction section.

Column chromatography (1:2.8 EtOAc/40:60 petrol) to give the product as an orange solid (33%). $^1$H NMR (400 MHz, CDCl$_3$) δ 4.06 (bs, 2H), 6.71 (d, J=8.5 Hz, 2H), 7.16 (d, J=8.5 Hz, 1H), 7.79 (d, J=8.5 Hz, 1H), 7.86 (d, J=8.5 Hz, 2H), 7.77-7.88 (hidden, 1H).

4-[6-(Trifluoromethoxy)-1,3-benzothiazol-2-yl]aniline

Book No.: LS-T201

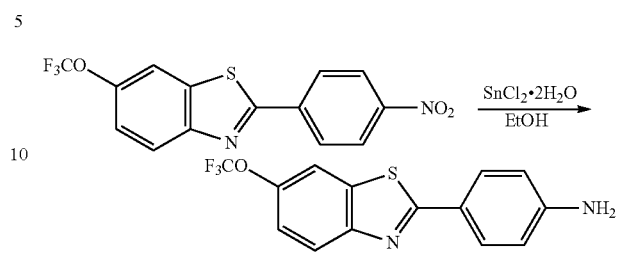

Prepared as described in the Nitro Reduction section.

Yellow solid (37%). $^1$H NMR (250 MHz, CDCl$_3$) δ 4.02 (bs, 2H), 6.72 (d, J=Hz, 8.5 Hz, 2H), 7.31 (d, J=8.9 Hz, 1H), 7.72 (s, 1H), 7.86 (d, J=8.5 Hz, 2H), 7.93 (d, J=8.9 Hz, 1H); LRMS (ESI+) m/z 310.99 (M$^+$+H, 20%), 455.95 (100%).

4-[6 (Dimethylamino)-1,3-benzothiazol-2-yl]aniline

Book No.: LS-T247

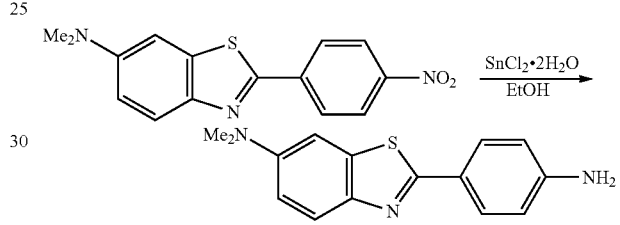

Prepared as described in the Nitro Reduction section.

Yellow solid (47%). $^1$H NMR (250 MHz, CDCl$_3$) δ 3.00 (s, 6H), 6.71 (d, J=8.5 Hz, 2H), 6.93 (dd, J=2.7 Hz, 8.9 Hz, 1H), 7.08 (d, J=2.7 Hz, 1H), 7.74-7.85 (m, 1H), 7.82 (d, J=8.5 Hz, 2H).

2-(4-{(E)-[4-(6-Methoxybenzothiazol-2-yl)phenyl]diazenyl}phenoxy)ethyl methane sulphonate Book No.: SC597

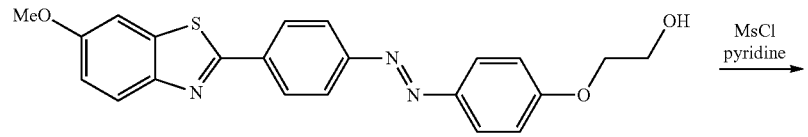

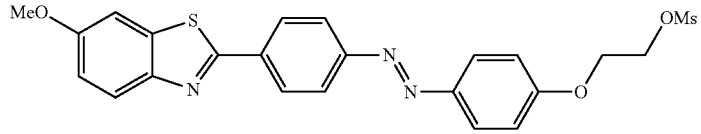

2-(4-{(E)-[4-(6-Methoxybenzothiazol-2-yl)phenyl]diazenyl}phenoxy)ethanol (260 mg, 0.642 mmol) was added to pyridine (26 ml) under N$_2$. Cooled to 6° C. and methane sulphonyl chloride (441 mg, 3.85 mmol)) was added dropwise. Allowed to warm to rt and then stirred for 6 h. H$_2$O (60 ml) added and the resulting precipitate collected by filtration, washed with H$_2$O (2×5 ml) and then dried under vacuum overnight to give the product as an orange solid. Yield: 251 mg, 81%; $^1$H NMR (250 MHz, DMSO-$d_6$) δ 3.26 (s, 3H), 3.87 (s, 3H), 4.39-4.41 (m, 2H), 4.57-4.59 (m, 2H), 7.12-7.26 (m, 3H), 7.75 (s, 1H), 7.88-8.06 (m, 5H), 8.23 (d, J=8.5 Hz, 2H).

Benzothiazole Compounds 2-(4-{(E)-[4-(2-Fluoroethoxy)phenyl] diazenyl}phenyl)-6-methoxy-1,3-benzothiazole Book No.: SC598

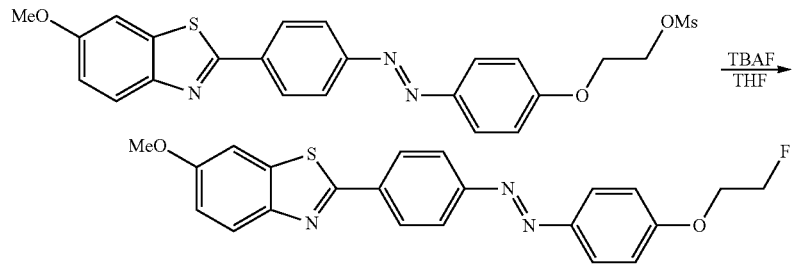

Dry THF (6 ml) was added to 2-(4-{(E)-[4-(6-methoxybenzothiazol-2-yl)phenyl]diazenyl}phenoxy)ethyl methane sulphonate (50 mg, 0.103 mmol) under $N_2$. TBAF (310 µl, 1 M in THF) was added and the reaction mixture heated to 50° C. for 1 h. Reaction cooled to rt and poured into $H_2O$ (15 ml). Solid collected by filtration, washed with $H_2O$ (2×2 ml) and dried under vacuum overnight. Column chromatography (3:7 EtOAc/Hexane) gave the product (24 mg, 57%) as an orange solid.

4-{(E)-[4-(6-Methyl-1,3-benzothiazol-2-yl)phenyl] diazenyl}-3-(trifluoromethyl)phenol Book No.: LS-T192

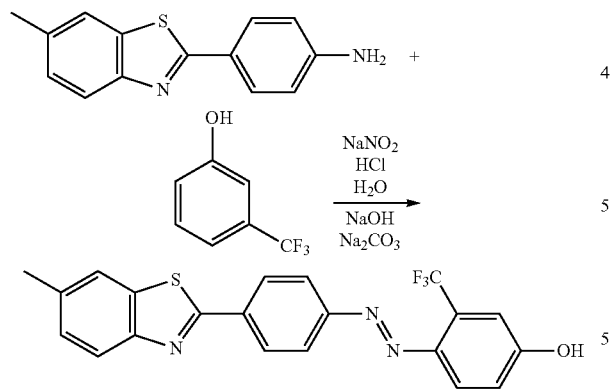

Prepared as described in the Diazo Coupling section.

Column chromatography (1:3 EtOAc/40:60 petrol) to give the product as a yellow solid (24%). IR (KBr)/cm$^{-1}$: 1616, 1481, 1326, 1263, 1225, 1167, 1126; $^1$H NMR (250 MHz, methanol-$d_4$) δ 2.52 (s, 3H), 7.09 (d, J=8.9 Hz, 1H), 7.26 (s, 1H), 7.38 (d, J=8.9 Hz, 1H), 7.83 (s, 1H), 7.91-7.98 (m, 2H), 8.02 (d, J=7.9 Hz, 2H), 8.25 (d, J=7.9 Hz, 2H); LRMS (ESI+) m/z 413.87 (M$^+$+H, 45%), 326.09 (100%).

2-{(E)-[4-(6-Methyl-1,3-benzothiazol-2-yl)phenyl] diazenyl}-4-(trifluoromethyl)phenol Book No.: LS-T191

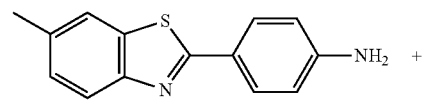

-continued

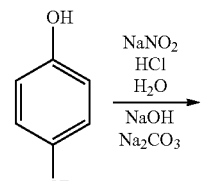

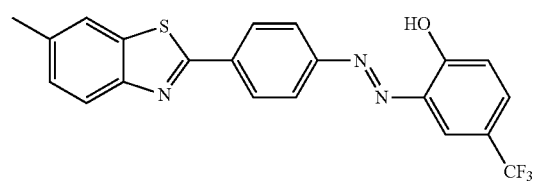

Prepared as described in the Diazo Coupling section.

Column chromatography (1:20 EtOAc/40:60 petrol to 100% EtOAc) to give the product as a yellow solid (29%). $^1$H NMR (250 MHz, CDCl$_3$) δ 2.50 (s, 3H), 7.13 (d, J=8.9 Hz, 1H), 7.32 (d, J=8.2 Hz, 1H), 7.59 (d, J=8.2 Hz, 1H), 7.71 (s, 1H), 7.91-8.04 (m, 3H), 8.17-8.29 (m, 3H), 13.07 (s, 1H); $^{13}$C NMR (62.5 MHz, CDCl$_3$) δ 21.6, 119.2, 121.5, 123.1, 127.9, 128.1, 128.4, 128.5, 129.0, 130.0 (2C), 130.8 (2C), 135.5, 136.1, 136.4, 136.7, 151.3, 152.4, 155.3, 165.2; LRMS (ESI−) m/z 411.99 (M$^+$−H, 100%).

4-{(E)-[4-(6-Methyl-1,3-benzothiazol-2-yl)phenyl] diazenyl}-3,5-bis(trifluoromethyl)phenol Book No.: LS-T214

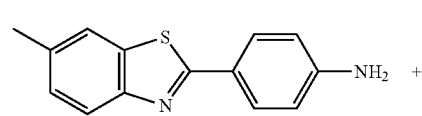

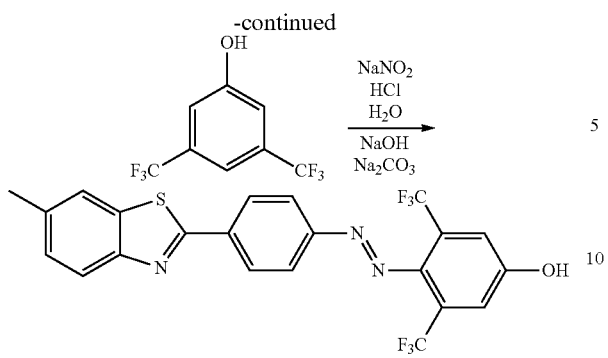

Prepared as described in the Diazo Coupling section.

Column chromatography (3:2 EtOAc/40:60 petrol) to give the product as an orange solid (20%). $^1$H NMR (250 MHz, CDCl$_3$) δ 2.51 (s, 3H), 7.32 (d, J=8.9 Hz, 1H), 7.53 (s, 1H), 7.62 (s, 1H), 7.72 (s, 1H), 7.98 (d, J=8.9 Hz, 1H), 8.02 (d, J=8.5 Hz, 2H), 8.26 (d, J=8.5 Hz, 2H); LRMS (ESI−) m/z 480.00 (M$^+$−H, 100%).

4-{(E)-[4-(6-Methoxy-1,3-benzothiazol-2-yl)phenyl]diazenyl}-3-(trifluoromethyl)phenol Book No.: LS-T209

Prepared as described in the Diazo Coupling section.

Column chromatography (1:3 EtOAc/40:60 petrol) to give the product as an orange solid (32%). IR (KBr)/cm$^{-1}$: 1604, 1484, 1326, 1264, 1226, 1165, 1127, 1043, 1029; $^1$H NMR (400 MHz, acetone-d$_6$) δ 3.89 (s, 3H), 7.13 (dd, J=2.4 Hz, 8.9 Hz, 1H), 7.21 (dd, J=2.4 Hz, 8.9 Hz, 1H), 7.34 (d, J=2.7 Hz, 1H), 7.61 (d, J=3.4 Hz, 1H), 7.93 (d, J=8.90 Hz, 1H), 8.01 (d, J=8.9 Hz, 2H), 8.25 (d, J=8.9 Hz, 2H), 9.80 (bs, 1H); $^{13}$C NMR (62.5 MHz, acetone-d$_6$) δ 60.7, 109.7, 118.6 (2C), 121.6, 123.5, 125.0, 129.0 (2C), 129.3, 133.4 (2C), 141.4, 142.2, 147.7, 154.2, 159.0, 163.8, 166.1, 168.9; LRMS (ESI+) m/z 429.96 (M$^+$+H, 100%).

Book No.: LS-T235A and LS-T235B

4-{(E)-[4-(5-Methoxy-1,3-benzothiazol-2-yl)phenyl]diazenyl}-3-(trifluoromethyl)phenol Book No.: LS-T235A Prepared as described in the Diazo Coupling section.

Column chromatography (1:1 EtOAc/40:60 petrol) to give the product as an orange solid (11%). $^1$H NMR (250 MHz, CDCl$_3$) δ 3.92 (s, 3H), 7.07 (d, J=7.6 Hz, 1H), 7.25-7.30 (m, 1H), 7.32 (d, J=6.1 Hz, 1H), 7.42 (s, 1H), 7.58 (d, J=1.9 Hz, 1H), 7.77 (d, J=8.8 Hz, 1H), 8.01 (d, J=8.5 Hz, 2H), 8.24 (d, J=8.5 Hz, 2H).

2-{(E)-[4-(5-Methoxy-1,3-benzothiazol-2-yl)phenyl]diazenyl}-5-(trifluoromethyl)phenol Book No.: LS-T235B Prepared as described in the Diazo Coupling section.

Column chromatography (1:1 EtOAc/40:60 petrol) to give the product as an orange solid (43%). $^1$H NMR (250 MHz, CDCl$_3$) δ 3.91 (s, 3H), 7.03 (dd, J=2.4 Hz, 8.9 Hz, 1H), 7.04-7.10 (m, 1H), 7.53-7.64 (m, 4H), 7.74 (d, J=8.9 Hz, 1H), 8.11 (d, J=8.5 Hz, 2H), 7.25-7.30 (m, 1H), 7.32 (d, J=6.1 Hz, 1H), 7.42 (s, 1H), 7.58 (d, J=1.9 Hz, 1H), 7.75-7.78 (m, 1H), 7.77 (1H, d, J=8.8 Hz, 1H), 8.01 (d, J=8.5 Hz, 2H), 8.24 (d, J=8.5 Hz, 2H).

4-{(E)-[4-(4-Methoxy-1,3-benzothiazol-2-yl)phenyl]diazenyl}-3-(trifluoromethyl)phenol Book No.: LS-T236

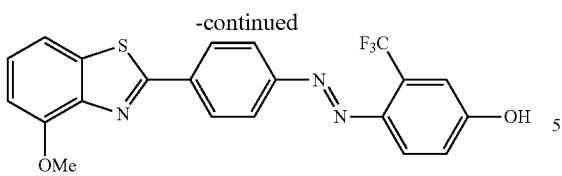

Prepared as described in the Diazo Coupling section.
Column chromatography (1:1 EtOAc/40:60 petrol) to give the product as an orange solid (40%). IR (KBr)/cm$^{-1}$: 3121, 1606, 1465, 1335, 1265, 1226, 1155, 1127; $^1$H NMR (400 MHz, acetone-d$_6$) δ 4.04 (s, 3H), 7.06 (dd, J=0.7 Hz, 8.2 Hz, 1H), 7.22 (dd, J=2.7 Hz, 8.9 Hz, 1H), 7.34 (d, J=27 Hz, 1H), 7.39 (t, J=8.0 Hz, 2H), 7.62 (dd, J=1.0 Hz, 8.2 Hz, 1H), 7.94 (d, J=8.9 Hz, 1H), 8.03 (d, J=8.9 Hz, 2H), 8.30 (d, J=8.5 Hz, 2H); $^{13}$C NMR (62.5 MHz, acetone-d$_6$) δ 55.8, 107.9, 108.1, 114.0, 118.1, 119.7, 123.6, 124.0, 128.3 (2C), 128.7 (2C), 130.8, 136.1, 137.2, 142.5, 144.7, 153.9, 154.4, 161.0, 164.4; LRMS (ESI+) m/z 430.41 (M$^+$+H, 70%), 64.42 (100%).

4-{(E)-[4-(6-Methoxy-1,3-benzothiazol-2-yl)phenyl]diazenyl}phenol

Book No.: LS-T210

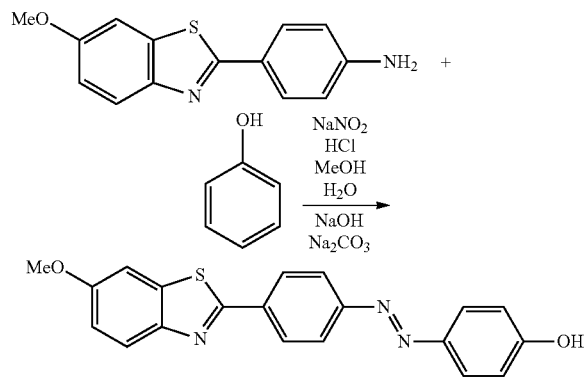

Prepared as described in the Diazo Coupling section.
Material is crystallised from acetone (80 vol) to give the product as an orange solid (70%). $^1$H NMR (250 MHz, DMSO-d$_6$) δ 3.85 (s, 3H), 6.96 (d, J=8.5 Hz, 2H), 7.14 (d, J=8.9 Hz, 1H), 7.71 (s, 1H), 7.84 (d, J=8.0 Hz, 2H), 7.84-7.95 (m, 3H), 8.19 (d, J=8.0 Hz, 2H);

4-[(E)-{4-[5-(Trifluoromethoxy)-1,3-benzothiazol-2-yl]phenyl}diazenyl]phenol

Book No.: LS-T229

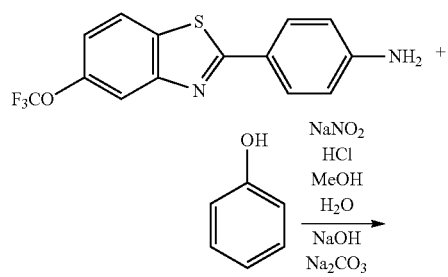

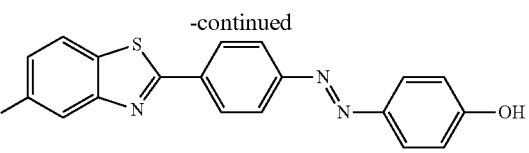

Prepared as described in the Diazo Coupling section.
Column chromatography (1:2 EtOAc/40:60 petrol) to give the product as an orange solid (37%). $^1$H NMR (250 MHz, acetone-d$_6$ and CDCl$_3$) δ 6.92 (d, J=8.9 Hz, 1H), 7.22 (m, 1H), 7.71-7.96 (m, 6H), 8.01-8.19 (m, 2H), 8.44 (bs, 1H).

4-[(E)-{4-[6-(Trifluoromethoxy)-1,3-benzothiazol-2-yl]phenyl}diazenyl]phenol

Book No.: LS-T210

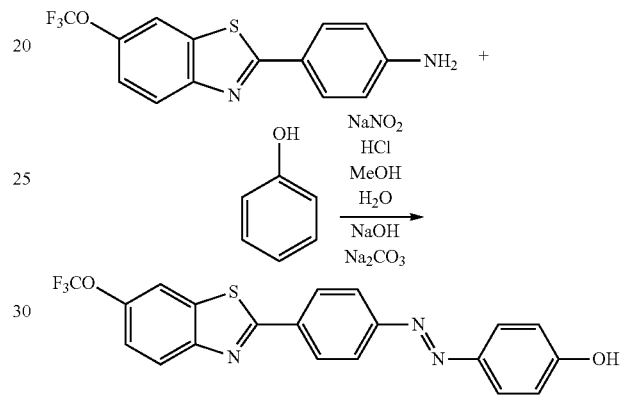

Prepared as described in the Diazo Coupling section.
Column chromatography (1:2 EtOAc/40:60 petrol) to give the product as an orange solid (32%). IR (KBr)/cm$^{-1}$: 1633, 1595, 1454, 1324, 1297, 1247, 1219, 1163, 1106; $^1$H NMR (250 MHz, acetone-d$_6$) δ 7.06, (d, J=8.9 Hz, 2H), 7.55 (d, J=9.2 Hz, 1H), 7.93 (d, J=8.5 Hz, 2H), 8.04 (d, J=8.5 Hz, 2H), 8.14-8.20 (m, 2H), 8.33 (d, J=8.2 Hz, 2H), 9.38 (bs, 1H); LRMS (ESI-) m/z 413.99 (M$^+$-H, 100%).

4-{(E)-[4-(6-Dimethylamino-1,3-benzothiazol-2-yl)phenyl]diazenyl}-3-(trifluoromethyl)phenol Book No.: LS-T256

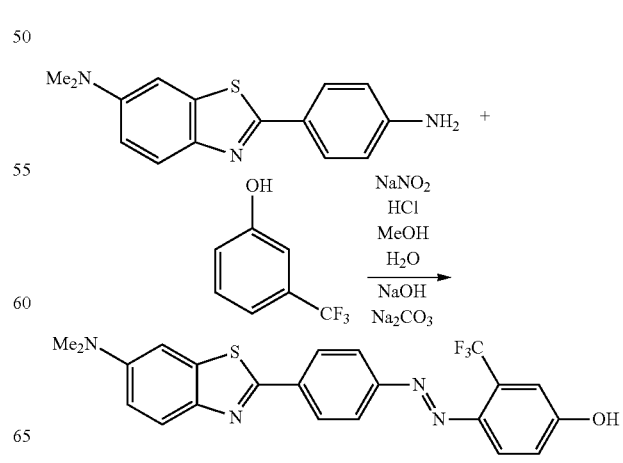

Prepared as described in the Diazo Coupling section.

Column chromatography (1:1 EtOAc/40:60 petrol) to give the product as an orange solid (26%). $^1$H NMR (250 MHz, acetone-$d_6$) δ 3.07 (s, 6H), 7.08 (dd, J=2.7 Hz, 9.1 Hz, 1H), 7.26 (dd, J=2.7 Hz, 9.1 Hz, 1H), 7.33 (d, J=2.7 Hz, 1H), 7.38 (d, J=2.4 Hz, 1H), 7.88 (d, J=9.1 Hz, 1H), 7.98 (d, J=9.1 Hz, 1H), 8.05 (d, J=8.5 Hz, 2H), 8.26 (d, J=8.5 Hz, 2H).

2-(4-{(E)-[4-(6-Methoxybenzothiazol-2-yl)phenyl]diazenyl}phenoxy)ethanol

Book No.: SC588

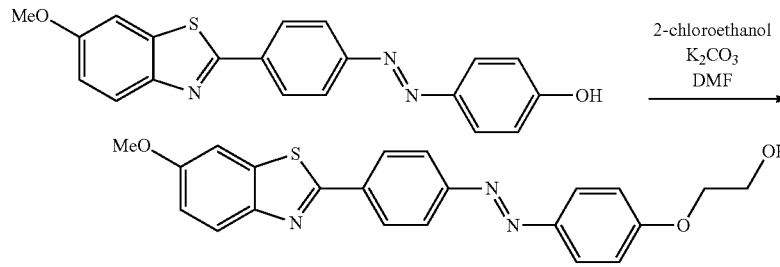

4-[(E)-{4-[6-(Trifluoromethoxy)-1,3-benzothiazol-2-yl]phenyl}diazenyl]-3-(trifluoromethyl)phenol (400 mg, 1.11 mmol) was added to DMF (5 ml). $K_2CO_3$ (535 mg, 3.88 mmol) followed by 2-chloroethanol (134 mg, 1.66 mmol) were then added and the reaction mixture heated to 80° C. for 48 h. Cooled to rt and $H_2O$ (20 ml) added. Resulting solid was collected by filtration, washed with $H_2O$ (2×5 ml) and dried under vacuum overnight to yield the product as an orange solid. Yield: 397 mg, 88%; $^1$H NMR (250 MHz, DMSO-$d_6$) δ 3.69-3.78 (m, 2H), 3.86 (s, 3H), 4.07-4.16 (m, 2H), 7.08-7.20 (m, 3H), 7.75 (s, 1H), 7.85-8.04 (m, 5H), 8.22 (d, J=8 Hz, 2H).

$^1$H NMR (250 MHz, DMSO-$d_6$) δ 3.69-3.78 (m, 2H), 3.86 (s, 3H), 4.07-4.16 (m, 2H), 7.08-7.20 (m, 3H), 7.75 (s, 1H), 7.85-8.04 (m, 5H), 8.22 (d, J=8 Hz, 2H).

4-{(E)-[4-(6-Hydroxy-1,3-benzothiazol-2-yl)phenyl]diazenyl}-3-(trifluoromethyl)phenol Book No.: LS-T213

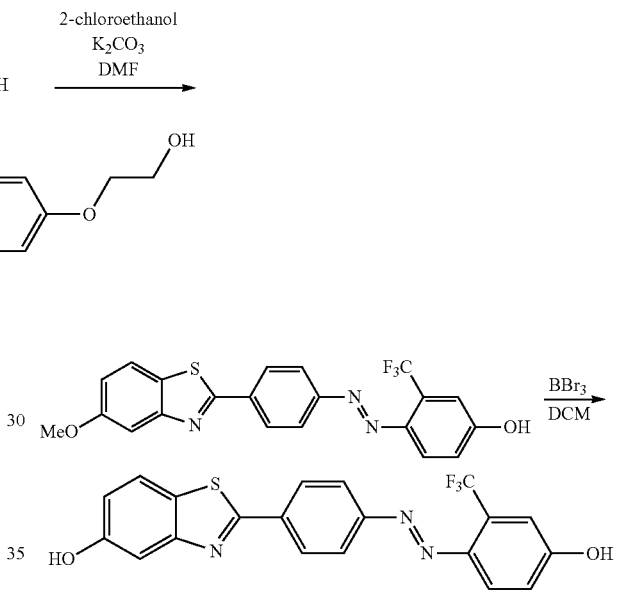

Prepared as described in Demethylation section.

Column chromatography (1:2 EtOAc/40:60 petrol) to give the product as an orange solid (36%). IR (KBr)/cm$^{-1}$: 1600, 1481, 1454, 1327, 1264, 1229, 1158, 1131, 1043; $^1$H NMR (400 MHz, acetone-$d_6$) δ 7.08 (dd, J=8.9 Hz, 2.4 Hz, 1H), 7.22 (dd, J=2.4 Hz, 8.9 Hz, 1H), 7.34 (d, J=2.7 Hz, 1H), 7.46 (d, J=2.4 Hz, 1H), 7.88 (d, J=8.9 Hz, 1H), 7.93 (d, J=8.9 Hz, 1H), 8.01 (d, J=8.5 Hz, 2H), 8.24 (d, J=8.9 Hz, 2H); $^{13}$C NMR (62.5 MHz, acetone-$d_6$) δ 106.9, 113.4, 116.7, 118.6, 119.7, 124.0 (2C), 124.4, 128.3 (2C), 130.8, 136.3, 137.1, 142.5, 148.5, 153.7, 156.4, 160.9, 163.0; LRMS (ESI−) m/z 414.05 (M$^+$−H, 100%).

4-{(E)-[4-(5-Hydroxy-1,3-benzothiazol-2-yl)phenyl]diazenyl}-3-(trifluoromethyl)phenol Book No.: LS-T245

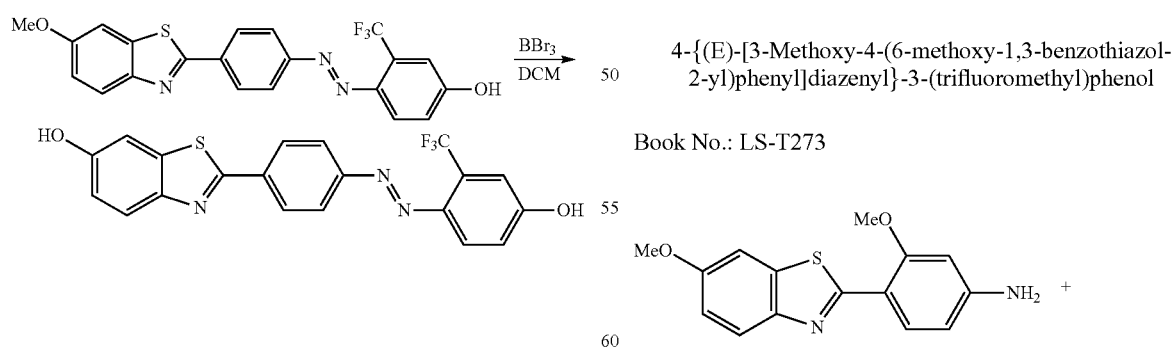

Prepared as described in Demethylation section.

Column chromatography (1:2 EtOAc/40:60 petrol) to give the product as an orange solid (39%). $^1$H NMR (250 MHz, acetone-$d_6$) δ 7.09 (dd, J=2.1 Hz, 8.5 Hz, 1H), 7.28 (dd, J=2.4 Hz, 8.85 Hz, 1H), 7.40 (d, J=2.4 Hz, 1H), 7.53 (d, J=2.1 Hz, 1H), 7.94 (d, J=8.9 Hz, 1H), 8.00 (d, J=8.9 Hz, 1H), 8.08 (d, J=8.5 Hz, 2H), 8.34 (d, J=8.5 Hz, 2H), 8.83 (s, 1H), 9.84 (s, 1H).

4-{(E)-[3-Methoxy-4-(6-methoxy-1,3-benzothiazol-2-yl)phenyl]diazenyl}-3-(trifluoromethyl)phenol Book No.: LS-T273

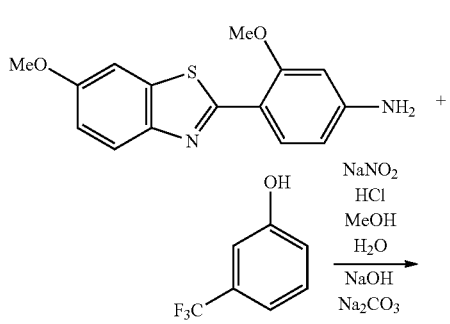

-continued

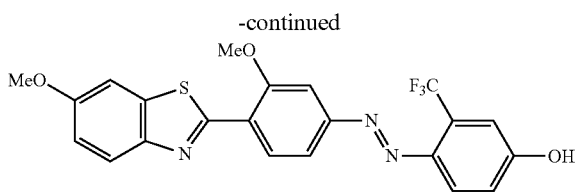

Prepared as described in the Diazo Coupling section.

Column chromatography (1:1 EtOAc/40:60 petrol) to give the product as a pink solid (25%). IR (KBr)/cm$^{-1}$: 1609, 1498, 1476, 1403, 1338, 1263, 1234, 1138, 1123, 1043, 1027; $^1$H NMR (400 MHz, acetone-d$_6$) δ 3.89 (s, 3H), 4.18 (s, 3H), 7.13 (dd, J=2.7 Hz, 8.8 Hz, 1H), 7.23 (dd, J=2.4 Hz, 8.8 Hz, 1H), 7.35 (d, J=2.7 Hz, 1H), 7.59 (d, J=2.7 Hz, 1H), 7.68 (dd, J=1.7 Hz, 8.8 Hz, 1H), 7.71 (d, J=1.7 Hz, 1H), 7.93 (d, J=8.9H, 2H), 8.66 (d, J=8.2 Hz, 1H); $^{13}$C NMR (100 MHz, acetone-d$_6$) δ 55.5, 55.7, 103.6, 105.9, 113.5, 116.3, 118.3, 119.8, 123.7, 124.8, 129.7, 138.0, 142.5, 147.1, 154.6, 157.8, 158.2, 159.2, 160.9.

4-{(E)-[3-Methoxy-4-(6-methoxy-1,3-benzothiazol-2-yl)phenyl]diazenyl}-3-(4,4,4-trifluorobutoxy)phenol Book No.: LS-T271

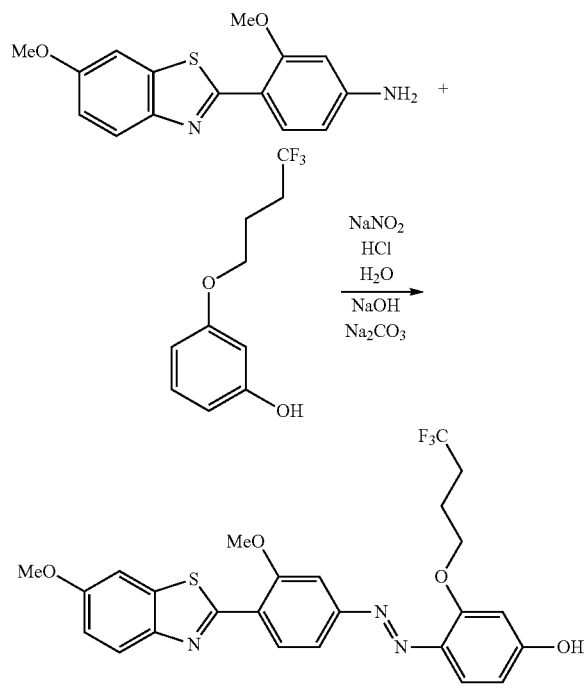

Prepared as described in the Diazo Coupling section.

Column chromatography (1:2 EtOAc/40:60 petrol) to give the product as a pink solid (3%). $^1$H NMR (250 MHz, acetone-d$_6$) δ 2.15-2.22 (m, 2H), 2.56-2.68 (m, 2H), 3.93 (s, 3H), 4.19 (s, 3H), 4.33 (t, J=6.0 Hz, 2H), 6.60 (dd, J=2.1 Hz, 8.5 Hz, 1H), 6.71 (d, J=2.1 Hz, 1H), 7.16 (dd, J=2.4 Hz, 8.5 Hz, 1H), 7.63-7.68 (m, 3H), 7.77 (d, J=8.5 Hz, 1H), 7.96 (d, J=8.9 Hz, 1H), 8.66 (d, J=8.9 Hz, 1H), 9.36 (bs, 1H).

4-{(E)-[2-Methoxy-4-(6-methoxy-1,3-benzothiazol-2-yl)phenyl]diazenyl}-3-(trifluoromethyl)phenol Book No.: LS-T286

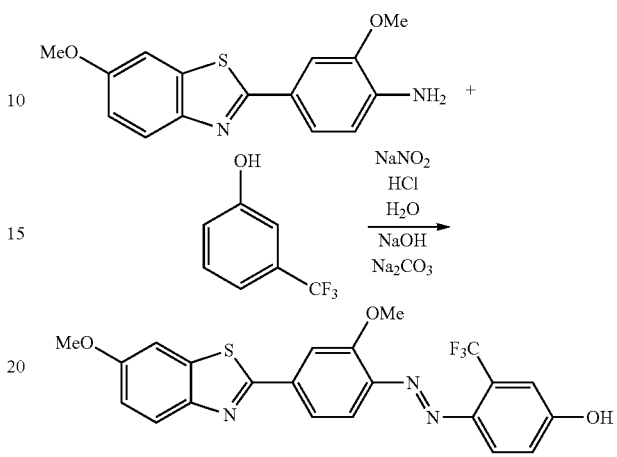

Prepared as described in the Diazo Coupling section.

Column chromatography (1:1 EtOAc/40:60 petrol) to give the product as a pink solid (21%). $^1$H NMR (250 MHz, acetone-d$_6$) δ 3.92 (s, 3H), 4.16 (s, 3H), 7.16 (d, J=8.9 Hz, 1H), 7.22 (d, J=8.5 Hz, 1H), 7.36 (s, 1H), 7.64 (s, 1H), 7.65-7.78 (m, 2H), 7.88-7.98 (m, 3H).

4-{(E)-[2-Methoxy-4-(6-methoxy-1,3-benzothiazol-2-yl)phenyl]diazenyl}-3-(trifluoromethoxy)phenol Book No.: LS-T287

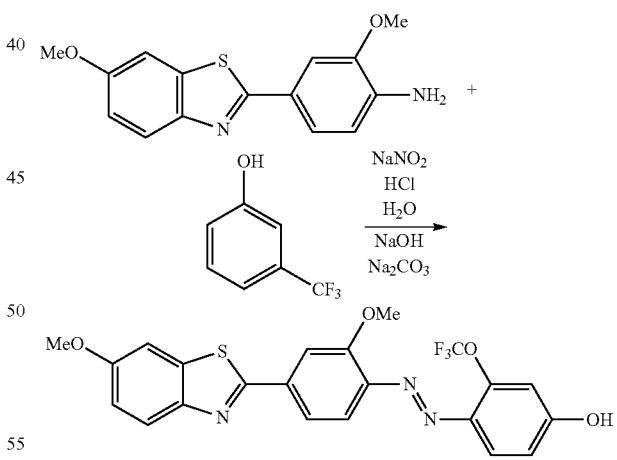

Prepared as described in the Diazo Coupling section.

Column chromatography (1:1 EtOAc/40:60 petrol) to give the product as a pink solid (24%). $^1$H NMR (400 MHz, acetone-d$_6$) δ 3.88 (s, 3H), 4.11 (s, 3H), 6.97-7.00 (m, 2H), 7.13 (dd, J=2.4 Hz, 8.9 Hz, 1H), 7.60 (d, J=2.4 Hz, 1H), 7.65-7.68 (m, 2H), 7.80 (d, J=9.2 Hz, 1H), 7.89 (d, J=1.4 Hz, 1H), 7.93 (d, J=8.9 Hz, 1H); NMR (100 MHz, acetone-d$_6$) δ 55.5, 56.1, 104.5, 109.6, 111.2, 115.5, 116.4, 117.4, 119.0, 119.6, 120.0, 122.2, 124.0, 137.0, 137.3, 139.1, 143.7, 148.6, 148.9, 157.7, 158.6, 161.8, 163.9.

4-{(E)-[3-Hydroxy-4-(6-hydroxy-1,3-benzothiazol-2-yl)phenyl]diazenyl}-3-(trifluoromethyl)phenol Book No.: LS-T274

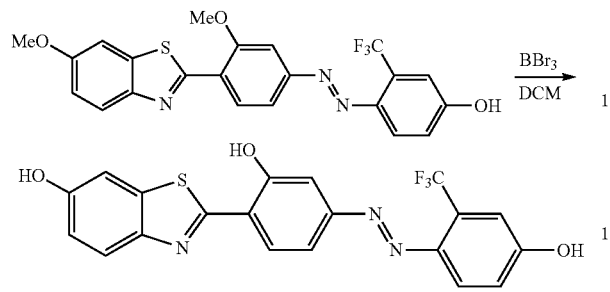

Prepared as described in Demethylation section.
Column chromatography (1:1 EtOAc/40:60 petrol) to give the product as a purple solid (31%). IR (KBr)/cm$^{-1}$: 1651, 1615, 1486, 1427, 1324, 1226, 1130, 1041; $^1$H NMR (250 MHz, acetone-d$_6$) δ 7.17 (dd, J=2.4 Hz, 8.9 Hz, 1H), 7.26 (dd, J=2.4 Hz, 8.9 Hz, 1H), 7.38 (d, J=2.1 Hz, 1H), 7.56 (m, 3H), 7.97 (m, 3H), 9.13 (bs, 1H).

4-{(E)-[3-Hydroxy-4-(6-hydroxy-1,3-benzothiazol-2-yl)phenyl]diazenyl}-3-(4,4,4-trifluorobutoxy)phenol Book No.: LS-T272

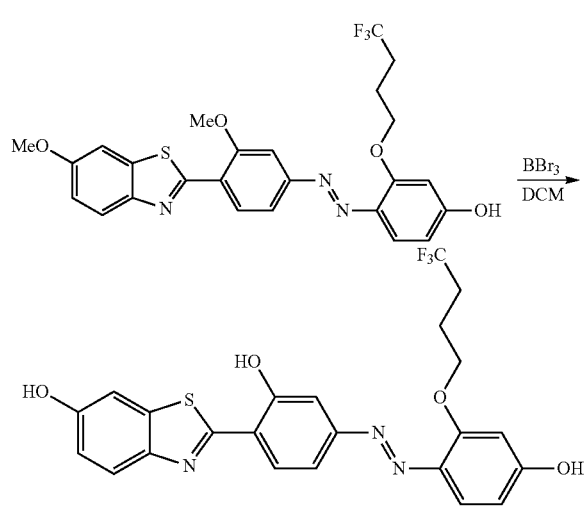

Prepared as described in Demethylation section.
Column chromatography (1:1 EtOAc/40:60 petrol) to give the product as a purple solid (29%). IR (KBr)/cm$^{-1}$: 1626, 1564, 1505, 1417, 1271, 1135, 1049, 1012; $^1$H NMR (400 MHz, acetone-d$_6$) δ 2.13 (m, 2H, 2.54 (m, 2H), 4.28 (t, J=6.2 Hz, 2H), 6.54 (dd, J=2.4 Hz, 8.8 Hz, 1H), 6.66 (d, J=2.4 Hz, 1H), 7.11 (dd, J=2.4 Hz, 8.9 Hz, 1H), 7.43 (d, J=1.7 Hz, 1H), 7.46 (dd, J=1.9 Hz, 8.9 Hz, 1H), 7.50 (d, J=2.4 Hz, 1H), 7.70 (d, J=8.9 Hz, 1H), 7.85 (d, J=8.55 Hz, 1H), 7.92 (d, J=8.9 Hz, 1H), 9.04 (bs, 1H), 9.34 (bs, 1H); $^{13}$C NMR (100 MHz, acetone-d$_6$) δ 22.4, 30.4, 67.7, 101.8, 107.0, 108.9, 110.6, 114.5, 116.8, 118.3, 123.1, 129.0, 134.7, 136.5, 145.8, 155.7, 156.6, 158.4, 159.4, 163.3, 165.5.

4-{(E)-[2-Hydroxy-4-(6-hydroxy-1,3-benzothiazol-2-yl)phenyl]diazenyl}-3-(trifluoromethyl)phenol Book No.: LS-T288

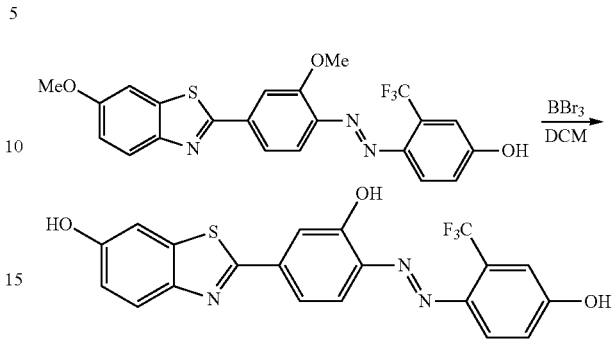

Prepared as described in Demethylation section.
Column chromatography (1:1 EtOAc/40:60 petrol) to give the product as a purple solid (31%). IR (KBr)/cm$^{-1}$: 1603, 1562, 1483, 1323, 1248, 1159, 1126, 1043; $^1$H NMR (250 MHz, acetone-d$_6$) δ 7.09-7.24 (m, 2H), 7.28 (d, J=8.6 Hz, 1H), 7.36 (s, 1H), 7.47 (s, 1H), 7.63 (s, 1H), 7.79 (d, J=8.9 Hz, 1H), 7.92 (d, J=8.6 Hz, 1H), 7.99-8.13 (m, 1H).

4-{(E)-[2-Hydroxy-4-(6-hydroxy-1,3-benzothiazol-2-yl)phenyl]diazenyl}-3-(trifluoromethoxy)phenol Book No.: LS-T289

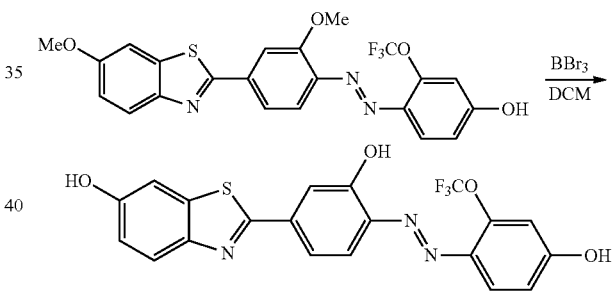

Prepared as described in Demethylation section.
Column chromatography (1:1 EtOAc/40:60 petrol) to give the product as a purple solid (20%). IR (KBr)/cm$^{-1}$: 1614, 1564, 1484, 1463, 1383, 1261, 1125, 1101; $^1$H NMR (250 MHz, acetone-d$_6$) δ 6.97-7.29 (m, 3H), 7.43 (s, 1H), 7.62 (s, 1H), 7.70-7.82 (m, 1H), 7.83-8.09 (m, 3H).

Imidazo[1,2-a]pyridine Compounds

N,N-dimethyl-4-{(E)-[4-(6-methylimidazo[1,2-a]pyridin-2-yl)phenyl]diazenyl}aniline Book No.: SKT05-163

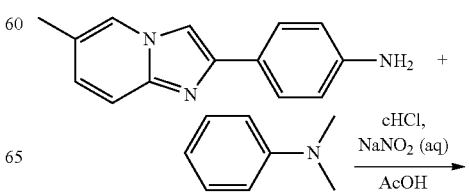

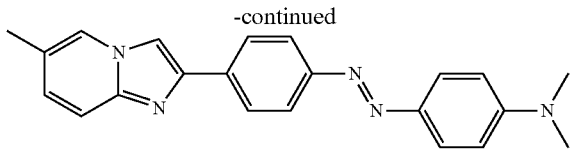

To a stirred solution of concentrated HCl (0.4 ml) in water (20 ml) at 0° C. was added a suspension of 4-(6-methylimidazo[1,2-a]pyridin-2-yl)aniline (80 mg, 0.359 mmol) in acetone (5 ml). The reaction mixture was stirred at 0° C. for 15 min, then a precooled solution of $NaNO_2$ (26 mg, 0.380 mmol) in water (2 ml) was added dropwise. After 15 min, a few crystals of urea were added. To this bright yellow solution was added dropwise a solution of N,N-dimethylaniline (43 mg, 0.359 mmol) in AcOH (1.5 ml). The reaction mixture was stirred for a further 10 min at 0° C., then a saturated solution of NaOAc (10 ml) was added and the orange precipitate was collected by filtration under vacuum and dried in air. The solid was purified by flash chromatography (1:1 DCM/EtOAc) to give the title compound (40 mg, 31%) as a red/orange solid.

$^1$H NMR (250 MHz, $CDCl_3$) δ 2.32 (s, 3H), 3.09 (s, 6H), 6.76 (d, J=9.2 Hz, 1H), 7.02 (d, J=9.5 Hz, 1H), 7.54 (d, J=9.2 Hz, 1H), 7.84-7.92 (m, 7H), 8.05 (d, J=8.5 Hz, 2H); $^{13}$C NMR (62.5 MHz, $CDCl_3$) δ 18.17, 40.36, 108.39, 111.56, 116.86, 122.31, 122.77, 123.35, 124.99, 126.45, 128.17, 128.73, 134.76, 143.86, 144.88, 152.40, 152.74.

Diagnostic Ligands

4-[$^{18}$F]Fluoro-N-[4-(6-methoxy-benzothiazol-2-yl)-phenyl]-3-nitro-benzamide

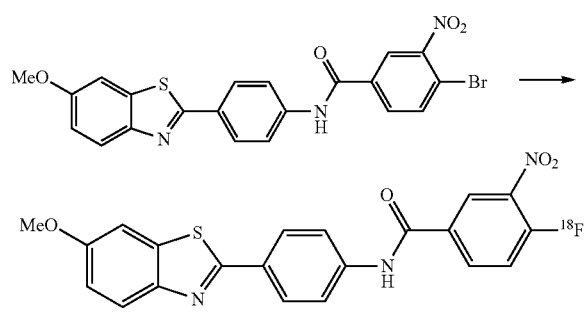

Aqueous [$^{18}$F]Fluoride (1.8 GBq) was trapped on a QMA cartridge (Waters, Sep Pak Light QMA Part. No.: WAT023525) and eluted with 5 mg $K_{2.2.2}$ in 0.95 mL MeCN+1 mg $K_2CO_3$ in 50 µl water into a Wheaton vial (5 mL). The solvent was removed by heating at 120° C. for 10 min under a stream of nitrogen. Anhydrous MeCN (1 mL) was added and evaporated as before. A solution of precursor 4-bromo-3-nitro-N-[4-(6-methoxybenzothiazol-2-yl)-phenyl]-benzamide (SKT04-33) (5 mg) in 500 µL anhydrous DMSO was added. After heating at 180° C. for 20 min the crude reaction mixture was diluted with water/MeCN (1/1) to a total volume of 5 mL and purified by preparative HPLC: ACE 5-C18-HL 250 mm×10 mm, Advanced Chromatography Technologies; Cat. No.: ACE 321-2510; 50% acetonitrile in 0.1% trifluoroacetic acid to 80% acetonitrile in 0.1% trifluoroacetic acid in 20 min, 20 to 30 min isocratic 80% acetonitrile in 0.1% trifluoroacetic acid; flow: 4 ml/min; $t_R$=22.5 min. The collected HPLC fraction was diluted with 40 mL water and immobilized on a Sep-Pak light C18 cartridge (Waters, WAT023501), which was washed with 5 mL water and eluted with 1 mL ethanol to deliver 134 MBq of the product (12%, corrected for decay; radiochemical purity>95%). The desired product was characterized by co-injection with the non-radioactive F-19 fluoro standard (SKT03-99) using analytical HPLC: ACE3-C18 50 mm×4.6 mm; solvent gradient: start 5% acetonitrile-95% acetonitrile in 0.1% trifluoroacetic acid in 7 min., flow: 2 mL/min ($t_R$=5.6 min), RCP: >95% (HPLC).

6-[$^{18}$F]Fluoro-N-[4-(6-methoxy-benzothiazol-2-yl)-phenyl]-nicotinamide

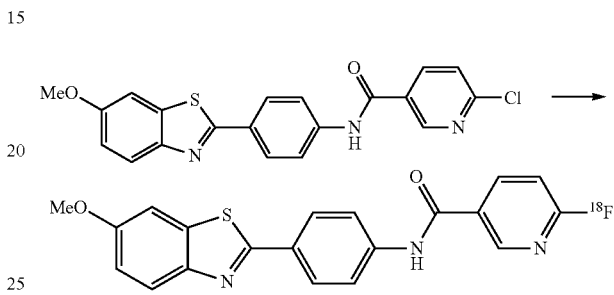

Aqueous [$^{18}$F]Fluoride (1.8 GBq) was trapped on a QMA cartridge (Waters, Sep Pak Light QMA Part. No.: WAT023525) and eluted with 5 mg $K_{2.2.2}$ in 0.95 mL MeCN+1 mg $K_2CO_3$ in 50 µl water into a Wheaton vial (5 mL). The solvent was removed by heating at 120° C. for 10 min under a stream of nitrogen. Anhydrous MeCN (1 mL) was added and evaporated as before. A solution of precursor 6-chloro-N-(4-[6-methoxy-1,3-benzothiazol-2-yl)phenyl] pyridine-3-carboxamide (SKT04-111) (5 mg) in 500 µL anhydrous DMSO was added. After heating at 180° C. for 20 min the crude reaction mixture was diluted with water/MeCN (1/1) to a total volume of 5 mL and purified by preparative HPLC: ACE 5-C18-HL 250 mm×10 mm, Advanced Chromatography Technologies; Cat. No.: ACE 321-2510; 50% acetonitrile in 0.1% trifluoroacetic acid to 80% acetonitrile in 0.1% trifluoroacetic acid in 20 min; flow: 4 ml/min; $t_R$=17.5 min. The collected HPLC fraction was diluted with 40 mL water and immobilized on a Sep-Pak light C18 cartridge (Waters, WAT023501), which was washed with 5 mL water and eluted with 1 mL ethanol to deliver 168 MBq of the product (15%, corrected for decay; radiochemical purity>95%). The desired product was characterized by co-injection with the non-radioactive F-19 fluoro standard (SKT04-137) using analytical HPLC: ACE3-C18 50 mm×4.6 mm; solvent gradient: start 5% acetonitrile-95% acetonitrile in 0.1% trifluoroacetic acid in 7 min., flow: 2 mL/min ($t_R$=5.1 min), RCP: >95% (HPLC).

4-[$^{18}$F]Fluoro-N-[4-(6-methyl-imidazo[1,2-a]pyridin-2-yl)-phenyl]-3-nitro-benzamide

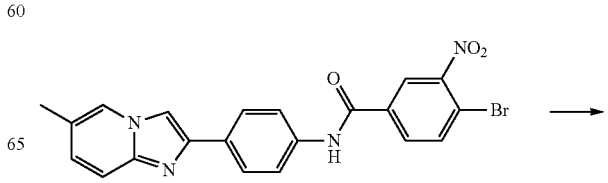

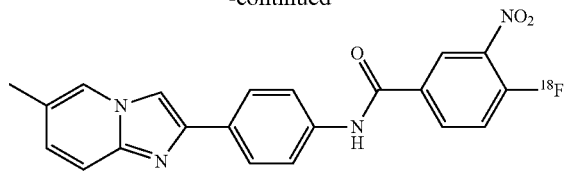

Aqueous [¹⁸F]Fluoride (2.4 GBq) was trapped on a QMA cartridge (Waters, Sep Pak Light QMA Part. No.: WAT023525) and eluted with 5 mg K$_{2.2.2}$ in 0.95 mL MeCN+1 mg K$_2$CO$_3$ in 50 µl water into a Wheaton vial (5 mL). The solvent was removed by heating at 120° C. for 10 min under a stream of nitrogen. Anhydrous MeCN (1 mL) was added and evaporated as beore. A solution of precursor 4-bromo-N-[4-(6-methylimidazo[1,2-a]pyridin-2-yl)phenyl]-3-nitrobenzamide (SKT08-153) (5 mg) in 500 µL anhydrous DMSO was added. After heating at 130° C. for 20 min the crude reaction mixture was diluted with water/MeCN (1/1) to a total volume of 5 mL and purified by preparative HPLC: ACE 5-C18-HL 250 mm×10 mm, Advanced Chromatography Technologies; Cat. No.: ACE 321-2510; 40% acetonitrile in 0.1% trifluoroacetic acid to 70% acetonitrile in 0.1% trifluoroacetic acid in 20 min; flow: 4 mL/min; t$_R$=9 min. The collected HPLC fraction was diluted with 40 mL water and immobilized on a Sep-Pak light C18 cartridge (Waters, WAT023501), which was washed with 5 mL water and eluted with 1 mL ethanol to deliver 80 MBq of the product (5%, corrected for decay; radiochemical purity>95%). The desired product was characterized by co-injection with the non-radioactive F-19 fluoro standard (SKT08-165) using analytical HPLC: ACE3-C18 50 mm×4.6 mm; solvent gradient: start 5% acetonitrile-95% acetonitrile in 0.1% trifluoroacetic acid in 7 min., flow: 2 mL/min (t$_R$=3.8 min), RCP: >95% (HPLC).

6-[¹⁸F]Fluoro-N-[4-(6-methyl-imidazo[1,2-a]pyridin-2-yl)-phenyl]-nicotinamide

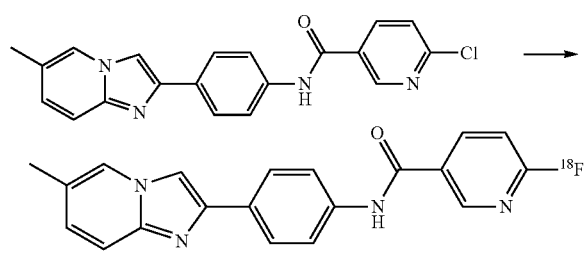

Aqueous [¹⁸F]Fluoride (1.1 GBq) was trapped on a QMA cartridge (Waters, Sep Pak Light QMA Part. No.: WAT023525) and eluted with 2 mL TBAOH-solution (8 µL TBAOH (40%) in 1.5 mL MeCN+0.5 mL water) into a Wheaton vial (5 mL). The solvent was removed by heating at 120° C. for 10 min under a stream of nitrogen. Anhydrous MeCN (1 mL) was added and evaporated as before. A solution of precursor 6-chloro-N-[4-(6-methylimidazo[1,2-a]pyridin-2-yl)phenyl]pyridine-3-carboxamide (SKT06-13) (5 mg) in 500 µL anhydrous DMSO was added. After heating at 180° C. for 10 min the crude reaction mixture was diluted with water/MeCN (1/1) to a total volume of 5 mL and purified by preparative HPLC: ACE 5-C18-HL 250 mm×10 mm, Advanced Chromatography Technologies; Cat. No.: ACE 321-2510; 30% acetonitrile in 0.1% trifluoroacetic acid to 70% acetonitrile in 0.1% trifluoroacetic acid in 20 min; flow: 4 mL/min; t$_R$=7 min. The collected HPLC fraction was diluted with 40 mL water and immobilized on a Sep-Pak light C18 cartridge (Waters, WAT023501), which was washed with 5 mL water and eluted with 1 mL ethanol to deliver 296 MBq of the product (38%, corrected for decay; radiochemical purity>99%). The desired product was characterized by co-injection with the non-radioactive F-19 fluoro standard (SKT05-169) using analytical HPLC: ACE3-C18 50 mm×4.6 mm; solvent gradient: start 5% acetonitrile-95% acetonitrile in 0.1 M K$_2$HPO$_4$ in 7 min., flow: 2 mL/min (t$_R$=5.0 min), RCP: >99% (HPLC).

2-(4-{(E)-2-[2-(2-[¹⁸F]Fluoro-ethoxy)-4-nitro-phenyl]-vinyl}-phenyl)-6-methyl-3H-imidazo[1,2-a]pyridine

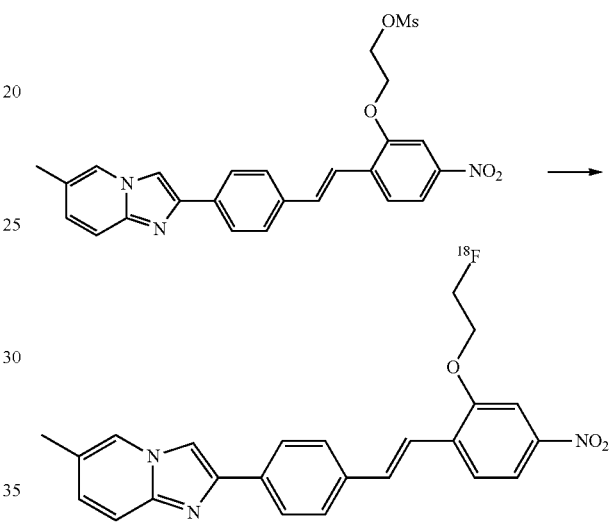

Aqueous [¹⁸F]Fluoride (0.255 GBq) was trapped on a QMA cartridge (Waters, Sep Pak Light QMA Part. No.: WAT023525) and eluted with 1.5 mL K$_{222}$/K$_2$CO$_3$-solution (5 mg K$_{222}$ in 0.95 mL MeCN, 1 mg K$_2$CO$_3$ in 0.05 mL water) into a Wheaton vial (5 mL). The solvent was removed by heating at 120° C. for 10 min under a stream of nitrogen. Anhydrous MeCN (1 mL) was added and evaporated as before. A solution of precursor methanesulphonic acid 2-(2-{(E)-2-[4-(6-methyl-1H-imidazo[1,2-a]pyridin-2-yl)phenyl]vinyl}-5-nitrophenoxy)ethyl ester (SKT08-175) (3 mg) in 500 µL anhydrous DMF was added. After heating at 130° C. for 15 min the crude reaction mixture was diluted with water/MeCN (1/1) to a total volume of 5 mL and purified by preparative HPLC: ACE 5-C18-HL 250 mm×10 mm, Advanced Chromatography Technologies; Cat. No.: ACE 321-2510; 40% acetonitrile in 0.1% trifluoroacetic acid to 70% acetonitrile in 0.1% trifluoroacetic acid in 20 min; flow: 4 mL/min; t$_R$=14 min. The collected HPLC fraction was diluted with 40 mL water and immobilized on a Sep-Pak Plus tC18 cartridge (Waters, WAT036810), which was washed with 5 mL water and eluted with 2 mL ethanol to deliver 55 MBq of the product (40%, corrected for decay; radiochemical purity>95%). The desired product was characterized by co-injection with the non-radioactive F-19 fluoro standard (SKT07-115) using analytical HPLC: ACE3-C18 50 mm×4.6 mm; solvent gradient: start 5% acetonitrile-95% acetonitrile in 10 mM Na$_2$HPO$_4$; (pH 7.4) in 7 min, flow: 2 mL/min (t$_R$=5.7 min), RCP: >95% (HPLC).

2-(4-{(E)-2-[4-(2-[$^{18}$F]Fluoro-ethoxy)-phenyl]-vinyl}-phenyl)-6-methoxy-benzothiazole

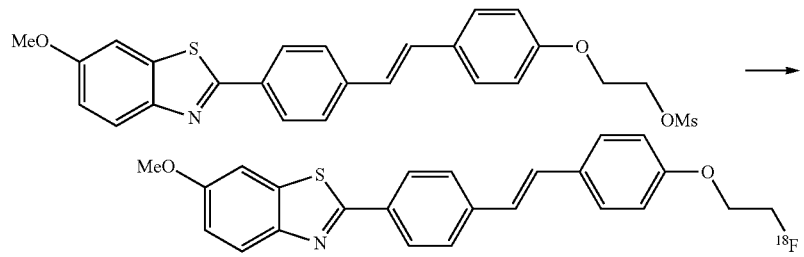

Aqueous [$^{18}$F]Fluoride (0.250 GBq) was trapped on a QMA cartridge (Waters, Sep Pak Light QMA Part. No.: WAT023525) and eluted with 1.5 mL $K_{222}/K_2CO_3$-solution (5 mg $K_{222}$ in 0.95 mL MeCN, 1 mg $K_2CO_3$ in 0.05 mL water) into a Wheaton vial (5 mL). The solvent was removed by heating at 120° C. for 10 min under a stream of nitrogen. Anhydrous MeCN (1 mL) was added and evaporated as before. A solution of precursor methanesulphonic acid 2-(4-{(E)-2-[4-(6-methoxy-1,3-benzothiazol-2-yl)phenyl]vinyl}phenoxy)ethyl ester (SKT08-179) (3 mg) in 500 µL anhydrous DMF was added. After heating at 130° C. for 15 min the crude reaction mixture was diluted with water/MeCN (1/1) to a total volume of 5 mL and purified by preparative HPLC: ACE 5-C18-HL 250 mm×10 mm, Advanced Chromatography Technologies; Cat. No.: ACE 321-2510; 60% acetonitrile in 0.1% trifluoroacetic acid to 90% acetonitrile in 0.1% trifluoroacetic acid in 30 min; 30-40 min 100% acetonitrile (0.1% trifluoroacetic acid), flow: 4 mL/min; $t_R$=31 min. The collected HPLC fraction was diluted with 40 mL water and immobilized on a Sep-Pak Plus tC18 cartridge (Waters, WAT036810), which was washed with 5 mL water and eluted with 2 mL ethanol to deliver 13 MBq of the product (9%, corrected for decay; radiochemical purity>95%). The desired product was characterized by co-injection with the non-radioactive F-19 fluoro standard (SKT03-77) using analytical HPLC: ACE3-C18 50 mm×4.6 mm; solvent gradient: start 5% acetonitrile-95% acetonitrile in 10 mM $Na_2HPO_4$; (pH 7.4) in 7 min, flow: 2 mL/min ($t_R$=6.9 min), RCP: >95% (HPLC).

[4-(2-[$^{18}$F]Fluoro-ethoxy)-phenyl]-[4-(6-methoxy-benzothiazol-2-yl)-phenyl]-diazene

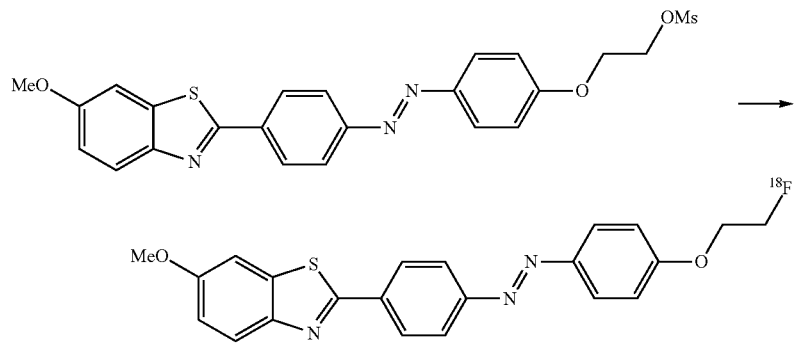

Aqueous [$^{18}$F]Fluoride (0.350 GBq) was trapped on a QMA cartridge (Waters, Sep Pak Light QMA Part. No.: WAT023525) and eluted with 1.5 mL $K_{222}/K_2CO_3$-solution (5 mg $K_{222}$ in 0.95 ml MeCN, 1 mg $K_2CO_3$ in 0.05 mL water) into a Wheaton vial (5 mL). The solvent was removed by heating at 120° C. for 10 min under a stream of nitrogen. Anhydrous MeCN (1 mL) was added and evaporated as before. A solution of precursor 2-(4-{(E)-[4-(6-methoxybenzothiazol-2-yl)phenyl]diazenyl}phenoxy)ethyl methane sulphonate (SC597) (1 mg) in 500 µL anhydrous DMF was added. After heating at 130° C. for 10 min the crude reaction mixture was diluted with water/MeCN (1/1) to a total volume of 5 mL and purified by preparative HPLC: Phenomenex Synergy Hydro-RP 250 mm×10 mm; 80% acetonitrile in 0.1% trifluoroacetic acid to 85% acetonitrile in 0.1% trifluoroacetic acid in 20 min; flow: 4 mL/min; $t_R$=19 min. The collected HPLC fraction was diluted with 40 mL water and immobilized on a Sep-Pak Plus tC18 cartridge (Waters, WAT036810), which was washed with 5 mL water and eluted with 2 mL ethanol to deliver 65 MBq of the product (35%, corrected for decay; radiochemical purity>85%). The desired product was characterized by co-injection with the non-radioactive F-19 fluoro standard (SC598) using analytical HPLC: ACE3-C18 50 mm×4.6 mm; solvent gradient: start 5% acetonitrile-95% acetonitrile in 10 mM $Na_2HPO_4$; (pH 7.4) in 7 min, flow: 2 mL/min ($t_R$=7.1 min), RCP: >85% (HPLC).

Biological Results

Competitive Binding Assay

The DSB compounds were tested for their ability to bind to PHF in a competition-style assay.

The ligand assay uses a reference ligand that shows increased fluorescence when that ligand binds to PHF. If a test compound that also binds to PHFs with the same or greater affinity is added, it will displace the reference ligand and reduce the fluorescence signal. In the present assay, the reference compound is primulin, which was added at 1 µM. Test compounds were added at concentrations from 0.05 to 1 µM. The $P_{50}$ for a test compound is defined as the concentration of compound that reduces the primulin signal to 50% of the control value. This value is, therefore, not an absolute affinity, but a relative affinity compared to the affinity of primulin.

Method

PHFs were isolated from the brain of an Alzheimer's disease patient essentially as described by Wischik et al. (Neurobiology of Aging, Vol. 16, pp. 409-431, 1995). The IFII fraction was isolated by centrifugation on a sucrose gradient as described in the PhD thesis of C. M. Wischik, and was further extracted into an 'abc sup' as described by C. M. Wischik (Thesis "The structure and biochemistry of paired helical filaments in Alzheimer's disease" Part I and II; Cambridge University, 1989).

The assay for ligand activity was performed in 96 well plates (Nunc Cat. No. 236108). The test compound at the required concentration was mixed with PHFs, then primulin was added to give a final concentration of 1 µM and a total volume of 100 µl. The concentration of PHFs added was determined for each preparation to give an adequate fluorescence signal, and was typically in the range 1-2 µl/100 µl. The test compounds were typically dissolved in DMSO to give a final concentration of 10% DMSO in the assay. The control fluorescence, in the absence of PHFs, was also measured in the presence of 10% DMSO.

The fluorescence was measured in a Varian Carey Eclipse Fluorescence Spectrophotometer, with the emission wavelength at 480 nm. Excitation spectra were recorded and corrected by subtraction of the signal measured in the absence of PHFs, using the Varian software. The fluorescence signal at the peak emission wavelength of 420 nm was measured from the corrected spectra. The fluorescence values were plotted as a function of concentration of test compound, and the value for $P_{50}$ measured from the graph.

$P_{50}$ Values $P_{50}$ data in brackets were measured in 10% DMSO

Reference Compound

| Code | Compound | $P_{50}$ (µM) |
|---|---|---|
| Primulin | SO₃Na structure with benzothiazole-benzothiazole-phenyl-NH₂ | (1) |

DSB Compounds

Compounds where -Q- is —NHC(O)—; C(O)—; —C(O)NH—; or —C(O)NR¹—

Benzothiazole Compounds

Non-Fluorinated Methoxy-Amides

| Code | Book No. | $P_{50}$ (µM) |
|---|---|---|
| ABMA-04 | SKT01-99 | 0.87 |
| ABMA-05 | SKT01-41 | 0.85 |
| ABMA-06 | SKT01-21 | 0.37 |
| ABMA-07 | SKT01-103 | 1.35 |
| ABMA-08 | SKT01-63 | ~1.2 |
| ABMA-09 | SKT01-61 | 0.17 |

-continued

| Code | Book No. | $P_{50}$ (µM) |
|---|---|---|
| ABMA-10 | SKT01-155 | 0.31 |
| ABMA-11 | SKT01-161 | 0.43 |
| ABMA-13 | SKT04-89 | 0.31 |

Fluorinated Methoxy-Amides

| Code | Book No. | $P_{50}$ (µM) |
|---|---|---|
| ABFMA-01 | SK2033-50 | no effect |
| ABFMA-02 | SK2033-49 | no effect |
| ABFMA-03 | SK2033-47 | no effect |
| ABFMA-10 | SKT05-21 | no effect |
| ABFMA-12 | SKT02-103 | 0.17 |
| ABFMA-13 | SKT02-169 | no effect |
| ABFMA-15 | SKT01-157 | 0.43 |
| ABFMA-16 | SKT01-149 | no effect |
| ABFMA-16a | SKT01-149a | no effect |
| ABFMA-16b | SKT01-149b | no effect |
| ABFMA-18 | SKT01-159 | no effect |
| ABFMA-19 | SKT02-25 | no effect |

Monofluoro Methoxy-Amides

| Code | Book No. | $P_{50}$ (µM) |
|---|---|---|
| ABMFMA-01 | SKT02-135 | no effect |
| ABMFMA-02 | SKT04-137 | 0.89 |
| ABMFMA-03 | SKT04-111 | 0.34 |
| ABMFMA-05 | SKT03-99 | 0.20 |
| ABMFMA-06 | SKT03-75 | no effect |
| ABMFMA-08 | SKT04-33 | >1 |

-continued

| Code | Book No. | $P_{50}$ (µM) |
|---|---|---|
| ABMFMA-09 | SKT04-29 | 0.21 |

Non-Fluorinated Hydroxy-Amides

| Code | Book No. | $P_{50}$ (µM) |
|---|---|---|
| ABHA-01 | SKT01-101 | 0.90 |
| ABHA-02 | SKT01-77 | 0.56 |

-continued

| Code | Book No. | $P_{50}$ (μM) |
|---|---|---|
| ABHA-03 | SKT01-57 | 0.45 |
| ABHA-04 | SKT01-111 | no effect |

Fluorinated Hydroxy-Amides

| Code | Book No. | $P_{50}$ (μM) |
|---|---|---|
| ABFHA-01 | SKT03-07 | 0.19 |
| ABFHA-02 | SKT02-45 | 0.34 |
| ABFHA-03 | SKT02-149 | 0.1 |
| ABFHA-04 | SKT03-41 | no effect |
| ABFHA-05 | SKT02-171 | 0.4 |
| ABFHA-06 | SKT05-39 | 0.39 |
| ABFHA-07 | SKT02-163 | 0.1 |
| ABFHA-08 | SKT05-17 | >1 |
| ABFHA-09 | SKT05-13 | >1 |
| ABFHA-10 | SKT04-179 | >1 |
| ABFHA-11 | SKT03-129 | 0.31 |

Non-Fluorinated Methyl-Amides

| Code | Book No. | $P_{50}$ (μM) |
|---|---|---|
| ABAA-04 | SK2033-55 | no effect |
| ABAA-05 | SK2033-72 | no effect |
| ABAA-06 | LS-T107 | 0.52 |
| ABAA-07 | SKT01-5 | no effect |
| ABAA-08 | SK2033-93 | no effect |
| ABAA-10 | SK696-32 | ~1.2 |
| ABAA-11 | SK696-54 | ~1.2 |
| ABAA-12 | SK2033-94 | no effect |

Dimethylamine-Amides

| Code | Book No. | $P_{50}$ (μM) |
|---|---|---|
| ABDMAA-01 | SKT03-171 | 0.98 |
| ABDMAA-02 | SKT03-171.01 | >1 |

Unsubstituted-Amides

| Code | Book No. | $P_{50}$ (μM) |
|---|---|---|
| AUB-01 | SKT04-127 | >1 |
| AUB-02 | SKT04-143 | >1 |
| AUB-03 | SKT04-163 | >1 |

Imidazo[2,1-a]pyridine Compounds

| Code | Book No. | $P_{50}$ (μM) |
|---|---|---|
| AIPN-01 | SKT05-123 | >1 |
| AIPN-02 | SKT05-93 | 0.31 |
| AIPN-03 | SKT05-107 | no effect |
| AIPN-04 | SKT05-171 | no effect |
| AIPN-05 | SKT06-5 | 0.51 |
| AIPN-06 | SKT05-169 | no effect |
| AIPN-07 | SKT06-53 | >1 |
| AIPN-08 | SKT06-63 | 0.10 |
| AIPN-09 | SKT05-165 | 0.34 |
| AIPN-10 | SKT05-173 | 0.18 |
| AIPN-11 | SKT06-71 | 0.66 |
| AIPN-12 | SKT06-67 | 0.33 |
| AIPN-13 | SKT06-7 | 0.63 |
| AIPN-14 | SKT06-11 | 0.5 |
| AIPN-16 | SKT06-29 | >1 |
| AIPN-17 | SKT06-15 | no effect |
| AIPN-18 | SKT06-13 | >1 |
| AIPN-20 | SKT06-55 | 0.27 |
| AIPN-21 | SKT06-59 | 0.46 |
| AIPN-22 | SKT06-39 | 0.76 |
| AIPN-23 | SKT06-49 | 0.95 |
| AIPN-24 | SKT06-45 | ~1.0 |
| AIPN-25 | SKT06-79 | >1 |
| AIPN-26 | SKT06-51 | >1 |
| AIPN-27 | SKT06-57 | >1 |
| AIPN-28 | SKT06-61 | >1 |
| AIPN-29 | SKT06-103 | 0.70 |

Imidazo[2,1-a]pyrimidine Compounds

| Code | Book No. | $P_{50}$ (μM) |
|---|---|---|
| AIPM-01 | SKT05-95 | no effect |

Compounds where -Q- is —CH═CH—; —CR$^1$═CH—; —CH═CR$^1$—; or —CR$^1$═CR$^1$—

Benzothaizole Compounds

Non-Fluorinated Methyl-Alkenes

| Code | Book No. | $P_{50}$ (μM) |
|---|---|---|
| BEMA-01 | SK696-39 | no effect |
| BEMA-05 | SKT01-55 | no effect |
| BEMA-06 | SKT01-69 | no effect |
| BEMA-08 | SK2033-30 | fl |
| BEMA-09 | SK696-62 | no effect |
| BEMA-10 | SK696-57 | ~1.2 |
| BEMA-11 | SK696-43 | no effect |
| BEMA-12 | SK2033-29 | no effect | fl indicates that the compound is fluorescent. Consequently, binding levels for the compound in the competition binding assay cannot be determined by fluorescent spectroscopy. Alternatively, the binding of the ligand to aggregated tau may be determined using a cell based-assay or analysis of tissue sections exposed to the ligand, as described herein.

Non-Fluorinated Methoxy-Alkenes

| Code | Book No. | $P_{50}$ (μM) |
|---|---|---|
| BEMOA-03 | SKT02-67 | 0.04 |
| BEMOA-05 | SKT01-107 | 0.28 |
| BEMOA-06 | SKT01-189 | no effect |
| BEMOA-09 | SKT03-107 | 0.03 |

Fluorinated Methoxy-Alkenes

| Code | Book No. | $P_{50}$ ($\mu$M) |
|---|---|---|
| BEFA-01 | SK2033-44 | no effect |
| BEFA-02 | SK2033-42 | no effect |
| BEFA-03 | SK2033-40 | no effect |
| BEFA-04 | SKT02-17 | no effect |
| BEFA-06 | SKT02-117 | fl |
| BEFA-09 | SKT02-81 | no effect |
| BEFA-10 | SKT02-137 | fl |
| BEFA-12 | SKT03-77 | no effect | fl indicates that the compound is fluorescent. Consequently, binding levels for the compound in the competition binding assay cannot be determined by fluorescent spectroscopy. Alternatively, the binding of the ligand to aggregated tau may be determined using a cell based-assay or analysis of tissue sections exposed to the ligand, as described herein.

Monofluoro and Fluorinated Hydroxy-Alkenes

| Code | Book No. | $P_{50}$ ($\mu$M) |
|---|---|---|
| BEHF-01 | SKT02-165 | fl |
| BEHF-02 | SKT02-155 | fl |
| BEHF-04 | SKT02-111 | no effect |
| BEHF-06 | SKT05-05 | fl |
| BEHF-07 | SKT04-169 | fl | fl indicates that the compound is fluorescent. Consequently, binding levels for the compound in the competition binding assay cannot be determined by fluorescent spectroscopy. Alternatively, the binding of the ligand to aggregated tau may be determined using a cell based-assay or analysis of tissue sections exposed to the ligand, as described herein.

Imidazo[1,2-a]pyridine Compounds

| Code | Book No. | $P_{50}$ ($\mu$M) |
|---|---|---|
| IEPN-01 | SKT06-117 | 0.05 |

Compounds where -Q- is —N═N—
Benzothiazole Compounds

| Code | Book No. | $P_{50}$ ($\mu$M) |
|---|---|---|
| BDF-01 | LS-T192 | 0.29 |
| BDF-02 | LS-T191 | 0.46 |
| BDF-03 | LS-T209 | 0.13 |
| BDF-04 | LS-T213 | 0.08 |
| BDF-05 | LS-T245 | 0.09 |
| BDF-06 | LS-T256 | 0.04 |
| BDF-07 | LS-T210 | 0.72 |
| BDF-08 | LS-T214 | no effect |
| BDF-09 | LS-T229 | no effect |
| BDF-10 | LS-T235A | 0.87 |
| BDF-11 | LS-T235B | 0.6 |
| BDF-12 | LS-T236A | 0.70 |
| BDF-13 | LS-T236B | 0.35 |
| BDF-14 | LS-T274 | 0.02 |
| BDF-15 | LS-T272 | 0.14 |
| BDF-16 | LS-T288 | 0.03 |
| BDF-17 | LS-T289 | 0.03 |

Imidazo[1,2-a]pyridine Compounds

| Code | Book No. | $P_{50}$ ($\mu$M) |
|---|---|---|
| DPN-001 | SKT05-163 | 0.03 |

Calculated Log P and TPSA ($A^2$)

Molecular polar surface area (PSA) or total polar surface area (TPSA) i.e. surface belonging to polar atoms (mainly N, O and associated hydrogens), is a descriptor that has been shown to correlate well with passive molecular transport through membranes, and therefore allows prediction of transport properties of drugs. It has been successfully applied for the prediction of intestinal absorption and blood-brain barrier crossing. The differences in CNS and non-CNS drugs have been examined using PSA and it has been shown that on average the PSA for drugs that act upon the CNS is smaller.

Computational methods for log P estimation are high throughput but are database limited in that the values computed for each structure depend on the information contained in the program library. In addition, most estimates reflect only partitioning of the neutral species, and therefore often log P is estimated to be higher than the experimental values for a given compound.

Various protocols have been reported to calculate the PSA, differing in definition of "polar atoms", different methodologies for generating the 3D structure, or the surface itself. However, the results of these various approaches are highly correlated, even when absolute values may differ due to differences in computational protocols and different sets of atomic radii used. The calculation of a topological PSA (TPSA) is based on a summation of tabulated surface contributions of polar fragments (i.e. atoms regarding also their bonding pattern) and allows the fast, straightforward calculation of PSA from a 2D structure. A preferred system is that of "molinspirations cheminformatics" http://www.molinspiration.com/).

Thus, in the tables below, miLog P refers to the Log P values calculated using the Molinspiration calculator.

Imidazo[1,2-a]pyridine Compounds

| Code | Book No. | miLog P | TPSA ($Å^2$) |
|---|---|---|---|
| AIPN-02 | SKT05-93 | 4.37 | 49.6 |
| AIPN-03 | SKT05-107 | 2.97 | 59.3 |
| AIPN-04 | SKT05-171 | 3.03 | 59.3 |
| AIPN-05 | SKT06-5 | 3.09 | 59.3 |
| AIPN-06 | SKT05-169 | 3.53 | 59.3 |
| AIPN-07 | SKT06-53 | 3.6 | 59.3 |
| AIPN-08 | SKT06-63 | 4.22 | 92.2 |
| AIPN-09 | SKT05-165 | 5.05 | 92.2 |
| AIPN-10 | SKT05-173 | 4.63 | 78.7 |
| AIPN-11 | SKT06-71 | 3.34 | 72.4 |
| AIPN-12 | SKT06-67 | 4.12 | 58.4 |
| AIPN-13 | SKT06-7 | 4.32 | 55.6 |
| AIPN-14 | SKT06-11 | 3.78 | 66.6 |
| AIPN-16 | SKT06-29 | 4.55 | 49.6 |
| AIPN-18 | SKT06-13 | 4.05 | 59.3 |
| AIPN-20 | SKT06-55 | 4.21 | 58.4 |
| AIPN-21 | SKT06-59 | 4.30 | 58.4 |
| AIPN-22 | SKT06-39 | 4.46 | 49.6 |
| AIPN-23 | SKT06-49 | 4.41 | 55.6 |
| AIPN-24 | SKT06-45 | 4.50 | 55.6 |
| AIPN-26 | SKT06-51 | 4.23 | 66.6 |

-continued

| Code | Book No. | miLog P | TPSA (Å$^2$) |
|---|---|---|---|
| AIPN-27 | SKT06-57 | 4.41 | 66.6 |
| AIPN-28 | SKT06-61 | 5.14 | 55.6 |

Tissue Section and Cell Assays

The binding of ligands to aggregated tau in tissue sections or cells containing such aggregates can also be used to test whether such compounds can (i) enter cells, and (ii) bind to aggregated tau. In addition, it is a suitable means to test fluorescent ligands that cannot be tested in the fluorescent competition binding assay.

Brain tissue sections were used from transgenic mice expressing full-length human tau, that contained a double mutation P301S/G335D (line 66 mouse). Aggregated tau pathology accumulates in neurons in these animals. Fixed tissue was used either after embedding in paraffin or after freezing in the presence of cryoprotectant.

The aggregated tau was prepared in cell lines as described in WO02/055720. In essence, fibroblast cells (3T6) express full-length tau ("T40") under control of an inducible promotor, and low constitutive levels of the PHF-core tau fragment (12 kD fragment). Then T40 expression is induced, it undergoes aggregation-dependent truncation within the cell, N-terminally at ~αα295 and C-terminally at ~αα390, thereby producing higher levels of the 12 kD PHF-core domain fragment.

Paraffin-Embedded Brain Sections

Sections from the brains of mice expressing full-length tau, that contain a double mutation P301S/G335D, associated with frontotemporal de brains were cut 5 μm thick. Sections were dewaxed and rehydrated into water. Inherent fluorescence was quenched with sodium permanganate followed by sodium borohydride. Primulin or SK2033-30 was added in 50% ethanol. In a second experiment, SK2033-30 was added in 50% ethanol containing 10% DMSO. Sections were compared with those stained by standard immunohistochemistry using mAb 7/51, an antibody recognising truncated tau repeat domain (Novak et al. (1993); Wischik et al. (1996)).

Figure 2A:
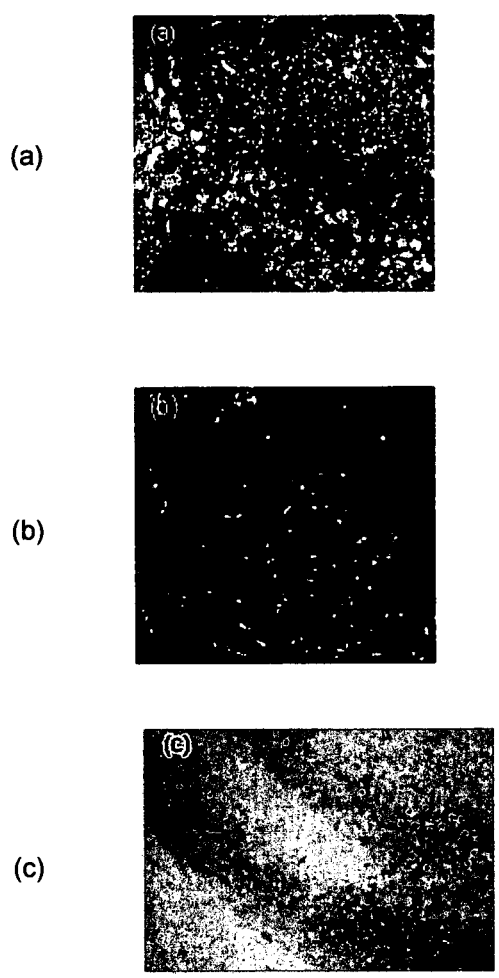
FIG. 2A shows the binding of primulin (a), SK2033-30 (BEMA-08) (b) and mAb 7/51 (c) to paraffin-embedded forebrain sections from line 66 mice.
Figure 2B:
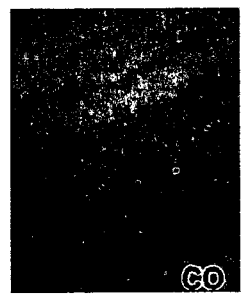
FIG. 2B shows the binding of SK2033-30 (BEMA-08) and mAb 7/51 to paraffin-embedded forebrain sections from line 66 mice. CO-1 and CO-2 are the cortex sections stained with mAb 7/51 and SK2033-30 respectively, and HC-1 and HC-2 are hippocampal formation sections stained with mAb 7/51 and SK2033-30 respectively.
Figure 2B:
Figure 2B:
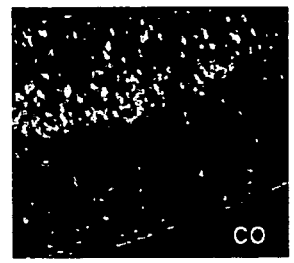
Figure 2B:
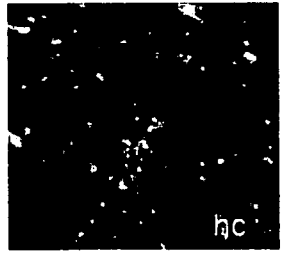

The compound SK2033-30 is fluorescent, but there was little evidence for its uptake into cells in a section from a line 66 mouse brain, when compared with either primulin or immunostaining with antibodies (FIG. 2A). When the solubility of the compound was increased, by inclusion of DMSO (10%), the SK2033-30 showed a staining pattern similar to that observed with primulin or antibody (FIG. 2B).

Frozen Brain Sections

Sections were taken from line 66 mice that had been fixed with 4% paraformaldehyde and then cryoprotected in 30% sucrose. Sections (30 μm) were cut and used free-floating. The ligand LST-213 was dissolved in either 1% triton or in 50% ethanol (the residual DMSO concentration from the stock solution was 1%).

Figure 3:
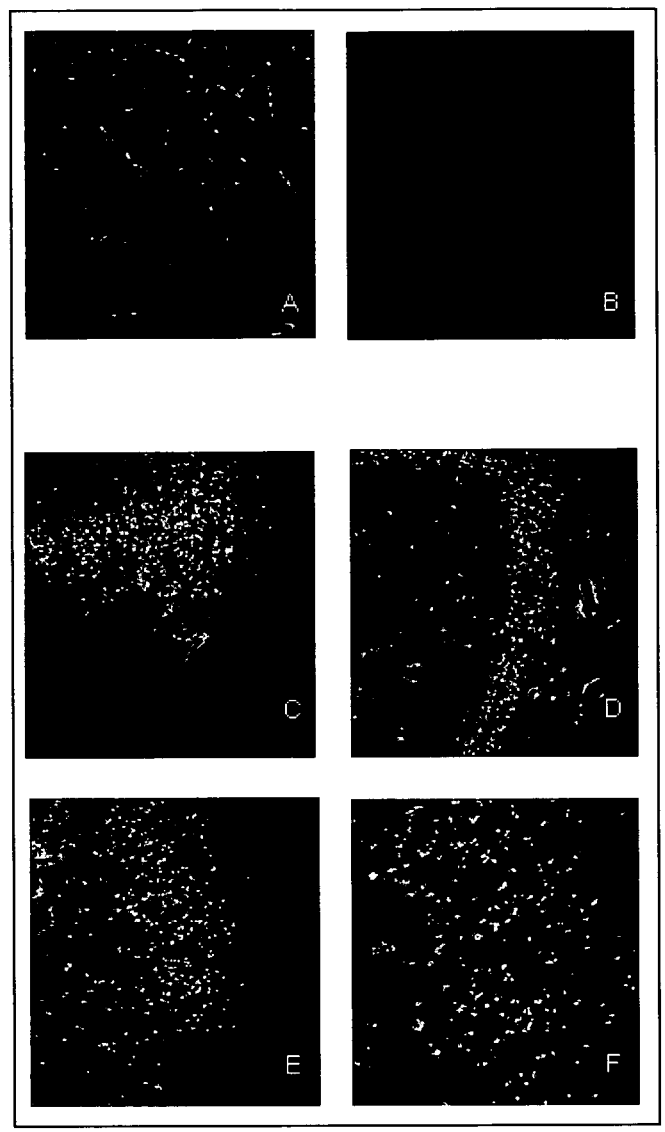
FIG. 3 shows the binding of LST-213 (BDF-04) to frozen mouse brain sections. Minimal fluorescence is seen in tissue from wild-type mice (A, cortex; B, amygdala) when compared with tissue from transgenic line 66 mice (C and E, cortex; D and F, amygdala) in which the fluorescent ligand was abundant. The lower panel (E and F) represents a higher power magnification of the sections shown in the panel above (C and D). The labelled structures exhibit the same pattern of distribution as tau-positive neurons (as seen in FIG. 1).

When frozen brain sections were incubated with LST-213, they became yellow over time and, by 24 hrs, had absorbed almost the entire compound. This was indicated by the medium becoming colourless. These sections were looked at using a BioRad confocal laser scanning microscope with the settings used for fluoroscein detection. Definite staining of structures in the cortex and in the hippocampus were observed (FIG. 3) and these would be consistent with the pattern of tau-positive neurons in such sections.

Tissue Culture Cells

The tissue culture assay uses 3T6 mouse cells engineered to express both full-length human tau protein (htau40) under the control of an inducible promoter (pOPRSVI), and to express low levels of truncated tau (295-390, dGA) under the control of a constitutive promoter (pcDNA3.1). Expression of large quantities of htau40 is induced by the addition of isopropyl β-D-1-thiogalactopyranoside (IPTG; 10-50 μM), which in turn leads to the production of additional truncated tau by a process in which aggregation and processing of the full-length tau occurs in the presence of dGA tau which acts as template. The aggregation of tau in this assay is depicted in FIG. 1.

Murine 3T6 fibroblast cells were grown to ~80% confluency in a 10-cm dish, before splitting into 2×24 well plates, and allowed to grow for a further 24 hrs when IPTG was added. After overnight incubation, the medium was removed and the cells were washed with PBS.

Figure 4:
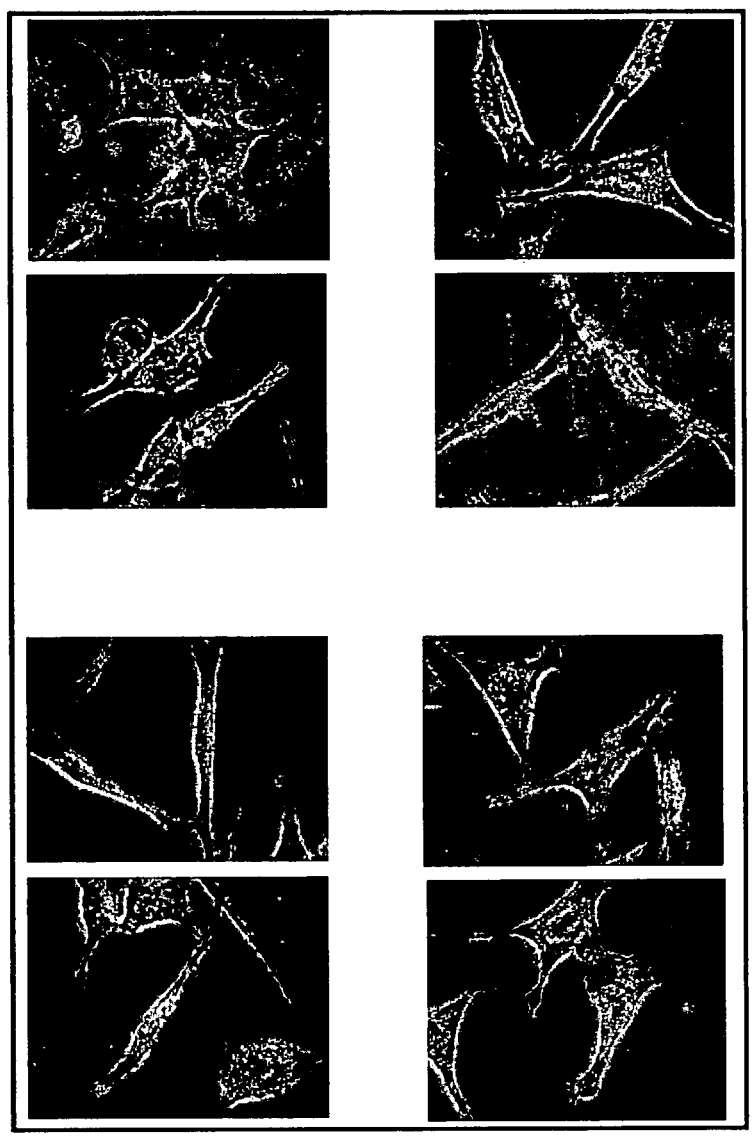
FIG. 4 shows the uptake of LST-213 (BDF-04) in cell culture. Cells were incubated in the presence of LST-213 for 18 hrs. Considerable insoluble material can be seen in the background as well as intracellular uptake (upper panel). Uptake can be clearly seen following washes with PBS, which removed most of the insoluble material from the outside of the cells (lower panel).

There was a marked increase in the uptake of LST-213 by cultured cells after 24 hrs as compared with 2-4 hrs when examined by light microscopy (FIG. 4). In the upper panels of the figure, one can see a great deal of insoluble material in the surrounding medium. After washing, however, it is clear that some of the compound is taken up by the cells.

A similar experiment was performed with cells seeded on to cover slips in a 24-well plate. After 24 hrs, the cells were incubated with ligand for 20 hrs in the presence or absence of IPTG (100 μM) i.e. induced or uninduced.

Figure 5:
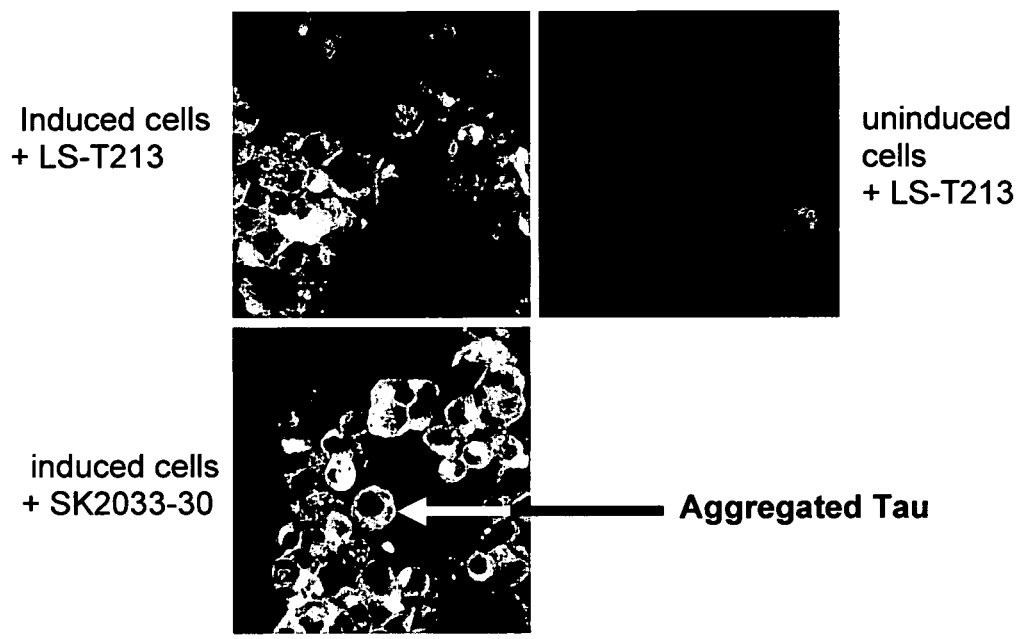
FIG. 5 shows the selective binding of two different ligands of the invention (LS-T213 [BDF-04] and SK2033-30 [BEMA-08]) to aggregated tau within cells. The ligands are visualized by fluorescence microscopy. The top left panel shows the binding of LS-T213 to aggregated tau within induced cells. The bottom left panel shows the binding of SK2033-30 to aggregated tau within induced cells. The top right panel is a control image showing uninduced cells that have been exposed to LS-T213.

LST-213 showed much stronger staining in the cells following IPTG-induction than in uninduced cells (FIG. 5). LST-213, in the presence of β-cyclodextrin (used to assist transport of hydrophobic compounds across membranes), showed no significant improvement in this labelling. Uptake and labelling of aggregated tau in induced cells was also demonstrated for SK2033-30 (FIG. 5).

Ligands can be demonstrated to bind to aggregated tau in vivo and that they are capable of being taken up into cells. This can be shown for aggregated tau using both fixed tissue and cells growing in culture.

Biodistribution Assay

Biodistribution and excretion studies for ligands were performed in male NMRI mice (body weight app. 30 g; 3 animals per time point). The animals were kept under normal laboratory conditions at a temperature of 22±2° C. and a dark/light rhythm of 12 hours. Food and water were provided ad libitium. During an acclimatisation period of at least 3 days before the beginning of the study, animals were clinically examined to ascertain the absence of abnormal clinical signs.

At 2, 5, 30, 60 and 120 min post intravenous injection via the tail vein of ca. 150 kBq in 100 μl of the test compound, urine and faeces were quantitatively collected. At the same time points, animals were anaesthetised with isoflurane, sacrificed by decapitation and the following organs and tissues were removed for the determination of radioactivity using a gamma-counter: spleen, liver, kidney, lung, bone, heart, brain, fat, thyroid, muscle, skin, blood, tail, stomach (without content), testicle, intestine (with content), pancreas, adrenals, skull, and the remaining body. For the analysis, the decay corrected percentage of the injected dose per tissue weight (% ID/g±standard deviation) was calculated.

The biodistribution of $^{18}$F-labelled SKT04-137 (shown below) in mice shows a good brain uptake (3.99% injected dose/g tissue after 2 min), and a significant brain wash-out (still 1.43% injected dose/g tissue after 60 min; i.e. 64% washout).

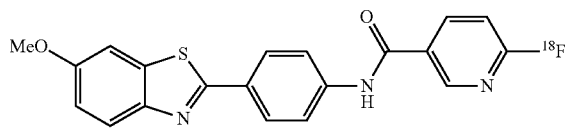 [SMILES: COc1ccc2nc(-c3ccc(NC(=O)c4ccc([18F])nc4)cc3)sc2c1]

Organ Distribution of F-18 Signal of SKT04-137 in Mice (% ID, % Injected Dose)

|  | Time | | | | | | | | | |
|---|---|---|---|---|---|---|---|---|---|---|
|  | 2 min | | 5 min | | 30 min | | 60 min | | 120 min | |
| Organ | % ID/g | S.D. | % ID/g | S.D. | % ID/g | S.D. | % ID/g | S.D. | % ID/g | S.D. |
| Spleen | 2.95 | 0.84 | 2.44 | 0.12 | 1.19 | 0.11 | 0.60 | 0.10 | 0.30 | 0.03 |
| Liver | 11.52 | 3.10 | 13.30 | 2.37 | 7.03 | 1.69 | 4.26 | 0.79 | 2.41 | 1.14 |
| Kidney | 9.60 | 2.82 | 7.10 | 0.50 | 6.38 | 0.70 | 3.78 | 0.69 | 1.49 | 0.52 |
| Lung | 6.91 | 2.25 | 4.55 | 0.08 | 1.83 | 0.25 | 0.97 | 0.06 | 0.40 | 0.01 |
| Bone | 1.54 | 0.37 | 1.50 | 0.34 | 1.20 | 0.10 | 1.96 | 0.24 | 1.65 | 0.22 |
| Heart | 6.68 | 1.98 | 3.72 | 0.18 | 1.62 | 0.26 | 0.81 | 0.04 | 0.39 | 0.04 |
| Brain | 3.99 | 0.62 | 3.54 | 0.45 | 3.19 | 0.42 | 1.43 | 0.18 | 0.60 | 0.10 |
| Fat | 1.25 | 0.51 | 1.57 | 0.51 | 7.21 | 1.41 | 4.51 | 0.41 | 1.76 | 0.25 |
| Thyroid | 3.97 | 3.09 | 2.59 | 1.04 | 1.06 | 0.07 | 0.59 | 0.11 | 0.37 | 0.07 |
| Muscle | 1.98 | 0.50 | 1.80 | 0.13 | 1.11 | 0.14 | 0.63 | 0.06 | 0.20 | 0.02 |
| Skin | 1.01 | 0.25 | 1.28 | 0.18 | 1.87 | 0.17 | 1.11 | 0.08 | 0.45 | 0.06 |
| Blood | 1.69 | 0.41 | 1.12 | 0.02 | 0.74 | 0.13 | 0.39 | 0.04 | 0.16 | 0.01 |
| Tail | 15.89 | 10.06 | 7.40 | 1.02 | 3.74 | 1.26 | 7.70 | 6.06 | 4.93 | 2.66 |
| Stomach | 3.67 | 0.57 | 2.28 | 0.46 | 2.48 | 1.14 | 2.17 | 0.68 | 0.98 | 0.57 |
| Testes | 0.97 | 0.10 | 1.10 | 0.19 | 1.68 | 0.19 | 1.18 | 0.40 | 0.61 | 0.17 |
| Adrenals | 10.84 | 5.50 | 9.59 | 4.97 | 5.62 | 0.96 | 2.83 | 0.55 | 1.04 | 0.07 |
| Intestine | 1.99 | 0.39 | 2.45 | 0.24 | 9.36 | 0.23 | 17.43 | 1.23 | 20.08 | 2.55 |
| Pancreas | 4.34 | 0.88 | 3.17 | 0.39 | 1.74 | 0.08 | 1.11 | 0.43 | 0.33 | 0.05 |
| Skull | 1.93 | 0.55 | 1.28 | 0.31 | 0.95 | 0.15 | 1.44 | 0.11 | 1.04 | 0.28 |

REFERENCES

Andreasen, N, Minthon, L, Davidsson, P, Vanmechelen, E, Vanderstichele, H et al. (2001) Evaluation of CSF-tau and CSF-Aβ42 as diagnostic markers for Alzheimer disease in clinical practice. Arch. Neurol. 58:373-379.

Bondareff, W, Harrington, C, Wischik, C M, Hauser, D L, Roth, M (1994) Immunohistochemical staging of neurofibrillary degeneration in Alzheimer's disease. J. Neuropathol. Exptl. Neurol. 53:158-164.

Boschelli, Diane H.; Wu, Biqi; Sosa, Ana Carolina Barrios; Chen, Joan J.; Golas, Jennifer M.; Boschelli, Frank; Bioorganic & Medicinal Chemistry Letters, 2005, 15, 4681-4684.

Carretero, M T, Harrington, C R, Wischik, C M (1995) Changes in a CSF antigen associated with dementia. Dementia 6:281-285.

Clark, C M, Xie, S, Chittams, J, Ewbank, D, Peskind, E et al. (2003) Cerebrospinal fluid tau and β-amyloid: how well do these biomarkers reflect autopsy-confirmed dementia diagnoses? Arch. Neurol. 60:1696-1702.

Cong, Zhi-Qi; Wang, Chun-Ian; Chen, Tie; Yin, Bing-Zhu; Synthetic Communications, 2006, 36, 679-683. Efficient and rapid method for the oxidation of electron-rich aromatic aldehydes to carboxylic acids using improved basic hydrogen peroxide.

Engelborghs, S, De Vreese, K, Van de Casteele, T, Vanderstichele, H, Van Everbroeck, A et al. (2008) Diagnostic performance of a CSF-biomarker panel in autopsy-confirmed dementia. Neurobiol. Aging 29:1143-1159.

Ermert, J.; Hamacher, K.; Coenen, H. H.; J. Labelled Cpd. Radiopharm. 2000, 43, 1345-1363. N.C.A. $^{18}$F-labelled norepinephrine derivatives via α-aminopropiophenones.

Galasko, D, Chang, L, Motter, R, Clark, C M, Kaye, J et al. (1998) High cerebrospinal fluid tau and low amyloid β42 levels in the clinical diagnosis of Alzheimer disease and relation to apolipoprotein E genotype. Arch. Neural. 55:937-945.

Grossman, M, Farmer, J, Leight, S, Work, M, Moore, P et al. (2005) Cerebrospinal fluid profile in frontotemporal dementia and Alzheimer's disease Ann. Neurol. 57:721-729.

Goedert, M, Spillantini, M G, Jakes, R, Rutherford, D, Crowther, R A (1989) Multiple isoforms of human microtubule-associated protein tau: sequences and localisation in neurofibrillary tangles of Alzheimer's disease. Neuron 3:519-526.

Goedert, M, Spillantini, M G, Potier, M C, Ulrich, J, Crowther, R A (1989) Cloning and sequencing of the cDNA encoding an isoform of microtubule-associated protein tau containing four tandem repeats: differential expressing of tau protein mRNAs in human brain. EMBO J. 8:393-399.

Hampel, H, Buerger, K, Zinkowski, R, Teipel, S J, Goernitz, A et al. (2004) Measurement of phosphorylated tau epitopes in the differential diagnosis of Alzheimer disease: a comparative cerebrospinal fluid study. Arch. Gen. Psychiatry 61:95-102.

Haugwitz, R. D.; Angel, R. G.; Jacobs, G. A.; Maurer, B. V.; Narayanan, V. L.; Cruthers, L. R.; Szanto, J.; J. Med. Chem., 1982, 25, 8, 969-974. Antiparasitic agents. 5. Synthesis and anthelmintic activities of novel 2-heteroaromatic-substituted isothiocyanatobenzoxazoles and benzothiazoles.

Hodges, J R, Spatt, J, Patterson, K (1999) "What" and "how": Evidence for the dissociation of object knowledge and mechanical problem-solving skills in the human brain. Proc. Natl. Acad. Sci. USA 96:9444-9448.

Hulstaert, F, Blennow, K, Ivanoiu, A, Schoonderwaldt, H C, Riemenschneider, M et al. (1999) Improved discrimination of AD patients using β-amyloid$_{(1-42)}$ and tau levels in CSF. Neurology 52:1555-1562.

Idoux, John P.; Gupton, John T.; McCurry, Cynthia K.; Crews, Donald; Jurss, Cindy D.; Colon, Cesar; Rampi, Richard C.; J. Org. Chem., 1983, 48, 3771-3773. Aromatic fluoroalkoxylation via direct aromatic nucleophilic substitution.

Idoux, John P.; Madenwald, Mark L.; Garcia, Brent S.; Chu, Der-Lun; *J. Org. Chem.*, 1985, 50, 1876-1878. Aromatic fluoroalkoxylation via direct displacement of a nitro or fluoro group.

Imamoto, Tsuneo; Matsumoto, Teruyo; Yokoyama, Hideki; Yokoyama, Masataka; Yamaguchi, Kei-ichi; *J. Org. Chem.*, 1984, 49, 1105-1110. Preparation and synthetic use of trimethylsilyl polyphosphate. A new stereoselective aldol-type reaction in the presence of trimethylsilyl polyphosphate.

Jakes, R, Novak, M, Davison, M, Wischik, C M (1991) Identification of 3- and 4-repeat tau isoforms within the PHF in Alzheimer's disease. *EMBO J.* 10:2725-2729

Kang J., Lemaire H.-G., Unterbeck A., Salbaum J. M., Masters C. L., Grzeschik K.-H., Multhaup G., Beyreuther K. and Müller-Hill B. (1987) The precursor of Alzheimer's disease amyloid A4 protein resembles a cell-surface receptor. Nature, 325, 733-736.

Kashiyama, Eiji; Hutchinson, Ian; Chua, Mei-Sze; Stinson, Sherman F.; Phillips, Lawrence R.; Kaur, Gurmeet; Sausville, Edward A.; Bradshaw, Tracey D.; Westwell, Andrew D.; Stevens, Malcolm F. G.; *J. Med. Chem.*, 42; 1999, 20, 4172-4184. Antitumor benzothiazoles. 8. Synthesis, metabolic formation, and biological properties of the C- and N-oxidation products of antitumor 2-(4-aminophenyl)benzothiazoles.

Kuller L H, Shemanski L, Manolio T, Haan M, Fried L, Bryan N, Burke G L, Tracy R, Bhadelia R. Relationship between ApoE, MRI findings, and cognitive function in the Cardiovascular Health Study. Stroke. 1998 29:388-398.

Kuwabe, Shin-itsu; Torraca, Karen E.; and Buchwald, Stephen L. *J. Am. Chem. Soc.* 2001, 123, 12202-12206

Lai, R Y K, Gertz, H-J, Wischik, D J, Xuereb, J H, Mukaetova-Ladinska, E B et al. (1995) Examination of phosphorylated tau protein as a PHF-precursor at early stage Alzheimer's disease. *Neurobiol. Aging* 16:433-445

Lakmache, Y, Lassonde, M, Gauthier, S, Frigon, J-Y, Lepore, F. (1998) Interhemispheric disconnection syndrome in Alzheimer's disease. Proceedings of the National Academy of Sciences USA 95:9042-9046

Lo Meo, Paolo; D'Anna, Francesca; Gruttadauria, Michelangelo; Riela, Serena and Noto, Renato Tetrahedron 60 (2004) 9099-9111

Malamas, Michael S.; Carlson, Richard P.; Grimes, David; Howell, Ralph; Glaser, Keith; Gunawan, Iwan; Nelson, James A.; Kanzelberger, Mira; Shah, Uresh; Hartman, David A.; *J. Med. Chem.*, 1996, 39, 237-245. Azole phenoxy hydroxyureas as selective and orally active inhibitors of 5-lipoxygenase.

Mann, John; Baron, Anne; Opoku-Boahen, Yaw; Johansson, Eric; Parkinson, Gary; Kelland, Lloyd R.; Neidle, Stephen; *J. Med. Chem.*, 2001, 44, 138-144. A new class of symmetric bisbenzimidazole-based DNA minor groove-binding agents showing antitumour activity.

Marin D B, Breuer B, Marin M L, Silverman J, Schmeidler J, Greenberg D, Flynn S, Mare M, Lantz M, Libow L, Neufeld R, Altstiel L, Davis K L, Mohs R C. The relationship between apolipoprotein E, dementia, and vascular illness. Atherosclerosis. 1998 140:173-180.

Mathis, Chester A.; Wang, Yanming; Holt, Daniel P.; Huang, Guo-Feng; Debnath, Manik L.; Klunk, William E.; *J. Med. Chem.*, 2003, 46, 13, 2740-2754. Synthesis and evaluation of C-11-labeled 6-substituted 2-arylbenzothiazoles as amyloid imaging agents.

Mena, R, Edwards, P, Pérez-Olvera, O, Wischik, C M (1995) Monitoring pathological assembly of tau and β-amyloid proteins in Alzheimer's disease. *Acta Neuropathol.* 89:50-56.

Mena, R, Edwards, P C, Harrington, C R, Mukaetova-Ladinska, E B, Wischik, C M (1996) Staging the pathological assembly of truncated tau protein into paired helical filaments in Alzheimer's disease. *Acta Neuropathol.* 91:633-641.

Mukaetova-Ladinska, E B, Garcia-Sierra, F, Hurt, J, Gertz, H J, Xuereb, J H et al. (2000) Staging of cytoskeletal and β-amyloid changes in human isocortex reveals biphasic synaptic protein response during progression of Alzheimer's disease. *Am. J. Pathol.* 157:623-636.

Novak, M, Kabat, J, Wischik, C M (1993) Molecular characterization of the minimal protease resistant tau unit of the Alzheimer's disease paired helical filament. *EMBO J.* 12:365-370.

Ono, Masahiro; Wilson, Alan; Nobrega, Jose; Westaway, David; Verhoeff, Paul; Zhuang, Zhi-Ping; Kung, Mei-Ping; Kung, Hank F.; *Nuclear Medicine and Biology*, 2003, 30, 565-571. C-11-labeled stilbene derivatives as Aβ-aggregate-specific PET imaging agents for Alzheimer's disease.

Pez, Didier; Leal, Isabel; Zuccotto, Fabio; Boussard, Cyrille; Brun, Reto; Croft, Simon L.; Yardley, Vanessa; Ruiz Perez, Luis M.; Pacanowska, Dolores Gonzalez; Gilbert, Ian H.; *Bioorganic & Medicinal Chemistry*, 2003, 11, 4693-4711. 2,4-Aminopyrimidines as Inhibitors of Leishmanial and Trypanosomal Dihydrofolate Reductase.

Shi, Dong-Fang; Bradshaw, Tracey D.; Wrigley, Samantha; McCall, Carol J.; Lelieveld, Peter; Fichtner, Iduna; Stevens, Malcolm F. G.; *J. Med. Chem.*, 1996, 39, 17, 3375-3384. Antitumor benzothiazoles. 3. Synthesis of 2-(4-aminophenyl)benzothiazoles and evaluation of their activities against breast cancer cell lines in vitro and in vivo.

Vargha-Khadem F, Gadian D G, Watkins K E, Connelly A, Van Paesschen W, Mishkin M. Differential effects of early hippocampal pathology on episodic and semantic memory. Science. 1997 277:376-380.

Villareal, D T, Morris, J C (1998) The diagnosis of Alzheimer's disease. *Alzheimer's Dis. Rev.* 3:142-152

Willingham D. B. (1997) Systems of memory in the human brain. Neuron, 18, 5-8.

Wischik, C M; Thesis "The structure and biochemistry of paired helical filaments in Alzheimer's disease" Part I and II; Cambridge University, 1989.

Wischik, C M, Novak, M, Thøgersen, H C, Edwards, P C, Runswick, M J et al. (1988) Isolation of a fragment of tau derived from the core of the paired helical filament of Alzheimer's disease. *Proc. Natl. Acad. Sci. USA* 85:4506-4510.

Wischik, C M, Edwards, P C, Lai, R Y K, Roth, M, Harrington, C R (1996) Selective inhibition of Alzheimer disease-like tau aggregation by phenothiazines. *Proc. Natl. Acad. Sci. USA* 93:11213-11218.

Wischik, C M, Novak, M, Edwards, P C, Klug, A, Tichelaar, W, Crowther, R A (1988) Structural characterization of the core of the paired helical filament of Alzheimer disease. *Proc. Natl. Acad. Sci. USA* 85:4884-4888.

Wischik C. W. et al., (1989), Curr. Opin. Cell Biol. 1, 115-122.

Wischik, C M, Lai, R Y K, Harrington, C R. 1997. Modelling prion-like processing of tau protein in Alzheimer's disease for pharmaceutical development. In *Microtubule-Associ-* ated *Proteins: Modifications in Disease.*, ed. J. Avila, R. Brandt, K. S. Kosik. pp. 185-241. Amsterdam: Harwood Academic Publishers.

Wischik, C M, Theuring, F, Harrington, C R. (2001). The molecular basis of tau protein pathology in Alzheimer's disease and related neurodegenerative dementias. In: "Neurobiology of Alzheimer's Disease", Eds. Dawbarn, D and Allen, S J, The Molecular and Cellular Neurobiology Series, Bios Scientific Publishers, Oxford).

WO02/055720

Yoshino, Kohichiro; Kohno, Toshihiko; Uno, Toshio; Morita, Tominori; and Tsukamoto, Goro *J. Med. Chem.,* 1986, 29, 820-825. Organic phosphorus compounds. 1. 4-(Benzothiazol-2-yl)benzylphosphonate as potent calcium antagonistic vasodilator.

Zhang, Wei; Oya, Shunichi; Kung, Mei-Ping; Hou, Catherine; Maier, Donna L.; Kung, Hank F.; *Nuclear Medicine and Biology,* 2005, 32, 799-809. F-18 Polyethyleneglycol stilbenes as PET imaging agents targeting Aβ aggregates in the brain.

The invention claimed is:

1. A compound having the formula:

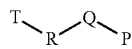

wherein

—R— is independently selected from:

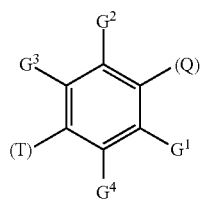

wherein (T) indicates the point of attachment to -T;
and (Q) indicates the point of attachment to -Q-;

-Q- is independently selected from:
—N=N—;
—CH=CH—; —CR$^1$=CH—; —CH=CR$^1$—; —CR$^1$=CR$^1$—;

each —R$^1$ is independently unsubstituted saturated aliphatic C$_{1-4}$-alkyl;

—P is independently selected from:

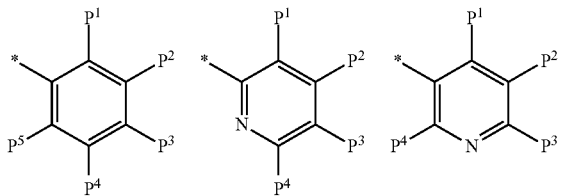

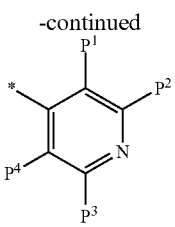

where the asterisk indicates the point of attachment;
-T is independently selected from:

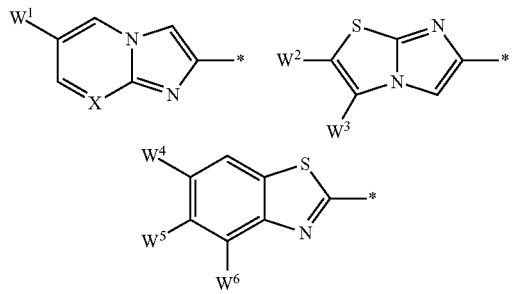

where the asterisk indicates the point of attachment;
and X is independently CH;
—W$^1$ is independently —W$^A$;
—W$^2$ is independently —H or —W$^A$;
—W$^3$ is independently —H or —W$^A$;
—W$^4$ is independently —H or —W$^A$;
—W$^5$ is independently —H or —W$^A$;
—W$^6$ is independently —H or —W$^A$;
with the proviso that at least one of —W$^4$, —W$^5$ and —W$^6$ is —W$^A$;
where —W$^A$ is independently selected from:
—F, —Cl, —Br, —I,
—OH, —W$^{A1}$, —O—W$^{A1}$,
—NH$_2$, —NHW$^{A1}$, and —N(W$^{A1}$)$_2$;
and —W$^{A1}$ is independently selected from:
unsubstituted saturated aliphatic C$_{1-4}$-alkyl,
—CF$_3$,
—CH$_2$CH$_2$OH, and
—CH$_2$CH$_2$N(Me)$_2$;
-G$^1$ is independently —H or -G$^A$;
-G$^2$ is independently —H or -G$^A$;
where -G$^A$ is independently selected from:
—F, —Cl, —Br, —I,
—CF$_3$, —OCF$_3$,
—OH, —OR$^2$;
—[O—CH$_2$CH$_2$]$_n$—R$^{B2}$, where n is 2 to 6;
-G$^3$ is independently —H or -G$^B$;
-G$^4$ is independently —H or -G$^B$
where -G$^B$ is independently selected from:
—F, —Cl, —Br, —I,
—CF$_3$, —OCF$_3$,
—OH, —OR$^2$;
—[O—CH$_2$CH$_2$]$_n$—R$^{B2}$, where n is 2 to 6;
wherein:
—P$^1$ is independently —H or —P$^A$;
—P$^2$ is independently —H or —P$^B$;
—P$^3$ is independently —H or —P$^C$;
—P$^4$ is independently —H or —P$^B$;
—P$^5$ is independently —H or —P$^A$;

and wherein:
each —$P^A$, each —$P^B$, and each —$P^C$ is independently:
—F, —Cl, —Br, —I,
—$R^2$,
—$CF_3$, —$OCF_3$,
—OH, -$L^1$-OH,
—$OR^2$, -$L^1$-$OR^2$, —O-$L^1$-$OR^2$,
—SH, —$SR^2$,
—CN,
—$NO_2$,
—$NH_2$, —$NHR^2$, —$NR^2{}_2$, —$NR^3R^4$,
—NHOH,
-$L^1$-$NH_2$, -$L^1$-$NHR^2$, -$L^1$-$NR^2{}_2$, -$L^1$-$NR^3R^4$,
—O-$L^1$-$NH_2$, —O-$L^1$-$NHR^2$, —O-$L^1$-$NR^2{}_2$, —O-$L^1$-$NR^3R^4$,
—C(=O)OH, —C(=O)$OR^2$,
—OC(=O)$R^2$,
—C(=O)$NH_2$, —C(=O)$NHR^2$, —C(=O)$NR^2{}_2$, —C(=O)$NR^3R^4$,
—NHC(=O)$R^2$, —$NR^2$C(=O)$R^2$,
—C(=O)$NHOR^2$, —C(=O)$NR^2OR^2$,
—NHC(=O)$OR^2$, —$NR^2$C(=O)$OR^2$,
—OC(=O)$NH_2$, —OC(=O)$NHR^2$, —OC(=O)$NR^2{}_2$, —OC(=O)$NR^3R^4$,
—C(=O)$R^2$,
—NHC(=O)$NH_2$, —NHC(=O)$NHR^2$,
—NHC(=O)$NR^2{}_2$, —NHC(=O)$NR^3R^4$,
—$NR^2$C(=O)$NH_2$, —$NR^2$C(=O)$NHR^2$,
—$NR^2$C(=O)$NR^2{}_2$, —$NR^2$C(=O)$NR^3R^4$,
—NHS(=O)$_2R^2$, —$NR^2$S(=O)$_2R^2$,
—S(=O)$_2NH_2$, —S(=O)$_2NHR^2$, —S(=O)$_2NR^2{}_2$, —S(=O)$_2NR^3R^4$,
—S(=O)$R^2$, —S(=O)$_2R^2$, —OS(=O)$_2R^2$, or —S(=O)$_2OR^2$
wherein:
each -$L^1$- is independently saturated aliphatic $C_{1-5}$alkylene;
in each group —$NR^3R^4$, —$R^3$ and —$R^4$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N, O, or S;
each —$R^2$ is independently:
—$R^{A1}$, —$R^{A2}$, —$R^{A3}$, —$R^{A4}$, —$R^{A5}$, —$R^{A6}$, —$R^{A7}$, —$R^{A8}$,
$L^A$-$R^{A4}$, -$L^A$-$R^{A5}$, -$L^A$-$R^{A6}$, -$L_A$-$R^{A7}$, or -$L^A$-$R^{A8}$;
wherein:
each —$R^{A1}$ is independently saturated aliphatic $C_{1-6}$alkyl;
each —$R^{A2}$ is independently aliphatic $C_{2-6}$alkenyl;
each —$R^{A3}$ is independently aliphatic $C_{2-6}$alkynyl;
each —$R^{A4}$ is independently saturated $C_{3-6}$cycloalkyl;
each —$R^{A5}$ is independently $C_{3-6}$cycloalkenyl;
each —$R^{A6}$ is independently non-aromatic $C_{3-7}$heterocyclyl;
each —$R^{A7}$ is independently $C_{6-10}$-carboaryl;
each —$R^{A8}$ is independently $C_{5-10}$heteroaryl;
each -$L^A$- is independently saturated aliphatic $C_{1-3}$alkylene;
and wherein:
each —$R^{A4}$, —$R^{A5}$, —$R^{A6}$, —$R^{A7}$, and —$R^{A8}$ is optionally substituted, for example, with one or more substituents —$R^{B1}$ and/or one or more substituents —$R^{B2}$, and each —$R^{A1}$, —$R^{A2}$, —$R^{A3}$, and -$L^A$- is optionally substituted, for example, with one or more substituents —$R^{B2}$,
wherein:
each —$R^{B1}$ is independently saturated aliphatic $C_{1-4}$-alkyl, phenyl, or benzyl;
each —$R^{B2}$ is independently:
—F, —Cl, —Br, —I,
—$CF_3$, —$OCF_3$,
—OH, -$L^C$-OH, —O-$L^C$-OH,
—$OR^{C1}$, -$L^C$-$OR^{C1}$, —O-$L^C$-$OR^{C1}$,
—SH, —$SR^{C1}$,
—CN,
—$NO_2$,
—$NH_2$, —$NHR^{C1}$, —$NR^{C1}{}_2$, —$NR^{C2}R^{C3}$,
-$L^C$-$NH_2$, -$L^C$-$NHR^{C1}$, -$L^C$-$NR^{C1}{}_2$, or -$L^C$-$NR^{C2}R^{C3}$,
—O-$L^C$-$NH_2$, —O-$L^C$-$NHR^{C1}$, —O-$L^C$-$NR^{C1}{}_2$, —O-$L^C$-$NR^{C2}R^{C3}$,
—C(=O)OH, —C(=O)$OR^{C1}$,
—OC(=O)$R^{C1}$,
—C(=O)$R^{C1}$,
—C(=O)$NH_2$, —C(=O)$NHR^{C1}$, —C(=O)$NR^{C1}{}_2$, —C(=O)$NR^{C2}R^{C3}$,
—NHC(=O)$R^{C1}$, —$NR^{C1}$C(=O)$R^{C1}$,
—NHS(=O)$_2R^{C1}$, —$NR^{C1}$S(=O)$_2R^{C1}$,
—S(=O)$_2NH_2$, —S(=O)$_2NHR^{C1}$, —S(=O)$_2NR^{C1}{}_2$, —S(=O)$_2NR^{C2}R^{C3}$, or
—S(=O)$_2R^{C1}$;
wherein:
each —$R^{C1}$ is independently unsubstituted saturated aliphatic $C_{1-4}$-alkyl, phenyl, or benzyl;
each -$L^C$- is independently unsubstituted saturated aliphatic $C_{1-5}$alkylene; and
in each group —$NR^{C2}R^{C3}$, —$R^{C2}$ and —$R^{C3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N, O, or S,
and pharmaceutically and physiologically acceptable salts thereof,
with the proviso that the compound is not a compound:
(a) P-002 through P-015; and
(b) where -T is:

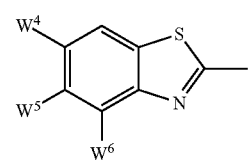

—R— is:

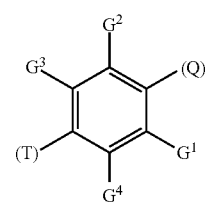

and —P is:

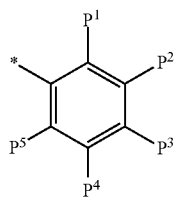

and —W⁴ is —H, -Q- is —CH═CH—, -G¹, -G², -G³, and -G⁴ are all —H, and
(i) —P¹, —P², —P⁴ and —P⁵ are all —H, and —P³ is —R^A1; or
(ii) one of —P¹, —P², —P³, P⁴ and —P⁵ is —R^A7, and the others of —P¹, —P², —P³, P⁴ and —P⁵ are —H.

2. A compound of formula:

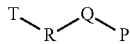

wherein
—R— is independently selected from:

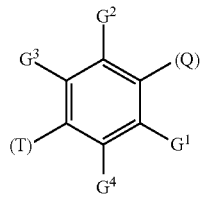

wherein (T) indicates the point of attachment to -T;
and (Q) indicates the point of attachment to -Q-;
-Q- is independently selected from:
—NHC(O)—; —NR¹C(O)—;
each —R¹ is independently unsubstituted saturated aliphatic $C_{1-4}$-alkyl;
—P is independently selected from:

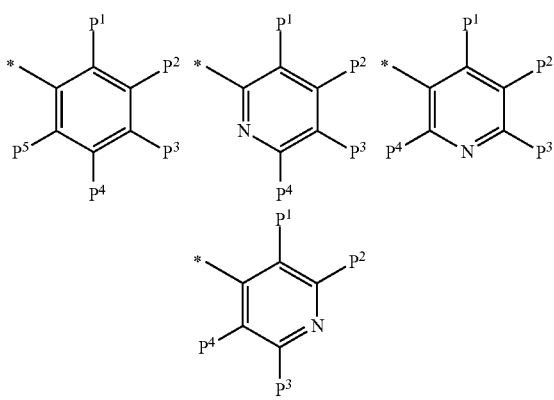

where the asterisk indicates the point of attachment;
-T is independently selected from:

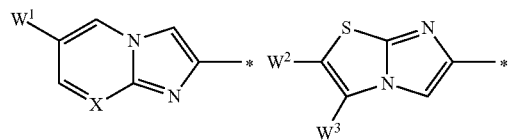

where the asterisk indicates the point of attachment;
and X is independently CH;
—W¹ is independently —W^A;
—W² is independently —H or —W^A;
—W³ is independently —H or —W^A;
where —W^A is independently selected from:
—F, —Cl, —Br, —I,
—OH, —W^A1, —O—W^A1,
—NH₂, —NHW^A1, and —N(W^A1)₂;
and —W^A1 is independently selected from:
unsubstituted saturated aliphatic $C_{1-4}$-alkyl,
—CF₃,
—CH₂CH₂OH, and
—CH₂CH₂N(Me)₂;
-G¹ is independently —H or -G^A;
-G² is independently —H or -G^A;
where -G^A is independently selected from:
—F, —Cl, —Br, —I,
—CF₃, —OCF₃,
—OH, —OR²;
—[O—CH₂CH₂]ₙ—R^B2, where n is 2 to 6;
-G³ is independently —H or -G^B;
-G⁴ is independently —H or -G^B
where -G^B is independently selected from:
—F, —Cl, —Br, —I,
—CF₃, —OCF₃,
—OH, —OR²;
—[O—CH₂CH₂]ₙ—R^B2, where n is 2 to 6;
wherein:
—P¹ is independently —H or —P^A;
—P² is independently —H or —P^B;
—P³ is independently —H or —P^C;
—P⁴ is independently —H or —P^B;
—P⁵ is independently —H or —P^A;
and wherein:
each —P^A, each —P^B, and each —P^C is independently:
—F, —Cl, —Br, —I,
—R²,
—CF₃, —OCF₃,
—OH, -L¹-OH,
—OR², -L¹-OR², —O-L¹-OR²,
—SH, —SR²,
—CN,
—NO₂,
—NH₂, —NHR², —NR²₂, —NR³R⁴,
—NHOH,
-L¹-NH₂, -L¹-NHR², -L¹-NR²₂, -L¹-NR³R⁴,
—O-L¹-NH₂, —O-L¹-NHR², —O-L¹-NR²₂, —O-L¹-NR³R⁴,
—C(═O)OH, —C(═O)OR²,
—OC(═O)R²,
—C(═O)NH₂, —C(═O)NHR², —C(═O)NR²₂,
—C(═O)NR³R⁴,
—NHC(═O)R², —NR²C(═O)R²,
—C(═O)NHOR², —C(═O)NR²OR²,
—NHC(═O)OR², —NR²C(═O)OR², —OC(=O)NH$_2$, —OC(=O)NHR$^2$, —OC(=O)NR$^2_2$,
—OC(=O)NR$^3$R$^4$,
—C(=O)R$^2$,
—NHC(=O)NH$_2$, —NHC(=O)NHR$^2$,
—NHC(=O)NR$^2_2$, —NHC(=O)NR$^3$R$^4$,
—NR$^2$C(=O)NH$_2$, —NR$^2$C(=O)NHR$^2$,
—NR$^2$C(=O)NR$^2_2$, —NR$^2$C(=O)NR$^3$R$^4$,
—NHS(=O)$_2$R$^2$, —NR$^2$S(=O)$_2$R$^2$,
—S(=O)$_2$NH$_2$, —S(=O)$_2$NHR$^2$, —S(=O)$_2$NR$^2_2$, —S(=O)$_2$NR$^3$R$^4$,
—S(=O)R$^2$, —S(=O)$_2$R$^2$, —OS(=O)$_2$R$^2$, or —S(=O)$_2$OR$^2$ wherein:
  each -L$^1$- is independently saturated aliphatic C$_{1-5}$alkylene;
  in each group —NR$^3$R$^4$, —R$^3$ and —R$^4$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N, O, or S;
  each —R$^2$ is independently:
    —R$^{A1}$, —R$^{A2}$, —R$^{A3}$, —R$^{A4}$, —R$^{A5}$, —R$^{A6}$, —R$^{A7}$, —R$^{A8}$,
    -L$^A$-R$^{A4}$, -L$^A$-R$^{A5}$, -L$^A$-R$^{A6}$, L$^A$-R$^{A7}$, or -L$^A$-R$^{A8}$;
  wherein:
    each —R$^{A1}$ is independently saturated aliphatic C$_{1-6}$alkyl;
    each —R$^{A2}$ is independently aliphatic C$_{2-6}$alkenyl;
    each —R$^{A3}$ is independently aliphatic C$_{2-6}$alkynyl;
    each —R$^{A4}$ is independently saturated C$_{3-6}$cycloalkyl;
    each —R$^{A5}$ is independently C$_{3-6}$cycloalkenyl;
    each —R$^{A6}$ is independently non-aromatic C$_{3-7}$heterocyclyl;
    each —R$^{A7}$ is independently C$_{6-10}$-carboaryl;
    each —R$^{A8}$ is independently C$_{5-10}$heteroaryl;
    each -L$^A$- is independently saturated aliphatic C$_{1-3}$alkylene;
  and wherein:
    each —R$^{A4}$, —R$^{A5}$, —R$^{A6}$, —R$^{A7}$, and —R$^{A8}$ is optionally substituted, for example, with one or more substituents —R$^{B1}$ and/or one or more substituents —R$^{B2}$, and
    each —R$^{A1}$, —R$^{A2}$, —R$^{A3}$, and -L$^A$- is optionally substituted, for example, with one or more substituents —R$^{B2}$,
wherein:
each —R$^{B1}$ is independently saturated aliphatic C$_{1-4}$-alkyl, phenyl, or benzyl;
each —R$^{B2}$ is independently:
  —F, —Cl, —Br, —I,
  —CF$_3$, —OCF$_3$,
  —OH, -L$^C$-OH, —O-L$^C$-OH,
  —OR$^{C1}$, -L$^C$-OR$^{C1}$, —O-L$^C$-OR$^{C1}$,
  —SH, —SR$^{C1}$,
  —CN,
  —NO$_2$,
  —NH$_2$, —NHR$^{C1}$, —NR$^{C1}_2$, —NR$^{C2}$R$^{C3}$,
  -L$^C$-NH$_2$, -L$^C$-NHR$^{C1}$, -L$^C$-NR$^{C1}_2$, or -L$^C$-NR$^{C2}$R$^{C3}$,
  —O-L$^C$-NH$_2$, —O-L$^C$-NHR$^{C1}$, —O-L$^C$-NR$^{C1}_2$,
  —O-L$^C$-NR$^{C2}$R$^{C3}$,
  —C(=O)OH, —C(=O)OR$^{C1}$,
  —OC(=O)R$^{C1}$,
  —C(=O)R$^{C1}$,
  —C(=O)NH$_2$, —C(=O)NHR$^{C1}$, —C(=O)NR$^{C1}_2$,
  —C(=O)NR$^{C2}$R$^{C3}$,
  —NHC(=O)R$^{C1}$, —NR$^{C1}$C(=O)R$^{C1}$,
  —NHS(=O)$_2$R$^{C1}$, —NR$^{C1}$S(=O)$_2$R$^{C1}$,
  —S(=O)$_2$NH$_2$, —S(=O)$_2$NHR$^{C1}$, —S(=O)$_2$NR$^{C1}_2$,
  —S(=O)$_2$NR$^{C2}$R$^{C3}$, or
  —S(=O)$_2$R$^{C1}$;
wherein:
  each —R$^{C1}$ is independently unsubstituted saturated aliphatic C$_{1-4}$-alkyl, phenyl, or benzyl;
  each -L$^C$- is independently unsubstituted saturated aliphatic C$_{1-5}$alkylene; and
  in each group —NR$^{C2}$R$^{C3}$, —R$^{C2}$ and —R$^{C3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N, O, or S,
and pharmaceutically and physiologically acceptable salts thereof.

3. A compound of formula:

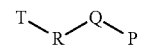

wherein
—R— is independently selected from:

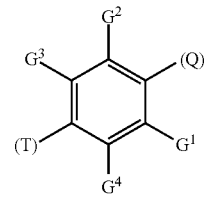

wherein (T) indicates the point of attachment to -T; and (Q) indicates the point of attachment to -Q-;
-Q- is independently selected from:
  —NHC(O)—; —NR$^1$C(O)—;
each —R$^1$ is independently unsubstituted saturated aliphatic C$_{1-4}$-alkyl;
—P is independently selected from:

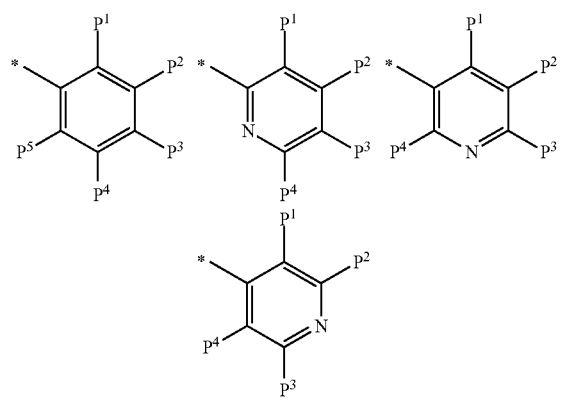

where the asterisk indicates the point of attachment;

-T is independently selected from:

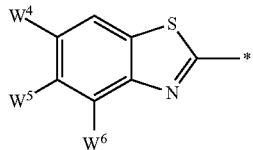

where the asterisk indicates the point of attachment;
—$W^4$ is independently —H or —$W^A$;
—$W^5$ is independently —H or —$W^A$;
—$W^6$ is independently —H or —$W^A$;
with the proviso that at least one of —$W^4$, —$W^5$ and —$W^6$ is —$W^A$;
where —$W^A$ is independently selected from:
—F, —Cl, —Br, —I,
—OH, —$W^{A1}$, —O—$W^{A1}$,
—$NH_2$, —$NHW^{A1}$, and —$N(W^{A1})_2$;
and —$W^{A1}$ is independently selected from:
unsubstituted saturated aliphatic $C_{1-4}$-alkyl,
—$CF_3$,
—$CH_2CH_2OH$, and
—$CH_2CH_2N(Me)_2$;
-$G^1$ is independently —H or -$G^A$;
-$G^2$ is independently —H or -$G^A$;
where -$G^A$ is independently selected from:
—F, —Cl, —Br, —I,
—$CF_3$, —$OCF_3$,
—OH, —$OR^2$;
—$[O—CH_2CH_2]_n$—$R^{B2}$, where n is 2 to 6;
-$G^3$ is independently —H or -$G^B$;
-$G^4$ is independently —H or -$G^B$
where -$G^B$ is independently selected from:
—F, —Cl, —Br, —I,
—$CF_3$, —$OCF_3$,
—OH, —$OR^2$;
—$[O—CH_2CH_2]_n$—$R^{B2}$, where n is 2 to 6;
wherein:
—$P^1$ is independently —H or —$P^A$;
—$P^2$ is independently —H or —$P^B$;
—$P^3$ is independently —H or —$P^C$;
—$P^4$ is independently —H or —$P^B$;
—$P^5$ is independently —H or —$P^A$;
and wherein:
each —$P^A$, each —$P^B$, and each —$P^C$ is independently:
—F, —Cl, —Br, —I,
—$R^2$,
—$CF_3$, —$OCF_3$,
—OH, -$L^1$-OH,
—$OR^2$, -$L^1$-$OR^2$, —O-$L^1$-$OR^2$,
—SH, —$SR^2$,
—CN,
—$NO_2$,
—$NH_2$, —$NHR^2$, —$NR^2_2$, —$NR^3R^4$,
—NHOH,
-$L^1$-$NH_2$, -$L^1$-$NHR^2$, -$L^1$-$NR^2_2$, -$L^1$-$NR^3R^4$,
—O-$L^1$-$NH_2$, —O-$L^1$-$NHR^2$, —O-$L^1$-$NR^2_2$, —O-$L^1$-$NR^3R^4$,
—C(=O)OH, —C(=O)$OR^2$,
—OC(=O)$R^2$,
—C(=O)$NH_2$, —C(=O)$NHR^2$, —C(=O)$NR^2_2$, —C(=O)$NR^3R^4$,
—NHC(=O)$R^2$, —$NR^2$C(=O)$R^2$,
—C(=O)$NHOR^2$, —C(=O)$NR^2OR^2$,
—NHC(=O)$OR^2$, —$NR^2$C(=O)$OR^2$,
—OC(=O)$NH_2$, —OC(=O)$NHR^2$, —OC(=O)$NR^2_2$, —OC(=O)$NR^3R^4$,
—C(=O)$R^2$,
—NHC(=O)$NH_2$, —NHC(=O)$NHR^2$,
—NHC(=O)$NR^2_2$, —NHC(=O)$NR^3R^4$,
—$NR^2$C(=O)$NH_2$, —$NR^2$C(=O)$NHR^2$,
—$NR^2$C(=O)$NR^2_2$, —$NR^2$C(=O)$NR^3R^4$,
—NHS(=O)$_2R^2$, —$NR^2$S(=O)$_2R^2$,
—S(=O)$_2NH_2$, —S(=O)$_2NHR^2$, —S(=O)$_2NR^2_2$, —S(=O)$_2NR^3R^4$,
—S(=O)$R^2$, —S(=O)$_2R^2$, —OS(=O)$_2R^2$, or —S(=O)$_2OR^2$
wherein:
each -$L^1$- is independently saturated aliphatic $C_{1-5}$alkylene;
in each group —$NR^3R^4$, —$R^3$ and —$R^4$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N, O, or S;
each —$R^2$ is independently:
—$R^{A1}$, —$R^{A2}$, —$R^{A3}$, —$R^{A4}$, —$R^{A5}$, —$R^{A6}$, —$R^{A7}$, —$R^{A8}$,
-$L^A$-$R^{A4}$, -$L^A$-$R^{A5}$, -$L^A$-$R^{A6}$, -$L^A$-$R^{A7}$, or -$L^A$-$R^{A8}$;
wherein:
each —$R^{A1}$ is independently saturated aliphatic $C_{1-6}$alkyl;
each —$R^{A2}$ is independently aliphatic $C_{2-6}$alkenyl;
each —$R^{A3}$ is independently aliphatic $C_{2-6}$alkynyl;
each —$R^{A4}$ is independently saturated $C_{3-6}$cycloalkyl;
each —$R^{A5}$ is independently $C_{3-6}$cycloalkenyl;
each —$R^{A6}$ is independently non-aromatic $C_{3-7}$heterocyclyl;
each —$R^{A7}$ is independently $C_{6-10}$-carboaryl;
each —$R^{A8}$ is independently $C_{5-10}$heteroaryl;
each -$L^A$- is independently saturated aliphatic $C_{1-3}$alkylene;
and wherein:
each —$R^{A4}$, —$R^{A5}$, —$R^{A6}$, —$R^{A7}$, and —$R^{A8}$ is optionally substituted, for example, with one or more substituents —$R^{B1}$ and/or one or more substituents —$R^{B2}$, and
each —$R^{A1}$, —$R^{A2}$, —$R^{A3}$, and -$L^A$- is optionally substituted, for example, with one or more substituents —$R^{B2}$,
wherein:
each —$R^{B1}$ is independently saturated aliphatic $C_{1-4}$-alkyl, phenyl, or benzyl;
each —$R^{B2}$ is independently:
—F, —Cl, —Br, —I,
—$CF_3$, —$OCF_3$,
—OH, -$L^C$-OH, —O-$L^C$-OH,
—$OR^{C1}$, -$L^C$-$OR^{C1}$, —O-$L^C$-$OR^{C1}$,
—SH, —$SR^{C1}$,
—CN,
—$NO_2$,
—$NH_2$, —$NHR^{C1}$, —$NR^{C1}_2$, —$NR^{C2}R^{C3}$,
-$L^C$-$NH_2$, -$L^C$-$NHR^{C1}$, -$L^C$-$NR^{C1}_2$, or -$L^C$-$NR^{C2}R^{C3}$,
—O-$L^C$-$NH_2$, —O-$L^C$-$NHR^{C1}$, —O-$L^C$-$NR^{C1}_2$, —O-$L^C$-$NR^{C2}R^{C3}$,
—C(=O)OH, —C(=O)$OR^{C1}$,
—OC(=O)$R^{C1}$,
—C(=O)$R^{C1}$, —C(=O)NH$_2$, —C(=O)NHR$^{C1}$, —C(=O)NR$^{C1}$$_2$,
—C(=O)NR$^{C2}$R$^{C3}$,
—NHC(=O)R$^{C1}$, —NR$^{C1}$C(=O)R$^{C1}$,
—NHS(=O)$_2$R$^{C1}$, —NR$^{C1}$S(=O)$_2$R$^{C1}$,
—S(=O)$_2$NH$_2$, —S(=O)$_2$NHR$^{C1}$, —S(=O)$_2$NR$^{C1}$$_2$,
—S(=O)$_2$NR$^{C2}$R$^{C3}$, or
—S(=O)$_2$R$^{C1}$;

wherein:
each —R$^{C1}$ is independently unsubstituted saturated aliphatic C$_{1-4}$-alkyl, phenyl, or benzyl;
each -L$^C$- is independently unsubstituted saturated aliphatic C$_{1-5}$alkylene; and
in each group —NR$^{C2}$R$^{C3}$, —R$^{C2}$ and —R$^{C3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N, O, or S;

wherein the compound contains a —F group;
and pharmaceutically and physiologically acceptable salts thereof;
with the proviso that the compound is not compound P-001.

4. A compound of formula:

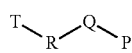

wherein
—R— is independently selected from:

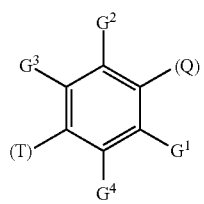

wherein (T) indicates the point of attachment to -T;
and (Q) indicates the point of attachment to -Q-;
-Q- is independently selected from:
—NHC(O)—; —NR$^1$C(O)—;
—N=N—;
—CH=CH—; —CR$^1$=CH—; —CH=CR$^1$—;
—CR$^1$=CR$^1$—;
each —R$^1$ is independently unsubstituted saturated aliphatic C$_{1-4}$-alkyl;
—P is independently selected from:

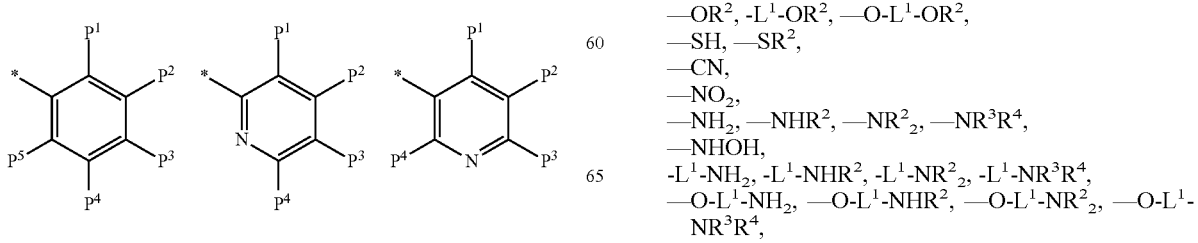

where the asterisk indicates the point of attachment;
-T is independently selected from:

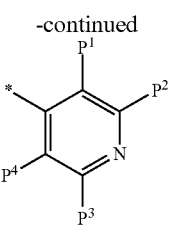

where the asterisk indicates the point of attachment;
and X is independently N;
—W$^1$ is independently H or —W$^A$;
where —W$^A$ is independently selected from:
—F, —Cl, —Br, —I,
—OH, —W$^{41}$, —O—W$^{41}$,
—NH$_2$, —NHW$^{41}$, and —N(W$^{41}$)$_2$;
and —W$^{41}$ is independently selected from:
unsubstituted saturated aliphatic C$_{1-4}$-alkyl,
—CF$_3$,
—CH$_2$CH$_2$OH, and
—CH$_2$CH$_2$N(Me)$_2$;
-G$^1$ is independently —H or -G$^A$;
-G$^2$ is independently —H or -G$^A$;
where -G$^A$ is independently selected from:
—F, —Cl, —Br, —I,
—CF$_3$, —OCF$_3$,
—OH, —OR$^2$;
—[O—CH$_2$CH$_2$]$_n$—R$^{B2}$, where n is 2 to 6;
-G$^3$ is independently —H or -G$^B$;
-G$^4$ is independently —H or -G$^B$
where -G$^B$ is independently selected from:
—F, —Cl, —Br, —I,
—CF$_3$, —OCF$_3$,
—OH, —OR$^2$;
—[O—CH$_2$CH$_2$]$_n$—R$^{B2}$, where n is 2 to 6;
wherein:
—P$^1$ is independently —H or —P$^A$;
—P$^2$ is independently —H or —P$^B$;
—P$^3$ is independently —H or —P$^C$;
—P$^4$ is independently —H or —P$^B$;
—P$^5$ is independently —H or —P$^A$;
and wherein:
each —P$^A$, each —P$^B$, and each —P$^C$ is independently:
—F, —Cl, —Br, —I,
—R$^2$,
—CF$_3$, —OCF$_3$,
—OH, -L$^1$-OH,
—OR$^2$, -L$^1$-OR$^2$, —O-L$^1$-OR$^2$,
—SH, —SR$^2$,
—CN,
—NO$_2$,
—NH$_2$, —NHR$^2$, —NR$^2$$_2$, —NR$^3$R$^4$,
—NHOH,
-L$^1$-NH$_2$, -L$^1$-NHR$^2$, -L$^1$-NR$^2$$_2$, -L$^1$-NR$^3$R$^4$,
—O-L$^1$-NH$_2$, —O-L$^1$-NHR$^2$, —O-L$^1$-NR$^2$$_2$, —O-L$^1$-NR$^3$R$^4$, —C(=O)OH, —C(=O)OR², 
—OC(=O)R², 
—C(=O)NH₂, —C(=O)NHR², —C(=O)NR²₂, 
—C(=O)NR³R⁴, 
—NHC(=O)R², —NR²C(=O)R², 
—C(=O)NHOR², —C(=O)NR²OR², 
—NHC(=O)OR², —NR²C(=O)OR², 
—OC(=O)NH₂, —OC(=O)NHR², —OC(=O)NR²₂, 
—OC(=O)NR³R⁴, 
—C(=O)R², 
—NHC(=O)NH₂, —NHC(=O)NHR², 
—NHC(=O)NR²₂, —NHC(=O)NR³R⁴, 
—NR²C(=O)NH₂, —NR²C(=O)NHR², 
—NR²C(=O)NR²₂, —NR²C(=O)NR³R⁴, 
—NHS(=O)₂R², —NR²S(=O)₂R², 
—S(=O)₂NH₂, —S(=O)₂NHR², —S(=O)₂NR²₂, 
—S(=O)₂NR³R⁴, 
—S(=O)R², —S(=O)₂R², —OS(=O)₂R², or 
—S(=O)₂OR² wherein: 
each -L¹- is independently saturated aliphatic C₁₋₅alkylene; 
in each group —NR³R⁴, —R³ and —R⁴, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N, O, or S; 
each —R² is independently: 
—R^{A1}, —R^{A2}, —R^{A3}, —R^{A4}, —R^{A5}, —R^{A6}, —R^{A7}, —R^{A8}, 
-L^A-R^{A4}, -L^A-R^{A5}, -L^A-R^{A6}, -L^A-R^{A7}, or -L^A-R^{A8}; 
wherein: 
each —R^{A1} is independently saturated aliphatic C₁₋₆alkyl; 
each —R^{A2} is independently aliphatic C₂₋₆alkenyl; 
each —R^{A3} is independently aliphatic C₂₋₆alkynyl; 
each —R^{A4} is independently saturated C₃₋₆cycloalkyl; 
each —R^{A5} is independently C₃₋₆cycloalkenyl; 
each —R^{A6} is independently non-aromatic C₃₋₇heterocyclyl; 
each —R^{A7} is independently C₆₋₁₀-carboaryl; 
each —R^{A8} is independently C₅₋₁₀heteroaryl; 
each -L^A- is independently saturated aliphatic C₁₋₃alkylene; 
and wherein: 
each —R^{A4}, —R^{A5}, —R^{A6}, —R^{A7}, and R^{A8} is optionally substituted, for example, with one or more substituents —R^{B1} and/or one or more substituents —R^{B2}, and 
each —R^{A1}, —R^{A2}, —R^{A3}, and -L^A- is optionally substituted, for example, with one or more substituents —R^{B2}, wherein: 
each —R^{B1} is independently saturated aliphatic C₁₋₄-alkyl, phenyl, or benzyl; 
each —R^{B2} is independently: 
—F, —Cl, —Br, —I, 
—CF₃, —OCF₃, 
—OH, -L^C-OH, —O-L^C-OH, 
—OR^{C1}, -L^C-OR^{C1}, —O-L^C-OR^{C1}, 
—SH, —SR^{C1}, 
—CN, 
—NO₂, 
—NH₂, —NHR^{C1}, —NR^{C1}₂, —NR^{C2}R^{C3}, 
-L^C-NH₂, -L^C-NHR^{C1}, -L^C-NR^{C1}₂, or -L^C-NR^{C2}R^{C3}, 
—O-L^C-NH₂, —O-L^C-NHR^{C1}, —O-L^C-NR^{C1}₂, 
—O-L^C-NR^{C2}R^{C3}, 
—C(=O)OH, —C(=O)OR^{C1}, 
—OC(=O)R^{C1}, 
—C(=O)R^{C1}, 
—C(=O)NH₂, —C(=O)NHR^{C1}, —C(=O)NR^{C1}₂, 
—C(=O)NR^{C2}R^{C3}, 
—NHC(=O)R^{C1}, —NR^{C1}C(=O)R^{C1}, 
—NHS(=O)₂R^{C1}, —NR^{C1}S(=O)₂R^{C1}, 
—S(=O)₂NH₂, —S(=O)₂NHR^{C1}, —S(=O)₂NR^{C1}₂, 
—S(=O)₂NR^{C2}R^{C3}, or 
—S(=O)₂R^{C1}; 
wherein: 
each —R^{C1} is independently unsubstituted saturated aliphatic C₁₋₄-alkyl, phenyl, or benzyl; and 
each -L^C- is independently unsubstituted saturated aliphatic C₁₋₅alkylene; and 
in each group —NR^{C2}R^{C3}, —R^{C2} and —R^{C3}, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N, O, or S, and pharmaceutically and physiologically acceptable salts thereof.

5. A compound according to any one of claims 1 to 4, wherein -G^A is independently selected from: 
—F, 
—CF₃, —OCF₃, 
—OH, and —OR².

6. A compound according to any one of claims 1 to 4, wherein -G^B is independently selected from: 
—F, 
—CF₃, —OCF₃, 
—OH, —OR²; and 
—[O—CH₂CH₂]ₙ—R^{B2}, where n is 2 to 6.

7. A compound according to any one of claims 1 to 4, wherein -G^B is independently —OCH₂CH₂N(Me)₂ or [O—CH₂CH₂]ₙ—R^{B2}, where n is 2 to 6.

8. A compound according to any one of claims 1 to 4, wherein —P is independently:

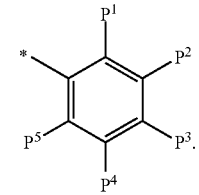

9. A compound according to claim 8, wherein —P¹ and —P⁵ are independently —H or —P^A.

10. A compound according to claim 8, wherein —P² and —P⁴ are independently —H or —P^B.

11. A compound according to claim 8, wherein —P³ is independently —H or —P^C.

12. A compound according to claim 9, wherein —P^A is independently selected from: 
—F, 
—CF₃, —OCF₃, 
—OH, 
—OR², 
—NO₂, 
—NH₂, —NHR², —NR²₂, and —NR³R⁴.

13. A compound according to claim 10, wherein —$P^B$ is independently selected from:
—F,
—$CF_3$, —$OCF_3$,
—$NO_2$,
—$NH_2$, —$NHR^2$, —$NR^2{}_2$, and —$NR^3R^4$.

14. A compound according to claim 11, wherein —$P^C$ is independently selected from:
—F, —Cl, —Br, —I,
—$CF_3$, —$OCF_3$,
—OH, —$OR^2$,
—$NO_2$,
—$NH_2$, —$NHR^2$, —$NR^2{}_2$, —$NR^3R^4$,
—NHOH,
—OC(=O)$R^2$, and
—NHC(=O)$R^2$.

15. A compound according to claim 8, wherein at least one of —$P^1$, —$P^2$, —$P^3$, $P^4$, and —$P^5$ is not —H.

16. A compound according to any one of claims 1 to 4 wherein —P is independently selected from:

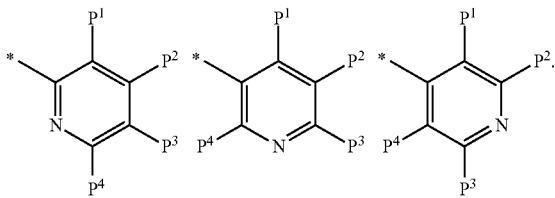

17. A compound according to claim 16, wherein —$P^2$, —$P^3$, and —$P^4$ are each independently —H.

18. A compound according to claim 1 or claim 3, wherein —$W^5$ is independently —H.

19. A compound according to claim 18, wherein —$W^6$ is independently —H.

20. A compound according to claim 18, wherein —$W^4$ is independently —H or —$W^A$.

21. A compound according to claim 20 wherein —$W^A$ is independently selected from —OH, —$W^{A1}$, and —O—$W^{A1}$.

22. A compound according to claim 21, wherein —$W^{A1}$ is independently -Me.

23. A compound according to claim 1, claim 2 or claim 4 wherein —$W^1$ is independently —H or —$W^A$.

24. A compound according to claim 23, wherein —$W^A$ is independently —$W^{A1}$.

25. A compound according to claim 24, wherein —$W^{A1}$ is independently -Me.

26. A compound according to claim 1 or claim 2 wherein —$W^2$ is independently —H or —$W^A$.

27. A compound according to claim 26, wherein —$W^A$ is independently -Me.

28. A compound according to claim 1 or claim 2, wherein —$W^3$ is independently —H or —$W^A$.

29. A compound according to claim 28, wherein —$W^A$ is independently -Me.

30. A compound according to any one of claims 1 to 4, wherein the compound has a molecular weight of 500 or less.

31. A compound according to any one of claims 1 to 4, wherein the compound has a miLog P of from 2.0 to 5.0.

32. A compound according to any one of claims 1 to 4, wherein the compound has a Log D of from 2.0 to 5.0.

33. A compound according to any one of claims 1 to 4, wherein the compound has a topological polar surface area of 90 Å$^2$ or less.

34. A compound according to any one of claims 1 to 4, wherein the compound has 3 or less hydrogen bond donors.

35. A method of detecting and/or visualizing paired helical filaments (PHFs), the method comprising
(a) contacting the PHFs with a compound which binds to said PHFs; and
(b) detecting the presence of said compound;
wherein the compound which binds to said PHFs is a compound as defined in any one of claims 1 to 4.

36. A method of detecting and/or visualizing aggregated tau molecules, the method comprising
(a) contacting the aggregated tau molecules with a compound which binds to said aggregated tau molecules; and
(b) detecting the presence of said compound;
wherein the compound which binds to said aggregated tau molecules is a compound as defined in any one of claims 1 to 4.

* * * * *